(12) United States Patent
Leimbach et al.

(10) Patent No.: US 9,913,642 B2
(45) Date of Patent: Mar. 13, 2018

(54) SURGICAL INSTRUMENT COMPRISING A SENSOR SYSTEM

(71) Applicant: Ethicon Endo-Surgery, Inc., Cincinnati, OH (US)

(72) Inventors: Richard L. Leimbach, Cincinnati, OH (US); Shane R. Adams, Lebanon, OH (US); Mark D. Overmyer, Cincinnati, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 680 days.

(21) Appl. No.: 14/226,142

(22) Filed: Mar. 26, 2014

(65) Prior Publication Data
US 2015/0272575 A1 Oct. 1, 2015

(51) Int. Cl.
*A61B 17/072* (2006.01)
*A61B 90/98* (2016.01)
(Continued)

(52) U.S. Cl.
CPC ...... *A61B 17/072* (2013.01); *A61B 17/07207* (2013.01); *A61B 90/98* (2016.02); *A61B 18/1445* (2013.01); *A61B 34/30* (2016.02); *A61B 2017/00017* (2013.01); *A61B 2017/00022* (2013.01); *A61B 2017/0046* (2013.01); *A61B 2017/00075* (2013.01); *A61B 2017/00084* (2013.01); *A61B 2017/00115* (2013.01); *A61B 2017/00123* (2013.01); *A61B 2017/00199* (2013.01); *A61B 2017/00212* (2013.01);
(Continued)

(58) Field of Classification Search
CPC ................ A61B 17/068; A61B 17/072; A61B 2017/00017; A61B 2017/00022
USPC ...................... 227/19, 175.1, 176.1; 606/139
See application file for complete search history.

(56) References Cited

U.S. PATENT DOCUMENTS

| 66,052 A | 6/1867 | Smith |
|---|---|---|
| 662,587 A | 11/1900 | Blake |

(Continued)

FOREIGN PATENT DOCUMENTS

| AU | 2008207624 A1 | 3/2009 |
|---|---|---|
| AU | 2010214687 A1 | 9/2010 |

(Continued)

OTHER PUBLICATIONS

International Search Report and Written Opinion for Application No. PCT/US2015/019817, dated Jul. 23, 2015 (15 pages).

(Continued)

*Primary Examiner* — Nathaniel Chukwurah

(57) ABSTRACT

A surgical instrument can comprise a handle, a shaft assembly, a first sensor configured to detect a condition of the surgical instrument, and a second sensor configured to detect the condition of the surgical instrument. The surgical instrument can further comprise a processor, wherein the first sensor and the second sensor are in signal communication with the processor, wherein the processor receives a first signal from the first sensor, wherein the processor receives a second signal from the second sensor, wherein the processor is configured to utilize the first signal and the second signal to determine the condition, and wherein the processor is configured to communicate instructions to the surgical instrument in view of the condition.

18 Claims, 119 Drawing Sheets

(51) Int. Cl.
*A61B 17/00* (2006.01)
*H01M 10/42* (2006.01)
*A61B 18/14* (2006.01)
*A61B 90/00* (2016.01)
*A61B 34/30* (2016.01)
*H01M 2/10* (2006.01)

(52) U.S. Cl.
CPC ............... *A61B 2017/00221* (2013.01); *A61B 2017/00398* (2013.01); *A61B 2017/00477* (2013.01); *A61B 2017/00734* (2013.01); *A61B 2017/07271* (2013.01); *A61B 2017/07285* (2013.01); *A61B 2090/081* (2016.02); *A61B 2090/0803* (2016.02); *A61B 2090/0807* (2016.02); *A61B 2090/0811* (2016.02); *H01M 2/1055* (2013.01); *H01M 2010/4278* (2013.01); *H01M 2220/30* (2013.01)

(56) References Cited

U.S. PATENT DOCUMENTS

| | | |
|---|---|---|
| 670,748 A | 3/1901 | Weddeler |
| 951,393 A | 3/1910 | Hahn |
| 1,306,107 A | 6/1919 | Elliott |
| 1,314,601 A | 9/1919 | McCaskey |
| 1,677,337 A | 7/1928 | Grove |
| 1,794,907 A | 3/1931 | Kelly |
| 2,037,727 A | 4/1936 | La Chapelle |
| 2,132,295 A | 10/1938 | Hawkins |
| 2,161,632 A | 6/1939 | Nattenheimer |
| 2,211,117 A | 8/1940 | Hess |
| 2,214,870 A | 9/1940 | West |
| 2,318,379 A | 5/1943 | Davis et al. |
| 2,329,440 A | 9/1943 | La Place |
| 2,441,096 A | 5/1948 | Happe |
| 2,448,741 A | 9/1948 | Scott et al. |
| 2,450,527 A | 10/1948 | Smith et al. |
| 2,526,902 A | 10/1950 | Rublee |
| 2,527,256 A | 10/1950 | Jackson |
| 2,578,686 A | 12/1951 | Fish |
| 2,674,149 A | 4/1954 | Benson |
| 2,711,461 A | 6/1955 | Happe |
| 2,804,848 A | 9/1957 | O'Farrell et al. |
| 2,808,482 A | 10/1957 | Zanichkowsky et al. |
| 2,853,074 A | 9/1958 | Olson |
| 2,887,004 A | 5/1959 | Stewart |
| 2,959,974 A | 11/1960 | Emrick |
| 3,032,769 A | 5/1962 | Palmer |
| 3,075,062 A | 1/1963 | Iaccarino |
| 3,078,465 A | 2/1963 | Bobrov |
| 3,079,606 A | 3/1963 | Bobrov et al. |
| 3,166,072 A | 1/1965 | Sullivan, Jr. |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,275,211 A | 9/1966 | Hirsch et al. |
| 3,317,103 A | 5/1967 | Cullen et al. |
| 3,317,105 A | 5/1967 | Astafjev et al. |
| 3,357,296 A | 12/1967 | Lefever |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,598,943 A | 8/1971 | Barrett |
| 3,608,549 A | 9/1971 | Merrill |
| 3,640,317 A | 2/1972 | Panfili |
| 3,643,851 A | 2/1972 | Green et al. |
| 3,661,666 A | 5/1972 | Foster et al. |
| 3,662,939 A | 5/1972 | Bryan |
| 3,695,646 A | 10/1972 | Mommsen |
| 3,709,221 A | 1/1973 | Riely |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,751,902 A | 8/1973 | Kingsbury et al. |
| 3,799,151 A | 3/1974 | Fukaumi et al. |
| 3,819,100 A | 6/1974 | Noiles et al. |
| 3,821,919 A | 7/1974 | Knohl |
| 3,841,474 A | 10/1974 | Maier |
| 3,851,196 A | 11/1974 | Hinds |
| 3,885,491 A | 5/1975 | Curtis |
| 3,892,228 A | 7/1975 | Mitsui |
| 3,894,174 A | 7/1975 | Cartun |
| 3,940,844 A | 3/1976 | Colby et al. |
| 3,950,686 A | 4/1976 | Randall |
| 3,955,581 A | 5/1976 | Spasiano et al. |
| RE28,932 E | 8/1976 | Noiles et al. |
| 3,981,051 A | 9/1976 | Brumlik |
| 4,054,108 A | 10/1977 | Gill |
| 4,060,089 A | 11/1977 | Noiles |
| 4,106,446 A | 8/1978 | Yamada et al. |
| 4,111,206 A | 9/1978 | Vishnevsky et al. |
| 4,129,059 A | 12/1978 | Van Eck |
| 4,169,990 A | 10/1979 | Lerdman |
| 4,180,285 A | 12/1979 | Reneau |
| 4,198,734 A | 4/1980 | Brumlik |
| 4,198,982 A | 4/1980 | Fortner et al. |
| 4,207,898 A | 6/1980 | Becht |
| 4,213,562 A | 7/1980 | Garrett et al. |
| 4,226,242 A | 10/1980 | Jarvik |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,275,813 A | 6/1981 | Noiles |
| 4,289,133 A | 9/1981 | Rothfuss |
| 4,296,654 A | 10/1981 | Mercer |
| 4,304,236 A | 12/1981 | Conta et al. |
| 4,305,539 A | 12/1981 | Korolkov et al. |
| 4,312,685 A | 1/1982 | Riedl |
| 4,317,451 A | 3/1982 | Cerwin et al. |
| 4,321,002 A | 3/1982 | Froehlich |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,373,147 A | 2/1983 | Carlson, Jr. |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,408,692 A | 10/1983 | Siegel et al. |
| 4,409,057 A | 10/1983 | Molenda et al. |
| 4,415,112 A | 11/1983 | Green |
| 4,416,276 A | 11/1983 | Newton et al. |
| 4,428,376 A | 1/1984 | Mericle |
| 4,429,695 A | 2/1984 | Green |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,454,887 A | 6/1984 | Krüger |
| 4,467,805 A | 8/1984 | Fukuda |
| 4,470,414 A | 9/1984 | Imagawa et al. |
| 4,473,077 A | 9/1984 | Noiles et al. |
| 4,475,679 A | 10/1984 | Fleury, Jr. |
| 4,485,816 A | 12/1984 | Krumme |

(56) References Cited

U.S. PATENT DOCUMENTS

| | | |
|---|---|---|
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,499,895 A | 2/1985 | Takayama |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,531,522 A | 7/1985 | Bedi et al. |
| 4,532,927 A | 8/1985 | Miksza, Jr. |
| 4,548,202 A | 10/1985 | Duncan |
| 4,565,109 A | 1/1986 | Tsay |
| 4,565,189 A | 1/1986 | Mabuchi |
| 4,566,620 A | 1/1986 | Green et al. |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |
| 4,585,153 A | 4/1986 | Failla et al. |
| 4,589,416 A | 5/1986 | Green |
| 4,591,085 A | 5/1986 | Di Giovanni |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,619,391 A | 10/1986 | Sharkany et al. |
| 4,628,459 A | 12/1986 | Shinohara et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,641,076 A | 2/1987 | Linden |
| 4,643,731 A | 2/1987 | Eckenhoff |
| 4,646,722 A | 3/1987 | Silverstein et al. |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,445 A | 6/1987 | Barker et al. |
| 4,676,245 A | 6/1987 | Fukuda |
| 4,684,051 A | 8/1987 | Akopov et al. |
| 4,691,703 A | 9/1987 | Auth et al. |
| 4,693,248 A | 9/1987 | Failla |
| 4,700,703 A | 10/1987 | Resnick et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,815,460 A | 3/1989 | Porat et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,830,855 A | 5/1989 | Stewart |
| 4,834,720 A | 5/1989 | Blinkhorn |
| 4,844,068 A | 7/1989 | Arata et al. |
| 4,848,637 A | 7/1989 | Pruitt |
| 4,865,030 A | 9/1989 | Polyak |
| 4,868,530 A | 9/1989 | Ahs |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,896,678 A | 1/1990 | Ogawa |
| 4,900,303 A | 2/1990 | Lemelson |
| 4,903,697 A | 2/1990 | Resnick et al. |
| 4,915,100 A | 4/1990 | Green |
| 4,930,503 A | 6/1990 | Pruitt |
| 4,930,674 A | 6/1990 | Barak |
| 4,931,047 A | 6/1990 | Broadwin et al. |
| 4,932,960 A | 6/1990 | Green et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,951,860 A | 8/1990 | Peters et al. |
| 4,955,959 A | 9/1990 | Tompkins et al. |
| 4,965,709 A | 10/1990 | Ngo |
| 4,973,274 A | 11/1990 | Hirukawa |
| 4,978,049 A | 12/1990 | Green |
| 4,978,333 A | 12/1990 | Broadwin et al. |
| 4,986,808 A | 1/1991 | Broadwin et al. |
| 4,988,334 A | 1/1991 | Hornlein et al. |
| 5,002,543 A | 3/1991 | Bradshaw et al. |
| 5,002,553 A | 3/1991 | Shiber |
| 5,005,754 A | 4/1991 | Van Overloop |
| 5,009,661 A | 4/1991 | Michelson |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,671 A | 6/1991 | Tu et al. |
| 5,027,834 A | 7/1991 | Pruitt |
| 5,031,814 A | 7/1991 | Tompkins et al. |
| 5,035,040 A | 7/1991 | Kerrigan et al. |
| 5,038,109 A | 8/1991 | Goble et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |

(56) References Cited

U.S. PATENT DOCUMENTS

| | | |
|---|---|---|
| 5,094,247 A | 3/1992 | Hernandez et al. |
| 5,100,420 A | 3/1992 | Green et al. |
| 5,104,025 A | 4/1992 | Main et al. |
| 5,104,397 A | 4/1992 | Vasconcelos et al. |
| 5,106,008 A | 4/1992 | Tompkins et al. |
| 5,108,368 A | 4/1992 | Hammerslag et al. |
| 5,111,987 A | 5/1992 | Moeinzadeh et al. |
| 5,116,349 A | 5/1992 | Aranyi |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,171,253 A | 12/1992 | Klieman et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,192,288 A | 3/1993 | Thompson et al. |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,263,629 A | 11/1993 | Trumbull et al. |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,289,963 A | 3/1994 | McGarry et al. |
| 5,290,271 A | 3/1994 | Jernberg |
| 5,292,053 A | 3/1994 | Bilotti et al. |
| 5,297,714 A | 3/1994 | Kramer |
| 5,304,204 A | 4/1994 | Bregen |
| 5,307,976 A | 5/1994 | Olson et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,314,445 A | 5/1994 | Heidmueller et al. |
| 5,314,466 A | 5/1994 | Stern et al. |
| 5,318,221 A | 6/1994 | Green et al. |
| 5,330,487 A | 7/1994 | Thornton et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,381 A | 8/1994 | Tidemand |
| 5,342,395 A | 8/1994 | Jarrett et al. |
| 5,342,396 A | 8/1994 | Cook |
| 5,343,391 A | 8/1994 | Mushabac |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,360,305 A | 11/1994 | Kerrigan |
| 5,360,428 A | 11/1994 | Hutchinson, Jr. |
| 5,364,001 A | 11/1994 | Bryan |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |

(56) References Cited

U.S. PATENT DOCUMENTS

| | | |
|---|---|---|
| 5,395,034 A | 3/1995 | Allen et al. |
| 5,395,312 A | 3/1995 | Desai |
| 5,395,384 A | 3/1995 | Duthoit |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman |
| 5,409,498 A | 4/1995 | Braddock et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson, IV et al. |
| 5,415,335 A | 5/1995 | Knodell, Jr. |
| 5,417,203 A | 5/1995 | Tovey et al. |
| 5,417,361 A | 5/1995 | Williamson, IV |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,431,322 A | 7/1995 | Green et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Schichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,444,113 A | 8/1995 | Sinclair et al. |
| 5,445,155 A | 8/1995 | Sieben |
| 5,445,304 A | 8/1995 | Plyley et al. |
| 5,445,644 A | 8/1995 | Pietrafitta et al. |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,009 A | 11/1995 | Rodak |
| 5,470,010 A | 11/1995 | Rothfuss et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,542,949 A | 8/1996 | Yoon |
| 5,543,119 A | 8/1996 | Sutter et al. |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |

(56) References Cited

U.S. PATENT DOCUMENTS

| | | |
|---|---|---|
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,609,285 A | 3/1997 | Grant et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,709,706 A | 1/1998 | Kienzle et al. |
| 5,711,472 A | 1/1998 | Bryan |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Costellessa |
| 5,718,714 A | 2/1998 | Livneh |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,110 A | 3/1998 | Vidal et al. |
| 5,728,121 A | 3/1998 | Bimbo et al. |
| 5,730,758 A | 3/1998 | Allgeyer |

(56) References Cited

U.S. PATENT DOCUMENTS

| | | |
|---|---|---|
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,748 A | 6/1998 | Eyerly et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,849,011 A | 12/1998 | Jones et al. |
| 5,849,023 A | 12/1998 | Mericle |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,947,984 A | 9/1999 | Whipple |
| 5,948,030 A | 9/1999 | Miller et al. |
| 5,951,516 A | 9/1999 | Bunyan |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,394 A | 10/1999 | Robertson |
| 5,964,774 A | 10/1999 | McKean et al. |
| 5,971,916 A | 10/1999 | Koren |
| 5,973,221 A | 10/1999 | Collyer et al. |
| 5,977,746 A | 11/1999 | Hershberger et al. |
| 5,984,949 A | 11/1999 | Levin |
| 5,988,479 A | 11/1999 | Palmer |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |

(56) References Cited

U.S. PATENT DOCUMENTS

| | | |
|---|---|---|
| 6,010,054 A | 1/2000 | Johnson et al. |
| 6,010,513 A | 1/2000 | Törmälä et al. |
| 6,012,494 A | 1/2000 | Balazs |
| 6,013,076 A | 1/2000 | Goble et al. |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,037,724 A | 3/2000 | Buss et al. |
| 6,039,733 A | 3/2000 | Buysse et al. |
| 6,039,734 A | 3/2000 | Goble |
| 6,042,601 A | 3/2000 | Smith |
| 6,045,560 A | 4/2000 | McKean et al. |
| 6,047,861 A | 4/2000 | Vidal et al. |
| 6,049,145 A | 4/2000 | Austin et al. |
| 6,050,472 A | 4/2000 | Shibata |
| 6,050,990 A | 4/2000 | Tankovich et al. |
| 6,050,996 A | 4/2000 | Schmaltz et al. |
| 6,053,390 A | 4/2000 | Green et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,062,360 A | 5/2000 | Shields |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,074,401 A | 6/2000 | Gardiner et al. |
| 6,077,286 A | 6/2000 | Cuschieri et al. |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,104,304 A | 8/2000 | Clark et al. |
| 6,106,511 A | 8/2000 | Jensen |
| 6,109,500 A | 8/2000 | Alli et al. |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,139,546 A | 10/2000 | Koenig et al. |
| 6,149,660 A | 11/2000 | Laufer et al. |
| 6,152,935 A | 11/2000 | Kammerer et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,330 B1 | 3/2001 | Benderev et al. |
| 6,202,914 B1 | 3/2001 | Geiste et al. |
| 6,206,897 B1 | 3/2001 | Jamiolkowski et al. |
| 6,206,904 B1 | 3/2001 | Ouchi |
| 6,210,403 B1 | 4/2001 | Klicek |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,081 B1 | 5/2001 | Goble |
| 6,228,083 B1 | 5/2001 | Lands et al. |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,305,891 B1 | 10/2001 | Burlingame |
| 6,306,134 B1 | 10/2001 | Goble et al. |
| 6,306,149 B1 | 10/2001 | Meade |
| 6,309,403 B1 | 10/2001 | Minor et al. |
| 6,315,184 B1 | 11/2001 | Whitman |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |

(56) References Cited

U.S. PATENT DOCUMENTS

| | | |
|---|---|---|
| 6,343,731 B1 | 2/2002 | Adams et al. |
| 6,346,077 B1 | 2/2002 | Taylor et al. |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,370,981 B2 | 4/2002 | Watarai |
| 6,373,152 B1 | 4/2002 | Wang et al. |
| 6,383,201 B1 | 5/2002 | Dong |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,398,781 B1 | 6/2002 | Goble et al. |
| 6,398,797 B2 | 6/2002 | Bombard et al. |
| 6,402,766 B2 | 6/2002 | Bowman et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,413,274 B1 | 7/2002 | Pedros |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| RE37,814 E | 8/2002 | Allgeyer |
| 6,428,070 B1 | 8/2002 | Takanashi et al. |
| 6,429,611 B1 | 8/2002 | Li |
| 6,430,298 B1 | 8/2002 | Kettl et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| 6,443,973 B1 | 9/2002 | Whitman |
| 6,447,518 B1 | 9/2002 | Krause et al. |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,468,275 B1 | 10/2002 | Wampler et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,200 B2 | 11/2002 | Shippert |
| 6,485,490 B2 | 11/2002 | Wampler et al. |
| 6,485,667 B1 | 11/2002 | Tan |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,512,360 B1 | 1/2003 | Goto et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,527,782 B2 | 3/2003 | Hogg et al. |
| 6,527,785 B2 | 3/2003 | Sancoff et al. |
| 6,533,157 B1 | 3/2003 | Whitman |
| 6,533,784 B2 | 3/2003 | Truckai et al. |
| 6,535,764 B2 | 3/2003 | Imran et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,587,750 B2 | 7/2003 | Gerbi et al. |
| 6,588,643 B2 | 7/2003 | Bolduc et al. |
| 6,588,931 B2 | 7/2003 | Betzner et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,605,078 B2 | 8/2003 | Adams |
| 6,605,669 B2 | 8/2003 | Awokola et al. |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,269 B2 | 1/2004 | Swanson |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |

(56) References Cited

U.S. PATENT DOCUMENTS

| | | |
|---|---|---|
| 6,682,528 B2 | 1/2004 | Frazier et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,695,198 B2 | 2/2004 | Adams et al. |
| 6,695,199 B2 | 2/2004 | Whitman |
| 6,695,774 B2 | 2/2004 | Hale et al. |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,726,706 B2 | 4/2004 | Dominguez |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,762,339 B1 | 7/2004 | Klun et al. |
| 6,764,445 B2 | 7/2004 | Ramans et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,802,843 B2 | 10/2004 | Truckai et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,850,817 B1 | 2/2005 | Green |
| 6,853,879 B2 | 2/2005 | Sunaoshi |
| 6,858,005 B2 | 2/2005 | Ohline et al. |
| RE38,708 E | 3/2005 | Bolanos et al. |
| 6,861,142 B1 | 3/2005 | Wilkie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,899,538 B2 | 5/2005 | Matoba |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,926,716 B2 | 8/2005 | Baker et al. |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,945,981 B2 | 9/2005 | Donofrio et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,971,988 B2 | 12/2005 | Orban, III |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |

(56) References Cited

U.S. PATENT DOCUMENTS

| | | |
|---|---|---|
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,993,413 B2 | 1/2006 | Sunaoshi |
| 6,994,708 B2 | 2/2006 | Manzo |
| 6,995,729 B2 | 2/2006 | Govari et al. |
| 6,997,931 B2 | 2/2006 | Sauer et al. |
| 6,998,816 B2 | 2/2006 | Wieck et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,018,357 B2 | 3/2006 | Emmons |
| 7,018,390 B2 | 3/2006 | Turovskiy et al. |
| 7,021,669 B1 | 4/2006 | Lindermeir et al. |
| 7,025,743 B2 | 4/2006 | Mann et al. |
| 7,029,435 B2 | 4/2006 | Nakao |
| 7,029,439 B2 | 4/2006 | Roberts et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,048,745 B2 | 5/2006 | Tierney et al. |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,137,980 B2 | 11/2006 | Buysse et al. |
| 7,137,981 B2 | 11/2006 | Long |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,172,593 B2 | 2/2007 | Trieu et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,188,758 B2 | 3/2007 | Viola et al. |
| 7,189,207 B2 | 3/2007 | Viola |
| 7,195,627 B2 | 3/2007 | Amoah et al. |
| 7,199,537 B2 | 4/2007 | Okamura et al. |
| 7,202,653 B2 | 4/2007 | Pai |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |

(56) References Cited

U.S. PATENT DOCUMENTS

| | | |
|---|---|---|
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapius |
| 7,252,660 B2 | 8/2007 | Kunz |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,286,850 B2 | 10/2007 | Frielink et al. |
| 7,287,682 B1 | 10/2007 | Ezzat et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,048 B2 | 2/2008 | Lohr |
| 7,336,184 B2 | 2/2008 | Smith et al. |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,348,763 B1 | 3/2008 | Reinhart et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,195 B2 | 4/2008 | Schwartz et al. |
| 7,364,060 B2 | 4/2008 | Milliman |
| 7,364,061 B2 | 4/2008 | Swayze et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,400,752 B2 | 7/2008 | Zacharias |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,494,501 B2 | 2/2009 | Ahlberg et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |

(56) References Cited

U.S. PATENT DOCUMENTS

| | | |
|---|---|---|
| 7,507,202 B2 | 3/2009 | Schoellhorn |
| 7,510,107 B2 | 3/2009 | Timm et al. |
| 7,510,566 B2 | 3/2009 | Jacobs et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,530,984 B2 | 5/2009 | Sonnenschein et al. |
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,542,807 B2 | 6/2009 | Bertolero et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,562,910 B2 | 7/2009 | Kertesz et al. |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,597,229 B2 | 10/2009 | Boudreaux et al. |
| 7,597,230 B2 | 10/2009 | Racenet et al. |
| 7,597,693 B2 | 10/2009 | Garrison |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,288 B2 | 2/2010 | Bauman et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,659,219 B2 | 2/2010 | Biran et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,682,307 B2 | 3/2010 | Danitz et al. |
| 7,682,367 B2 | 3/2010 | Shah et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,758 B2 | 5/2010 | Lee et al. |
| 7,714,239 B2 | 5/2010 | Smith |
| 7,717,312 B2 | 5/2010 | Beetel |
| 7,717,313 B2 | 5/2010 | Criscuolo et al. |
| 7,717,846 B2 | 5/2010 | Zirps et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shelton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,748,587 B2 | 7/2010 | Haramiishi et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,207 B2 | 8/2010 | Mather et al. |
| 7,766,209 B2 | 8/2010 | Baxter, III et al. |

(56) References Cited

U.S. PATENT DOCUMENTS

| | | |
|---|---|---|
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,776,037 B2 | 8/2010 | Odom |
| 7,776,060 B2 | 8/2010 | Mooradian et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,884 B2 | 10/2010 | Lee et al. |
| 7,819,886 B2 | 10/2010 | Whitfield et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,838,789 B2 | 11/2010 | Stoffers et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,149 B2 | 12/2010 | Jankowski |
| 7,850,642 B2 | 12/2010 | Moll et al. |
| 7,850,982 B2 | 12/2010 | Stopek et al. |
| 7,854,736 B2 | 12/2010 | Ryan |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,891,531 B1 | 2/2011 | Ward |
| 7,891,532 B2 | 2/2011 | Mastri et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,877 B2 | 3/2011 | Hall et al. |
| 7,896,895 B2 | 3/2011 | Boudreaux et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,889 B2 | 3/2011 | Catanese, III et al. |
| 7,905,902 B2 | 3/2011 | Huitema et al. |
| 7,909,191 B2 | 3/2011 | Baker et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,848 B2 | 4/2011 | Lau et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,927,328 B2 | 4/2011 | Orszulak et al. |
| 7,928,281 B2 | 4/2011 | Augustine |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban et al. |
| 7,954,682 B2 * | 6/2011 | Giordano ......... A61B 17/07207 227/175.1 |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,955,257 B2 | 6/2011 | Frasier et al. |
| 7,955,322 B2 | 6/2011 | Devengenzo et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,963 B2 | 6/2011 | Francischelli et al. |
| 7,963,964 B2 | 6/2011 | Santilli et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |

(56) References Cited

U.S. PATENT DOCUMENTS

| | | |
|---|---|---|
| 7,967,181 B2 | 6/2011 | Viola et al. |
| 7,967,839 B2 | 6/2011 | Flock et al. |
| 7,972,298 B2 | 7/2011 | Wallace et al. |
| 7,980,443 B2 | 7/2011 | Scheib et al. |
| 7,987,405 B2 | 7/2011 | Turner et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,511 B2 | 8/2011 | Brock et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,028,883 B2 | 10/2011 | Stopek |
| 8,028,884 B2 | 10/2011 | Sniffin et al. |
| 8,028,885 B2 | 10/2011 | Smith et al. |
| 8,034,077 B2 | 10/2011 | Smith et al. |
| 8,034,363 B2 | 10/2011 | Li et al. |
| 8,037,591 B2 | 10/2011 | Spivey et al. |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,047,236 B2 | 11/2011 | Perry |
| 8,048,503 B2 | 11/2011 | Farnsworth et al. |
| 8,056,787 B2 | 11/2011 | Boudreaux et al. |
| 8,056,788 B2 | 11/2011 | Mastri et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,576 B2 | 11/2011 | Cappola |
| 8,062,330 B2 | 11/2011 | Prommersberger et al. |
| 8,063,619 B2 | 11/2011 | Zhu et al. |
| 8,066,167 B2 | 11/2011 | Measamer et al. |
| 8,066,168 B2 | 11/2011 | Vidal et al. |
| D650,074 S | 12/2011 | Hunt et al. |
| 8,070,033 B2 | 12/2011 | Milliman et al. |
| 8,070,035 B2 | 12/2011 | Holsten et al. |
| 8,070,743 B2 | 12/2011 | Kagan et al. |
| 8,075,571 B2 | 12/2011 | Vitali et al. |
| 8,079,950 B2 | 12/2011 | Stern et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,085,013 B2 | 12/2011 | Wei et al. |
| 8,087,563 B2 | 1/2012 | Milliman et al. |
| 8,089,509 B2 | 1/2012 | Chatenever et al. |
| 8,091,756 B2 | 1/2012 | Viola |
| 8,092,443 B2 | 1/2012 | Bischoff |
| 8,092,932 B2 | 1/2012 | Phillips et al. |
| 8,096,458 B2 | 1/2012 | Hessler |
| 8,097,017 B2 | 1/2012 | Viola |
| 8,100,310 B2 | 1/2012 | Zemlok |
| 8,100,872 B2 | 1/2012 | Patel |
| 8,102,278 B2 | 1/2012 | Deck et al. |
| 8,105,350 B2 | 1/2012 | Lee et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,410 B2 | 2/2012 | Hall et al. |
| 8,114,100 B2 | 2/2012 | Smith et al. |
| 8,123,103 B2 | 2/2012 | Milliman |
| 8,123,766 B2 | 2/2012 | Bauman et al. |
| 8,123,767 B2 | 2/2012 | Bauman et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,132,703 B2 | 3/2012 | Milliman et al. |
| 8,132,706 B2 | 3/2012 | Marczyk et al. |
| 8,134,306 B2 | 3/2012 | Drader et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,425 B2 | 3/2012 | Eggers |
| 8,146,790 B2 | 4/2012 | Milliman |
| 8,147,485 B2 | 4/2012 | Wham et al. |
| 8,152,041 B2 | 4/2012 | Kostrzewski |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,840 B2 | 5/2012 | Milliman |
| 8,186,555 B2 | 5/2012 | Shelton, IV et al. |
| 8,186,560 B2 | 5/2012 | Hess et al. |
| 8,191,752 B2 | 6/2012 | Scirica |
| 8,192,460 B2 | 6/2012 | Orban, III et al. |
| 8,196,795 B2 | 6/2012 | Moore et al. |
| 8,196,796 B2 | 6/2012 | Shelton, IV et al. |
| 8,201,720 B2 | 6/2012 | Hessler |
| 8,201,721 B2 | 6/2012 | Zemlok et al. |
| 8,205,779 B2 | 6/2012 | Ma |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,424 B2 | 7/2012 | Cha |

(56) References Cited

U.S. PATENT DOCUMENTS

| | | |
|---|---|---|
| 8,225,799 B2 | 7/2012 | Bettuchi |
| 8,226,715 B2 | 7/2012 | Hwang et al. |
| 8,227,946 B2 | 7/2012 | Kim |
| 8,228,048 B2 | 7/2012 | Spencer |
| 8,231,040 B2 | 7/2012 | Zemlok et al. |
| 8,231,041 B2 | 7/2012 | Marczyk et al. |
| 8,231,042 B2 | 7/2012 | Hessler et al. |
| 8,231,043 B2 | 7/2012 | Tarinelli et al. |
| 8,236,010 B2 | 8/2012 | Ortiz et al. |
| 8,241,271 B2 | 8/2012 | Millman et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,391 B2 | 9/2012 | Orban, III et al. |
| 8,262,655 B2 | 9/2012 | Ghabrial et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,273,404 B2 | 9/2012 | Dave et al. |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,286,845 B2 | 10/2012 | Perry et al. |
| 8,287,561 B2 | 10/2012 | Nunez et al. |
| 8,292,147 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,161 B2 | 10/2012 | Vargas |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,046 B2 | 11/2012 | Prommersberger |
| 8,308,659 B2 | 11/2012 | Scheibe et al. |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,323,789 B2 | 12/2012 | Rozhin et al. |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,764 B2 | 12/2012 | Francischelli et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,348,123 B2 | 1/2013 | Scirica et al. |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,376,865 B2 | 2/2013 | Forster et al. |
| 8,377,044 B2 | 2/2013 | Coe et al. |
| 8,388,633 B2 | 3/2013 | Rousseau et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,398,633 B2 | 3/2013 | Mueller |
| 8,398,673 B2 | 3/2013 | Hinchliffe et al. |
| 8,403,138 B2 | 3/2013 | Weisshaupt et al. |
| 8,403,198 B2 | 3/2013 | Sorrentino et al. |
| 8,403,832 B2 | 3/2013 | Cunningham et al. |
| 8,403,945 B2 | 3/2013 | Whitfield et al. |
| 8,408,439 B2 | 4/2013 | Huang et al. |
| 8,408,442 B2 | 4/2013 | Racenet et al. |
| 8,409,079 B2 | 4/2013 | Oakamoto et al. |
| 8,409,174 B2 | 4/2013 | Omori |
| 8,409,222 B2 | 4/2013 | Whitfield et al. |
| 8,409,223 B2 | 4/2013 | Sorrentino et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,418,909 B2 | 4/2013 | Kostrzewski |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,430,292 B2 | 4/2013 | Patel et al. |
| 8,430,892 B2 | 4/2013 | Bindra et al. |
| 8,430,898 B2 | 4/2013 | Wiener et al. |
| 8,439,246 B1 | 5/2013 | Knodel et al. |
| 8,444,036 B2 | 5/2013 | Shelton, IV |
| 8,444,549 B2 | 5/2013 | Viola et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,628 B2 | 6/2013 | Smith et al. |
| 8,457,757 B2 | 6/2013 | Cauller et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |

(56) References Cited

U.S. PATENT DOCUMENTS

| | | |
|---|---|---|
| 8,465,502 B2 | 6/2013 | Zergiebel |
| 8,469,973 B2 | 6/2013 | Meade et al. |
| 8,474,677 B2 | 7/2013 | Woodard, Jr. et al. |
| 8,475,453 B2 | 7/2013 | Marczyk et al. |
| 8,475,474 B2 | 7/2013 | Bombard et al. |
| 8,479,969 B2 | 7/2013 | Shelton, IV |
| 8,480,703 B2 | 7/2013 | Nicholas et al. |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,491,581 B2 | 7/2013 | Deville et al. |
| 8,496,156 B2 | 7/2013 | Sniffin et al. |
| 8,496,683 B2 | 7/2013 | Prommersberger et al. |
| 8,499,992 B2 | 8/2013 | Whitman et al. |
| 8,499,993 B2 | 8/2013 | Shelton, IV et al. |
| 8,500,762 B2 | 8/2013 | Sholev et al. |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,521,273 B2 | 8/2013 | Kliman |
| 8,523,043 B2 | 9/2013 | Ullrich et al. |
| 8,523,881 B2 | 9/2013 | Cabiri et al. |
| 8,523,900 B2 | 9/2013 | Jinno et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,534,528 B2 | 9/2013 | Shelton, IV |
| 8,535,304 B2 | 9/2013 | Sklar et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,540,735 B2 | 9/2013 | Mitelberg et al. |
| 8,551,076 B2 | 10/2013 | Duval et al. |
| 8,556,151 B2 | 10/2013 | Viola |
| 8,556,918 B2 | 10/2013 | Bauman et al. |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV et al. |
| 8,574,199 B2 | 11/2013 | von Bülow et al. |
| 8,574,263 B2 | 11/2013 | Mueller |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,585,721 B2 | 11/2013 | Kirsch |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,603,135 B2 | 12/2013 | Mueller |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,736 B2 | 1/2014 | Yates et al. |
| 8,636,766 B2 | 1/2014 | Milliman et al. |
| 8,640,788 B2 | 2/2014 | Dachs, II et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,662,370 B2 | 3/2014 | Takei |
| 8,663,192 B2 | 3/2014 | Hester et al. |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,673,210 B2 | 3/2014 | Deshays |
| 8,678,263 B2 | 3/2014 | Viola |
| 8,679,093 B2 | 3/2014 | Farra |
| 8,679,098 B2 | 3/2014 | Hart |
| 8,679,137 B2 | 3/2014 | Bauman et al. |
| 8,679,454 B2 | 3/2014 | Guire et al. |
| 8,684,250 B2 | 4/2014 | Bettuchi et al. |
| 8,684,253 B2 | 4/2014 | Giordano et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,211 B2 | 4/2014 | Zemlok et al. |
| 8,708,213 B2 | 4/2014 | Shelton, IV et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,728,119 B2 | 5/2014 | Cummins |
| 8,733,613 B2 | 5/2014 | Huitema et al. |
| 8,733,614 B2 | 5/2014 | Ross et al. |
| 8,734,478 B2 | 5/2014 | Widenhouse et al. |
| 8,739,033 B2 | 5/2014 | Rosenberg |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,747,238 B2 | 6/2014 | Shelton, IV et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,235 B2 | 6/2014 | Jaworek |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,771,169 B2 | 7/2014 | Whitman et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,684 B2 | 7/2014 | Dave et al. |
| 8,794,496 B2 | 8/2014 | Scirica |
| 8,794,497 B2 | 8/2014 | Zingman |
| 8,795,276 B2 | 8/2014 | Dietz et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |

(56) References Cited

U.S. PATENT DOCUMENTS

| | | |
|---|---|---|
| 8,801,735 B2 | 8/2014 | Shelton, IV et al. |
| 8,801,752 B2 | 8/2014 | Fortier et al. |
| 8,806,973 B2 | 8/2014 | Ross et al. |
| 8,807,414 B2 | 8/2014 | Ross et al. |
| 8,808,294 B2 | 8/2014 | Fox et al. |
| 8,808,311 B2 | 8/2014 | Heinrich et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,827,133 B2 | 9/2014 | Shelton, IV et al. |
| 8,827,903 B2 | 9/2014 | Shelton, IV et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,852,199 B2 | 10/2014 | Deslauriers et al. |
| 8,857,693 B2 | 10/2014 | Schuckmann et al. |
| 8,857,694 B2 | 10/2014 | Shelton, IV et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,870,050 B2 | 10/2014 | Hodgkinson |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,893,946 B2 | 11/2014 | Boudreaux et al. |
| 8,893,949 B2 | 11/2014 | Shelton, IV et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,905,977 B2 | 12/2014 | Shelton et al. |
| 8,911,426 B2 | 12/2014 | Coppeta et al. |
| 8,911,471 B2 | 12/2014 | Spivey et al. |
| 8,920,438 B2 | 12/2014 | Aranyi et al. |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,598 B2 | 1/2015 | Mollere et al. |
| 8,931,682 B2 | 1/2015 | Timm et al. |
| 8,936,614 B2 | 1/2015 | Allen, IV |
| 8,939,343 B2 | 1/2015 | Milliman et al. |
| 8,939,344 B2 | 1/2015 | Olson et al. |
| 8,955,732 B2 | 2/2015 | Zemlok et al. |
| 8,960,520 B2 | 2/2015 | McCuen |
| 8,960,521 B2 | 2/2015 | Kostrzewski |
| 8,961,504 B2 | 2/2015 | Hoarau et al. |
| 8,967,443 B2 | 3/2015 | McCuen |
| 8,967,446 B2 | 3/2015 | Beardsley et al. |
| 8,968,276 B2 | 3/2015 | Zemlok et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,970,507 B2 | 3/2015 | Holbein et al. |
| 8,973,803 B2 | 3/2015 | Hall et al. |
| 8,973,804 B2 | 3/2015 | Hess et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,890 B2 | 3/2015 | Boudreaux |
| 8,982,195 B2 | 3/2015 | Claus et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 9,005,230 B2 | 4/2015 | Yates et al. |
| 9,011,471 B2 | 4/2015 | Timm et al. |
| 9,016,540 B2 | 4/2015 | Whitman et al. |
| 9,016,542 B2 | 4/2015 | Shelton, IV et al. |
| 9,017,331 B2 | 4/2015 | Fox |
| 9,017,371 B2 | 4/2015 | Whitman et al. |
| 9,023,014 B2 | 5/2015 | Chowaniec et al. |
| 9,027,817 B2 | 5/2015 | Milliman et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,038,881 B1 | 5/2015 | Schaller et al. |
| 9,039,690 B2 | 5/2015 | Kersten et al. |
| 9,039,720 B2 | 5/2015 | Madan |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,050,100 B2 | 6/2015 | Yates et al. |
| 9,055,941 B2 | 6/2015 | Schmid et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,072,515 B2 | 7/2015 | Hall et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,084,601 B2 | 7/2015 | Moore et al. |
| 9,084,602 B2 | 7/2015 | Glieman |
| 9,086,875 B2 | 7/2015 | Harrat et al. |
| 9,089,330 B2 | 7/2015 | Widenhouse et al. |
| 9,095,339 B2 | 8/2015 | Moore et al. |
| 9,095,362 B2 | 8/2015 | Dachs, II et al. |
| 9,096,033 B2 | 8/2015 | Holop et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,873 B2 | 8/2015 | Marczyk et al. |
| 9,113,874 B2 | 8/2015 | Shelton, IV et al. |
| 9,113,880 B2 | 8/2015 | Zemlok et al. |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,123,286 B2 | 9/2015 | Park |
| 9,125,654 B2 | 9/2015 | Aronhalt et al. |
| 9,125,662 B2 | 9/2015 | Shelton, IV |
| 9,131,940 B2 | 9/2015 | Huitema et al. |
| 9,131,957 B2 | 9/2015 | Sharbnik et al. |
| 9,138,225 B2 | 9/2015 | Huang et al. |
| 9,149,274 B2 | 10/2015 | Spivey et al. |
| 9,149,325 B2 | 10/2015 | Worrell et al. |
| 9,161,803 B2 | 10/2015 | Yates et al. |
| 9,168,038 B2 | 10/2015 | Shelton, IV et al. |
| 9,168,054 B2 | 10/2015 | Turner et al. |
| 9,168,144 B2 | 10/2015 | Rivin et al. |
| 9,179,911 B2 | 11/2015 | Morgan et al. |
| 9,179,912 B2 | 11/2015 | Yates et al. |
| 9,186,143 B2 | 11/2015 | Timm et al. |
| 9,192,380 B2 | 11/2015 | (Tarinelli) Racenet et al. |
| 9,192,384 B2 | 11/2015 | Bettuchi |
| 9,193,045 B2 | 11/2015 | Saur et al. |
| 9,198,661 B2 | 12/2015 | Swensgard |
| 9,198,662 B2 | 12/2015 | Barton et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,019 B2 | 12/2015 | Schmid et al. |
| 9,220,500 B2 | 12/2015 | Swayze et al. |
| 9,220,501 B2 | 12/2015 | Baxter, III et al. |
| 9,226,750 B2 | 1/2016 | Weir et al. |

(56) References Cited

U.S. PATENT DOCUMENTS

| | | |
|---|---|---|
| 9,226,751 B2 | 1/2016 | Shelton, IV et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,237,891 B2 | 1/2016 | Shelton, IV |
| 9,241,714 B2 | 1/2016 | Timm et al. |
| 9,259,274 B2 | 2/2016 | Prisco |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,277,922 B2 | 3/2016 | Carter et al. |
| 9,282,962 B2 | 3/2016 | Schmid et al. |
| 9,282,966 B2 | 3/2016 | Shelton, IV et al. |
| 9,282,974 B2 | 3/2016 | Shelton, IV |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,295,464 B2 | 3/2016 | Shelton, IV et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,986 B2 | 4/2016 | Hall et al. |
| 9,307,988 B2 | 4/2016 | Shelton, IV |
| 9,308,011 B2 | 4/2016 | Chao et al. |
| 9,314,246 B2 | 4/2016 | Shelton, IV et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,730 B2 | 5/2016 | Schmid et al. |
| 9,358,003 B2 | 6/2016 | Hall et al. |
| 9,358,005 B2 | 6/2016 | Shelton, IV et al. |
| 9,364,230 B2 | 6/2016 | Shelton, IV et al. |
| 9,364,233 B2 | 6/2016 | Alexander, III et al. |
| 9,364,279 B2 | 6/2016 | Houser et al. |
| 9,370,358 B2 | 6/2016 | Shelton, IV et al. |
| 9,370,364 B2 | 6/2016 | Smith et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,015 B2 | 7/2016 | Laurent et al. |
| 9,398,911 B2 | 7/2016 | Auld |
| 9,402,626 B2 | 8/2016 | Ortiz et al. |
| 9,408,604 B2 | 8/2016 | Shelton, IV et al. |
| 9,408,606 B2 | 8/2016 | Shelton, IV |
| 9,414,838 B2 | 8/2016 | Shelton, IV et al. |
| 9,433,419 B2 | 9/2016 | Gonzalez et al. |
| 9,445,813 B2 | 9/2016 | Shelton, IV et al. |
| 9,451,958 B2 | 9/2016 | Shelton, IV et al. |
| 9,480,476 B2 | 11/2016 | Aldridge et al. |
| 2001/0020937 A1* | 9/2001 | Rosenberg ............ G01B 5/008 345/184 |
| 2001/0025183 A1 | 9/2001 | Shahidi |
| 2001/0044637 A1 | 11/2001 | Jacobs et al. |
| 2002/0014510 A1 | 2/2002 | Richter et al. |
| 2002/0022836 A1 | 2/2002 | Goble et al. |
| 2002/0026126 A1 | 2/2002 | Burdorff et al. |
| 2002/0029032 A1 | 3/2002 | Arkin |
| 2002/0029036 A1 | 3/2002 | Goble et al. |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0128552 A1 | 9/2002 | Nowlin et al. |
| 2002/0134811 A1 | 9/2002 | Napier et al. |
| 2002/0143340 A1 | 10/2002 | Kaneko |
| 2002/0157481 A1 | 10/2002 | Kogiso et al. |
| 2002/0165541 A1 | 11/2002 | Whitman |
| 2002/0188170 A1 | 12/2002 | Santamore et al. |
| 2002/0193808 A1 | 12/2002 | Belef et al. |
| 2003/0023316 A1 | 1/2003 | Brown et al. |
| 2003/0078647 A1 | 4/2003 | Vallana et al. |
| 2003/0084983 A1 | 5/2003 | Rangachari et al. |
| 2003/0093103 A1 | 5/2003 | Malackowski et al. |
| 2003/0096158 A1 | 5/2003 | Takano et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0153968 A1 | 8/2003 | Geis et al. |
| 2003/0163085 A1 | 8/2003 | Tanner et al. |
| 2003/0181900 A1 | 9/2003 | Long |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0220660 A1 | 11/2003 | Kortenbach et al. |
| 2003/0236505 A1 | 12/2003 | Bonadio et al. |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0006861 A1 | 1/2004 | Haytayan |
| 2004/0030333 A1 | 2/2004 | Goble |
| 2004/0032345 A1 | 2/2004 | Kazuya et al. |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068224 A1 | 4/2004 | Couvillon, Jr. et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0098040 A1 | 5/2004 | Taniguchi et al. |
| 2004/0101822 A1 | 5/2004 | Weisner et al. |
| 2004/0102783 A1 | 5/2004 | Sutterlin, III et al. |
| 2004/0108357 A1 | 6/2004 | Milliman et al. |
| 2004/0110439 A1 | 6/2004 | Chaikof et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0133095 A1 | 7/2004 | Dunki-Jacobs et al. |
| 2004/0143297 A1 | 7/2004 | Ramsey |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0225186 A1 | 11/2004 | Horne, Jr. et al. |
| 2004/0230214 A1 | 11/2004 | Donofrio et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0247415 A1 | 12/2004 | Mangone, Jr. |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0254608 A1 | 12/2004 | Huitema et al. |

(56) References Cited

U.S. PATENT DOCUMENTS

| | | |
|---|---|---|
| 2004/0260315 A1 | 12/2004 | Dell et al. |
| 2004/0267297 A1 | 12/2004 | Malackowski |
| 2004/0267310 A1 | 12/2004 | Racenet et al. |
| 2005/0010213 A1 | 1/2005 | Stad et al. |
| 2005/0032511 A1 | 2/2005 | Malone et al. |
| 2005/0033352 A1 | 2/2005 | Zeph et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080454 A1 | 4/2005 | Drews et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0116673 A1 | 6/2005 | Carl et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0125897 A1 | 6/2005 | Wyslucha et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0143769 A1 | 6/2005 | White et al. |
| 2005/0145675 A1 | 7/2005 | Hartwick et al. |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159184 A1 | 7/2005 | Kerner et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240178 A1 | 10/2005 | Morley et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256452 A1 | 11/2005 | DeMarchi et al. |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0272973 A1 | 12/2005 | Kawano et al. |
| 2005/0274768 A1 | 12/2005 | Cummins et al. |
| 2005/0283188 A1 | 12/2005 | Loshakove et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020258 A1 | 1/2006 | Strauss et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0041188 A1 | 2/2006 | Dirusso et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079115 A1 | 4/2006 | Aranyi et al. |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100643 A1 | 5/2006 | Laufer et al. |
| 2006/0108393 A1 | 5/2006 | Heinrich et al. |
| 2006/0111711 A1 | 5/2006 | Goble |
| 2006/0111723 A1 | 5/2006 | Chapolini et al. |
| 2006/0116634 A1 | 6/2006 | Shachar |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0178556 A1 | 8/2006 | Hasser et al. |
| 2006/0180634 A1 | 8/2006 | Shelton, IV et al. |
| 2006/0185682 A1 | 8/2006 | Marczyk |
| 2006/0200123 A1 | 9/2006 | Ryan |
| 2006/0201989 A1 | 9/2006 | Ojeda |
| 2006/0206100 A1 | 9/2006 | Eskridge et al. |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235368 A1 | 10/2006 | Oz |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0252993 A1 | 11/2006 | Freed et al. |
| 2006/0253069 A1 | 11/2006 | Li et al. |
| 2006/0258904 A1 | 11/2006 | Stefanchik et al. |
| 2006/0258910 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0010702 A1 | 1/2007 | Wang et al. |
| 2007/0010838 A1 | 1/2007 | Shelton, IV et al. |
| 2007/0023476 A1 | 2/2007 | Whitman et al. |
| 2007/0023477 A1 | 2/2007 | Whitman et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027472 A1 | 2/2007 | Hiles et al. |
| 2007/0027551 A1 | 2/2007 | Farnsworth et al. |
| 2007/0027553 A1 | 2/2007 | Biran et al. |
| 2007/0034668 A1 | 2/2007 | Holsten et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055219 A1 | 3/2007 | Whitman et al. |
| 2007/0066981 A1 | 3/2007 | Meagher |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0083193 A1 | 4/2007 | Werneth et al. |
| 2007/0084897 A1 | 4/2007 | Shelton, IV et al. |
| 2007/0090788 A1 | 4/2007 | Hansford et al. |

(56) References Cited

U.S. PATENT DOCUMENTS

| | | |
|---|---|---|
| 2007/0093869 A1 | 4/2007 | Bloom et al. |
| 2007/0102472 A1 | 5/2007 | Shelton, IV |
| 2007/0106113 A1 | 5/2007 | Ravo |
| 2007/0106317 A1 | 5/2007 | Shelton, IV et al. |
| 2007/0118175 A1 | 5/2007 | Butler et al. |
| 2007/0129605 A1 | 6/2007 | Schaaf |
| 2007/0135686 A1 | 6/2007 | Pruitt, Jr. et al. |
| 2007/0135803 A1 | 6/2007 | Belson |
| 2007/0155010 A1 | 7/2007 | Farnsworth et al. |
| 2007/0158358 A1 | 7/2007 | Mason, II et al. |
| 2007/0170225 A1 | 7/2007 | Shelton, IV et al. |
| 2007/0173687 A1 | 7/2007 | Shima et al. |
| 2007/0173806 A1 | 7/2007 | Orszulak et al. |
| 2007/0173813 A1 | 7/2007 | Odom |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0181632 A1 | 8/2007 | Milliman |
| 2007/0190110 A1 | 8/2007 | Pameijer et al. |
| 2007/0191868 A1 | 8/2007 | Theroux et al. |
| 2007/0194079 A1 | 8/2007 | Hueil et al. |
| 2007/0194082 A1 | 8/2007 | Morgan et al. |
| 2007/0198039 A1 | 8/2007 | Jones et al. |
| 2007/0203510 A1 | 8/2007 | Bettuchi |
| 2007/0213750 A1 | 9/2007 | Weadock |
| 2007/0219571 A1 | 9/2007 | Balbierz et al. |
| 2007/0225562 A1 | 9/2007 | Spivey et al. |
| 2007/0233163 A1 | 10/2007 | Bombard et al. |
| 2007/0239028 A1 | 10/2007 | Houser et al. |
| 2007/0243227 A1 | 10/2007 | Gertner |
| 2007/0244471 A1 | 10/2007 | Malackowski |
| 2007/0246505 A1 | 10/2007 | Pace-Floridia et al. |
| 2007/0249999 A1 | 10/2007 | Sklar et al. |
| 2007/0250113 A1 | 10/2007 | Hegeman et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0287993 A1 | 12/2007 | Hinman et al. |
| 2007/0288044 A1 | 12/2007 | Jinno et al. |
| 2007/0299427 A1 | 12/2007 | Yeung et al. |
| 2008/0003196 A1 | 1/2008 | Jonn et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0051833 A1 | 2/2008 | Gramuglia et al. |
| 2008/0065153 A1 | 3/2008 | Allard et al. |
| 2008/0071328 A1 | 3/2008 | Haubrich et al. |
| 2008/0078802 A1 | 4/2008 | Hess et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083808 A1 | 4/2008 | Scirica |
| 2008/0083813 A1 | 4/2008 | Zemlok et al. |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0097563 A1 | 4/2008 | Petrie et al. |
| 2008/0108443 A1 | 5/2008 | Jinno et al. |
| 2008/0114315 A1 | 5/2008 | Voegele et al. |
| 2008/0114385 A1 | 5/2008 | Byrum et al. |
| 2008/0128469 A1 | 6/2008 | Dalessandro et al. |
| 2008/0129253 A1 | 6/2008 | Shiue et al. |
| 2008/0140115 A1 | 6/2008 | Stopek |
| 2008/0154299 A1 | 6/2008 | Livnveh |
| 2008/0167671 A1* | 7/2008 | Giordano ......... A61B 17/07207 606/167 |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0200835 A1 | 8/2008 | Monson et al. |
| 2008/0200933 A1 | 8/2008 | Bakos et al. |
| 2008/0200949 A1 | 8/2008 | Hiles et al. |
| 2008/0228029 A1 | 9/2008 | Mikkaichi et al. |
| 2008/0241667 A1 | 10/2008 | Kohn et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0281171 A1 | 11/2008 | Fennell et al. |
| 2008/0281254 A1 | 11/2008 | Humayun et al. |
| 2008/0283570 A1 | 11/2008 | Boyden et al. |
| 2008/0287944 A1 | 11/2008 | Pearson et al. |
| 2008/0287988 A1 | 11/2008 | Smith et al. |
| 2008/0290134 A1 | 11/2008 | Bettuchi et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0018553 A1 | 1/2009 | McLean et al. |
| 2009/0020958 A1 | 1/2009 | Soul |
| 2009/0047329 A1 | 2/2009 | Stucky et al. |
| 2009/0048589 A1 | 2/2009 | Takashino et al. |
| 2009/0048612 A1 | 2/2009 | Farritor et al. |
| 2009/0054908 A1 | 2/2009 | Zand et al. |
| 2009/0069842 A1 | 3/2009 | Lee et al. |
| 2009/0076506 A1 | 3/2009 | Baker |
| 2009/0078736 A1 | 3/2009 | Van Lue |
| 2009/0082789 A1 | 3/2009 | Milliman et al. |
| 2009/0088659 A1 | 4/2009 | Graham et al. |
| 2009/0088774 A1 | 4/2009 | Swarup et al. |
| 2009/0090763 A1* | 4/2009 | Zemlok ............ A61B 17/07207 227/175.2 |
| 2009/0092651 A1 | 4/2009 | Shah et al. |
| 2009/0093728 A1 | 4/2009 | Hyde et al. |
| 2009/0099579 A1 | 4/2009 | Nentwick et al. |
| 2009/0099876 A1 | 4/2009 | Whitman |
| 2009/0108048 A1 | 4/2009 | Zemlok et al. |
| 2009/0112229 A1 | 4/2009 | Omori et al. |
| 2009/0114701 A1 | 5/2009 | Zemlok et al. |
| 2009/0119011 A1 | 5/2009 | Kondo et al. |
| 2009/0137952 A1 | 5/2009 | Ramamurthy et al. |
| 2009/0143805 A1 | 6/2009 | Palmer et al. |
| 2009/0143855 A1 | 6/2009 | Weber et al. |
| 2009/0149871 A9 | 6/2009 | Kagan et al. |
| 2009/0157067 A1 | 6/2009 | Kane et al. |
| 2009/0157087 A1 | 6/2009 | Wei et al. |
| 2009/0171147 A1 | 7/2009 | Lee et al. |
| 2009/0177226 A1 | 7/2009 | Reinprecht et al. |
| 2009/0179757 A1 | 7/2009 | Cohn et al. |
| 2009/0188964 A1 | 7/2009 | Orlov |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |

(56) References Cited

U.S. PATENT DOCUMENTS

| | | |
|---|---|---|
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0213685 A1 | 8/2009 | Mak et al. |
| 2009/0234273 A1 | 9/2009 | Intoccia et al. |
| 2009/0242610 A1 | 10/2009 | Shelton, IV et al. |
| 2009/0247901 A1 | 10/2009 | Zimmer |
| 2009/0248007 A1 | 10/2009 | Falkenstein et al. |
| 2009/0248038 A1 | 10/2009 | Blumenkranz et al. |
| 2009/0253959 A1 | 10/2009 | Yoshie et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0262078 A1 | 10/2009 | Pizzi |
| 2009/0270895 A1 | 10/2009 | Churchill et al. |
| 2009/0277949 A1 | 11/2009 | Viola et al. |
| 2009/0290016 A1 | 11/2009 | Suda |
| 2009/0292283 A1 | 11/2009 | Odom |
| 2009/0308907 A1 | 12/2009 | Nalagatla et al. |
| 2010/0010511 A1 | 1/2010 | Harris et al. |
| 2010/0012704 A1 | 1/2010 | Tarinelli Racenet et al. |
| 2010/0016852 A1 | 1/2010 | Manzo et al. |
| 2010/0016888 A1 | 1/2010 | Calabrese et al. |
| 2010/0023024 A1 | 1/2010 | Zeiner et al. |
| 2010/0036370 A1 | 2/2010 | Mirel et al. |
| 2010/0041945 A1 | 2/2010 | Isbell, Jr. |
| 2010/0049084 A1 | 2/2010 | Nock et al. |
| 2010/0057087 A1 | 3/2010 | Cha |
| 2010/0057107 A1 | 3/2010 | Sorrentino et al. |
| 2010/0069942 A1 | 3/2010 | Shelton, IV |
| 2010/0072254 A1 | 3/2010 | Aranyi et al. |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0087840 A1 | 4/2010 | Ebersole et al. |
| 2010/0094289 A1 | 4/2010 | Taylor et al. |
| 2010/0096431 A1 | 4/2010 | Smith et al. |
| 2010/0100124 A1 | 4/2010 | Calabrese et al. |
| 2010/0108740 A1 | 5/2010 | Pastorelli et al. |
| 2010/0108741 A1 | 5/2010 | Hessler et al. |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0147923 A1 | 6/2010 | D'Agostino et al. |
| 2010/0163598 A1 | 7/2010 | Belzer |
| 2010/0179022 A1 | 7/2010 | Shirokoshi |
| 2010/0179540 A1 | 7/2010 | Marczyk et al. |
| 2010/0180711 A1 | 7/2010 | Kilibarda et al. |
| 2010/0186219 A1 | 7/2010 | Smith |
| 2010/0191292 A1 | 7/2010 | DeMeo et al. |
| 2010/0193566 A1 | 8/2010 | Schieb et al. |
| 2010/0200637 A1 | 8/2010 | Beetel |
| 2010/0204717 A1 | 8/2010 | Knodel |
| 2010/0222901 A1 | 9/2010 | Swayze et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0249497 A1 | 9/2010 | Peine et al. |
| 2010/0249519 A1 | 9/2010 | Park et al. |
| 2010/0249759 A1 | 9/2010 | Hinman et al. |
| 2010/0258611 A1 | 10/2010 | Smith et al. |
| 2010/0267662 A1 | 10/2010 | Fielder et al. |
| 2010/0268030 A1 | 10/2010 | Viola et al. |
| 2010/0274160 A1 | 10/2010 | Yachi et al. |
| 2010/0276471 A1 | 11/2010 | Whitman |
| 2010/0292540 A1 | 11/2010 | Hess et al. |
| 2010/0294827 A1 | 11/2010 | Boyden et al. |
| 2010/0298636 A1 | 11/2010 | Casto et al. |
| 2010/0312261 A1 | 12/2010 | Suzuki et al. |
| 2010/0320252 A1 | 12/2010 | Viola et al. |
| 2010/0331856 A1 | 12/2010 | Carlson et al. |
| 2010/0331880 A1 | 12/2010 | Stopek |
| 2011/0003528 A1 | 1/2011 | Lam |
| 2011/0006101 A1 | 1/2011 | Hall et al. |
| 2011/0009890 A1 | 1/2011 | Palmer et al. |
| 2011/0011916 A1 | 1/2011 | Levine |
| 2011/0016960 A1 | 1/2011 | Debrailly |
| 2011/0017799 A1 | 1/2011 | Whitman et al. |
| 2011/0021871 A1 | 1/2011 | Berkelaar |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0034910 A1 | 2/2011 | Ross et al. |
| 2011/0034918 A1 | 2/2011 | Reschke |
| 2011/0036887 A1 | 2/2011 | Zemlok et al. |
| 2011/0036890 A1 | 2/2011 | Ma |
| 2011/0036891 A1 | 2/2011 | Zemlok et al. |
| 2011/0045047 A1 | 2/2011 | Bennett et al. |
| 2011/0046666 A1 | 2/2011 | Sorrentino et al. |
| 2011/0046667 A1 | 2/2011 | Culligan et al. |
| 2011/0060356 A1 | 3/2011 | Reschke et al. |
| 2011/0060363 A1 | 3/2011 | Hess et al. |
| 2011/0082538 A1 | 4/2011 | Dahlgren et al. |
| 2011/0084112 A1 | 4/2011 | Kostrzewski |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0101065 A1 | 5/2011 | Milliman |
| 2011/0112517 A1 | 5/2011 | Peine et al. |
| 2011/0114697 A1 | 5/2011 | Baxter, III et al. |
| 2011/0118778 A1 | 5/2011 | Burbank |
| 2011/0121049 A1 | 5/2011 | Malinouskas et al. |
| 2011/0125138 A1* | 5/2011 | Malinouskas ........ A61B 17/068 606/1 |
| 2011/0125176 A1 | 5/2011 | Yates et al. |
| 2011/0144640 A1 | 6/2011 | Heinrich et al. |
| 2011/0147433 A1 | 6/2011 | Shelton, IV et al. |
| 2011/0155786 A1 | 6/2011 | Shelton, IV |
| 2011/0163146 A1 | 7/2011 | Ortiz et al. |
| 2011/0167619 A1 | 7/2011 | Smith et al. |
| 2011/0174099 A1 | 7/2011 | Ross et al. |
| 2011/0174861 A1 | 7/2011 | Shelton, IV et al. |
| 2011/0178536 A1 | 7/2011 | Kostrzewski |
| 2011/0184459 A1 | 7/2011 | Malkowski et al. |
| 2011/0192882 A1 | 8/2011 | Hess et al. |
| 2011/0208093 A1 | 8/2011 | Gross et al. |
| 2011/0210156 A1 | 9/2011 | Smith et al. |
| 2011/0241597 A1 | 10/2011 | Zhu et al. |
| 2011/0253765 A1 | 10/2011 | Nicholas et al. |
| 2011/0257650 A1 | 10/2011 | Deville et al. |
| 2011/0264119 A1 | 10/2011 | Bayon et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0282446 A1 | 11/2011 | Schulte et al. |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2011/0307023 A1 | 12/2011 | Tweden et al. |
| 2011/0309128 A1* | 12/2011 | Okoniewski ..... A61B 17/07207 227/176.1 |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0016413 A1 | 1/2012 | Timm et al. |
| 2012/0018326 A1 | 1/2012 | Racenet et al. |
| 2012/0022523 A1 | 1/2012 | Smith et al. |
| 2012/0022630 A1 | 1/2012 | Wübbeling |
| 2012/0029272 A1 | 2/2012 | Shelton, IV et al. |
| 2012/0033360 A1 | 2/2012 | Hsu |
| 2012/0045303 A1 | 2/2012 | Macdonald |
| 2012/0046692 A1 | 2/2012 | Smith et al. |
| 2012/0074200 A1 | 3/2012 | Schmid et al. |
| 2012/0078071 A1 | 3/2012 | Bohm et al. |
| 2012/0078244 A1 | 3/2012 | Worrell et al. |
| 2012/0078278 A1 | 3/2012 | Bales, Jr. et al. |
| 2012/0080336 A1 | 4/2012 | Shelton, IV et al. |

(56) References Cited

U.S. PATENT DOCUMENTS

| | | |
|---|---|---|
| 2012/0080340 A1 | 4/2012 | Shelton, IV et al. |
| 2012/0080344 A1 | 4/2012 | Shelton, IV |
| 2012/0080475 A1 | 4/2012 | Smith et al. |
| 2012/0080478 A1 | 4/2012 | Morgan et al. |
| 2012/0080498 A1 | 4/2012 | Shelton, IV et al. |
| 2012/0089131 A1 | 4/2012 | Zemlok et al. |
| 2012/0110810 A1 | 5/2012 | Houser et al. |
| 2012/0116265 A1 | 5/2012 | Houser et al. |
| 2012/0116367 A1 | 5/2012 | Houser et al. |
| 2012/0116388 A1 | 5/2012 | Houser et al. |
| 2012/0116391 A1 | 5/2012 | Houser et al. |
| 2012/0116395 A1 | 5/2012 | Madan et al. |
| 2012/0123203 A1 | 5/2012 | Riva |
| 2012/0125792 A1 | 5/2012 | Cassivi |
| 2012/0138658 A1 | 6/2012 | Ullrich et al. |
| 2012/0175398 A1 | 7/2012 | Sandborn et al. |
| 2012/0187179 A1 | 7/2012 | Gleiman |
| 2012/0209289 A1 | 8/2012 | Duque et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0241492 A1 | 9/2012 | Shelton, IV et al. |
| 2012/0241493 A1 | 9/2012 | Baxter, III et al. |
| 2012/0248167 A1 | 10/2012 | Flanagan et al. |
| 2012/0248169 A1 | 10/2012 | Widenhouse et al. |
| 2012/0253329 A1 | 10/2012 | Zemlok et al. |
| 2012/0265176 A1 | 10/2012 | Braun |
| 2012/0271285 A1 | 10/2012 | Sholev et al. |
| 2012/0273550 A1 | 11/2012 | Scirica |
| 2012/0277780 A1 | 11/2012 | Smith et al. |
| 2012/0283707 A1 | 11/2012 | Giordano et al. |
| 2012/0286021 A1 | 11/2012 | Kostrzewski et al. |
| 2012/0289979 A1 | 11/2012 | Eskaros et al. |
| 2012/0292367 A1 | 11/2012 | Morgan et al. |
| 2012/0296333 A1 | 11/2012 | Twomey |
| 2012/0298722 A1 | 11/2012 | Hess et al. |
| 2012/0310255 A1 | 12/2012 | Brisson et al. |
| 2012/0310256 A1 | 12/2012 | Brisson |
| 2012/0312860 A1 | 12/2012 | Ming et al. |
| 2012/0318842 A1 | 12/2012 | Anim et al. |
| 2012/0325892 A1 | 12/2012 | Kostrzewski |
| 2013/0012983 A1 | 1/2013 | Kleyman |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0026973 A1 | 1/2013 | Luke et al. |
| 2013/0030608 A1 | 1/2013 | Taylor et al. |
| 2013/0032626 A1 | 2/2013 | Smith et al. |
| 2013/0037596 A1 | 2/2013 | Bear et al. |
| 2013/0046290 A1 | 2/2013 | Palmer et al. |
| 2013/0060278 A1 | 3/2013 | Bozung et al. |
| 2013/0062391 A1 | 3/2013 | Boudreaux et al. |
| 2013/0075446 A1 | 3/2013 | Wang et al. |
| 2013/0079814 A1 | 3/2013 | Hess et al. |
| 2013/0087597 A1 | 4/2013 | Shelton, IV et al. |
| 2013/0087599 A1 | 4/2013 | Krumanaker et al. |
| 2013/0087602 A1 | 4/2013 | Olson et al. |
| 2013/0090534 A1 | 4/2013 | Burns et al. |
| 2013/0098970 A1 | 4/2013 | Racenet et al. |
| 2013/0103023 A1 | 4/2013 | Monson et al. |
| 2013/0103024 A1 | 4/2013 | Monson et al. |
| 2013/0105548 A1 | 5/2013 | Hodgkinson et al. |
| 2013/0116668 A1 | 5/2013 | Shelton, IV et al. |
| 2013/0116669 A1 | 5/2013 | Shelton, IV et al. |
| 2013/0119108 A1 | 5/2013 | Altman et al. |
| 2013/0123822 A1 | 5/2013 | Wellman et al. |
| 2013/0126379 A1 | 5/2013 | Medhal et al. |
| 2013/0131651 A1 | 5/2013 | Strobl et al. |
| 2013/0146641 A1 | 6/2013 | Shelton, IV et al. |
| 2013/0146642 A1 | 6/2013 | Shelton, IV et al. |
| 2013/0150832 A1 | 6/2013 | Belson et al. |
| 2013/0153633 A1 | 6/2013 | Casasanta, Jr. et al. |
| 2013/0153634 A1 | 6/2013 | Carter et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153641 A1 | 6/2013 | Shelton, IV et al. |
| 2013/0161374 A1 | 6/2013 | Swayze et al. |
| 2013/0168431 A1 | 7/2013 | Zemlok et al. |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0214025 A1 | 8/2013 | Zemlok et al. |
| 2013/0214030 A1 | 8/2013 | Aronhalt et al. |
| 2013/0221059 A1 | 8/2013 | Racenet et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233906 A1 | 9/2013 | Hess et al. |
| 2013/0233908 A1 | 9/2013 | Knodel et al. |
| 2013/0238021 A1 | 9/2013 | Gross et al. |
| 2013/0256371 A1 | 10/2013 | Shelton, IV et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0267945 A1 | 10/2013 | Behnke et al. |
| 2013/0270322 A1 | 10/2013 | Scheib et al. |
| 2013/0277412 A1 | 10/2013 | Gresham et al. |
| 2013/0310873 A1 | 11/2013 | Stopek et al. |
| 2013/0313304 A1 | 11/2013 | Shelton, IV et al. |
| 2013/0313306 A1 | 11/2013 | Shelton, IV et al. |
| 2013/0319706 A1 | 12/2013 | Nicholas et al. |
| 2013/0324981 A1 | 12/2013 | Smith et al. |
| 2013/0324982 A1 | 12/2013 | Smith et al. |
| 2013/0327809 A1 | 12/2013 | Shelton, IV et al. |
| 2013/0327810 A1 | 12/2013 | Swayze et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005681 A1 | 1/2014 | Gee et al. |
| 2014/0005693 A1 | 1/2014 | Shelton, IV et al. |
| 2014/0005694 A1 | 1/2014 | Shelton, IV et al. |
| 2014/0005702 A1 | 1/2014 | Timm et al. |
| 2014/0005703 A1 | 1/2014 | Stulen et al. |
| 2014/0005718 A1 | 1/2014 | Shelton, IV et al. |
| 2014/0008414 A1 | 1/2014 | Shelton, IV et al. |
| 2014/0012237 A1 | 1/2014 | Pribanic et al. |
| 2014/0012238 A1 | 1/2014 | Chen et al. |
| 2014/0014705 A1 | 1/2014 | Baxter, III |
| 2014/0015782 A1 | 1/2014 | Kim et al. |
| 2014/0018832 A1 | 1/2014 | Shelton, IV |
| 2014/0025046 A1 | 1/2014 | Williams et al. |
| 2014/0042205 A1 | 2/2014 | Baxter, III et al. |

(56) References Cited

U.S. PATENT DOCUMENTS

| | | |
|---|---|---|
| 2014/0048580 A1 | 2/2014 | Merchant et al. |
| 2014/0061279 A1 | 3/2014 | Laurent et al. |
| 2014/0061280 A1 | 3/2014 | Ingmanson et al. |
| 2014/0100558 A1 | 4/2014 | Schmitz et al. |
| 2014/0103093 A1 | 4/2014 | Koch, Jr. et al. |
| 2014/0107640 A1 | 4/2014 | Yates et al. |
| 2014/0110455 A1 | 4/2014 | Ingmanson et al. |
| 2014/0128850 A1 | 5/2014 | Kerr et al. |
| 2014/0138423 A1 | 5/2014 | Whitfield et al. |
| 2014/0151431 A1 | 6/2014 | Hodgkinson et al. |
| 2014/0151433 A1 | 6/2014 | Shelton, IV et al. |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0175154 A1 | 6/2014 | Shelton, IV et al. |
| 2014/0191014 A1 | 7/2014 | Shelton, IV |
| 2014/0191015 A1 | 7/2014 | Shelton, IV |
| 2014/0203061 A1 | 7/2014 | Hodgkinson |
| 2014/0205637 A1 | 7/2014 | Widenhouse et al. |
| 2014/0207125 A1 | 7/2014 | Applegate et al. |
| 2014/0207166 A1 | 7/2014 | Shelton, IV et al. |
| 2014/0224857 A1 | 8/2014 | Schmid |
| 2014/0230595 A1 | 8/2014 | Butt et al. |
| 2014/0232316 A1 | 8/2014 | Philipp |
| 2014/0236184 A1 | 8/2014 | Leimbach et al. |
| 2014/0239036 A1 | 8/2014 | Zerkle et al. |
| 2014/0239038 A1 | 8/2014 | Leimbach et al. |
| 2014/0243865 A1 | 8/2014 | Swayze et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0249557 A1 | 9/2014 | Koch, Jr. et al. |
| 2014/0252066 A1 | 9/2014 | Shelton, IV et al. |
| 2014/0252068 A1 | 9/2014 | Shelton, IV et al. |
| 2014/0259591 A1 | 9/2014 | Shelton, IV et al. |
| 2014/0263538 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263552 A1 | 9/2014 | Hall et al. |
| 2014/0263554 A1 | 9/2014 | Leimbach et al. |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263572 A1 | 9/2014 | Shelton, IV et al. |
| 2014/0277017 A1 | 9/2014 | Leimbach et al. |
| 2014/0284371 A1 | 9/2014 | Morgan et al. |
| 2014/0284373 A1 | 9/2014 | Shelton, IV et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |
| 2014/0299648 A1 | 10/2014 | Shelton, IV et al. |
| 2014/0303645 A1 | 10/2014 | Morgan et al. |
| 2014/0303646 A1 | 10/2014 | Morgan et al. |
| 2014/0305987 A1 | 10/2014 | Parihar et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305994 A1 | 10/2014 | Parihar et al. |
| 2014/0309665 A1 | 10/2014 | Parihar et al. |
| 2014/0309666 A1 | 10/2014 | Shelton, IV et al. |
| 2014/0330161 A1 | 11/2014 | Swayze et al. |
| 2014/0339286 A1 | 11/2014 | Motooka et al. |
| 2014/0352463 A1 | 12/2014 | Parihar |
| 2014/0353358 A1 | 12/2014 | Shelton, IV et al. |
| 2014/0367447 A1 | 12/2014 | Woodard, Jr. et al. |
| 2014/0378950 A1 | 12/2014 | Chiu |
| 2015/0008248 A1 | 1/2015 | Giordano et al. |
| 2015/0034696 A1 | 2/2015 | Shelton, IV et al. |
| 2015/0038986 A1 | 2/2015 | Swensgard et al. |
| 2015/0041518 A1 | 2/2015 | Shelton, IV et al. |
| 2015/0053737 A1 | 2/2015 | Leimbach et al. |
| 2015/0053738 A1 | 2/2015 | Morgan et al. |
| 2015/0053739 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0080868 A1 | 3/2015 | Kerr |
| 2015/0083780 A1 | 3/2015 | Shelton, IV et al. |
| 2015/0083781 A1 | 3/2015 | Giordano et al. |
| 2015/0083782 A1 | 3/2015 | Scheib et al. |
| 2015/0083783 A1 | 3/2015 | Shelton, IV et al. |
| 2015/0090759 A1 | 4/2015 | Spivey et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090763 A1 | 4/2015 | Murray et al. |
| 2015/0108199 A1 | 4/2015 | Shelton, IV et al. |
| 2015/0122869 A1 | 5/2015 | Aronhalt et al. |
| 2015/0136830 A1 | 5/2015 | Baxter, III et al. |
| 2015/0136831 A1 | 5/2015 | Baxter, III et al. |
| 2015/0136832 A1 | 5/2015 | Baxter, III et al. |
| 2015/0136833 A1 | 5/2015 | Shelton, IV et al. |
| 2015/0136835 A1 | 5/2015 | Shelton, IV et al. |
| 2015/0157354 A1 | 6/2015 | Bales, Jr. et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173749 A1 | 6/2015 | Shelton, IV et al. |
| 2015/0173750 A1 | 6/2015 | Shelton, IV et al. |
| 2015/0173751 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0173762 A1 | 6/2015 | Shelton, IV et al. |
| 2015/0173789 A1 | 6/2015 | Baxter, III et al. |
| 2015/0182220 A1 | 7/2015 | Yates et al. |
| 2015/0182222 A1 | 7/2015 | Swayze et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0196347 A1 | 7/2015 | Yates et al. |
| 2015/0196348 A1 | 7/2015 | Yates et al. |
| 2015/0201932 A1 | 7/2015 | Swayze et al. |
| 2015/0201935 A1 | 7/2015 | Weisenburgh, II et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209031 A1 | 7/2015 | Shelton, IV et al. |
| 2015/0209038 A1 | 7/2015 | Shelton, IV et al. |
| 2015/0209039 A1 | 7/2015 | Shelton, IV et al. |
| 2015/0209041 A1 | 7/2015 | Milliman et al. |
| 2015/0223809 A1 | 8/2015 | Scheib et al. |

(56) References Cited

U.S. PATENT DOCUMENTS

| | | |
|---|---|---|
| 2015/0223816 A1 | 8/2015 | Morgan et al. |
| 2015/0230783 A1 | 8/2015 | Shelton, IV et al. |
| 2015/0230784 A1 | 8/2015 | Shelton, IV et al. |
| 2015/0231409 A1 | 8/2015 | Racenet et al. |
| 2015/0238185 A1 | 8/2015 | Schellin et al. |
| 2015/0238186 A1 | 8/2015 | Aronhalt et al. |
| 2015/0238187 A1 | 8/2015 | Schellin et al. |
| 2015/0238188 A1 | 8/2015 | Vendely et al. |
| 2015/0238191 A1 | 8/2015 | Schellin et al. |
| 2015/0239180 A1 | 8/2015 | Schellin et al. |
| 2015/0265276 A1 | 9/2015 | Huitema et al. |
| 2015/0265357 A1 | 9/2015 | Shelton, IV et al. |
| 2015/0272557 A1 | 10/2015 | Overmyer et al. |
| 2015/0272569 A1 | 10/2015 | Leimbach et al. |
| 2015/0272570 A1 | 10/2015 | Lytle, IV et al. |
| 2015/0272571 A1 | 10/2015 | Leimbach et al. |
| 2015/0272572 A1 | 10/2015 | Overmyer et al. |
| 2015/0272574 A1 | 10/2015 | Leimbach et al. |
| 2015/0272578 A1 | 10/2015 | Leimbach et al. |
| 2015/0272579 A1 | 10/2015 | Leimbach et al. |
| 2015/0272580 A1 | 10/2015 | Leimbach et al. |
| 2015/0272581 A1 | 10/2015 | Leimbach et al. |
| 2015/0272582 A1 | 10/2015 | Leimbach et al. |
| 2015/0272583 A1 | 10/2015 | Leimbach et al. |
| 2015/0277471 A1 | 10/2015 | Leimbach et al. |
| 2015/0280384 A1 | 10/2015 | Leimbach et al. |
| 2015/0280424 A1 | 10/2015 | Leimbach et al. |
| 2015/0282809 A1 | 10/2015 | Shelton, IV et al. |
| 2015/0282810 A1 | 10/2015 | Shelton, IV et al. |
| 2015/0289873 A1 | 10/2015 | Shelton, IV et al. |
| 2015/0289874 A1 | 10/2015 | Leimbach et al. |
| 2015/0297210 A1 | 10/2015 | Widenhouse et al. |
| 2015/0297217 A1 | 10/2015 | Huitema et al. |
| 2015/0297218 A1 | 10/2015 | Shelton, IV et al. |
| 2015/0297219 A1 | 10/2015 | Shelton, IV et al. |
| 2015/0297221 A1 | 10/2015 | Kerr et al. |
| 2015/0297222 A1 | 10/2015 | Huitema et al. |
| 2015/0297223 A1 | 10/2015 | Huitema et al. |
| 2015/0297224 A1 | 10/2015 | Hall et al. |
| 2015/0297225 A1 | 10/2015 | Huitema et al. |
| 2015/0297226 A1 | 10/2015 | Hall et al. |
| 2015/0297227 A1 | 10/2015 | Huitema et al. |
| 2015/0297228 A1 | 10/2015 | Huitema et al. |
| 2015/0297229 A1 | 10/2015 | Schellin et al. |
| 2015/0297230 A1 | 10/2015 | Schellin et al. |
| 2015/0297231 A1 | 10/2015 | Huitema et al. |
| 2015/0297232 A1 | 10/2015 | Huitema et al. |
| 2015/0297233 A1 | 10/2015 | Huitema et al. |
| 2015/0297234 A1 | 10/2015 | Schellin et al. |
| 2015/0297235 A1 | 10/2015 | Harris et al. |
| 2015/0297236 A1 | 10/2015 | Harris et al. |
| 2015/0305744 A1 | 10/2015 | Moore et al. |
| 2015/0305745 A1 | 10/2015 | Baxter, III et al. |
| 2015/0313591 A1 | 11/2015 | Baxter, III et al. |
| 2015/0313594 A1 | 11/2015 | Shelton, IV et al. |
| 2015/0327853 A1 | 11/2015 | Aronhalt et al. |
| 2015/0327864 A1 | 11/2015 | Hodgkinson et al. |
| 2015/0335328 A1 | 11/2015 | Shelton, IV et al. |
| 2015/0335329 A1 | 11/2015 | Shelton, IV et al. |
| 2015/0342606 A1 | 12/2015 | Schmid et al. |
| 2015/0342607 A1 | 12/2015 | Shelton, IV et al. |
| 2015/0359536 A1 | 12/2015 | Cropper et al. |
| 2015/0374367 A1 | 12/2015 | Hall et al. |
| 2015/0374368 A1 | 12/2015 | Swayze et al. |
| 2015/0374369 A1 | 12/2015 | Yates et al. |
| 2015/0374374 A1 | 12/2015 | Shelton, IV et al. |
| 2015/0374375 A1 | 12/2015 | Shelton, IV et al. |
| 2015/0374376 A1 | 12/2015 | Shelton, IV |
| 2015/0374377 A1 | 12/2015 | Shelton, IV |
| 2015/0374378 A1 | 12/2015 | Giordano et al. |
| 2015/0374379 A1 | 12/2015 | Shelton, IV |
| 2016/0000430 A1 | 1/2016 | Ming et al. |
| 2016/0000431 A1 | 1/2016 | Giordano et al. |
| 2016/0000432 A1 | 1/2016 | Huang et al. |
| 2016/0000437 A1 | 1/2016 | Giordano et al. |
| 2016/0000438 A1 | 1/2016 | Swayze et al. |
| 2016/0000439 A1 | 1/2016 | Weisenburgh, II et al. |
| 2016/0000440 A1 | 1/2016 | Weisenburgh, II et al. |
| 2016/0000441 A1 | 1/2016 | Shelton, IV et al. |
| 2016/0000442 A1 | 1/2016 | Shelton, IV |
| 2016/0000452 A1 | 1/2016 | Yates et al. |
| 2016/0000453 A1 | 1/2016 | Yates et al. |
| 2016/0000513 A1 | 1/2016 | Shelton, IV et al. |
| 2016/0007992 A1 | 1/2016 | Yates et al. |
| 2016/0008023 A1 | 1/2016 | Yates et al. |
| 2016/0015390 A1 | 1/2016 | Timm et al. |
| 2016/0015391 A1 | 1/2016 | Shelton, IV et al. |
| 2016/0051257 A1 | 2/2016 | Shelton, IV et al. |
| 2016/0058443 A1 | 3/2016 | Yates et al. |
| 2016/0066909 A1 | 3/2016 | Baber et al. |
| 2016/0066910 A1 | 3/2016 | Baber et al. |
| 2016/0066911 A1 | 3/2016 | Baber et al. |
| 2016/0066912 A1 | 3/2016 | Baber et al. |
| 2016/0066913 A1 | 3/2016 | Swayze et al. |
| 2016/0066914 A1 | 3/2016 | Baber et al. |
| 2016/0066915 A1 | 3/2016 | Baber et al. |
| 2016/0066916 A1 | 3/2016 | Overmyer et al. |
| 2016/0069449 A1 | 3/2016 | Kanai et al. |
| 2016/0074038 A1 | 3/2016 | Leimbach et al. |
| 2016/0074040 A1 | 3/2016 | Widenhouse et al. |
| 2016/0089137 A1 | 3/2016 | Hess et al. |
| 2016/0089141 A1 | 3/2016 | Harris et al. |
| 2016/0089142 A1 | 3/2016 | Harris et al. |
| 2016/0089143 A1 | 3/2016 | Harris et al. |
| 2016/0089146 A1 | 3/2016 | Harris et al. |
| 2016/0089147 A1 | 3/2016 | Harris et al. |
| 2016/0089148 A1 | 3/2016 | Harris et al. |
| 2016/0089149 A1 | 3/2016 | Harris et al. |
| 2016/0100837 A1 | 4/2016 | Huang et al. |
| 2016/0106426 A1 | 4/2016 | Shelton, IV et al. |
| 2016/0106427 A1 | 4/2016 | Shelton, IV et al. |
| 2016/0106431 A1 | 4/2016 | Shelton, IV et al. |
| 2016/0113653 A1 | 4/2016 | Zingman |
| 2016/0120544 A1 | 5/2016 | Shelton, IV et al. |
| 2016/0120545 A1 | 5/2016 | Shelton, IV et al. |
| 2016/0120547 A1 | 5/2016 | Schmid et al. |
| 2016/0128694 A1 | 5/2016 | Baxter, III et al. |
| 2016/0135812 A1 | 5/2016 | Shelton, IV et al. |
| 2016/0166256 A1 | 6/2016 | Baxter, III et al. |
| 2016/0174969 A1 | 6/2016 | Kerr et al. |
| 2016/0174970 A1 | 6/2016 | Shelton, IV et al. |
| 2016/0174971 A1 | 6/2016 | Baxter, III et al. |
| 2016/0174972 A1 | 6/2016 | Shelton, IV et al. |
| 2016/0174973 A1 | 6/2016 | Shelton, IV et al. |
| 2016/0174974 A1 | 6/2016 | Schmid et al. |
| 2016/0174975 A1 | 6/2016 | Shelton, IV et al. |
| 2016/0174976 A1 | 6/2016 | Morgan et al. |
| 2016/0174977 A1 | 6/2016 | Lytle, IV et al. |
| 2016/0174978 A1 | 6/2016 | Overmyer et al. |
| 2016/0174983 A1 | 6/2016 | Shelton, IV et al. |
| 2016/0174984 A1 | 6/2016 | Smith et al. |
| 2016/0174985 A1 | 6/2016 | Baxter, III et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0183945 A1 | 6/2016 | Shelton, IV et al. |
| 2016/0183947 A1 | 6/2016 | Shelton, IV et al. |
| 2016/0183948 A1 | 6/2016 | Shelton, IV et al. |
| 2016/0183950 A1 | 6/2016 | Shelton, IV et al. |
| 2016/0184039 A1 | 6/2016 | Shelton, IV et al. |
| 2016/0192916 A1 | 7/2016 | Shelton, IV et al. |
| 2016/0192917 A1 | 7/2016 | Shelton, IV et al. |
| 2016/0192918 A1 | 7/2016 | Shelton, IV et al. |
| 2016/0192929 A1 | 7/2016 | Schmid et al. |
| 2016/0192933 A1 | 7/2016 | Shelton, IV |
| 2016/0192936 A1 | 7/2016 | Leimbach et al. |
| 2016/0192996 A1 | 7/2016 | Spivey et al. |
| 2016/0192997 A1 | 7/2016 | Spivey et al. |
| 2016/0199059 A1 | 7/2016 | Shelton, IV et al. |
| 2016/0199061 A1 | 7/2016 | Shelton, IV et al. |
| 2016/0199063 A1 | 7/2016 | Mandakolathur Vasudevan et al. |
| 2016/0199064 A1 | 7/2016 | Shelton, IV et al. |
| 2016/0199088 A1 | 7/2016 | Shelton, IV et al. |
| 2016/0199089 A1 | 7/2016 | Hess et al. |

(56) References Cited

U.S. PATENT DOCUMENTS

| | | | |
|---|---|---|---|
| 2016/0199956 A1 | 7/2016 | Shelton, IV et al. |
| 2016/0206309 A1 | 7/2016 | Hess et al. |
| 2016/0206310 A1 | 7/2016 | Shelton, IV |
| 2016/0206314 A1 | 7/2016 | Scheib et al. |
| 2016/0220246 A1 | 8/2016 | Timm et al. |
| 2016/0220247 A1 | 8/2016 | Timm et al. |
| 2016/0220248 A1 | 8/2016 | Timm et al. |
| 2016/0220249 A1 | 8/2016 | Shelton, IV et al. |
| 2016/0220254 A1 | 8/2016 | Baxter, III et al. |
| 2016/0220266 A1 | 8/2016 | Shelton, IV et al. |
| 2016/0220268 A1 | 8/2016 | Shelton, IV et al. |
| 2016/0235403 A1 | 8/2016 | Shelton, IV et al. |
| 2016/0235404 A1 | 8/2016 | Shelton, IV |
| 2016/0235405 A1 | 8/2016 | Shelton, IV et al. |
| 2016/0235406 A1 | 8/2016 | Shelton, IV et al. |
| 2016/0235408 A1 | 8/2016 | Shelton, IV et al. |
| 2016/0235409 A1 | 8/2016 | Shelton, IV et al. |
| 2016/0235494 A1 | 8/2016 | Shelton, IV et al. |
| 2016/0238108 A1 | 8/2016 | Kanai et al. |
| 2016/0242768 A1 | 8/2016 | Moore et al. |
| 2016/0242769 A1 | 8/2016 | Moore et al. |
| 2016/0242770 A1 | 8/2016 | Moore et al. |
| 2016/0242775 A1 | 8/2016 | Shelton, IV et al. |
| 2016/0242776 A1 | 8/2016 | Shelton, IV et al. |
| 2016/0242777 A1 | 8/2016 | Shelton, IV et al. |
| 2016/0242780 A1 | 8/2016 | Shelton, IV et al. |
| 2016/0242781 A1 | 8/2016 | Shelton, IV et al. |
| 2016/0242782 A1 | 8/2016 | Shelton, IV et al. |
| 2016/0242783 A1 | 8/2016 | Shelton, IV et al. |
| 2016/0249908 A1 | 9/2016 | Shelton, IV et al. |
| 2016/0249909 A1 | 9/2016 | Shelton, IV et al. |
| 2016/0249910 A1 | 9/2016 | Shelton, IV et al. |
| 2016/0249911 A1 | 9/2016 | Timm et al. |
| 2016/0249915 A1 | 9/2016 | Beckman et al. |
| 2016/0249916 A1 | 9/2016 | Shelton, IV et al. |
| 2016/0249917 A1 | 9/2016 | Beckman et al. |
| 2016/0249918 A1 | 9/2016 | Shelton, IV et al. |
| 2016/0249919 A1 | 9/2016 | Savage et al. |
| 2016/0249922 A1 | 9/2016 | Morgan et al. |
| 2016/0249927 A1 | 9/2016 | Beckman et al. |
| 2016/0249930 A1 | 9/2016 | Hall et al. |
| 2016/0249945 A1 | 9/2016 | Shelton, IV et al. |
| 2016/0256071 A1 | 9/2016 | Shelton, IV et al. |
| 2016/0256153 A1 | 9/2016 | Shelton, IV et al. |
| 2016/0256154 A1 | 9/2016 | Shelton, IV et al. |
| 2016/0256155 A1 | 9/2016 | Shelton, IV et al. |
| 2016/0256156 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256186 A1 | 9/2016 | Shelton, IV et al. |
| 2016/0256187 A1 | 9/2016 | Shelton, IV et al. |
| 2016/0256229 A1 | 9/2016 | Morgan et al. |
| 2016/0262745 A1 | 9/2016 | Morgan et al. |
| 2016/0262746 A1 | 9/2016 | Shelton, IV et al. |
| 2016/0262760 A1 | 9/2016 | Shelton, IV et al. |
| 2016/0270780 A1 | 9/2016 | Hall et al. |
| 2016/0287249 A1 | 10/2016 | Alexander, III et al. |
| 2016/0287250 A1 | 10/2016 | Shelton, IV et al. |
| 2016/0287251 A1 | 10/2016 | Shelton, IV et al. |
| 2016/0287253 A1 | 10/2016 | Shelton, IV et al. |
| 2016/0287254 A1 | 10/2016 | Baxter, III et al. |

FOREIGN PATENT DOCUMENTS

| | | |
|---|---|---|
| AU | 2012200178 B2 | 7/2013 |
| CA | 2458946 A1 | 3/2003 |
| CA | 2477181 A1 | 4/2004 |
| CA | 2512960 A1 | 1/2006 |
| CA | 2514274 A1 | 1/2006 |
| CA | 2639177 A1 | 2/2009 |
| CN | 1163558 A | 10/1997 |
| CN | 2488482 Y | 5/2002 |
| CN | 1523725 A | 8/2004 |
| CN | 1545154 A | 11/2004 |
| CN | 1634601 A | 7/2005 |
| CN | 2716900 Y | 8/2005 |
| CN | 2738962 Y | 11/2005 |
| CN | 1726874 A | 2/2006 |
| CN | 1868411 A | 11/2006 |
| CN | 1915180 A | 2/2007 |
| CN | 2868212 Y | 2/2007 |
| CN | 1960679 A | 5/2007 |
| CN | 101011286 A | 8/2007 |
| CN | 101095621 A | 1/2008 |
| CN | 101111196 A | 1/2008 |
| CN | 101137402 A | 3/2008 |
| CN | 101507620 A | 8/2009 |
| CN | 101507622 A | 8/2009 |
| CN | 101507623 A | 8/2009 |
| CN | 101507625 A | 8/2009 |
| CN | 101507628 A | 8/2009 |
| CN | 101541251 A | 9/2009 |
| CN | 101675898 A | 3/2010 |
| CN | 101683280 A | 3/2010 |
| CN | 101028205 A | 1/2011 |
| CN | 101934098 A | 5/2011 |
| CN | 201949071 U | 8/2011 |
| CN | 101336835 B | 9/2011 |
| CN | 102188270 A | 9/2011 |
| CN | 101534723 B | 1/2012 |
| CN | 101310680 B | 4/2012 |
| CN | 101317782 B | 10/2012 |
| CN | 101507633 B | 2/2013 |
| CN | 101023879 B | 3/2013 |
| CN | 101327137 B | 6/2013 |
| CN | 101401736 B | 6/2013 |
| CN | 101332110 B | 7/2013 |
| CN | 101683281 B | 1/2014 |
| CN | 103648408 A | 3/2014 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 9412228 U1 | 9/1994 |
| DE | 19509116 A1 | 9/1996 |
| DE | 19707373 C1 | 2/1998 |
| DE | 19851291 A1 | 1/2000 |
| DE | 19924311 A | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314827 B3 | 4/2004 |
| DE | 10314072 A1 | 10/2004 |
| DE | 202004012389 U1 | 11/2004 |
| DE | 202007003114 U1 | 6/2007 |
| EP | 0000756 A1 | 2/1979 |
| EP | 0122046 A1 | 10/1984 |
| EP | 0070230 B1 | 10/1985 |
| EP | 0156774 A2 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0379721 B1 | 8/1990 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0548998 A1 | 6/1993 |
| EP | 0277959 B1 | 10/1993 |
| EP | 0591946 A1 | 10/1993 |
| EP | 0233940 B1 | 11/1993 |
| EP | 0261230 B1 | 11/1993 |
| EP | 0639349 A2 | 2/1994 |

(56) References Cited

FOREIGN PATENT DOCUMENTS

| | | | |
|---|---|---|---|
| EP | 0324636 | B1 | 3/1994 |
| EP | 0593920 | A1 | 4/1994 |
| EP | 0594148 | A1 | 4/1994 |
| EP | 0427949 | B1 | 6/1994 |
| EP | 0523174 | B1 | 6/1994 |
| EP | 0600182 | A2 | 6/1994 |
| EP | 0310431 | B1 | 11/1994 |
| EP | 0375302 | B1 | 11/1994 |
| EP | 0376562 | B1 | 11/1994 |
| EP | 0630612 | A1 | 12/1994 |
| EP | 0630614 | A1 | 12/1994 |
| EP | 0634144 | A1 | 1/1995 |
| EP | 0646356 | A2 | 4/1995 |
| EP | 0646357 | A1 | 4/1995 |
| EP | 0505036 | B1 | 5/1995 |
| EP | 0653189 | A2 | 5/1995 |
| EP | 0669104 | A1 | 8/1995 |
| EP | 0387980 | B1 | 10/1995 |
| EP | 0511470 | B1 | 10/1995 |
| EP | 0674876 | A2 | 10/1995 |
| EP | 0679367 | A2 | 11/1995 |
| EP | 0392547 | B1 | 12/1995 |
| EP | 0685204 | A1 | 12/1995 |
| EP | 0364216 | B1 | 1/1996 |
| EP | 0699418 | A1 | 3/1996 |
| EP | 0702937 | A1 | 3/1996 |
| EP | 0488768 | B1 | 4/1996 |
| EP | 0705571 | A1 | 4/1996 |
| EP | 0528478 | B1 | 5/1996 |
| EP | 0711611 | A2 | 5/1996 |
| EP | 0484677 | B2 | 6/1996 |
| EP | 0541987 | B1 | 7/1996 |
| EP | 0667119 | B1 | 7/1996 |
| EP | 0737446 | A1 | 10/1996 |
| EP | 0748614 | A1 | 12/1996 |
| EP | 0708618 | B1 | 3/1997 |
| EP | 0770355 | A1 | 5/1997 |
| EP | 0503662 | B1 | 6/1997 |
| EP | 0447121 | B1 | 7/1997 |
| EP | 0621009 | B1 | 7/1997 |
| EP | 0625077 | B1 | 7/1997 |
| EP | 0633749 | B1 | 8/1997 |
| EP | 0710090 | B1 | 8/1997 |
| EP | 0578425 | B1 | 9/1997 |
| EP | 0621006 | B1 | 10/1997 |
| EP | 0625335 | B1 | 11/1997 |
| EP | 0552423 | B1 | 1/1998 |
| EP | 0592244 | B1 | 1/1998 |
| EP | 0648476 | B1 | 1/1998 |
| EP | 0649290 | B1 | 3/1998 |
| EP | 0598618 | B1 | 9/1998 |
| EP | 0676173 | B1 | 9/1998 |
| EP | 0678007 | B1 | 9/1998 |
| EP | 0869104 | A1 | 10/1998 |
| EP | 0603472 | B1 | 11/1998 |
| EP | 0605351 | B1 | 11/1998 |
| EP | 0878169 | A1 | 11/1998 |
| EP | 0879742 | A1 | 11/1998 |
| EP | 0695144 | B1 | 12/1998 |
| EP | 0722296 | B1 | 12/1998 |
| EP | 0760230 | B1 | 2/1999 |
| EP | 0623316 | B1 | 3/1999 |
| EP | 0650701 | B1 | 3/1999 |
| EP | 0537572 | B1 | 6/1999 |
| EP | 0923907 | A1 | 6/1999 |
| EP | 0640317 | A1 | 9/1999 |
| EP | 0843906 | B1 | 3/2000 |
| EP | 0552050 | B1 | 5/2000 |
| EP | 0833592 | B1 | 5/2000 |
| EP | 0832605 | B1 | 6/2000 |
| EP | 0830094 | B1 | 9/2000 |
| EP | 1034747 | A1 | 9/2000 |
| EP | 1034748 | A1 | 9/2000 |
| EP | 0694290 | B1 | 11/2000 |
| EP | 1050278 | A1 | 11/2000 |
| EP | 1053719 | A1 | 11/2000 |
| EP | 1053720 | A1 | 11/2000 |
| EP | 1055399 | A1 | 11/2000 |
| EP | 1055400 | A1 | 11/2000 |
| EP | 1058177 | A1 | 12/2000 |
| EP | 1080694 | A1 | 3/2001 |
| EP | 1090592 | A1 | 4/2001 |
| EP | 1095627 | A1 | 5/2001 |
| EP | 1256318 | B1 | 5/2001 |
| EP | 0806914 | B1 | 9/2001 |
| EP | 0768840 | B1 | 12/2001 |
| EP | 0908152 | B1 | 1/2002 |
| EP | 0717959 | B1 | 2/2002 |
| EP | 0872213 | B1 | 5/2002 |
| EP | 0862386 | B1 | 6/2002 |
| EP | 0949886 | B1 | 9/2002 |
| EP | 1238634 | A2 | 9/2002 |
| EP | 0858295 | B1 | 12/2002 |
| EP | 0656188 | B1 | 1/2003 |
| EP | 0717960 | B1 | 2/2003 |
| EP | 1284120 | A1 | 2/2003 |
| EP | 1287788 | A1 | 3/2003 |
| EP | 0717966 | B1 | 4/2003 |
| EP | 0869742 | B1 | 5/2003 |
| EP | 0829235 | B1 | 6/2003 |
| EP | 0887046 | B1 | 7/2003 |
| EP | 1323384 | A2 | 7/2003 |
| EP | 0852480 | B1 | 8/2003 |
| EP | 0891154 | B1 | 9/2003 |
| EP | 0813843 | B1 | 10/2003 |
| EP | 0873089 | B1 | 10/2003 |
| EP | 0856326 | B1 | 11/2003 |
| EP | 1374788 | A1 | 1/2004 |
| EP | 0741996 | B1 | 2/2004 |
| EP | 0814712 | B1 | 2/2004 |
| EP | 1402837 | A1 | 3/2004 |
| EP | 0705570 | B1 | 4/2004 |
| EP | 0959784 | B1 | 4/2004 |
| EP | 1407719 | A2 | 4/2004 |
| EP | 1411626 | A2 | 4/2004 |
| EP | 1086713 | B1 | 5/2004 |
| EP | 0996378 | B1 | 6/2004 |
| EP | 1426012 | A1 | 6/2004 |
| EP | 0833593 | B2 | 7/2004 |
| EP | 1442694 | A1 | 8/2004 |
| EP | 0888749 | B1 | 9/2004 |
| EP | 0959786 | B1 | 9/2004 |
| EP | 1453432 | A2 | 9/2004 |
| EP | 1459695 | A1 | 9/2004 |
| EP | 1254636 | B1 | 10/2004 |
| EP | 1473819 | A1 | 11/2004 |
| EP | 1477119 | A1 | 11/2004 |
| EP | 1479345 | A1 | 11/2004 |
| EP | 1479347 | A1 | 11/2004 |
| EP | 1479348 | A1 | 11/2004 |
| EP | 0754437 | B2 | 12/2004 |
| EP | 1025807 | B1 | 12/2004 |
| EP | 1001710 | B1 | 1/2005 |
| EP | 1496805 | A2 | 1/2005 |
| EP | 1520521 | A1 | 4/2005 |
| EP | 1520522 | A1 | 4/2005 |
| EP | 1520523 | A1 | 4/2005 |
| EP | 1520525 | A1 | 4/2005 |
| EP | 1522264 | A1 | 4/2005 |
| EP | 1523942 | A2 | 4/2005 |
| EP | 1550408 | A1 | 7/2005 |
| EP | 1557129 | A1 | 7/2005 |
| EP | 1064883 | B1 | 8/2005 |
| EP | 1067876 | B1 | 8/2005 |
| EP | 0870473 | B1 | 9/2005 |
| EP | 1157666 | B1 | 9/2005 |
| EP | 0880338 | B1 | 10/2005 |
| EP | 1158917 | B1 | 11/2005 |
| EP | 1344498 | B1 | 11/2005 |
| EP | 0906764 | B1 | 12/2005 |
| EP | 1330989 | B1 | 12/2005 |
| EP | 0771176 | B2 | 1/2006 |
| EP | 1621138 | A2 | 2/2006 |
| EP | 1621139 | A2 | 2/2006 |

(56) References Cited

FOREIGN PATENT DOCUMENTS

| | | | |
|---|---|---|---|
| EP | 1621141 | A2 | 2/2006 |
| EP | 1621143 | A2 | 2/2006 |
| EP | 1621145 | A2 | 2/2006 |
| EP | 1621151 | A2 | 2/2006 |
| EP | 1034746 | B1 | 3/2006 |
| EP | 1201196 | B1 | 3/2006 |
| EP | 1632191 | A2 | 3/2006 |
| EP | 1647231 | A1 | 4/2006 |
| EP | 1065981 | B1 | 5/2006 |
| EP | 1082944 | B1 | 5/2006 |
| EP | 1230899 | B1 | 5/2006 |
| EP | 1652481 | A2 | 5/2006 |
| EP | 1382303 | B1 | 6/2006 |
| EP | 1253866 | B1 | 7/2006 |
| EP | 1032318 | B1 | 8/2006 |
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1256317 | B1 | 12/2006 |
| EP | 1285633 | B1 | 12/2006 |
| EP | 1728473 | A1 | 12/2006 |
| EP | 1728475 | A2 | 12/2006 |
| EP | 1736105 | A1 | 12/2006 |
| EP | 1011494 | B1 | 1/2007 |
| EP | 1479346 | B1 | 1/2007 |
| EP | 1484024 | B1 | 1/2007 |
| EP | 1749485 | A1 | 2/2007 |
| EP | 1754445 | A2 | 2/2007 |
| EP | 1759812 | A1 | 3/2007 |
| EP | 1767157 | A1 | 3/2007 |
| EP | 1767163 | A1 | 3/2007 |
| EP | 1563792 | B1 | 4/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1790294 | A1 | 5/2007 |
| EP | 1563793 | B1 | 6/2007 |
| EP | 1800610 | A1 | 6/2007 |
| EP | 1300117 | B1 | 8/2007 |
| EP | 1813199 | A1 | 8/2007 |
| EP | 1813200 | A2 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1815950 | A1 | 8/2007 |
| EP | 1330991 | B1 | 9/2007 |
| EP | 1806103 | B1 | 9/2007 |
| EP | 1837041 | A1 | 9/2007 |
| EP | 0922435 | B1 | 10/2007 |
| EP | 1487359 | B1 | 10/2007 |
| EP | 1599146 | B1 | 10/2007 |
| EP | 1839596 | A1 | 10/2007 |
| EP | 2110083 | A2 | 10/2007 |
| EP | 1679096 | B1 | 11/2007 |
| EP | 1857057 | A2 | 11/2007 |
| EP | 1402821 | B1 | 12/2007 |
| EP | 1872727 | A1 | 1/2008 |
| EP | 1550410 | B1 | 2/2008 |
| EP | 1671593 | B1 | 2/2008 |
| EP | 1897502 | A1 | 3/2008 |
| EP | 1611856 | B1 | 4/2008 |
| EP | 1908417 | A2 | 4/2008 |
| EP | 1917929 | A1 | 5/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943959 | A1 | 7/2008 |
| EP | 1943962 | A2 | 7/2008 |
| EP | 1943964 | A1 | 7/2008 |
| EP | 1943976 | A2 | 7/2008 |
| EP | 1593337 | B1 | 8/2008 |
| EP | 1970014 | A1 | 9/2008 |
| EP | 1974678 | A2 | 10/2008 |
| EP | 1980213 | A2 | 10/2008 |
| EP | 1980214 | A2 | 10/2008 |
| EP | 1759645 | B1 | 11/2008 |
| EP | 1987780 | A2 | 11/2008 |
| EP | 1990014 | A2 | 11/2008 |
| EP | 1552795 | B1 | 12/2008 |
| EP | 1693008 | B1 | 12/2008 |
| EP | 1759640 | B1 | 12/2008 |
| EP | 1997439 | A2 | 12/2008 |
| EP | 2000101 | A2 | 12/2008 |
| EP | 2000102 | A2 | 12/2008 |
| EP | 2005894 | A2 | 12/2008 |
| EP | 2005897 | A2 | 12/2008 |
| EP | 2005901 | A1 | 12/2008 |
| EP | 2008595 | A2 | 12/2008 |
| EP | 1736104 | B1 | 3/2009 |
| EP | 1749486 | B1 | 3/2009 |
| EP | 1782743 | B1 | 3/2009 |
| EP | 2039302 | A2 | 3/2009 |
| EP | 2039308 | A2 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 2055243 | A2 | 5/2009 |
| EP | 1550409 | B1 | 6/2009 |
| EP | 1550413 | B1 | 6/2009 |
| EP | 1719461 | B1 | 6/2009 |
| EP | 1834594 | B1 | 6/2009 |
| EP | 1709911 | B1 | 7/2009 |
| EP | 2077093 | A2 | 7/2009 |
| EP | 1745748 | B1 | 8/2009 |
| EP | 2090231 | A1 | 8/2009 |
| EP | 2090237 | A1 | 8/2009 |
| EP | 2090241 | A1 | 8/2009 |
| EP | 2090244 | B1 | 8/2009 |
| EP | 2090245 | A1 | 8/2009 |
| EP | 2090254 | A1 | 8/2009 |
| EP | 2090256 | A2 | 8/2009 |
| EP | 2095777 | A2 | 9/2009 |
| EP | 2098170 | A2 | 9/2009 |
| EP | 2110082 | A1 | 10/2009 |
| EP | 2110084 | A2 | 10/2009 |
| EP | 2111803 | A2 | 10/2009 |
| EP | 1762190 | B8 | 11/2009 |
| EP | 1813208 | B1 | 11/2009 |
| EP | 1908426 | B1 | 11/2009 |
| EP | 2116195 | A1 | 11/2009 |
| EP | 2116197 | A2 | 11/2009 |
| EP | 1607050 | B1 | 12/2009 |
| EP | 1815804 | B1 | 12/2009 |
| EP | 1875870 | B1 | 12/2009 |
| EP | 1878395 | B1 | 1/2010 |
| EP | 2151204 | A1 | 2/2010 |
| EP | 1813211 | B1 | 3/2010 |
| EP | 2165656 | A2 | 3/2010 |
| EP | 2165660 | A2 | 3/2010 |
| EP | 2165664 | A1 | 3/2010 |
| EP | 1566150 | B1 | 4/2010 |
| EP | 1813206 | B1 | 4/2010 |
| EP | 1769754 | B1 | 6/2010 |
| EP | 1854416 | B1 | 6/2010 |
| EP | 1911408 | B1 | 6/2010 |
| EP | 2198787 | A1 | 6/2010 |
| EP | 1647286 | B1 | 9/2010 |
| EP | 1825821 | B1 | 9/2010 |
| EP | 1535565 | B1 | 10/2010 |
| EP | 1702570 | B1 | 10/2010 |
| EP | 1785098 | B1 | 10/2010 |
| EP | 2005896 | B1 | 10/2010 |

(56) References Cited

FOREIGN PATENT DOCUMENTS

| | | |
|---|---|---|
| EP | 2030578 B1 | 11/2010 |
| EP | 2036505 B1 | 11/2010 |
| EP | 2245993 A2 | 11/2010 |
| EP | 2253280 A1 | 11/2010 |
| EP | 1627605 B1 | 12/2010 |
| EP | 2027811 B1 | 12/2010 |
| EP | 2130498 B1 | 12/2010 |
| EP | 2263568 A2 | 12/2010 |
| EP | 1994890 B1 | 1/2011 |
| EP | 2005900 B1 | 1/2011 |
| EP | 2283780 A2 | 2/2011 |
| EP | 2286738 A2 | 2/2011 |
| EP | 1690502 B1 | 3/2011 |
| EP | 1884201 B1 | 3/2011 |
| EP | 2292153 A1 | 3/2011 |
| EP | 1769755 B1 | 4/2011 |
| EP | 2090240 B1 | 4/2011 |
| EP | 2305135 A1 | 4/2011 |
| EP | 2308388 A1 | 4/2011 |
| EP | 2314254 A2 | 4/2011 |
| EP | 2316345 A1 | 5/2011 |
| EP | 2316366 A2 | 5/2011 |
| EP | 1813205 B1 | 6/2011 |
| EP | 2090243 B1 | 6/2011 |
| EP | 2329773 A1 | 6/2011 |
| EP | 2090239 B1 | 7/2011 |
| EP | 2340771 A2 | 7/2011 |
| EP | 2353545 A1 | 8/2011 |
| EP | 2361562 A1 | 8/2011 |
| EP | 1836986 B1 | 11/2011 |
| EP | 1908414 B1 | 11/2011 |
| EP | 2153781 B1 | 11/2011 |
| EP | 2389928 A2 | 11/2011 |
| EP | 1847225 B1 | 12/2011 |
| EP | 2397079 A1 | 12/2011 |
| EP | 2399538 A2 | 12/2011 |
| EP | 1785102 B1 | 1/2012 |
| EP | 2415416 A | 2/2012 |
| EP | 2090253 B1 | 3/2012 |
| EP | 2430986 A2 | 3/2012 |
| EP | 1347638 B1 | 5/2012 |
| EP | 2446834 A1 | 5/2012 |
| EP | 2455007 A2 | 5/2012 |
| EP | 2457519 A1 | 5/2012 |
| EP | 2462878 A1 | 6/2012 |
| EP | 2462880 A2 | 6/2012 |
| EP | 1813204 B1 | 7/2012 |
| EP | 2189121 B1 | 7/2012 |
| EP | 2248475 B1 | 7/2012 |
| EP | 2005895 B1 | 8/2012 |
| EP | 2090248 B1 | 8/2012 |
| EP | 2481359 A1 | 8/2012 |
| EP | 2486860 A2 | 8/2012 |
| EP | 2486862 A2 | 8/2012 |
| EP | 1908412 B1 | 9/2012 |
| EP | 1935351 B1 | 9/2012 |
| EP | 2497431 A1 | 9/2012 |
| EP | 1550412 B2 | 10/2012 |
| EP | 1616549 B1 | 10/2012 |
| EP | 2030579 B1 | 10/2012 |
| EP | 2090252 B1 | 10/2012 |
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 2526877 A1 | 11/2012 |
| EP | 2526883 A1 | 11/2012 |
| EP | 1884206 B1 | 3/2013 |
| EP | 2090238 B1 | 4/2013 |
| EP | 2586380 A1 | 5/2013 |
| EP | 1982657 B1 | 7/2013 |
| EP | 2614782 A2 | 7/2013 |
| EP | 2090234 B1 | 9/2013 |
| EP | 2633830 A1 | 9/2013 |
| EP | 2644124 A1 | 10/2013 |
| EP | 2644209 A2 | 10/2013 |
| EP | 2649948 A1 | 10/2013 |
| EP | 2649949 A1 | 10/2013 |
| EP | 2700367 A1 | 2/2014 |
| EP | 2713902 A1 | 4/2014 |
| EP | 1772105 B1 | 5/2014 |
| EP | 2759267 A2 | 7/2014 |
| EP | 2777538 A2 | 9/2014 |
| EP | 2446835 B1 | 1/2015 |
| EP | 2923660 A2 | 9/2015 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A1 | 1/1999 |
| FR | 2815842 A1 | 10/2000 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GB | 2423199 B | 5/2009 |
| GR | 930100110 A | 11/1993 |
| JP | S 47-11908 Y1 | 5/1972 |
| JP | 50-33988 U | 4/1975 |
| JP | S 56-112235 A | 9/1981 |
| JP | S 58500053 A | 1/1983 |
| JP | S 58-501360 A | 8/1983 |
| JP | S 59-174920 A | 3/1984 |
| JP | 60-100955 A | 6/1985 |
| JP | 60-212152 A | 10/1985 |
| JP | 61-98249 A | 5/1986 |
| JP | S 61502036 A | 9/1986 |
| JP | S 62-170011 U | 10/1987 |
| JP | S 63-59764 A | 3/1988 |
| JP | S 63-147449 A | 6/1988 |
| JP | 63-203149 A | 8/1988 |
| JP | H 02-279149 A | 11/1990 |
| JP | 3-12126 A | 1/1991 |
| JP | H 04-215747 A | 8/1992 |
| JP | H 4-131860 U | 12/1992 |
| JP | H 05-084252 A | 4/1993 |
| JP | H 05-123325 A | 5/1993 |
| JP | 5-212039 A | 8/1993 |
| JP | 6007357 A | 1/1994 |
| JP | H 6-30945 A | 2/1994 |
| JP | H 06-54857 A | 3/1994 |
| JP | H 06-63054 A | 3/1994 |
| JP | H06-26812 U | 4/1994 |
| JP | H 6-121798 A | 5/1994 |
| JP | H 6-125913 A | 5/1994 |
| JP | H 06-197901 A | 7/1994 |
| JP | H 06-237937 A | 8/1994 |
| JP | H 06-327684 A | 11/1994 |
| JP | 7-31623 A | 2/1995 |
| JP | 7051273 A | 2/1995 |
| JP | H 07-9622 U | 2/1995 |
| JP | H 7-47070 A | 2/1995 |
| JP | H 07-124166 A | 5/1995 |
| JP | H 7-163574 A | 6/1995 |
| JP | 07-171163 A | 7/1995 |
| JP | 7-255735 A | 10/1995 |
| JP | H 7-285089 A | 10/1995 |
| JP | 8-33642 A | 2/1996 |
| JP | 8033641 A | 2/1996 |
| JP | 8-164141 A | 6/1996 |
| JP | H 08-182684 A | 7/1996 |
| JP | H 08-507708 A | 8/1996 |
| JP | 8229050 A | 9/1996 |
| JP | H 8-336540 A | 12/1996 |

(56) References Cited

FOREIGN PATENT DOCUMENTS

| | | |
|---|---|---|
| JP | H 08-336544 A | 12/1996 |
| JP | H 09-501081 A | 2/1997 |
| JP | H 09-501577 A | 2/1997 |
| JP | H 09-164144 A | 6/1997 |
| JP | H 10-113352 A | 5/1998 |
| JP | H 10-118090 A | 5/1998 |
| JP | 10-512469 A | 12/1998 |
| JP | 2000-14632 A | 1/2000 |
| JP | 2000033071 A | 2/2000 |
| JP | 2000-112002 A | 4/2000 |
| JP | 2000-166932 A | 6/2000 |
| JP | 2000171730 A | 6/2000 |
| JP | 2000287987 A | 10/2000 |
| JP | 2000325303 A | 11/2000 |
| JP | 2001-046384 A | 2/2001 |
| JP | 2001-87272 A | 4/2001 |
| JP | 2001-514541 A | 9/2001 |
| JP | 2001-276091 A | 10/2001 |
| JP | 2001-517473 A | 10/2001 |
| JP | 2001286477 A | 10/2001 |
| JP | 2002-51974 A | 2/2002 |
| JP | 2002-085415 A | 3/2002 |
| JP | 2002143078 A | 5/2002 |
| JP | 2002-204801 A | 7/2002 |
| JP | 2002-528161 A | 9/2002 |
| JP | 2002-314298 A | 10/2002 |
| JP | 2002369820 A | 12/2002 |
| JP | 2003-500153 A | 1/2003 |
| JP | 2003000603 A | 1/2003 |
| JP | 2003-504104 A | 2/2003 |
| JP | 2003-135473 A | 5/2003 |
| JP | 2003-148903 A | 5/2003 |
| JP | 2003-164066 A | 6/2003 |
| JP | 2003-521301 A | 7/2003 |
| JP | 2003-523251 A | 8/2003 |
| JP | 2003-523254 A | 8/2003 |
| JP | 2003-300416 A | 10/2003 |
| JP | 2004-147701 A | 5/2004 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-337617 A | 12/2004 |
| JP | 2004-344662 A | 12/2004 |
| JP | 2004-344663 A | 12/2004 |
| JP | 2005-013573 A | 1/2005 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005-505334 A | 2/2005 |
| JP | 2005505322 T | 2/2005 |
| JP | 2005-80702 A | 3/2005 |
| JP | 2005-103280 A | 4/2005 |
| JP | 2005-103281 A | 4/2005 |
| JP | 2005-511131 A | 4/2005 |
| JP | 2005-511137 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-137919 A | 6/2005 |
| JP | 2005-144183 A | 6/2005 |
| JP | 2005-516714 A | 6/2005 |
| JP | 2005137423 A | 6/2005 |
| JP | 2005152416 A | 6/2005 |
| JP | 2005-521109 A | 7/2005 |
| JP | 2005-523105 A | 8/2005 |
| JP | 4461008 B2 | 8/2005 |
| JP | 2005524474 A | 8/2005 |
| JP | 2005-296412 A | 10/2005 |
| JP | 2005-328882 A | 12/2005 |
| JP | 2005-335432 A | 12/2005 |
| JP | 2005-342267 A | 12/2005 |
| JP | 2006-034975 A | 2/2006 |
| JP | 2006-34977 A | 2/2006 |
| JP | 2006-034978 A | 2/2006 |
| JP | 2006-034980 A | 2/2006 |
| JP | 2006-506106 A | 2/2006 |
| JP | 2006-510879 A | 3/2006 |
| JP | 2006-187649 A | 7/2006 |
| JP | 2006-218297 A | 8/2006 |
| JP | 2006-223872 A | 8/2006 |
| JP | 2006-281405 A | 10/2006 |
| JP | 2006-289064 A | 10/2006 |
| JP | 2006-334412 A | 12/2006 |
| JP | 2006-334417 A | 12/2006 |
| JP | 2006-346445 A | 12/2006 |
| JP | 2007-000634 A | 1/2007 |
| JP | 2007-050253 A | 3/2007 |
| JP | 2007-61628 A | 3/2007 |
| JP | 2007-083051 A | 4/2007 |
| JP | 2007-098130 A | 4/2007 |
| JP | 2007-105481 A | 4/2007 |
| JP | 3906843 B2 | 4/2007 |
| JP | 2007-117725 A | 5/2007 |
| JP | 2007-130471 A | 5/2007 |
| JP | 2007-130479 A | 5/2007 |
| JP | 2007-222615 A | 6/2007 |
| JP | 3934161 B2 | 6/2007 |
| JP | 2007-203049 A | 8/2007 |
| JP | 2007-203051 A | 8/2007 |
| JP | 2007-203055 A | 8/2007 |
| JP | 2007-203057 A | 8/2007 |
| JP | 2007-524435 A | 8/2007 |
| JP | 2007-229448 A | 9/2007 |
| JP | 2007-252916 A | 10/2007 |
| JP | 4001860 B2 | 10/2007 |
| JP | 2007-307373 A | 11/2007 |
| JP | 2007-325922 A | 12/2007 |
| JP | 2008-68073 A | 3/2008 |
| JP | 2008-206967 A | 9/2008 |
| JP | 2008-212637 A | 9/2008 |
| JP | 2008-212638 A | 9/2008 |
| JP | 2008-220956 A | 9/2008 |
| JP | 2008-237881 A | 10/2008 |
| JP | 2008-259860 A | 10/2008 |
| JP | 2008-264535 A | 11/2008 |
| JP | 2008-283459 A | 11/2008 |
| JP | 2009-006137 A | 1/2009 |
| JP | 2009-502351 A | 1/2009 |
| JP | 2009-502352 A | 1/2009 |
| JP | 2009-022742 A | 2/2009 |
| JP | 2009-506799 A | 2/2009 |
| JP | 2009-507526 A | 2/2009 |
| JP | 2009-72599 A | 4/2009 |
| JP | 2009-090113 A | 4/2009 |
| JP | 2009-106752 A | 5/2009 |
| JP | 2009-189836 A | 8/2009 |
| JP | 2009-189837 A | 8/2009 |
| JP | 2009-189838 A | 8/2009 |
| JP | 2009-201998 A | 9/2009 |
| JP | 2009-536082 A | 10/2009 |
| JP | 2009-261944 A | 11/2009 |
| JP | 2009-268908 A | 11/2009 |
| JP | 2009-539420 A | 11/2009 |
| JP | 2009-291604 A | 12/2009 |
| JP | 2010-504808 A | 2/2010 |
| JP | 2010-504809 A | 2/2010 |
| JP | 2010-504846 A | 2/2010 |
| JP | 2010-505524 A | 2/2010 |
| JP | 2010-069310 A | 4/2010 |
| JP | 2010-075695 A | 4/2010 |
| JP | 2010-088876 A | 4/2010 |
| JP | 2010-098844 A | 4/2010 |
| JP | 2010-214166 A | 9/2010 |
| JP | 4549018 B2 | 9/2010 |
| JP | 2010-540192 A | 12/2010 |
| JP | 2011-524199 A | 9/2011 |

(56) References Cited

FOREIGN PATENT DOCUMENTS

| | | |
|---|---|---|
| JP | 4783373 B2 | 9/2011 |
| JP | 5140421 B2 | 2/2013 |
| JP | 5162595 B2 | 3/2013 |
| JP | 2013-128791 A | 7/2013 |
| JP | 5333899 B2 | 11/2013 |
| KR | 20110003229 A | 1/2011 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/01080 A1 | 1/1998 |
| WO | WO 98/17180 A1 | 4/1998 |
| WO | WO 98/22154 A2 | 5/1998 |
| WO | WO 98/27880 A1 | 7/1998 |
| WO | WO 98/30153 A1 | 7/1998 |
| WO | WO 98/47436 A1 | 10/1998 |
| WO | WO 98/58589 A1 | 12/1998 |
| WO | WO 99/02090 A1 | 1/1999 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/057796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 00/78222 A1 | 12/2000 |
| WO | WO 01/03587 A1 | 1/2001 |
| WO | WO 01/05702 A1 | 1/2001 |
| WO | WO 01/010482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62163 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |

(56) References Cited

FOREIGN PATENT DOCUMENTS

| | | |
|---|---|---|
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/065933 A2 | 8/2002 |
| WO | WO 02/067785 A2 | 9/2002 |
| WO | WO 02/080781 A2 | 10/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 2003/079909 A3 | 3/2003 |
| WO | WO 03/030743 A2 | 4/2003 |
| WO | WO 03/037193 A1 | 5/2003 |
| WO | WO 2003/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 2003/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 2003/094746 A1 | 11/2003 |
| WO | WO 2003/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/014238 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/050971 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |
| WO | WO 2005/044078 A2 | 5/2005 |
| WO | WO 2005/048809 A1 | 6/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/087128 A1 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A1 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/049852 A2 | 5/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A2 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/059233 A2 | 5/2007 |
| WO | WO 2007/074430 A1 | 7/2007 |
| WO | WO 2007/089603 A2 | 8/2007 |
| WO | WO 2007/098220 A2 | 8/2007 |
| WO | WO 2007/121579 A1 | 11/2007 |
| WO | WO 2007/129121 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/146987 A2 | 12/2007 |
| WO | WO 2007/147439 A1 | 12/2007 |
| WO | WO 2008/020964 A2 | 2/2008 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/101228 A2 | 8/2008 |
| WO | WO 2008/103797 A2 | 8/2008 |
| WO | WO 2008/109125 A1 | 9/2008 |
| WO | WO 2008/112912 A2 | 9/2008 |
| WO | WO 2008/124748 A1 | 10/2008 |
| WO | WO 2009/005969 A2 | 1/2009 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/067649 A2 | 5/2009 |
| WO | WO 2009/091497 A2 | 7/2009 |
| WO | WO 2009/120944 A2 | 10/2009 |
| WO | WO 2009/137761 A2 | 11/2009 |
| WO | WO 2009/143092 A1 | 11/2009 |

(56) References Cited

FOREIGN PATENT DOCUMENTS

| WO | WO 2009/143331 A1 | 11/2009 |
|---|---|---|
| WO | WO 2009/150650 A2 | 12/2009 |
| WO | WO 2009/152307 A1 | 12/2009 |
| WO | WO 2010/028332 A2 | 3/2010 |
| WO | WO 2010/030434 A1 | 3/2010 |
| WO | WO 2010/045425 A1 | 4/2010 |
| WO | WO 2010/050771 A2 | 5/2010 |
| WO | WO 2010/054404 A1 | 5/2010 |
| WO | WO 2010/056714 A1 | 5/2010 |
| WO | WO 2010/063795 A1 | 6/2010 |
| WO | WO 2010/090940 A1 | 8/2010 |
| WO | WO 2010/093333 A1 | 8/2010 |
| WO | WO 2010/098871 A2 | 9/2010 |
| WO | WO 2011/008672 A2 | 1/2011 |
| WO | WO 2011/013103 A1 | 2/2011 |
| WO | WO 2011/044343 A2 | 4/2011 |
| WO | WO 2011/060311 A2 | 5/2011 |
| WO | WO 2012/006306 A2 | 1/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044597 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/044853 A1 | 4/2012 |
| WO | WO 2012/058213 A2 | 5/2012 |
| WO | WO 2012/068156 A2 | 5/2012 |
| WO | WO 2012/127462 A1 | 9/2012 |
| WO | WO 2012/135705 A1 | 10/2012 |
| WO | WO 2012/143913 A2 | 10/2012 |
| WO | WO 2012/148667 A2 | 11/2012 |
| WO | WO 2012/148703 A2 | 11/2012 |
| WO | WO 2012/160163 A1 | 11/2012 |
| WO | WO 2013/009699 A2 | 1/2013 |
| WO | WO 2013/036409 A1 | 3/2013 |
| WO | WO 2013/043707 A2 | 3/2013 |
| WO | WO 2013/043717 A1 | 3/2013 |
| WO | WO 2013/043721 A2 | 3/2013 |
| WO | WO 2013/062978 A2 | 5/2013 |
| WO | WO 2013/148762 A2 | 10/2013 |
| WO | WO 2013/167427 A1 | 11/2013 |
| WO | WO 2014/004199 A1 | 1/2014 |

OTHER PUBLICATIONS

U.S. Appl. No. 12/031,573, filed Feb. 14, 2008.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).
Datasheet for Panasonic TK Relays Ultra Low Profile 2 a Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
Peppas, Editor "Hydrogels in Medicine and Pharmacy," vol. I, Fundamentals, CRC Press, 1986.
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Seils et al., Covidien Summary: Clinical Study "UCONN Biodynamics: Final Report on Results," (2 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien brochure "iDrive™ Ultra Powered Stapling System," (6 pages).

(56) References Cited

OTHER PUBLICATIONS

"Indian Standard: Automotive Vehicles—Brakes and Braking Systems (IS 11852-1:2001)", Mar. 1, 2001.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.

* cited by examiner

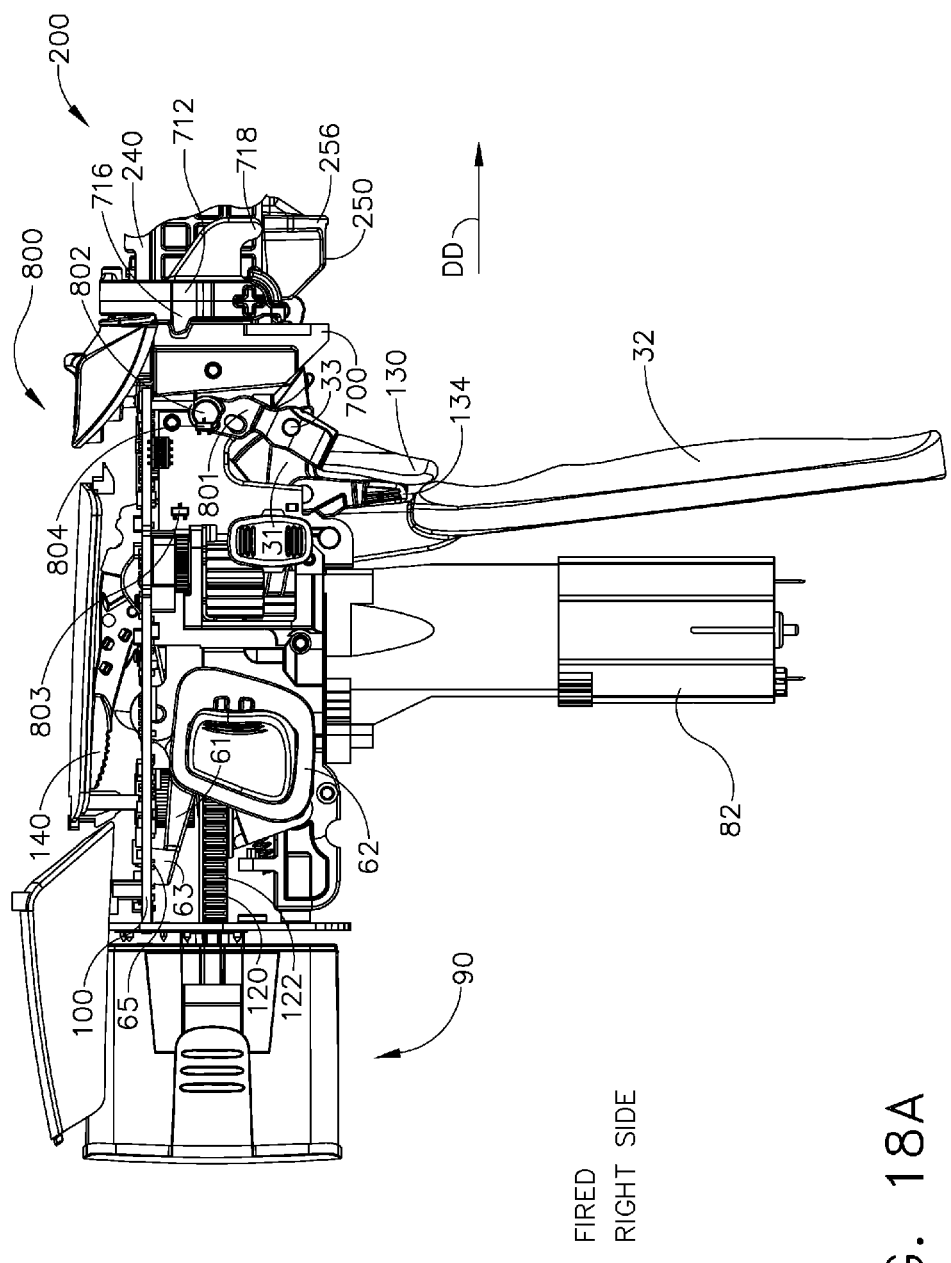

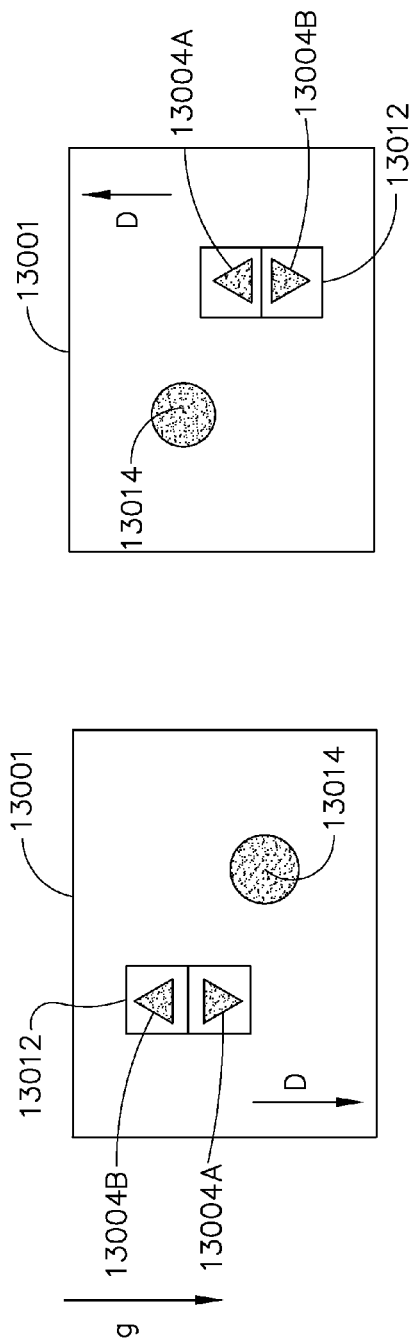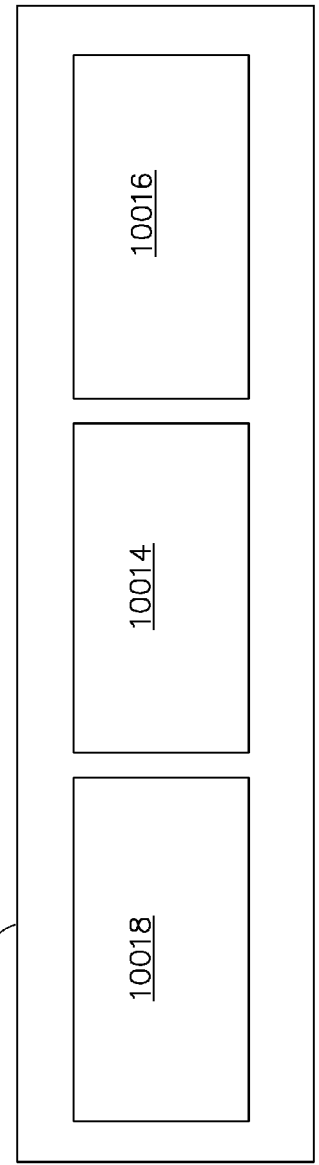

SURGICAL INSTRUMENT COMPRISING A SENSOR SYSTEM

BACKGROUND

The present invention relates to surgical instruments and, in various circumstances, to surgical stapling and cutting instruments and staple cartridges therefor that are designed to staple and cut tissue.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 18A is a right side elevational view of the interchangeable shaft assembly of FIG. 11 operably coupled to a portion of the surgical instrument of FIG. 1 illustrated with the closure trigger thereof in an actuated position and the firing trigger thereof in an actuated position;

FIG. 33, which is divided into

FIG. 71, which is divided into

FIG. 72, which is divided into

FIG. 73, which is divided into

FIG. 78, which is divided into

FIG. 100A is a side view of the handle assembly of FIG. 96 in an upright position;

FIG. 100B is a side view of the handle assembly of FIG. 96 in an upside down position;

FIG. 101 is a schematic illustration of the display of FIG. 96 showing a plurality of icons;

FIG. 110 is an exploded, perspective view of the modular surgical instrument of FIG. 109;

FIG. 111 is a schematic depicting the control systems of a modular surgical system according to various embodiments of the present disclosure;

FIG. 112 is a flowchart depicting a method for updating a component of a modular surgical system according to various embodiments of the present disclosure;

FIG. 113 is a flowchart depicting a method for updating a component of a modular surgical system according to various embodiments of the present disclosure;

Figure 114A:
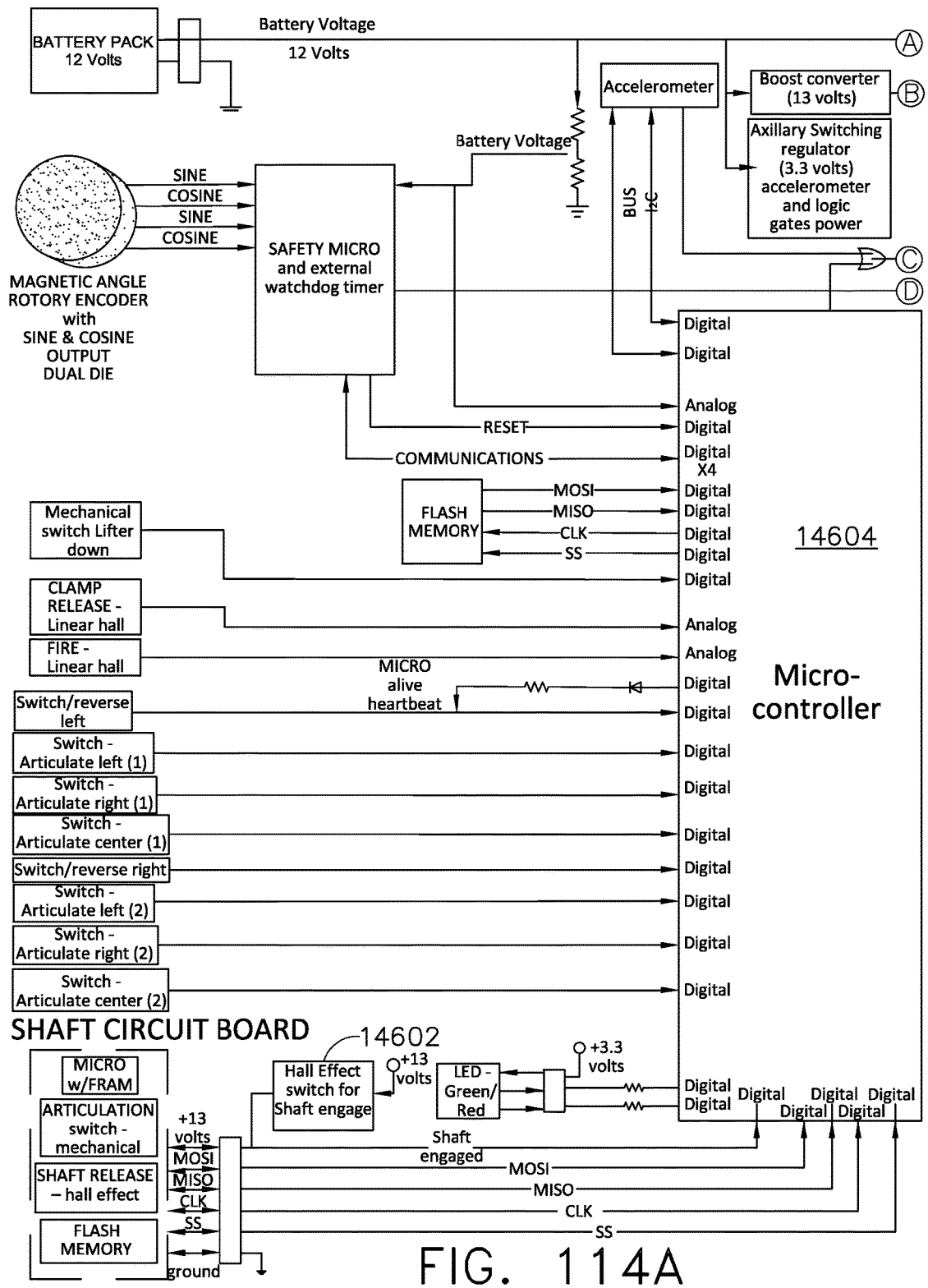
Figure 114B:
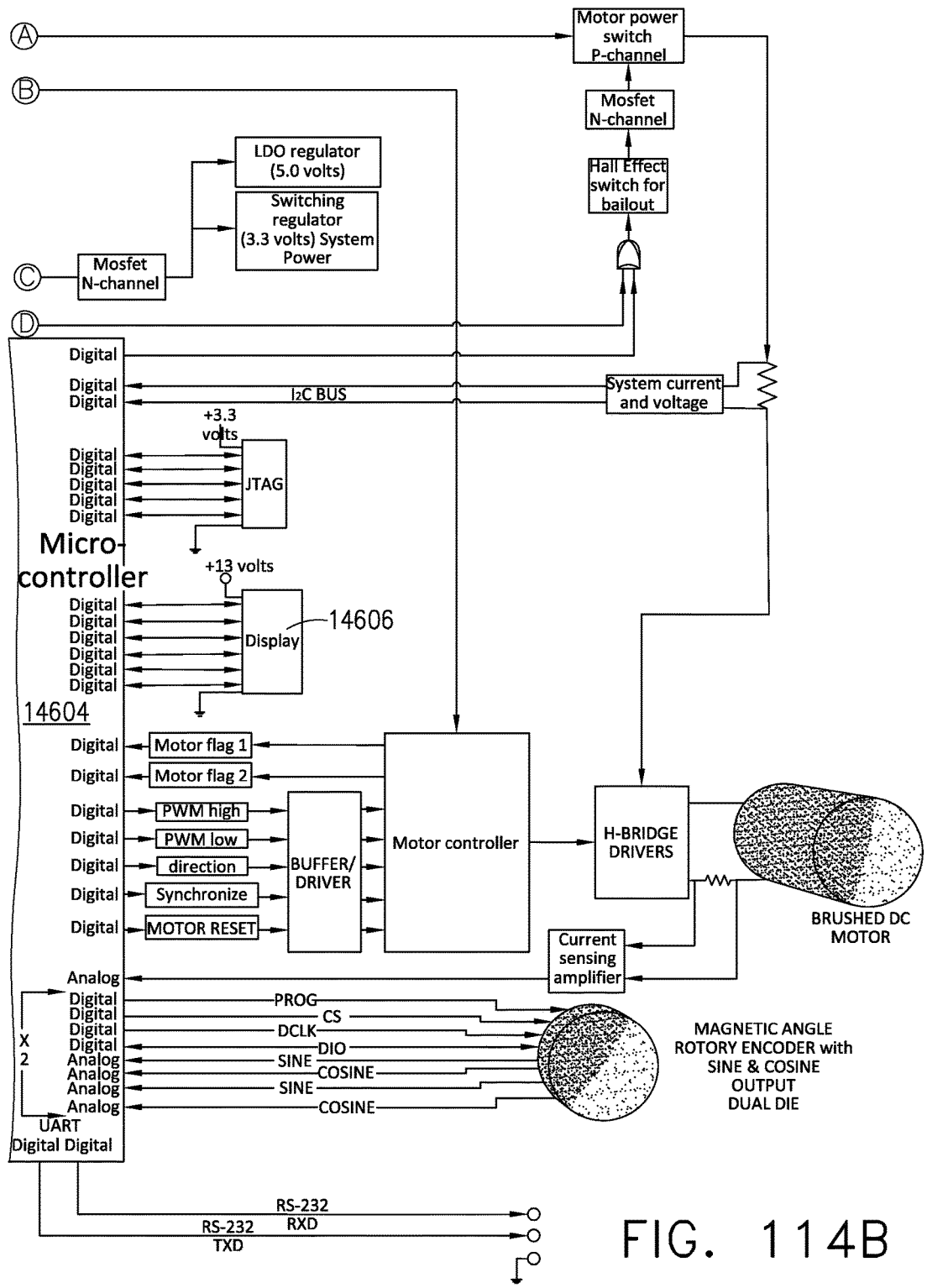
Figure 115A:
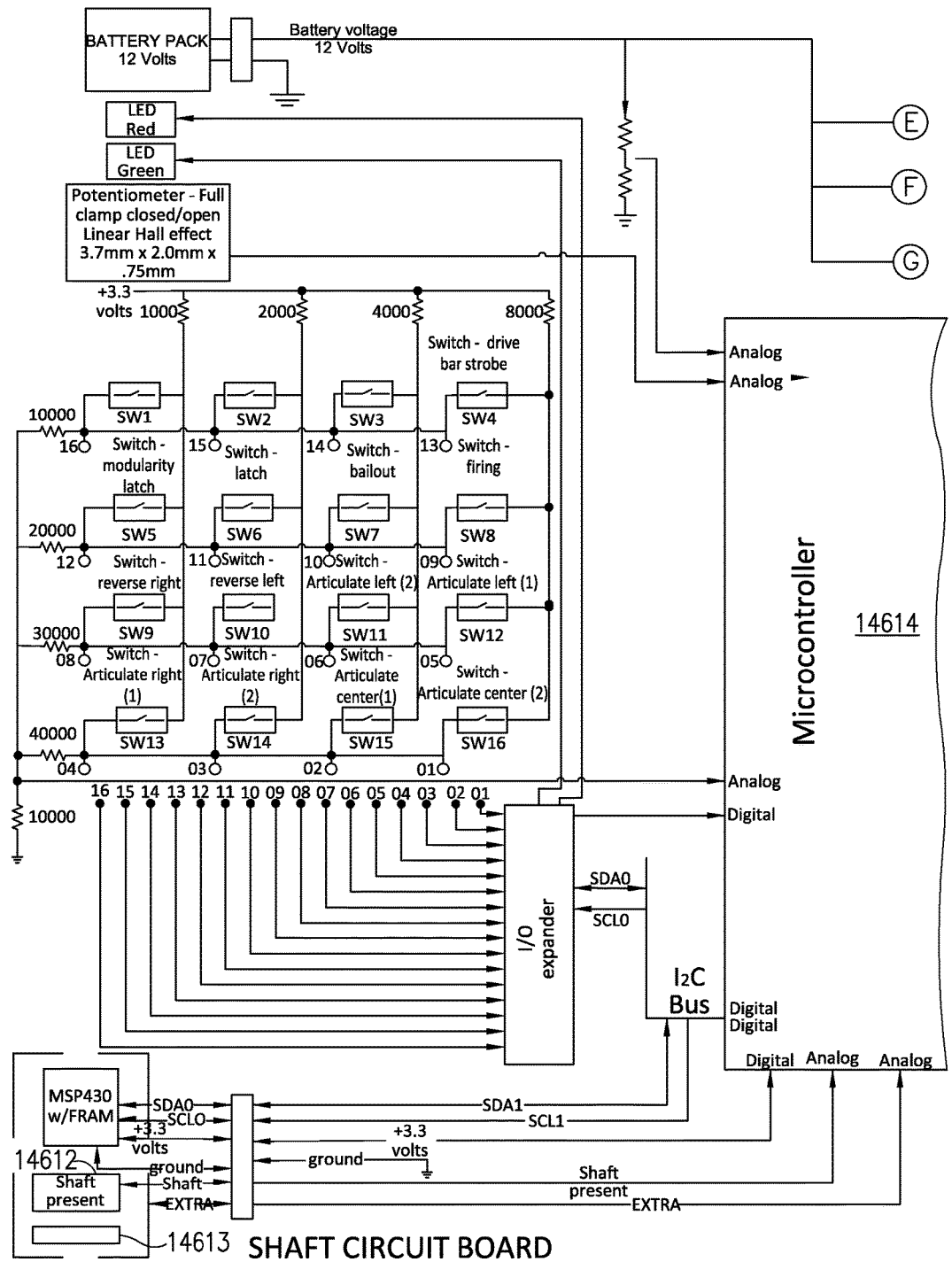
Figure 115B:
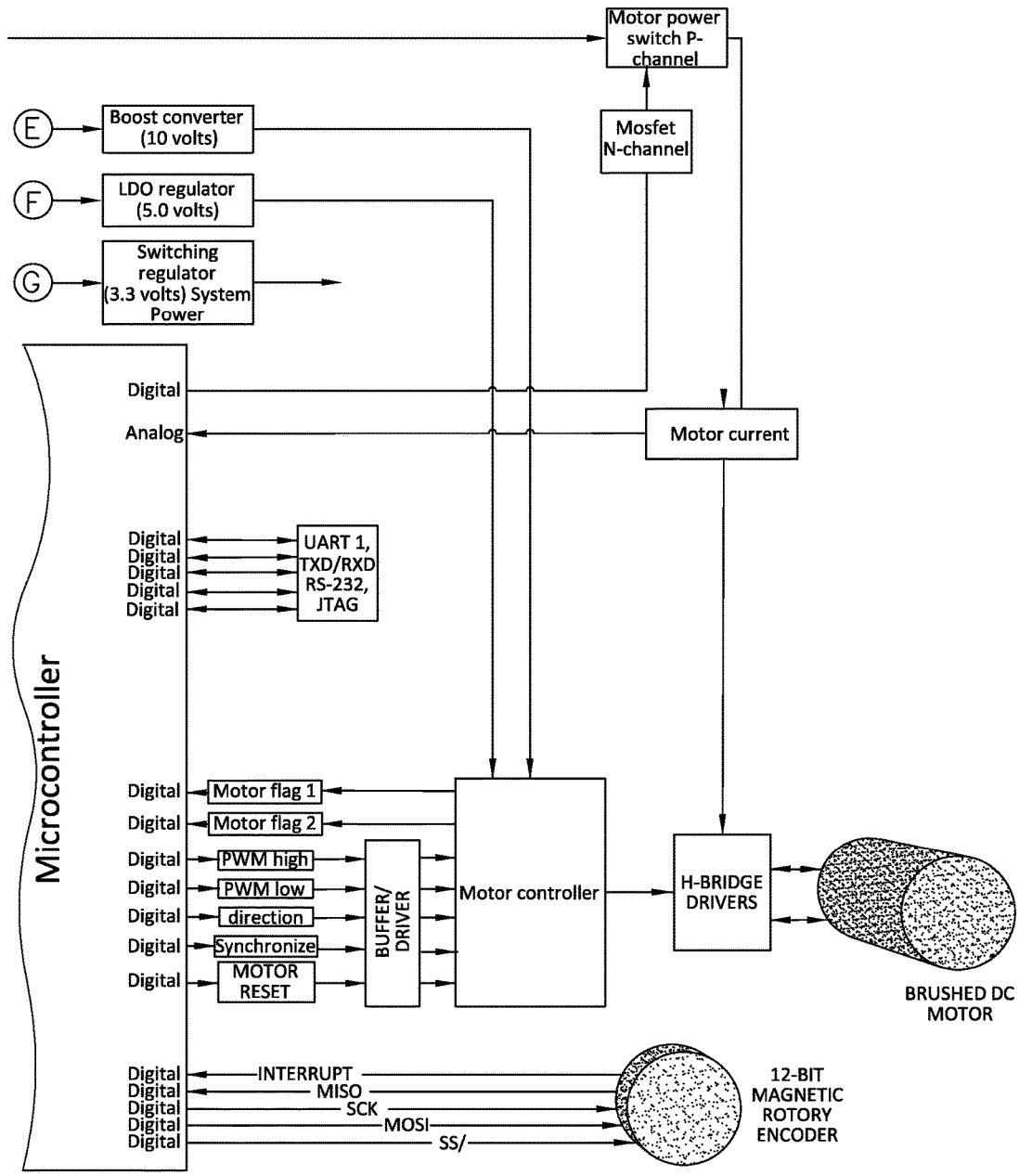
Figure 116:
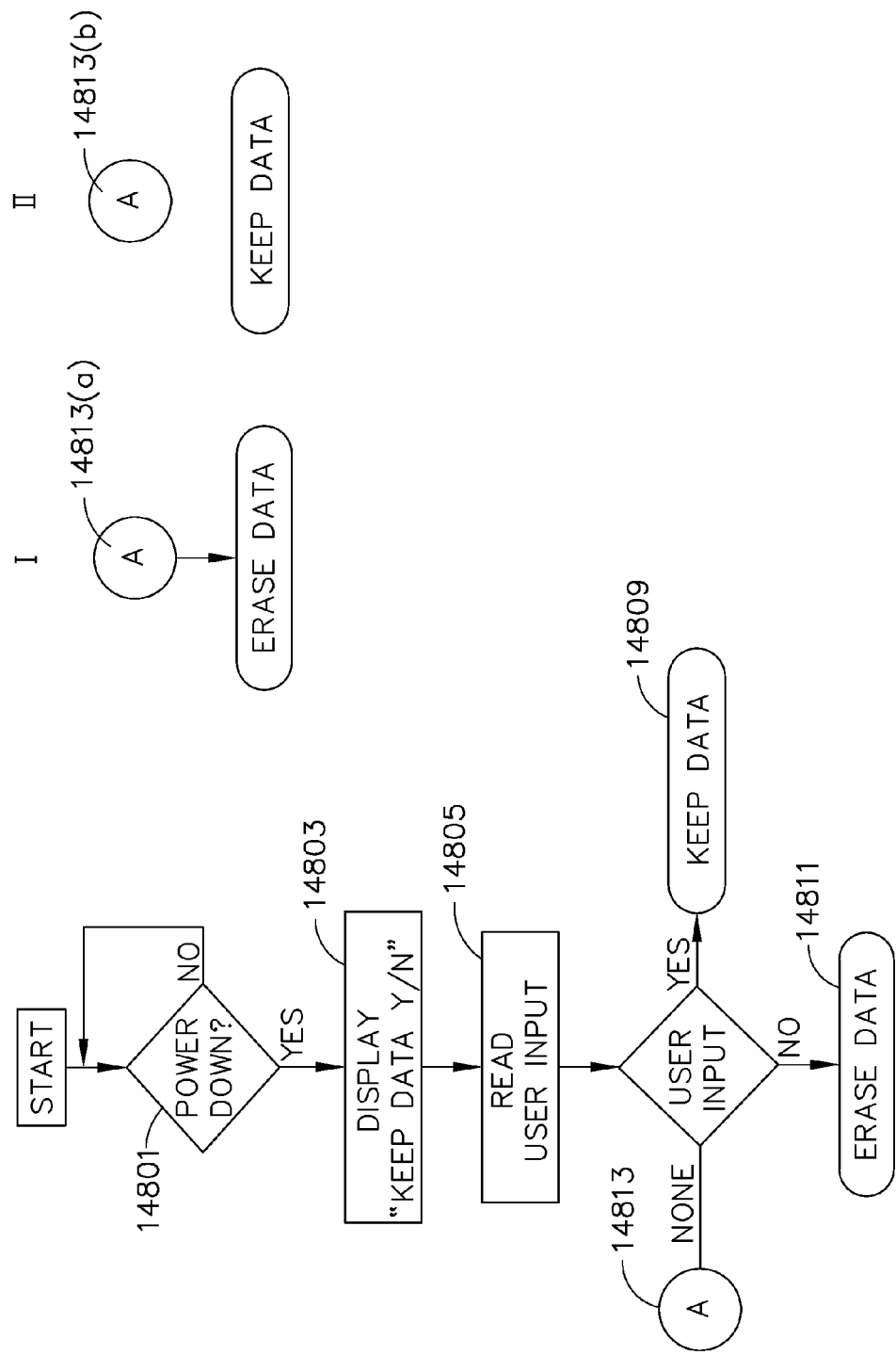
Figure 117:
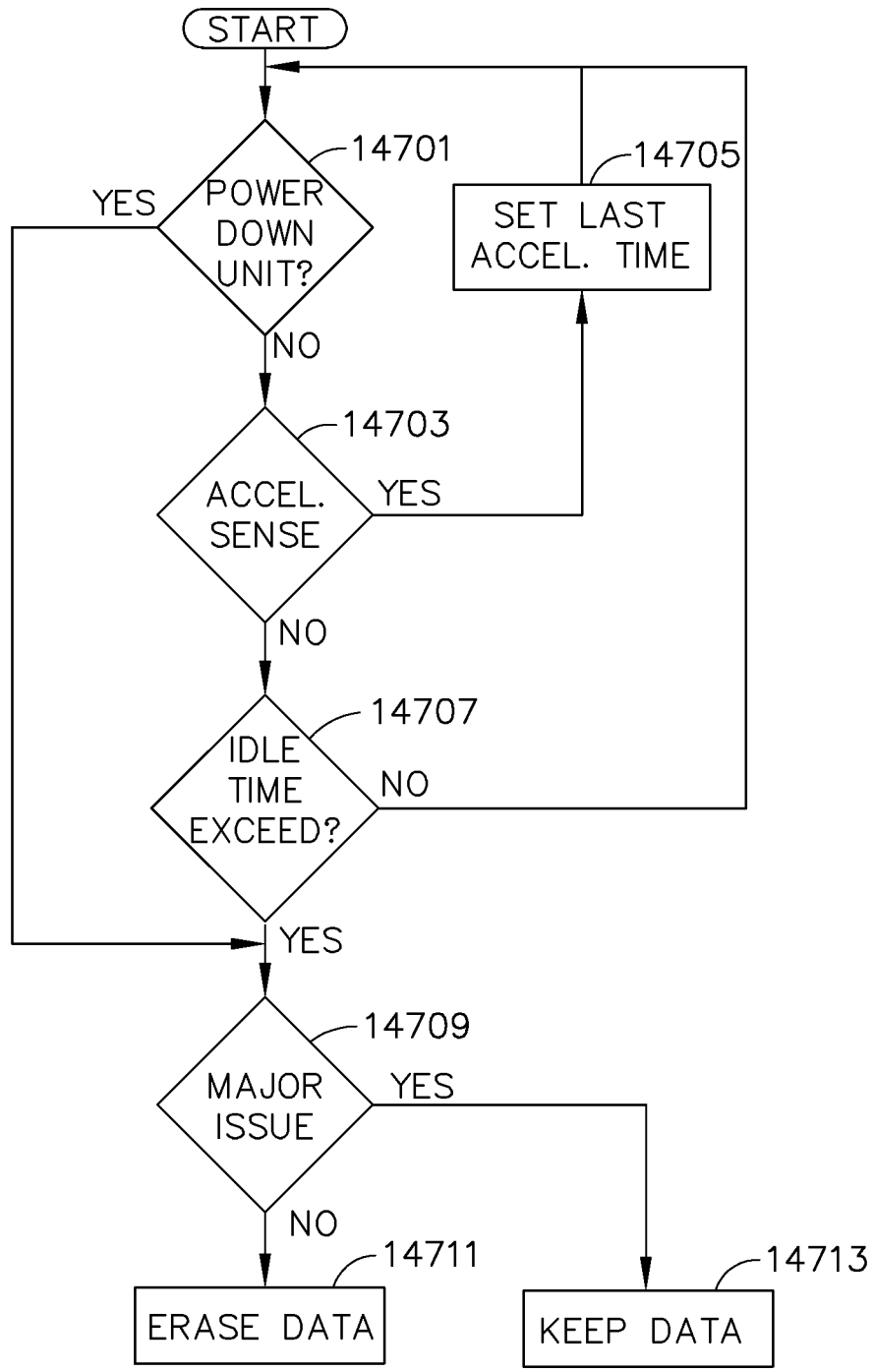
Figure 118:
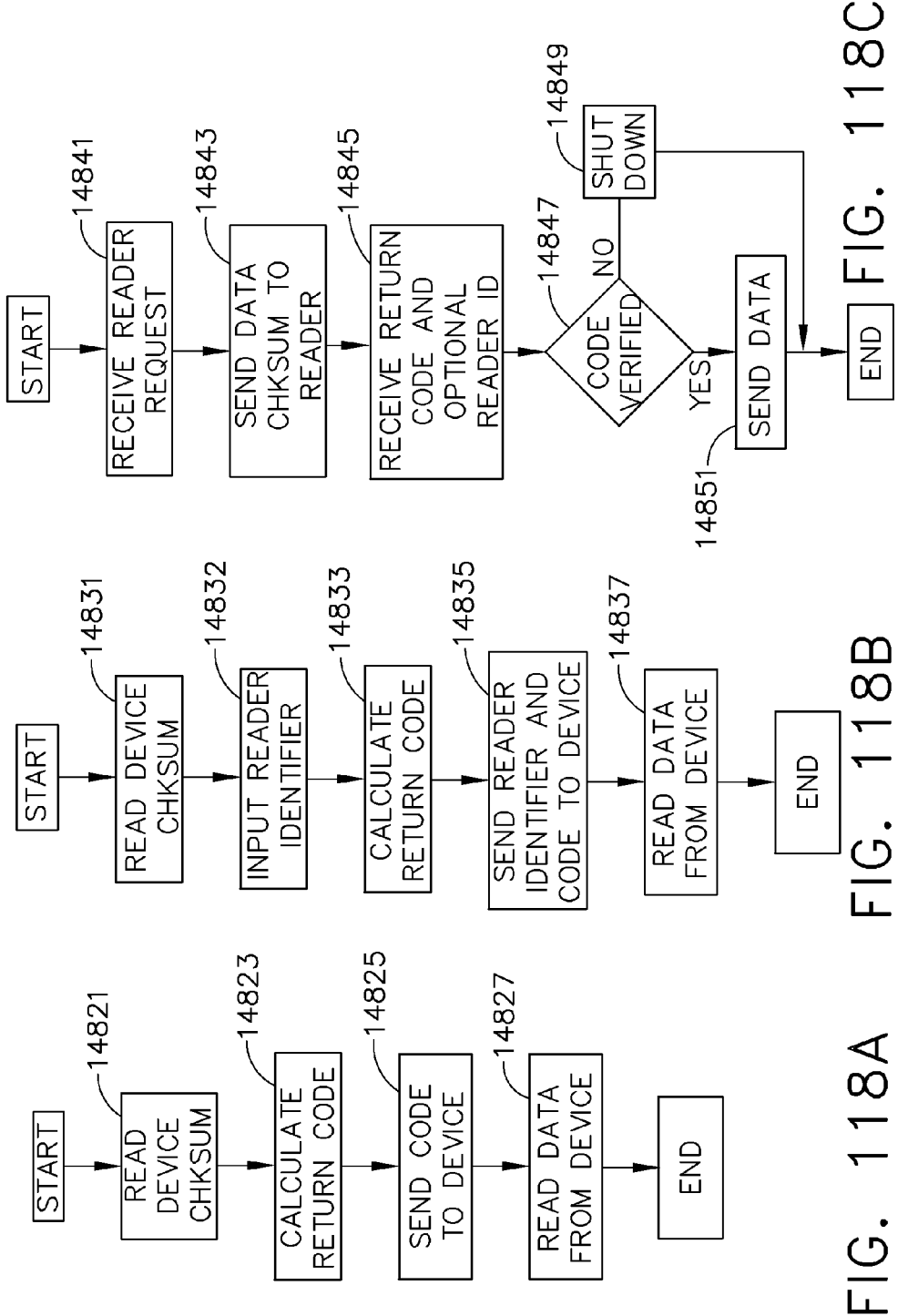
Figure 119:
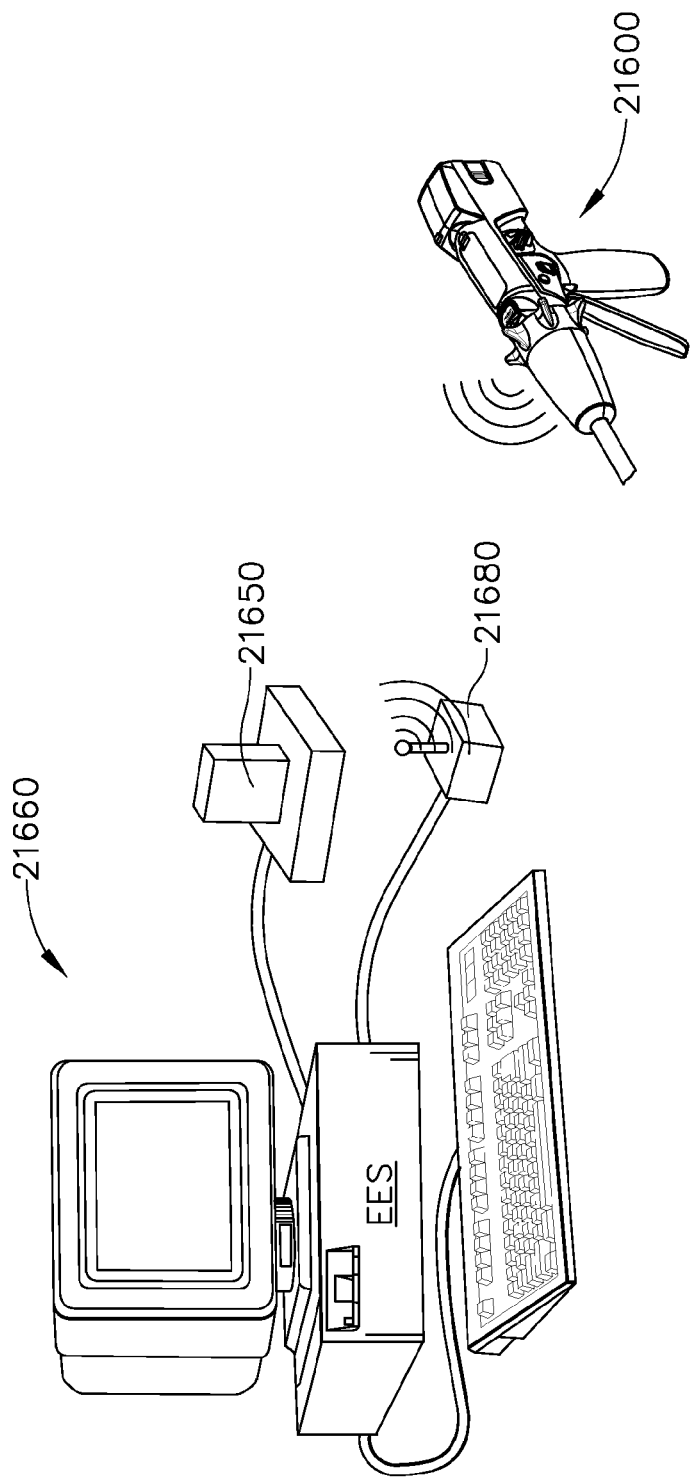
Figure 120:
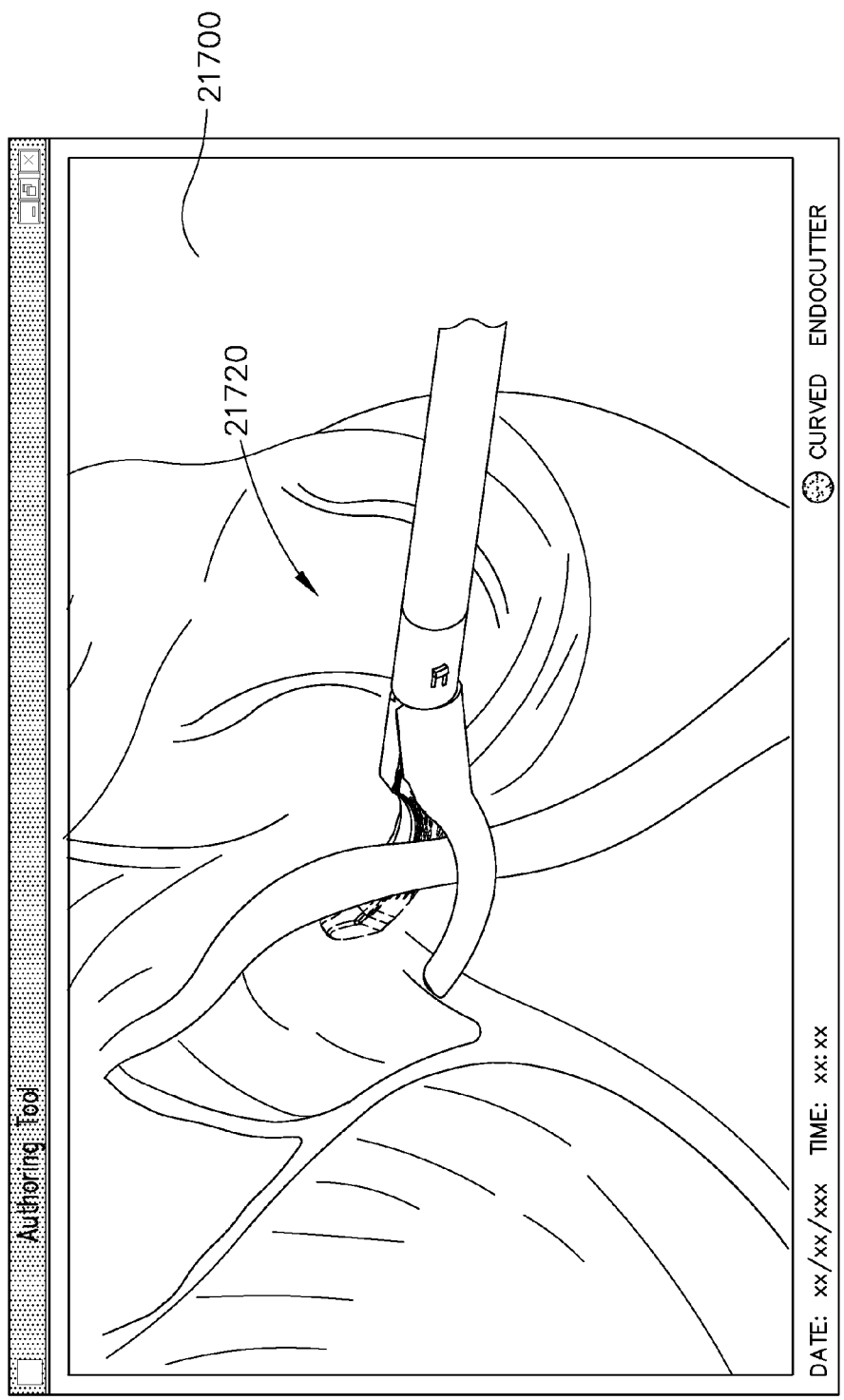
Figure 121:
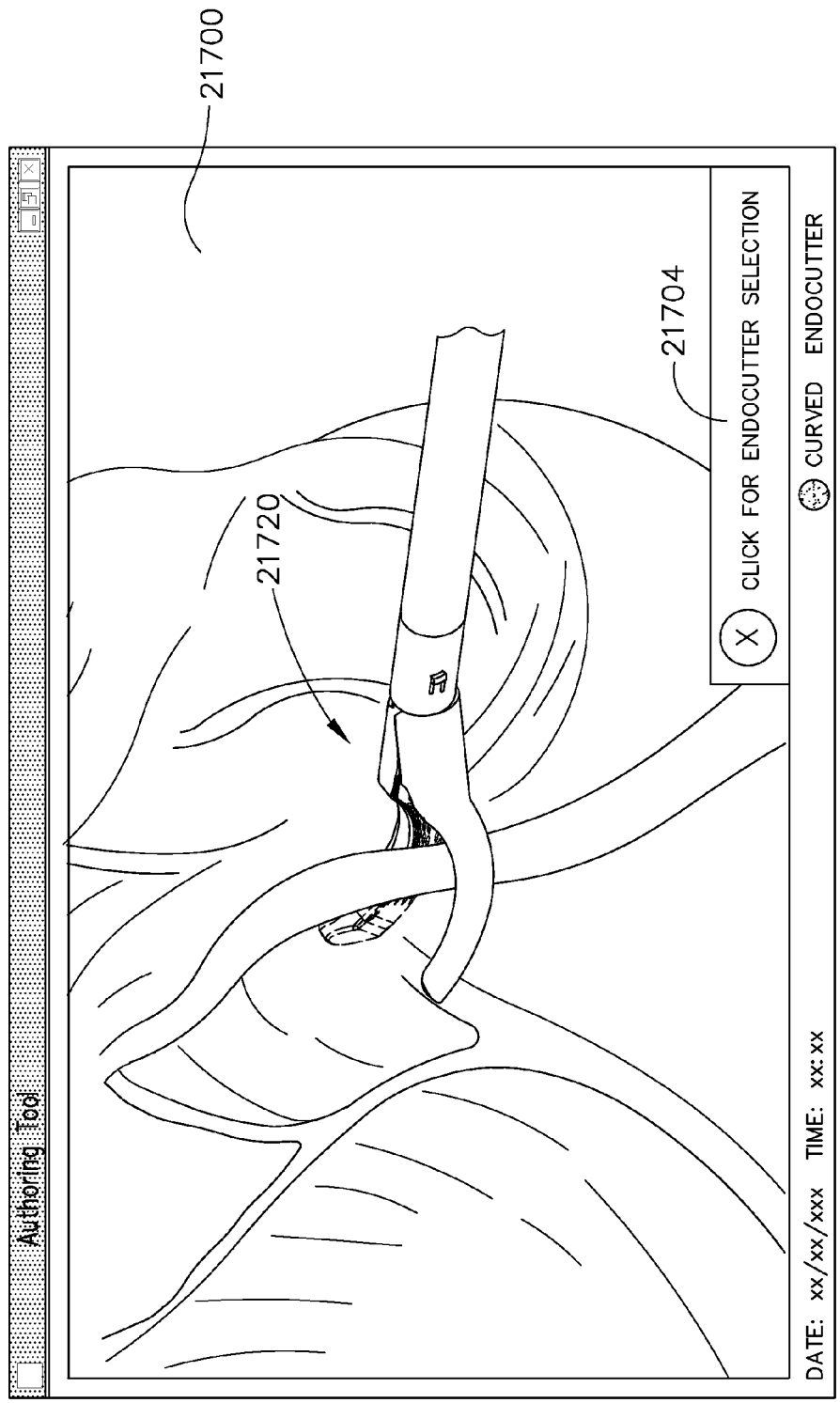
Figure 122:
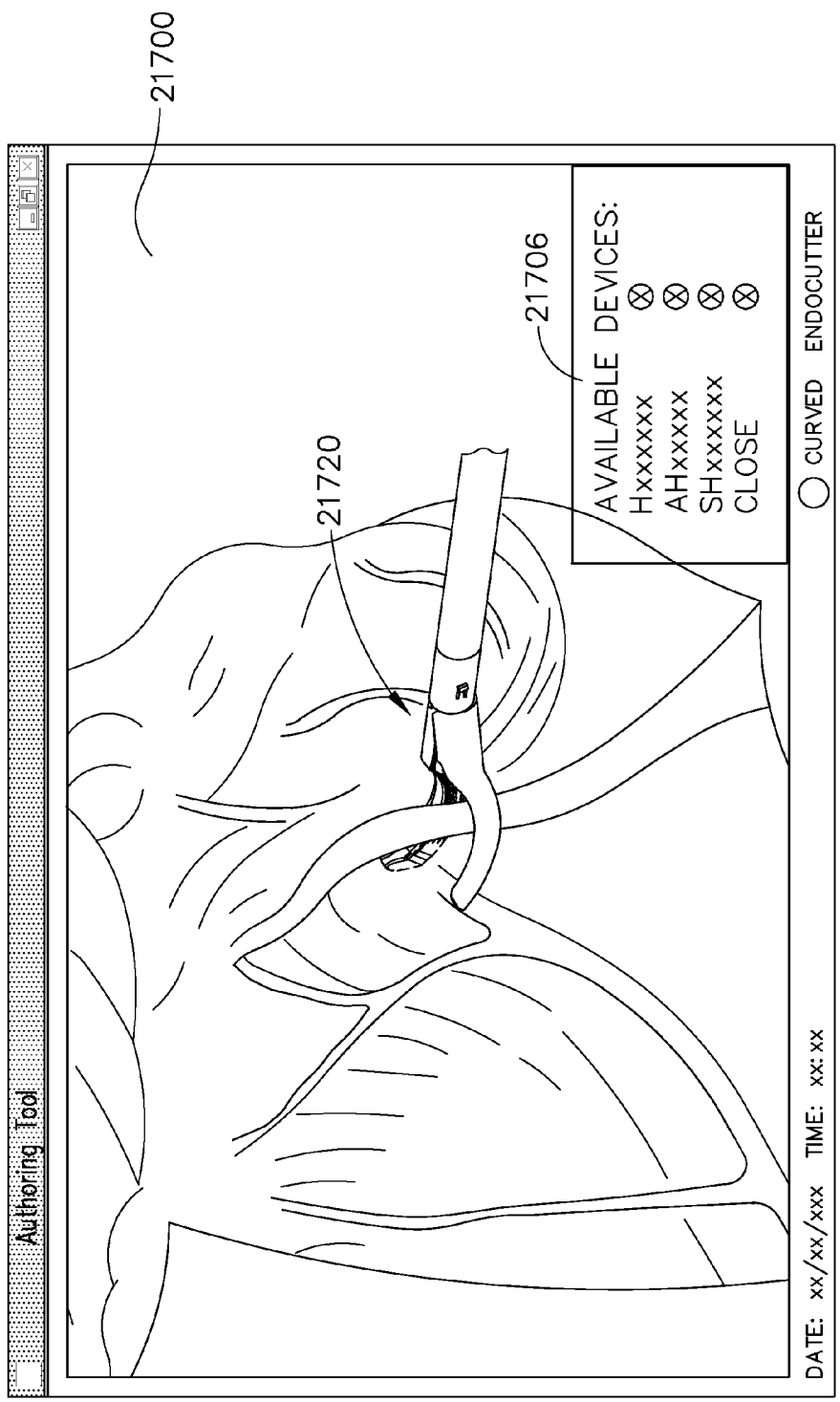

FIGS. 114(A) and 114(B) are schematics depicting a control circuit according to various embodiments of the present disclosure;

FIGS. 115(A) and 115(B) are schematics depicting a control circuit according to various embodiments of the present disclosure;

FIG. 116 is a flow chart depicting a method for processing data recorded by a surgical instrument according to various embodiments of the present disclosure;

FIG. 117 is a flow chart depicting a method for processing data recorded by a surgical instrument according to various embodiments of the present disclosure;

FIGS. 118(A)-118(C) are flow charts depicting various methods for processing data recorded by a surgical instrument according to various embodiments of the present disclosure;

FIG. 119 is a schematic depicting a surgical system having wireless communication capabilities according to various embodiments of the present disclosure;

FIG. 120 is an elevation view of an external screen depicting an end effector at a surgical site according to various embodiments of the present disclosure;

FIG. 121 is an elevation view of the external screen of FIG. 120 depicting a notification according to various embodiments of the present disclosure; and FIG. 122 is an elevation view of the external screen of FIG. 120 depicting a selection menu according to various embodiments of the present disclosure.

DETAILED DESCRIPTION

Applicant of the present application owns the following patent applications that were filed on Mar. 1, 2013 and which are each herein incorporated by reference in their respective entireties:

U.S. patent application Ser. No. 13/782,295, entitled ARTICULATABLE SURGICAL INSTRUMENTS WITH CONDUCTIVE PATHWAYS FOR SIGNAL COMMUNICATION;

U.S. patent application Ser. No. 13/782,323, entitled ROTARY POWERED ARTICULATION JOINTS FOR SURGICAL INSTRUMENTS;

U.S. patent application Ser. No. 13/782,338, entitled THUMBWHEEL SWITCH ARRANGEMENTS FOR SURGICAL INSTRUMENTS;

U.S. patent application Ser. No. 13/782,499, entitled ELECTROMECHANICAL SURGICAL DEVICE WITH SIGNAL RELAY ARRANGEMENT;

U.S. patent application Ser. No. 13/782,460, entitled MULTIPLE PROCESSOR MOTOR CONTROL FOR MODULAR SURGICAL INSTRUMENTS;

U.S. patent application Ser. No. 13/782,358, entitled JOYSTICK SWITCH ASSEMBLIES FOR SURGICAL INSTRUMENTS;

U.S. patent application Ser. No. 13/782,481, entitled SENSOR STRAIGHTENED END EFFECTOR DURING REMOVAL THROUGH TROCAR;

U.S. patent application Ser. No. 13/782,518, entitled CONTROL METHODS FOR SURGICAL INSTRUMENTS WITH REMOVABLE IMPLEMENT PORTIONS;

U.S. patent application Ser. No. 13/782,375, entitled ROTARY POWERED SURGICAL INSTRUMENTS WITH MULTIPLE DEGREES OF FREEDOM; and U.S. patent application Ser. No. 13/782,536, entitled SURGICAL INSTRUMENT SOFT STOP are hereby incorporated by reference in their entireties.

Applicant of the present application also owns the following patent applications that were filed on Mar. 14, 2013 and which are each herein incorporated by reference in their respective entireties:

U.S. patent application Ser. No. 13/803,097, entitled ARTICULATABLE SURGICAL INSTRUMENT COMPRISING A FIRING DRIVE;

U.S. patent application Ser. No. 13/803,193, entitled CONTROL ARRANGEMENTS FOR A DRIVE MEMBER OF A SURGICAL INSTRUMENT;

U.S. patent application Ser. No. 13/803,053, entitled INTERCHANGEABLE SHAFT ASSEMBLIES FOR USE WITH A SURGICAL INSTRUMENT;

U.S. patent application Ser. No. 13/803,086, entitled ARTICULATABLE SURGICAL INSTRUMENT COMPRISING AN ARTICULATION LOCK;

U.S. patent application Ser. No. 13/803,210, entitled SENSOR ARRANGEMENTS FOR ABSOLUTE POSITIONING SYSTEM FOR SURGICAL INSTRUMENTS;

U.S. patent application Ser. No. 13/803,148, entitled MULTI-FUNCTION MOTOR FOR A SURGICAL INSTRUMENT;

U.S. patent application Ser. No. 13/803,066, entitled DRIVE SYSTEM LOCKOUT ARRANGEMENTS FOR MODULAR SURGICAL INSTRUMENTS;

U.S. patent application Ser. No. 13/803,117, entitled ARTICULATION CONTROL SYSTEM FOR ARTICULATABLE SURGICAL INSTRUMENTS;

U.S. patent application Ser. No. 13/803,130, entitled DRIVE TRAIN CONTROL ARRANGEMENTS FOR MODULAR SURGICAL INSTRUMENTS; and U.S. patent application Ser. No. 13/803,159, entitled METHOD AND SYSTEM FOR OPERATING A SURGICAL INSTRUMENT.

Applicant of the present application also owns the following patent applications that were filed on Mar. 26, 2014 and are each herein incorporated by reference in their respective entireties:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Patent Application Publication No. 2015/0272581;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Patent Application Publication No. 2015/0272574;

U.S. patent application Ser. No. 14/226,075, entitled MODULAR POWERED SURGICAL INSTRUMENT WITH DETACHABLE SHAFT ASSEMBLIES, now U.S. Patent Application Publication No. 2015/0272579;

U.S. patent application Ser. No. 14/226,093, entitled FEEDBACK ALGORITHMS FOR MANUAL BAILOUT SYSTEMS FOR SURGICAL INSTRUMENTS, U.S. Patent Application Publication No. 2015/0272569;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Patent Application Publication No. 2015/0272578;

U.S. patent application Ser. No. 14/226,097, entitled SURGICAL INSTRUMENT COMPRISING INTERACTIVE SYSTEMS, now U.S. Patent Application Publication No. 2015/0272570;

U.S. patent application Ser. No. 14/226,126, entitled INTERFACE SYSTEMS FOR USE WITH SURGICAL INSTRUMENTS, now U.S. Patent Application Publication No. 2015/0272572;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Patent Application Publication No. 2015/0277471;

U.S. patent application Ser. No. 14/226,076, entitled POWER MANAGEMENT THROUGH SEGMENTED CIRCUIT AND VARIABLE VOLTAGE PROTECTION, now U.S. Patent Application Publication No. 2015/0280424;

U.S. patent application Ser. No. 14/226,111, entitled SURGICAL STAPLING INSTRUMENT SYSTEM, now U.S. Patent Application Publication No. 2015/0272583; and U.S. patent application Ser. No. 14/226,125, entitled SURGICAL INSTRUMENT COMPRISING A ROTATABLE SHAFT, now U.S. Patent Application Publication No. 2015/0280384.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

FIGS. 1-6 depict a motor-driven surgical cutting and fastening instrument 10 that may or may not be reused. In the illustrated embodiment, the instrument 10 includes a housing 12 that comprises a handle 14 that is configured to be grasped, manipulated and actuated by the clinician. The housing 12 is configured for operable attachment to an interchangeable shaft assembly 200 that has a surgical end effector 300 operably coupled thereto that is configured to perform one or more surgical tasks or procedures. As the present Detailed Description proceeds, it will be understood that the various unique and novel arrangements of the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. US 2012/0298719. U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. US 2012/0298719, is incorporated by reference herein in its entirety.

Figure 1:
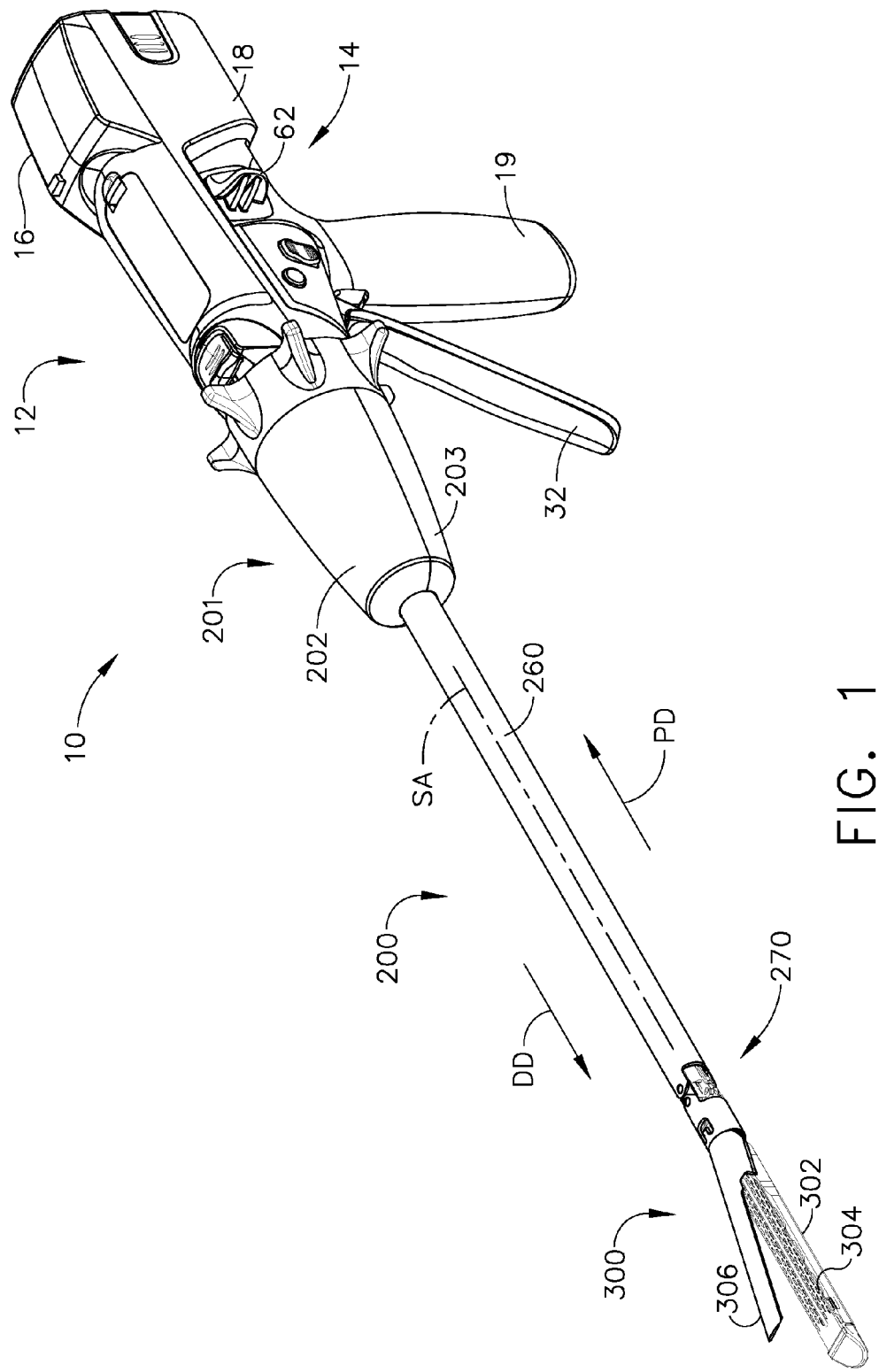
FIG. 1 is a perspective view of a surgical instrument that has an interchangeable shaft assembly operably coupled thereto.
Figure 2:
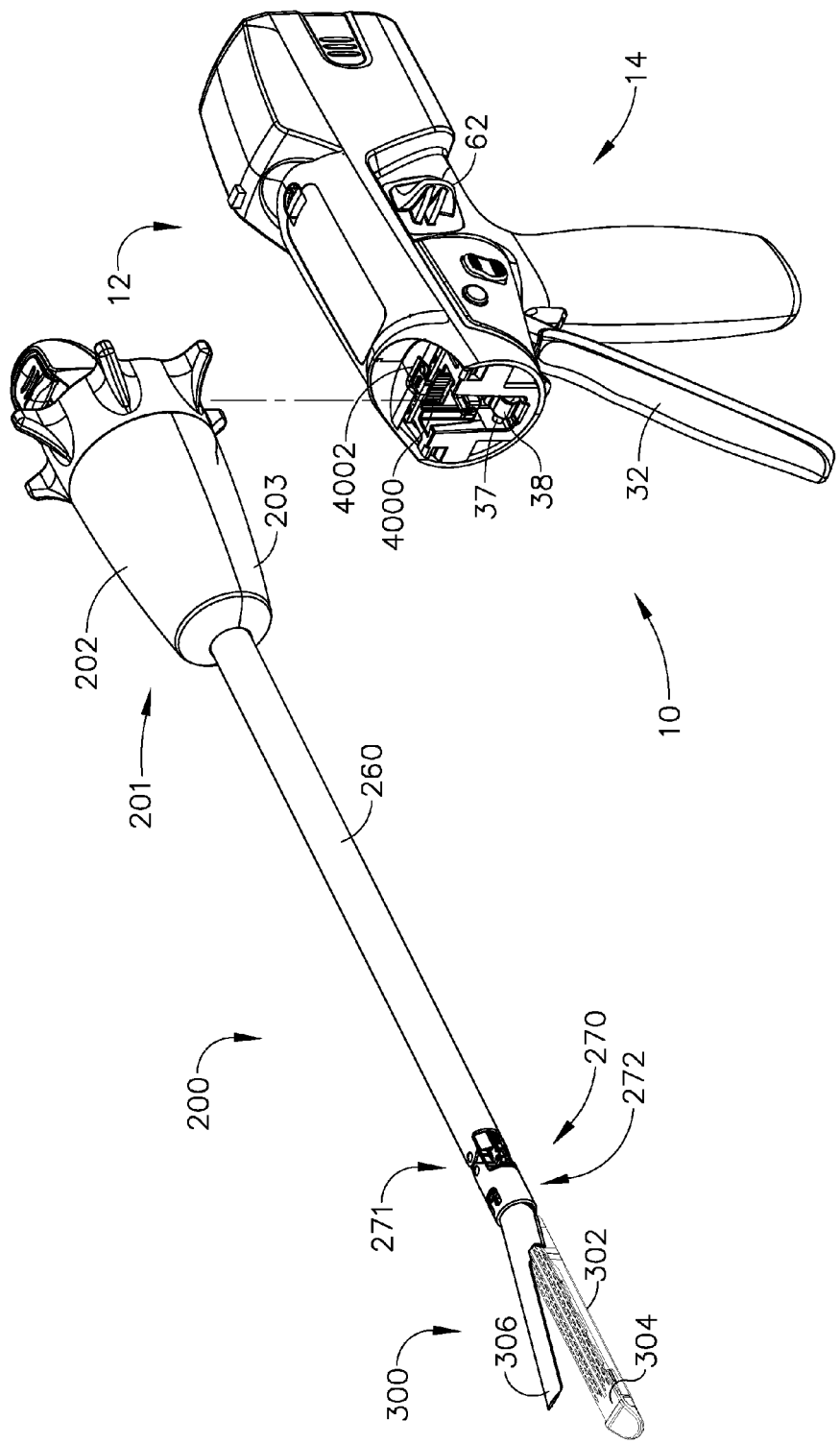
FIG. 2 is an exploded assembly view of the interchangeable shaft assembly and surgical instrument of FIG. 1.
Figure 3:
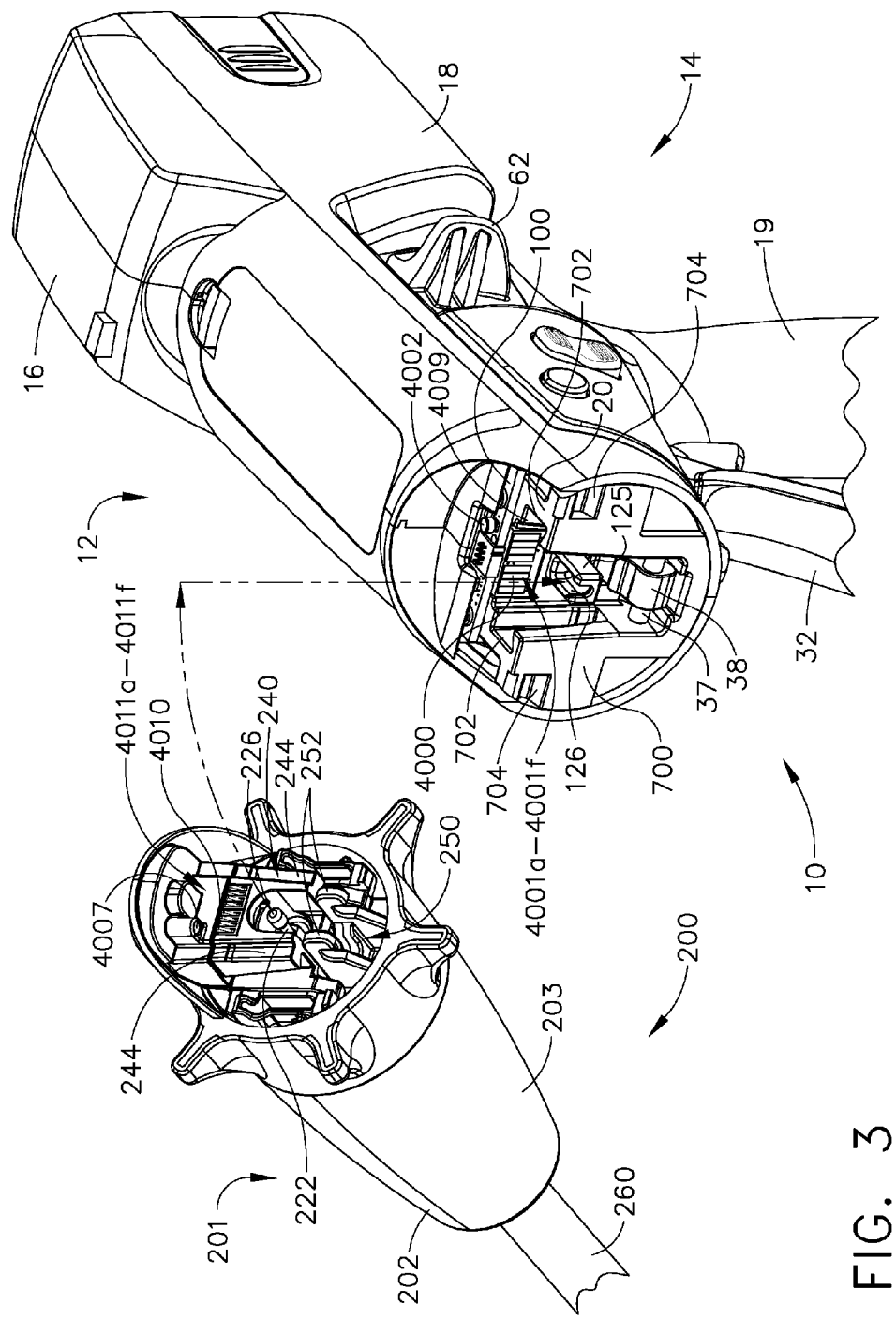
FIG. 3 is another exploded assembly view showing portions of the interchangeable shaft assembly and surgical instrument of FIGS. 1 and 2.

The housing 12 depicted in FIGS. 1-3 is shown in connection with an interchangeable shaft assembly 200 that includes an end effector 300 that comprises a surgical cutting and fastening device that is configured to operably support a surgical staple cartridge 304 therein. The housing 12 may be configured for use in connection with interchangeable shaft assemblies that include end effectors that are adapted to support different sizes and types of staple cartridges, have different shaft lengths, sizes, and types, etc. In addition, the housing 12 may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

Figure 4:
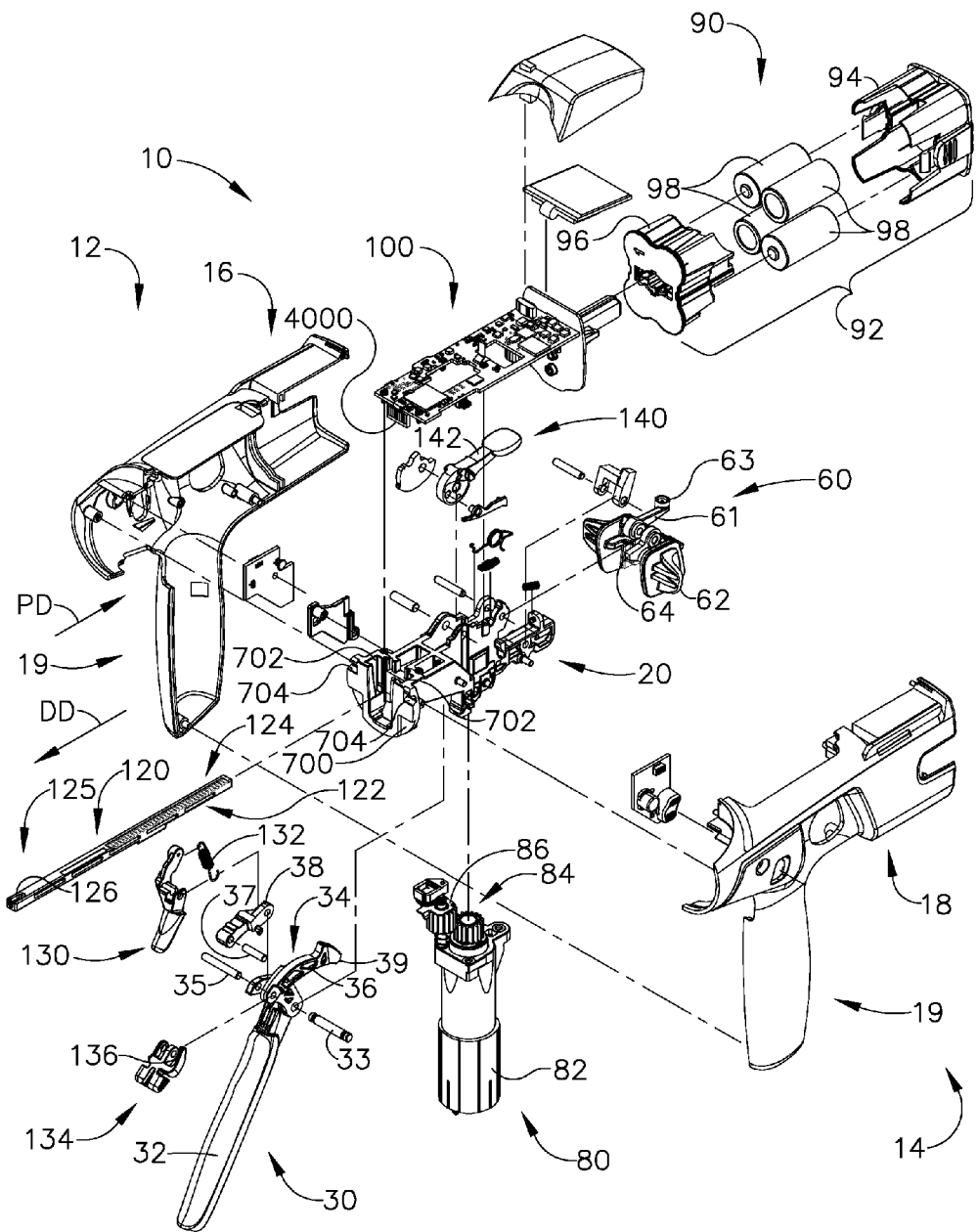
FIG. 4 is an exploded assembly view of a portion of the surgical instrument of FIGS. 1-3.
Figure 5:
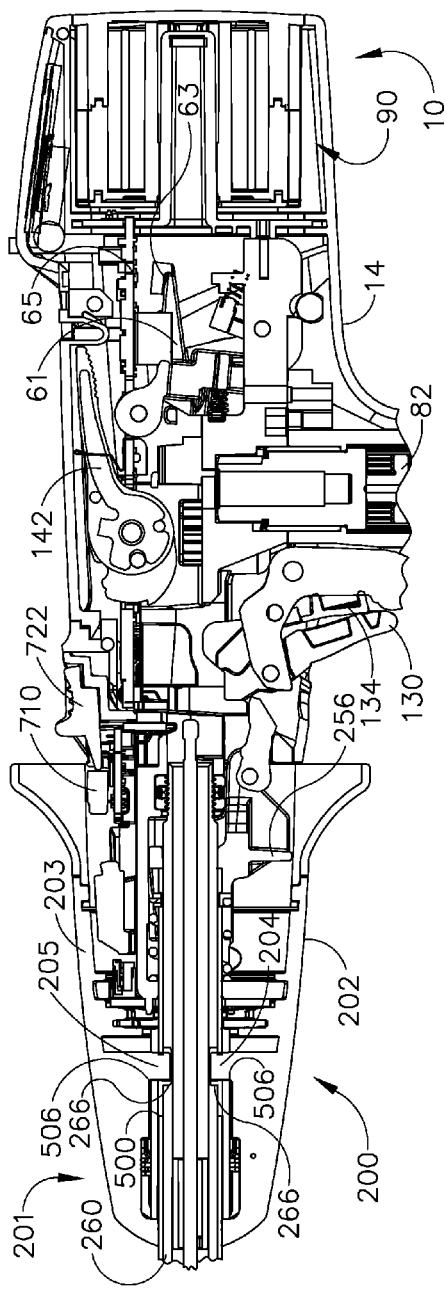
FIG. 5 is a cross-sectional side view of a portion of the surgical instrument of FIG. 4 with the firing trigger in a fully actuated position.
Figure 6:
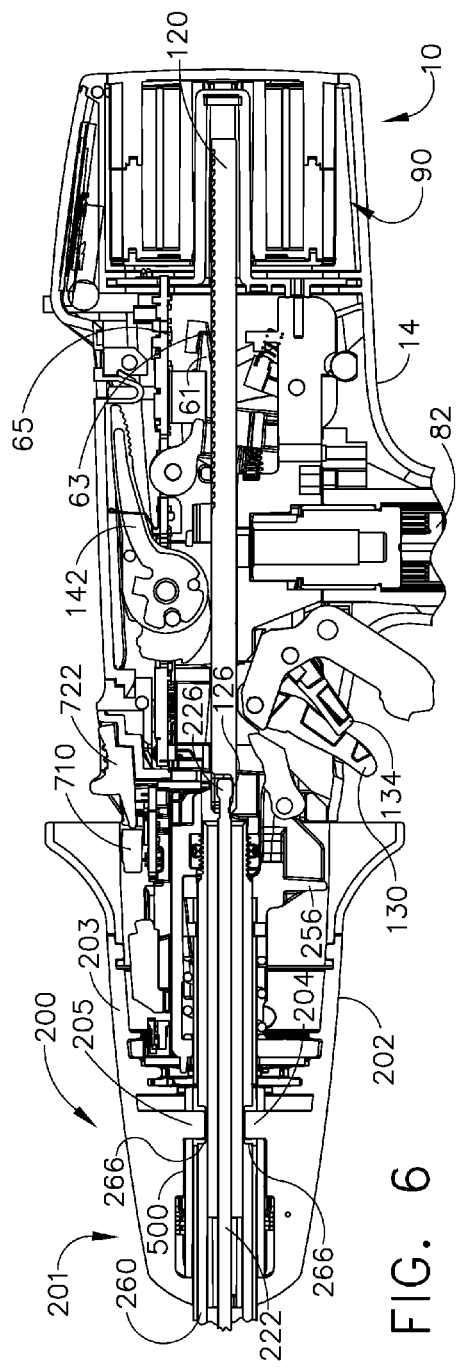
FIG. 6 is another cross-sectional view of a portion of the surgical instrument of FIG. 5 with the firing trigger in an unactuated position.

FIG. 1 illustrates the surgical instrument 10 with an interchangeable shaft assembly 200 operably coupled thereto. FIGS. 2 and 3 illustrate attachment of the interchangeable shaft assembly 200 to the housing 12 or handle 14. As can be seen in FIG. 4, the handle 14 may comprise a pair of interconnectable handle housing segments 16 and 18 that may be interconnected by screws, snap features, adhesive, etc. In the illustrated arrangement, the handle housing segments 16, 18 cooperate to form a pistol grip portion 19 that can be gripped and manipulated by the clinician. As will be discussed in further detail below, the handle 14 operably supports a plurality of drive systems therein that are configured to generate and apply various control motions to corresponding portions of the interchangeable shaft assembly that is operably attached thereto.

Referring now to FIG. 4, the handle 14 may further include a frame 20 that operably supports a plurality of drive systems. For example, the frame 20 can operably support a "first" or closure drive system, generally designated as 30, which may be employed to apply closing and opening motions to the interchangeable shaft assembly 200 that is operably attached or coupled thereto. In at least one form, the closure drive system 30 may include an actuator in the form of a closure trigger 32 that is pivotally supported by the frame 20. More specifically, as illustrated in FIG. 4, the closure trigger 32 is pivotally coupled to the housing 14 by a pin 33. Such arrangement enables the closure trigger 32 to be manipulated by a clinician such that when the clinician grips the pistol grip portion 19 of the handle 14, the closure trigger 32 may be easily pivoted from a starting or "unactuated" position to an "actuated" position and more particularly to a fully compressed or fully actuated position. The closure trigger 32 may be biased into the unactuated position by spring or other biasing arrangement (not shown). In various forms, the closure drive system 30 further includes a closure linkage assembly 34 that is pivotally coupled to the closure trigger 32. As can be seen in FIG. 4, the closure linkage assembly 34 may include a first closure link 36 and a second closure link 38 that are pivotally coupled to the closure trigger 32 by a pin 35. The second closure link 38 may also be referred to herein as an "attachment member" and include a transverse attachment pin 37.

Still referring to FIG. 4, it can be observed that the first closure link 36 may have a locking wall or end 39 thereon that is configured to cooperate with a closure release assembly 60 that is pivotally coupled to the frame 20. In at least one form, the closure release assembly 60 may comprise a release button assembly 62 that has a distally protruding locking pawl 64 formed thereon. The release button assembly 62 may be pivoted in a counterclockwise direction by a release spring (not shown). As the clinician depresses the closure trigger 32 from its unactuated position towards the pistol grip portion 19 of the handle 14, the first closure link 36 pivots upward to a point wherein the locking pawl 64 drops into retaining engagement with the locking wall 39 on the first closure link 36 thereby preventing the closure trigger 32 from returning to the unactuated position. See FIG. 18. Thus, the closure release assembly 60 serves to lock the closure trigger 32 in the fully actuated position. When the clinician desires to unlock the closure trigger 32 to permit it to be biased to the unactuated position, the clinician simply pivots the closure release button assembly 62 such that the locking pawl 64 is moved out of engagement with the locking wall 39 on the first closure link 36. When the locking pawl 64 has been moved out of engagement with the first closure link 36, the closure trigger 32 may pivot back to the unactuated position. Other closure trigger locking and release arrangements may also be employed.

Figure 13:
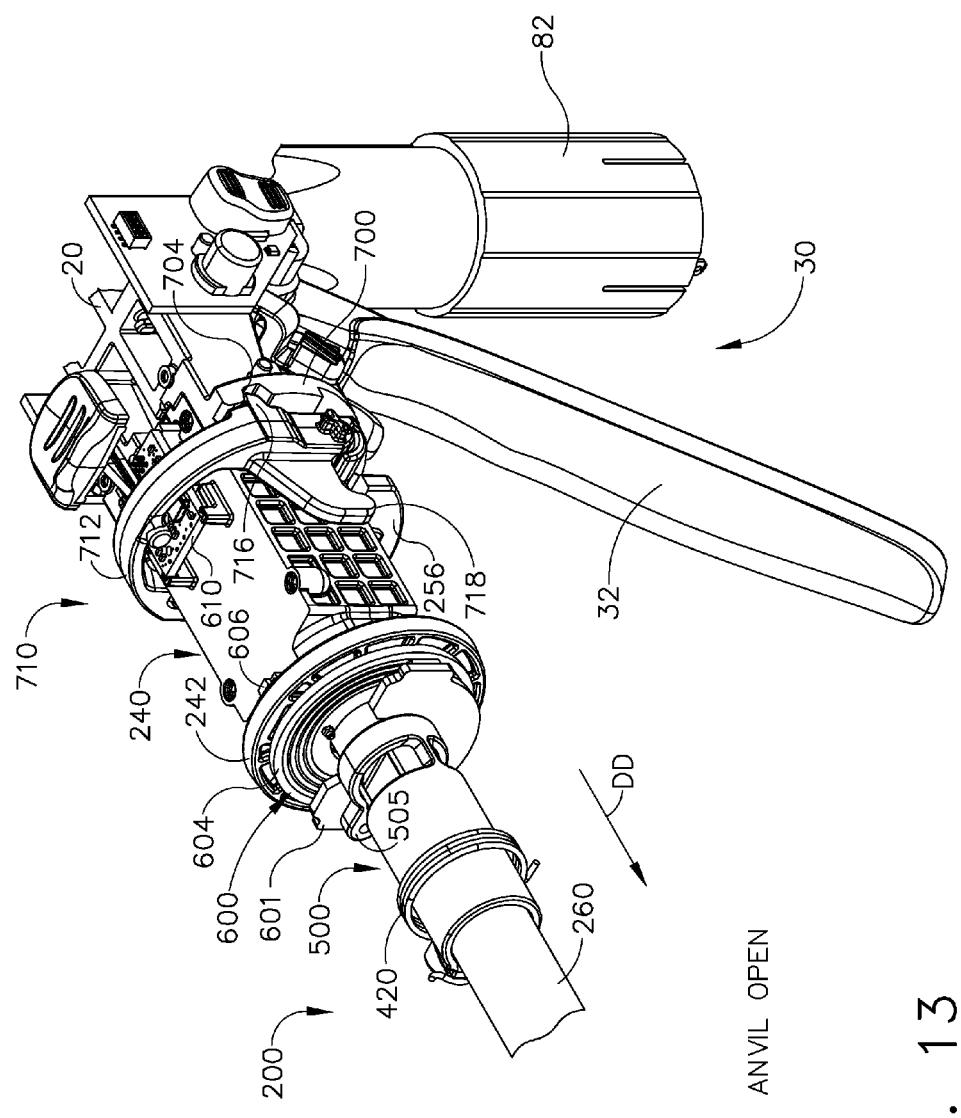
FIG. 13 is a perspective view of a portion of the interchangeable shaft assembly of FIG. 11 operably coupled to a portion of the surgical instrument of FIG. 1 illustrated with the closure trigger thereof in an unactuated position.
Figure 14:
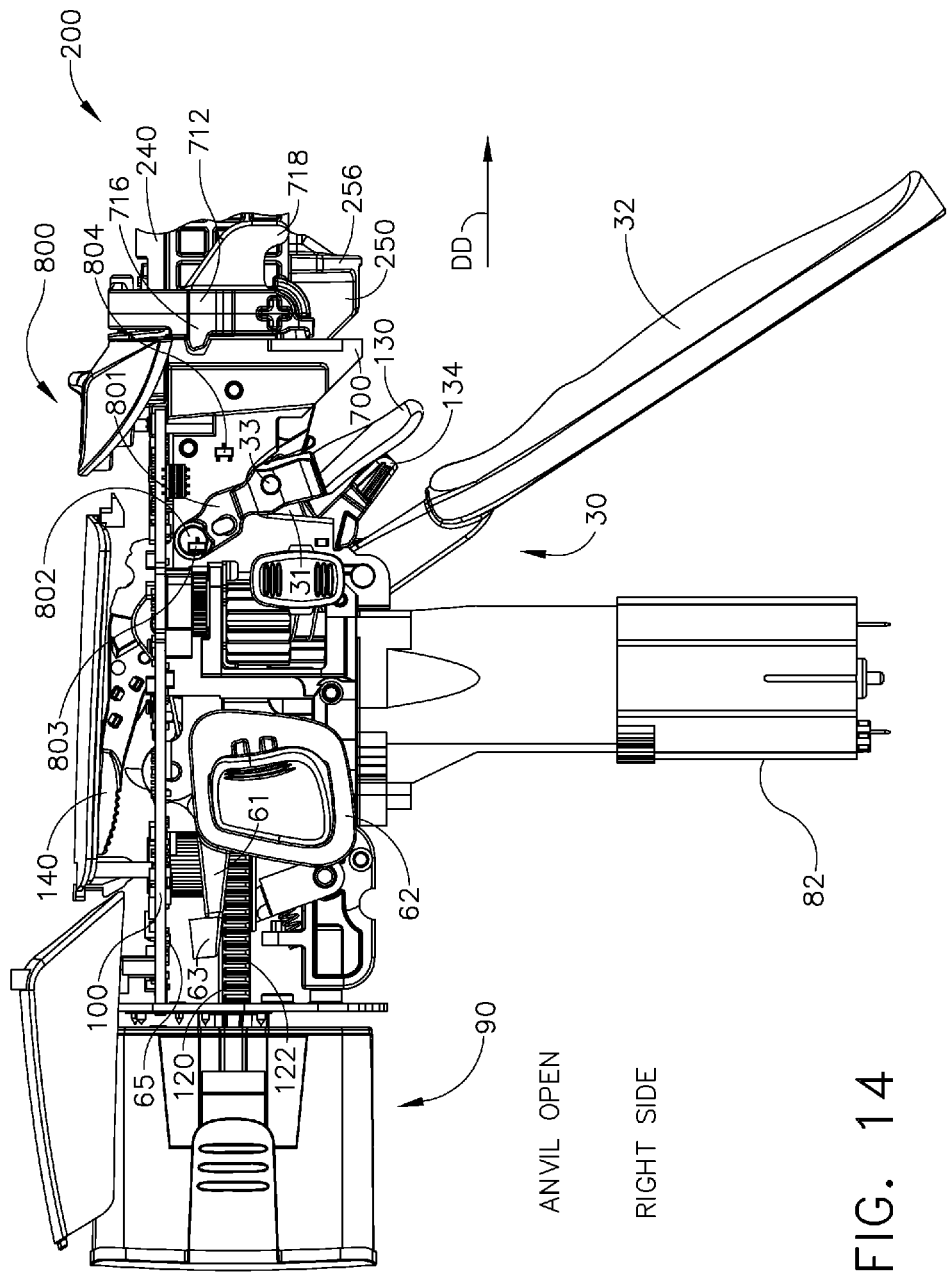
FIG. 14 is a right side elevational view of the interchangeable shaft assembly and surgical instrument of FIG. 13.
Figure 15:
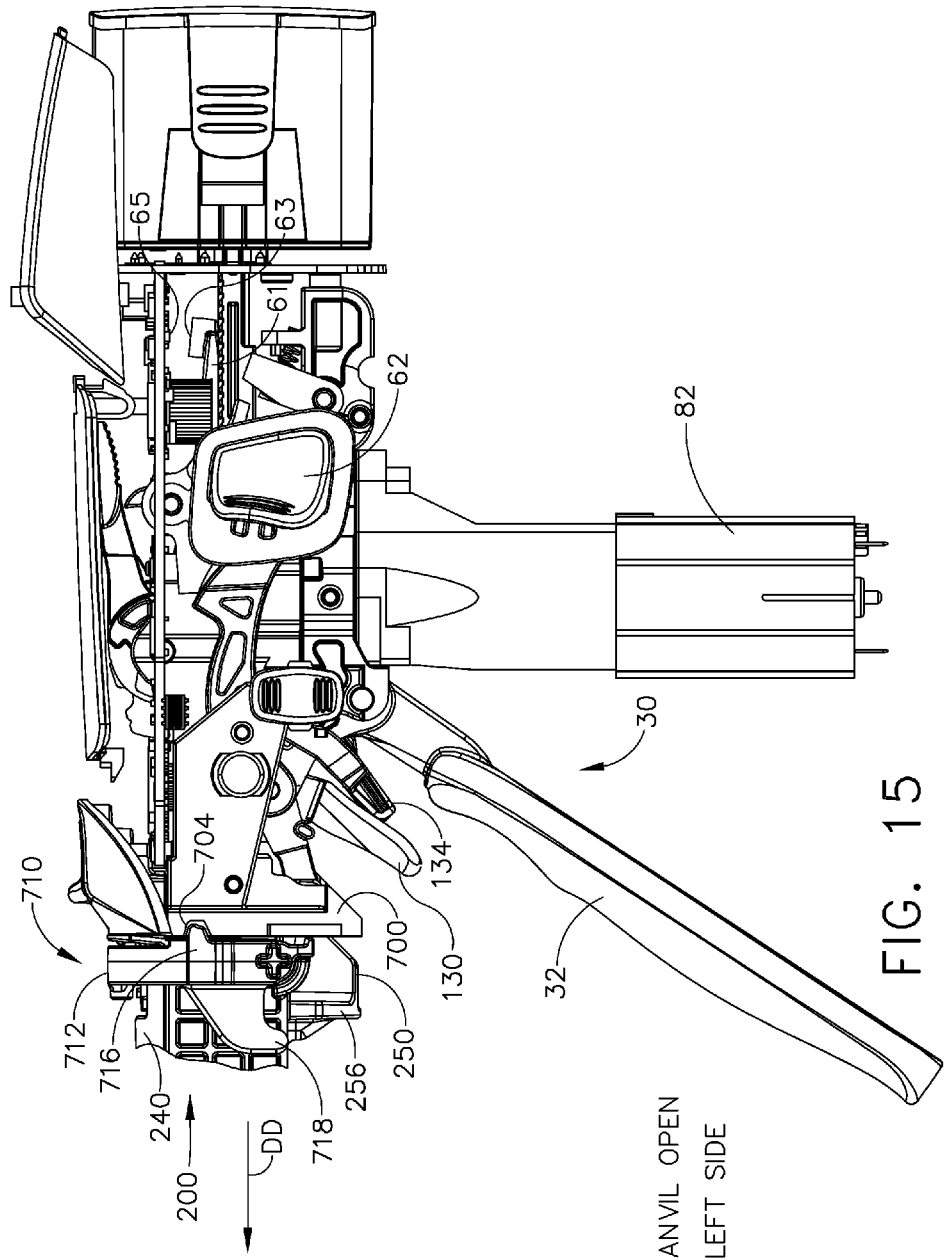
FIG. 15 is a left side elevational view of the interchangeable shaft assembly and surgical instrument of FIGS. 13 and 14.
Figure 16:
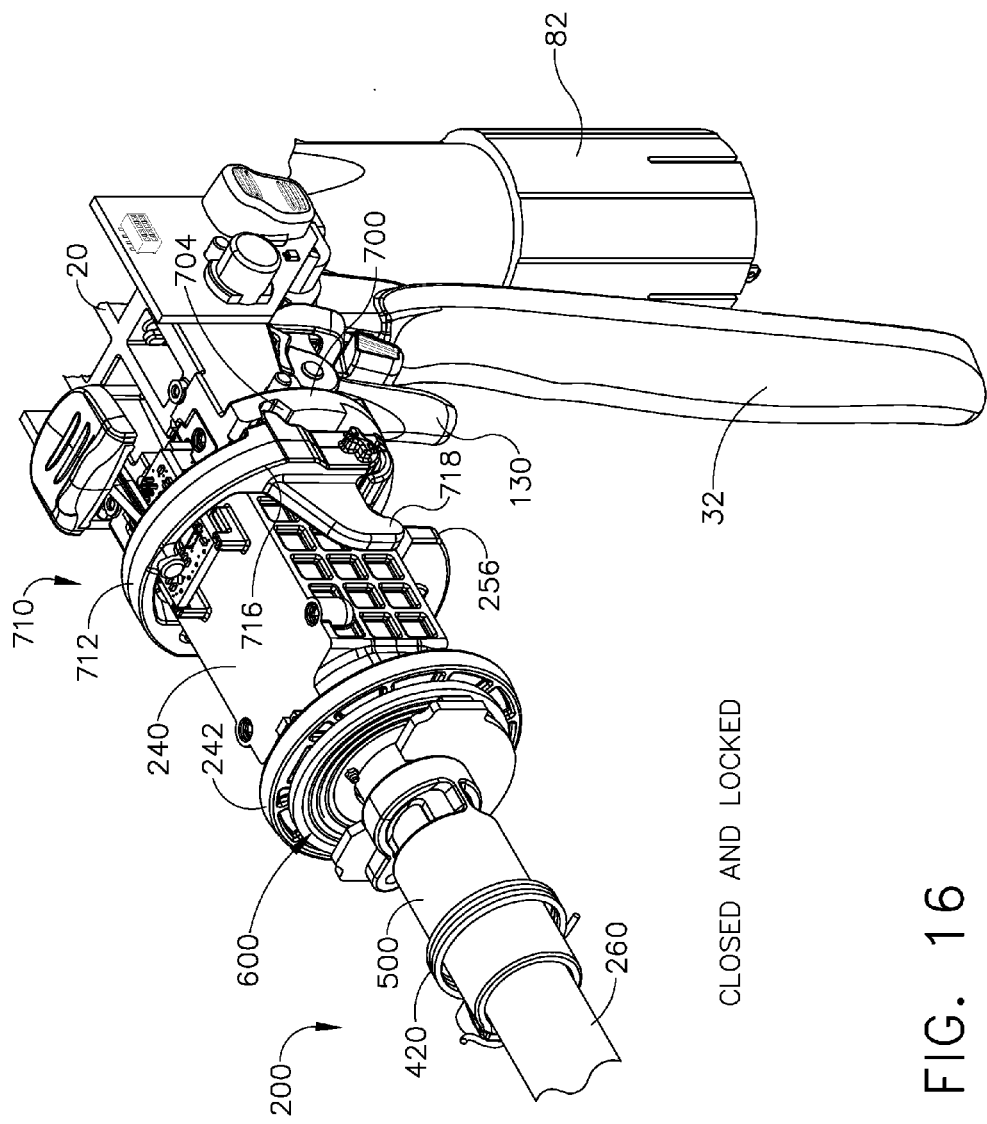
FIG. 16 is a perspective view of a portion of the interchangeable shaft assembly of FIG. 11 operably coupled to a portion of the surgical instrument of FIG. 1 illustrated with the closure trigger thereof in an actuated position and a firing trigger thereof in an unactuated position.
Figure 17:
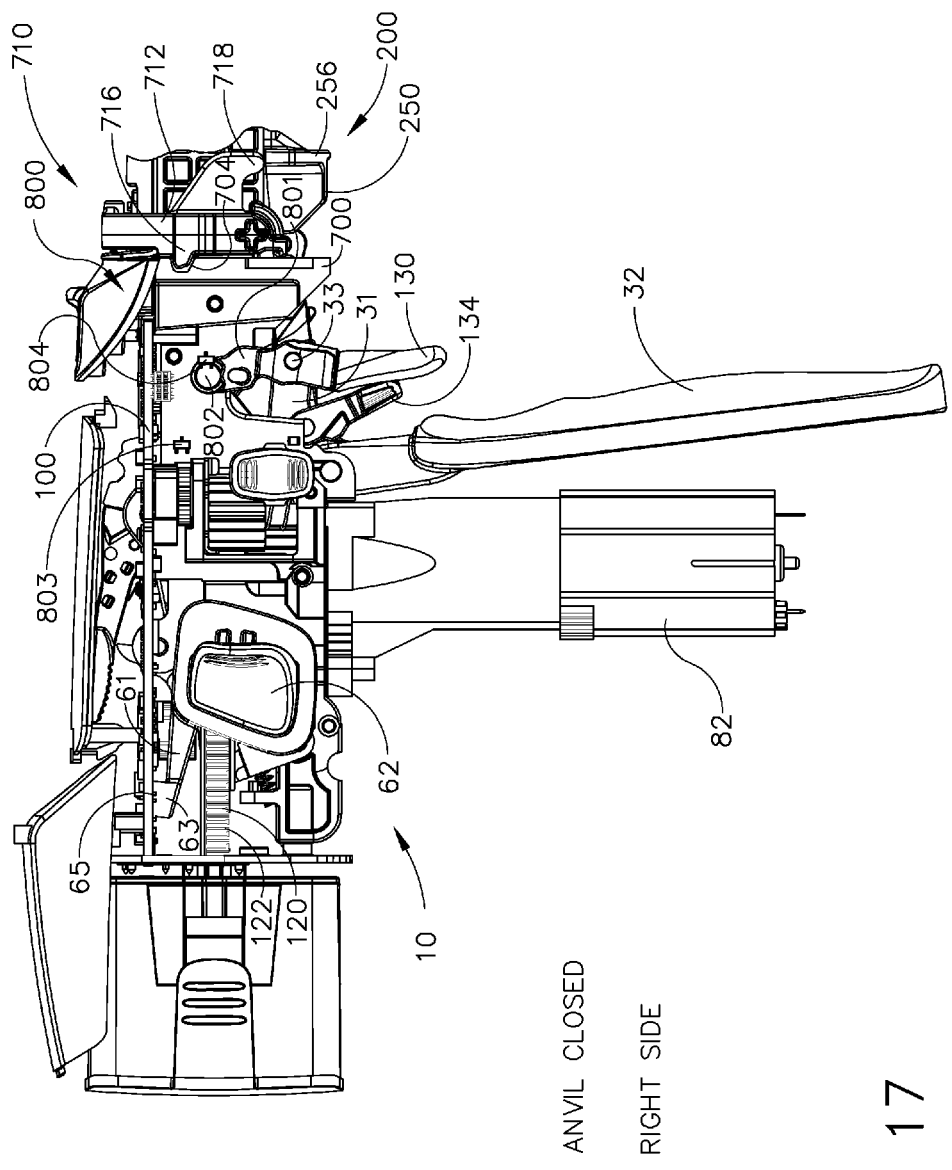
FIG. 17 is a right side elevational view of the interchangeable shaft assembly and surgical instrument of FIG. 16.
Figure 18:
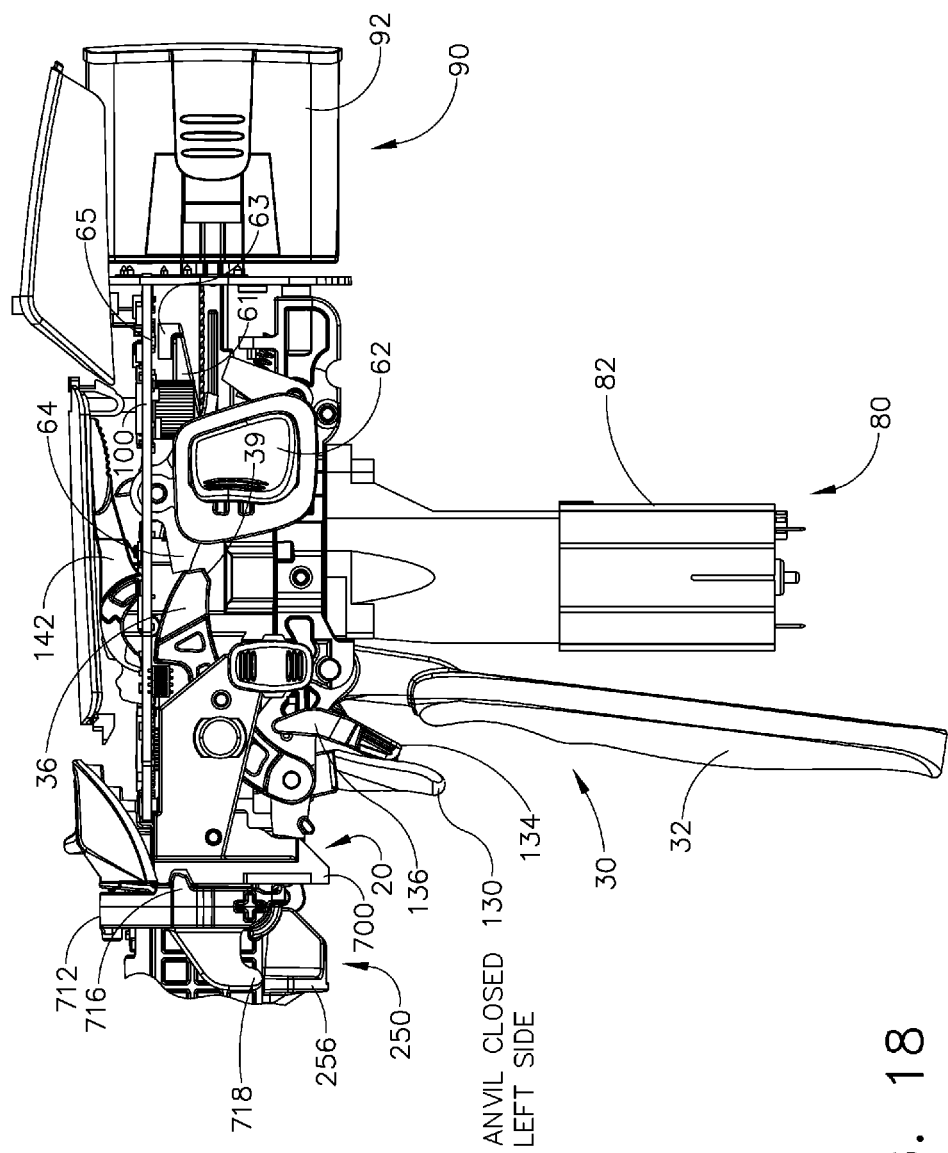
FIG. 18 is a left side elevational view of the interchangeable shaft assembly and surgical instrument of FIGS. 16 and 17.
Figure 19:
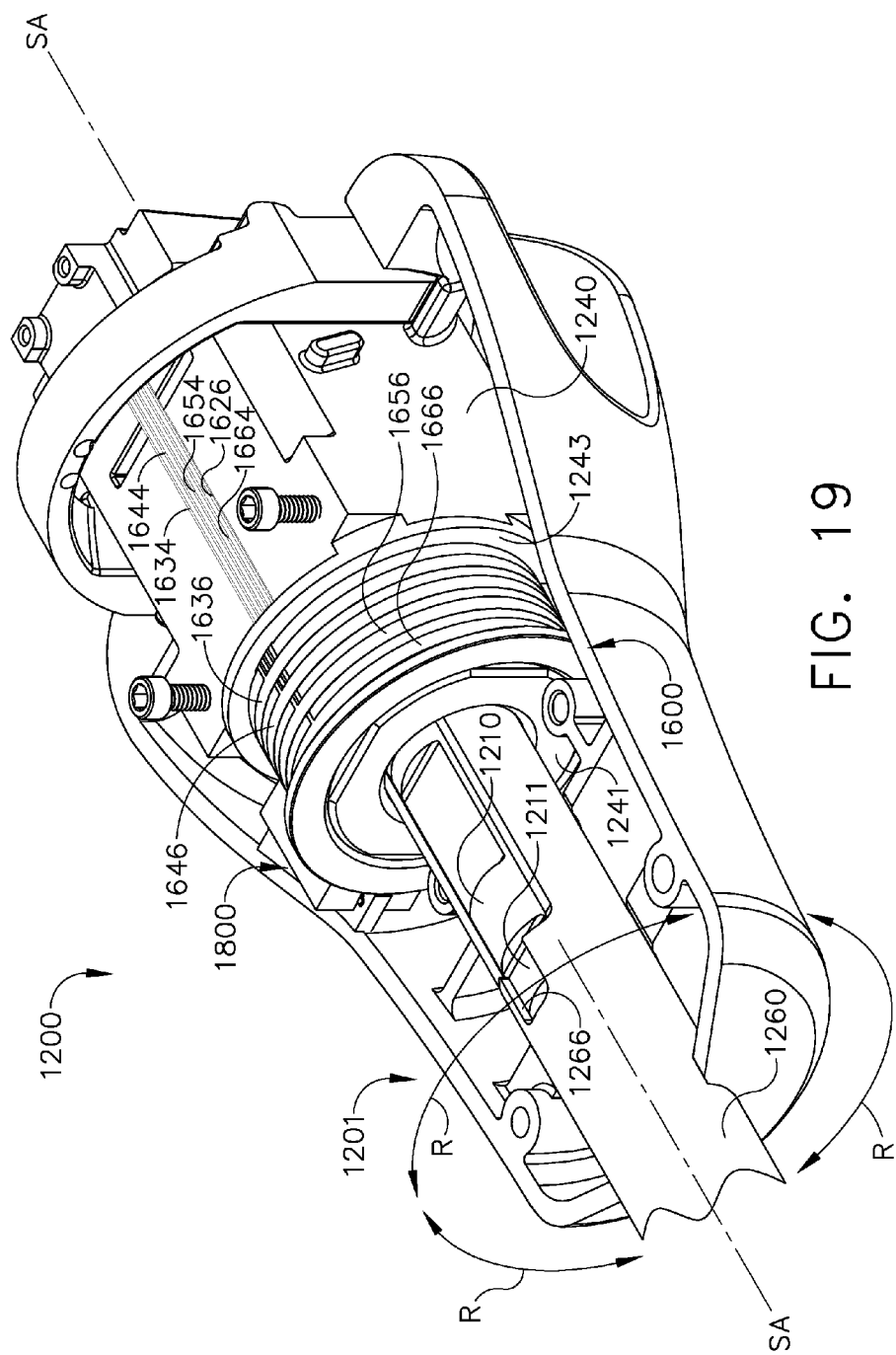
FIG. 19 is a perspective view of a portion of an interchangeable shaft assembly showing an electrical coupler arrangement.
Figure 20:
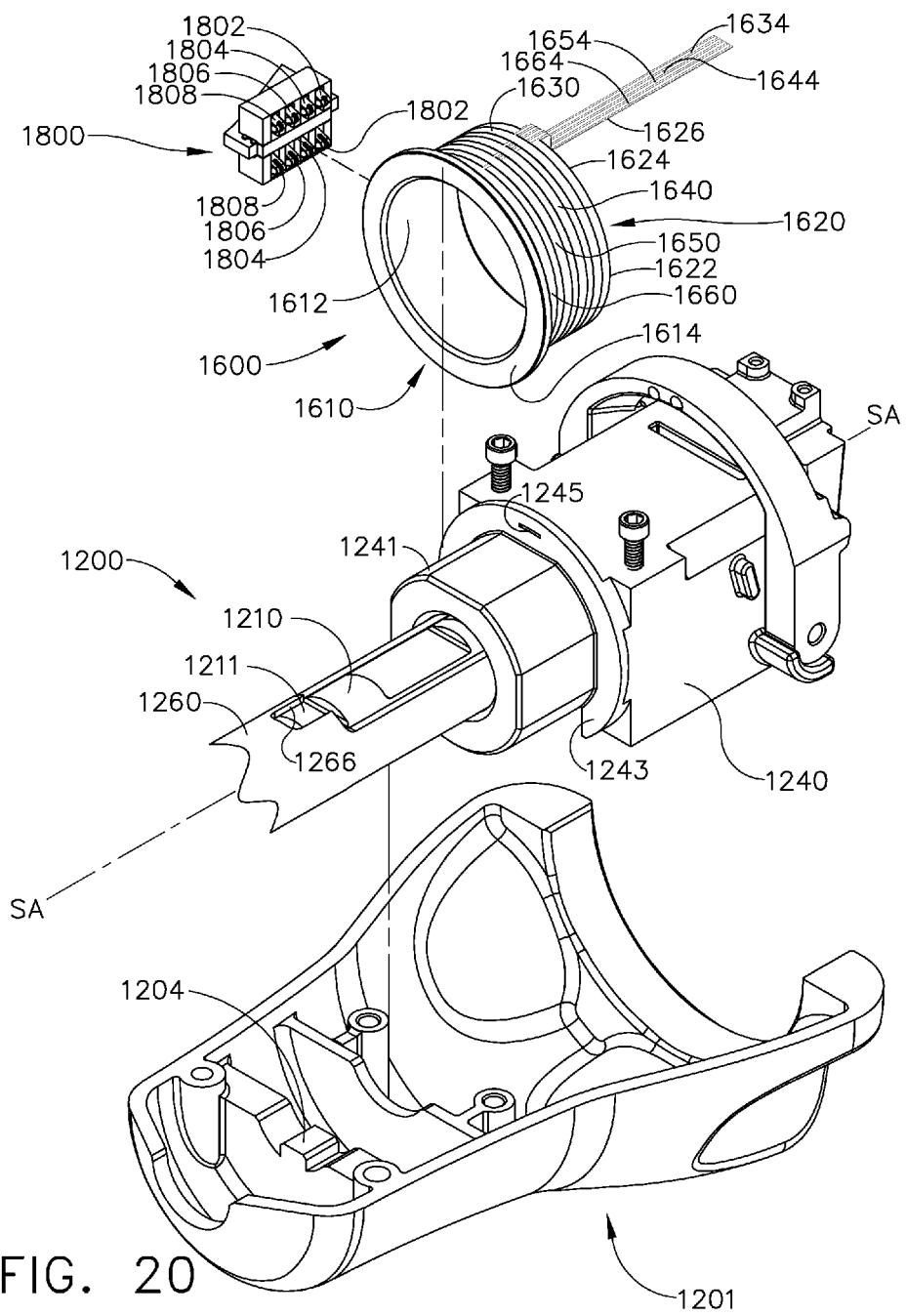
FIG. 20 is an exploded assembly view of portions of the interchangeable shaft assembly and electrical coupler of FIG. 19.

Further to the above, FIGS. 13-15 illustrate the closure trigger 32 in its unactuated position which is associated with an open, or unclamped, configuration of the shaft assembly 200 in which tissue can be positioned between the jaws of the shaft assembly 200. FIGS. 16-18 illustrate the closure trigger 32 in its actuated position which is associated with a closed, or clamped, configuration of the shaft assembly 200 in which tissue is clamped between the jaws of the shaft assembly 200. Upon comparing FIGS. 14 and 17, the reader will appreciate that, when the closure trigger 32 is moved from its unactuated position (FIG. 14) to its actuated position (FIG. 17), the closure release button 62 is pivoted between a first position (FIG. 14) and a second position (FIG. 17). The rotation of the closure release button 62 can be referred to as being an upward rotation; however, at least a portion of the closure release button 62 is being rotated toward the circuit board 100. Referring to FIG. 4, the closure release button 62 can include an arm 61 extending therefrom and a magnetic element 63, such as a permanent magnet, for example, mounted to the arm 61. When the closure release button 62 is rotated from its first position to its second position, the magnetic element 63 can move toward the circuit board 100. The circuit board 100 can include at least one sensor configured to detect the movement of the magnetic element 63. In at least one embodiment, a Hall effect sensor 65, for example, can be mounted to the bottom surface of the circuit board 100. The Hall effect sensor 65 can be configured to detect changes in a magnetic field surrounding the Hall effect sensor 65 caused by the movement of the magnetic element 63. The Hall effect sensor 65 can be in signal communication with a microcontroller 7004 (FIG. 59), for example, which can determine whether the closure release button 62 is in its first position, which is associated with the unactuated position of the closure trigger 32 and the open configuration of the end effector, its second position, which is associated with the actuated position of the closure trigger 32 and the closed configuration of the end effector, and/or any position between the first position and the second position.

In at least one form, the handle 14 and the frame 20 may operably support another drive system referred to herein as a firing drive system 80 that is configured to apply firing motions to corresponding portions of the interchangeable shaft assembly attached thereto. The firing drive system may 80 also be referred to herein as a "second drive system". The firing drive system 80 may employ an electric motor 82, located in the pistol grip portion 19 of the handle 14. In various forms, the motor 82 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor 82 may be powered by a power source 90 that in one form may comprise a removable power pack 92. As can be seen in FIG. 4, for example, the power pack 92 may comprise a proximal housing portion 94 that is configured for attachment to a distal housing portion 96. The proximal housing portion 94 and the distal housing portion 96 are configured to operably support a plurality of batteries 98 therein. Batteries 98 may each comprise, for example, a Lithium Ion ("LI") or other suitable battery. The distal housing portion 96 is configured for removable operable attachment to a control circuit board assembly 100 which is also operably coupled to the motor 82. A number of batteries 98 may be connected in series may be used as the power source for the surgical instrument 10. In addition, the power source 90 may be replaceable and/or rechargeable.

As outlined above with respect to other various forms, the electric motor 82 can include a rotatable shaft (not shown) that operably interfaces with a gear reducer assembly 84 that is mounted in meshing engagement with a with a set, or rack, of drive teeth 122 on a longitudinally-movable drive member 120. In use, a voltage polarity provided by the power source 90 can operate the electric motor 82 in a clockwise direction wherein the voltage polarity applied to the electric motor by the battery can be reversed in order to operate the electric motor 82 in a counter-clockwise direction. When the electric motor 82 is rotated in one direction, the drive member 120 will be axially driven in the distal direction "DD". When the motor 82 is driven in the opposite rotary direction, the drive member 120 will be axially driven in a proximal direction "PD". The handle 14 can include a switch which can be configured to reverse the polarity applied to the electric motor 82 by the power source 90. As with the other forms described herein, the handle 14 can also include a sensor that is configured to detect the position of the drive member 120 and/or the direction in which the drive member 120 is being moved.

Actuation of the motor 82 can be controlled by a firing trigger 130 that is pivotally supported on the handle 14. The firing trigger 130 may be pivoted between an unactuated position and an actuated position. The firing trigger 130 may be biased into the unactuated position by a spring 132 or other biasing arrangement such that when the clinician releases the firing trigger 130, it may be pivoted or otherwise returned to the unactuated position by the spring 132 or biasing arrangement. In at least one form, the firing trigger 130 can be positioned "outboard" of the closure trigger 32 as was discussed above. In at least one form, a firing trigger safety button 134 may be pivotally mounted to the closure trigger 32 by pin 35. The safety button 134 may be positioned between the firing trigger 130 and the closure trigger 32 and have a pivot arm 136 protruding therefrom. See FIG. 4. When the closure trigger 32 is in the unactuated position, the safety button 134 is contained in the handle 14 where the clinician cannot readily access it and move it between a safety position preventing actuation of the firing trigger 130 and a firing position wherein the firing trigger 130 may be fired. As the clinician depresses the closure trigger 32, the safety button 134 and the firing trigger 130 pivot down wherein they can then be manipulated by the clinician.

As discussed above, the handle 14 can include a closure trigger 32 and a firing trigger 130. Referring to FIGS. 14-18A, the firing trigger 130 can be pivotably mounted to the closure trigger 32. The closure trigger 32 can include an arm 31 extending therefrom and the firing trigger 130 can be pivotably mounted to the arm 31 about a pivot pin 33. When the closure trigger 32 is moved from its unactuated position (FIG. 14) to its actuated position (FIG. 17), the firing trigger 130 can descend downwardly, as outlined above. After the safety button 134 has been moved to its firing position, referring primarily to FIG. 18A, the firing trigger 130 can be depressed to operate the motor of the surgical instrument firing system. In various instances, the handle 14 can include a tracking system, such as system 800, for example, configured to determine the position of the closure trigger 32 and/or the position of the firing trigger 130. With primary reference to FIGS. 14, 17, and 18A, the tracking system 800 can include a magnetic element, such as permanent magnet 802, for example, which is mounted to an arm 801 extending from the firing trigger 130. The tracking system 800 can comprise one or more sensors, such as a first Hall effect sensor 803 and a second Hall effect sensor 804, for example, which can be configured to track the position of the magnet 802. Upon comparing FIGS. 14 and 17, the reader will appreciate that, when the closure trigger 32 is moved from its unactuated position to its actuated position, the magnet 802 can move between a first position adjacent the first Hall effect sensor 803 and a second position adjacent the second Hall effect sensor 804. Upon comparing FIGS. 17 and 18A, the reader will further appreciate that, when the firing trigger 130 is moved from an unfired position (FIG. 17) to a fired position (FIG. 18A), the magnet 802 can move relative to the second Hall effect sensor 804. The sensors 803 and 804 can track the movement of the magnet 802 and can be in signal communication with a microcontroller on the circuit board 100. With data from the first sensor 803 and/or the second sensor 804, the microcontroller can determine the position of the magnet 802 along a predefined path and, based on that position, the microcontroller can determine whether the closure trigger 32 is in its unactuated position, its actuated position, or a position therebetween. Similarly, with data from the first sensor 803 and/or the second sensor 804, the microcontroller can determine the position of the magnet 802 along a predefined path and, based on that position, the microcontroller can determine whether the firing trigger 130 is in its unfired position, its fully fired position, or a position therebetween.

As indicated above, in at least one form, the longitudinally movable drive member 120 has a rack of teeth 122 formed thereon for meshing engagement with a corresponding drive gear 86 of the gear reducer assembly 84. At least one form also includes a manually-actuatable "bailout" assembly 140 that is configured to enable the clinician to manually retract the longitudinally movable drive member 120 should the motor 82 become disabled. The bailout assembly 140 may include a lever or bailout handle assembly 142 that is configured to be manually pivoted into ratcheting engagement with teeth 124 also provided in the drive member 120. Thus, the clinician can manually retract the drive member 120 by using the bailout handle assembly 142 to ratchet the drive member 120 in the proximal direction "PD". U.S. Patent Application Publication No. US 2010/0089970 discloses bailout arrangements and other components, arrangements and systems that may also be employed with the various instruments disclosed herein. U.S. patent application Ser. No. 12/249,117, entitled POWERED SURGICAL CUTTING AND STAPLING APPARATUS WITH MANUALLY RETRACTABLE FIRING SYSTEM, now U.S. Patent Application Publication No. 2010/0089970, is hereby incorporated by reference in its entirety.

Figure 7:
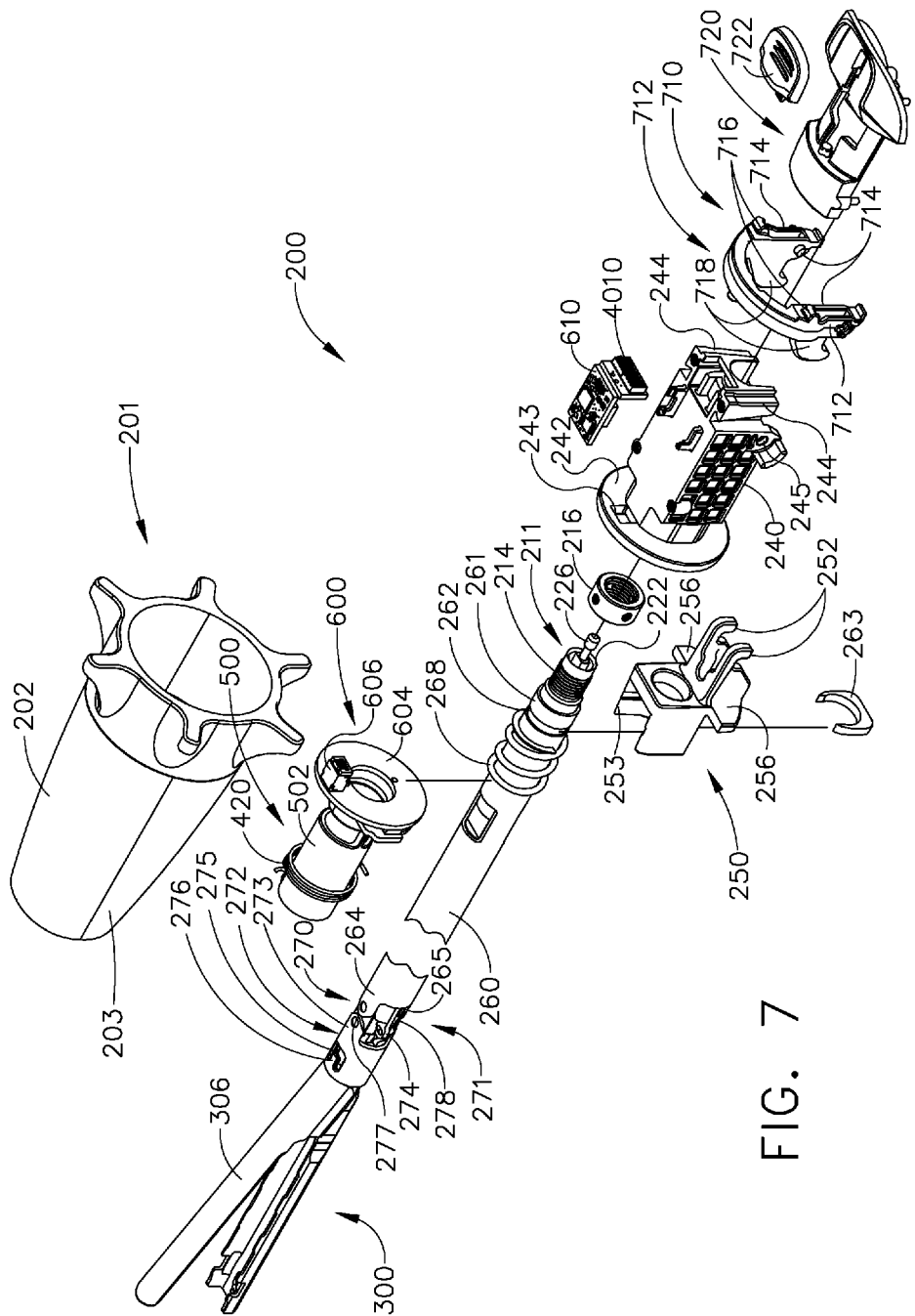
FIG. 7 is an exploded assembly view of one form of an interchangeable shaft assembly.
Figure 8:
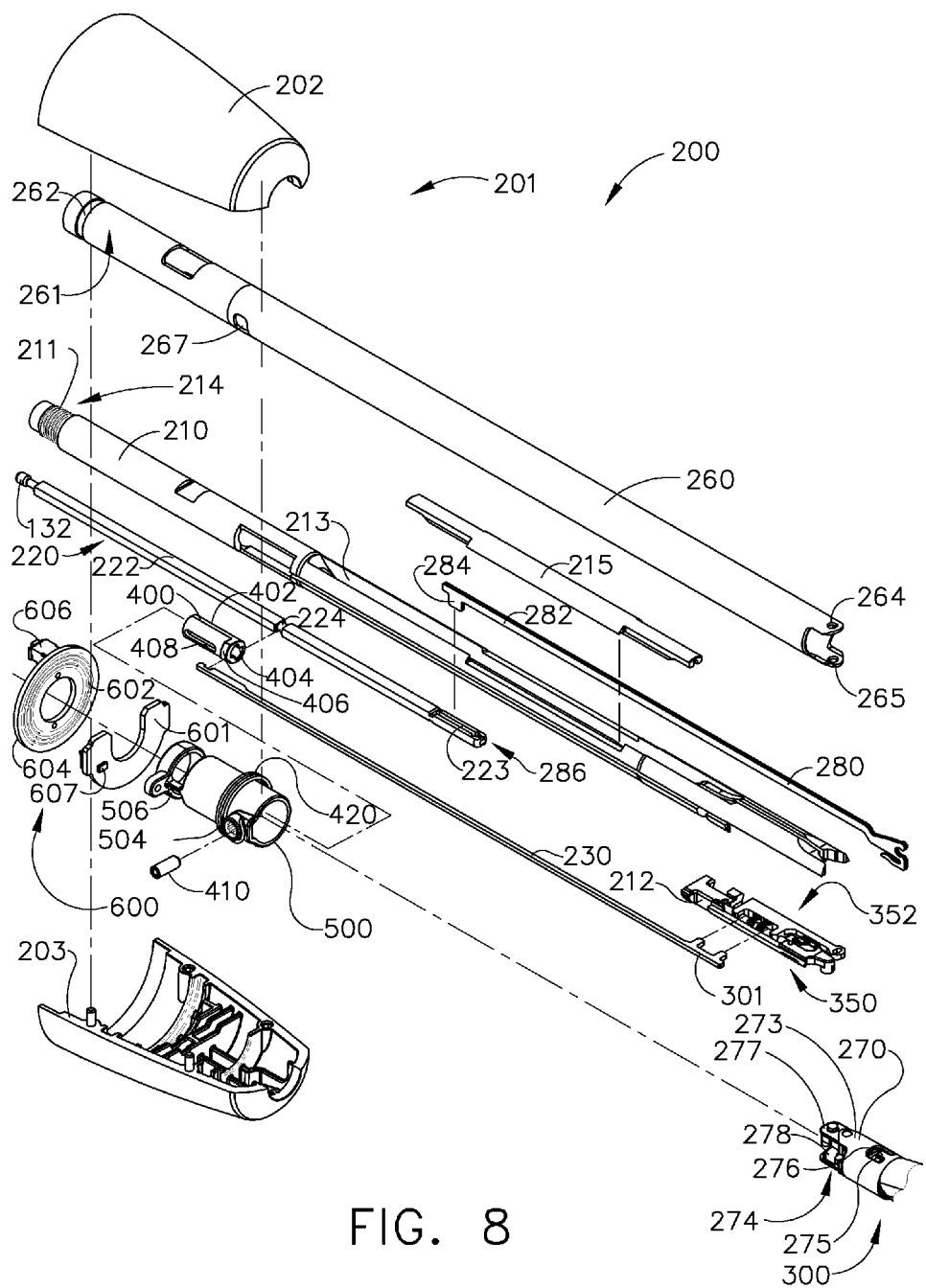
FIG. 8 is another exploded assembly view of portions of the interchangeable shaft assembly of FIG. 7.

Turning now to FIGS. 1 and 7, the interchangeable shaft assembly 200 includes a surgical end effector 300 that comprises an elongated channel 302 that is configured to operably support a staple cartridge 304 therein. The end effector 300 may further include an anvil 306 that is pivotally supported relative to the elongated channel 302. The interchangeable shaft assembly 200 may further include an articulation joint 270 and an articulation lock 350 (FIG. 8) which can be configured to releasably hold the end effector 300 in a desired position relative to a shaft axis SA-SA. Details regarding the construction and operation of the end effector 300, the articulation joint 270 and the articulation lock 350 are set forth in U.S. patent application Ser. No. 13/803,086, filed Mar. 14, 2013, entitled ARTICULATABLE SURGICAL INSTRUMENT COMPRISING AN ARTICULATION LOCK. The entire disclosure of U.S. patent application Ser. No. 13/803,086, filed Mar. 14, 2013, entitled ARTICULATABLE SURGICAL INSTRUMENT COMPRISING AN ARTICULATION LOCK is hereby incorporated by reference herein. As can be seen in FIGS. 7 and 8, the interchangeable shaft assembly 200 can further include a proximal housing or nozzle 201 comprised of nozzle portions 202 and 203. The interchangeable shaft assembly 200 can further include a closure tube 260 which can be utilized to close and/or open the anvil 306 of the end effector 300. Primarily referring now to FIGS. 8 and 9, the shaft assembly 200 can include a spine 210 which can be configured to fixably support a shaft frame portion 212 of the articulation lock 350. See FIG. 8. The spine 210 can be configured to, one, slidably support a firing member 220 therein and, two, slidably support the closure tube 260 which extends around the spine 210. The spine 210 can also be configured to slidably support a proximal articulation driver 230. The articulation driver 230 has a distal end 231 that is configured to operably engage the articulation lock 350. The articulation lock 350 interfaces with an articulation frame 352 that is adapted to operably engage a drive pin (not shown) on the end effector frame (not shown). As indicated above, further details regarding the operation of the articulation lock 350 and the articulation frame may be found in U.S. patent application Ser. No. 13/803,086. In various circumstances, the spine 210 can comprise a proximal end 211 which is rotatably supported in a chassis 240. In one arrangement, for example, the proximal end 211 of the spine 210 has a thread 214 formed thereon for threaded attachment to a spine bearing 216 configured to be supported within the chassis 240. See FIG. 7. Such an arrangement facilitates rotatable attachment of the spine 210 to the chassis 240 such that the spine 210 may be selectively rotated about a shaft axis SA-SA relative to the chassis 240.

Referring primarily to FIG. 7, the interchangeable shaft assembly 200 includes a closure shuttle 250 that is slidably supported within the chassis 240 such that it may be axially moved relative thereto. As can be seen in FIGS. 3 and 7, the closure shuttle 250 includes a pair of proximally-protruding hooks 252 that are configured for attachment to the attachment pin 37 that is attached to the second closure link 38 as will be discussed in further detail below. A proximal end 261 of the closure tube 260 is coupled to the closure shuttle 250 for relative rotation thereto. For example, a U shaped connector 263 is inserted into an annular slot 262 in the proximal end 261 of the closure tube 260 and is retained within vertical slots 253 in the closure shuttle 250. See FIG. 7. Such an arrangement serves to attach the closure tube 260 to the closure shuttle 250 for axial travel therewith while enabling the closure tube 260 to rotate relative to the closure shuttle 250 about the shaft axis SA-SA. A closure spring 268 is journaled on the closure tube 260 and serves to bias the closure tube 260 in the proximal direction "PD" which can serve to pivot the closure trigger into the unactuated position when the shaft assembly is operably coupled to the handle 14.

In at least one form, the interchangeable shaft assembly 200 may further include an articulation joint 270. Other interchangeable shaft assemblies, however, may not be capable of articulation. As can be seen in FIG. 7, for example, the articulation joint 270 includes a double pivot closure sleeve assembly 271. According to various forms, the double pivot closure sleeve assembly 271 includes an end effector closure sleeve assembly 272 having upper and lower distally projecting tangs 273, 274. An end effector closure sleeve assembly 272 includes a horseshoe aperture 275 and a tab 276 for engaging an opening tab on the anvil 306 in the various manners described in U.S. patent application Ser. No. 13/803,086, filed Mar. 14, 2013, entitled ARTICULATABLE SURGICAL INSTRUMENT COMPRISING AN ARTICULATION LOCK which has been incorporated by reference herein. As described in further detail therein, the horseshoe aperture 275 and tab 276 engage a tab on the anvil when the anvil 306 is opened. An upper double pivot link 277 includes upwardly projecting distal and proximal pivot pins that engage respectively an upper distal pin hole in the upper proximally projecting tang 273 and an upper proximal pin hole in an upper distally projecting tang 264 on the closure tube 260. A lower double pivot link 278 includes upwardly projecting distal and proximal pivot pins that engage respectively a lower distal pin hole in the lower proximally projecting tang 274 and a lower proximal pin hole in the lower distally projecting tang 265. See also FIG. 8.

In use, the closure tube 260 is translated distally (direction "DD") to close the anvil 306, for example, in response to the actuation of the closure trigger 32. The anvil 306 is closed by distally translating the closure tube 260 and thus the shaft closure sleeve assembly 272, causing it to strike a proximal surface on the anvil 360 in the manner described in the aforementioned reference U.S. patent application Ser. No. 13/803,086. As was also described in detail in that reference, the anvil 306 is opened by proximally translating the closure tube 260 and the shaft closure sleeve assembly 272, causing tab 276 and the horseshoe aperture 275 to contact and push against the anvil tab to lift the anvil 306. In the anvil-open position, the shaft closure tube 260 is moved to its proximal position.

As indicated above, the surgical instrument 10 may further include an articulation lock 350 of the types and construction described in further detail in U.S. patent application Ser. No. 13/803,086 which can be configured and operated to selectively lock the end effector 300 in position. Such arrangement enables the end effector 300 to be rotated, or articulated, relative to the shaft closure tube 260 when the articulation lock 350 is in its unlocked state. In such an unlocked state, the end effector 300 can be positioned and pushed against soft tissue and/or bone, for example, surrounding the surgical site within the patient in order to cause the end effector 300 to articulate relative to the closure tube 260. The end effector 300 may also be articulated relative to the closure tube 260 by an articulation driver 230.

Figure 9:
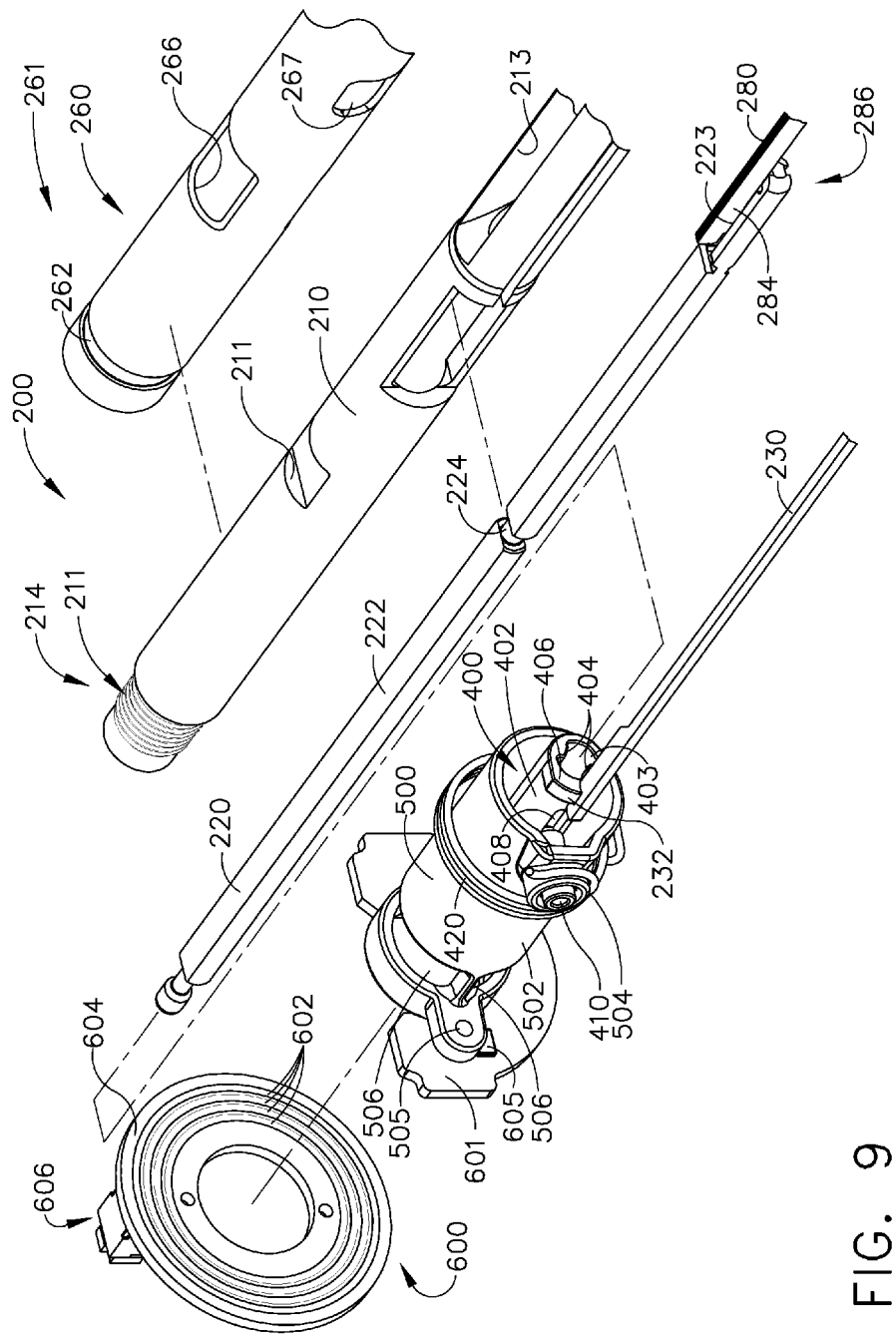
FIG. 9 is another exploded assembly view of portions of the interchangeable shaft assembly of FIGS. 7 and 8.

As was also indicated above, the interchangeable shaft assembly 200 further includes a firing member 220 that is supported for axial travel within the shaft spine 210. The firing member 220 includes an intermediate firing shaft portion 222 that is configured for attachment to a distal cutting portion or knife bar 280. The firing member 220 may also be referred to herein as a "second shaft" and/or a "second shaft assembly". As can be seen in FIGS. 8 and 9, the intermediate firing shaft portion 222 may include a longitudinal slot 223 in the distal end thereof which can be configured to receive a tab 284 on the proximal end 282 of the distal knife bar 280. The longitudinal slot 223 and the proximal end 282 can be sized and configured to permit relative movement therebetween and can comprise a slip joint 286. The slip joint 286 can permit the intermediate firing shaft portion 222 of the firing drive 220 to be moved to articulate the end effector 300 without moving, or at least substantially moving, the knife bar 280. Once the end effector 300 has been suitably oriented, the intermediate firing shaft portion 222 can be advanced distally until a proximal sidewall of the longitudinal slot 223 comes into contact with the tab 284 in order to advance the knife bar 280 and fire the staple cartridge positioned within the channel 302 As can be further seen in FIGS. 8 and 9, the shaft spine 210 has an elongate opening or window 213 therein to facilitate assembly and insertion of the intermediate firing shaft portion 222 into the shaft frame 210. Once the intermediate firing shaft portion 222 has been inserted therein, a top frame segment 215 may be engaged with the shaft frame 212 to enclose the intermediate firing shaft portion 222 and knife bar 280 therein. Further description of the operation of the firing member 220 may be found in U.S. patent application Ser. No. 13/803,086.

Further to the above, the shaft assembly 200 can include a clutch assembly 400 which can be configured to selectively and releasably couple the articulation driver 230 to the firing member 220. In one form, the clutch assembly 400 includes a lock collar, or sleeve 402, positioned around the firing member 220 wherein the lock sleeve 402 can be rotated between an engaged position in which the lock sleeve 402 couples the articulation driver 360 to the firing member 220 and a disengaged position in which the articulation driver 360 is not operably coupled to the firing member 200. When lock sleeve 402 is in its engaged position, distal movement of the firing member 220 can move the articulation driver 360 distally and, correspondingly, proximal movement of the firing member 220 can move the articulation driver 230 proximally. When lock sleeve 402 is in its disengaged position, movement of the firing member 220 is not transmitted to the articulation driver 230 and, as a result, the firing member 220 can move independently of the articulation driver 230. In various circumstances, the articulation driver 230 can be held in position by the articulation lock 350 when the articulation driver 230 is not being moved in the proximal or distal directions by the firing member 220.

Referring primarily to FIG. 9, the lock sleeve 402 can comprise a cylindrical, or an at least substantially cylindrical, body including a longitudinal aperture 403 defined therein configured to receive the firing member 220. The lock sleeve 402 can comprise diametrically-opposed, inwardly-facing lock protrusions 404 and an outwardly-facing lock member 406. The lock protrusions 404 can be configured to be selectively engaged with the firing member 220. More particularly, when the lock sleeve 402 is in its engaged position, the lock protrusions 404 are positioned within a drive notch 224 defined in the firing member 220 such that a distal pushing force and/or a proximal pulling force can be transmitted from the firing member 220 to the lock sleeve 402. When the lock sleeve 402 is in its engaged position, the second lock member 406 is received within a drive notch 232 defined in the articulation driver 230 such that the distal pushing force and/or the proximal pulling force applied to the lock sleeve 402 can be transmitted to the articulation driver 230. In effect, the firing member 220, the lock sleeve 402, and the articulation driver 230 will move together when the lock sleeve 402 is in its engaged position. On the other hand, when the lock sleeve 402 is in its disengaged position, the lock protrusions 404 may not be positioned within the drive notch 224 of the firing member 220 and, as a result, a distal pushing force and/or a proximal pulling force may not be transmitted from the firing member 220 to the lock sleeve 402. Correspondingly, the distal pushing force and/or the proximal pulling force may not be transmitted to the articulation driver 230. In such circumstances, the firing member 220 can be slid proximally and/or distally relative to the lock sleeve 402 and the proximal articulation driver 230.

Figure 10:
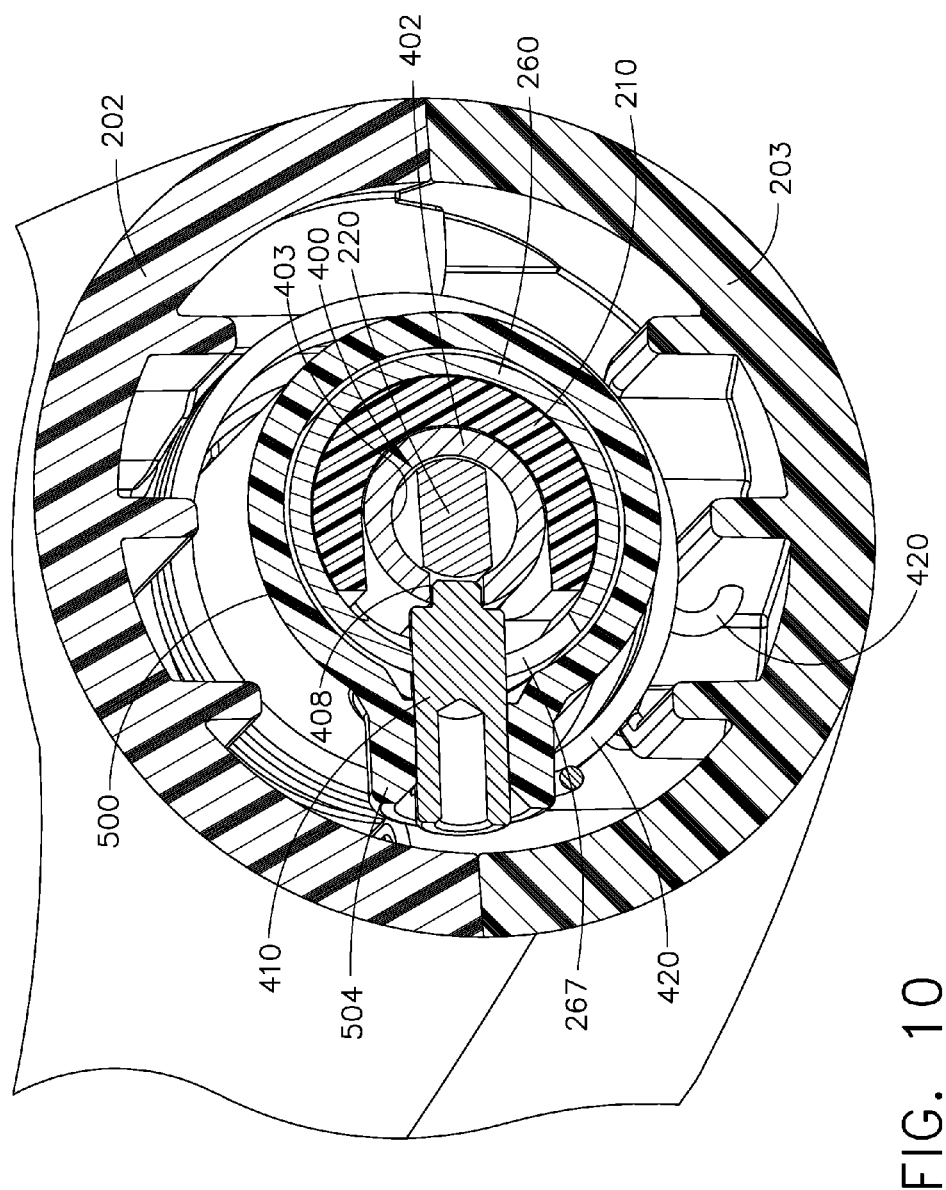
FIG. 10 is a cross-sectional view of a portion of the interchangeable shaft assembly of FIGS. 7-9.

As can be seen in FIGS. 8-12, the shaft assembly 200 further includes a switch drum 500 that is rotatably received on the closure tube 260. The switch drum 500 comprises a hollow shaft segment 502 that has a shaft boss 504 formed thereon for receive an outwardly protruding actuation pin 410 therein. In various circumstances, the actuation pin 410 extends through a slot 267 into a longitudinal slot 408 provided in the lock sleeve 402 to facilitate axial movement of the lock sleeve 402 when it is engaged with the articulation driver 230. A rotary torsion spring 420 is configured to engage the boss 504 on the switch drum 500 and a portion of the nozzle housing 203 as shown in FIG. 10 to apply a biasing force to the switch drum 500. The switch drum 500 can further comprise at least partially circumferential openings 506 defined therein which, referring to FIGS. 5 and 6, can be configured to receive circumferential mounts 204, 205 extending from the nozzle halves 202, 203 and permit relative rotation, but not translation, between the switch drum 500 and the proximal nozzle 201. As can be seen in those Figures, the mounts 204 and 205 also extend through openings 266 in the closure tube 260 to be seated in recesses 211 in the shaft spine 210. However, rotation of the nozzle 201 to a point where the mounts 204, 205 reach the end of their respective slots 506 in the switch drum 500 will result in rotation of the switch drum 500 about the shaft axis SA-SA. Rotation of the switch drum 500 will ultimately result in the rotation of the actuation pin 410 and the lock sleeve 402 between its engaged and disengaged positions. Thus, in essence, the nozzle 201 may be employed to operably engage and disengage the articulation drive system with the firing drive system in the various manners described in further detail in U.S. patent application Ser. No. 13/803,086.

As also illustrated in FIGS. 8-12, the shaft assembly 200 can comprise a slip ring assembly 600 which can be configured to conduct electrical power to and/or from the end effector 300 and/or communicate signals to and/or from the end effector 300, for example. The slip ring assembly 600 can comprise a proximal connector flange 604 mounted to a chassis flange 242 extending from the chassis 240 and a distal connector flange 601 positioned within a slot defined in the shaft housings 202, 203. The proximal connector flange 604 can comprise a first face and the distal connector flange 601 can comprise a second face which is positioned adjacent to and movable relative to the first face. The distal connector flange 601 can rotate relative to the proximal connector flange 604 about the shaft axis SA-SA. The proximal connector flange 604 can comprise a plurality of concentric, or at least substantially concentric, conductors 602 defined in the first face thereof. A connector 607 can be mounted on the proximal side of the connector flange 601 and may have a plurality of contacts (not shown) wherein each contact corresponds to and is in electrical contact with one of the conductors 602. Such an arrangement permits relative rotation between the proximal connector flange 604 and the distal connector flange 601 while maintaining electrical contact therebetween. The proximal connector flange 604 can include an electrical connector 606 which can place the conductors 602 in signal communication with a shaft circuit board 610 mounted to the shaft chassis 240, for example. In at least one instance, a wiring harness comprising a plurality of conductors can extend between the electrical connector 606 and the shaft circuit board 610. The electrical connector 606 may extend proximally through a connector opening 243 defined in the chassis mounting flange 242. See FIG. 7. U.S. patent application Ser. No. 13/800,067, entitled STAPLE CARTRIDGE TISSUE THICKNESS SENSOR SYSTEM, filed on Mar. 13, 2013, is incorporated by reference in its entirety. U.S. patent application Ser. No. 13/800,025, entitled STAPLE CARTRIDGE TISSUE THICKNESS SENSOR SYSTEM, filed on Mar. 13, 2013, is incorporated by reference in its entirety. Further details regarding slip ring assembly 600 may be found in U.S. patent application Ser. No. 13/803,086.

Figure 11:
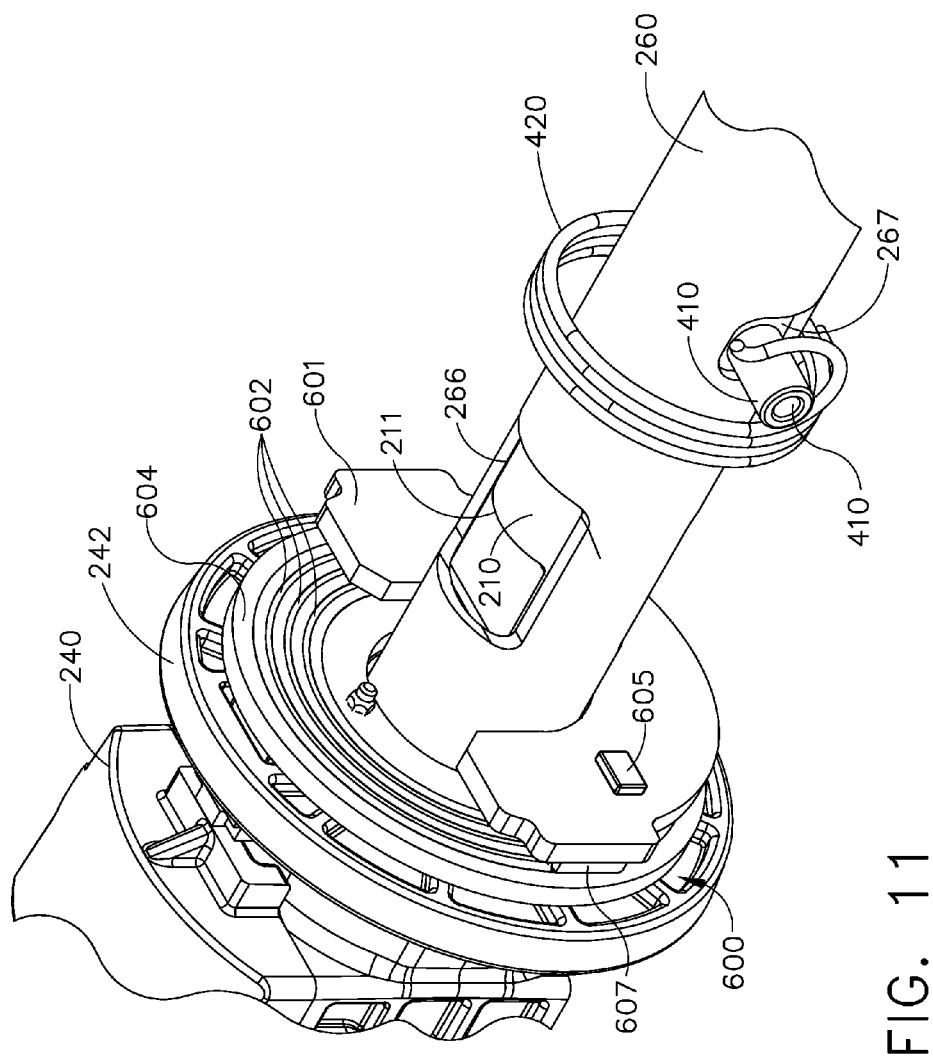
FIG. 11 is a perspective view of a portion of the shaft assembly of FIGS. 7-10 with the switch drum omitted for clarity.
Figure 12:
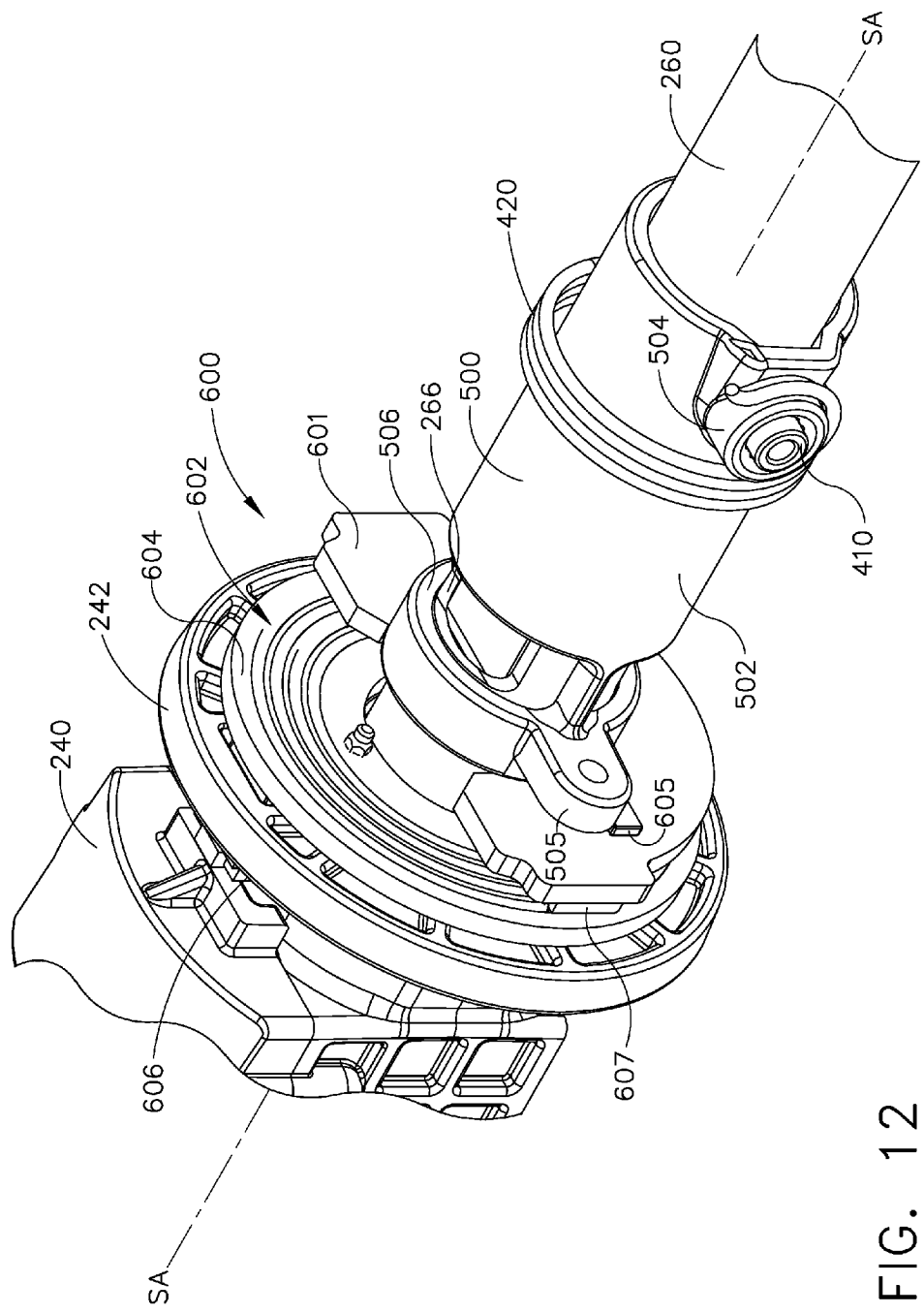
FIG. 12 is another perspective view of the portion of the interchangeable shaft assembly of FIG. 11 with the switch drum mounted thereon.

As discussed above, the shaft assembly 200 can include a proximal portion which is fixably mounted to the handle 14 and a distal portion which is rotatable about a longitudinal axis. The rotatable distal shaft portion can be rotated relative to the proximal portion about the slip ring assembly 600, as discussed above. The distal connector flange 601 of the slip ring assembly 600 can be positioned within the rotatable distal shaft portion. Moreover, further to the above, the switch drum 500 can also be positioned within the rotatable distal shaft portion. When the rotatable distal shaft portion is rotated, the distal connector flange 601 and the switch drum 500 can be rotated synchronously with one another. In addition, the switch drum 500 can be rotated between a first position and a second position relative to the distal connector flange 601. When the switch drum 500 is in its first position, the articulation drive system may be operably disengaged from the firing drive system and, thus, the operation of the firing drive system may not articulate the end effector 300 of the shaft assembly 200. When the switch drum 500 is in its second position, the articulation drive system may be operably engaged with the firing drive system and, thus, the operation of the firing drive system may articulate the end effector 300 of the shaft assembly 200. When the switch drum 500 is moved between its first position and its second position, the switch drum 500 is moved relative to distal connector flange 601. In various instances, the shaft assembly 200 can comprise at least one sensor configured to detect the position of the switch drum 500. Turning now to FIGS. 11 and 12, the distal connector flange 601 can comprise a Hall effect sensor 605, for example, and the switch drum 500 can comprise a magnetic element, such as permanent magnet 505, for example. The Hall effect sensor 605 can be configured to detect the position of the permanent magnet 505. When the switch drum 500 is rotated between its first position and its second position, the permanent magnet 505 can move relative to the Hall effect sensor 605. In various instances, Hall effect sensor 605 can detect changes in a magnetic field created when the permanent magnet 505 is moved. The Hall effect sensor 605 can be in signal communication with the shaft circuit board 610 and/or the handle circuit board 100, for example. Based on the signal from the Hall effect sensor 605, a microcontroller on the shaft circuit board 610 and/or the handle circuit board 100 can determine whether the articulation drive system is engaged with or disengaged from the firing drive system.

Referring again to FIGS. 3 and 7, the chassis 240 includes at least one, and preferably two, tapered attachment portions 244 formed thereon that are adapted to be received within corresponding dovetail slots 702 formed within a distal attachment flange portion 700 of the frame 20. Each dovetail slot 702 may be tapered or, stated another way, be somewhat V-shaped to seatingly receive the attachment portions 244 therein. As can be further seen in FIGS. 3 and 7, a shaft attachment lug 226 is formed on the proximal end of the intermediate firing shaft 222. As will be discussed in further detail below, when the interchangeable shaft assembly 200 is coupled to the handle 14, the shaft attachment lug 226 is received in a firing shaft attachment cradle 126 formed in the distal end 125 of the longitudinal drive member 120. See FIGS. 3 and 6.

Various shaft assembly embodiments employ a latch system 710 for removably coupling the shaft assembly 200 to the housing 12 and more specifically to the frame 20. As can be seen in FIG. 7, for example, in at least one form, the latch system 710 includes a lock member or lock yoke 712 that is movably coupled to the chassis 240. In the illustrated embodiment, for example, the lock yoke 712 has a U-shape with two spaced downwardly extending legs 714. The legs 714 each have a pivot lug 716 formed thereon that are adapted to be received in corresponding holes 245 formed in the chassis 240. Such arrangement facilitates pivotal attachment of the lock yoke 712 to the chassis 240. The lock yoke 712 may include two proximally protruding lock lugs 714 that are configured for releasable engagement with corresponding lock detents or grooves 704 in the distal attachment flange 700 of the frame 20. See FIG. 3. In various forms, the lock yoke 712 is biased in the proximal direction by spring or biasing member (not shown). Actuation of the lock yoke 712 may be accomplished by a latch button 722 that is slidably mounted on a latch actuator assembly 720 that is mounted to the chassis 240. The latch button 722 may be biased in a proximal direction relative to the lock yoke 712. As will be discussed in further detail below, the lock yoke 712 may be moved to an unlocked position by biasing the latch button the in distal direction which also causes the lock yoke 712 to pivot out of retaining engagement with the distal attachment flange 700 of the frame 20. When the lock yoke 712 is in "retaining engagement" with the distal attachment flange 700 of the frame 20, the lock lugs 716 are retainingly seated within the corresponding lock detents or grooves 704 in the distal attachment flange 700.

When employing an interchangeable shaft assembly that includes an end effector of the type described herein that is adapted to cut and fasten tissue, as well as other types of end effectors, it may be desirable to prevent inadvertent detachment of the interchangeable shaft assembly from the housing during actuation of the end effector. For example, in use the clinician may actuate the closure trigger 32 to grasp and manipulate the target tissue into a desired position. Once the target tissue is positioned within the end effector 300 in a desired orientation, the clinician may then fully actuate the closure trigger 32 to close the anvil 306 and clamp the target tissue in position for cutting and stapling. In that instance, the first drive system 30 has been fully actuated. After the target tissue has been clamped in the end effector 300, it may be desirable to prevent the inadvertent detachment of the shaft assembly 200 from the housing 12. One form of the latch system 710 is configured to prevent such inadvertent detachment.

As can be most particularly seen in FIG. 7, the lock yoke 712 includes at least one and preferably two lock hooks 718 that are adapted to contact corresponding lock lug portions 256 that are formed on the closure shuttle 250. Referring to FIGS. 13-15, when the closure shuttle 250 is in an unactuated position (i.e., the first drive system 30 is unactuated and the anvil 306 is open), the lock yoke 712 may be pivoted in a distal direction to unlock the interchangeable shaft assembly 200 from the housing 12. When in that position, the lock hooks 718 do not contact the lock lug portions 256 on the closure shuttle 250. However, when the closure shuttle 250 is moved to an actuated position (i.e., the first drive system 30 is actuated and the anvil 306 is in the closed position), the lock yoke 712 is prevented from being pivoted to an unlocked position. See FIGS. 16-18. Stated another way, if the clinician were to attempt to pivot the lock yoke 712 to an unlocked position or, for example, the lock yoke 712 was inadvertently bumped or contacted in a manner that might otherwise cause it to pivot distally, the lock hooks 718 on the lock yoke 712 will contact the lock lugs 256 on the closure shuttle 250 and prevent movement of the lock yoke 712 to an unlocked position.

Attachment of the interchangeable shaft assembly 200 to the handle 14 will now be described with reference to FIG. 3. To commence the coupling process, the clinician may position the chassis 240 of the interchangeable shaft assembly 200 above or adjacent to the distal attachment flange 700 of the frame 20 such that the tapered attachment portions 244 formed on the chassis 240 are aligned with the dovetail slots 702 in the frame 20. The clinician may then move the shaft assembly 200 along an installation axis IA that is perpendicular to the shaft axis SA-SA to seat the attachment portions 244 in "operable engagement" with the corresponding dovetail receiving slots 702. In doing so, the shaft attachment lug 226 on the intermediate firing shaft 222 will also be seated in the cradle 126 in the longitudinally movable drive member 120 and the portions of pin 37 on the second closure link 38 will be seated in the corresponding hooks 252 in the closure yoke 250. As used herein, the term "operable engagement" in the context of two components means that the two components are sufficiently engaged with each other so that upon application of an actuation motion thereto, the components may carry out their intended action, function and/or procedure.

As discussed above, at least five systems of the interchangeable shaft assembly 200 can be operably coupled with at least five corresponding systems of the handle 14. A first system can comprise a frame system which couples and/or aligns the frame or spine of the shaft assembly 200 with the frame 20 of the handle 14. Another system can comprise a closure drive system 30 which can operably connect the closure trigger 32 of the handle 14 and the closure tube 260 and the anvil 306 of the shaft assembly 200. As outlined above, the closure tube attachment yoke 250 of the shaft assembly 200 can be engaged with the pin 37 on the second closure link 38. Another system can comprise the firing drive system 80 which can operably connect the firing trigger 130 of the handle 14 with the intermediate firing shaft 222 of the shaft assembly 200. As outlined above, the shaft attachment lug 226 can be operably connected with the cradle 126 of the longitudinal drive member 120. Another system can comprise an electrical system which can signal to a controller in the handle 14, such as microcontroller, for example, that a shaft assembly, such as shaft assembly 200, for example, has been operably engaged with the handle 14 and/or, two, conduct power and/or communication signals between the shaft assembly 200 and the handle 14. For instance, the shaft assembly 200 can include an electrical connector 4010 that is operably mounted to the shaft circuit board 610. The electrical connector 4010 is configured for mating engagement with a corresponding electrical connector 4000 on the handle control board 100. Further details regaining the circuitry and control systems may be found in U.S. patent application Ser. No. 13/803,086, the entire disclosure of which was previously incorporated by reference herein. The fifth system may consist of the latching system for releasably locking the shaft assembly 200 to the handle 14.

Figure 59:
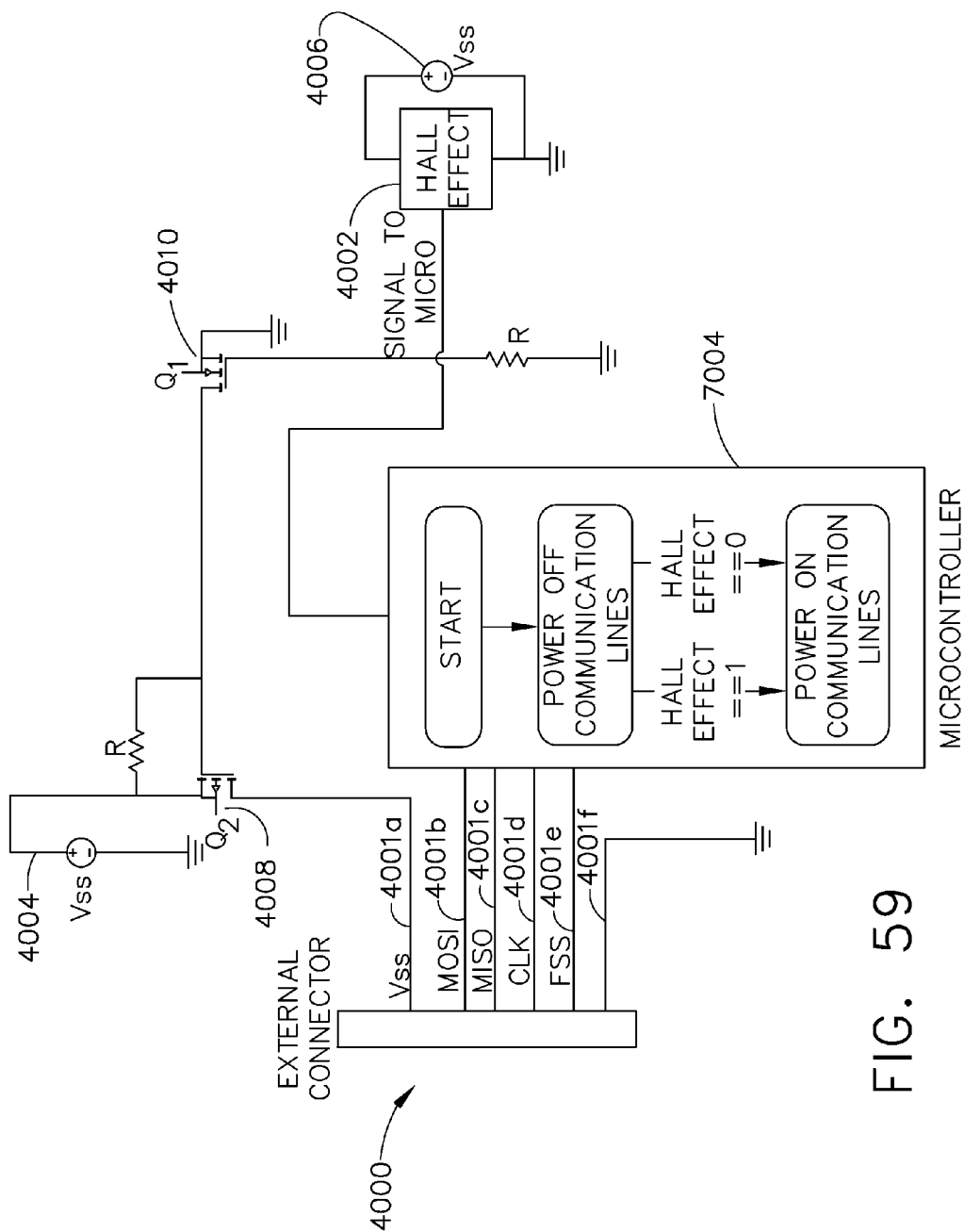
FIG. 59 is a schematic of a system for powering down an electrical connector of a surgical instrument handle when a shaft assembly is not coupled thereto.

Referring again to FIGS. 2 and 3, the handle 14 can include an electrical connector 4000 comprising a plurality of electrical contacts. Turning now to FIG. 59, the electrical connector 4000 can comprise a first contact 4001a, a second contact 4001b, a third contact 4001c, a fourth contact 4001d, a fifth contact 4001e, and a sixth contact 4001f, for example. While the illustrated embodiment utilizes six contacts, other embodiments are envisioned which may utilize more than six contacts or less than six contacts. As illustrated in FIG. 59, the first contact 4001a can be in electrical communication with a transistor 4008, contacts 4001b-4001e can be in electrical communication with a microcontroller 7004, and the sixth contact 4001f can be in electrical communication with a ground. In certain circumstances, one or more of the electrical contacts 4001b-4001e may be in electrical communication with one or more output channels of the microcontroller 7004 and can be energized, or have a voltage potential applied thereto, when the handle 1042 is in a powered state. In some circumstances, one or more of the electrical contacts 4001b-4001e may be in electrical communication with one or more input channels of the microcontroller 7004 and, when the handle 14 is in a powered state, the microcontroller 7004 can be configured to detect when a voltage potential is applied to such electrical contacts. When a shaft assembly, such as shaft assembly 200, for example, is assembled to the handle 14, the electrical contacts 4001a-4001f may not communicate with each other. When a shaft assembly is not assembled to the handle 14, however, the electrical contacts 4001a-4001f of the electrical connector 4000 may be exposed and, in some circumstances, one or more of the contacts 4001a-4001f may be accidentally placed in electrical communication with each other. Such circumstances can arise when one or more of the contacts 4001a-4001f come into contact with an electrically conductive material, for example. When this occurs, the microcontroller 7004 can receive an erroneous input and/or the shaft assembly 200 can receive an erroneous output, for example. To address this issue, in various circumstances, the handle 14 may be unpowered when a shaft assembly, such as shaft assembly 200, for example, is not attached to the handle 14. In other circumstances, the handle 1042 can be powered when a shaft assembly, such as shaft assembly 200, for example, is not attached thereto. In such circumstances, the microcontroller 7004 can be configured to ignore inputs, or voltage potentials, applied to the contacts in electrical communication with the microcontroller 7004, i.e., contacts 4001b-4001e, for example, until a shaft assembly is attached to the handle 14. Even though the microcontroller 7004 may be supplied with power to operate other functionalities of the handle 14 in such circumstances, the handle 14 may be in a powered-down state. In a way, the electrical connector 4000 may be in a powered-down state as voltage potentials applied to the electrical contacts 4001b-4001e may not affect the operation of the handle 14. The reader will appreciate that, even though contacts 4001b-4001e may be in a powered-down state, the electrical contacts 4001a and 4001f, which are not in electrical communication with the microcontroller 7004, may or may not be in a powered-down state. For instance, sixth contact 4001f may remain in electrical communication with a ground regardless of whether the handle 14 is in a powered-up or a powered-down state. Furthermore, the transistor 4008, and/or any other suitable arrangement of transistors, such as transistor 4010, for example, and/or switches may be configured to control the supply of power from a power source 4004, such as a battery 90 within the handle 14, for example, to the first electrical contact 4001a regardless of whether the handle 14 is in a powered-up or a powered-down state. In various circumstances, the shaft assembly 200, for example, can be configured to change the state of the transistor 4008 when the shaft assembly 200 is engaged with the handle 14. In certain circumstances, further to the below, a Hall effect sensor 4002 can be configured to switch the state of transistor 4010 which, as a result, can switch the state of transistor 4008 and ultimately supply power from power source 4004 to first contact 4001a. In this way, both the power circuits and the signal circuits to the connector 4000 can be powered down when a shaft assembly is not installed to the handle 14 and powered up when a shaft assembly is installed to the handle 14.

In various circumstances, referring again to FIG. 59, the handle 14 can include the Hall effect sensor 4002, for example, which can be configured to detect a detectable element, such as a magnetic element 4007 (FIG. 3), for example, on a shaft assembly, such as shaft assembly 200, for example, when the shaft assembly is coupled to the handle 14. The Hall effect sensor 4002 can be powered by a power source 4006, such as a battery, for example, which can, in effect, amplify the detection signal of the Hall effect sensor 4002 and communicate with an input channel of the microcontroller 7004 via the circuit illustrated in FIG. 59. Once the microcontroller 7004 has a received an input indicating that a shaft assembly has been at least partially coupled to the handle 14, and that, as a result, the electrical contacts 4001a-4001f are no longer exposed, the microcontroller 7004 can enter into its normal, or powered-up, operating state. In such an operating state, the microcontroller 7004 will evaluate the signals transmitted to one or more of the contacts 4001b-4001e from the shaft assembly and/or transmit signals to the shaft assembly through one or more of the contacts 4001b-4001e in normal use thereof. In various circumstances, the shaft assembly 1200 may have to be fully seated before the Hall effect sensor 4002 can detect the magnetic element 4007. While a Hall effect sensor 4002 can be utilized to detect the presence of the shaft assembly 200, any suitable system of sensors and/or switches can be utilized to detect whether a shaft assembly has been assembled to the handle 14, for example. In this way, further to the above, both the power circuits and the signal circuits to the connector 4000 can be powered down when a shaft assembly is not installed to the handle 14 and powered up when a shaft assembly is installed to the handle 14.

In various embodiments, any number of magnetic sensing elements may be employed to detect whether a shaft assembly has been assembled to the handle 14, for example. For example, the technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

Referring to FIG. 59, the microcontroller 7004 may generally comprise a microprocessor ("processor") and one or more memory units operationally coupled to the processor. By executing instruction code stored in the memory, the processor may control various components of the surgical instrument, such as the motor, various drive systems, and/or a user display, for example. The microcontroller 7004 may be implemented using integrated and/or discrete hardware elements, software elements, and/or a combination of both. Examples of integrated hardware elements may include processors, microprocessors, microcontrollers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, microcontrollers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the microcontroller 7004 may include a hybrid circuit comprising discrete and integrated circuit elements or components on one or more substrates, for example.

Referring to FIG. 59, the microcontroller 7004 may be an LM 4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available. Other microcontrollers may be readily substituted for use with the present disclosure. Accordingly, the present disclosure should not be limited in this context.

As discussed above, the handle 14 and/or the shaft assembly 200 can include systems and configurations configured to prevent, or at least reduce the possibility of, the contacts of the handle electrical connector 4000 and/or the contacts of the shaft electrical connector 4010 from becoming shorted out when the shaft assembly 200 is not assembled, or completely assembled, to the handle 14. Referring to FIG. 3, the handle electrical connector 4000 can be at least partially recessed within a cavity 4009 defined in the handle frame 20. The six contacts 4001a-4001f of the electrical connector 4000 can be completely recessed within the cavity 4009. Such arrangements can reduce the possibility of an object accidentally contacting one or more of the contacts 4001a-4001f. Similarly, the shaft electrical connector 4010 can be positioned within a recess defined in the shaft chassis 240 which can reduce the possibility of an object accidentally contacting one or more of the contacts 4011a-4011f of the shaft electrical connector 4010. With regard to the particular embodiment depicted in FIG. 3, the shaft contacts 4011a-4011f can comprise male contacts. In at least one embodiment, each shaft contact 4011a-4011f can comprise a flexible projection extending therefrom which can be configured to engage a corresponding handle contact 4001a-4001f, for example. The handle contacts 4001a-4001f can comprise female contacts. In at least one embodiment, each handle contact 4001a-4001f can comprise a flat surface, for example, against which the male shaft contacts 4001a-4001f can wipe, or slide, against and maintain an electrically conductive interface therebetween. In various instances, the direction in which the shaft assembly 200 is assembled to the handle 14 can be parallel to, or at least substantially parallel to, the handle contacts 4001a-4001f such that the shaft contacts 4011a-4011f slide against the handle contacts 4001a-4001f when the shaft assembly 200 is assembled to the handle 14. In various alternative embodiments, the handle contacts 4001a-4001f can comprise male contacts and the shaft contacts 4011a-4011f can comprise female contacts. In certain alternative embodiments, the handle contacts 4001a-4001f and the shaft contacts 4011a-4011f can comprise any suitable arrangement of contacts.

In various instances, the handle 14 can comprise a connector guard configured to at least partially cover the handle electrical connector 4000 and/or a connector guard configured to at least partially cover the shaft electrical connector 4010. A connector guard can prevent, or at least reduce the possibility of, an object accidentally touching the contacts of an electrical connector when the shaft assembly is not assembled to, or only partially assembled to, the handle. A connector guard can be movable. For instance, the connector guard can be moved between a guarded position in which it at least partially guards a connector and an unguarded position in which it does not guard, or at least guards less of, the connector. In at least one embodiment, a connector guard can be displaced as the shaft assembly is being assembled to the handle. For instance, if the handle comprises a handle connector guard, the shaft assembly can contact and displace the handle connector guard as the shaft assembly is being assembled to the handle. Similarly, if the shaft assembly comprises a shaft connector guard, the handle can contact and displace the shaft connector guard as the shaft assembly is being assembled to the handle. In various instances, a connector guard can comprise a door, for example. In at least one instance, the door can comprise a beveled surface which, when contacted by the handle or shaft, can facilitate the displacement of the door in a certain direction. In various instances, the connector guard can be translated and/or rotated, for example. In certain instances, a connector guard can comprise at least one film which covers the contacts of an electrical connector. When the shaft assembly is assembled to the handle, the film can become ruptured. In at least one instance, the male contacts of a connector can penetrate the film before engaging the corresponding contacts positioned underneath the film.

As described above, the surgical instrument can include a system which can selectively power-up, or activate, the contacts of an electrical connector, such as the electrical connector 4000, for example. In various instances, the contacts can be transitioned between an unactivated condition and an activated condition. In certain instances, the contacts can be transitioned between a monitored condition, a deactivated condition, and an activated condition. For instance, the microcontroller 7004, for example, can monitor the contacts 4001a-4001f when a shaft assembly has not been assembled to the handle 14 to determine whether one or more of the contacts 4001a-4001f may have been shorted. The microcontroller 7004 can be configured to apply a low voltage potential to each of the contacts 4001a-4001f and assess whether only a minimal resistance is present at each of the contacts. Such an operating state can comprise the monitored condition. In the event that the resistance detected at a contact is high, or above a threshold resistance, the microcontroller 7004 can deactivate that contact, more than one contact, or, alternatively, all of the contacts. Such an operating state can comprise the deactivated condition. If a shaft assembly is assembled to the handle 14 and it is detected by the microcontroller 7004, as discussed above, the microcontroller 7004 can increase the voltage potential to the contacts 4001a-4001f. Such an operating state can comprise the activated condition.

The various shaft assemblies disclosed herein may employ sensors and various other components that require electrical communication with the controller in the housing. These shaft assemblies generally are configured to be able to rotate relative to the housing necessitating a connection that facilitates such electrical communication between two or more components that may rotate relative to each other. When employing end effectors of the types disclosed herein, the connector arrangements must be relatively robust in nature while also being somewhat compact to fit into the shaft assembly connector portion.

FIGS. 19-22 depict one form of electric coupler or slip ring connector 1600 that may be employed with, for example an interchangeable shaft assembly 1200 or a variety of other applications that require electrical connections between components that rotate relative to each other. The shaft assembly 1200 may be similar to shaft assembly 200 described herein and include a closure tube or outer shaft 1260 and a proximal nozzle 1201 (the upper half of nozzle 1201 is omitted for clarity). In the illustrated example, the outer shaft 1260 is mounted on a shaft spine 1210 such that the outer tube 1260 may be selectively axially movable thereon. The proximal ends of the shaft spine 1210 and the outer tube 1260 may be rotatably coupled to a chassis 1240 for rotation relative thereto about a shaft axis SA-SA. As was discussed above, the proximal nozzle 1201 may include mounts or mounting lugs 1204 (FIG. 20) that protrude inwardly from the nozzle portions and extend through corresponding openings 1266 in the outer tube 1260 to be seated in corresponding recesses 1211 in the shaft spine 1210. Thus, to rotate the outer shaft 1260 and spine shaft 1210 and presumably an end effector (not shown) coupled thereto about the shaft axis SA-SA relative to the chassis 1240, the clinician simply rotates the nozzle 1201 as represented by arrows "R" in FIG. 19.

When sensors are employed at the end effector or at locations within or on the shaft assembly for example, conductors such as wires and/or traces (not shown) may be received or mounted within the outer tube 1260 or could even be routed along the outer tube 1260 from the sensors to a distal electrical component 1800 mounted within the nozzle 1201. Thus, the distal electrical component 1800 is rotatable with the nozzle 1201 about the shaft axis SA-SA. In the embodiment illustrated in FIG. 20, the electrical component 1800 comprises a connector, battery, etc. that includes contacts 1802, 1804, 1806, and 1808 that are laterally displaced from each other.

The slip ring connector 1600 further includes a mounting member 1610 that includes a cylindrical body portion 1612 that defines an annular mounting surface 1613. A distal flange 1614 may be formed on at least one end of the cylindrical body portion 1612. The body portion 1612 of the mounting member 1610 is sized to be non-rotatably mounted on a mounting hub 1241 on the chassis 1240. In the illustrated embodiment, one distal flange 1614 is provided on one end of the body portion 1612. A second flange 1243 is formed on the chassis 1240 such that when the body portion 1612 is fixedly (non-rotatably) mounted thereon, the second flange 1243 abuts the proximal end of the body portion 1612.

Figure 21:
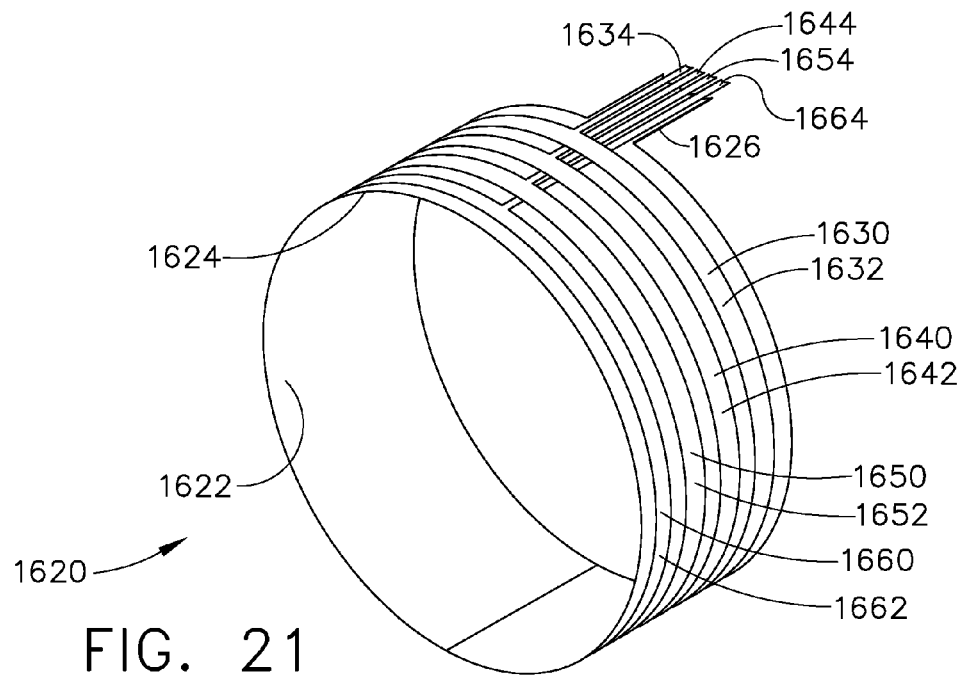
FIG. 21 is a perspective view of circuit trace assembly.
Figure 22:
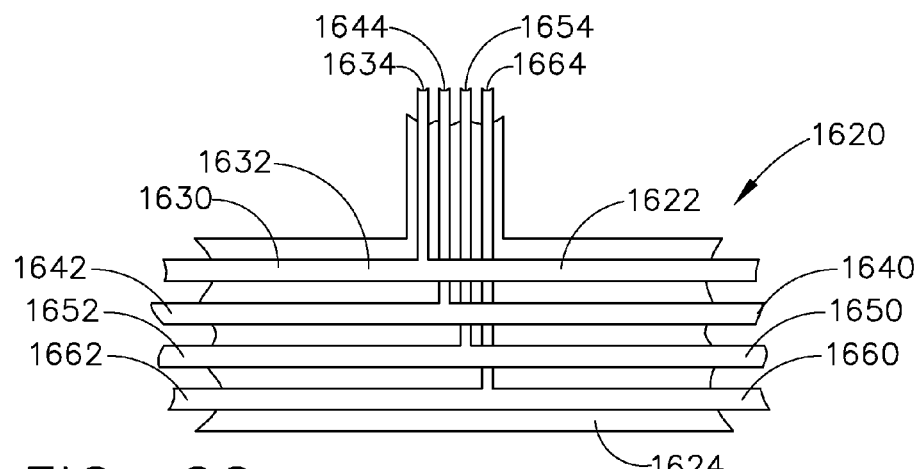
FIG. 22 is a plan view of a portion of the circuit trace assembly of FIG. 21.

The slip ring connector 1600 also employs a unique and novel annular circuit trace assembly 1620 that is wrapped around the annular mounting surface 1613 of the body portion 1612 such that it is received between the first and second flanges 1614 and 1243. Referring now to FIGS. 21 and 22, the circuit trace assembly 1620 may comprise an adhesive-backed flexible substrate 1622 that may be wrapped around the circumference of the body portion 1612 (i.e., the annular mounting surface 1613). Prior to being wrapped around the body portion 1612, the flexible substrate 1622 may have a "T-shape" with a first annular portion 1624 and a lead portion 1626. As can also be seen in FIGS. 19-21, the circuit trace assembly 1620 may further include circuit traces 1630, 1640, 1650, 1660 that may comprise, for example, electrically-conductive gold-plated traces. However, other electrically-conductive materials may also be used. Each electrically-conductive circuit trace includes an "annular portion" that will form an annular part of the trace when the substrate is wrapped around the body portion 1612 as well as another "lead portion" that extends transversely from or perpendicular from the annular portion. More specifically, referring to FIG. 22, first electrically-conductive circuit trace 1630 has a first annular portion 1632 and first lead portion 1634. The second electrically-conductive circuit trace 1640 has a second annular portion 1642 and a second lead portion 1644 extending transversely or perpendicularly therefrom. The third electrically conductive circuit trace 1650 has a third annular portion 1652 and a third lead portion 1654 extending transversely or perpendicularly therefrom. The fourth electrically-conductive circuit trace has a fourth annular portion 1662 and a fourth lead portion 1664 extending transversely or perpendicularly therefrom. The electrically-conductive circuit traces 1630, 1640, 1650, 1660 may be applied to the flexible substrate 1622 while the substrate is in a planar orientation (i.e., prior to being wrapped onto the annular body portion 1612 of the mounting member 1610) using conventional manufacturing techniques. As can be seen in FIG. 22, the annular portions 1632, 1642, 1652, 1662 are laterally displaced from each other. Likewise, the lead portions 1634, 1644, 1654, 1664 are laterally displaced from each other.

When the circuit trace assembly 1620 is wrapped around the annular mounting surface 1613 and attached thereto by adhesive, double-stick tape, etc., the ends of the portion of the substrate that contains the annular portions 1632, 1642, 1652, 1664 are butted together such that the annular portions 1632, 1642, 1652, 1664 form discrete continuous annular electrically-conductive paths 1636, 1646, 1656, 1666, respectively that extend around the shaft axis SA-SA. Thus, the electrically-conductive paths 1636, 1646, 1656, and 1666 are laterally or axially displaced from each other along the shaft axis SA-SA. The lead portion 1626 may extend through a slot 1245 in the flange 1243 and be electrically coupled to a circuit board (see e.g., FIG. 7—circuit board 610) or other suitable electrical component(s).

In the depicted embodiment for example, the electrical component 1800 is mounted within the nozzle 1261 for rotation about the mounting member 1610 such that: contact 1802 is in constant electrical contact with the first annular electrically-conductive path 1636; contact 1804 is in constant electrical contact with the second annular electrically-conductive path 1646; contact 1806 is in constant electrical contact with the third annular electrically-conductive path 1656; and contact 1808 is in constant electrical contact with the fourth electrically-conductive path 1666. It will be understood however, that the various advantages of the slip ring connector 1600 may also be obtained in applications wherein the mounting member 1610 is supported for rotation about the shaft axis SA-SA and the electrical component 1800 is fixedly mounted relative thereto. It will be further appreciated that the slip ring connector 1600 may be effectively employed in connection with a variety of different components and applications outside the field of surgery wherein it is desirable to provide electrical connections between components that rotate relative to each other.

The slip ring connector 1600 comprises a radial slip ring that provides a conductive contact means of passing signal(s) and power to and from any radial position and after shaft rotation. In applications wherein the electrical component comprises a battery contact, the battery contact position can be situated relative to the mounting member to minimize any tolerance stack up between those components. The coupler arrangement may represent a low cost coupling arrangement that can be assembled with minimal manufacturing costs. The gold plated traces may also minimize the likelihood of corrosion. The unique and novel contact arrangement facilitates complete clockwise and counter-clockwise rotation about the shaft axis SA-SA while remaining in electrical contact with the corresponding annular electrically-conductive paths.

Figure 23:
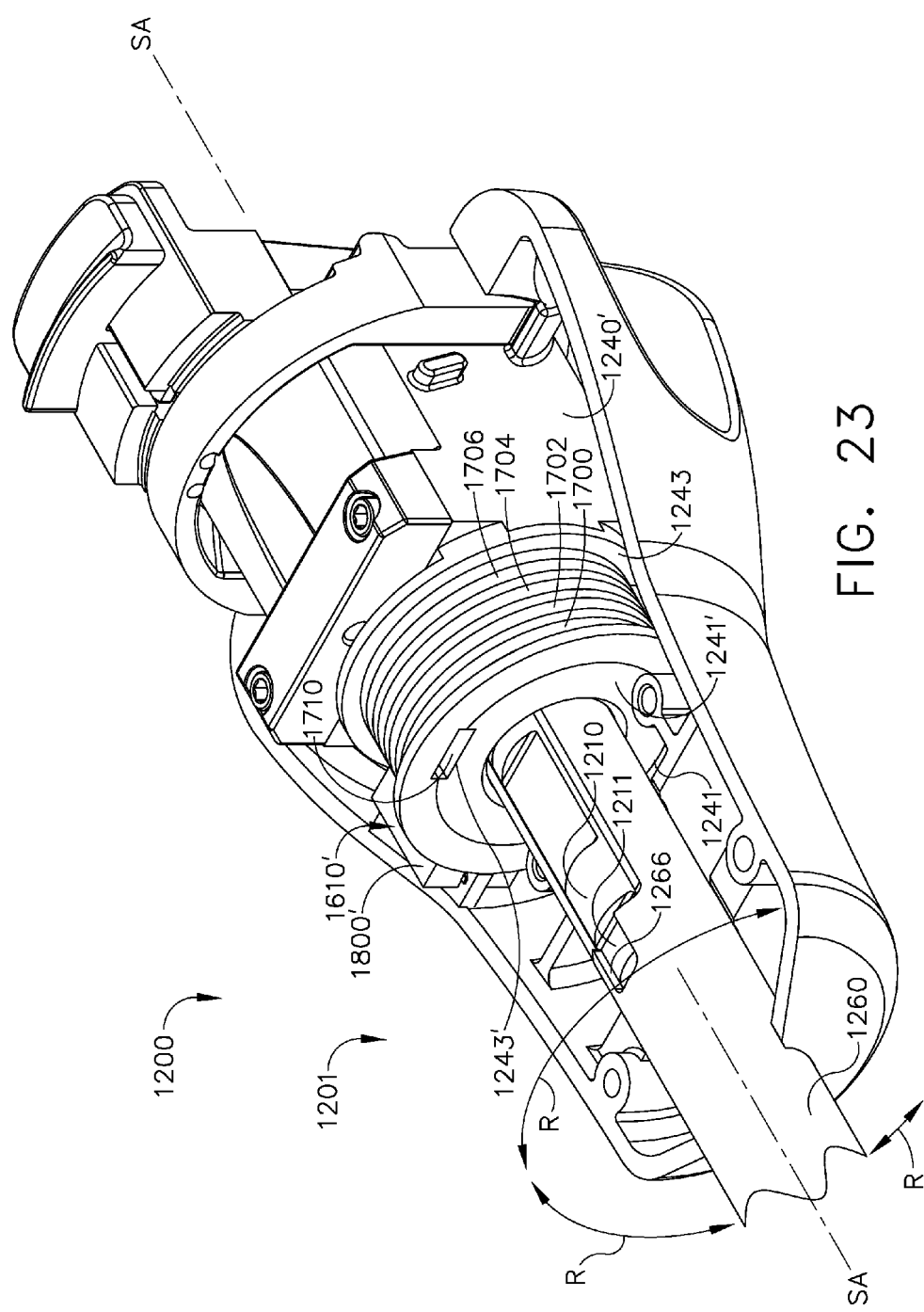
FIG. 23 is a perspective view of a portion of another interchangeable shaft assembly showing another electrical coupler arrangement.
Figure 24:
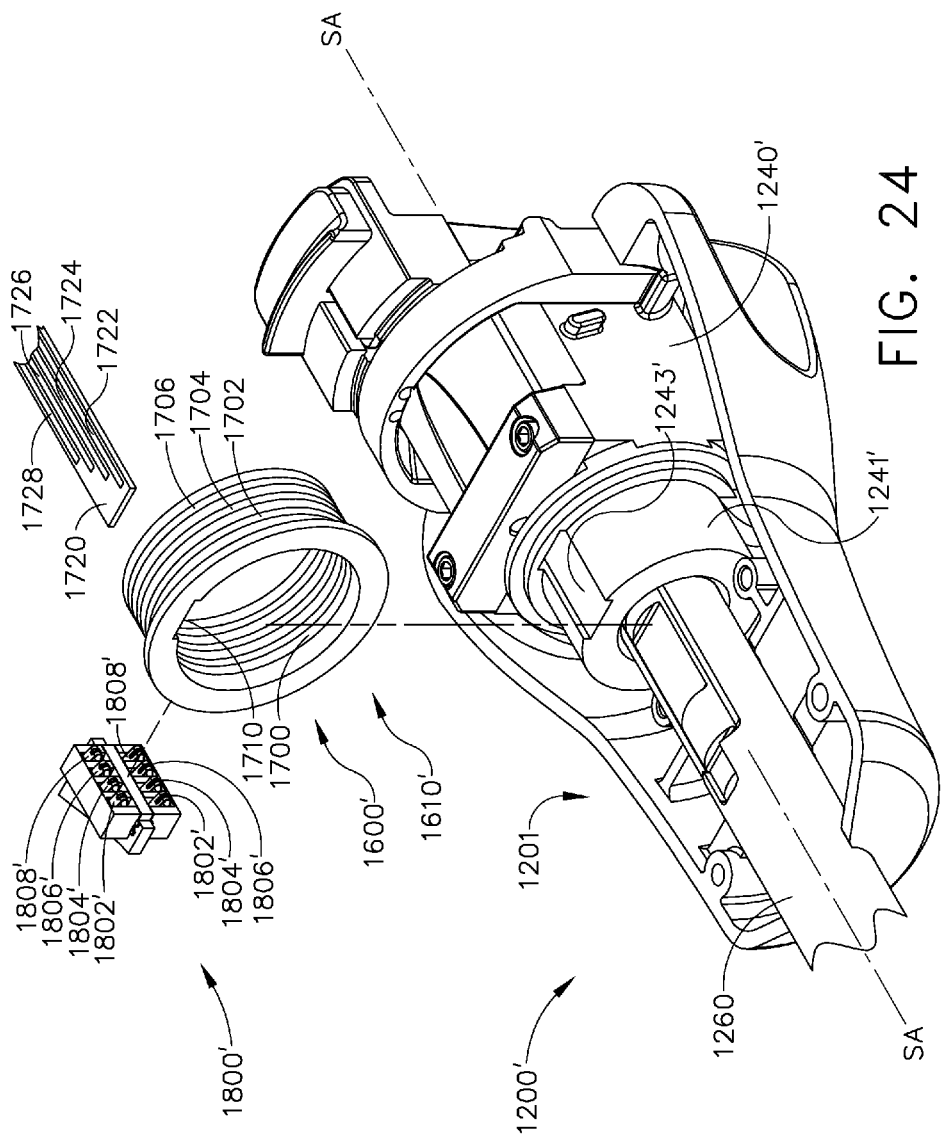
FIG. 24 is an exploded assembly view of portions of the interchangeable shaft assembly and electrical coupler of FIG. 23.
Figure 25:
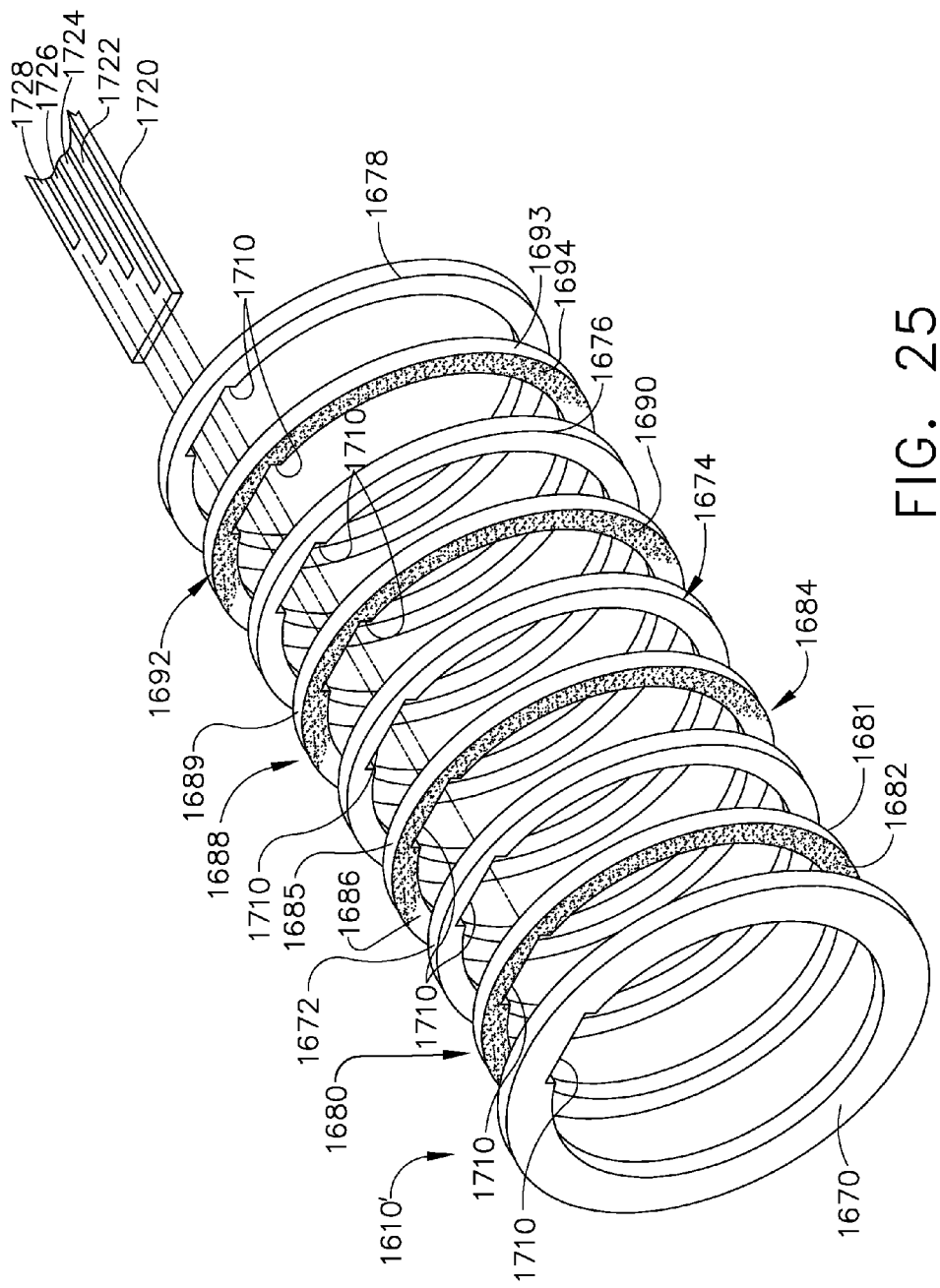
FIG. 25 is an exploded slip ring assembly of the electrical coupler of FIGS. 23 and 24.

FIGS. 23-25 depict one form of electric coupler or slip ring connector 1600' that may be employed with, for example an interchangeable shaft assembly 1200' or a variety of other applications that require electrical connections between components that rotate relative to each other. The shaft assembly 1200' may be similar to shaft assembly 1200 described herein and include a closure tube or outer shaft 1260 and a proximal nozzle 1201 (the upper half of nozzle 1201 is omitted for clarity). In the illustrated example, the outer shaft 1260 is mounted on a shaft spine 1210 such that the outer tube 1260 may be selectively axially movable thereon. The proximal ends of the shaft spine 1210 and the outer tube 1260 may be rotatably coupled to a chassis 1240' for rotation relative thereto about a shaft axis SA-SA. As was discussed above, the proximal nozzle 1201 may include mounts or mounting lugs that protrude inwardly from the nozzle portions and extend through corresponding openings 1266 in the outer tube 1260 to be seated in corresponding recesses 1211 in the shaft spine 1210. Thus, to rotate the outer shaft 1260 and spine shaft 1210 and presumably an end effector (not shown) coupled thereto about the shaft axis SA-SA relative to the chassis 1240', the clinician simply rotates the nozzle 1201 as represented by arrows "R" in FIG. 23.

When sensors are employed at the end effector or at locations within or on the shaft assembly for example, conductors such as wires and/or traces (not shown) may be received or mounted within the outer tube 1260 or could even be routed along the outer tube 1260 from the sensors to a distal electrical component 1800' mounted within the nozzle 1201. Thus, the distal electrical component 1800' is rotatable with the nozzle 1201 and the wires/traces attached thereto. In the embodiment illustrated in FIG. 23, the electrical component 1800 comprises a connector, battery, etc. that includes contacts 1802', 1804', 1806', 1808' that are laterally displaced from each other.

The slip ring connector 1600' further includes a laminated slip ring assembly 1610' that is fabricated from a plurality of conductive rings that are laminated together. More specifically and with reference to FIG. 25, one form of slip ring assembly 1610' may comprise a first non-electrically conductive flange 1670 that forms a distal end of the slip ring assembly 1610'. The flange 1670 may be fabricated from a high-heat resistant material, for example. A first electrically conductive ring 1680 is positioned immediately adjacent the first flange 1670. The first electrically conductive ring 1680 may comprise a first copper ring 1681 that has a first gold plating 1682 thereon. A second non-electrically conductive ring 1672 is adjacent to the first electrically-conductive ring 1680. A second electrically-conductive ring 1684 is adjacent to the second non-electrically-conductive ring 1672. The second electrically-conductive ring 1684 may comprise a second copper ring 1685 that has a second gold plating 1686 thereon. A third non-electrically-conductive ring 1674 is adjacent to the second electrically-conductive ring 1684. A third electrically conductive ring 1688 is adjacent to the third non-electrically conductive ring 1674. The third electrically conductive ring 1688 may comprise a third copper ring 1689 that has a third gold plating 1690 thereon. A fourth non-electrically conductive ring 1676 is adjacent to the third electrically-conductive ring 1688. A fourth electrically conductive ring 1692 is adjacent to the fourth non-electrically-conductive ring 1676. The fourth electrically-conductive ring 1692 is adjacent to the fourth non-electrically conductive ring 1676. A fifth non-electrically conductive ring 1678 is adjacent to the fourth electrically-conductive ring 1692 and forms the proximal end of the mounting member 1610'. The non-electrically conductive rings 1670, 1672, 1674, 1676, and 1678 may be fabricated from the same material. The first electrically-conductive ring 1680 forms a first annular electrically-conductive pathway 1700. The second electrically-conductive ring 1682 forms a second annular electrically-conductive pathway 1702 that is laterally or axially spaced from the first annular electrically-conductive pathway 1700. The third electrically-conductive ring 1688 forms a third annular electrically conductive pathway 1704 that is laterally or axially spaced from the second annular electrically-conductive pathway 1702. The fourth electrically-conductive ring 1692 forms a fourth annular electrically-conductive pathway 1706 that is laterally or axially spaced from the third annular electrically-conductive pathway 1704. The slip ring assembly 1610' comprises a one piece molded high temperature resistant, non-conductive material with molded in channels for electromagnetic forming (EMF-Magneformed) copper rings.

As can be seen in FIG. 24, the slip ring connector 1600' further includes a non-conductive transverse mounting member 1720 that is adapted to be inserted into axially-aligned notches 1710 in each of the rings 1670, 1680, 1672, 1684, 1674, 1688, 1676, 1692, and 1678. The transverse mounting member 1720 has a first circuit trace 1722 thereon that is adapted for electrical contact with the first annular electrically-conductive pathway 1700 when the transverse mounting member 1672 is mounted within the notches 1710. Likewise, a second circuit trace 1724 is printed on the transverse mounting member 1720 and is configured for electrical contact with the second annular electrically conductive pathway 1702. A third circuit trace 1726 is printed on the transverse mounting member 1720 and is configured for electrical contact with the third annular electrically-conductive pathway 1704. A fourth circuit trace 1728 is printed on the transverse mounting member 1720 and is configured for electrical contact with the fourth annular electrically-conductive pathway 1706.

In the arrangement depicted in FIGS. 23-25, the slip ring assembly 1610' is configured to be fixedly (non-rotatably) received on a mounting hub 1241' on the chassis 1240'. The transverse mounting member 1720 is received within groove 1243' formed in the mounting hub 1241' which acts as a keyway for the transverse mounting member 1720 and which serves to prevent the slip ring assembly 1610' from rotating relative to the mounting hub 1241'.

In the depicted embodiment for example, the electrical component 1800' is mounted within the nozzle 1201 for rotation about the slip ring assembly 1610' such that: contact 1802' is in constant electrical contact with the first annular electrically-conductive path 1700; contact 1804' is in constant electrical contact with the second annular electrically-conductive path 1702; contact 1806' is in constant electrical contact with the third annular electrically-conductive path 1704; and contact 1808' is in constant electrical contact with the fourth electrically-conductive path 1706. It will be understood however, that the various advantages of the slip ring connector 1600' may also be obtained in applications wherein the slip ring assembly 1610' is supported for rotation about the shaft axis SA-SA and the electrical component 1800' is fixedly mounted relative thereto. It will be further appreciated that the slip ring connector 1600' may be effectively employed in connection with a variety of different components and applications outside the field of surgery wherein it is desirable to provide electrical connections between components that rotate relative to each other.

The slip ring connector 1600' comprises a radial slip ring that provides a conductive contact means of passing signal(s) and power to and from any radial position and after shaft rotation. In applications wherein the electrical component comprises a battery contact, the battery contact position can be situated relative to the mounting member to minimize any tolerance stack-up between those components. The slip ring connector 1600' represents a low cost coupling arrangement that can be assembled with minimal manufacturing costs. The gold plated traces may also minimize the likelihood of corrosion. The unique and novel contact arrangement facilitates complete clockwise and counterclockwise rotation about the shaft axis while remaining in electrical contact with the corresponding annular electrically-conductive paths.

FIGS. 26-30 depict another form of electric coupler or slip ring connector 1600" that may be employed with, for example an interchangeable shaft assembly 1200" or a variety of other applications that require electrical connections between components that rotate relative to each other. The shaft assembly 1200" may be similar to shaft assemblies 1200 and/or 1200' described herein except for the differences noted below. The shaft assembly 1200" may include a closure tube or outer shaft 1260 and a proximal nozzle 1201 (the upper half of nozzle 1201 is omitted for clarity). In the illustrated example, the outer shaft 1260 is mounted on a shaft spine 1210 such that the outer tube 1260 may be selectively axially movable thereon. The proximal ends of the shaft spine 1210 and the outer tube 1260 may be rotatably coupled to a chassis 1240" for rotation relative thereto about a shaft axis SA-SA. As was discussed above, the proximal nozzle 1201 may include mounts or mounting lugs that protrude inwardly from the nozzle portions and extend through corresponding openings 1266 in the outer tube 1260 to be seated in corresponding recesses 1211 in the shaft spine 1210. Thus, to rotate the outer shaft 1260 and spine shaft 1210 and presumably an end effector (not shown) coupled thereto about the shaft axis SA-SA relative to the chassis 1240", the clinician simply rotates the nozzle 1201.

When sensors are employed at the end effector or at locations within or on the shaft assembly for example, conductors such as wires and/or traces (not shown) may be received or mounted within the outer tube 1260 or could even be routed along the outer tube 1260 from the sensors to a distal electrical component 1800''' mounted within the nozzle 1201. In the illustrated embodiment, for example, the electrical component 1800" is mounted in the nozzle 1201 such that it is substantially aligned with the shaft axis SA-SA. The distal electrical component 1800" is rotatable about the shaft axis SA-SA with the nozzle 1201 and the wires/traces attached thereto. The electrical component 1800" may comprise a connector, a battery, etc. that includes four contacts 1802", 1804", 1806", 1808" that are laterally displaced from each other.

The slip ring connector 1600" further includes a slip ring assembly 1610" that includes a base ring 1900 that is fabricated from a non-electrically conductive material and has a central mounting bore 1902 therethrough. The mounting bore 1902 has a flat surface 1904 and is configured for non-rotational attachment to a mounting flange assembly 1930 that is supported at a distal end of the chassis 1240". A distal side 1905 of the base ring 1900 has a series of concentric electrical-conductive rings 1906, 1908, 1910, and 1912 attached or laminated thereto. The rings 1906, 1908, 1910, and 1912 may be attached to the base ring 1900 by any suitable method.

Figure 28:
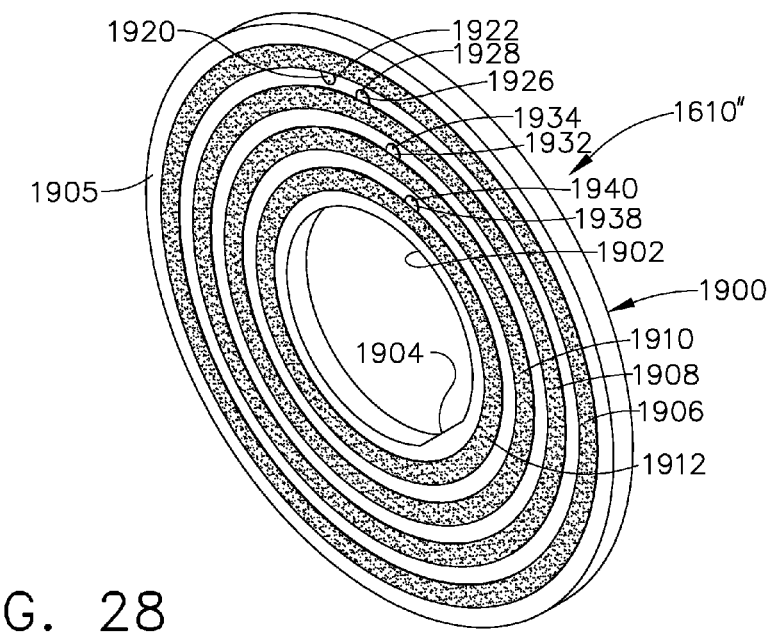
FIG. 28 is a front perspective view of a portion of the slip ring assembly of the electrical coupler of FIGS. 26 and 27.
Figure 29:
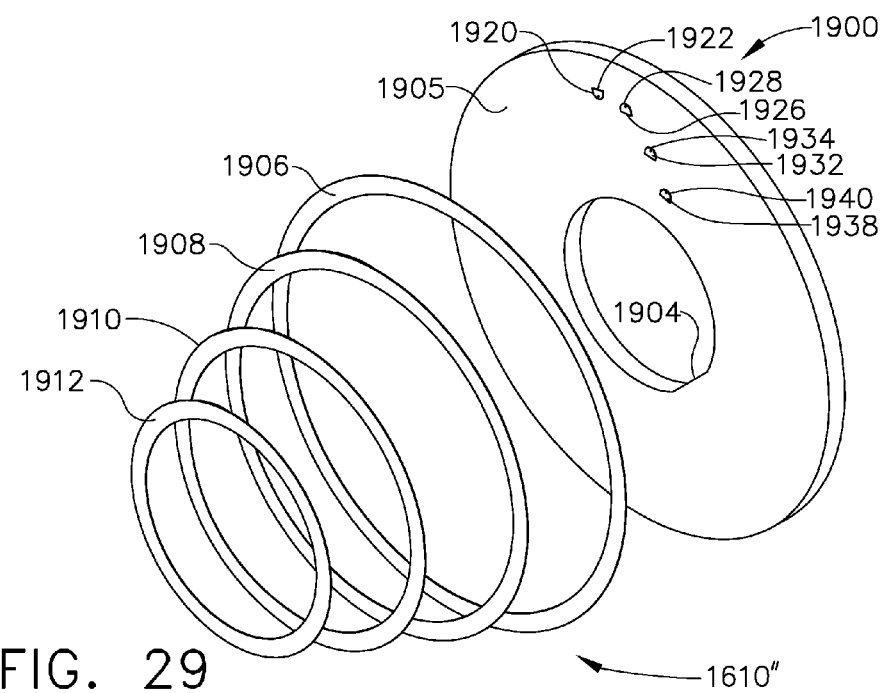
FIG. 29 is an exploded assembly view of the slip ring assembly portion of FIG. 28.
Figure 30:
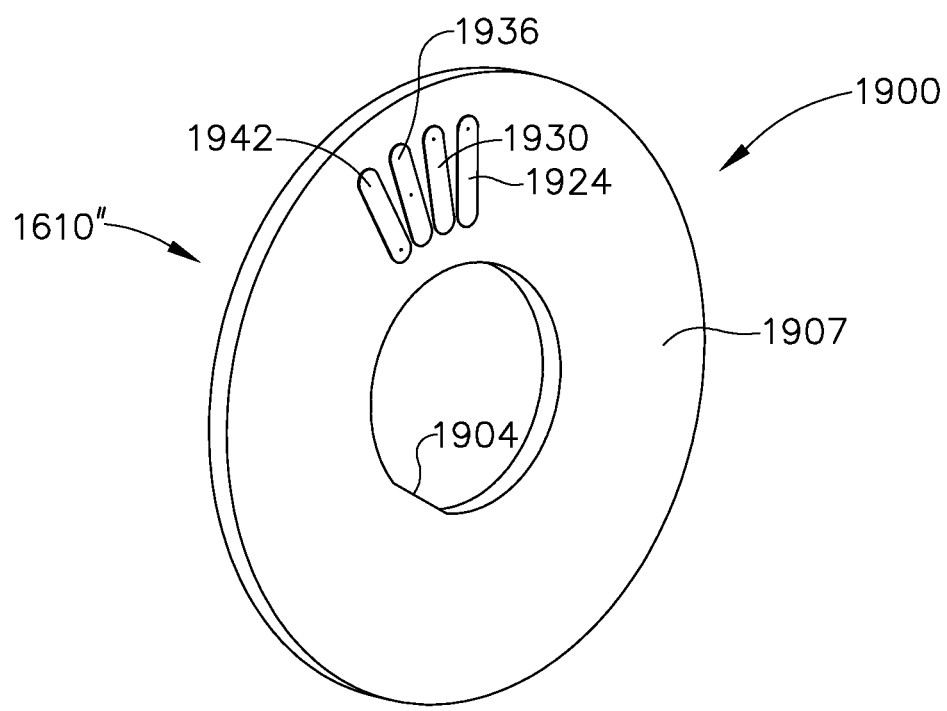
FIG. 30 is a rear perspective view of the portion of slip ring assembly of FIGS. 28 and 29.

The base ring 1900 may further include a circuit trace extending therethrough that is coupled to each of the electrically-conductive rings 1906, 1908, 1910, and 1912. Referring now to FIGS. 28-30, a first circuit trace 1922 extends through a first hole 1920 in the base ring 1900 and is coupled to the first electrically conductive ring 1906. The first circuit trace 1922 terminates in a first proximal contact portion 1924 on the proximal side 1907 of the base ring 1900. See FIG. 30. Similarly, a second circuit trace 1928 extends through a second hole 1926 in the base ring 1900 and is coupled to the second electrically-conductive ring 1908. The second circuit trace 1928 terminates in a second proximal contact 1930 on the proximal side 1907 of the base ring 1900. A third circuit trace 1934 extends through a third hole 1932 in the base ring and is attached to the third electrically-conductive ring 1910. The third circuit trace 1934 terminates in a third proximal contact 1936 on the proximal side 1907 of the base ring. A fourth circuit trace 1940 extends through a fourth hole 1938 in the base ring 1900 to be attached to the fourth electrically-conductive ring 1912. The fourth circuit trace 1940 terminates in a fourth proximal contact 1942 on the proximal side 1907 of the base ring 1900.

Figure 26:
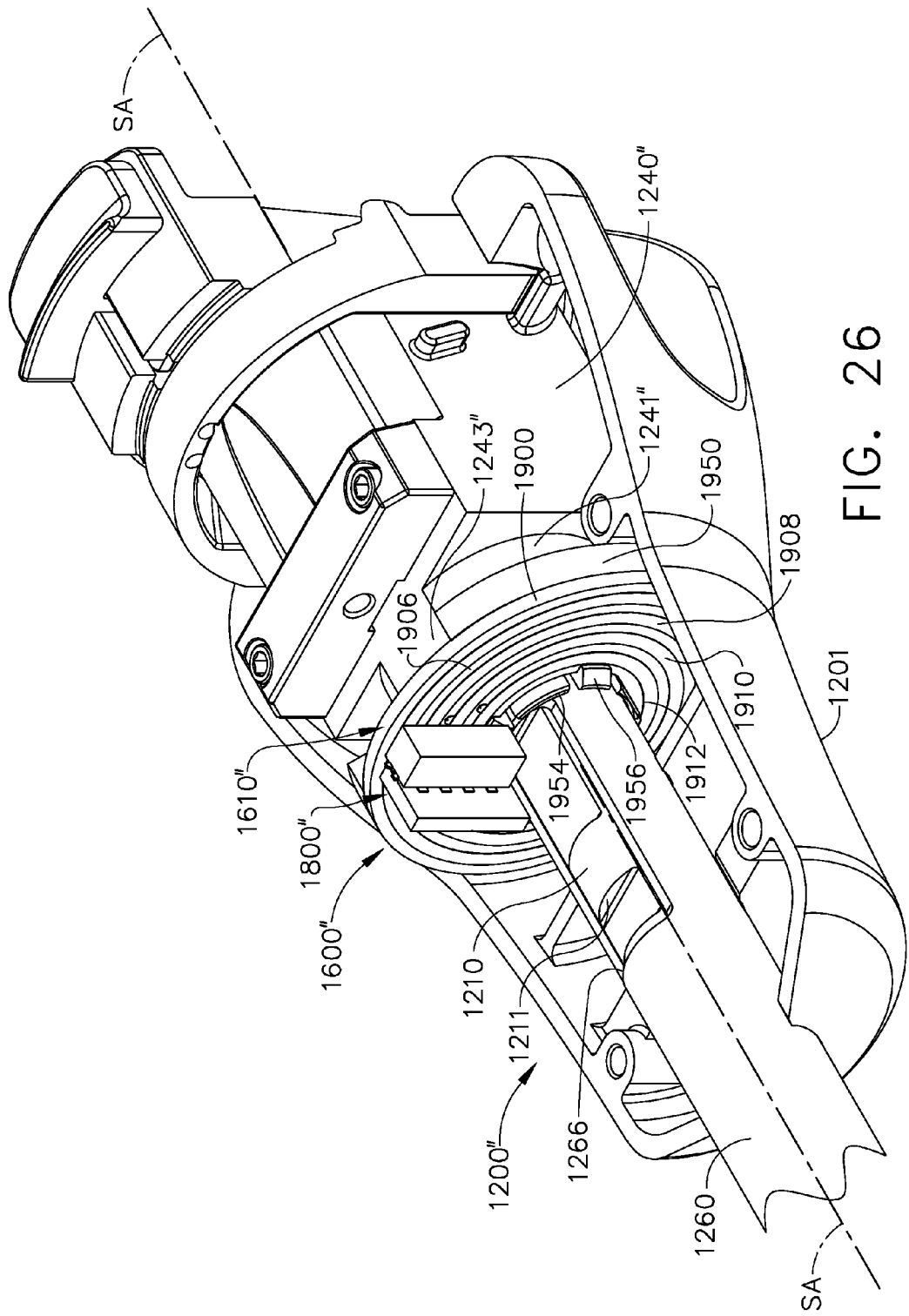
FIG. 26 is a perspective view of a portion of another interchangeable shaft assembly showing another electrical coupler arrangement.
Figure 27:
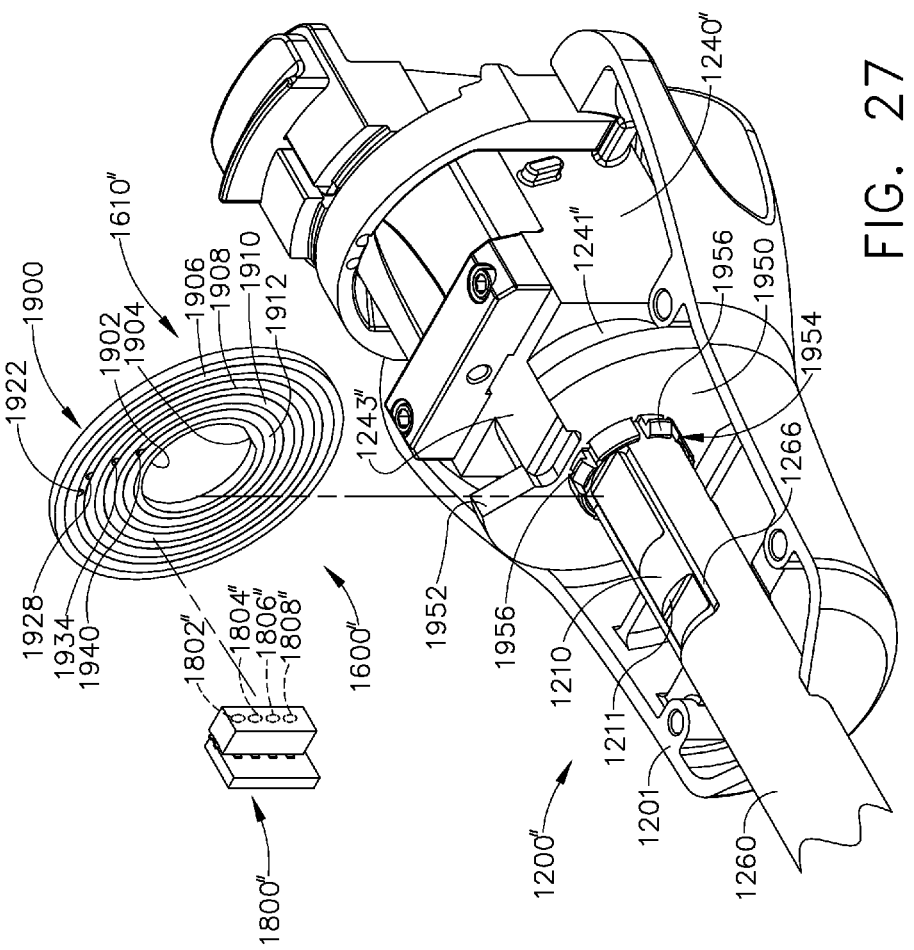
FIG. 27 is an exploded assembly view of portions of the interchangeable shaft assembly and electrical coupler of FIG. 26.

Referring now to FIG. 27, the base ring 1900 is configured to be non-rotatably supported within the nozzle 1201 by a mounting flange 1950 that is non-rotatably coupled to the mounting hub portion 1241" of the chassis 1240". The mounting hub portion 1241" may be formed with a flat surface 1243" for supporting a transverse mounting member of the type, for example, described above that includes a plurality (preferably four) leads that may be coupled to, for example, a circuit board or other corresponding electrical components supported on the chassis in the various manners and arrangements described herein as well as in U.S. patent application Ser. No. 13/803,086. The transverse support member has been omitted for clarity in FIGS. 26 and 27. However, as can be seen in FIGS. 26 and 27, the mounting flange 1950 has a notch 1952 therein that is adapted to engage a portion of the flat surface 1243" on the mounting hub portion 1241". As can be seen in FIG. 27, the mounting flange 1950 may further include a flange hub portion 1954 that comprises a series of spring tabs 1956 that serve to fixedly attach the base ring 1900 to the mounting flange 1950. It will be understood that the closure tube 1260 and spine 1210 extend through the flange hub 1954 and are rotatable relative thereto with the nozzle 1201.

In the depicted embodiment for example, the electrical component 1800" is mounted within the nozzle 1201 for rotation about the slip ring assembly 1610" such that, for example, contact 1802" in the component 1800" is in constant electrical contact with rings 1906; contact 1804" is in contact with ring 1908; contact 1806" is in contact with ring 1910; and contact 1808" is in contact with ring 1912 even when the nozzle 1201 is rotated relative to the chassis 1240". It will be understood however, that the various advantages of the slip ring connector 1600" may also be obtained in applications wherein the slip ring assembly 1610" is supported for rotation about the shaft axis SA-SA and the electrical component 1800" is fixedly mounted relative thereto. It will be further appreciated that the slip ring connector 1600" may be effectively employed in connection with a variety of different components and applications outside the field of surgery wherein it is desirable to provide electrical connections between components that rotate relative to each other.

The slip ring connector 1600" comprises a radial slip ring that provides a conductive contact means of passing signal(s) and power to and from any radial position and after shaft rotation. In applications wherein the electrical component comprises a battery contact, the battery contact position can be situated relative to the mounting member to minimize any tolerance stack-up between those components. The slip ring connector 1600" represents a low cost and compact coupling arrangement that can be assembled with minimal manufacturing costs. The unique and novel contact arrangement facilitates complete clockwise and counterclockwise rotation about the shaft axis while remaining in electrical contact with the corresponding annular electrically-conductive rings.

Figure 31:
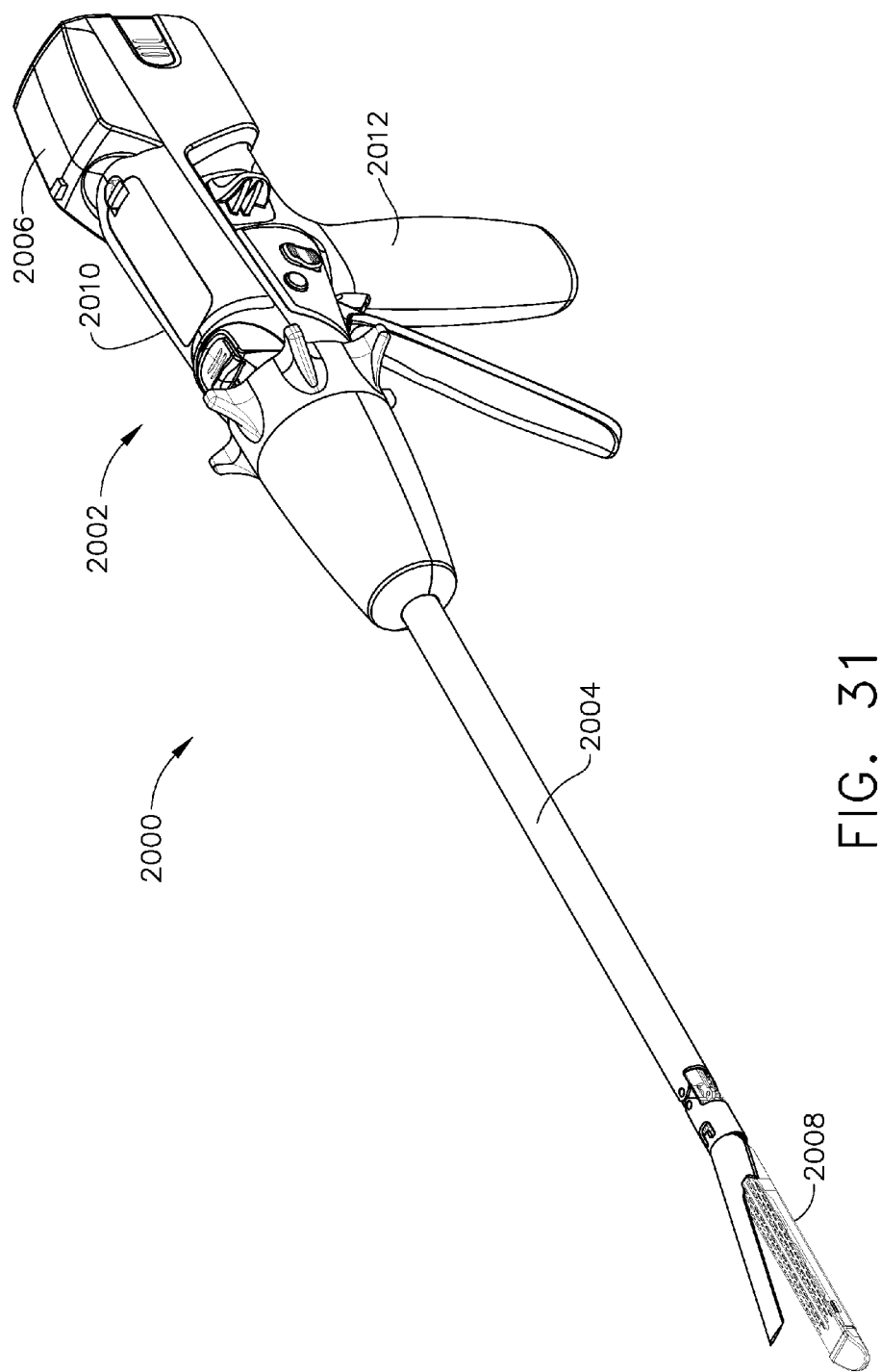
FIG. 31 is a perspective view of a surgical instrument comprising a power assembly, a handle assembly, and an interchangeable shaft assembly.
Figure 32:
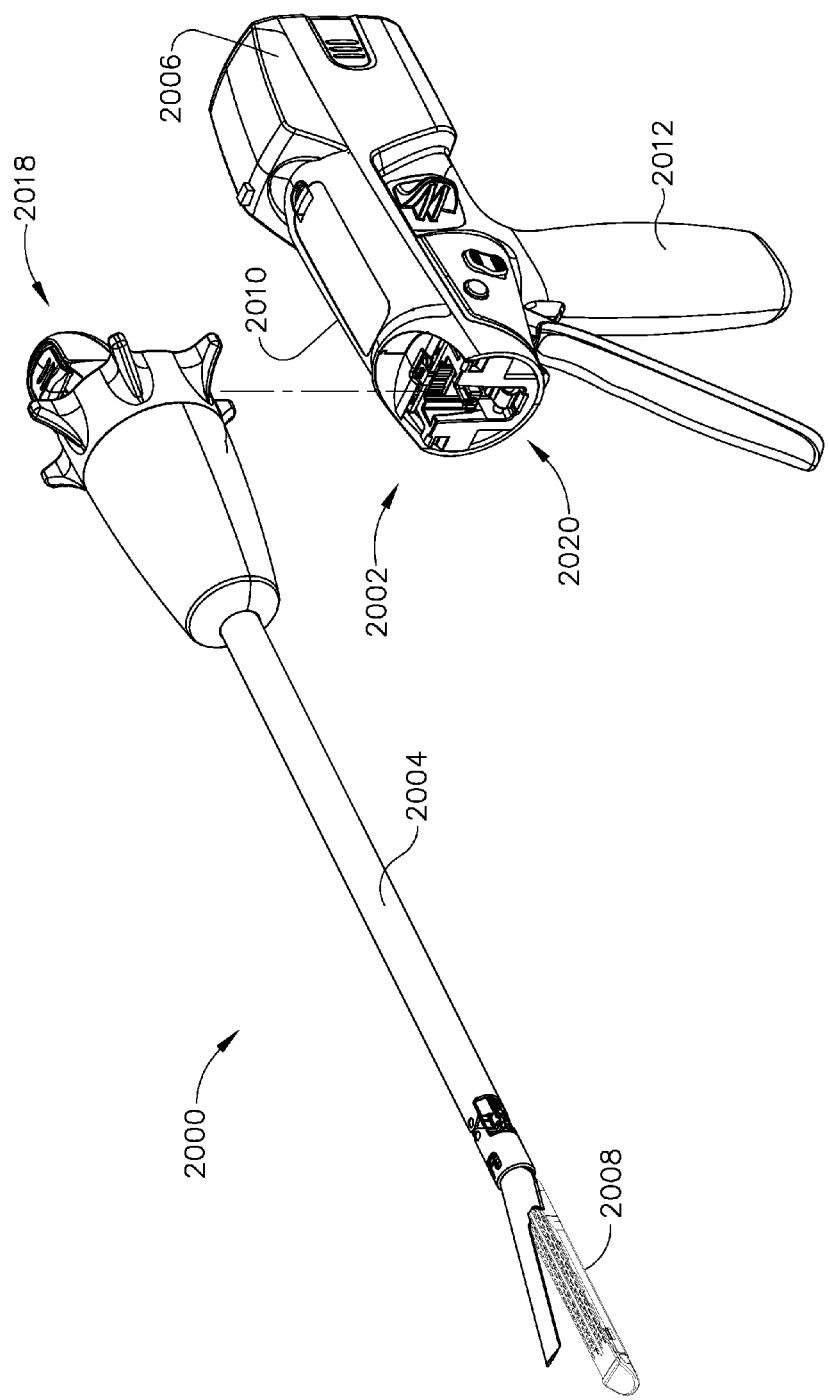
FIG. 32 is perspective view of the surgical instrument of FIG. 31 with the interchangeable shaft assembly separated from the handle assembly.

FIGS. 31-36 generally depict a motor-driven surgical fastening and cutting instrument 2000. As illustrated in FIGS. 31 and 32, the surgical instrument 2000 may include a handle assembly 2002, a shaft assembly 2004, and a power assembly 2006 (or "power source" or "power pack"). The shaft assembly 2004 may include an end effector 2008 which, in certain circumstances, can be configured to act as an endocutter for clamping, severing, and/or stapling tissue, although, in other instances, different types of end effectors may be used, such as end effectors for other types of surgical devices, graspers, cutters, staplers, clip appliers, access devices, drug/gene therapy devices, ultrasound devices, RF device, and/or laser devices, for example. Several RF devices may be found in U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL FASTENING AND CUTTING INSTRUMENT HAVING RF ELECTRODES, filed Feb. 14, 2008. The entire disclosures of U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL FASTENING AND CUTTING INSTRUMENT HAVING RF ELECTRODES, filed Feb. 14, 2008, are incorporated herein by reference in their entirety.

Referring primarily to FIGS. 32 and 33, the handle assembly 2002 can be employed with a plurality of interchangeable shaft assemblies such as, for example, the shaft assembly 2004. Such interchangeable shaft assemblies may comprise surgical end effectors such as, for example, the end effector 2008 that can be configured to perform one or more surgical tasks or procedures. Examples of suitable interchangeable shaft assemblies are disclosed in U.S. Provisional Patent Application Ser. No. 61/782,866, entitled CONTROL SYSTEM OF A SURGICAL INSTRUMENT, filed Mar. 14, 2013. The entire disclosure of U.S. Provisional Patent Application Ser. No. 61/782,866, entitled CONTROL SYSTEM OF A SURGICAL INSTRUMENT, filed Mar. 14, 2013, is hereby incorporated by reference herein in its entirety.

Referring primarily to FIG. 32, the handle assembly 2002 may comprise a housing 2010 that consists of a handle 2012 that may be configured to be grasped, manipulated and actuated by a clinician. However, it will be understood that the various unique and novel arrangements of the various forms of interchangeable shaft assemblies disclosed herein also may be effectively employed in connection with robotically-controlled surgical systems. Thus, the term "housing" also may encompass a housing or similar portion of a robotic system that houses or otherwise operably supports at least one drive system that is configured to generate and apply at least one control motion which could be used to actuate the interchangeable shaft assemblies disclosed herein and their respective equivalents. For example, the interchangeable shaft assemblies disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719. U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719 is incorporated by reference herein in its entirety.

Referring again to FIG. 32, the handle assembly 2002 may operably support a plurality of drive systems therein that can be configured to generate and apply various control motions to corresponding portions of the interchangeable shaft assembly that is operably attached thereto. For example, the handle assembly 2002 can operably support a first or closure drive system, which may be employed to apply closing and opening motions to the shaft assembly 2004 while operably attached or coupled to the handle assembly 2002. In at least one form, the handle assembly 2002 may operably support a firing drive system that can be configured to apply firing motions to corresponding portions of the interchangeable shaft assembly attached thereto.

Figure 33A:
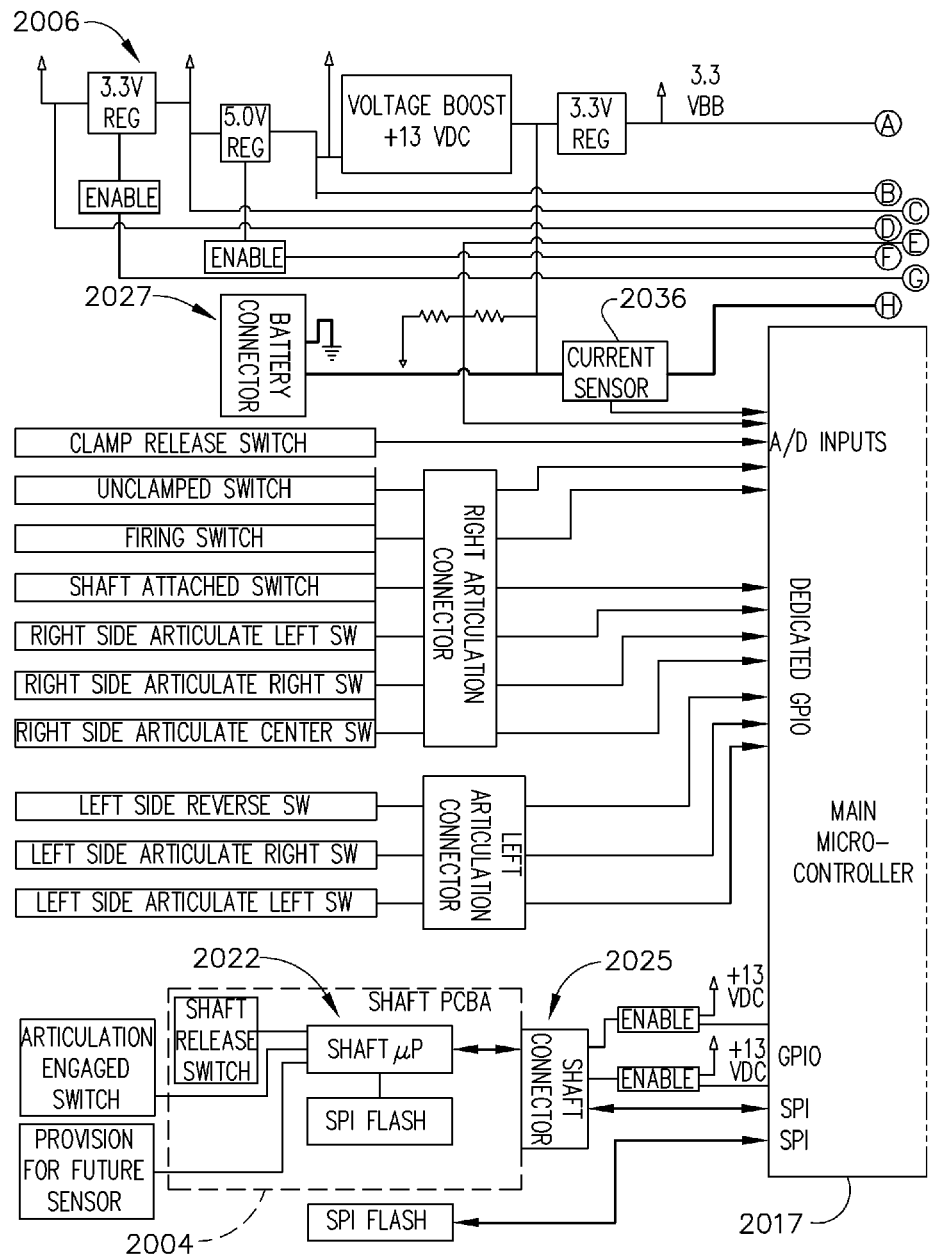
FIGS. 33A and 33B, is a circuit diagram of the surgical instrument of FIG. 31.
Figure 33B:
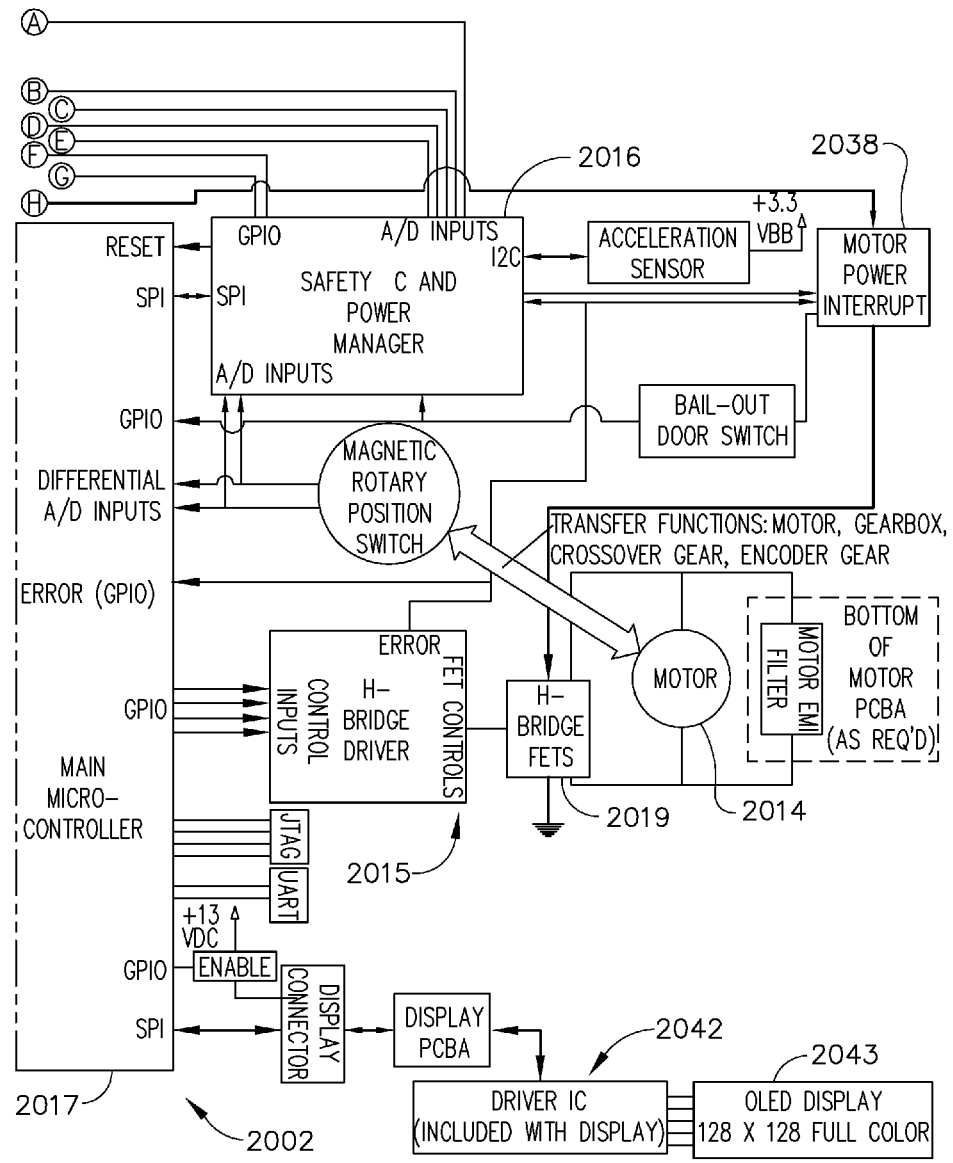

Referring primarily to FIGS. 33A and 33B, the handle assembly 2002 may include a motor 2014 which can be controlled by a motor driver 2015 and can be employed by the firing system of the surgical instrument 2000. In various forms, the motor 2014 may be a DC brushed driving motor having a maximum rotation of, approximately, 25,000 RPM, for example. In other arrangements, the motor 2014 may include a brushless motor, a cordless motor, a synchronous motor, a stepper motor, or any other suitable electric motor. In certain circumstances, the motor driver 2015 may comprise an H-Bridge FETs 2019, as illustrated in FIGS. 33A and 33B, for example. The motor 2014 can be powered by the power assembly 2006 (FIG. 35), which can be releasably mounted to the handle assembly 2002, power assembly 2006 being configured to supply control power to the surgical instrument 2000. The power assembly 2006 may comprise a battery 2007 (FIG. 36) which may include a number of battery cells connected in series that can be used as the power source to power the surgical instrument 2000. In such configuration, the power assembly 2006 may be referred to as a battery pack. In certain circumstances, the battery cells of the power assembly 2006 may be replaceable and/or rechargeable. In at least one example, the battery cells can be Lithium-Ion batteries which can be separably couplable to the power assembly 2006.

Examples of drive systems and closure systems that are suitable for use with the surgical instrument 2000 are disclosed in U.S. Provisional Patent Application Ser. No. 61/782,866, entitled CONTROL SYSTEM OF A SURGICAL INSTRUMENT, and filed Mar. 14, 2013, the entire disclosure of which is incorporated by reference herein in its entirety. For example, the electric motor 2014 can include a rotatable shaft (not shown) that may operably interface with a gear reducer assembly that can be mounted in meshing engagement with a set, or rack, of drive teeth on a longitudinally-movable drive member. In use, a voltage polarity provided by the battery 2007 (FIG. 36) can operate the electric motor 2014 to drive the longitudinally-movable drive member to effectuate the end effector 2008. For example, the motor 2014 can be configured to drive the longitudinally-movable drive member to advance a firing mechanism to fire staples into tissue captured by the end effector 2008 from a staple cartridge assembled with the end effector 2008 and/or advance a cutting member 2011 (FIG. 34) to cut tissue captured by the end effector 2008, for example.

Figure 35:
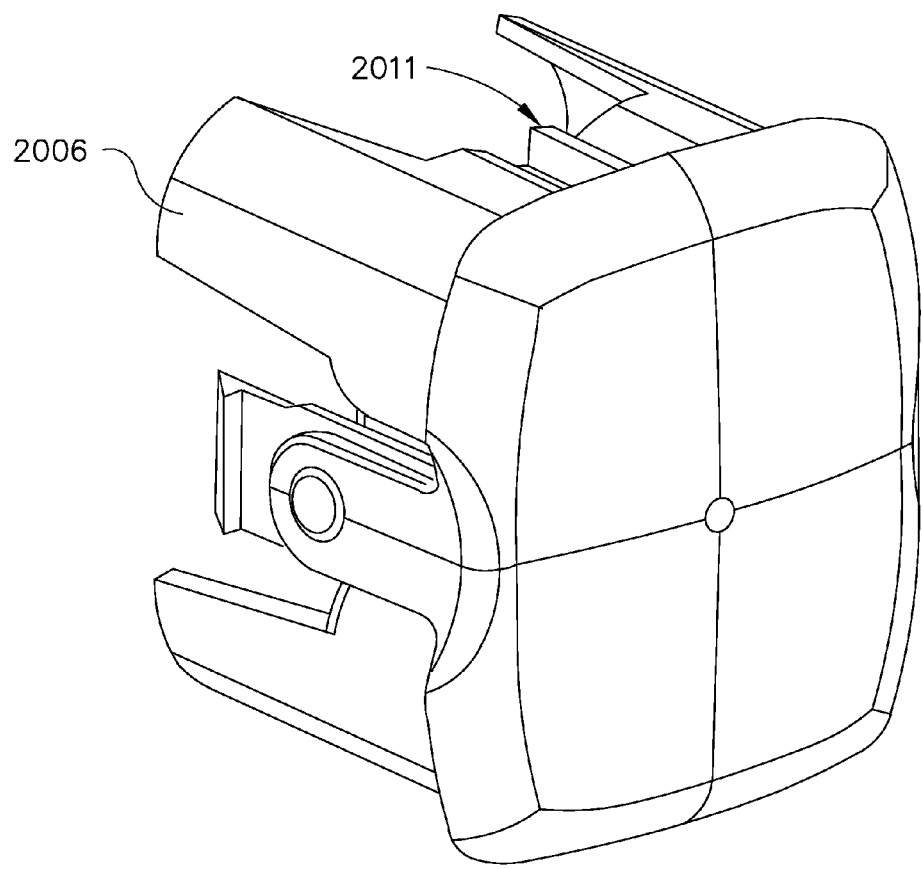
FIG. 35 is a perspective view of the power assembly of the surgical instrument of FIG. 31 separated from the handle assembly.

In certain circumstances, the surgical instrument 2000 may comprise a lockout mechanism to prevent a user from coupling incompatible handle assemblies and power assemblies. For example, as illustrated in FIG. 35, the power assembly 2006 may include a mating element 2011. In certain circumstances, the mating element 2011 can be a tab extending from the power assembly 2006. In certain instances, the handle assembly 2002 may comprise a corresponding mating element (not shown) for mating engagement with the mating element 2011. Such an arrangement can be useful in preventing a user from coupling incompatible handle assemblies and power assemblies.

Figure 34:
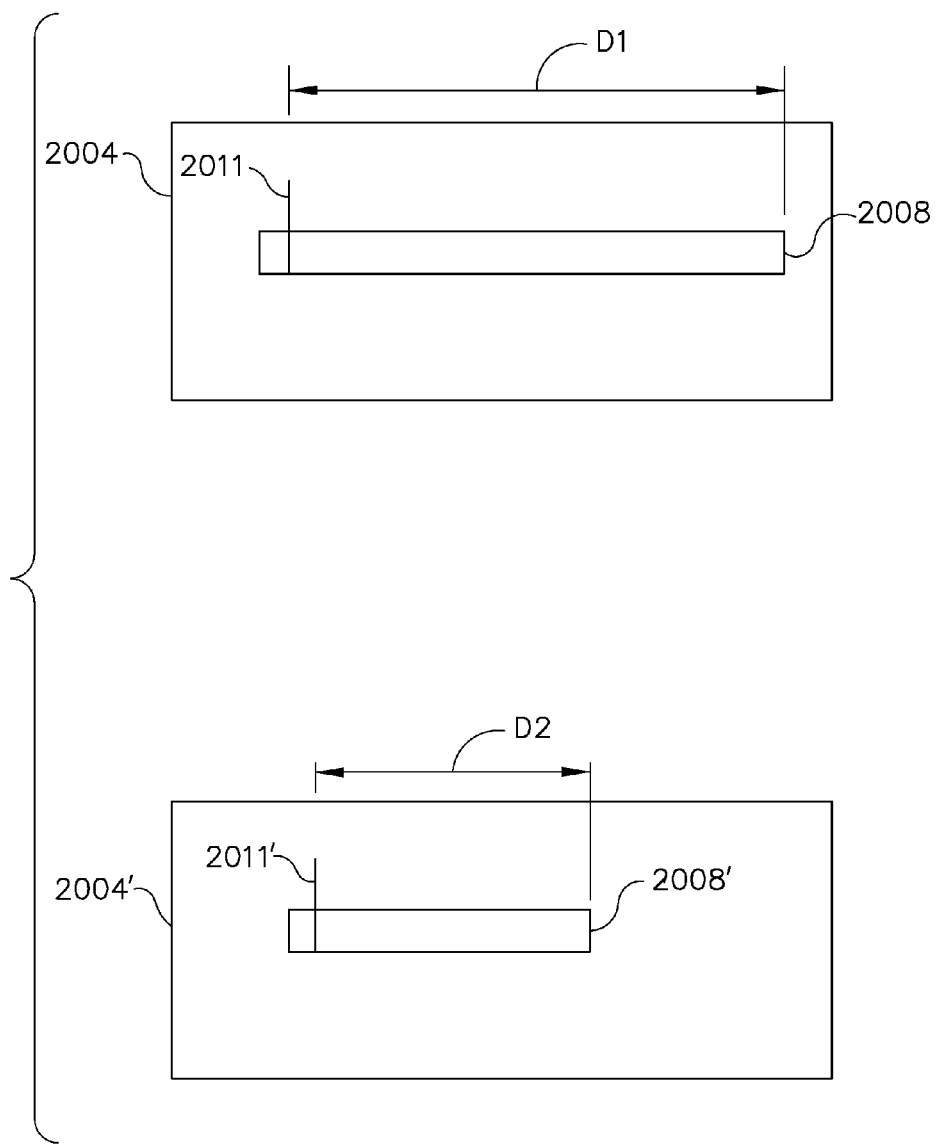
FIG. 34 is a block diagram of interchangeable shaft assemblies for use with the surgical instrument of FIG. 31.

The reader will appreciate that different interchangeable shaft assemblies may possess different power requirements. The power required to advance a cutting member through an end effector and/or to fire staples may depend, for example, on the distance traveled by the cutting member, the staple cartridge being used, and/or the type of tissue being treated. That said, the power assembly 2006 can be configured to meet the power requirements of various interchangeable shaft assemblies. For example, as illustrated in FIG. 34, the cutting member 2011 of the shaft assembly 2004 can be configured to travel a distance D1 along the end effector 2008. On the other hand, another interchangeable shaft assembly 2004' may include a cutting member 2011' which can be configured to travel a distance D2, different from the distance D1, along an end effector 2008' of the interchangeable shaft assembly 2004'. The power assembly 2006 can be configured to provide a first power output sufficient to power the motor 2014 to advance the cutting member 2011 the distance D1 while the interchangeable shaft assembly 2004 is coupled to the handle assembly 2002 and can be configured to provide a second power output, different from the first power output, which is sufficient to power the motor 2014 to advance the cutting member 2011' the distance D2 while the interchangeable shaft assembly 2004' is coupled to the handle assembly 2002, for example. As illustrated in FIGS. 33A and 33B and as described below in greater detail, the power assembly 2006 may include a power management controller 2016 (FIG. 36) which can be configured to modulate the power output of the power assembly 2006 to deliver a first power output to power the motor 2014 to advance the cutting member 2011 the distance D1 while the interchangeable shaft assembly 2004 is coupled to the handle assembly 2002 and to deliver a second power output to power the motor 2014 to advance the cutting member 2011' the distance D2 while the interchangeable shaft assembly 2004' is coupled to the handle assembly 2002, for example. Such modulation can be beneficial in avoiding transmission of excessive power to the motor 2014 beyond the requirements of an interchangeable shaft assembly that is coupled to the handle assembly 2002.

Referring again to FIGS. 32-36, the handle assembly 2002 can be releasably coupled or attached to an interchangeable shaft assembly such as, for example, the shaft assembly 2004. In certain instances, the handle assembly 2002 can be releasably coupled or attached to the power assembly 2006. Various coupling means can be utilized to releasably couple the handle assembly 2002 to the shaft assembly 2004 and/or to the power assembly 2006. Exemplary coupling mechanisms are described in U.S. Provisional Patent Application Ser. No. 61/782,866, entitled CONTROL SYSTEM OF A SURGICAL INSTRUMENT, and filed Mar. 14, 2013. For example, the shaft assembly 2004 may include a shaft attachment module 2018 (FIG. 32) which may further include a latch actuator assembly that may be configured to cooperate with a lock yoke that is pivotally coupled to the shaft attachment module 2018 for selective pivotal travel relative thereto, wherein the lock yoke may include proximally protruding lock lugs that are configured for releasable engagement with corresponding lock detents or grooves formed in a hand assembly attachment module 2020 of the handle assembly 2002.

Referring now primarily to FIGS. 33A-36, the shaft assembly 2004 may include a shaft assembly controller 2022 which can communicate with the power management controller 2016 through an interface 2024 while the shaft assembly 2004 and the power assembly 2006 are coupled to the handle assembly 2002. For example, the interface 2024 may comprise a first interface portion 2025 which may include one or more electric connectors 2026 for coupling engagement with corresponding shaft assembly electric connectors 2028 and a second interface portion 2027 which may include one or more electric connectors 2030 for coupling engagement with corresponding power assembly electric connectors 2032 to permit electrical communication between the shaft assembly controller 2022 and the power management controller 2016 while the shaft assembly 2004 and the power assembly 2006 are coupled to the handle assembly 2002. One or more communication signals can be transmitted through the interface 2024 to communicate one or more of the power requirements of the attached interchangeable shaft assembly 2004 to the power management controller 2016. In response, the power management controller may modulate the power output of the battery 2007 of the power assembly 2006, as described below in greater detail, in accordance with the power requirements of the attached shaft assembly 2004. In certain circumstances, one or more of the electric connectors 2026, 2028, 2030, and/or 2032 may comprise switches which can be activated after mechanical coupling engagement of the handle assembly 2002 to the shaft assembly 2004 and/or to the power assembly 2006 to allow electrical communication between the shaft assembly controller 2022 and the power management controller 2016.

In certain circumstances, the interface 2024 can facilitate transmission of the one or more communication signals between the power management controller 2016 and the shaft assembly controller 2022 by routing such communication signals through a main controller 2017 (FIGS. 33A and 33B) residing in the handle assembly 2002, for example. In other circumstances, the interface 2024 can facilitate a direct line of communication between the power management controller 2016 and the shaft assembly controller 2022 through the handle assembly 2002 while the shaft assembly 2004 and the power assembly 2006 are coupled to the handle assembly 2002.

In one instance, the main microcontroller 2017 may be any single core or multicore processor such as those known under the trade name ARM Cortex by Texas Instruments. In one instance, the surgical instrument 2000 may comprise a power management controller 2016 such as, for example, a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one instance, the safety processor 1004 may be configured specifically for IEC 61508 and ISO 26262 safety critical applications, among others, to provide advanced integrated safety features while delivering scalable performance, connectivity, and memory options.

In certain instances, the microcontroller 2017 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet. The present disclosure should not be limited in this context.

Figure 36:
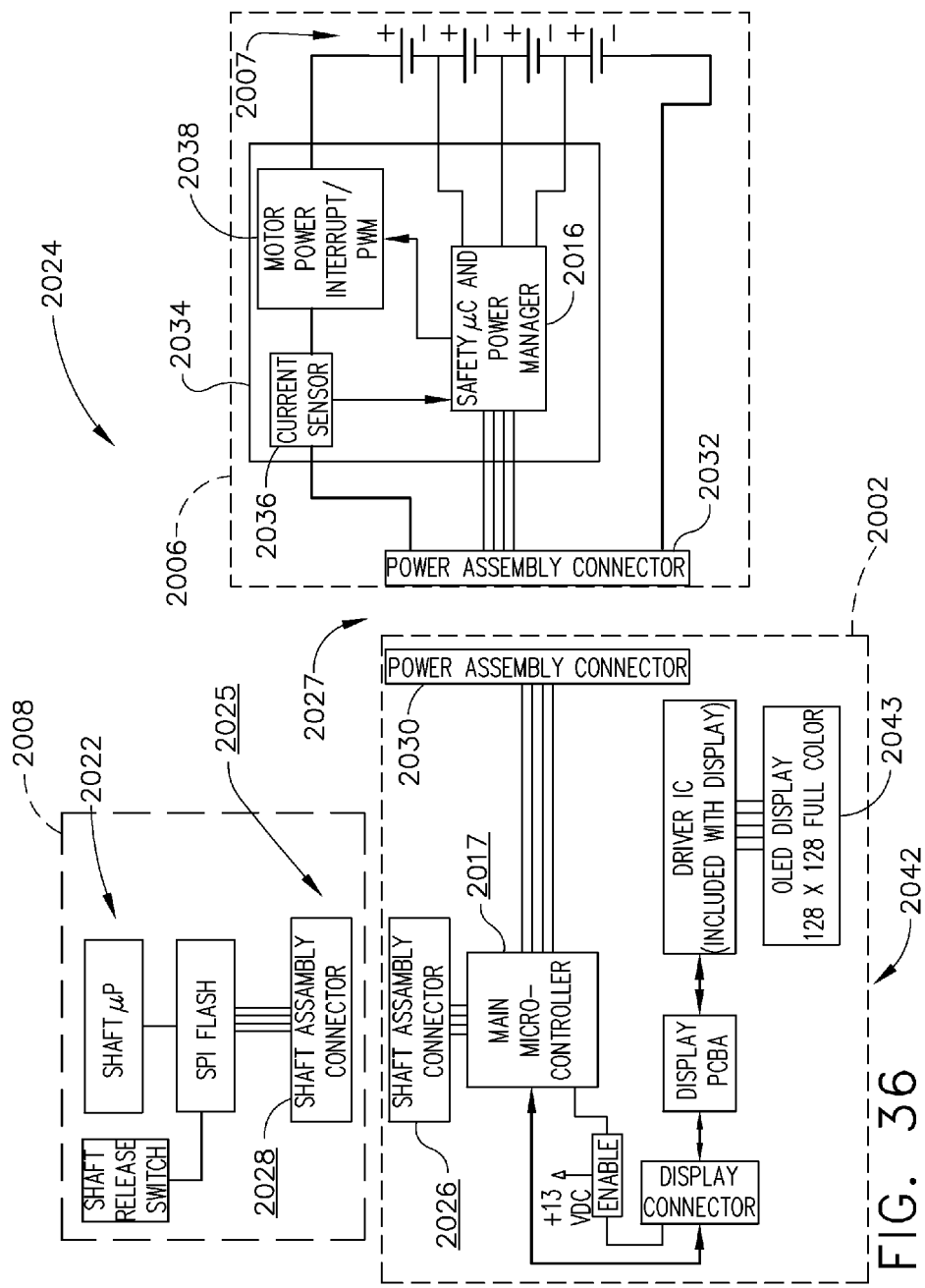
FIG. 36 is a block diagram the surgical instrument of FIG. 31 illustrating interfaces between the handle assembly and the power assembly and between the handle assembly and the interchangeable shaft assembly.
Figure 37:
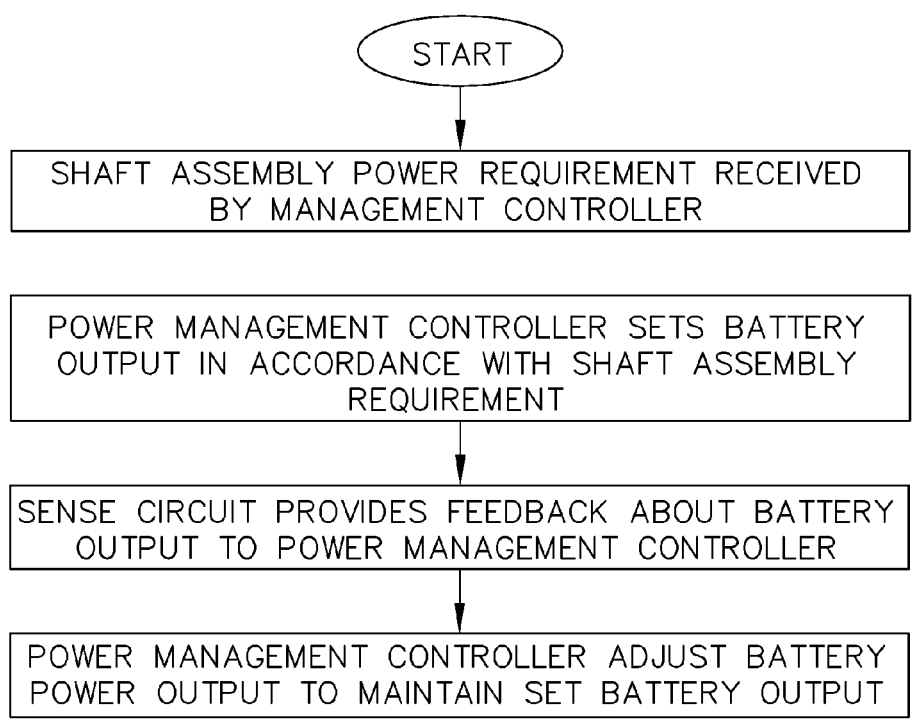
FIG. 37 is a power management module of the surgical instrument of FIG. 31.

Referring now primarily to FIGS. 36 and 37, the power assembly 2006 may include a power management circuit 2034 which may comprise the power management controller 2016, a power modulator 2038, and a current sense circuit 2036. The power management circuit 2034 can be configured to modulate power output of the battery 2007 based on the power requirements of the shaft assembly 2004 while the shaft assembly 2004 and the power assembly 2006 are coupled to the handle assembly 2002. For example, the power management controller 2016 can be programmed to control the power modulator 2038 of the power output of the power assembly 2006 and the current sense circuit 2036 can be employed to monitor power output of the power assembly 2006 to provide feedback to the power management controller 2016 about the power output of the battery 2007 so that the power management controller 2016 may adjust the power output of the power assembly 2006 to maintain a desired output, as illustrated in FIG. 37.

It is noteworthy that the power management controller 2016 and/or the shaft assembly controller 2022 each may comprise one or more processors and/or memory units which may store a number of software modules. Although certain modules and/or blocks of the surgical instrument 2000 may be described by way of example, it can be appreciated that a greater or lesser number of modules and/or blocks may be used. Further, although various instances may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In certain instances, the surgical instrument 2000 may comprise an output device 2042 which may include one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 2042 may comprise a display 2043 which may be included in the handle assembly 2002, as illustrated in FIG. 36. The shaft assembly controller 2022 and/or the power management controller 2016 can provide feedback to a user of the surgical instrument 2000 through the output device 2042. The interface 2024 can be configured to connect the shaft assembly controller 2022 and/or the power management controller 2016 to the output device 2042. The reader will appreciate that the output device 2042 can instead be integrated with the power assembly 2006. In such circumstances, communication between the output device 2042 and the shaft assembly controller 2022 may be accomplished through the interface 2024 while the shaft assembly 2004 is coupled to the handle assembly 2002.

Figure 38:
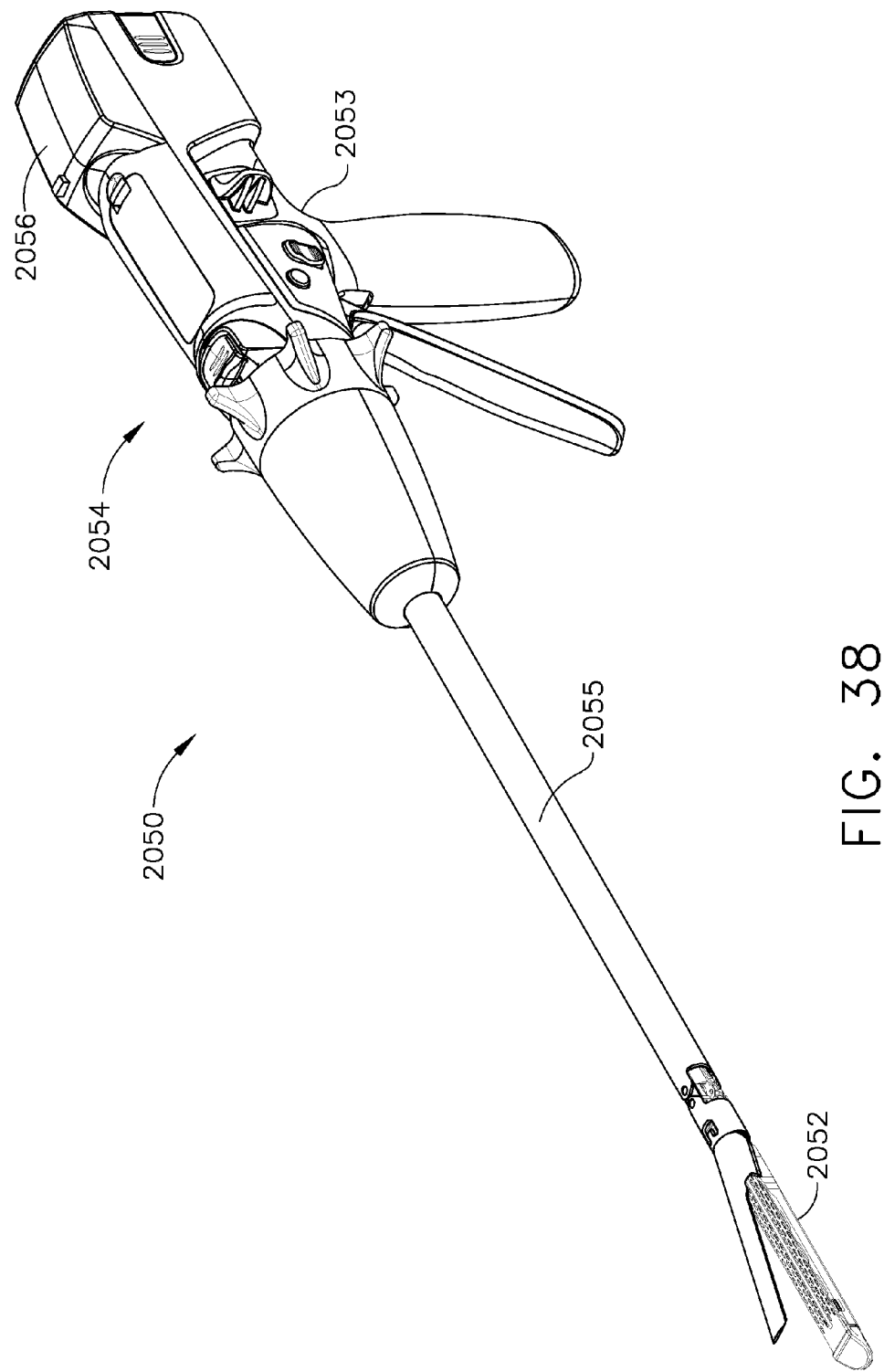
FIG. 38 is a perspective view of a surgical instrument comprising a power assembly and an interchangeable working assembly assembled with the power assembly.
Figure 39:
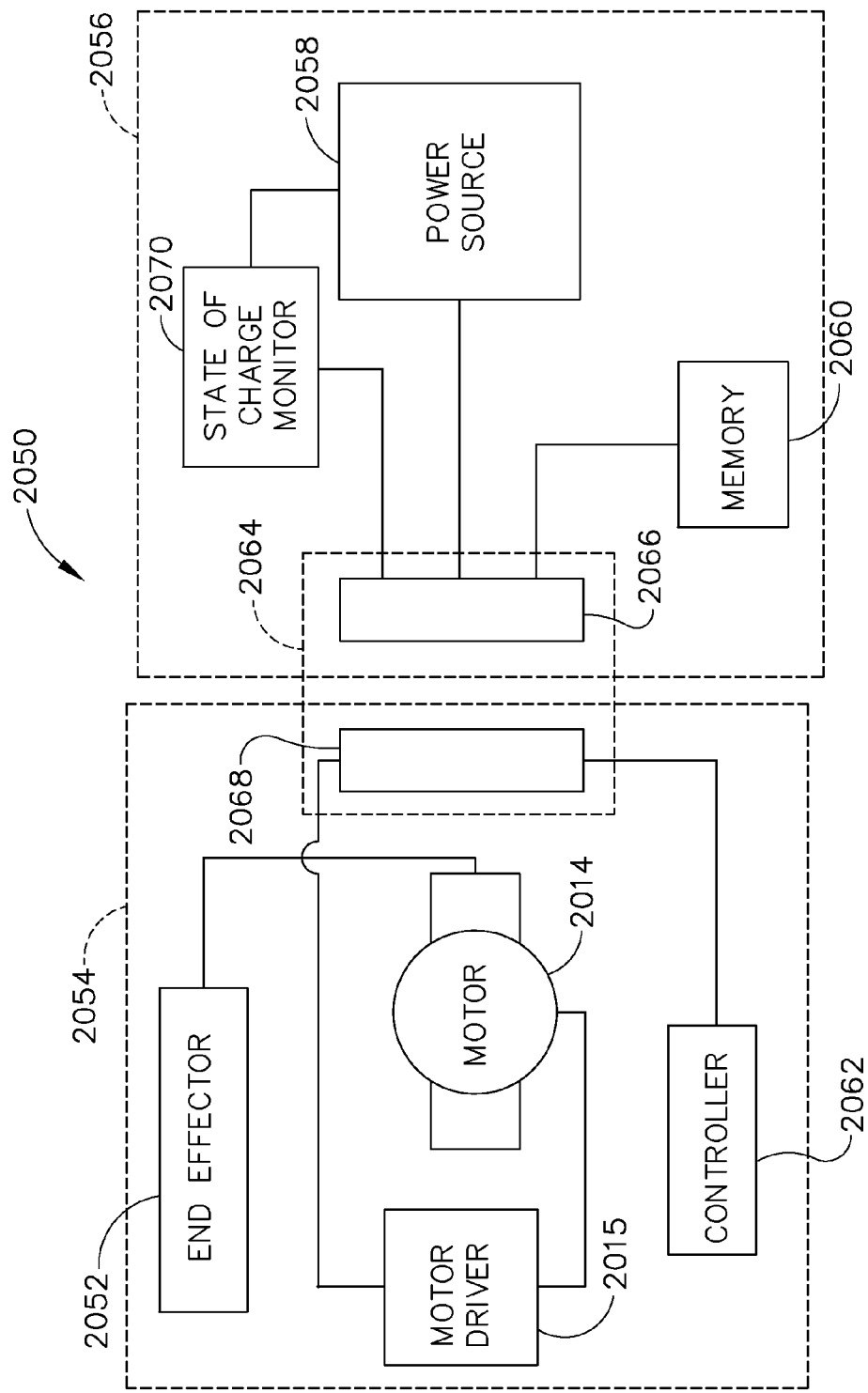
FIG. 39 is a block diagram of the surgical instrument of FIG. 38 illustrating an interface between the interchangeable working assembly and the power assembly.

Referring to FIGS. 38 and 39, a surgical instrument 2050 is illustrated. The surgical instrument 2050 is similar in many respects to the surgical fastening and cutting instrument 2000 (FIG. 31). For example, the surgical instrument 2050 may include an end effector 2052 which is similar in many respects to the end effector 2008. For example, the end effector 2052 can be configured to act as an endocutter for clamping, severing, and/or stapling tissue.

Further to the above, the surgical instrument 2050 may include an interchangeable working assembly 2054 which may include a handle assembly 2053 and a shaft 2055 extending between the handle assembly 2053 and the end effector 2052, as illustrated in FIG. 38. In certain instances, the surgical instrument 2050 may include a power assembly 2056 which can be employed with a plurality of interchangeable working assemblies such as, for example, the interchangeable working assembly 2054. Such interchangeable working assemblies may include surgical end effectors such as, for example, the end effector 2052 that can be configured to perform one or more surgical tasks or procedures. In certain circumstances, the handle assembly 2053 and the shaft 2055 may be integrated into a single unit. In other circumstances, the handle assembly 2053 and the shaft 2055 may be separably couplable to each other.

Similar to the surgical instrument 2000, the surgical instrument 2050 may operably support a plurality of drive systems which can be powered by the power assembly 2056 while the power assembly 2056 is coupled to the interchangeable working assembly 2054. For example, the interchangeable working assembly 2054 can operably support a closure drive system, which may be employed to apply closing and opening motions to the end effector 2052. In at least one form, the interchangeable working assembly 2054 may operably support a firing drive system that can be configured to apply firing motions to the end effector 2052. Examples of drive systems suitable for use with the surgical instrument 2050 are described in U.S. Provisional Patent Application Ser. No. 61/782,866, entitled CONTROL SYS- TEM OF A SURGICAL INSTRUMENT, and filed Mar. 14, 2013, the entire disclosure of which is incorporated by reference herein in its entirety.

Referring to FIG. 39, the power assembly 2056 of the surgical instrument 2050 can be separably coupled to an interchangeable working assembly such as, for example, the interchangeable working assembly 2054. Various coupling means can be utilized to releasably couple the power assembly 2056 to the interchangeable working assembly 2054. Exemplary coupling mechanisms are described herein and are described in U.S. Provisional Patent Application Ser. No. 61/782,866, entitled CONTROL SYSTEM OF A SURGICAL INSTRUMENT, and filed Mar. 14, 2013, the entire disclosure of which is incorporated by reference herein in its entirety.

Still referring to FIG. 39, the power assembly 2056 may include a power source 2058 such as, for example, a battery which can be configured to power the interchangeable working assembly 2054 while coupled to the power assembly 2056. In certain instances, the power assembly 2056 may include a memory 2060 which can be configured to receive and store information about the battery 2058 and/or the interchangeable working assembly 2054 such as, for example, the state of charge of the battery 2058, the number of treatment cycles performed using the battery 2058, and/or identification information for the interchangeable working assemblies coupled to the power assembly 2056 during the life cycle of the battery 2058. Further to the above, the interchangeable working assembly 2054 may include a controller 2062 which can be configured to provide the memory 2060 with such information about the battery 2058 and/or the interchangeable working assembly 2054.

Still referring to FIG. 39, the power assembly 2056 may include an interface 2064 which can be configured to facilitate electrical communication between the memory 2060 of the power assembly 2056 and a controller of an interchangeable working assembly that is coupled to the power assembly 2056 such as, for example, the controller 2062 of the interchangeable working assembly 2054. For example, the interface 2064 may comprise one or more connectors 2066 for coupling engagement with corresponding working assembly connectors 2068 to permit electrical communication between the controller 2062 and the memory 2060 while the interchangeable working assembly 2054 is coupled to the power assembly 2056. In certain circumstances, one or more of the electric connectors 2066 and/or 2068 may comprise switches which can be activated after coupling engagement of the interchangeable working assembly 2054 and the power assembly 2056 to allow electric communication between the controller 2062 and the memory 2060.

Still referring to FIG. 39, the power assembly 2056 may include a state of charge monitoring circuit 2070. In certain circumstances, the state of charge monitoring circuit 2070 may comprise a coulomb counter. The controller 2062 can be in communication with the state of charge monitoring circuit 2070 while the interchangeable working assembly 2054 is coupled to the power assembly 2056. The state of charge monitoring circuit 2070 can be operable to provide for accurate monitoring of charge states of the battery 2058.

Figure 40:
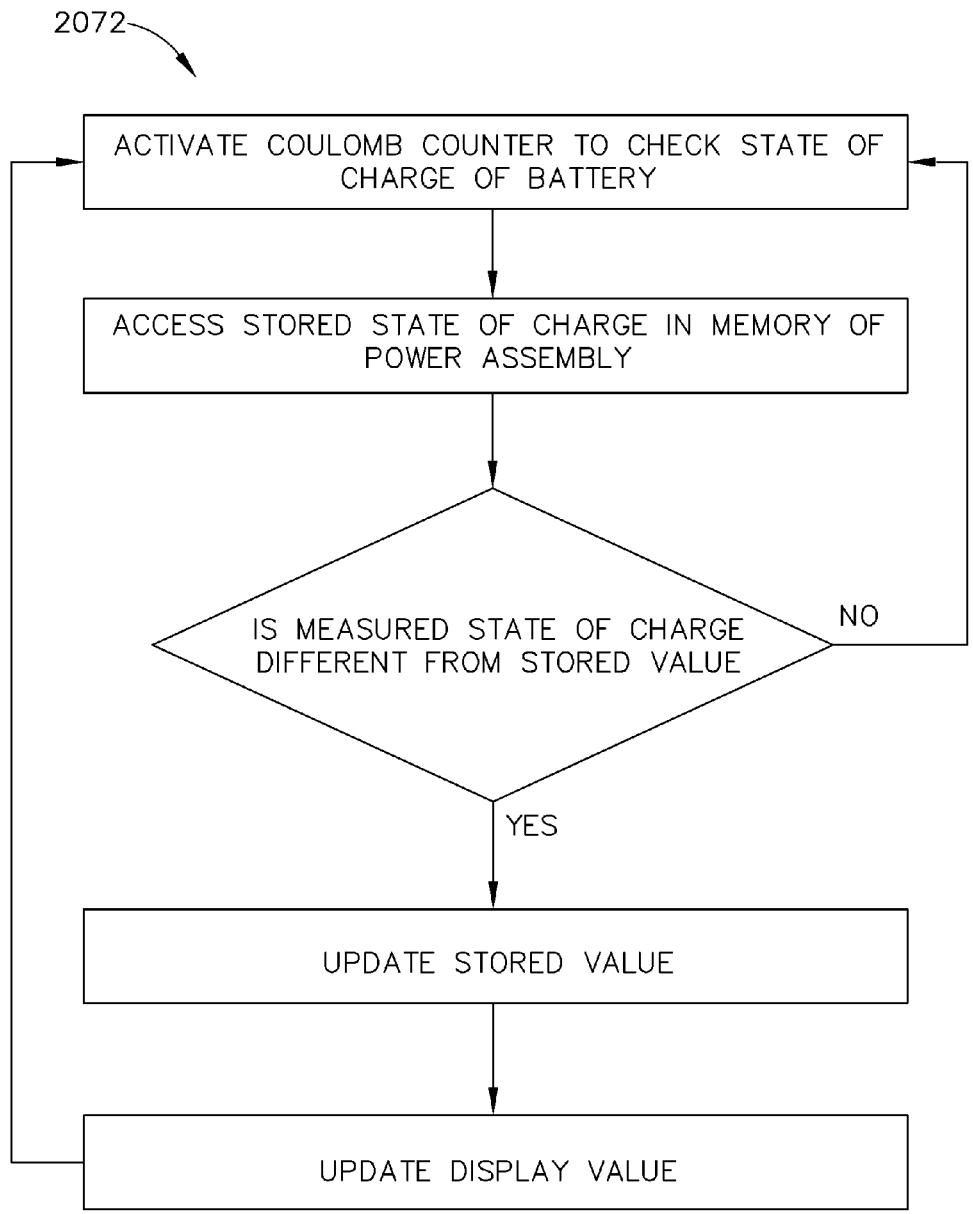
FIG. 40 is a block diagram illustrating a module of the surgical instrument of FIG. 38.

FIG. 40 depicts an exemplary module 2072 for use with a controller of an interchangeable working assembly such as, for example, the controller 2062 of the interchangeable working assembly 2054 while coupled to the power assembly 2056. For example, the controller 2062 may comprise one or more processors and/or memory units which may store a number of software modules such as, for example, the module 2072. Although certain modules and/or blocks of the surgical instrument 2050 may be described by way of example, it can be appreciated that a greater or lesser number of modules and/or blocks may be used. Further, although various instances may be described in terms of modules and/or blocks to facilitate description, such modules and/or blocks may be implemented by one or more hardware components, e.g., processors, DSPs, PLDs, ASICs, circuits, registers and/or software components, e.g., programs, subroutines, logic and/or combinations of hardware and software components.

In any event, upon coupling the interchangeable working assembly 2054 to the power assembly 2056, the interface 2064 may facilitate communication between the controller 2062 and the memory 2060 and/or the state of charge monitoring circuit 2070 to execute the module 2072, as illustrated in FIG. 40. For example, the controller 2062 of the interchangeable working assembly 2054 may utilize the state of charge monitoring circuit 2070 to measure the state of charge of the battery 2058. The controller 2062 may then access the memory 2060 and determine whether a previous value for the state of charge of the battery 2058 is stored in the memory 2060. When a previous value is detected, the controller 2060 may compare the measured value to the previously stored value. When the measured value is different from the previously stored value, the controller 2060 may update the previously stored value. When no value is previously recorded, the controller 2060 may store the measured value into the memory 2060. In certain circumstances, the controller 2060 may provide visual feedback to a user of the surgical instrument 2050 as to the measured state of charge of the battery 2058. For example, the controller 2060 may display the measured value of the state of charge of the battery 2058 on an LCD display screen which, in some circumstances, can be integrated with the interchangeable working assembly 2054.

Further to the above, the module 2072 also can be executed by other controllers upon coupling the interchangeable working assemblies of such other controllers to the power assembly 2056. For example, a user may disconnect the interchangeable working assembly 2054 from the power assembly 2056. The user may then connect another interchangeable working assembly comprising another controller to the power assembly 2056. Such controller may in turn utilize the coulomb counting circuit 2070 to measure the state of charge of the battery 2058 and may then access the memory 2060 and determine whether a previous value for the state of charge of the battery 2058 is stored in the memory 2060 such as, for example, a value entered by the controller 2060 while the interchangeable working assembly 2054 was coupled to the power assembly 2056. When a previous value is detected, the controller may compare the measured value to the previously stored value. When the measured value is different from the previously stored value, the controller may update the previously stored value.

Figure 41:
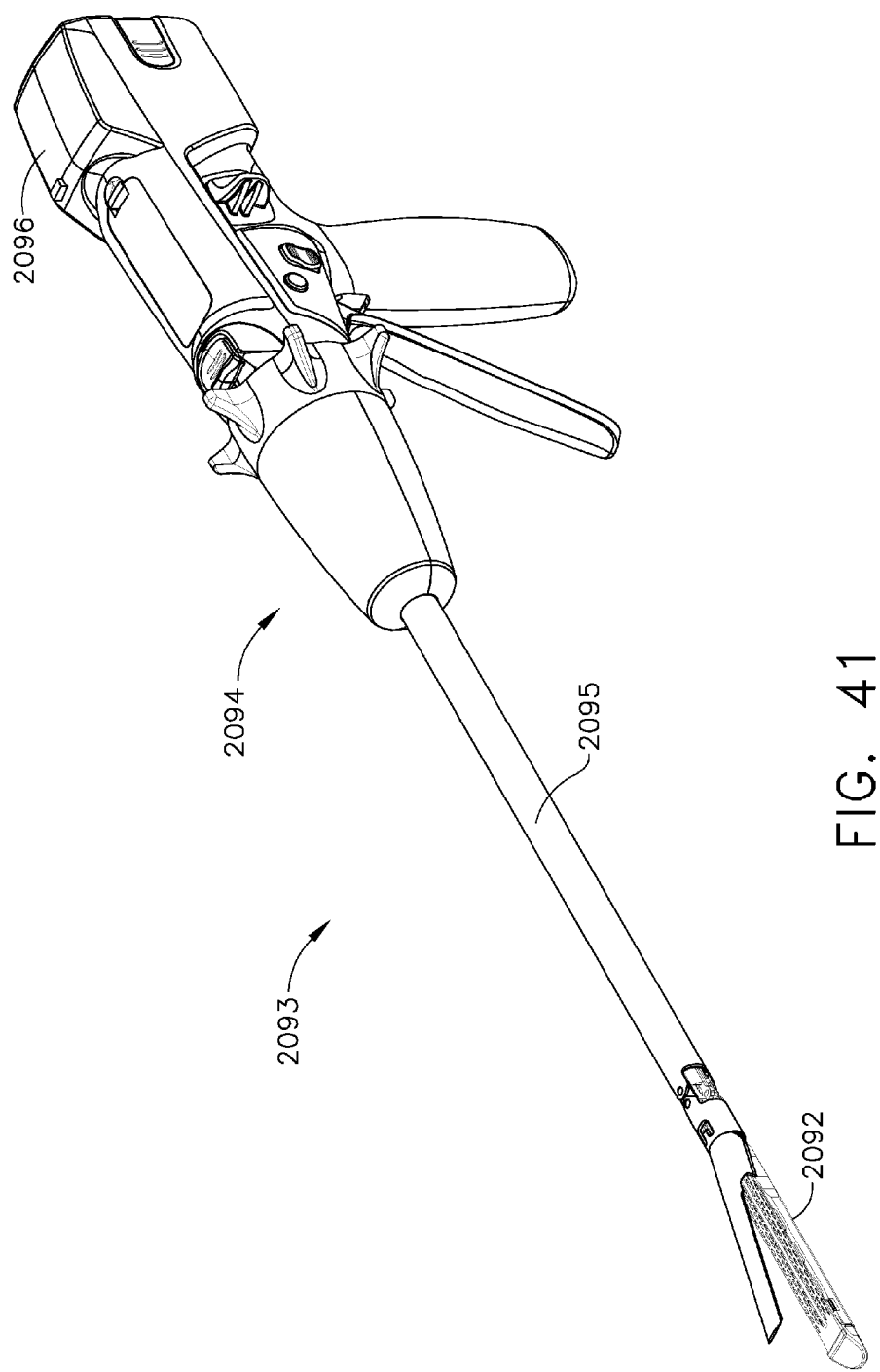
FIG. 41 is a perspective view of a surgical instrument comprising a power assembly and a interchangeable working assembly assembled with the power assembly.

FIG. 41 depicts a surgical instrument 2090 which is similar in many respects to the surgical instrument 2000 (FIG. 31) and/or the surgical instrument 2050 (FIG. 38). For example, the surgical instrument 2090 may include an end effector 2092 which is similar in many respects to the end effector 2008 and/or the end effector 2052. For example, the end effector 2092 can be configured to act as an endocutter for clamping, severing, and/or stapling tissue.

Further to the above, the surgical instrument 2090 may include an interchangeable working assembly 2094 which may include a handle assembly 2093 and a shaft 2095 which may extend between the handle assembly 2093 and the end effector 2092. In certain instances, the surgical instrument 2090 may include a power assembly 2096 which can be employed with a plurality of interchangeable working assemblies such as, for example, the interchangeable working assembly 2094. Such interchangeable working assemblies may comprise surgical end effectors such as, for example, the end effector 2092 that can be configured to perform one or more surgical tasks or procedures. In certain circumstances, the handle assembly 2093 and the shaft 2095 may be integrated into a single unit. In other circumstances, the handle assembly 2093 and the shaft 2095 can be separably couplable to each other.

Furthermore, the power assembly 2096 of the surgical instrument 2090 can be separably couplable to an interchangeable working assembly such as, for example, the interchangeable working assembly 2094. Various coupling means can be utilized to releasably couple the power assembly 2096 to the interchangeable working assembly 2094. Similar to the surgical instrument 2050 and/or the surgical instrument 2000, the surgical instrument 2090 may operably support one or more drive systems which can be powered by the power assembly 2096 while the power assembly 2096 is coupled to the interchangeable working assembly 2094. For example, the interchangeable working assembly 2094 may operably support a closure drive system, which may be employed to apply closing and/or opening motions to the end effector 2092. In at least one form, the interchangeable working assembly 2094 may operably support a firing drive system that can be configured to apply firing motions to the end effector 2092. Exemplary drive systems and coupling mechanisms for use with the surgical instrument 2090 are described in greater detail U.S. Provisional Patent Application Ser. No. 61/782,866, entitled CONTROL SYSTEM OF A SURGICAL INSTRUMENT, and filed Mar. 14, 2013, the entire disclosure of which is incorporated by reference herein in its entirety.

Figure 42:
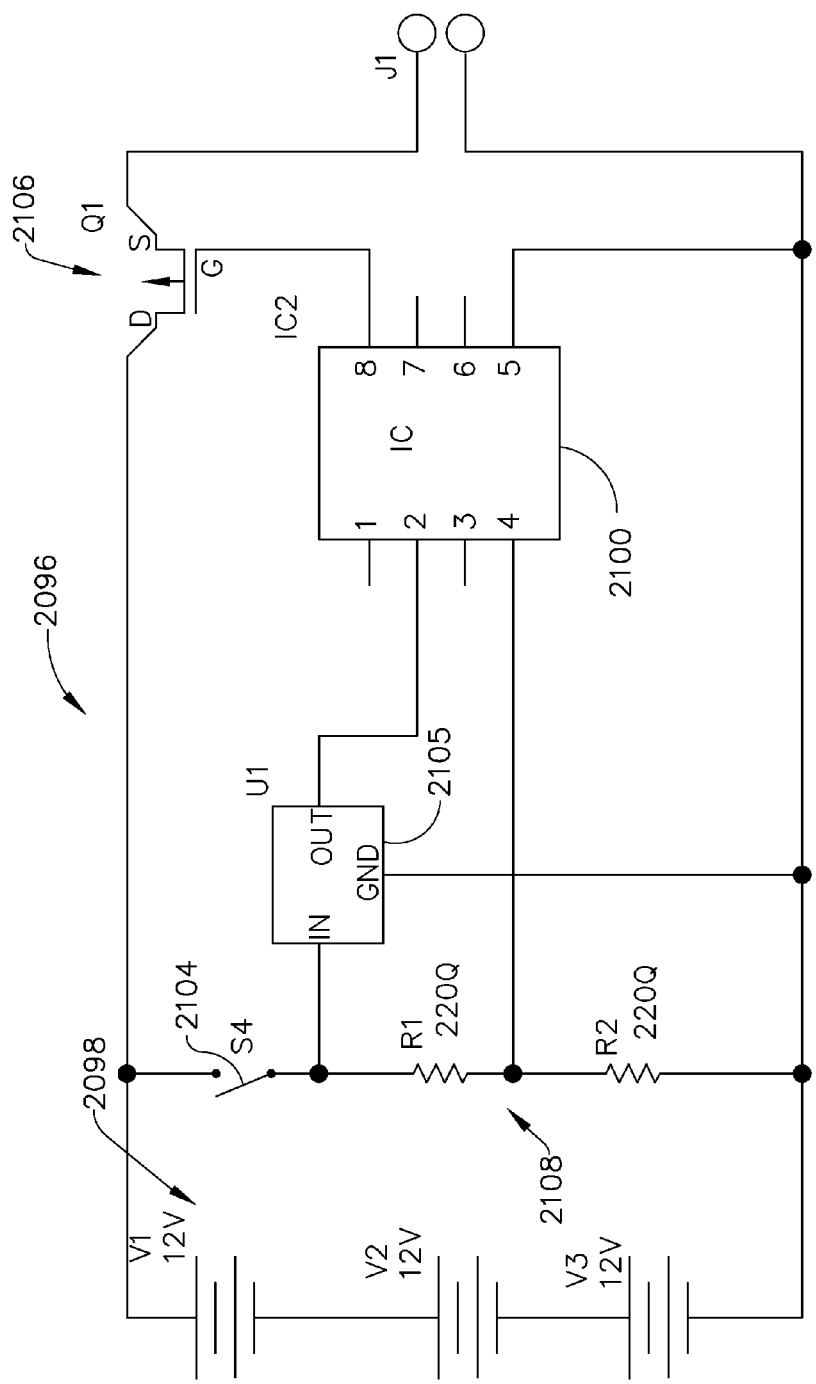
FIG. 42 is a circuit diagram of an exemplary power assembly of the surgical instrument of FIG. 41.
Figure 43:
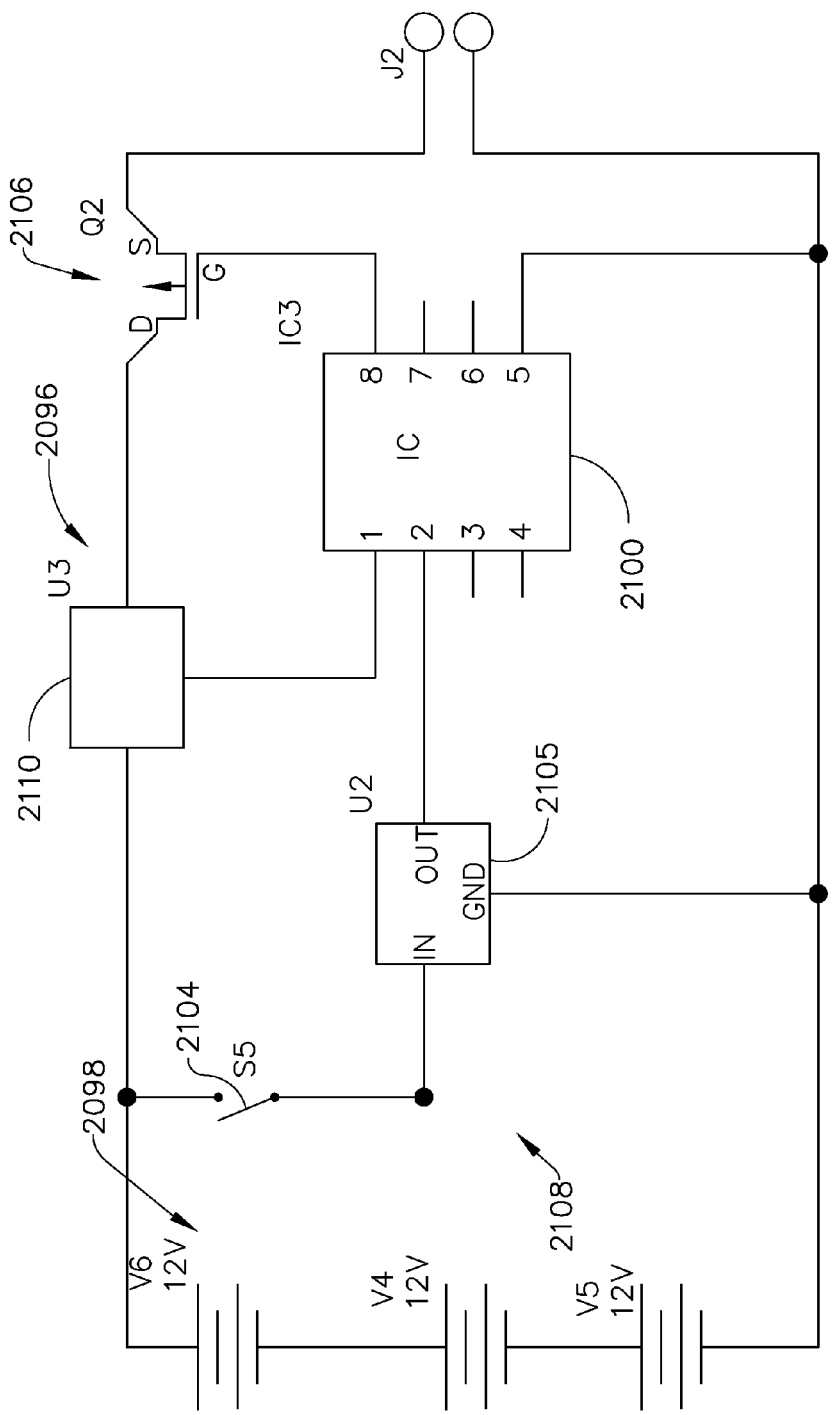
FIG. 43 is a circuit diagram of an exemplary power assembly of the surgical instrument of FIG. 41.

Referring to FIGS. 41-45, the interchangeable working assembly 2094 may include a motor such as, for example, the motor 2014 (FIG. 44) and a motor driver such as, for example, the motor driver 2015 (FIG. 44) which can be employed to motivate the closure drive system and/or the firing drive system of the interchangeable working assembly 2094, for example. The motor 2014 can be powered by a battery 2098 (FIG. 42) which may reside in the power assembly 2096. As illustrated in FIGS. 42 and 43, the battery 2098 may include a number of battery cells connected in series that can be used as a power source to power the motor 2014. In certain instances, the battery cells of the power assembly 2096 may be replaceable and/or rechargeable. The battery cells can be Lithium-Ion batteries which can be separably couplable to the power assembly 2096, for example. In use, a voltage polarity provided by the power assembly 2096 can operate the motor 2014 to drive a longitudinally-movable drive member to effectuate the end effector 2092. For example, the motor 2014 can be configured to drive the longitudinally-movable drive member to advance a cutting member to cut tissue captured by the end effector 2092 and/or a firing mechanism to fire staples from a staple cartridge assembled with the end effector 2092, for example. The staples can be fired into tissue captured by the end effector 2092, for example.

Referring now to FIGS. 41-45, the interchangeable working assembly 2094 may include a working assembly controller 2102 (FIGS. 44 and 45) and the power assembly 2096 may include a power assembly controller 2100 (FIGS. 42 and 43). The working assembly controller 2102 can be configured to generate one or more signals to communicate with the power assembly controller 2100. In certain instances, the working assembly controller 2102 may generate the one or more signals to communicate with the power assembly controller 2100 by modulating power transmission from the power assembly 2096 to the interchangeable working assembly 2094 while the power assembly 2096 is coupled to the interchangeable working assembly 2094.

Furthermore, the power assembly controller 2100 can be configured to perform one or more functions in response to receiving the one or more signals generated by the working assembly controller 2102. For example, the interchangeable working assembly 2094 may comprise a power requirement and the working assembly controller 2102 may be configured to generate a signal to instruct the power assembly controller 2100 to select a power output of the battery 2098 in accordance with the power requirement of the interchangeable working assembly 2094; the signal can be generated, as described above, by modulating power transmission from the power assembly 2096 to the interchangeable working assembly 2094 while the power assembly 2096 is coupled to the interchangeable working assembly 2094. In response to receiving the signal, the power assembly controller 2100 may set the power output of the battery 2098 to accommodate the power requirement of the interchangeable working assembly 2094. The reader will appreciate that various interchangeable working assemblies may be utilized with the power assembly 2096. The various interchangeable working assemblies may comprise various power requirements and may generate signals unique to their power requirements during their coupling engagement with the power assembly 2096 to alert the power assembly controller 2100 to set the power output of the battery 2098 in accordance with their power requirements.

Referring now primarily to FIGS. 42 and 43, the power assembly 2096 may include a power modulator control 2106 which may comprise, for example, one or more field-effect transistors (FETs), a Darlington array, an adjustable amplifier, and/or any other power modulator. The power assembly controller 2100 may actuate the power modulator control 2106 to set the power output of the battery 2098 to the power requirement of the interchangeable working assembly 2094 in response to the signal generated by working assembly controller 2102 while the interchangeable working assembly 2094 is coupled to the power assembly 2096.

Still referring primarily to FIGS. 42 and 43, the power assembly controller 2100 can be configured to monitor power transmission from the power assembly 2096 to the interchangeable working assembly 2094 for the one or more signals generated by the working assembly controller 2102 of the interchangeable working assembly 2094 while he interchangeable working assembly 2094 is coupled to the power assembly 2096. As illustrated in FIG. 42, the power assembly controller 2100 may utilize a voltage monitoring mechanism for monitoring the voltage across the battery 2098 to detect the one or more signals generated by the working assembly controller 2102, for example. In certain instances, a voltage conditioner can be utilized to scale the voltage of the battery 2098 to be readable by an Analog to Digital Converter (ADC) of the power assembly controller 2100. As illustrated in FIG. 42, the voltage conditioner may comprise a voltage divider 2108 which can create a reference voltage or a low voltage signal proportional to the voltage of the battery 2098 which can be measured and reported to the power assembly controller 2100 through the ADC, for example.

In other circumstances, as illustrated in FIG. 43, the power assembly 2096 may comprise a current monitoring mechanism for monitoring current transmitted to the interchangeable working assembly 2094 to detect the one or more signals generated by the working assembly controller 2102, for example. In certain instances, the power assembly 2096 may comprise a current sensor 2110 which can be utilized to monitor current transmitted to the interchangeable working assembly 2094. The monitored current can be reported to the power assembly controller 2100 through an ADC, for example. In other circumstances, the power assembly controller 2100 may be configured to simultaneously monitor both of the current transmitted to the interchangeable working assembly 2094 and the corresponding voltage across the battery 2098 to detect the one or more signals generated by the working assembly controller 2102. The reader will appreciate that various other mechanisms for monitoring current and/or voltage can be utilized by the power assembly controller 2100 to detect the one or more signals generated by the working assembly controller 2102; all such mechanisms are contemplated by the present disclosure.

Figure 44:
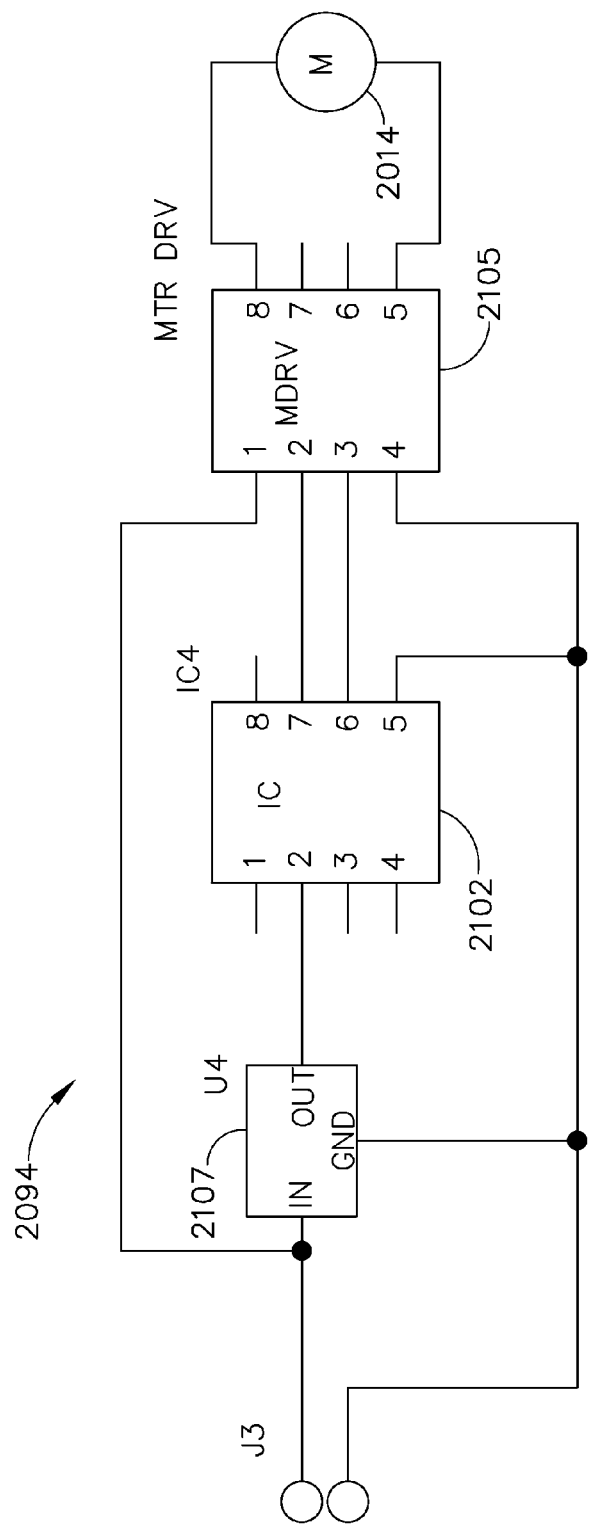
FIG. 44 is a circuit diagram of an exemplary interchangeable working assembly of the surgical instrument of FIG. 41.

As illustrated in FIG. 44, the working assembly controller 2102 can be configured to generate the one or more signals for communication with the power assembly controller 2100 by effectuating the motor driver 2015 to modulate the power transmitted to the motor 2014 from the battery 2098. In result, the voltage across the battery 2098 and/or the current drawn from the battery 2098 to power the motor 2014 may form discrete patterns or waveforms that represent the one or more signals. As described above, the power assembly controller 2100 can be configured to monitor the voltage across the battery 2098 and/or the current drawn from the battery 2098 for the one or more signals generated by the working assembly controller 2102.

Upon detecting a signal, the power assembly controller 2100 can be configured to perform one or more functions that correspond to the detected signal. In at least one example, upon detecting a first signal, the power assembly controller 2100 can be configured to actuate the power modulator control 2106 to set the power output of the battery 2098 to a first duty cycle. In at least one example, upon detecting a second signal, the power assembly controller 2100 can be configured to actuate the power modulator control 2106 to set the power output of the battery 2098 to a second duty cycle different from the first duty cycle.

Figure 45:
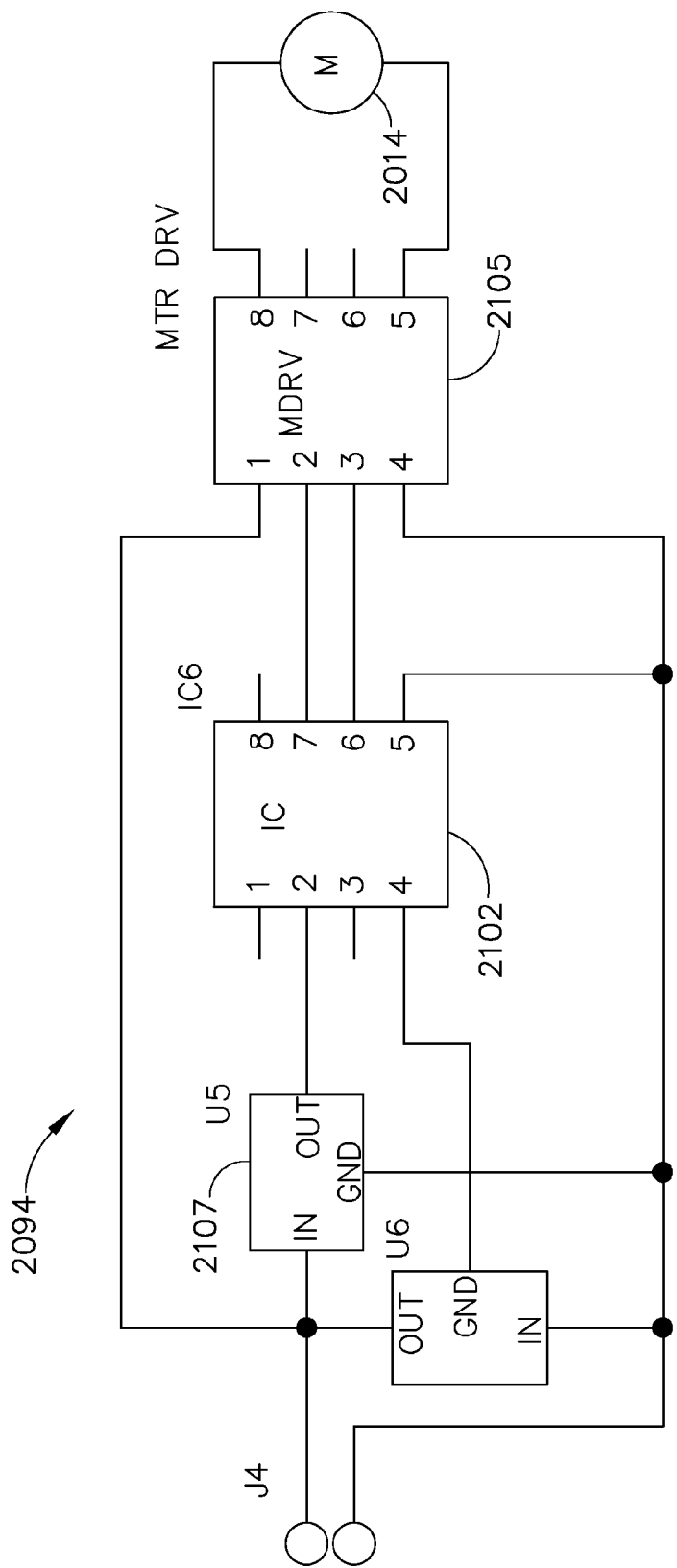
FIG. 45 is a circuit diagram of an exemplary interchangeable working assembly of the surgical instrument of FIG. 41.

In certain circumstances, as illustrated in FIG. 45, the interchangeable working assembly 2094 may include a power modulation circuit 2012 which may comprise one or more field-effect transistors (FETs) which can be controlled by the working assembly controller 2102 to generate a signal or a waveform recognizable by the power assembly controller 2100. For example, in certain circumstances, the working assembly controller 2102 may operate the power modulation circuit 2012 to amplify the voltage higher than the voltage of the battery 2098 to trigger a new power mode of the power assembly 2096, for example.

Referring now primarily to FIGS. 42 and 43, the power assembly 2096 may comprise a switch 2104 which can be switchable between an open position and a closed position. The switch 2104 can be transitioned from the open position to the closed positioned when the power assembly 2096 is coupled with the interchangeable working assembly 2094, for example. In certain instances, the switch 2104 can be manually transitioned from the open position to the closed position after the power assembly 2096 is coupled with the interchangeable working assembly 2094, for example. While the switch 2104 is in the open position, components of the power assembly 2096 may draw sufficiently low or no power to retain capacity of the battery 2098 for clinical use. The switch 2104 can be a mechanical, reed, hall, or any other suitable switching mechanism. Furthermore, in certain circumstances, the power assembly 2096 may include an optional power supply 2105 which may be configured to provide sufficient power to various components of the power assembly 2096 during use of the battery 2098. Similarly, the interchangeable working assembly 2094 also may include an optional power supply 2107 which can be configured to provide sufficient power to various components of the interchangeable working assembly 2094.

Figure 46:
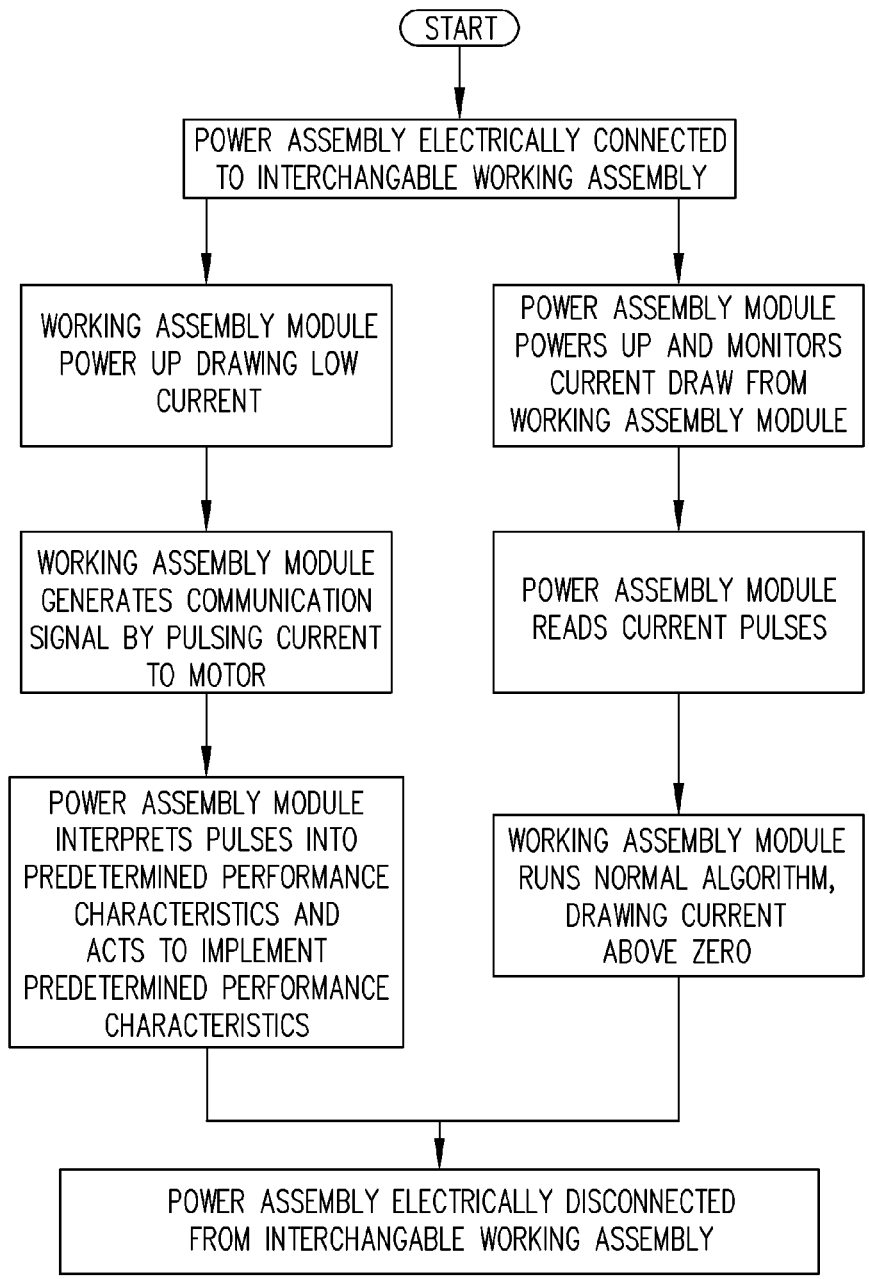
FIG. 46 is a block diagram depicting an exemplary module of the surgical instrument of FIG. 41.

In use, as illustrated in FIG. 46, the power assembly 2096 can be coupled to the interchangeable working assembly 2094. In certain instances, as described above, the switch 2104 can be transitioned to the closed configuration to electrically connect the interchangeable working assembly 2094 to the power assembly 2096. In response, the interchangeable working assembly 2094 may power up and may, at least initially, draw relatively low current from the battery 2098. For example, the interchangeable working assembly 2094 may draw less than or equal to 1 ampere to power various components of the interchangeable working assembly 2094. In certain instances, the power assembly 2096 also may power up as the switch 2014 is transitioned to the closed position. In response, the power assembly controller 2100 may begin to monitor current draw from the interchangeable working assembly 2094, as described in greater detail above, by monitoring voltage across the battery 2098 and/or current transmission from the battery 2098 to the interchangeable working assembly 2094, for example.

Figure 47A:
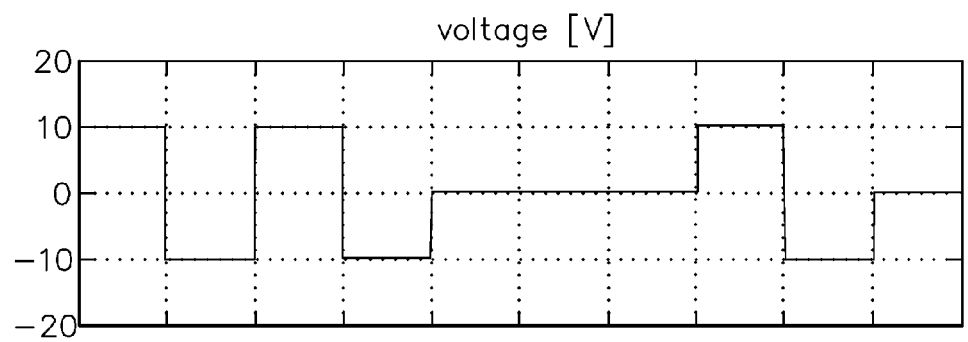
FIG. 47A is a graphical representation of an exemplary communication signal generated by a working assembly controller of the interchangeable working assembly of the surgical instrument of FIG. 41 as detected by a voltage monitoring mechanism.
Figure 47B:
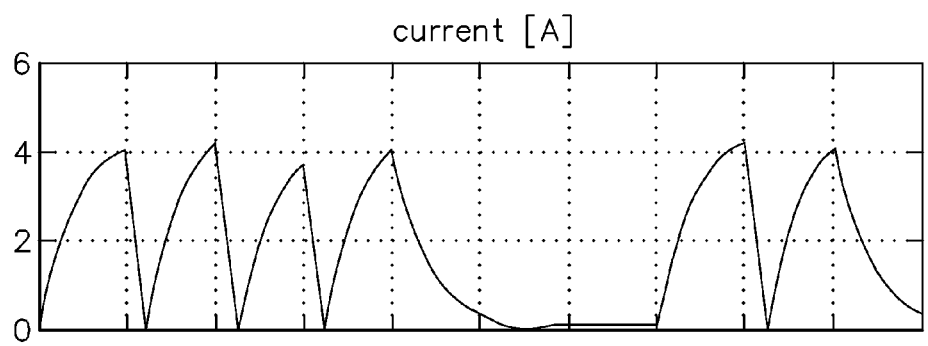
FIG. 47B is a graphical representation of an exemplary communication signal generated by a working assembly controller of the interchangeable working assembly of the surgical instrument of FIG. 41 as detected by a current monitoring mechanism.
Figure 47C:
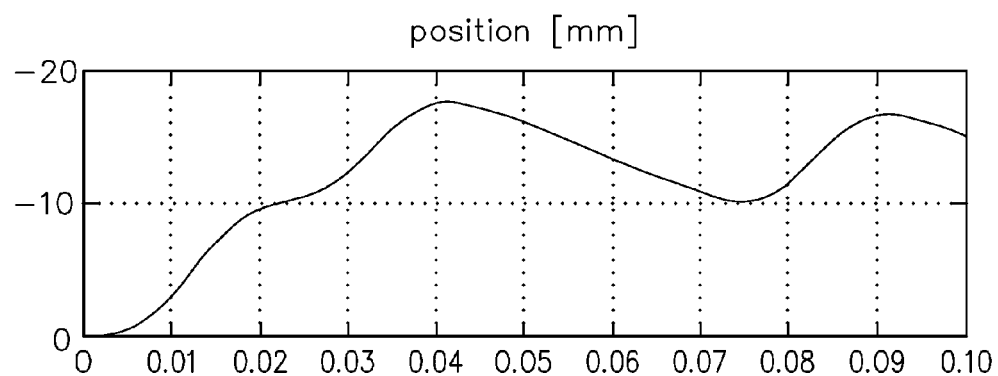
FIG. 47C is a graphical representation of effective motor displacement of a motor of the interchangeable working assembly of FIG. 41 in response to the communication signal generated by the working assembly controller of FIG. 47A.

To generate and transmit a communication signal to the power assembly controller 2100 via power modulation, the working assembly controller 2102 may employ the motor drive 2015 to pulse power to the motor 2014 in patterns or waveforms of power spikes, for example. In certain circumstances, the working assembly controller 2102 can be configured to communicate with the motor driver 2015 to rapidly switch the direction of motion of the motor 2014 by rapidly switching the voltage polarity across the windings of the motor 2014 to limit the effective current transmission to the motor 2014 resulting from the power spikes. In result, as illustrated in FIG. 47C, the effective motor displacement resulting from the power spikes can be reduced to minimize effective displacement of a drive system of the surgical instrument 2090 that is coupled to the motor 2014 in response to the power spikes.

Further to the above, the working assembly controller 2102 may communicate with the power assembly controller 2100 by employing the motor driver 2015 to draw power from the battery 2098 in spikes arranged in predetermined packets or groups which can be repeated over predetermined time periods to form patterns detectable by the power assembly controller 2100. For example, as illustrated in FIGS. 47A and 47B, the power assembly controller 2100 can be configured to monitor voltage across the battery 2100 for predetermined voltage patterns such as, for example, the voltage pattern 2103 (FIG. 47A) and/or predetermined current patterns such as, for example, the current pattern 2109 (FIG. 47B) using voltage and/or current monitoring mechanisms as described in greater detail above. Furthermore, the power assembly controller 2100 can be configured to perform one or more functions upon detecting of a pattern. The reader will appreciate that the communication between the power assembly controller 2100 and the working assembly controller 2102 via power transmission modulation may reduce the number of connection lines needed between the interchangeable working assembly 2094 and the power assembly 2096.

In certain circumstances, the power assembly 2096 can be employed with various interchangeable working assemblies of multiple generations which may comprise different power requirements. Some of the various interchangeable workings assemblies may comprise communication systems, as described above, while others may lack such communication systems. For example, the power assembly 2096 can be utilized with a first generation interchangeable working assembly which lacks the communication system described above. Alternatively, the power assembly 2096 can be utilized with a second generation interchangeable working assembly such as, for example, the interchangeable working assembly 2094 which comprises a communication system, as described above.

Further to the above, the first generation interchangeable working assembly may comprise a first power requirement and the second generation interchangeable working assembly may comprise a second power requirement which can be different from the first power requirement. For example, the first power requirement may be less than the second power requirement. To accommodate the first power requirement of the first generation interchangeable working assembly and the second power requirement of the second generation interchangeable working assembly, the power assembly 2096 may comprise a first power mode for use with the first generation interchangeable working assembly and a second power mode for use with the second generation interchangeable working assembly. In certain instances, the power assembly 2096 can be configured to operate at a default first power mode corresponding to the power requirement of the first generation interchangeable working assembly. As such, when a first generation interchangeable working assembly is connected to the power assembly 2096, the default first power mode of the power assembly 2096 may accommodate the first power requirement of the first generation interchangeable working assembly. However, when a second generation interchangeable working assembly such as, for example, the interchangeable working assembly 2094 is connected to the power assembly 2096, the working assembly controller 2102 of the interchangeable working assembly 2094 may communicate, as described above, with the power assembly controller 2100 of the power assembly 2096 to switch the power assembly 2096 to the second power mode to accommodate the second power requirement of the interchangeable working assembly 2094. The reader will appreciate that since the first generation interchangeable working assembly lacks the ability to generate a communication signal, the power assembly 2096 will remain in the default first power mode while connected to the first generation interchangeable working assembly.

As described above, the battery 2098 can be rechargeable. In certain circumstances, it may be desirable to drain the battery 2098 prior to shipping the power assembly 2096. A dedicated drainage circuit can be activated to drain the battery 2098 in preparation for shipping of the power assembly 2096. Upon reaching its final destination, the battery 2098 can be recharged for use during a surgical procedure. However, the drainage circuit may continue to consume energy from the battery 2098 during clinical use. In certain circumstances, the interchangeable working assembly controller 2102 can be configured to transmit a drainage circuit deactivation signal to the power assembly controller 2100 by modulating power transmission from the battery 2098 to the motor 2014, as described in greater detail above.

The power assembly controller 2100 can be programmed to deactivate the drainage circuit to prevent drainage of the battery 2098 by the drainage circuit in response to the drainage circuit deactivation signal, for example. The reader will appreciate that various communication signals can be generated by the working assembly controller 2102 to instruct the power assembly controller 2100 to perform various functions while the power assembly 2096 is coupled to the interchangeable working assembly 2094.

Referring again to FIGS. 42-45, the power assembly controller 2100 and/or the working assembly controller 2102 may comprise one or more processors and/or memory units which may store a number of software modules. Although certain modules and/or blocks of the surgical instrument 2050 may be described by way of example, it can be appreciated that a greater or lesser number of modules and/or blocks may be used. Further, although various instances may be described in terms of modules and/or blocks to facilitate description, such modules and/or blocks may be implemented by one or more hardware components, e.g., processors, DSPs, PLDs, ASICs, circuits, registers and/or software components, e.g., programs, subroutines, logic and/or combinations of hardware and software components.

Figure 48:
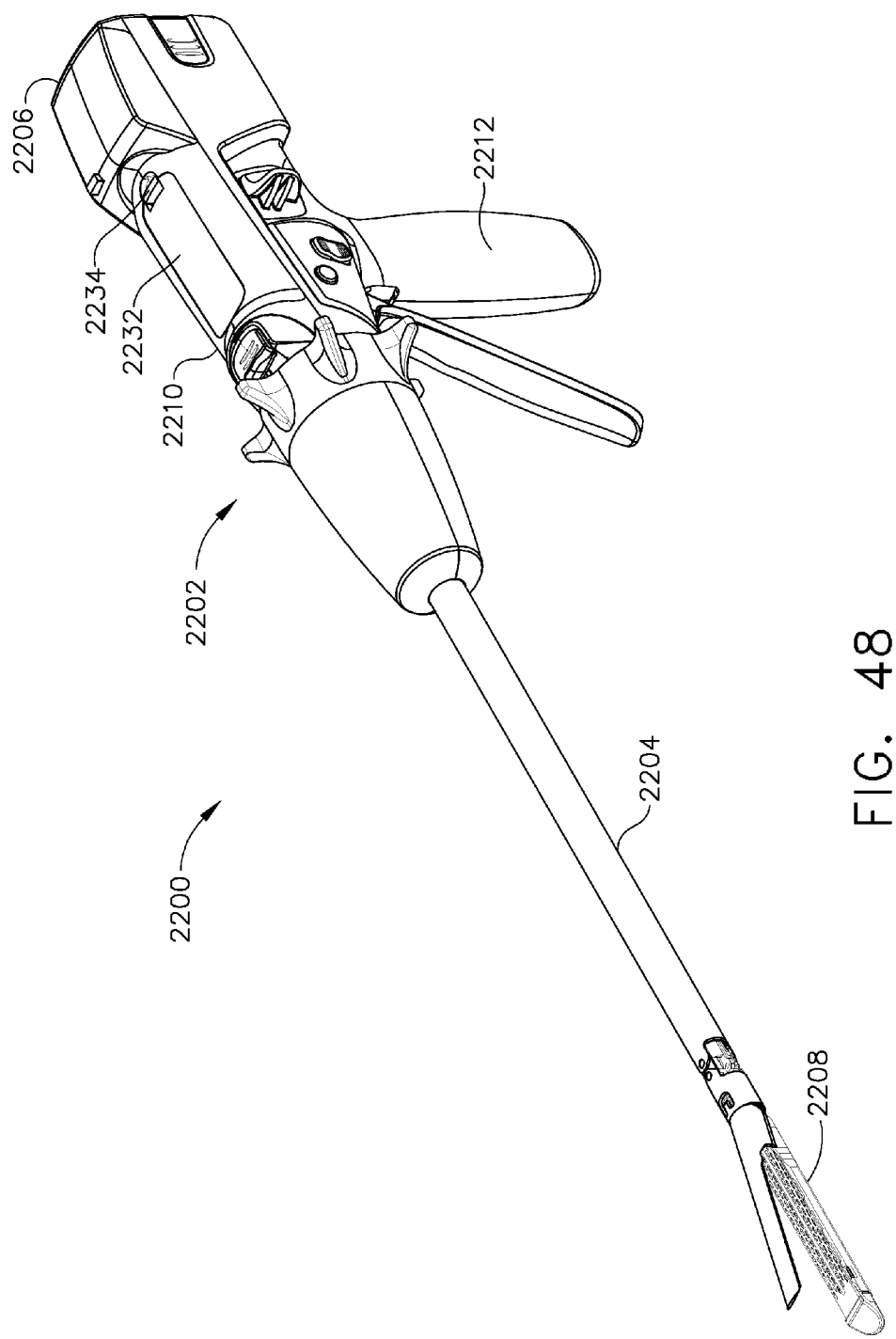
FIG. 48 is a perspective view of a surgical instrument comprising a handle assembly and a shaft assembly including an end effector.
Figure 49:
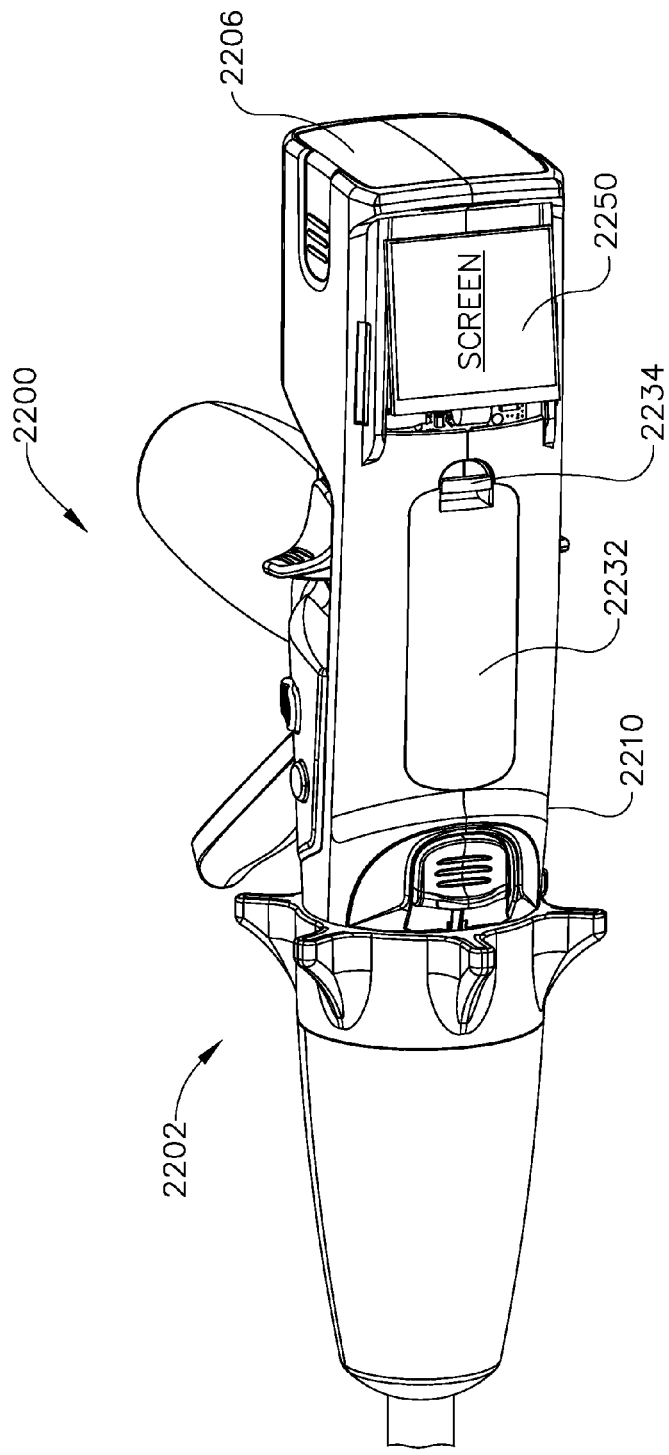
FIG. 49 is a perspective view of the handle assembly of the surgical instrument of FIG. 48.

FIG. 48 generally depicts a motor-driven surgical instrument 2200. In certain circumstances, the surgical instrument 2200 may include a handle assembly 2202, a shaft assembly 2204, and a power assembly 2206 (or "power source" or "power pack"). The shaft assembly 2204 may include an end effector 2208 which, in certain circumstances, can be configured to act as an endocutter for clamping, severing, and/or stapling tissue, although, in other circumstances, different types of end effectors may be used, such as end effectors for other types of surgical devices, graspers, cutters, staplers, clip appliers, access devices, drug/gene therapy devices, ultrasound, RF and/or laser devices, etc. Several RF devices may be found in U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL FASTENING AND CUTTING INSTRUMENT HAVING RF ELECTRODES, filed Feb. 14, 2008, the entire disclosures of which are incorporated herein by reference in their entirety.

In certain circumstances, the handle assembly 2202 can be separably couplable to the shaft assembly 2204, for example. In such circumstances, the handle assembly 2202 can be employed with a plurality of interchangeable shaft assemblies which may comprise surgical end effectors such as, for example, the end effector 2208 that can be configured to perform one or more surgical tasks or procedures. For example, one or more of the interchangeable shaft assemblies may employ end effectors that are adapted to support different sizes and types of staple cartridges, have different shaft lengths, sizes, and types, etc. Examples of suitable interchangeable shaft assemblies are disclosed in U.S. Provisional Patent Application Ser. No. 61/782,866, entitled CONTROL SYSTEM OF A SURGICAL INSTRUMENT, and filed Mar. 14, 2013, the entire disclosure of which is hereby incorporated by reference herein in its entirety.

Referring still to FIG. 48, the handle assembly 2202 may comprise a housing 2210 that consists of a handle 2212 that may be configured to be grasped, manipulated, and/or actuated by a clinician. However, it will be understood that the various unique and novel arrangements of the housing 2210 also may be effectively employed in connection with robotically-controlled surgical systems. Thus, the term "housing" also may encompass a housing or similar portion of a robotic system that houses or otherwise operably supports at least one drive system that is configured to generate and apply at least one control motion which could be used to actuate the shaft assembly 2204 disclosed herein and its respective equivalents. For example, the housing 2210 disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719, which is incorporated by reference herein in its entirety.

Figure 50:
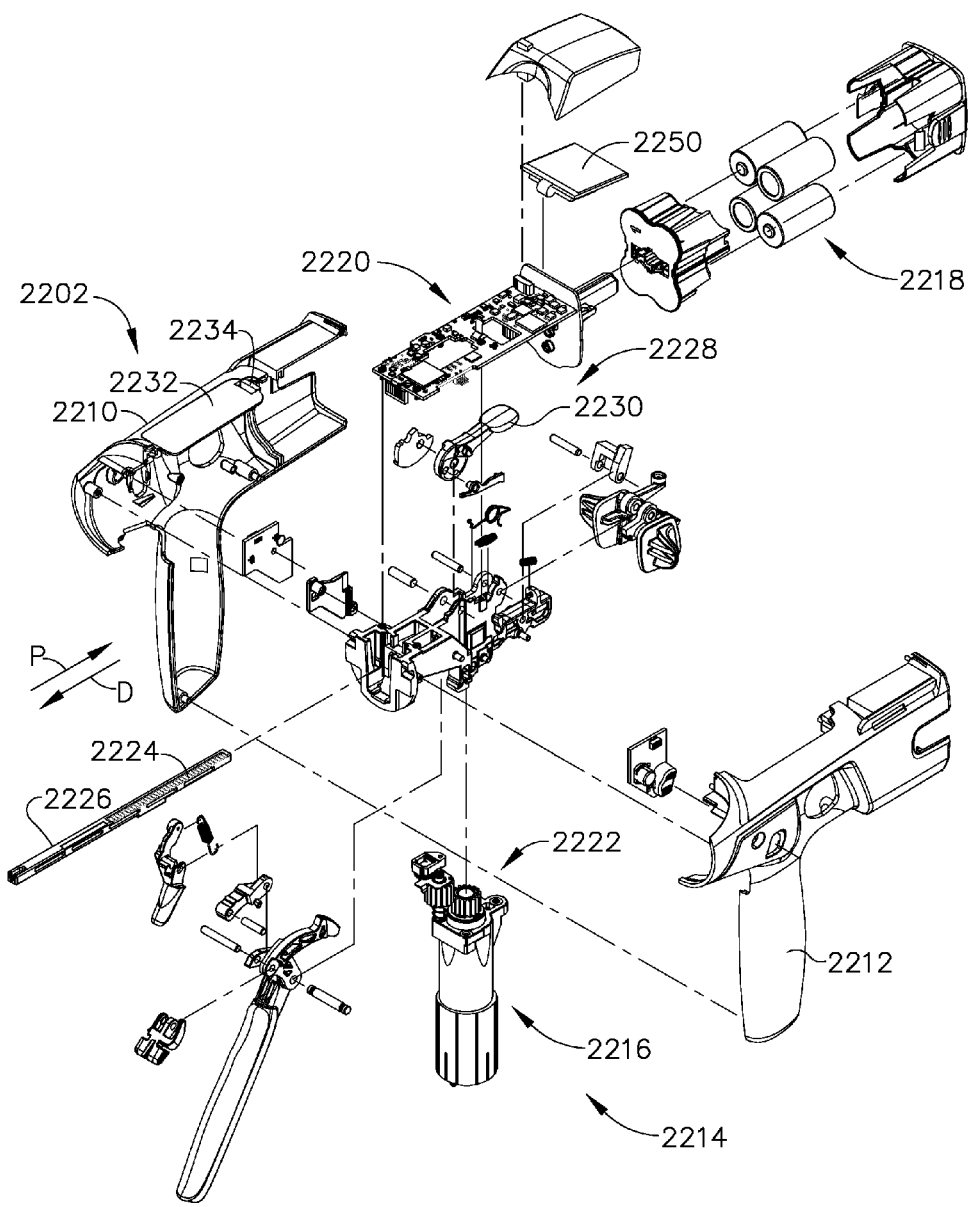
FIG. 50 is an exploded view of the handle assembly of the surgical instrument of FIG. 48.

In at least one form, the surgical instrument 2200 may be a surgical fastening and cutting instrument. Furthermore, the housing 2210 may operably support one or more drive systems. For example, as illustrated in FIG. 50, the housing 2210 may support a drive system referred to herein as firing drive system 2214 that is configured to apply firing motions to the end effector 2208. The firing drive system 2214 may employ an electric motor 2216, which can be located in the handle 2212, for example. In various forms, the motor 2216 may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. A battery 2218 (or "power source" or "power pack"), such as a Li ion battery, for example, may be coupled to the handle 2212 to supply power to a control circuit board assembly 2220 and ultimately to the motor 2216.

In certain circumstances, referring still to FIG. 50, the electric motor 2216 can include a rotatable shaft (not shown) that may operably interface with a gear reducer assembly 2222 that may be mounted in meshing engagement with a with a set, or rack, of drive teeth 2224 on a longitudinally-movable drive member 2226. In use, a voltage polarity provided by the battery 2218 can operate the electric motor 2216 in a clockwise direction wherein the voltage polarity applied to the electric motor by the battery 2218 can be reversed in order to operate the electric motor 2216 in a counter-clockwise direction. When the electric motor 2216 is rotated in one direction, the drive member 2226 will be axially driven in a distal direction "D", for example, and when the motor 2216 is driven in the opposite rotary direction, the drive member 2226 will be axially driven in a proximal direction "P", for example, as illustrated in FIG. 50. The handle 2212 can include a switch which can be configured to reverse the polarity applied to the electric motor 2216 by the battery 2218. As with the other forms described herein, the handle 2212 also can include a sensor that is configured to detect the position of the drive member 2226 and/or the direction in which the drive member 2226 is being moved.

As indicated above, in at least one form, the longitudinally movable drive member 2226 may include a rack of drive teeth 2224 formed thereon for meshing engagement with the gear reducer assembly 2222. In certain circumstances, as illustrated in FIG. 50, the surgical instrument 2200 may include a manually-actuatable "bailout" assembly 2228 that can be configured to enable a clinician to manually retract the longitudinally movable drive member 2226 when a bailout error is detected such as, for example, when the motor 2216 malfunctions during operation of the surgical instrument 2200 which may cause tissue captured by the end effector 2208 to be trapped.

Further to the above, as illustrated in FIG. 50, the bailout assembly 2228 may include a lever or bailout handle 2230 configured to be manually moved or pivoted into ratcheting engagement with the teeth 2224 in the drive member 2226. In such circumstances, the clinician can manually retract the drive member 2226 by using the bailout handle 2230 to ratchet the drive member 2226 in the proximal direction "P", for example, to release the trapped tissue from the end effector 2208, for example. Exemplary bailout arrangements and other components, arrangements and systems that may be employed with the various instruments disclosed herein are disclosed in U.S. patent application Ser. No. 12/249,117, entitled POWERED SURGICAL CUTTING AND STAPLING APPARATUS WITH MANUALLY RETRACTABLE FIRING SYSTEM, now U.S. Patent Application Publication No. 2010/0089970, which is hereby incorporated by reference herein in its entirety.

Further to the above, referring now primarily to FIGS. 48 and 50, the bailout handle 2230 of the bailout assembly 2228 may reside within the housing 2210 of the handle assembly 2202. In certain circumstances, access to the bailout handle 2230 can be controlled by a bailout door 2232. The bailout door 2232 can be releasably locked to the housing 2210 to control access to the bailout handle 2230. As illustrated in FIG. 48, the bailout door 2232 may include a locking mechanism such as, for example, a snap-type locking mechanism 2234 for locking engagement with the housing 2210. Other locking mechanisms for locking the bailout door 2232 to the housing 2210 are contemplated by the present disclosure. In use, a clinician may obtain access to the bailout handle 2230 by unlocking the locking mechanism 2234 and opening the bailout door 2232. In at least one example, the bailout door 2232 can be separably coupled to the housing 2232 and can be detached from the housing 2210 to provide access to the bailout handle 2230, for example. In another example, the bailout door 2232 can be pivotally coupled to the housing 2210 via hinges (not shown) and can be pivoted relative to the housing 2210 to provide access to the bailout handle 2230, for example. In yet another example, the bailout door 2232 can be a sliding door which can be slidably movable relative to the housing 2210 to provide access to the bailout handle 2230.

Figure 51:
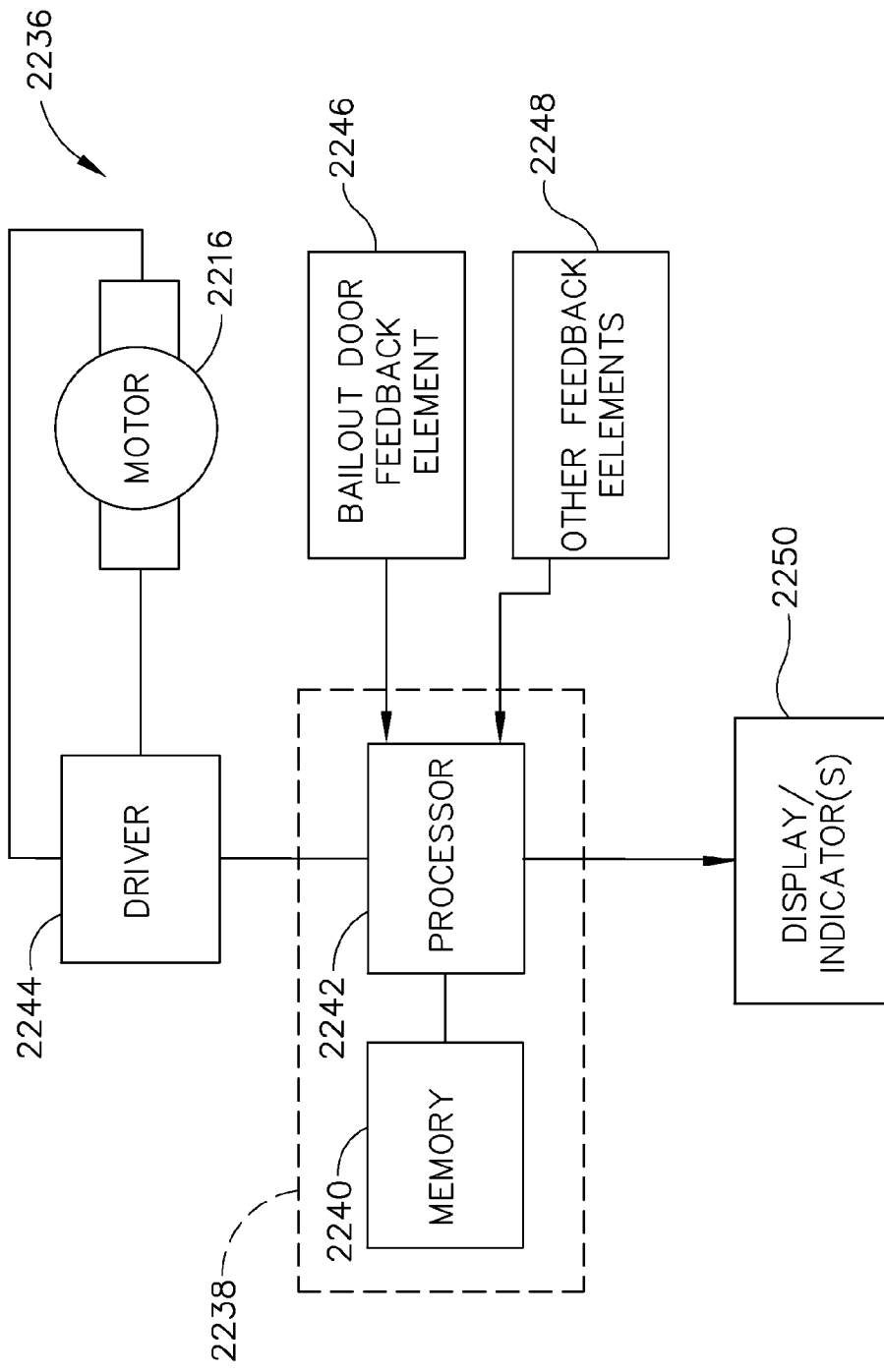
FIG. 51 is a schematic diagram of a bailout feedback system of the surgical instrument of FIG. 48.

Referring now to FIG. 51, the surgical instrument 2200 may include a bailout feedback system 2236 which can be configured to guide and/or provide feedback to a clinician through the various steps of utilizing the bailout assembly 2228, as described below in greater detail. In certain instances, the bailout feedback system 2236 may include a microcontroller 2238 and/or one or more bailout feedback elements. The electrical and electronic circuit elements associated with the bailout feedback system 2236 and/or the bailout feedback elements may be supported by the control circuit board assembly 2220, for example. The microcontroller 2238 may generally comprise a memory 2240 and a microprocessor 2242 ("processor") operationally coupled to the memory 2240. The processor 2242 may control a motor driver 2244 circuit generally utilized to control the position and velocity of the motor 2216. In certain instances, the processor 2242 can signal the motor driver 2244 to stop and/or disable the motor 2216, as described in greater detail below. In certain instances, the processor 2242 may control a separate motor override circuit which may comprise a motor override switch that can stop and/or disable the motor 2216 during operation of the surgical instrument 2200 in response to an override signal from the processor 2242. It should be understood that the term processor as used herein includes any suitable microprocessor, microcontroller, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 2242 may be any single core or multicore processor such as those known under the trade name ARM Cortex by Texas Instruments. In one instance, the surgical instrument 2200 may comprise a safety processor such as, for example, a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one instance, the safety processor 1004 may be configured specifically for IEC 61508 and ISO 26262 safety critical applications, among others, to provide advanced integrated safety features while delivering scalable performance, connectivity, and memory options.

In certain instances, the microcontroller 2238 may be an LM 4F230H5QR, available from Texas Instruments, for example. In at least one example, the Texas Instruments LM4F230H5QR is an ARM Cortex-M4F Processor Core comprising on-chip memory 2240 of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet. Other microcontrollers may be readily substituted for use in the bailout feedback system 2236. Accordingly, the present disclosure should not be limited in this context.

Referring again to FIG. 51, the bailout feedback system 2236 may include a bailout door feedback element 2246, for example. In certain instances, the bailout door feedback element 2246 can be configured to alert the processor 2242 that the locking mechanism 2234 is unlocked. In at least one example, the bailout door feedback element 2246 may comprise a switch circuit (not shown) operably coupled to the processor 2242; the switch circuit can be configured to be transitioned to an open configuration when the locking mechanism 2234 is unlocked by a clinician and/or transitioned to a closed configuration when the locking mechanism 2234 is locked by the clinician, for example. In at least one example, the bailout door feedback element 2246 may comprise at least one sensor (not shown) operably coupled to the processor 2242; the sensor can be configured to be triggered when the locking mechanism 2234 is transitioned to unlocked and/or locked configurations by the clinician, for example. The reader will appreciate that the bailout door feedback element 2246 may include other means for detecting the locking and/or unlocking of the locking mechanism 2234 by the clinician.

In certain instances, the bailout door feedback element 2246 may comprise a switch circuit (not shown) operably coupled to the processor 2242; the switch circuit can be configured to be transitioned to an open configuration when the bailout door 2232 is removed or opened, for example, and/or transitioned to a closed configuration when the bailout door 2232 is installed or closed, for example. In at least one example, the bailout door feedback element 2246 may comprise at least one sensor (not shown) operably coupled to the processor 2242; the sensor can be configured to be triggered when the bailout door 2232 is removed or opened, for example, and/or when the bailout door 2232 is closed or installed, for example. The reader will appreciate that the bailout door feedback element 2246 may include other means for detecting the locking and/or unlocking of the locking mechanism 2234 and/or the opening and/or closing of the bailout door 2232 by the clinician.

In certain instances, as illustrated in FIG. 51, the bailout feedback system 2236 may comprise one or more additional feedback elements 2248 which may comprise additional switch circuits and/or sensors in operable communication with the processor 2242; the additional switch circuits and/or sensors may be employed by the processor 2242 to measure other parameters associated with the bailout feedback system 2236. In certain instances, the bailout feedback system 2236 may comprise one or more interfaces which may include one or more devices for providing a sensory feedback to a user. Such devices may comprise, for example, visual feedback devices such as display screens and/or LED indicators, for example. In certain instances, such devices may comprise audio feedback devices such as speakers and/or buzzers, for example. In certain instances, such devices may comprise tactile feedback devices such as haptic actuators, for example. In certain instances, such devices may comprise combinations of visual feedback devices, audio feedback devices, and/or tactile feedback devices. In certain circumstances, as illustrated in FIG. 48, the one or more interfaces may comprise a display 2250 which may be included in the handle assembly 2202, for example. In certain instances, the processor 2242 may employ the display 2250 to alert, guide, and/or provide feedback to a user of the surgical instrument 2200 with regard to performing a manual bailout of the surgical instrument 2200 using the bailout assembly 2228.

Figure 52:
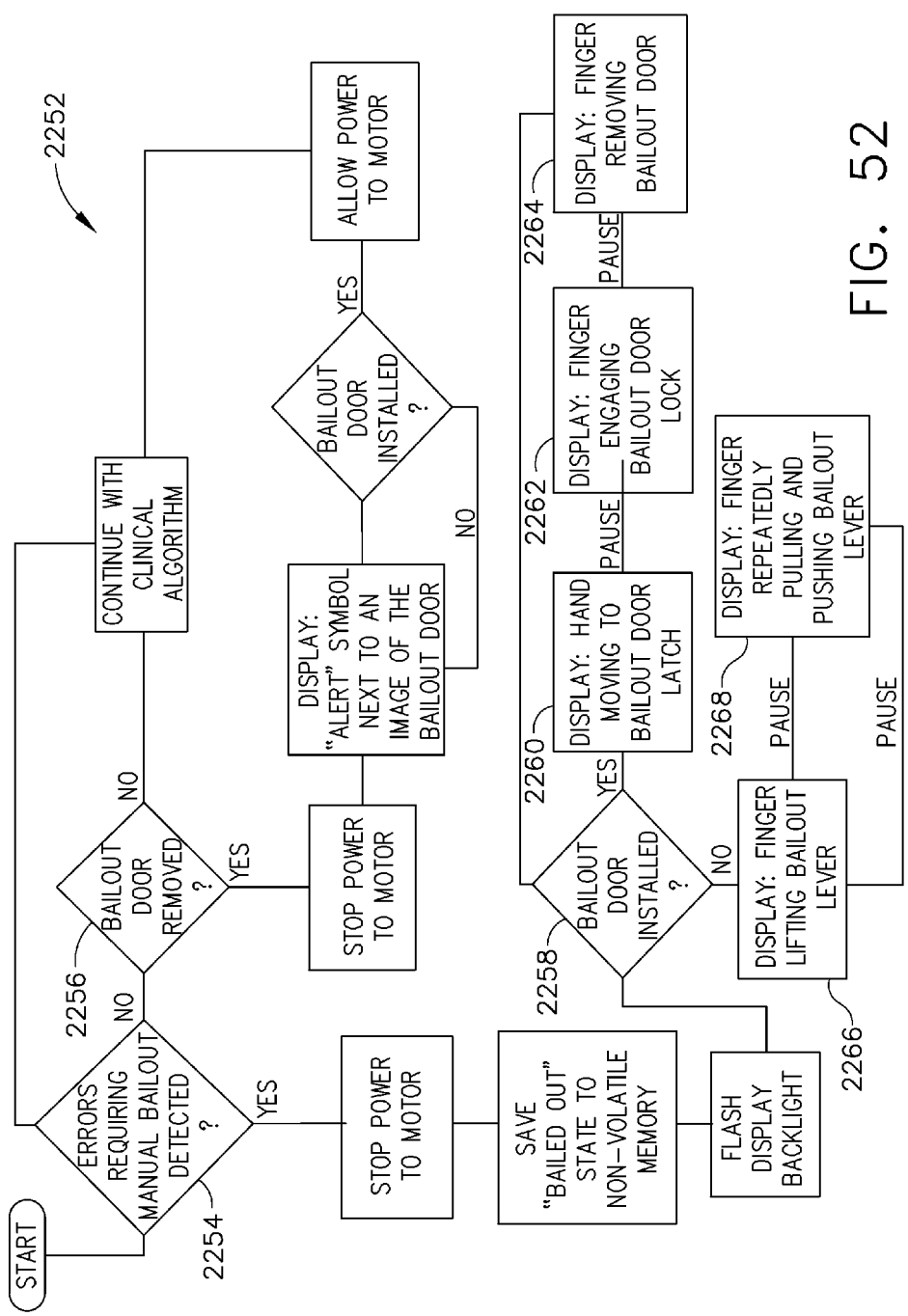
FIG. 52 is a block diagram of a module for use with the bailout feedback system of FIG. 51.

In certain instances, the bailout feedback system 2236 may comprise one or more embedded applications implemented as firmware, software, hardware, or any combination thereof. In certain instances, the bailout feedback system 2236 may comprise various executable modules such as software, programs, data, drivers, and/or application program interfaces (APIs), for example. FIG. 52 depicts an exemplary module 2252 that can be stored in the memory 2240, for example. The module 2252 can be executed by the processor 2242, for example, to alert, guide, and/or provide feedback to a user of the surgical instrument 2200 with regard to performing a manual bailout of the surgical instrument 2200 using the bailout assembly 2228.

As illustrated in FIG. 52, the module 2252 may be executed by the processor 2242 to provide the user with instructions as to how to access and/or use the bailout assembly 2228 to perform the manual bailout of the surgical instrument 2200, for example. In various instances, the module 2252 may comprise one or more decision-making steps such as, for example, a decision-making step 2254 with regard to the detection of one or more errors requiring the manual bailout of the surgical instrument 2200.

In various instances, the processor 2242 may be configured to detect a bailout error in response to the occurrence of one or more intervening events during the normal operation of the surgical instrument 2200, for example. In certain instances, the processor 2242 may be configured to detect a bailout error when one or more bailout error signals are received by the processor 2242; the bailout error signals can be communicated to the processor 2242 by other processors and/or sensors of the surgical instrument 2200, for example. In certain instances, a bailout error can be detected by the processor 2242 when a temperature of the surgical instrument 2200, as detected by a sensor (not shown), exceeds a threshold, for example. In certain instances, the surgical instrument 2200 may comprise a positioning system (not shown) for sensing and recording the position of the longitudinally-movable drive member 2226 during a firing stroke of the firing drive system 2214. In at least one example, the processor 2242 can be configured to detect a bailout error when one or more of the recorded positions of the longitudinally-movable drive member 2226 is not are accordance with a predetermined threshold, for example.

In any event, referring again to FIG. 52, when the processor 2242 detects a bailout error in the decision-making step 2254, the processor 2242 may respond by stopping and/or disabling the motor 2216, for example. In addition, in certain instances, the processor 2242 also may store a bailed out state in the memory 2240 after detecting the bailout error, as illustrated in FIG. 52. In other words, the processor 2242 may store in the memory 2240 a status indicating that a bailout error has been detected. As described above, the memory 2240 can be a non-volatile memory which may preserve the stored status that a bailout error has been detected when the surgical instrument 2200 is reset by the user, for example.

In various instances, the motor 2216 can be stopped and/or disabled by disconnecting the battery 2218 from the motor 2216, for example. In various instances, the processor 2242 may employ the driver 2244 to stop and/or disable the motor 2216. In certain instances, when the motor override circuit is utilized, the processor 2242 may employ the motor override circuit to stop and/or disable the motor 2216. In certain instances, stopping and/or disabling the motor 2216 may prevent a user of the surgical instrument 2200 from using the motor 2216 at least until the manual bailout is performed, for example. The reader will appreciate that stopping and/or disabling the motor 2216 in response to the detection of a bailout error can be advantageous in protecting tissue captured by the surgical instrument 2200.

Further to the above, referring still to FIG. 52, the module 2252 may include a decision-making step 2256 for detecting whether the bailout door 2232 is removed. As described above, the processor 2242 can be operationally coupled to the bailout door feedback element 2246 which can be configured to alert the processor 2242 as to whether the bailout door 2232 is removed. In certain instances, the processor 2242 can be programmed to detect that the bailout door 2232 is removed when the bailout door feedback element 2246 reports that the locking mechanism 2234 is unlocked, for example. In certain instances, the processor 2242 can be programmed to detect that the bailout door 2232 is removed when the bailout door feedback element 2246 reports that the bailout door 2232 is opened, for example. In certain instances, the processor 2242 can be programmed to detect that the bailout door 2232 is removed when the bailout door feedback element 2246 reports that the locking mechanism 2234 is unlocked and that the bailout door 2232 is opened, for example.

In various instances, referring still to FIG. 52, when the processor 2242 does not detect a bailout error in the decision-making step 2254 and does not detect that the bailout door 2232 is removed in the decision-making step 2256, the processor 2242 may not interrupt the normal operation of the surgical instrument 2200 and may proceed with various clinical algorithms. In certain instances, when the processor 2242 does not detect a bailout error in the decision-making step 2254 but detects that the bailout door 2232 is removed in the decision-making step 2256, the processor 2242 may respond by stopping and/or disabling the motor 2216, as described above. In addition, in certain instances, the processor 2242 also may provide the user with instructions to reinstall the bailout door 2232, as described in greater detail below. In certain instances, when the processor 2242 detects that the bailout door 2232 is reinstalled, while no bailout error is detected, the processor 2242 can be configured to reconnect the power to the motor 2216 and allow the user to continue with clinical algorithms, as illustrated in FIG. 52.

In certain instances, when the user does not reinstall the bailout door 2232, the processor 2242 may not reconnect power to the motor 2216 and may continue providing the user with the instructions to reinstall the bailout door 2232. In certain instances, when the user does not reinstall the bailout door 2232, the processor 2242 may provide the user with a warning that the bailout door 2232 needs to be reinstalled in order to continue with the normal operation of the surgical instrument 2200. In certain instances, the surgical instrument 2200 can be equipped with an override mechanism (not shown) to permit the user to reconnect power to the motor 2216 even when the bailout door 2216 is not installed.

In various instances, the processor 2242 can be configured to provide the user with a sensory feedback when the processor 2242 detects that the bailout door 2232 is removed. In various instances, the processor 2242 can be configured to provide the user with a sensory feedback when the processor 2242 detects that the bailout door 2232 is reinstalled. Various devices can be employed by the processor 2242 to provide the sensory feedback to the user. Such devices may comprise, for example, visual feedback devices such as display screens and/or LED indicators, for example. In certain instances, such devices may comprise audio feedback devices such as speakers and/or buzzers, for example. In certain instances, such devices may comprise tactile feedback devices such as haptic actuators, for example. In certain instances, such devices may comprise combinations of visual feedback devices, audio feedback devices, and/or tactile feedback devices. In certain instances, the processor 2242 may employ the display 2250 to instruct the user to reinstall the bailout door 2232. For example, the processor 2242 may present an alert symbol next to an image of the bailout door 2232 to the user through the display 2250, for example. In certain instances, the processor 2242 may present an animated image of the bailout door 2232 being installed, for example. Other images, symbols, and/or words can be displayed through the display 2250 to alert the user of the surgical instrument 2200 to reinstall the bailout door 2232.

Referring again to FIG. 52, when a bailout error is detected, the processor 2242 may signal the user of the surgical instrument 2200 to perform the manual bailout using the bailout handle 2230. In various instances, the processor 2242 can signal the user to perform the manual bailout by providing the user with a visual, audio, and/or tactile feedback, for example. In certain instances, as illustrated in FIG. 52, the processor 2242 can signal the user of the surgical instrument 2200 to perform the manual bailout by flashing a backlight of the display 2250. In any event, the processor 2242 may then provide the user with instructions to perform the manual bailout. In various instances, as illustrated in FIG. 52, the instructions may depend on whether the bailout door 2232 is installed; a decision making step 2258 may determine the type of instructions provided to the user. In certain instances, when the processor 2242 detects that the bailout door 2232 is installed, the processor 2242 may provide the user with instructions to remove the bailout door 2232 and instructions to operate the bailout handle 2230, for example. However, when the processor 2242 detects that the bailout door 2232 is removed, the processor 2242 may provide the user with the instructions to operate the bailout handle 2230 but not the instructions to remove the bailout door 2232, for example.

Referring again to FIG. 52, in various instances, the instructions provided by the processor 2242 to the user to remove the bailout door 2232 and/or to operate the bailout handle 2230 may comprise one or more steps; the steps may be presented to the user in a chronological order. In certain instances, the steps may comprise actions to be performed by the user. In such instances, the user may proceed through the steps of the manual bailout by performing the actions presented in each of the steps. In certain instances, the actions required in one or more of the steps can be presented to the user in the form of animated images displayed on the display 2250, for example. In certain instances, one or more of the steps can be presented to the user as messages which may include words, symbols, and/or images that guide the user through the manual bailout. In certain instances, one or more of the steps of performing the manual bailout can be combined in one or more messages, for example. In certain instances, each message may comprise a separate step, for example.

In certain instances, the steps and/or the messages providing the instructions for the manual bailout can be presented to the user in predetermined time intervals to allow the user sufficient time to comply with the presented steps and/or messages, for example. In certain instances, the processor 2242 can be programmed to continue presenting a step and/or a message until feedback is received by the processor 2242 that the step has been performed. In certain instances, the feedback can be provided to the processor 2242 by the bailout door feedback element 2246, for example. Other mechanisms and/or sensors can be employed by the processor 2242 to obtain feedback that a step has been completed. In at least one example, the user can be instructed to alert that processor 2242 when a step is completed by pressing an alert button, for example. In certain instances, the display 2250 may comprise a capacitive screen which may provide the user with an interface to alert the processor 2242 when a step is completed. For example, the user may press the capacitive screen to move to the next step of the manual bailout instructions after a current step is completed.

In certain instances, as illustrated in FIG. 52, after detecting that the bailout door 2232 is installed, the processor 2242 can be configured to employ the display 2250 to present an animated image 2260 depicting a hand moving toward the bailout door 2232. The processor 2242 may continue to display the animated image 2260 for a time interval sufficient for the user to engage the bailout door 2232, for example. In certain instances, the processor 2242 may then replace the animated image 2260 with an animated image 2262 depicting a finger engaging the bailout door locking mechanism 2234, for example. The processor 2242 may continue to display the animated image 2262 for a time interval sufficient for the user to unlock the locking mechanism 2234, for example. In certain instances, the processor 2242 may continue to display the animated image 2262 until the bailout door feedback element 2246 reports that the locking mechanism 2234 is unlocked, for example. In certain instances, the processor 2242 may continue to display the animated image 2262 until the user alerts the processor 2242 that the step of unlocking the locking mechanism 2234 is completed.

In any event, the processor 2242 may then replace the animated image 2262 with an animated image 2264 depicting a finger removing the bailout door 2232, for example. The processor 2242 may continue to display the animated image 2264 for a time interval sufficient for the user to remove the bailout door 2232, for example. In certain instances, the processor 2242 may continue to display the animated image 2264 until the bailout door feedback element 2246 reports that the bailout door 2232 is removed, for example. In certain instances, the processor 2242 may continue to display the animated image 2264 until the user alerts the processor 2242 that the step of removing the bailout door 2232 has been removed, for example. In certain instances, the processor 2242 can be configured to continue to repeat displaying the animated images 2260, 2262, and 2246 in their respective order when the processor 2242 continues to detect that the bailout door is installed at the decision making step 2258, for example.

Further to the above, after detecting that the bailout door 2232 is removed, the processor 2242 may proceed to guide the user through the steps of operating the bailout handle 2230. In certain instances, the processor 2242 may replace the animated image 2264 with an animated image 2266 depicting a finger lifting the bailout handle 2230, for example, into ratcheting engagement with the teeth 2224 in the drive member 2226, as described above. The processor 2242 may continue to display the animated image 2266 for a time interval sufficient for the user to lift the bailout handle 2230, for example. In certain instances, the processor 2242 may continue to display the animated image 2266 until the processor receives feedback that the bailout handle 2230 has been lifted. For example, the processor 2242 may continue to display the animated image 2266 until the user alerts the processor 2242 that the step of lifting the bailout handle 2230 has been removed.

In certain instances, as described above, the user can manually retract the drive member 2226 by using the bailout handle 2230 to ratchet the drive member 2226 in the proximal direction "P," for example, to release tissue trapped by the end effector 2208, for example. In such instances, the processor 2242 may replace the animated image 2266 with an animated image 2268 depicting a finger repeatedly pulling then pushing the bailout handle 2230, for example, to simulate the ratcheting of the bailout handle 2230. The processor 2242 may continue to display the animated image 2268 for a time interval sufficient for the user to ratchet the drive member 2226 to default position, for example. In certain instances, the processor 2242 may continue to display the animated image 2268 until the processor 2242 receives feedback that the drive member 2226 has been retracted.

Figure 53:
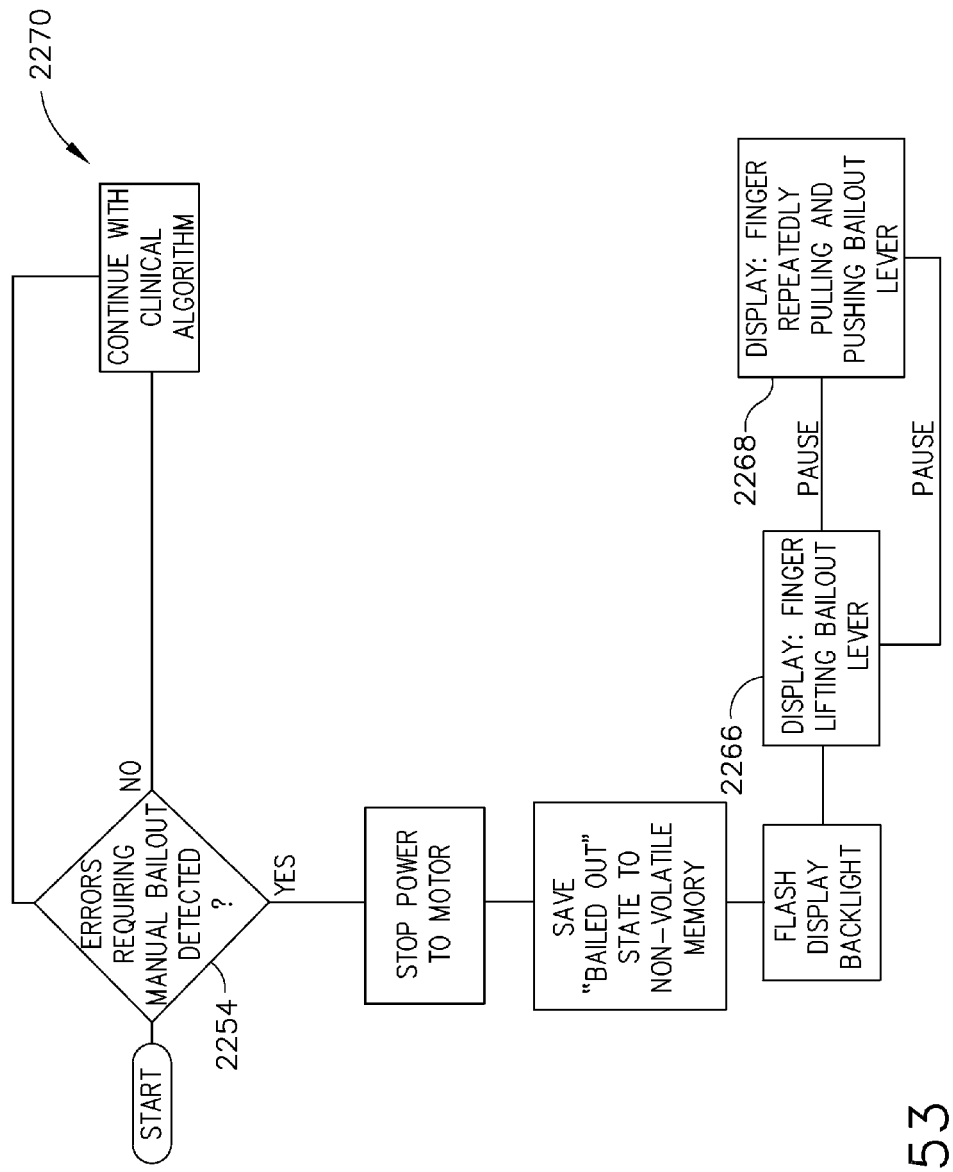
FIG. 53 is a block diagram of a module for use with the bailout feedback system of FIG. 51.

FIG. 53 depicts a module 2270 which is similar in many respects to the module 2258. For example, the module 2252 also can be stored in the memory 2240 and/or executed by the processor 2242, for example, to alert, guide, and/or provide feedback to a user of the surgical instrument 2200 with regard to performing a manual bailout of the surgical instrument 2200. In certain instances, the surgical instrument 2200 may not comprise a bailout door. In such circumstances, the module 2270 can be employed by the processor 2242 to provide the user with instructions as to how to operate the bailout handle 2230, for example.

Referring again to the module 2270 depicted in FIG. 53, when the processor 2242 does not detect a bailout error in the decision-making step 2254 of the module 2270, the processor 2242 may not interrupt the normal operation of the surgical instrument 2200 and may proceed with various clinical algorithms. However, when the processor 2242 detects a bailout error in the decision-making step 2254 of the module 2270, the processor 2242 may respond by stopping and/or disabling the motor 2216, for example. In addition, in certain instances, the processor 2242 also may store a bailed out state in the memory 2240 after detecting the bailout error, as illustrated in FIG. 53. In the absence of a bailout door, the processor 2242 may signal the user of the surgical instrument 2200 to perform the manual bailout, for example, by flashing the backlight of the display 2250; the processor 2242 may then proceed directly to providing the user with the instructions to operate the bailout handle 2230, as described above.

The reader will appreciate that the steps depicted in FIGS. 52 and/or 53 are illustrative examples of the instructions that can be provided to the user of the surgical instrument 2200 to perform a manual bailout. The modules 2252 and/or 2270 can be configured to provide more or less steps than those illustrated in FIGS. 52 and 53. The reader will also appreciate that the modules 2252 and/or 2270 are exemplary modules; various other modules can be executed by the processor 2242 to provide the user of the surgical instrument 2200 with instructions to perform the manual bailout.

In various instances, as described above, the processor 2242 can be configured to present to the user of the surgical instrument 2200 the steps and/or messages for performing a manual bailout in predetermined time intervals. Such time intervals may be the same or may vary depending on the complexity of the task to be performed by the user, for example. In certain instances, such time intervals can be any time interval in the range of about 1 second, for example, to about 10 minutes, for example. In certain instances, such time intervals can be any time interval in the range of about 1 second, for example, to about 1 minute, for example. Other time intervals are contemplated by the present disclosure.

In some instances, a power assembly, such as, for example the power assembly 2006 illustrated in FIGS. 31-33B, is configured to monitor the number of uses of the power assembly 2006 and/or a surgical instrument 2000 coupled to the power assembly 2006. The power assembly 2006 maintains a usage cycle count corresponding to the number of uses. The power assembly 2006 and/or the surgical instrument 2000 performs one or more actions based on the usage cycle count. For example, in some instances, when the usage cycle count exceeds a predetermined usage limit, the power assembly 2006 and/or a surgical instrument 2000 may disable the power assembly 2006, disable the surgical instrument 2000, indicate that a reconditioning or service cycle is required, provide a usage cycle count to an operator and/or a remote system, and/or perform any other suitable action. The usage cycle count is determined by any suitable system, such as, for example, a mechanical limiter, a usage cycle circuit, and/or any other suitable system coupled to the battery 2006 and/or the surgical instrument 2000.

Figure 54:
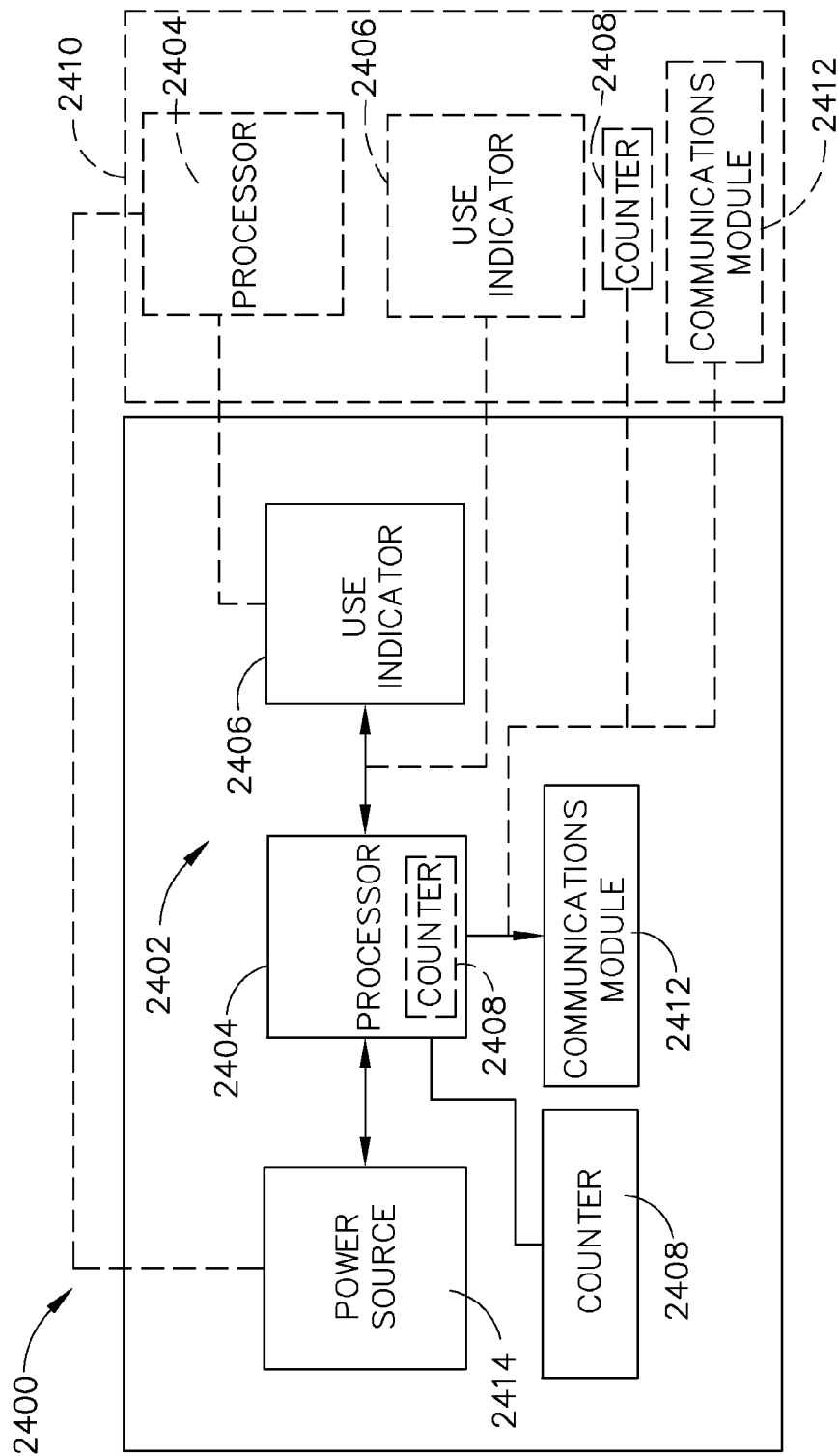
FIG. 54 illustrates one instance of a power assembly comprising a usage cycle circuit configured to generate a usage cycle count of the battery back.

FIG. 54 illustrates one example of a power assembly 2400 comprising a usage cycle circuit 2402 configured to monitor a usage cycle count of the power assembly 2400. The power assembly 2400 may be coupled to a surgical instrument 2410. The usage cycle circuit 2402 comprises a processor 2404 and a use indicator 2406. The use indicator 2406 is configured to provide a signal to the processor 2404 to indicate a use of the battery back 2400 and/or a surgical instrument 2410 coupled to the power assembly 2400. A "use" may comprise any suitable action, condition, and/or parameter such as, for example, changing a modular component of a surgical instrument 2410, deploying or firing a disposable component coupled to the surgical instrument 2410, delivering electrosurgical energy from the surgical instrument 2410, reconditioning the surgical instrument 2410 and/or the power assembly 2400, exchanging the power assembly 2400, recharging the power assembly 2400, and/or exceeding a safety limitation of the surgical instrument 2410 and/or the battery back 2400.

In some instances, a usage cycle, or use, is defined by one or more power assembly 2400 parameters. For example, in one instance, a usage cycle comprises using more than 5% of the total energy available from the power assembly 2400 when the power assembly 2400 is at a full charge level. In another instance, a usage cycle comprises a continuous energy drain from the power assembly 2400 exceeding a predetermined time limit. For example, a usage cycle may correspond to five minutes of continuous and/or total energy draw from the power assembly 2400. In some instances, the power assembly 2400 comprises a usage cycle circuit 2402 having a continuous power draw to maintain one or more components of the usage cycle circuit 2402, such as, for example, the use indicator 2406 and/or a counter 2408, in an active state.

The processor 2404 maintains a usage cycle count. The usage cycle count indicates the number of uses detected by the use indicator 2406 for the power assembly 2400 and/or the surgical instrument 2410. The processor 2404 may increment and/or decrement the usage cycle count based on input from the use indicator 2406. The usage cycle count is used to control one or more operations of the power assembly 2400 and/or the surgical instrument 2410. For example, in some instances, a power assembly 2400 is disabled when the usage cycle count exceeds a predetermined usage limit. Although the instances discussed herein are discussed with respect to incrementing the usage cycle count above a predetermined usage limit, those skilled in the art will recognize that the usage cycle count may start at a predetermined amount and may be decremented by the processor 2404. In this instance, the processor 2404 initiates and/or prevents one or more operations of the power assembly 2400 when the usage cycle count falls below a predetermined usage limit.

The usage cycle count is maintained by a counter 2408. The counter 2408 comprises any suitable circuit, such as, for example, a memory module, an analog counter, and/or any circuit configured to maintain a usage cycle count. In some instances, the counter 2408 is formed integrally with the processor 2404. In other instances, the counter 2408 comprises a separate component, such as, for example, a solid state memory module. In some instances, the usage cycle count is provided to a remote system, such as, for example, a central database. The usage cycle count is transmitted by a communications module 2412 to the remote system. The communications module 2412 is configured to use any suitable communications medium, such as, for example, wired and/or wireless communication. In some instances, the communications module 2412 is configured to receive one or more instructions from the remote system, such as, for example, a control signal when the usage cycle count exceeds the predetermined usage limit.

In some instances, the use indicator 2406 is configured to monitor the number of modular components used with a surgical instrument 2410 coupled to the power assembly 2400. A modular component may comprise, for example, a modular shaft, a modular end effector, and/or any other modular component. In some instances, the use indicator 2406 monitors the use of one or more disposable components, such as, for example, insertion and/or deployment of a staple cartridge within an end effector coupled to the surgical instrument 2410. The use indicator 2406 comprises one or more sensors for detecting the exchange of one or more modular and/or disposable components of the surgical instrument 2410.

In some instances, the use indicator 2406 is configured to monitor single patient surgical procedures performed while the power assembly 2400 is installed. For example, the use indicator 2406 may be configured to monitor firings of the surgical instrument 2410 while the power assembly 2400 is coupled to the surgical instrument 2410. A firing may correspond to deployment of a staple cartridge, application of electrosurgical energy, and/or any other suitable surgical event. The use indicator 2406 may comprise one or more circuits for measuring the number of firings while the power assembly 2400 is installed. The use indicator 2406 provides a signal to the processor 2404 when a single patient procedure is performed and the processor 2404 increments the usage cycle count.

In some instances, the use indicator 2406 comprises a circuit configured to monitor one or more parameters of the power source 2414, such as, for example, a current draw from the power source 2414. The one or more parameters of the power source 2414 correspond to one or more operations performable by the surgical instrument 2410, such as, for example, a cutting and sealing operation. The use indicator 2406 provides the one or more parameters to the processor 2404, which increments the usage cycle count when the one or more parameters indicate that a procedure has been performed.

In some instances, the use indicator 2406 comprises a timing circuit configured to increment a usage cycle count after a predetermined time period. The predetermined time period corresponds to a single patient procedure time, which is the time required for an operator to perform a procedure, such as, for example, a cutting and sealing procedure. When the power assembly 2400 is coupled to the surgical instrument 2410, the processor 2404 polls the use indicator 2406 to determine when the single patient procedure time has expired. When the predetermined time period has elapsed, the processor 2404 increments the usage cycle count. After incrementing the usage cycle count, the processor 2404 resets the timing circuit of the use indicator 2406.

Figure 55:
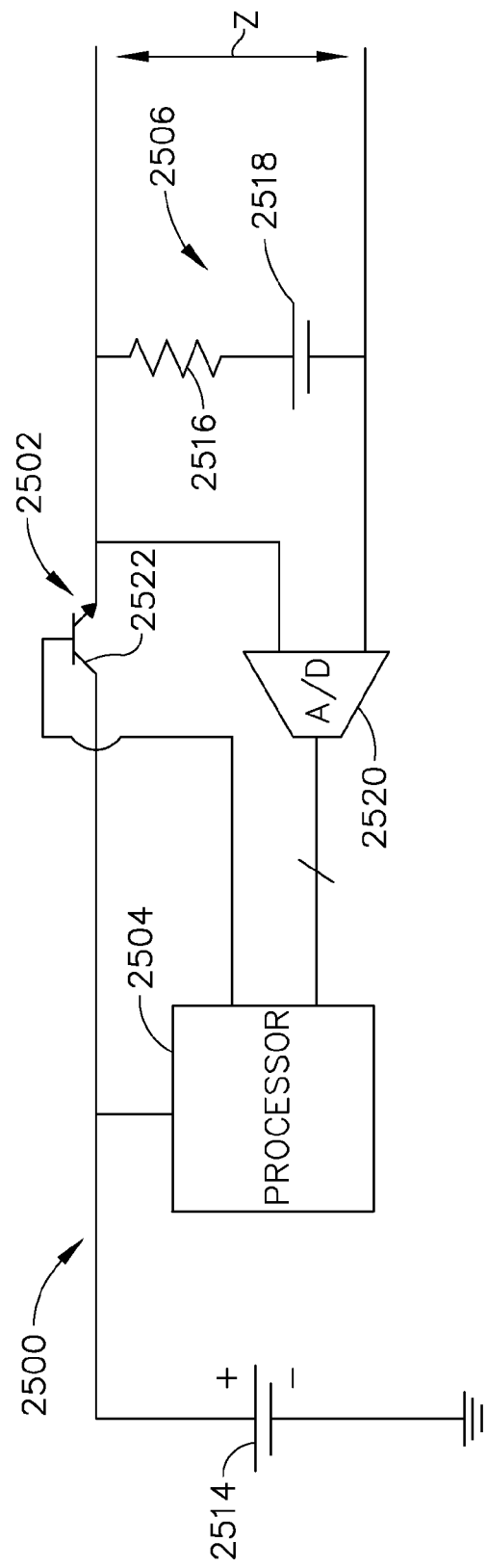
FIG. 55 illustrates one instance of a usage cycle circuit comprising a resistor-capacitor timer.

In some instances, the use indicator 2406 comprises a time constant that approximates the single patient procedure time. FIG. 55 illustrates one instance of power assembly 2500 comprising a usage cycle circuit 2502 having a resistor-capacitor (RC) timing circuit 2506. The RC timing circuit 2506 comprises a time constant defined by a resistor-capacitor pair. The time constant is defined by the values of the resistor 2518 and the capacitor 2516. When the power assembly 2500 is installed in a surgical instrument, a processor 2504 polls the RC timing circuit 2506. When one or more parameters of the RC timing circuit 2506 are below a predetermined threshold, the processor 2504 increments the usage cycle count. For example, the processor 2504 may poll the voltage of the capacitor 2518 of the resistor-capacitor pair 2506. When the voltage of the capacitor 2518 is below a predetermined threshold, the processor 2504 increments the usage cycle count. The processor 2504 may be coupled to the RC timing circuit 2506 by, for example, and ADC 2520. After incrementing the usage cycle count, the processor 2504 turns on a transistor 2522 to connect the RC timing circuit 2506 to a power source 2514 to charge the capacitor 2518 of the RC timing circuit 2506. Once the capacitor 2518 is fully charged, the transistor 2522 is opened and the RC timing circuit 2506 is allowed to discharge, as governed by the time constant, to indicate a subsequent single patient procedure.

Figure 56:
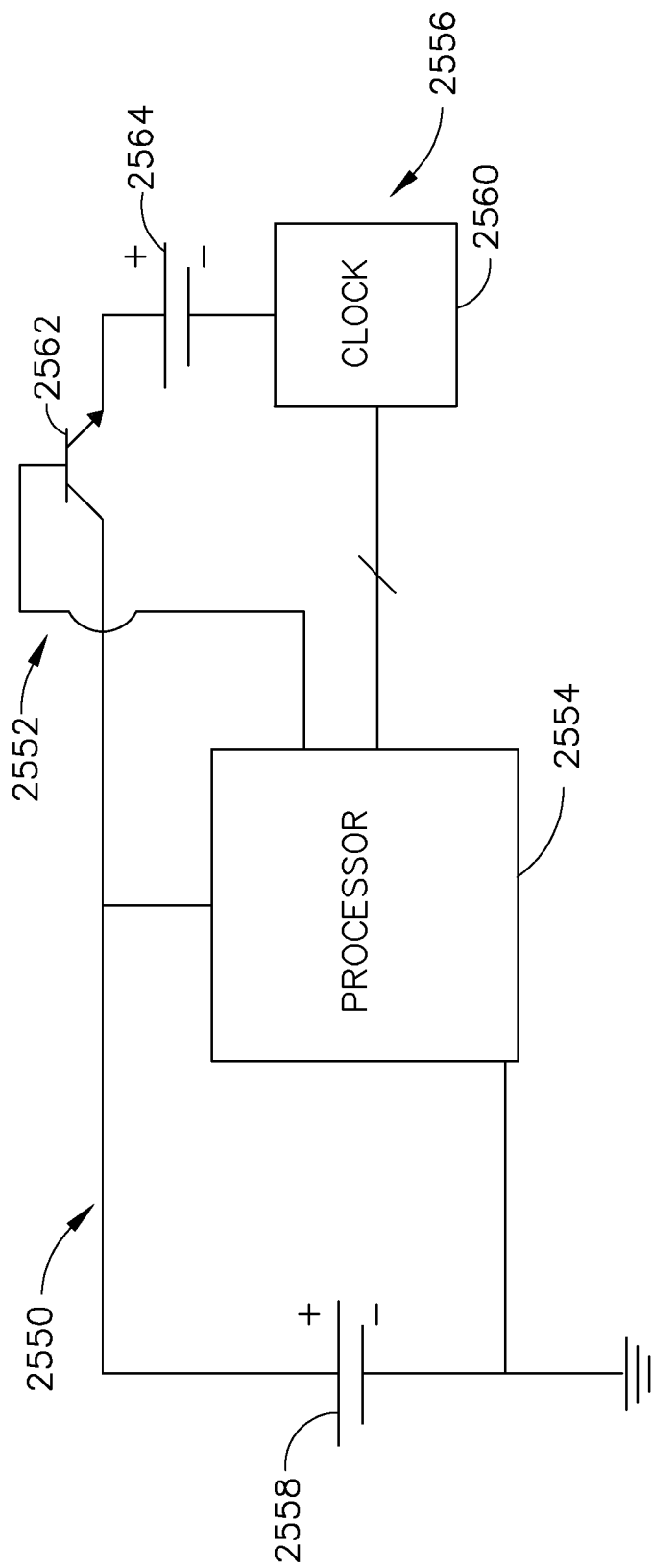
FIG. 56 illustrates one instance of a usage cycle circuit comprising a timer and a rechargeable battery.

FIG. 56 illustrates one instance of a power assembly 2550 comprising a usage cycle circuit 2552 having a rechargeable battery 2564 and a clock 2560. When the power assembly 2550 is installed in a surgical instrument, the rechargeable battery 2564 is charged by the power source 2558. The rechargeable battery 2564 comprises enough power to run the clock 2560 for at least the single patient procedure time. The clock 2560 may comprise a real time clock, a processor configured to implement a time function, or any other suitable timing circuit. The processor 2554 receives a signal from the clock 2560 and increments the usage cycle count when the clock 2560 indicates that the single patient procedure time has been exceeded. The processor 2554 resets the clock 2560 after incrementing the usage cycle count. For example, in one instance, the processor 2554 closes a transistor 2562 to recharge the rechargeable battery 2564. Once the rechargeable battery 2564 is fully charged, the processor 2554 opens the transistor 2562, and allows the clock 2560 to run while the rechargeable battery 2564 discharges.

Referring back to FIG. 54, in some instances, the use indicator 2406 comprises a sensor configured to monitor one or more environmental conditions experienced by the power assembly 2400. For example, the use indicator 2406 may comprise an accelerometer. The accelerometer is configured to monitor acceleration of the power assembly 2400. The power assembly 2400 comprises a maximum acceleration tolerance. Acceleration above a predetermined threshold indicates, for example, that the power assembly 2400 has been dropped. When the use indicator 2406 detects acceleration above the maximum acceleration tolerance, the processor 2404 increments a usage cycle count. In some instances, the use indicator 2406 comprises a moisture sensor. The moisture sensor is configured to indicate when the power assembly 2400 has been exposed to moisture. The moisture sensor may comprise, for example, an immersion sensor configured to indicate when the power assembly 2400 has been fully immersed in a cleaning fluid, a moisture sensor configured to indicate when moisture is in contact with the power assembly 2400 during use, and/or any other suitable moisture sensor.

In some instances, the use indicator 2406 comprises a chemical exposure sensor. The chemical exposure sensor is configured to indicate when the power assembly 2400 has come into contact with harmful and/or dangerous chemicals. For example, during a sterilization procedure, an inappropriate chemical may be used that leads to degradation of the power assembly 2400. The processor 2404 increments the usage cycle count when the use indicator 2406 detects an inappropriate chemical.

In some instances, the usage cycle circuit 2402 is configured to monitor the number of reconditioning cycles experienced by the power assembly 2400. A reconditioning cycle may comprise, for example, a cleaning cycle, a sterilization cycle, a charging cycle, routine and/or preventative maintenance, and/or any other suitable reconditioning cycle. The use indicator 2406 is configured to detect a reconditioning cycle. For example, the use indicator 2406 may comprise a moisture sensor to detect a cleaning and/or sterilization cycle. In some instances, the usage cycle circuit 2402 monitors the number of reconditioning cycles experienced by the power assembly 2400 and disables the power assembly 2400 after the number of reconditioning cycles exceeds a predetermined threshold.

The usage cycle circuit 2402 may be configured to monitor the number of power assembly 2400 exchanges. The usage cycle circuit 2402 increments the usage cycle count each time the power assembly 2400 is exchanged. When the maximum number of exchanges is exceeded, the usage cycle circuit 2402 locks out the power assembly 2400 and/or the surgical instrument 2410. In some instances, when the power assembly 2400 is coupled the surgical instrument 2410, the usage cycle circuit 2402 identifies the serial number of the power assembly 2400 and locks the power assembly 2400 such that the power assembly 2400 is usable only with the surgical instrument 2410. In some instances, the usage cycle circuit 2402 increments the usage cycle each time the power assembly 2400 is removed from and/or coupled to the surgical instrument 2410.

In some instances, the usage cycle count corresponds to sterilization of the power assembly 2400. The use indicator 2406 comprises a sensor configured to detect one or more parameters of a sterilization cycle, such as, for example, a temperature parameter, a chemical parameter, a moisture parameter, and/or any other suitable parameter. The processor 2404 increments the usage cycle count when a sterilization parameter is detected. The usage cycle circuit 2402 disables the power assembly 2400 after a predetermined number of sterilizations. In some instances, the usage cycle circuit 2402 is reset during a sterilization cycle, a voltage sensor to detect a recharge cycle, and/or any suitable sensor. The processor 2404 increments the usage cycle count when a reconditioning cycle is detected. The usage cycle circuit 2402 is disabled when a sterilization cycle is detected. The usage cycle circuit 2402 is reactivated and/or reset when the power assembly 2400 is coupled to the surgical instrument 2410. In some instances, the use indicator comprises a zero power indicator. The zero power indicator changes state during a sterilization cycle and is checked by the processor 2404 when the power assembly 2400 is coupled to a surgical instrument 2410. When the zero power indicator indicates that a sterilization cycle has occurred, the processor 2404 increments the usage cycle count.

A counter 2408 maintains the usage cycle count. In some instances, the counter 2408 comprises a non-volatile memory module. The processor 2404 increments the usage cycle count stored in the non-volatile memory module each time a usage cycle is detected. The memory module may be accessed by the processor 2404 and/or a control circuit, such as, for example, the control circuit 1100. When the usage cycle count exceeds a predetermined threshold, the processor 2404 disables the power assembly 2400. In some instances, the usage cycle count is maintained by a plurality of circuit components. For example, in one instance, the counter 2408 comprises a resistor (or fuse) pack. After each use of the power assembly 2400, a resistor (or fuse) is burned to an open position, changing the resistance of the resistor pack. The power assembly 2400 and/or the surgical instrument 2410 reads the remaining resistance. When the last resistor of the resistor pack is burned out, the resistor pack has a predetermined resistance, such as, for example, an infinite resistance corresponding to an open circuit, which indicates that the power assembly 2400 has reached its usage limit. In some instances, the resistance of the resistor pack is used to derive the number of uses remaining.

In some instances, the usage cycle circuit 2402 prevents further use of the power assembly 2400 and/or the surgical instrument 2410 when the usage cycle count exceeds a predetermined usage limit. In one instance, the usage cycle count associated with the power assembly 2400 is provided to an operator, for example, utilizing a screen formed integrally with the surgical instrument 2410. The surgical instrument 2410 provides an indication to the operator that the usage cycle count has exceeded a predetermined limit for the power assembly 2400, and prevents further operation of the surgical instrument 2410.

In some instances, the usage cycle circuit 2402 is configured to physically prevent operation when the predetermined usage limit is reached. For example, the power assembly 2400 may comprise a shield configured to deploy over contacts of the power assembly 2400 when the usage cycle count exceeds the predetermined usage limit. The shield prevents recharge and use of the power assembly 2400 by covering the electrical connections of the power assembly 2400.

In some instances, the usage cycle circuit 2402 is located at least partially within the surgical instrument 2410 and is configured to maintain a usage cycle count for the surgical instrument 2410. FIG. 54 illustrates one or more components of the usage cycle circuit 2402 within the surgical instrument 2410 in phantom, illustrating the alternative positioning of the usage cycle circuit 2402. When a predetermined usage limit of the surgical instrument 2410 is exceeded, the usage cycle circuit 2402 disables and/or prevents operation of the surgical instrument 2410. The usage cycle count is incremented by the usage cycle circuit 2402 when the use indicator 2406 detects a specific event and/or requirement, such as, for example, firing of the surgical instrument 2410, a predetermined time period corresponding to a single patient procedure time, based on one or more motor parameters of the surgical instrument 2410, in response to a system diagnostic indicating that one or more predetermined thresholds are met, and/or any other suitable requirement. As discussed above, in some instances, the use indicator 2406 comprises a timing circuit corresponding to a single patient procedure time. In other instances, the use indicator 2406 comprises one or more sensors configured to detect a specific event and/or condition of the surgical instrument 2410.

In some instances, the usage cycle circuit 2402 is configured to prevent operation of the surgical instrument 2410 after the predetermined usage limit is reached. In some instances, the surgical instrument 2410 comprises a visible indicator to indicate when the predetermined usage limit has been reached and/or exceeded. For example, a flag, such as a red flag, may pop-up from the surgical instrument 2410, such as from the handle, to provide a visual indication to the operator that the surgical instrument 2410 has exceeded the predetermined usage limit. As another example, the usage cycle circuit 2402 may be coupled to a display formed integrally with the surgical instrument 2410. The usage cycle circuit 2402 displays a message indicating that the predetermined usage limit has been exceeded. The surgical instrument 2410 may provide an audible indication to the operator that the predetermined usage limit has been exceeded. For example, in one instance, the surgical instrument 2410 emits an audible tone when the predetermined usage limit is exceeded and the power assembly 2400 is removed from the surgical instrument 2410. The audible tone indicates the last use of the surgical instrument 2410 and indicates that the surgical instrument 2410 should be disposed or reconditioned.

In some instances, the usage cycle circuit 2402 is configured to transmit the usage cycle count of the surgical instrument 2410 to a remote location, such as, for example, a central database. The usage cycle circuit 2402 comprises a communications module 2412 configured to transmit the usage cycle count to the remote location. The communications module 2412 may utilize any suitable communications system, such as, for example, wired or wireless communications system. The remote location may comprise a central database configured to maintain usage information. In some instances, when the power assembly 2400 is coupled to the surgical instrument 2410, the power assembly 2400 records a serial number of the surgical instrument 2410. The serial number is transmitted to the central database, for example, when the power assembly 2400 is coupled to a charger. In some instances, the central database maintains a count corresponding to each use of the surgical instrument 2410. For example, a bar code associated with the surgical instrument 2410 may be scanned each time the surgical instrument 2410 is used. When the use count exceeds a predetermined usage limit, the central database provides a signal to the surgical instrument 2410 indicating that the surgical instrument 2410 should be discarded.

The surgical instrument 2410 may be configured to lock and/or prevent operation of the surgical instrument 2410 when the usage cycle count exceeds a predetermined usage limit. In some instances, the surgical instrument 2410 comprises a disposable instrument and is discarded after the usage cycle count exceeds the predetermined usage limit. In other instances, the surgical instrument 2410 comprises a reusable surgical instrument which may be reconditioned after the usage cycle count exceeds the predetermined usage limit. The surgical instrument 2410 initiates a reversible lockout after the predetermined usage limit is met. A technician reconditions the surgical instrument 2410 and releases the lockout, for example, utilizing a specialized technician key configured to reset the usage cycle circuit 2402.

Figure 57:
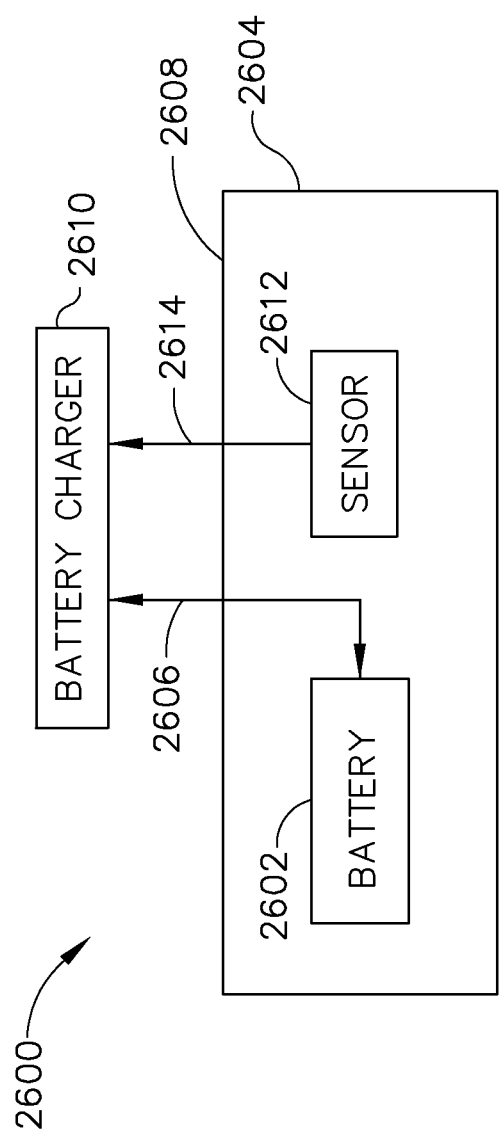
FIG. 57 illustrates one instance of a combination sterilization and charging system configured to sterilize and charge a power assembly simultaneously.

In some instances, the power assembly 2400 is charged and sterilized simultaneously prior to use. FIG. 57 illustrates one instance of a combined sterilization and charging system 2600 configured to charge and sterilize a battery 2602 simultaneously. The combined sterilization and charging system 2600 comprises a sterilization chamber 2604. A battery 2602 is placed within the sterilization chamber 2604. In some instances, the battery 2602 is coupled to a surgical instrument. A charging cable 2606 is mounted through a wall 2608 of the sterilization chamber 2604. The wall 2608 is sealed around the charging cable 2606 to maintain a sterile environment within the sterilization chamber 2604 during sterilization. The charging cable 2606 comprises a first end configured to couple to the power assembly 2602 within the sterilization chamber 2604 and a second end coupled to a battery charger 2610 located outside of the sterilization chamber 2604. Because the charging cable 2606 passes through the wall 2608 of the sterilization chamber 2604 while maintaining a sterile environment within the sterilization chamber 2604, the power assembly 2602 may be charged and sterilized simultaneously.

The charging profile applied by the battery charger 2610 is configured to match the sterilization cycle of the sterilization chamber 2604. For example, in one instance, a sterilization procedure time is about 28 to 38 minutes. The battery charger 2610 is configured to provide a charging profile that charges the battery during the sterilization procedure time. In some instances, the charging profile may extend over a cooling-off period following the sterilization procedure. The charging profile may be adjusted by the battery charger 2610 based on feedback from the power assembly 2602 and/or the sterilization chamber 2604. For example, in one instance, a sensor 2612 is located within the sterilization chamber 2604. The sensor 2612 is configured to monitor one or more characteristics of the sterilization chamber 2604, such as, for example, chemicals present in the sterilization chamber 2604, temperature of the sterilization chamber 2604, and/or any other suitable characteristic of the sterilization chamber 2604. The sensor 2612 is coupled to the battery charger 2610 by a cable 2614 extending through the wall 2608 of the sterilization chamber 2604. The cable 2614 is sealed such that the sterilization chamber 2604 may maintain a sterile environment. The battery charger 2610 adjusts the charging profile based on feedback from the sensor 2614. For example, in one instance, the battery charger 2610 receives temperature data from the sensor 2612 and adjusts the charging profile when the temperature of the sterilization chamber 2604 and/or the power assembly 2602 exceeds a predetermined temperature. As another example, the battery charger 2610 receives chemical composition information from the sensor 2612 and prevents charging of the power assembly 2602 when a chemical, such as, for example, $H_2O_2$, approaches explosive limits.

Figure 58:
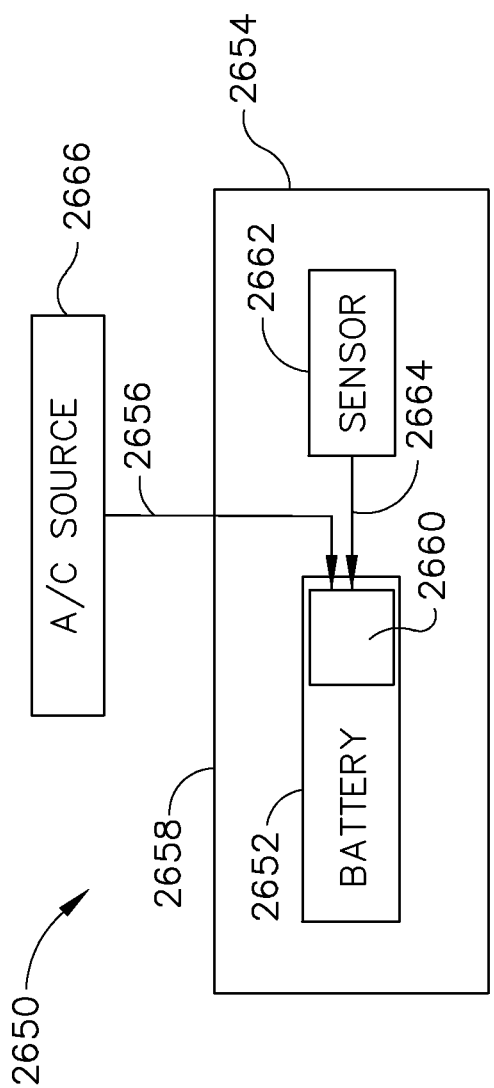
FIG. 58 illustrates one instance of a combination sterilization and charging system configured to sterilize and charge a power assembly having a battery charger formed integrally therein.

FIG. 58 illustrates one instance of a combination sterilization and charging system 2650 configured for a power assembly 2652 having a battery charger 2660 formed integrally therewith. An alternating current (AC) source 2666 is located outside of the sterilization chamber 2654 and is coupled the battery charger 2660 by an AC cable 2656 mounted through a wall 2658 of the sterilization chamber 2654. The wall 2658 is sealed around the AC cable 2656. The battery charger 2660 operates similar to the battery charger 2610 illustrated in FIG. 57. In some instances, the battery charger 2660 receives feedback from a sensor 2662 located within the sterilization chamber 2654 and coupled to the battery charger 2660 by a cable 2664.

Figure 62:
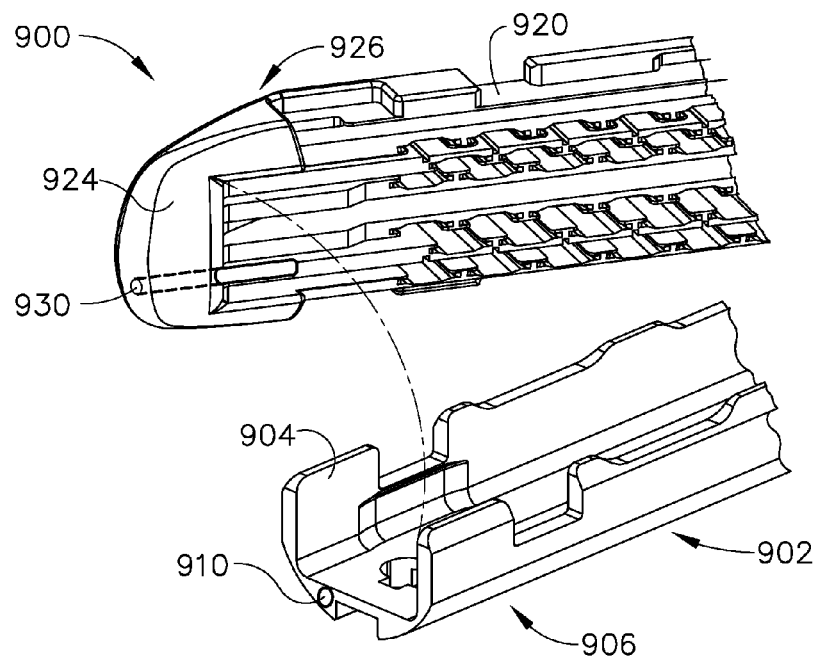
FIG. 62 is a partial, perspective view of an end effector and a fastener cartridge according to various embodiments of the present disclosure.

In various instances, a surgical system can include a magnet and a sensor. In combination, the magnet and the sensor can cooperate to detect various conditions of a fastener cartridge, such as the presence of a fastener cartridge in an end effector of the surgical instrument, the type of fastener cartridge loaded in the end effector, and/or the firing state of a loaded fastener cartridge, for example. Referring now to FIG. 62, a jaw 902 of an end effector 900 can comprise a magnet 910, for example, and a fastener cartridge 920 can comprise a sensor 930, for example. In various instances, the magnet 910 can be positioned at the distal end 906 of an elongate channel 904 sized and configured to receive the fastener cartridge 920. Furthermore, the sensor 930 can be at least partially embedded or retained in the distal end 926 of the nose 924 of the fastener cartridge 920, for example. In various instances, the sensor 924 can be in signal communication with the microcontroller of the surgical instrument.

In various circumstances, the sensor 930 can detect the presence of the magnet 910 when the fastener cartridge 920 is positioned in the elongate channel 904 of the jaw 902. The sensor 930 can detect when the fastener cartridge 920 is improperly positioned in the elongate channel 904 and/or not loaded into the elongate channel 904, for example, and can communicate the cartridge loading state to the microcontroller of the surgical system, for example. In certain instances, the magnet 910 can be positioned in the fastener cartridge 920, for example, and the sensor 930 can be positioned in the end effector 900, for example. In various instances, the sensor 930 can detect the type of fastener cartridge 920 loaded in the end effector 900. For example, different types of fastener cartridges can have different magnetic arrangements, such as different placement(s) relative to the cartridge body or other cartridge components, different polarities, and/or different magnetic strengths, for example. In such instances, the sensor 930 can detect the type of cartridge, e.g., the cartridge length, the number of fasteners and/or the fastener height(s), positioned in the jaw 902 based on the detected magnetic signal. Additionally or alternatively, the sensor 930 can detect if the fastener cartridge 920 is properly seated in the end effector 900. For example, the end effector 900 and the fastener cartridge 920 can comprise a plurality of magnets and/or a plurality of sensors and, in certain instances, the sensor(s) can detect whether the fastener cartridge 920 is properly positioned and/or aligned based on the position of multiple magnets relative to the sensor(s), for example.

Figure 63:
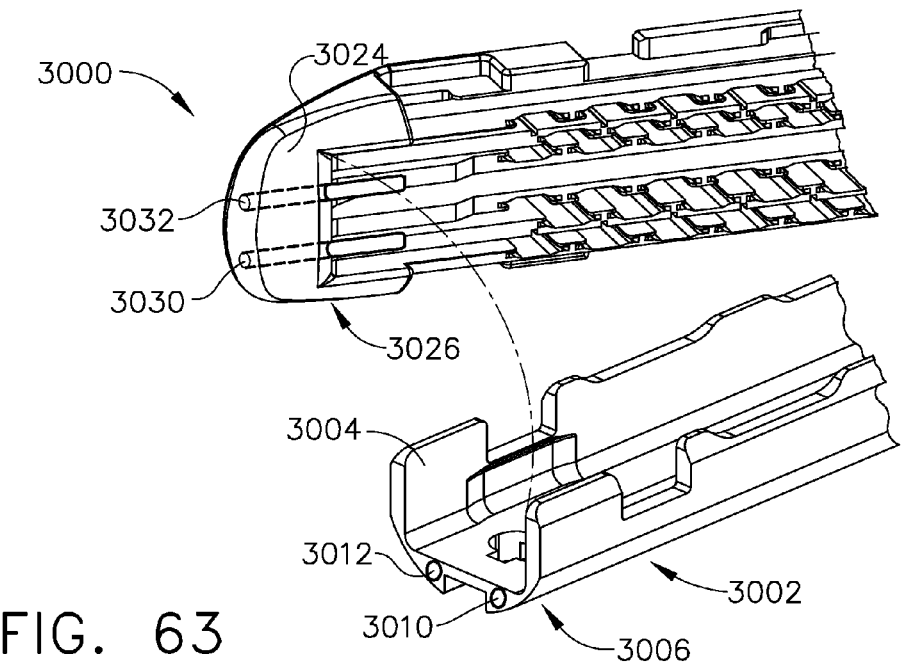
FIG. 63 is partial, perspective view of an end effector and a fastener cartridge according to various embodiments of the present disclosure.

Referring now to FIG. 63, in certain instances, an end effector 3000 can include a plurality of magnets and a plurality of sensors. For example, a jaw 3002 can include a plurality of magnets 3010, 3012 positioned at the distal end 3006 thereof. Moreover, the fastener cartridge 3020 can include a plurality of sensors 3030, 3032 positioned at the distal end 3026 of the nose 3024, for example. In certain instances, the sensors 3030, 3032 can detect the presence of the fastener cartridge 3020 in the elongate channel 3004 of the jaw 3002. In various instances, the sensors 3030, 3032 can comprise Hall Effect sensors, for example. Various sensors are described in U.S. Pat. No. 8,210,411, filed Sep. 23, 2008, and entitled MOTOR-DRIVEN SURGICAL CUTTING INSTRUMENT. U.S. Pat. No. 8,210,411, filed Sep. 23, 2008, and entitled MOTOR-DRIVEN SURGICAL CUTTING INSTRUMENT, is hereby incorporated by reference in its entirety. The addition of an additional sensor or sensors can provide a greater bandwidth signal, for example, which can provide further and/or improved information to the microcontroller of the surgical instrument. Additionally or alternatively, additional sensors can determine if the fastener cartridge 3020 is properly seated in the elongate channel of the jaw 3002, for example.

Figure 64:
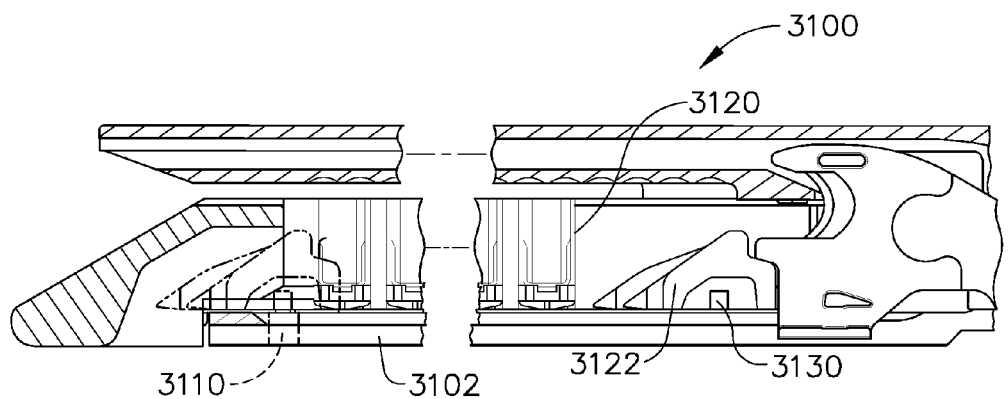
FIG. 64 is a cross-sectional, elevation view of an end effector and a fastener cartridge according to various embodiments of the present disclosure.
Figure 65:
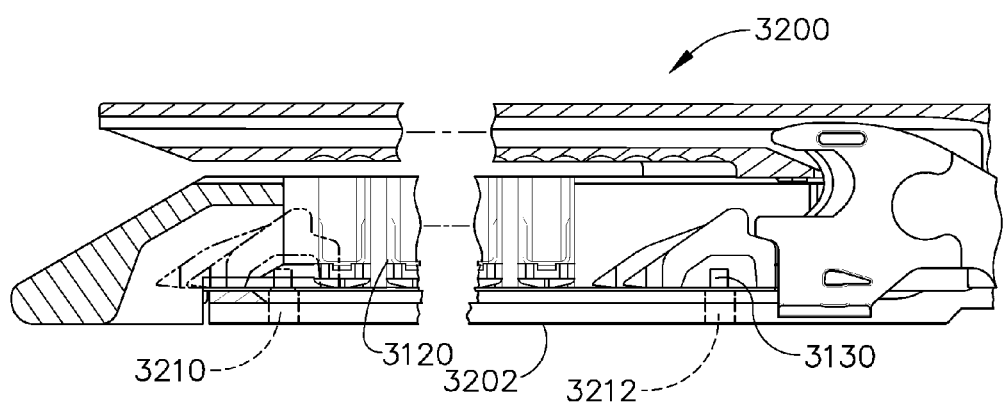
FIG. 65 is a cross-sectional, elevation view of an end effector and a fastener cartridge according to various embodiments of the present disclosure.

In various instances, a magnet can be positioned on a moveable component of a fastener cartridge. For example, a magnet can be positioned on a component of the fastener cartridge that moves during a firing stroke. In such instances, a sensor in the end effector can detect the firing state of the fastener cartridge. For example, referring now to FIG. 64, a magnet 3130 can be positioned on the sled 3122 of a fastener cartridge 3120. Moreover, a sensor 1110 can be positioned in the jaw 3102 of the end effector 3100. In various circumstances, the sled 3122 can translate during a firing stroke. Moreover, in certain instances, the sled 3120 can remain at the distal end of the fastener cartridge 3120 after the firing stroke. Stated differently, after the cartridge has been fired, the sled 3120 can remain at the distal end of the fastener cartridge 3120. Accordingly, the sensor 3110 can detect the position of the magnet 3130 and the corresponding sled 3120 to determine the firing state of the fastener cartridge 3120. For example, when the sensor 3110 detects the proximal position of the magnet 3130, the fastener cartridge 3120 can be unfired and ready to fire, for example, and when the sensor 3110 detects the distal position of the magnet 3130, the fastener cartridge 3120 can be spent, for example. Referring now to FIG. 65, in various instances, a jaw 3202 of an end effector 3200 can include a plurality of sensors 3210, 3212. For example, a proximal sensor 3212 can be positioned in the proximal portion of the jaw 3202, and a distal sensor 3210 can be positioned in the distal portion of the jaw 3202, for example. In such instances, the sensors 3210, 3212 can detect the position of the sled 3122 as the sled 3122 moves during a firing stroke, for example. In various instances, the sensors 3210, 3212 can comprise Hall Effect sensors, for example.

Figure 66:
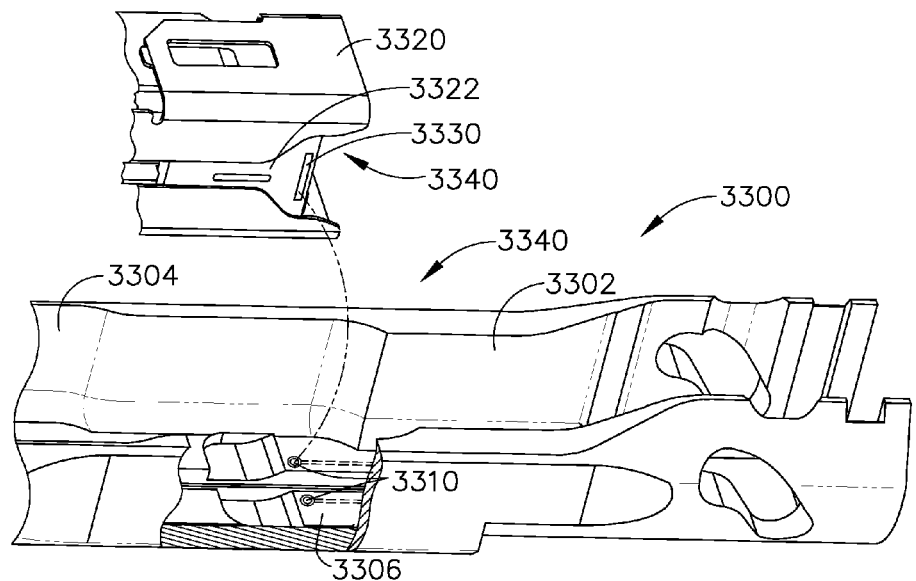
FIG. 66 is a partial, perspective view of an end effector with portions removed and a fastener cartridge according to various embodiments of the present disclosure.

Additionally or alternatively, an end effector can include a plurality of electrical contacts, which can detect the presence and/or firing state of a fastener cartridge. Referring now to FIG. 66, an end effector 3300 can include a jaw 3302 defining a channel 3304 configured to receive a fastener cartridge 3320. In various instances, the jaw 3302 and the fastener cartridge 3320 can comprise electrical contacts. For example, the elongate channel 3304 can define a bottom surface 3306, and an electrical contact 3310 can be positioned on the bottom surface 3306. In various instances, a plurality of electrical contacts 3310 can be defined in the elongate channel 3304. The electrical contacts 3310 can form part of a firing-state circuit 3340, which can be in signal communication with a microcontroller of the surgical system. For example, the electrical contacts 3310 can be electrically coupled to and/or in communication with a power supply, and can form electrically active ends of an open circuit, for example. In some instances, one of the electrical contacts 3310 can be powered such that a voltage potential is created intermediate the electrical contacts 3310. In certain instances, one of the contacts can be coupled to an output channel of the microprocessor, for example, which can apply a voltage potential to the contact. Another contact can be coupled to an input channel of the microprocessor, for example. In certain instances, the electrical contacts 3310 can be insulated from the frame 3306 of the jaw 3302. Referring still to FIG. 66, the fastener cartridge 3320 can also include an electrical contact 3330, or a plurality of electrical contacts, for example. In various instances, the electrical contact 3330 can be positioned on a moveable element of the fastener cartridge 3320. For example, the electrical contact 3330 can be positioned on the sled 3322 of the fastener cartridge 3320, and thus, the electrical contact 3330 can move in the fastener cartridge 3320 during a firing stroke.

In various instances, the electrical contact 3330 can comprise a metallic bar or plate on the sled 3320, for example. The electrical contact 3330 in the fastener cartridge 3320 can cooperate with the electrical contact(s) 3310 in the end effector 3300, for example. In certain circumstances, the electrical contact 3330 can contact the electrical contact(s) 3310 when the sled 3322 is positioned in a particular position, or a range of positions, in the fastener cartridge 3320. For example, the electrical contact 3330 can contact the electrical contacts 3310 when the sled 3322 is unfired, and thus, positioned in a proximal position in the fastener cartridge 3320. In such circumstances, the electrical contact 3330 can close the circuit between the electrical contacts 3310, for example. Moreover, the firing-state circuit 3340 can communicate the closed circuit, i.e., the unfired cartridge indication, to the microcontroller of the surgical system. In such instances, when the sled 3322 is fired distally during a firing stroke, the electrical contact 3330 can move out of electrically contact with the electrical contacts 3310, for example. Accordingly, the firing-state circuit 3340 can communicate the open circuit, i.e., the fired cartridge indication, to the microcontroller of the surgical system. In certain circumstances, the microcontroller may only initiate a firing stroke when an unspent cartridge is indicated by the firing-state circuit 3340, for example. In various instances, the electrical contact 3330 can comprise an electromechanical fuse. In such instances, the fuse can break or short when the sled 3322 is fired through a firing stroke, for example.

Figure 67:
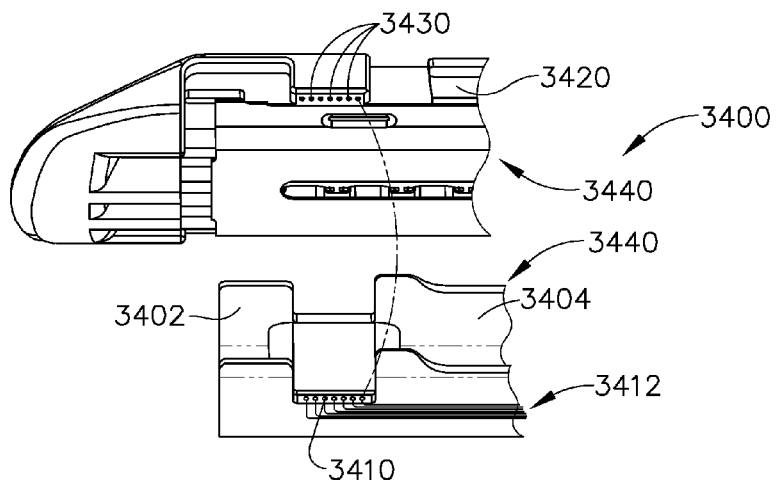
FIG. 67 is a partial, perspective view of an end effector with portions removed and a fastener cartridge according to various embodiments of the present disclosure.

Additionally or alternatively, referring now to FIG. 67, an end effector 3400 can include a jaw 3402 and a cartridge-present circuit 3440. In various instances, the jaw 3402 can comprise an electrical contact 3410, or a plurality of electrical contacts 3410, in an elongate channel 3404 thereof, for example. Furthermore, a fastener cartridge 3420 can include an electrical contact 3430, or a plurality of electrical contacts 3430, on an outer surface of the fastener cartridge 3420. In various instances, the electrical contacts 3430 can be positioned and/or mounted to a fixed or stationary component of the fastener cartridge 3420, for example. In various circumstances, the electrical contacts 3430 of the fastener cartridge 3420 can contact the electrical contacts 3410 of the end effector 3400 when the fastener cartridge 3420 is loaded into the elongate channel 3404, for example. Prior to placement of the fastener cartridge 3420 in the elongate channel 3404, the cartridge-present circuit 3440 can be an open circuit, for example. When the fastener cartridge 3420 is properly seated in the jaw 3402, the electrical contacts 3410 and 3430 can form the closed cartridge-present circuit 3440. In instances where the jaw 3402 and/or the fastener cartridge 3420 comprise a plurality of electrical contacts 3410, 3430, the cartridge-present circuit 3440 can comprise a plurality of circuits. Moreover, in certain instances, the cartridge-present circuit 3440 can identify the type of cartridge loaded in the jaw 3402 based on the number and/or arrangement of electrical contacts 3430 on the fastener cartridge 3420, for example, and the corresponding open and/or closed circuits of the cartridge-present circuit 3440, for example.

Moreover, the electrical contacts 3410 in the jaw 3402 can be in signal communication with the microcontroller of the surgical system. The electrical contacts 3410 can be wired to a power source, for example, and/or can communicate with the microcontroller via a wired and/or wireless connection, for example. In various instances, the cartridge-present circuit 3440 can communicate the cartridge presence or absence to the microcontroller of the surgical system. In various instances, a firing stroke may be prevented when the cartridge-present circuit 3440 indicates the absence of a fastener cartridge in the end effector jaw 3402, for example. Moreover, a firing stroke may be permitted when the cartridge-present circuit 3440 indicates the presence of a fastener cartridge 3420 in the end effector jaw 3402.

As described throughout the present disclosure, various sensors, programs, and circuits can detect and measure numerous characteristics of the surgical instrument and/or components thereof, surgical use or operation, and/or the tissue and/or operating site. For example, tissue thickness, the identification of the instrument components, usage and feedback data from surgical functions, and error or fault indications can be detected by the surgical instrument. In certain instances, the fastener cartridge can include a nonvolatile memory unit, which can be embedded or removably coupled to the fastener cartridge, for example. Such a nonvolatile memory unit can be in signal communication with the microcontroller via hardware, such as the electrical contacts described herein, radio frequency, or various other suitable forms of data transmission. In such instances, the microcontroller can communicate data and feedback to the nonvolatile memory unit in the fastener cartridge, and thus, the fastener cartridge can store information. In various instances, the information can be securely stored and access thereto can be restricted as suitable and appropriate for the circumstances.

In certain instances, the nonvolatile memory unit can comprise information regarding the fastener cartridge characteristics and/or the compatibility thereof with various other components of the modular surgical system. For example, when the fastener cartridge is loaded into an end effector, the nonvolatile memory unit can provide compatibility information to the microcontroller of the surgical system. In such instances, the microcontroller can verify the validity or compatibility of the modular assembly. For example, the microcontroller can confirm that the handle component can fire the fastener cartridge and/or that the fastener cartridge appropriate fits the end effector, for example. In certain circumstances, the microcontroller can communicate the compatibility or lack thereof to the operator of the surgical system, and/or may prevent a surgical function if the modular components are incompatible, for example.

Figures 68A, 68B, 68C:
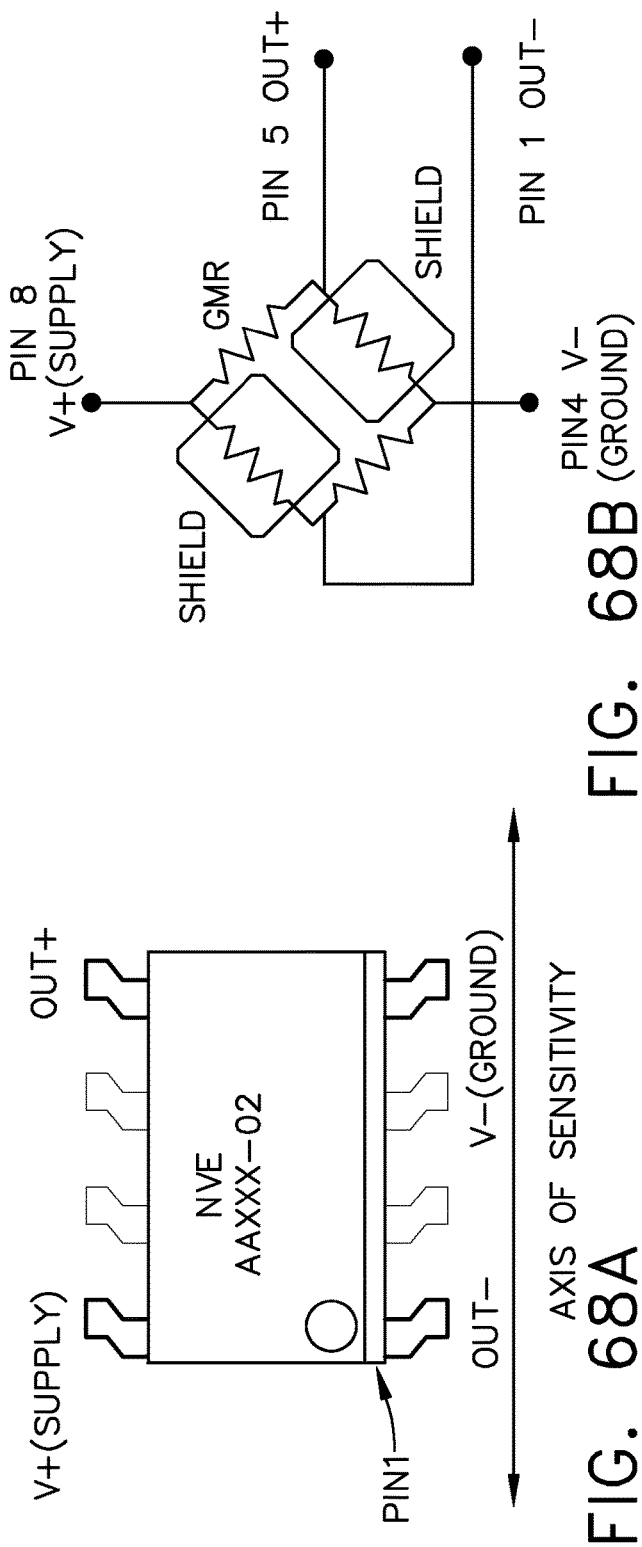
FIG. 68(A) is a schematic depicting an integrated circuit according to various embodiments of the present disclosure.
FIG. 68(B) is a schematic depicting a magnetoresistive circuit according to various embodiments of the present disclosure.
FIG. 68(C) is a table listing various specifications of a magnetoresistive sensor according to various embodiments of the present disclosure.

As described herein, the surgical instrument can include a sensor, which can cooperate with a magnet to detect various characteristics of the surgical instrument, operation, and surgical site. In certain instances, the sensor can comprise a Hall Effect sensor and, in other instances, the sensor can comprise a magnetoresistive sensor as depicted in FIGS. 68(A)-68(C), for example. As described in greater detail herein, a surgical end effector can comprise a first jaw, which can be configured to receive a fastener cartridge, and a second jaw. The first jaw and/or the fastener cartridge can comprise a magnetic element, such as a permanent magnet, for example, and the second jaw can comprise a magnetoresistive sensor, for example. In other instances, the first jaw and/or the fastener cartridge can comprise a magnetoresistive sensor, for example, and the second jaw can comprise a magnetic element. The magnetoresistive sensor may have various characteristics listed in the table in FIG. 68(C), for example, and/or similar specifications, for example. In certain instances, the change in resistance caused by movement of the magnetic element relative to the magnetoresistive sensor can affect and/or vary the properties of the magnetic circuit depicted in FIG. 68(B), for example.

In various instances, the magnetoresistive sensor can detect the position of the magnetic element, and thus, can detect the thickness of tissue clamped between the opposing first and second jaws, for example. The magnetoresistive sensor can be in signal communication with the microcontroller, and the magnetoresistive sensor can wirelessly transmit data to an antenna in signal communication with the microcontroller, for example. In various instances, a passive circuit can comprise the magnetoresistive sensor. Moreover, the antenna can be positioned in the end effector, and can detect a wireless signal from the magnetoresistive sensor and/or microprocessor operably coupled thereto, for example. In such circumstances, an exposed electrical connection between the end effector comprising the antenna, for example, and the fastener cartridge comprising the magnetoresistive sensor, for example, can be avoided. Furthermore, in various instances, the antenna can be wired and/or in wireless communication with the microcontroller of the surgical instrument.

Tissue can contain fluid and, when the tissue is compressed, the fluid may be pressed from the compressed tissue. For example, when tissue is clamped between opposing jaws of a surgical end effector, fluid may flow and/or be displaced from the clamped tissue. Fluid flow or displacement in clamped tissue can depend on various characteristics of the tissue, such as the thickness and/or type of tissue, as well as various characteristics of the surgical operation, such as the desired tissue compression and/or the elapsed clamping time, for example. In various instances, fluid displacement between the opposing jaws of an end effector may contribute to malformation of staples formed between the opposing jaws. For example, the displacement of fluid during and/or following staple formation can induce bending and/or other uncontrolled movement of a staple away from its desired or intended formation. Accordingly, in various instances, it may be desirable to control the firing stroke, e.g., to control the firing speed, in relationship to the detected fluid flow, or lack thereof, intermediate opposing jaws of a surgical end effector.

In various instances, the fluid displacement in clamped tissue can be determined or approximated by various measurable and/or detectable tissue characteristics. For example, the degree of tissue compression can correspond to the degree of fluid displacement in the clamped tissue. In various instances, a higher degree of tissue compression can correspond to more fluid flow, for example, and a reduced degree of tissue compression can correspond to less fluid flow, for example. In various circumstances, a sensor positioned in the end effector jaws can detect the force exerted on the jaws by the compressed tissue. Additionally or alternatively, a sensor on or operably associated with the cutting element can detect the resistance on the cutting element as the cutting element is advanced through, and transects, the clamped tissue. In such circumstances, the detected cutting and/or firing resistance can correspond to the degree of tissue compression. When tissue compression is high, for example, the cutting element resistance can be greater, and when tissue compression is lower, for example, the cutting element resistance can be reduced. Correspondingly, the cutting element resistance can indicate the amount of fluid displacement.

In certain instances, the fluid displacement in clamped tissue can be determined or approximated by the force required to fire the cutting element, i.e., the force-to-fire. The force-to-fire can correspond to the cutting element resistance, for example. Furthermore, the force-to-fire can be measured or approximated by a microcontroller in signal communication with the electric motor that drives the cutting element. For example, where the cutting element resistance is higher, the electric motor can require more current to drive the cutting element through the tissue. Similarly, if the cutting element resistance is lower, the electric motor can require less current to drive the cutting element through the tissue. In such instances, the microcontroller can detect the amount of current drawn by the electric motor during the firing stroke. For example, the microcontroller can include a current sensor, which can detect the current utilized to fire the cutting element through the tissue, for example.

Figure 60:
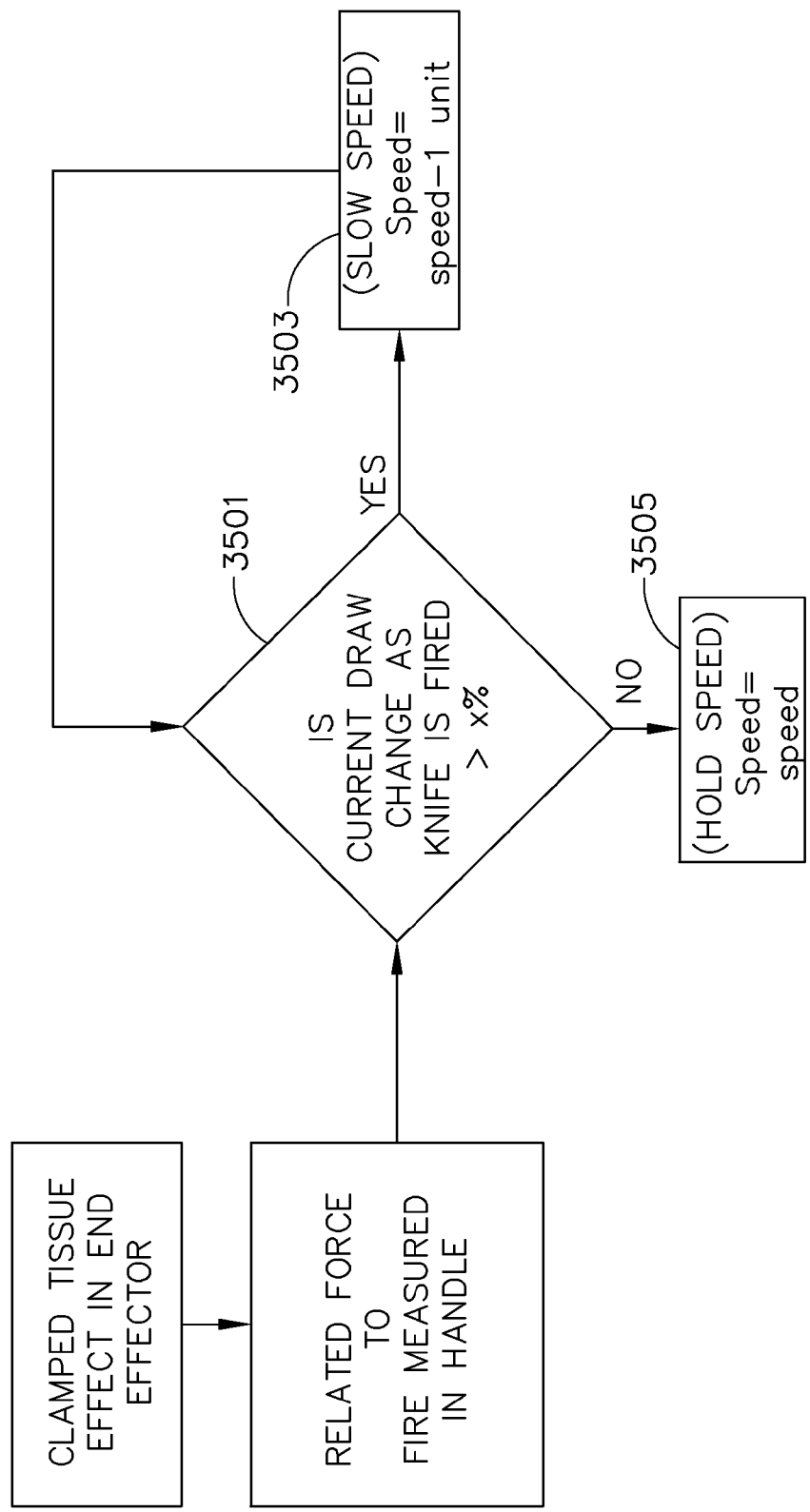
FIG. 60 is a flowchart depicting a method for adjusting the velocity of a firing element according to various embodiments of the present disclosure.

Referring now to FIG. 60, a surgical instrument assembly or system can be configured to detect the compressive force in the clamped tissue. For example, in various instances, an electric motor can drive the firing element, and a microcontroller can be in signal communication with the electric motor. As the electric motor drives the firing element, the microcontroller can determine the current drawn by the electric motor, for example. In such instances, the force-to-fire can correspond to the current drawn by the electric motor throughout the firing stroke, as described above. Referring still to FIG. 60, at step 3501, the microcontroller of the surgical instrument can determine if the current drawn by the electric motor increases during the firing stroke and, if so, can calculate the percentage increase of the current.

In various instances, the microcontroller can compare the current draw increase during the firing stroke to a predefined threshold value. For example, the predefined threshold value can be 5%, 10%, 25%, 50% and/or 100%, for example, and the microcontroller can compare the current increase detected during a firing stroke to the predefined threshold value. In other instances, the threshold increase can be a value or range of values between 5% and 100%, and, in still other instances, the threshold increase can be less than 5% or greater than 100%, for example. For example, if the predefined threshold value is 50%, the microcontroller can compare the percentage of current draw change to 50%, for example. In certain instances, the microcontroller can determine if the current drawn by the electric motor during the firing stroke exceeds a percentage of the maximum current or a baseline value. For example, the microcontroller can determine if the current exceeds 5%, 10%, 25%, 50% and/or 100% of the maximum motor current. In other instances, the microcontroller can compare the current drawn by the electric motor during the firing stroke to a predefined baseline value, for example.

In various instances, the microcontroller can utilize an algorithm to determine the change in current drawn by the electric motor during a firing stroke. For example, the current sensor can detect the current drawn by the electric motor at various times and/or intervals during the firing stroke. The current sensor can continually detect the current drawn by the electric motor and/or can intermittently detect the current draw by the electric motor. In various instances, the algorithm can compare the most recent current reading to the immediately proceeding current reading, for example. Additionally or alternatively, the algorithm can compare a sample reading within a time period X to a previous current reading. For example, the algorithm can compare the sample reading to a previous sample reading within a previous time period X, such as the immediately proceeding time period X, for example. In other instances, the algorithm can calculate the trending average of current drawn by the motor. The algorithm can calculate the average current draw during a time period X that includes the most recent current reading, for example, and can compare that average current draw to the average current draw during an immediately proceeding time period time X, for example.

Referring still to FIG. 60, if the microcontroller detects a current increase that is greater than the threshold change or value, the microcontroller can proceed to step 3503, and the firing speed of the firing element can be reduced. For example, the microcontroller can communicate with the electric motor to slow the firing speed of the firing element. For example, the firing speed can be reduced by a predefined step unit and/or a predefined percentage. In various instances, the microcontroller can comprise a velocity control module, which can affect changes in the cutting element speed and/or can maintain the cutting element speed. The velocity control module can comprise a resistor, a variable resistor, a pulse width modulation circuit, and/or a frequency modulation circuit, for example. Referring still to FIG. 60, if the current increase is less than the threshold value, the microcontroller can proceed to step 3505, wherein the firing speed of the firing element can be maintained, for example. In various circumstances, the microcontroller can continue to monitor the current drawn by the electric motor and changes thereto during at least a portion of the firing stroke. Moreover, the microcontroller and/or velocity control module thereof can adjust the firing element velocity throughout the firing stroke in accordance with the detected current draw. In such instances, controlling the firing speed based on the approximated fluid flow or displacement in the clamped tissue, for example, can reduce the incidence of staple malformation in the clamped tissue.

Figure 61:
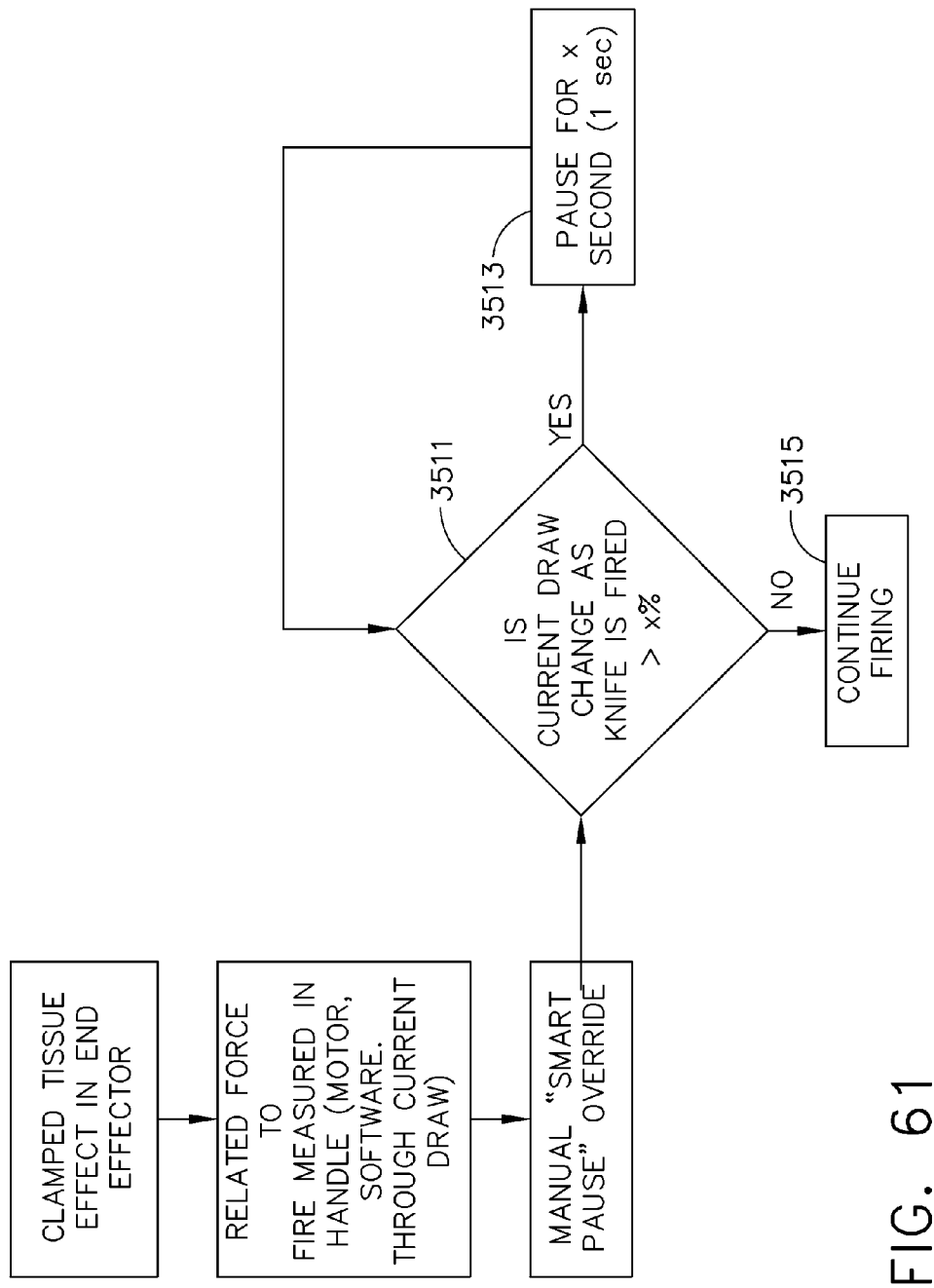
FIG. 61 is a flowchart depicting a method for adjusting the velocity of a firing element according to various embodiments of the present disclosure.

Referring now to FIG. 61, in various instances, the microcontroller can adjust the firing element velocity by pausing the firing element for a predefined period of time.

For example, similar to the embodiment depicted in FIG. 60, if the microcontroller detects a current draw that exceeds a predefined threshold value at step 3511, the microcontroller can proceed to step 3513 and the firing element can be paused. For example, the microcontroller can pause movement and/or translation of the firing element for one second if the current increase measured by the microcontroller exceeds the threshold value. In other instances, the firing stroke can be paused for a fraction of a second and/or more than one second, for example. Similar to the process described above, if the current draw increase is less than the threshold value, the microcontroller can proceed to step 3515 and the firing element can continue to progress through the firing stroke without adjusting the velocity of the firing element. In certain instances, the microcontroller can be configured to pause and slow the firing element during a firing stroke. For example, for a first increase in current draw, the firing element can be paused, and for a second, different increase in current draw, the velocity of the firing element can be reduced. In still other circumstances, the microcontroller can command an increase in the velocity of the firing element if the current draw decreases below a threshold value, for example.

As described herein, a surgical instrument, such as a surgical stapling instrument, for example, can include a processor, computer, and/or controller, for example, (herein collectively referred to as a "processor") and one or more sensors in signal communication with the processor, computer, and/or controller. In various instances, a processor can comprise a microcontroller and one or more memory units operationally coupled to the microcontroller. By executing instruction code stored in the memory, the processor may control various components of the surgical instrument, such as the motor, various drive systems, and/or a user display, for example. The processor may be implemented using integrated and/or discrete hardware elements, software elements, and/or a combination of both. Examples of integrated hardware elements may include processors, microprocessors, microcontrollers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, microcontrollers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the processor may include a hybrid circuit comprising discrete and integrated circuit elements or components on one or more substrates, for example.

The processor may be an LM 4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available. Other microcontrollers may be readily substituted for use with the present disclosure. Accordingly, the present disclosure should not be limited in this context.

Signal communication can comprise any suitable form of communication in which information is transmitted between a sensor and the processor. Such communication can comprise wired communication utilizing one or more conductors and/or wireless communication utilizing a wireless transmitter and receiver, for example. In various instances, a surgical instrument can include a first sensor configured to detect a first condition of the surgical instrument and a second sensor configured to detect a second condition of the surgical instrument. For instance, the surgical instrument can include a first sensor configured to detect whether a closure trigger of the surgical instrument has been actuated and a second sensor configured to detect whether a firing trigger of the surgical instrument has been actuated, for example.

Various embodiments are envisioned in which the surgical instrument can include two or more sensors configured to detect the same condition. In at least one such embodiment, the surgical instrument can comprise a processor, a first sensor in signal communication with the processor, and a second sensor in signal communication with the processor. The first sensor can be configured to communicate a first signal to the processor and the second sensor can be configured to communicate a second signal to the processor. In various instances, the processor can include a first input channel for receiving the first signal from the first sensor and a second input channel for receiving the second signal from the second sensor. In other instances, a multiplexer device can receive the first signal and the second signal and communicate the data of the first and second signals to the processor as part of a single, combined signal, for example. In some instances, a first conductor, such as a first insulated wire, for example, can connect the first sensor to the first input channel and a second conductor, such as a second insulated wire, for example, can connect the second sensor to the second input channel. As outlined above, the first sensor and/or the second sensor can communicate wirelessly with the processor. In at least one such instance, the first sensor can include a first wireless transmitter and the second sensor can include a second wireless transmitter, wherein the processor can include and/or can be in communication with at least one wireless signal receiver configured to receive the first signal and/or the second signal and transmit the signals to the processor.

In co-operation with the sensors, as described in greater detail below, the processor of the surgical instrument can verify that the surgical instrument is operating correctly. The first signal can include data regarding a condition of the surgical instrument and the second signal can include data regarding the same condition. The processor can include an algorithm configured to compare the data from the first signal to the data from the second signal and determine whether the data communicated by the two signals are the same or different. If the data from the two signals are the same, the processor may use the data to operate the surgical instrument. In such circumstances, the processor can assume that a fault condition does not exist. In various instances, the processor can determine whether the data from the first signal and the data from the second signal are within an acceptable, or recognized, range of data. If the data from the two signals are within the recognized range of data, the processor may use the data from one or both of the signals to operate the surgical instrument. In such circumstances, the processor can assume that a fault condition does not exist. If the data from the first signal is outside of the recognized range of data, the processor may assume that a fault condition exists with regard to the first sensor, ignore the first signal, and operate the surgical instrument in response to the data from the second signal. Likewise, if the data from the second signal is outside the recognized range of data, the processor may assume that a fault condition exists with regard to the second sensor, ignore the second signal, and operate the surgical instrument in response to the data from the first signal. The processor can be configured to selectively ignore the input from one or more sensors.

In various instances, further to the above, the processor can include a module configured to implement an algorithm configured to assess whether the data from the first signal is between a first value and a second value. Similarly, the algorithm can be configured to assess whether the data from the second signal is between the first value and the second value. In certain instances, a surgical instrument can include at least one memory device. A memory device can be integral with the processor, in signal communication with the processor, and/or accessible by the processor. In certain instances, the memory device can include a memory chip including data stored thereon. The data stored on the memory chip can be in the form of a lookup table, for example, wherein the processor can access the lookup table to establish the acceptable, or recognized, range of data. In certain instances, the memory device can comprise nonvolatile memory, such as bit-masked read-only memory (ROM) or flash memory, for example. Nonvolatile memory (NVM) may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

Further to the above, the first sensor and the second sensor can be redundant. The processor can be configured to compare the first signal from the first sensor to the second signal from the second sensor to determine what action, if any, to take. In addition to or in lieu of the above, the processor can be configured to compare the data from the first signal and/or the second signal to limits established by the algorithm and/or data stored within a memory device. In various circumstances, the processor can be configured to apply a gain to a signal it receives, such as the first signal and/or the second signal, for example. For instance, the processor can apply a first gain to the first signal and a second gain to the second signal. In certain instances, the first gain can be the same as the second gain. In other instances, the first gain and the second gain can be different. In some circumstances, the processor can be configured to calibrate the first gain and/or the second gain. In at least one such circumstance, the processor can modify a gain such that the amplified signal is within a desired, or acceptable, range. In various instances, the unmodified gain and/or the modified gain can be stored within a memory device which is integral to and/or accessible by the processor. In certain embodiments, the memory device can track the history of the gains applied to a signal. In any event, the processor can be configured to provide this calibration before, during, and/or after a surgical procedure.

In various embodiments, the first sensor can apply a first gain to the first signal and the second sensor can apply a second gain to the second signal. In certain embodiments, the processor can include one or more output channels and can communicate with the first and second sensors. For instance, the processor can include a first output channel in signal communication with the first sensor and a second output channel in signal communication with the second sensor. Further to the above, the processor can be configured to calibrate the first sensor and/or the second sensor. The processor can send a first calibration signal through said first output channel in order to modify a first gain that the first sensor is applying to the first signal. Similarly, the processor can send a second calibration signal through said second output channel in order to modify a second gain that the second sensor is applying to the second signal.

As discussed above, the processor can modify the operation of the surgical instrument in view of the data received from the first signal and/or the second signal. In some circumstances, the processor can ignore the signal from a redundant sensor that the processor deems to be faulty. In some circumstances, the processor can return the surgical instrument to a safe state and/or warn the user of the surgical instrument that one or both of the sensors may be faulty. In certain circumstances, the processor can disable the surgical instrument. In various circumstances, the processor can deactivate and/or modify certain functions of the surgical instrument when the processor detects that one or more of the sensors may be faulty. In at least one such circumstance, the processor may limit the operable controls to those controls which can permit the surgical instrument to be safely removed from the surgical site, for example, when the processor detects that one or more of the sensors may be faulty. In at least one circumstance, when the processor detects that one or more of the sensors may be faulty. In certain circumstances, the processor may limit the maximum speed, power, and/or torque that can be delivered by the motor of the surgical instrument, for example, when the processor detects that one or more of the sensors may be faulty. In various circumstances, the processor may enable a recalibration control which may allow the user of the surgical instrument to recalibrate the mal-performing or non-performing sensor, for example, when the processor detects that one or more of the sensors may be faulty. While various exemplary embodiments utilizing two sensors to detect the same condition are described herein, various other embodiments are envisioned which utilize more than two sensors. The principles applied to the two sensor system described herein can be adapted to systems including three or more sensors.

As discussed above, the first sensor and the second sensor can be configured to detect the same condition of the surgical instrument. For instance, the first sensor and the second sensor can be configured to detect whether an anvil of the surgical instrument is in an open condition, for example. In at least one such instance, the first sensor can detect the movement of a closure trigger into an actuated position and the second sensor can detect the movement of an anvil into a clamped position, for example. In some instances, the first sensor and the second sensor can be configured to detect the position of a firing member configured to deploy staples from an end effector of the surgical instrument. In at least one such instance, the first sensor can be configured to detect the position of a motor-driven rack in a handle of the surgical instrument and the second sensor can be configured to detect the position of a firing member in a shaft or an end effector of the surgical instrument which is operably coupled with the motor-driven rack, for example. In various instances, the first and second sensors could verify that the same event is occurring. The first and second sensors could be located in the same portion of the surgical instrument and/or in different portions of the surgical instrument. A first sensor can be located in the handle, for example, and a second sensor could be located in the shaft or the end effector, for example.

Further to the above, the first and second sensors can be utilized to determine whether two events are occurring at the same time. For example, whether the closure trigger and the anvil are moving, or have moved, concurrently. In certain instances, the first and second sensors can be utilized to determine whether two events are not occurring at the same time. For example, it may not be desirable for the anvil of the end effector to open while the firing member of the surgical instrument is being advanced to deploy the staples from the end effector. The first sensor can be configured to determine whether the anvil is in an clamped position and the second sensor can be configured to determine whether the firing member is being advanced. In the event that the first sensor detects that the anvil is in an unclamped position while the second sensor detects that the firing member is being advanced, the processor can interrupt the supply of power to the motor of the surgical instrument, for example. Similarly, the first sensor can be configured to detect whether an unclamping actuator configured to unclamp the end effector has been depressed and the second sensor can be configured to detect whether a firing actuator configured to operate the motor of the surgical instrument has been depressed. The processor of the surgical instrument can be configured to resolve these conflicting instructions by stopping the motor, reversing the motor to retract the firing member, and/or ignoring the instructions from the unclamping actuator, for example.

In some instances, further to the above, the condition detected can include the power consumed by the surgical instrument. In at least one such instance, the first sensor can be configured to monitor the current drawn from a battery of the surgical instrument and the second sensor can be configured to monitor the voltage of the battery. As discussed above, such information can be communicated from the first sensor and the second sensor to the processor. With this information, the processor can calculate the electrical power draw of the surgical instrument. Such a system could be referred to as 'supply side' power monitoring. In certain instances, the first sensor can be configured to detect the current drawn by a motor of the surgical instrument and the second sensor can be configured to detect the current drawn by a processor of the surgical instrument, for example. As discussed above, such information can be communicated from the first sensor and the second sensor to the processor. With this information, the processor can calculate the electrical power draw of the surgical instrument. To the extent that other components of the surgical instrument draw electrical power, a sensor could be utilized to detect the current drawn for each component and communicate that information to the processor. Such a system could be referred to as 'use side' power monitoring. Various embodiments are envisioned which utilize supply side power monitoring and use side power monitoring. In various instances, the processor, and/or an algorithm implemented by the processor, can be configured to calculate a state of the device using more than one sensor that may not be sensed directly by only one sensor. Based on this calculation, the processor can enable, block, and/or modify a function of the surgical instrument.

In various circumstances, the condition of the surgical instrument that can be detected by a processor and a sensor system can include the orientation of the surgical instrument. In at least one embodiment, the surgical instrument can include a handle, a shaft extending from the handle, and an end effector extending from the shaft. A first sensor can be positioned within the handle and a second sensor can be positioned within the shaft, for example. The first sensor can comprise a first tilt sensor and the second sensor can comprise a second tilt sensor, for example. The first tilt sensor can be configured to detect the instrument's orientation with respect to a first plane and the second tilt sensor can be configured to detect the instrument's orientation with respect to a second plane. The first plane and the second plane may or may not be orthogonal. The first sensor can comprise an accelerometer and/or a gyroscope, for example. The second sensor can comprise an accelerometer and/or a gyroscope, for example. Various embodiments are envisioned which comprise more than two sensors and each such sensor can comprise an accelerometer and/or a gyroscope, for example. In at least one implementation, a first sensor can comprise a first accelerometer arranged along a first axis and a second sensor can comprise a second accelerometer arranged along a second axis which is different than the first axis. In at least one such instance, the first axis can be transverse to the second axis.

Further to the above, the processor can utilize data from the first and second accelerometers to determine the direction in which gravity is acting with respect to the instrument, i.e., the direction of ground with respect to the surgical instrument. In certain instances, magnetic fields generated in the environment surrounding the surgical instrument may affect one of the accelerometers. Further to the above, the processor can be configured to ignore data from an accelerometer if the data from the accelerometers is inconsistent. Moreover, the processor can be configured to ignore data from an accelerometer if the accelerometer is dithering between two or more strong polarity orientations, for example. To the extent that an external magnetic field is affecting two or more, and/or all, of the accelerometers of a surgical instrument, the processor can deactivate certain functions of the surgical instrument which depend on data from the accelerometers. In various instances, a surgical instrument can include a screen configured to display images communicated to the screen by the processor, wherein the processor can be configured to change the orientation of the images displayed on the screen when the handle of the surgical instrument is reoriented, or at least when a reorientation of the handle is detected by the accelerometers. In at least one instance, the display on the screen can be flipped upside down when the handle is oriented upside down. In the event that the processor determines that orientation data from one or more of the accelerometers may be faulty, the processor may prevent the display from being reoriented away from its default position, for example.

Further to the above, the orientation of a surgical instrument may or may not be detectable from a single sensor. In at least one instance, the handle of the surgical instrument can include a first sensor and the shaft can include a second sensor, for example. Utilizing data from the first sensor and the second sensor, and/or data from any other sensor, the processor can determine the orientation of the surgical instrument. In some instances, the processor can utilize an algorithm configured to combine the data from the first sensor signal, the second sensor signal, and/or any suitable number of sensor signals to determine the orientation of the surgical instrument. In at least one instance, a handle sensor positioned within the handle can determine the orientation of the handle with respect to gravity. A shaft sensor positioned within the shaft can determine the orientation of the shaft with respect to gravity. In embodiments where the shaft, or at least a portion of the shaft, does not articulate relative to the handle, the processor can determine the direction in which the shaft, or the non-articulated shaft portion, is pointing. In some instances, a surgical instrument can include an end effector which can articulate relative to the shaft. The surgical instrument can include an articulation sensor which can determine the direction and the degree in which the end effector has been articulated relative to the shaft, for example. With data from the handle sensor, the shaft sensor, and the articulation sensor, the processor can determine the direction in which the end effector is pointing. With additional data including the length of the handle, the shaft, and/or the end effector, the processor can determine the position of the distal tip of the end effector, for example. With such information, the processor could enable, block, and/or modify a function of the surgical instrument.

In various instances, a surgical instrument can include a redundant processor in addition to a first processor. The redundant processor can be in signal communication with some or all of the sensors that the first processor is in signal communication with. The redundant processor can perform some or all of the same calculations that the first processor performs. The redundant processor can be in signal communication with the first processor. The first processor can be configured to compare the calculations that it has performed with the calculations that the redundant processor has performed. Similarly, the redundant processor can be configured to compare the calculations that it has performed with the calculations that the first processor has performed. In various instances, the first processor and the redundant processor can be configured to operate the surgical instrument independently of one another. In some instances, the first processor and/or the redundant processor can be configured to determine whether the other processor is faulty and/or deactivate the other processor if a fault within the other processor and/or within the surgical instrument is detected. The first processor and the redundant processor can both be configured to communicate with the operator of the surgical instrument such that, if one of the processors determines the other processor to be faulty, the non-faulty processor can communicate with the operator that a fault condition exists, for example.

In various embodiments, a surgical instrument can include a processor and one or more sensors in signal communication with the processor. The sensors can comprise digital sensors and/or analog sensors. A digital sensor can generate a measuring signal and can include an electronic chip. The electronic chip can convert the measuring signal into a digital output signal. The digital output signal can then be transmitted to the processor utilizing a suitable transmission means such as, for example, a conductive cable, a fiber optic cable, and/or a wireless emitter. An analog sensor can generate a measuring signal and communicate the measuring signal to the processor using an analog output signal. An analog sensor can include a Hall Effect sensor, a magnetoresistive sensor, an optical sensor, and/or any other suitable sensor, for example. A surgical instrument can include a signal filter which can be configured to receive and/or condition the analog output signal before the analog output signal reaches the processor. The signal filter can comprise a low-pass filter, for example, that passes signals to the processor having a low frequency which is at and/or below a cutoff frequency and that attenuates, or reduces the amplitude of, signals with high frequencies higher than the cutoff frequency. In some instances, the low-pass filter may eliminate certain high frequency signals that it receives or all of the high frequency signals that it receives. The low-pass filter may also attenuate, or reduce the amplitude of, certain or all of the low frequency signals, but such attenuation may be different than the attenuation that it applies to high frequency signals. Any suitable signal filter could be utilized. A high-pass filter, for example, could be utilized. A longpass filter could be utilized to receive and condition signals from optical sensors. In various instances, the processor can include an integral signal filter. In some instances, the processor can be in signal communication with the signal filter. In any event, the signal filter can be configured to reduce noise within the analog output signal, or signals, that it receives.

Further to the above, an analog output signal from a sensor can comprise a series of voltage potentials applied to an input channel of the processor. In various instances, the voltage potentials of the analog sensor output signal can be within a defined range. For instance, the voltage potentials can be between about 0V and about 12V, between about 0V and about 6V, between about 0V and about 3V, and/or between about 0V and about 1V, for example. In some instances, the voltage potentials can be less than or equal to 12V, less than or equal to 6V, less than or equal to 3V, and/or less than or equal to 1V, for example. In some instances, the voltage potentials can be between about 0V and about −12V, between about 0V and about −6V, between about 0V and about −3V, and/or between about 0V and about −1V, for example. In some instances, the voltage potentials can be greater than or equal to −12V, greater than or equal to −6V, greater than or equal to −3V, and/or greater than or equal to −1V, for example. In some instances, the voltage potentials can be between about 12V and about −12V, between about 6V and about −6V, between about 3V and about −3V, and/or between about 1V and about −1V, for example. In various instances, the sensor can supply voltage potentials to an input channel of the processor in a continuous stream. The processor may sample this stream of data at a rate which is less than rate in which data is delivered to the processor. In some instances, the sensor can supply voltage potentials to an input channel of the process intermittently or at periodic intervals. In any event, the processor can be configured to evaluate the voltage potentials applied to the input channel or channels thereof and operate the surgical instrument in response to the voltage potentials, as described in greater detail further below.

Further to the above, the processor can be configured to evaluate the analog output signal from a sensor. In various instances, the processor can be configured to evaluate every voltage potential of the analog output signal and/or sample the analog output signal. When sampling the analog output signal, the processor can make periodic evaluations of the signal to periodically obtain voltage potentials from the analog output signal. For each evaluation, the processor can compare the voltage potential obtained from the evaluation against a reference value. In various circumstances, the processor can calculate a digital value, such as 0 or 1, or on or off, for example, from this comparison. For instance, in the event that the evaluated voltage potential equals the reference value, the processor can calculate a digital value of 1. Alternatively, the processor can calculate a digital value of 0 if the evaluated voltage potential equals the reference value. With regard to a first embodiment, the processor can calculate a digital value of 1 if the evaluated voltage potential is less than the reference value and a digital value of 0 if the evaluated voltage potential is greater than the reference value. With regard to a second embodiment, the processor can calculate a digital value of 0 if the evaluated voltage potential is less than the reference value and a digital value of 1 if the evaluated voltage potential is greater than the reference value. In either event, the processor can convert the analog signal to a digital signal. When the processor is continuously evaluating the voltage potential of the sensor output signal, the processor can continuously compare the voltage potential to the reference value, and continuously calculate the digital value. When the processor is evaluating the voltage potential of the sensor output signal at periodic intervals, the processor can compare the voltage potential to the reference value at periodic intervals, and calculate the digital value at periodic intervals.

Further to the above, the reference value can be part of an algorithm utilized by the processor. The reference value can be pre-programmed in the algorithm. In some instances, the processor can obtain, calculate, and/or modify the reference value in the algorithm. In some instances, the reference value can be stored in a memory device which is accessible by and/or integral with the processor. The reference value can be pre-programmed in the memory device. In some instances, the processor can obtain, calculate, and/or modify the reference value in the memory device. In at least one instance, the reference value may be stored in non-volatile memory. In some instances, the reference value may be stored in volatile memory. The reference value may comprise a constant value. The reference value may or may not be changeable or overwritten. In certain instances, the reference value can be stored, changed, and/or otherwise determined as the result of a calibration procedure. The calibration procedure can be performed when manufacturing the surgical instrument, when initializing, or initially powering up, the instrument, when powering up the instrument from a sleep mode, when using the instrument, when placing the instrument into a sleep mode, and/or when completely powering down the instrument, for example.

Also further to the above, the processor can be configured to store the digital value. The digital value can be stored at an electronic logic gate. In various instances, the electronic logic gate can supply a binary output which can be referenced by the processor to assess a condition detected by the sensor, as described in greater detail further below. The processor can include the electronic logic gate. The binary output of the electronic logic gate can be updated. In various instances, the processor can include one or more output channels. The processor can supply the binary output to at least one of the output channels. The processor can apply a low voltage to such an output channel to indicate an off bit or a high voltage to the output channel to indicate an on bit, for example. The low voltage and the high voltage can be measured relative to a threshold value. In at least one instance, the low voltage can comprise no voltage, for example. In at least one other instance, the low voltage can comprise a voltage having a first polarity and the high voltage can comprise a voltage having an opposite polarity, for example.

In at least one instance, if the voltage potentials evaluated by the processor are consistently at or below the reference value, the electronic logic gate can maintain an output of 'on'. When an evaluated voltage potential exceeds the reference value, the output of the logic gate can be switched to 'off'. If the voltage potentials evaluated by the processor are consistently above the reference value, the electronic logic gate can maintain an output of 'off'. When an evaluated voltage potential is thereafter measured at or below the reference value, the output of the logic gate can be switched back to 'on', and so forth. In various instances, the electronic logic gate may not maintain a history of its output. In some instances, the processor can include a memory device configured to record the output history of the electronic logic gate, i.e., record a history of the calculated digital value. In various instances, the processor can be configured to access the memory device to ascertain the current digital value and/or at least one previously-existing digital value, for example.

In various instances, the processor can provide an immediate response to a change in the calculated digital value. When the processor first detects that the calculated digital value has changed from 'on' to 'off' or from 'off' to 'on', for example, the processor can immediately modify the operation of the surgical instrument. In certain instances, the processor may not immediately modify the operation of the surgical instrument upon detecting that the calculated digital value has changed from 'on' to 'off' or from 'off' to 'on', for example. The processor may employ a hysteresis algorithm. For instance, the processor may not modify the operation of the surgical instrument until after the digital value has been calculated the same way a certain number of consecutive times. In at least one such instance, the processor may calculate an 'on' value and display an 'on' binary value at the output logic gate and/or the output channel based on the data it has received from one or more surgical instrument sensors wherein, at some point thereafter, the processor may calculate an 'off' value based on the data it has received from one or more of the surgical instrument sensors; however, the processor may not immediately display an 'off' binary value at the output logic gate and/or the output channel. Rather, the processor may delay changing the binary value at the output logic gate and/or the output channel until after the processor has calculated the 'off' value a certain number of consecutive times, such as ten times, for example. Once the processor has changed the binary value at the output logic gate and/or the output channel, the processor may likewise delay changing the binary value at the output logic gate and/or the output channel until after the processor has calculated the 'on' value a certain number of consecutive times, such as ten times, for example, and so forth.

A hysteresis algorithm may be suitable for handling switch debounce. A surgical instrument can include a switch debouncer circuit which utilizes a capacitor to filter out any quick changes of signal response.

In the example provided above, the sampling delay for going from 'on' to 'off' was the same as the sampling delay for going from 'off' to 'on'. Embodiments are envisioned in which the sampling delays are not equal. For instance, if an 'on' value at an output channel activates the motor of the surgical instrument and an 'off' value at an output channel deactivates the motor, the 'on' delay may be longer than the 'off' delay, for example. In such instances, the processor may not suddenly activate the motor in response to accidental or incidental movements of the firing trigger while, on the other hand, the processor may react quickly to a release of the firing trigger to stop the motor. In at least one such instance, the processor may have an 'on' delay but no 'off' delay such that the motor can be stopped immediately after the firing trigger is released, for example. As discussed above, the processor may wait for a certain number of consecutive consistent binary output calculations before changing the binary output value. Other algorithms are contemplated. For instance, a processor may not require a certain number of consecutive consistent binary output calculations; rather, the processor may only require that a certain number, or percentage, of consecutive calculations be consistent in order to change the binary output.

As discussed above, a processor can convert an analog input signal to a digital output signal utilizing a reference value. As also discussed above, the processor can utilize the reference value to convert the analog input data, or samples of the analog input data, to 'on' values or 'off' values as part of its digital output signal. In various instances, a processor can utilize more than one reference value in order to determine whether to output an 'on' value or an 'off' value. One reference value can define two ranges. A range below the reference value and a range above the reference value. The reference value itself can be part of the first range or the second range, depending on the circumstances. The use of additional reference values can define additional ranges. For instance, a first reference value and a second reference value can define three ranges: a first range below the first reference value, a second range between the first reference value and the second reference value, and a third range above the second reference value. Again, the first reference value can be part of the first range or the second range and, similarly, the second reference value can be part of the second range or the third range, depending on the circumstances. For a given sample of data from an analog signal, the processor can determine whether the sample lies within the first range, the second range, or the third range. In at least one exemplary embodiment, the processor can assign an 'on' value to the binary output if the sample is in the first range and an 'off' value to the binary output if the sample is in the third range. Alternatively, the processor can assign an 'off' value to the binary output if the sample is in the first range and an 'on' value to the binary output if the sample is in the third range.

Further to the above, the processor can assign an 'on' value or an 'off' value to the binary output if the data sample is in the second range. In various instances, an analog data sample in the second range may not change the binary output value. For instance, if the processor has been receiving analog data above the second reference value and producing a certain binary output and, subsequently, the processor receives analog data between the first reference value and the second reference value, the processor may not change the binary output. If the processor, in this example, receives analog data below the first reference value, the processor may then change the binary output. Correspondingly, in this example, if the processor has been receiving analog data below the first reference value and producing a certain binary output and, subsequently, the processor receives analog data between the first reference value and the second reference value, the processor may not change the binary output. If the processor, in this example, receives analog data above the second reference value, the processor may then change the binary output. In various instances, the second range between the first reference value and the second reference value may comprise an observation window within which the processor may not change the binary output signal. In certain instances, the processor may utilize different sampling delays, depending on whether the analog input data jumps directly between the first range and the third range or whether the analog input data transitions into the second range before transitioning into the third range. For example, the sampling delay may be shorter if the analog input data transitions into the second range before transitioning into the first range or the third range as compared to when analog input data jumps directly between the first range and the third range.

As discussed above, an analog sensor, such as a Hall effect sensor, for example, can be utilized to detect a condition of a surgical instrument. In various instances, a Hall effect sensor can produce a linear analog output which can include a positive polarity and a negative polarity and, in certain instances, produce a wide range of analog output values. Such a wide range of values may not always be useful, or may not correspond to events which are actually possible for the surgical instrument. For instance, a Hall effect sensor can be utilized to track the orientation of the anvil of an end effector which, owing to certain physical constraints to the motion of the anvil, may only move through a small range of motion, such as about 30 degrees, for example. Although the Hall effect sensor could detect motion of the anvil outside this range of motion, as a practical matter, the Hall effect sensor will not need to and, as a result, a portion of the output range of the Hall effect sensor may not be utilized. The processor may be programmed to only recognize a range of output from the Hall effect sensor which corresponds to a possible range of motion of the anvil and, to the extent that the processor receives data from the Hall effect sensor which is outside of this range of output, whether above the range or below the range, the processor can ignore such data, generate a fault condition, modify the operation of the surgical instrument, and/or notify the user of the surgical instrument, for example. In such instances, the processor may recognize a valid range of data from the sensor and any data received from the sensor which is outside of this range may be deemed invalid by the processor. The valid range of data may be defined by a first reference value, or threshold, and a second reference value, or threshold. The valid range of data may include data having a positive polarity and a negative polarity. Alternatively, the valid range of data may only comprise data from the positive polarity or data from the negative polarity.

The first reference value and the second reference value, further to the above, can comprise fixed values. In certain circumstances, the first reference value and/or the second reference value can be calibrated. The first reference value and/or the second reference value can be calibrated when the surgical instrument is initially manufactured and/or subsequently re-manufactured. For instance, a trigger, such as the closure trigger, for example, can be moved through its entire range of motion during a calibration procedure and a Hall effect sensor, for example, positioned within the surgical instrument handle can detect the motion of the closure trigger, or at least the motion of a magnetic element, such as a permanent magnet, for example, positioned on the closure trigger. When the closure trigger is in its unclamped position, the reading taken by the Hall effect sensor can be stored as a first set point which corresponds with the unclamped position of the closure trigger. Similarly, when the closure trigger is in its fully clamped position, the reading taken by the Hall effect sensor can be stored as a second set point which corresponds with the fully clamped position of the closure trigger. Thereafter, the first set point can define the first reference value and the second set point can define the second reference value. Positions of the closure trigger between its unclamped position and its fully clamped position can correspond to the range of data between the first reference value and the second reference value. As outlined above, the processor can produce a digital output value in response to the data received from the analog sensor. In at least one instance, the processor can assign an 'off' value to its digital output when the data received from the analog sensor is at or above the first reference value. Alternatively, the processor can assign an 'off' value to its digital output when the data received from the analog sensor is above, at, or within about 20% of the range preceding first reference value, for example. Data from the analog sensor which is between the first reference value and about 20% of the range below the first reference value can correspond with a position of the closure trigger which is suitably close to is unclamped position. In at least one instance, the processor can assign an 'on' value to its digital output when the data received from the analog sensor is below the first reference value. Alternatively, the processor can assign an 'on' value to its digital output when the data received from the analog sensor is at, below, or within about 40% of the range above the second reference value can correspond with a position of the closure trigger when it has been pulled about ¾ through its range of motion, for example. The same or similar attributes could be applied to a firing trigger of the surgical instrument, for example.

Further to the above, a sensor can be calibrated in view of a reference value. For instance, if a reference value of +2V, for example, is associated with an unclamped position of the closure trigger and the processor detects a sensor output value which is different than +2V when the closure trigger is in its unclamped position, the processor can recalibrate the sensor, or the gain of the sensor, such that the sensor output matches, or at least substantially matches, the reference value. The processor may utilize an independent method of confirming that the closure trigger is in its unclamped position. In at least one such instance, the surgical instrument can include a second sensor in signal communication with the processor which can independently verify when the closure trigger is in its unclamped position. The second sensor could also comprise an analog sensor, such as a Hall effect sensor, for example. The second sensor could comprise a proximity sensor, a resistance based sensor, and/or any other suitable sensor, for example. The same or similar attributes could be applied to a firing trigger of the surgical instrument, for example.

As discussed above, referring to FIGS. 14-18A, a tracking system 800 can comprise one or more sensors, such as a first Hall effect sensor 803 and a second Hall effect sensor 804, for example, which can be configured to track the position of the magnet 802. Upon comparing FIGS. 14 and 17, the reader will appreciate that, when the closure trigger 32 is moved from its unactuated position to its actuated position, the magnet 802 can move between a first position adjacent the first Hall effect sensor 803 and a second position adjacent the second Hall effect sensor 804. When the magnet 802 is in its first position, the position of the magnet 802 can be detected by the first Hall effect sensor 803 and/or the second Hall effect sensor 804. The processor of the surgical instrument can use data from the first sensor 803 to determine the position of the magnet 802 and data from the second sensor 804 to independently determine the position of the magnet 802. In such instances, the processor can utilize data from the second sensor 804 to verify the integrity of the data from the first sensor 803. Alternatively, the processor could utilize the data from the first sensor 803 to verify the integrity of the data from the second sensor 804. The processor can utilize any suitable hierarchy for determining whether the data from a sensor should be used to provide a primary determination or a secondary determination of the position of the magnet 802. For instance, when the magnet 802 is in its first position, the magnet 802 may provide a larger disturbance to the magnetic field surrounding the first sensor 803 than to the magnetic field surrounding the second sensor 804 and, as a result, the processor may utilize the data from the first sensor 803 as a primary determination of the position of the magnet 802. When the magnet 802 is closer to the second sensor 804 than the first sensor 803, the magnet 802 may provide a larger disturbance to the magnetic field surrounding the second sensor 804 than to the magnetic field surrounding the first sensor 803 and, as a result, the processor may utilize the data from the second sensor 804 as a primary determination of the position of the magnet 802.

Further to the above, the path of the magnet 802 relative to the first sensor 803 can be determined when the magnet 802 moves along a first path segment when the closure trigger 32 is moved between its unclamped position and its clamped position and a second path segment when the firing trigger 130 is moved between its unfired position and its fired position. The range of outputs that the first sensor 803 will produce while tracking the magnet 802 as it moves along its first path segment can define a first valid range of data while the range of outputs that the first sensor 803 will produce while tracking the magnet 802 as it moves along its second path segment can define a second valid range of data. The first valid range of data may or may not be contiguous with the second valid range of data. In either event, the path of the magnet 802 relative to the second sensor 804 can also be determined when the magnet 802 moves along its first path segment and its second path segment. The range of outputs that the second sensor 804 will produce while tracking the magnet 802 as it moves along its first path segment can define a first valid range of data while the range of outputs that the second sensor 804 will produce while tracking the magnet 802 as it moves along its second path segment can define a second valid range of data. When the first sensor 803 and/or the second sensor 804 receives data outside of its respective first valid range of data and second valid range of data, the processor may assume that an error has occurred, modify the operation of the surgical instrument, and/or notify the operator of the surgical instrument. In certain instances, the processor can be configured to utilize data from the first sensor 803 and the second sensor 804 to determine whether the surgical instrument has been positioned within a strong external magnetic field which can affect the operation of the surgical instrument. For instance, the magnet 802 may move along a path such that the first sensor 803 and the second sensor 804 do not produce the same output at the same time and, in the event that first sensor 803 and the second sensor 804 produce the same output at the same time, the processor can determine that a fault condition exists, for example.

Figure 69:
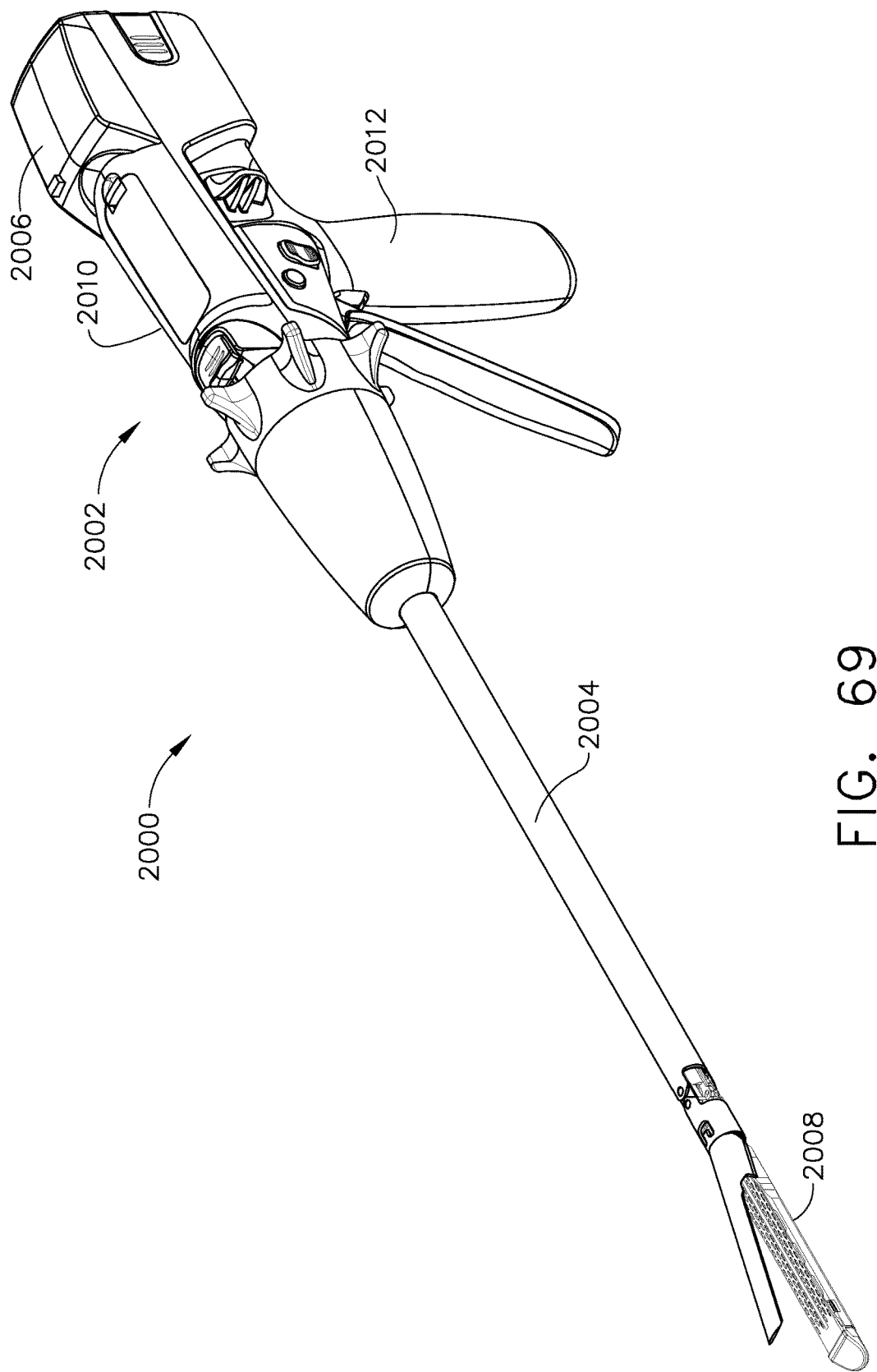
FIG. 69 is a perspective view of a surgical instrument comprising a power assembly, a handle assembly, and an interchangeable shaft assembly.
Figure 70:
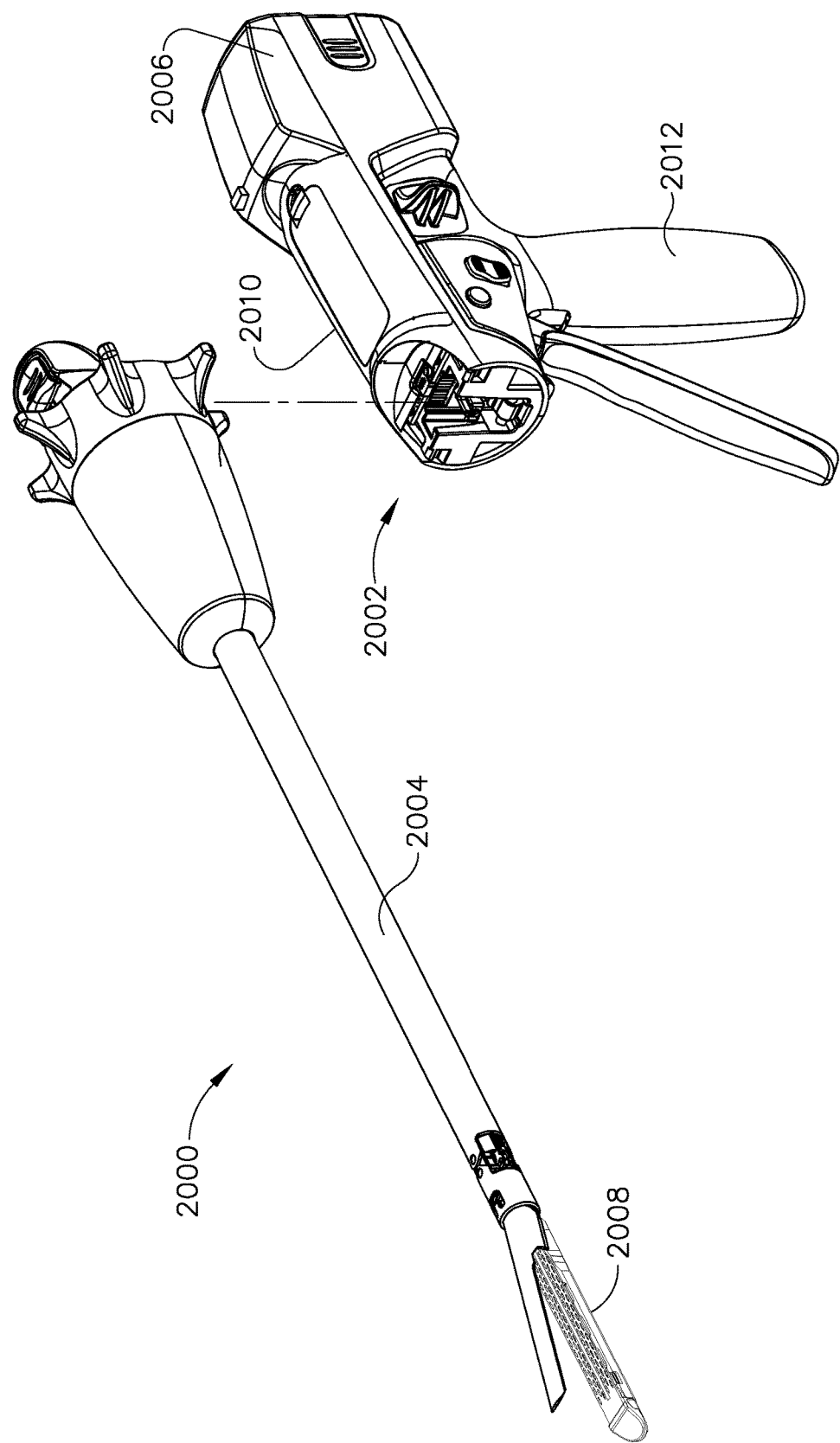
FIG. 70 is perspective view of the surgical instrument of FIG. 69 with the interchangeable shaft assembly separated from the handle assembly.

FIGS. 69-71B generally depict a motor-driven surgical fastening and cutting instrument 2000. As illustrated in FIGS. 69 and 70, the surgical instrument 2000 may include a handle assembly 2002, a shaft assembly 2004, and a power assembly 2006 ("power source," "power pack," or "battery pack"). The shaft assembly 2004 may include an end effector 2008 which, in certain circumstances, can be configured to act as an endocutter for clamping, severing, and/or stapling tissue, although, in other embodiments, different types of end effectors may be used, such as end effectors for other types of surgical devices, graspers, cutters, staplers, clip appliers, access devices, drug/gene therapy devices, ultrasound devices, RF device, and/or laser devices, for example. Several RF devices may be found in U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL FASTENING AND CUTTING INSTRUMENT HAVING RF ELECTRODES, filed Feb. 14, 2008, the entire disclosures of which are incorporated herein by reference in their entirety.

Figure 71A:
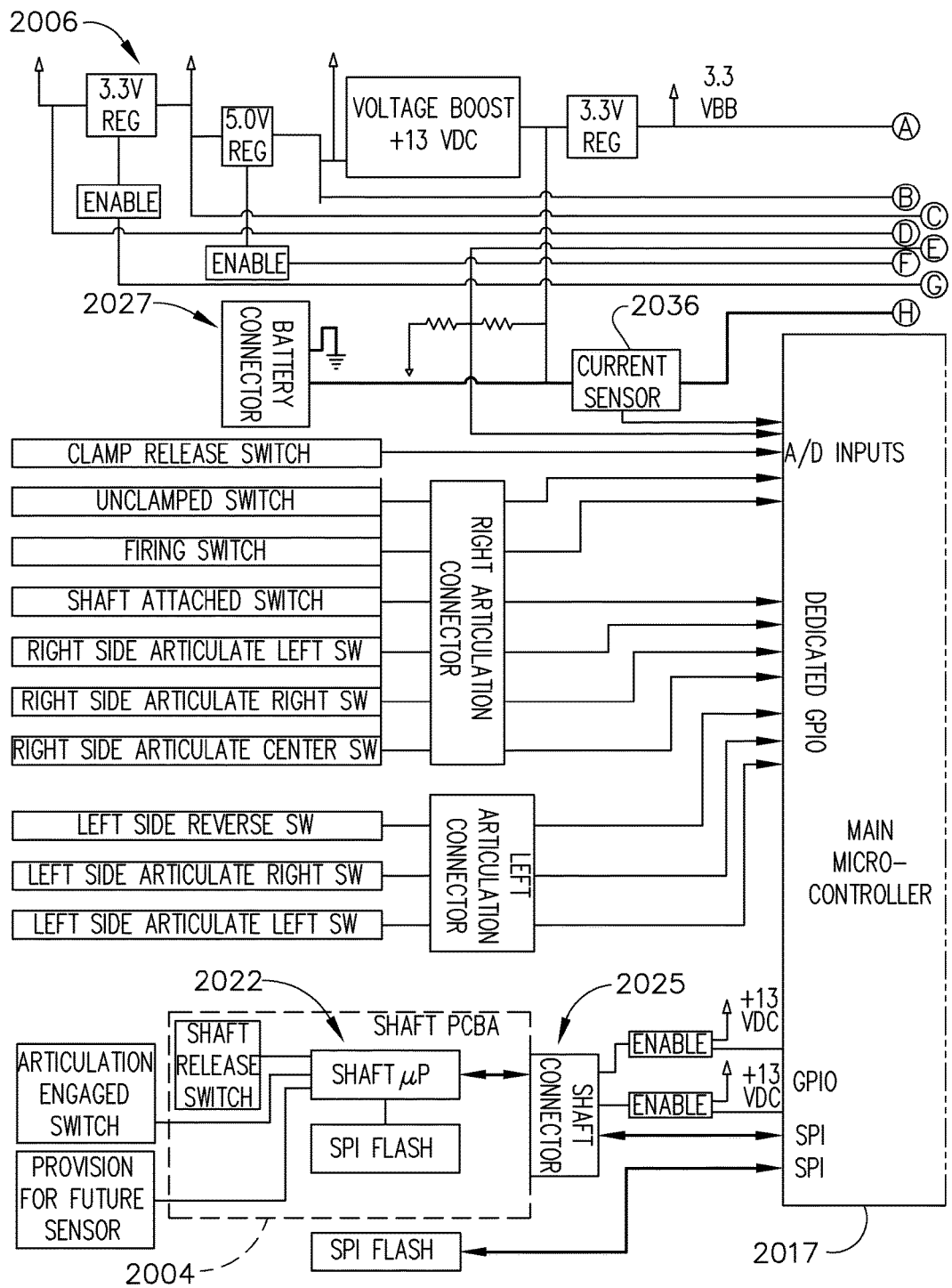
FIGS. 71A and 71B, is a circuit diagram of the surgical instrument of FIG. 69.
Figure 71B:
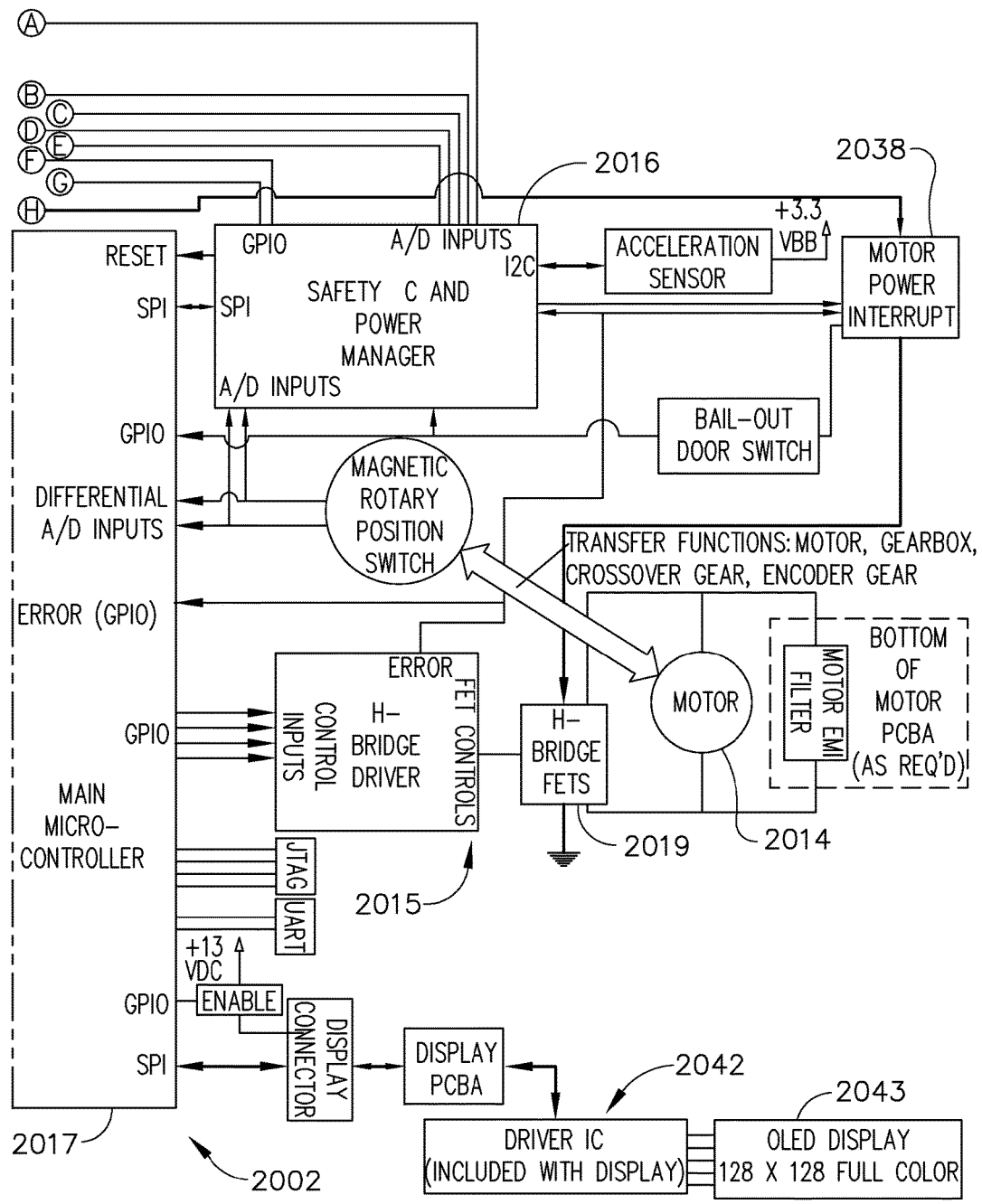

Referring primarily to FIGS. 70, 71A, and 71B, the handle assembly 2002 can be employed with a plurality of interchangeable shaft assemblies such as, for example, the shaft assembly 2004. Such interchangeable shaft assemblies may comprise surgical end effectors such as, for example, the end effector 2008 that can be configured to perform one or more surgical tasks or procedures. Examples of suitable interchangeable shaft assemblies are disclosed in U.S. Provisional Patent Application Ser. No. 61/782,866, entitled CONTROL SYSTEM OF A SURGICAL INSTRUMENT, and filed Mar. 14, 2013, the entire disclosure of which is hereby incorporated by reference herein in its entirety.

Referring primarily to FIG. 70, the handle assembly 2002 may comprise a housing 2010 that consists of a handle 2012 that may be configured to be grasped, manipulated and actuated by a clinician. However, it will be understood that the various unique and novel arrangements of the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the interchangeable shaft assemblies disclosed herein and their respective equivalents. For example, the interchangeable shaft assemblies disclosed herein may be employed with various robotic systems, instruments, components and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719, which is incorporated by reference herein in its entirety.

Referring again to FIG. 70, the handle assembly 2002 may operably support a plurality of drive systems therein that can be configured to generate and apply various control motions to corresponding portions of the interchangeable shaft assembly that is operably attached thereto. For example, the handle assembly 2002 can operably support a first or closure drive system, which may be employed to apply closing and opening motions to the shaft assembly 2004 while operably attached or coupled to the handle assembly 2002. In at least one form, the handle assembly 2002 may operably support a firing drive system that can be configured to apply firing motions to corresponding portions of the interchangeable shaft assembly attached thereto.

Referring primarily to FIGS. 71A and 71B, the handle assembly 2002 may include a motor 2014 which can be controlled by a motor driver 2015 and can be employed by the firing system of the surgical instrument 2000. In various forms, the motor 2014 may be a DC brushed driving motor having a maximum rotation of, approximately, 25,000 RPM, for example. In other arrangements, the motor 2014 may include a brushless motor, a cordless motor, a synchronous motor, a stepper motor, or any other suitable electric motor. In certain circumstances, the motor driver 2015 may comprise an H-Bridge field-effect transistors (FETs) 2019, as illustrated in FIGS. 71A and 71B, for example. The motor 2014 can be powered by the power assembly 2006 (FIGS. 71A and 71B) which can be releasably mounted to the handle assembly 2002 for supplying control power to the surgical instrument 2000. The power assembly 2006 may comprise a battery which may include a number of battery cells connected in series that can be used as the power source to power the surgical instrument 2000. In certain circumstances, the battery cells of the power assembly 2006 may be replaceable and/or rechargeable. In at least one example, the battery cells can be Lithium-Ion batteries which can be separably couplable to the power assembly 2006.

The shaft assembly 2004 may include a shaft assembly controller 2022 which can communicate with the power management controller 2016 through an interface while the shaft assembly 2004 and the power assembly 2006 are coupled to the handle assembly 2002. For example, the interface may comprise a first interface portion 2025 which may include one or more electric connectors for coupling engagement with corresponding shaft assembly electric connectors and a second interface portion 2027 which may include one or more electric connectors for coupling engagement with corresponding power assembly electric connectors to permit electrical communication between the shaft assembly controller 2022 and the power management controller 2016 while the shaft assembly 2004 and the power assembly 2006 are coupled to the handle assembly 2002. One or more communication signals can be transmitted through the interface to communicate one or more of the power requirements of the attached interchangeable shaft assembly 2004 to the power management controller 2016. In response, the power management controller may modulate the power output of the battery of the power assembly 2006, as described below in greater detail, in accordance with the power requirements of the attached shaft assembly 2004. In certain circumstances, one or more of the electric connectors may comprise switches which can be activated after mechanical coupling engagement of the handle assembly 2002 to the shaft assembly 2004 and/or to the power assembly 2006 to allow electrical communication between the shaft assembly controller 2022 and the power management controller 2016.

In certain circumstances, the interface can facilitate transmission of the one or more communication signals between the power management controller 2016 and the shaft assembly controller 2022 by routing such communication signals through a main controller 2017 residing in the handle assembly 2002, for example. In other circumstances, the interface can facilitate a direct line of communication between the power management controller 2016 and the shaft assembly controller 2022 through the handle assembly 2002 while the shaft assembly 2004 and the power assembly 2006 are coupled to the handle assembly 2002.

In one instance, the main microcontroller 2017 may be any single core or multicore processor such as those known under the trade name ARM Cortex by Texas Instruments. In one instance, the surgical instrument 2000 may comprise a power management controller 2016 such as, for example, a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one instance, the safety processor may be configured specifically for IEC 61508 and ISO 26262 safety critical applications, among others, to provide advanced integrated safety features while delivering scalable performance, connectivity, and memory options.

In certain instances, the microcontroller 2017 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet. The present disclosure should not be limited in this context.

The power assembly 2006 may include a power management circuit which may comprise the power management controller 2016, a power modulator 2038, and a current sense circuit 2036. The power management circuit can be configured to modulate power output of the battery based on the power requirements of the shaft assembly 2004 while the shaft assembly 2004 and the power assembly 2006 are coupled to the handle assembly 2002. For example, the power management controller 2016 can be programmed to control the power modulator 2038 of the power output of the power assembly 2006 and the current sense circuit 2036 can be employed to monitor power output of the power assembly 2006 to provide feedback to the power management controller 2016 about the power output of the battery so that the power management controller 2016 may adjust the power output of the power assembly 2006 to maintain a desired output.

It is noteworthy that the power management controller 2016 and/or the shaft assembly controller 2022 each may comprise one or more processors and/or memory units which may store a number of software modules. Although certain modules and/or blocks of the surgical instrument 2000 may be described by way of example, it can be appreciated that a greater or lesser number of modules and/or blocks may be used. Further, although various instances may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In certain instances, the surgical instrument 2000 may comprise an output device 2042 which may include one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 2042 may comprise a display 2043 which may be included in the handle assembly 2002. The shaft assembly controller 2022 and/or the power management controller 2016 can provide feedback to a user of the surgical instrument 2000 through the output device 2042. The interface 2024 can be configured to connect the shaft assembly controller 2022 and/or the power management controller 2016 to the output device 2042. The reader will appreciate that the output device 2042 can instead be integrated with the power assembly 2006. In such circumstances, communication between the output device 2042 and the shaft assembly controller 2022 may be accomplished through the interface 2024 while the shaft assembly 2004 is coupled to the handle assembly 2002.

Figure 72A:
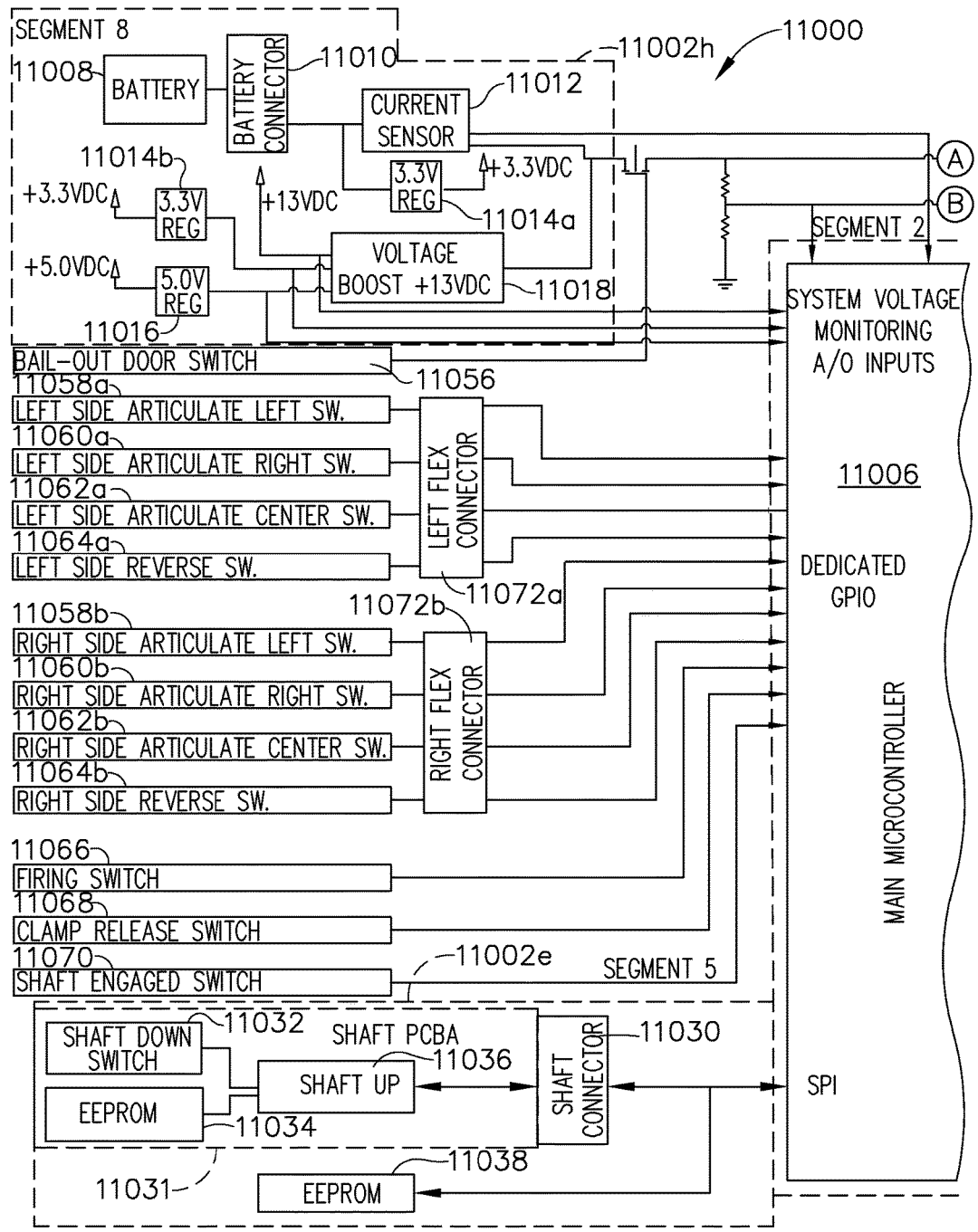
FIGS. 72A and 72B, illustrates one embodiment of a segmented circuit comprising a plurality of circuit segments configured to control a powered surgical instrument.
Figure 72B:
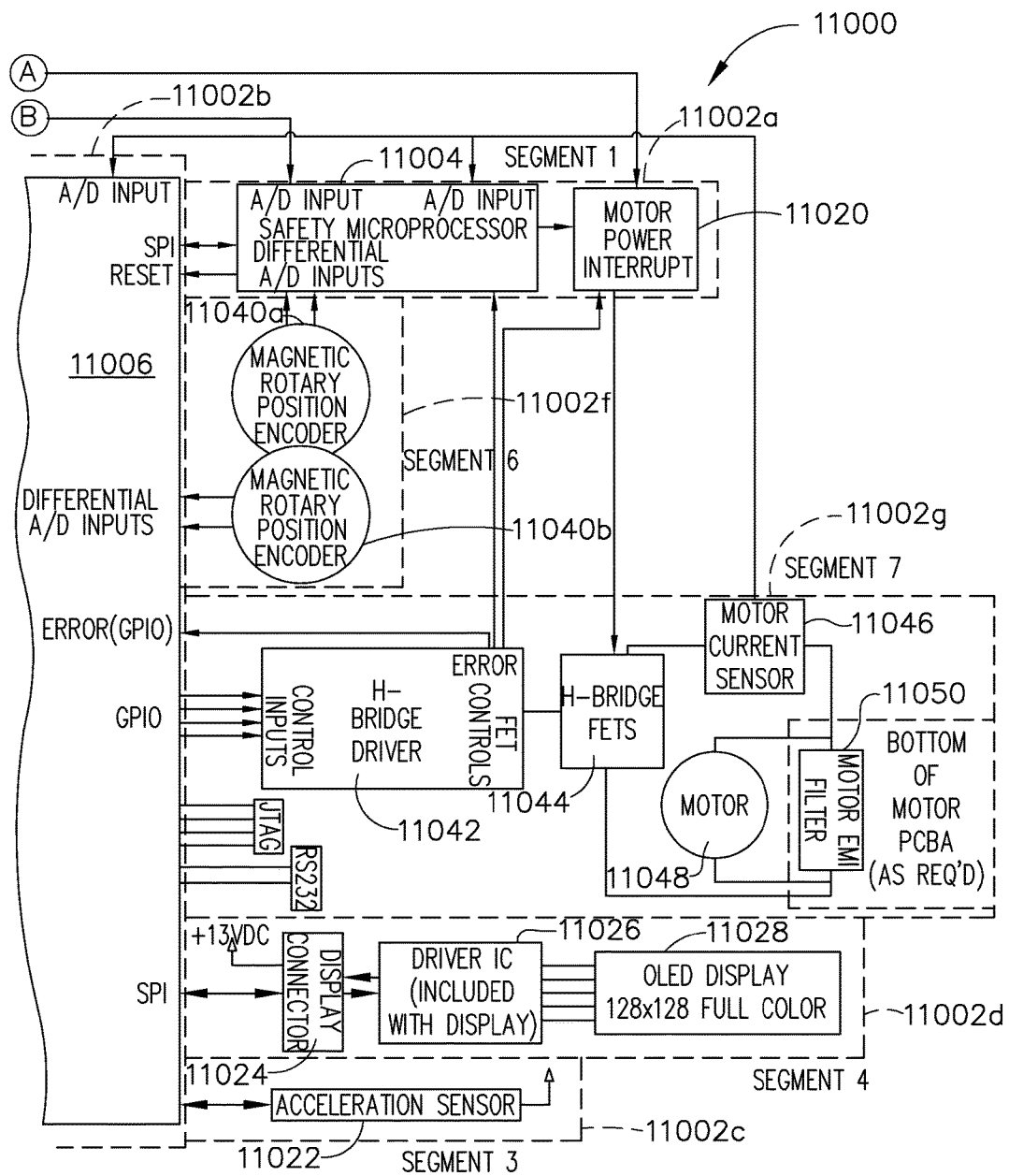

Having described a surgical instrument 2000 in general terms, the description now turns to a detailed description of various electrical/electronic component of the surgical instrument 2000. For expedience, any references hereinbelow to the surgical instrument 2000 should be construed to refer to the surgical instrument 2000 shown in connection with FIGS. 69-71B. Turning now to FIGS. 72A and 72B, where one embodiment of a segmented circuit 11000 comprising a plurality of circuit segments 11002a-11002g is illustrated. The segmented circuit 11000 comprising the plurality of circuit segments 11002a-11002g is configured to control a powered surgical instrument, such as, for example, the surgical instrument 2000 illustrated in FIGS. 69-71B, without limitation. The plurality of circuit segments 11002a-11002g is configured to control one or more operations of the powered surgical instrument 2000. A safety processor segment 11002a (Segment 1) comprises a safety processor 11004. A primary processor segment 11002b (Segment 2) comprises a primary processor 11006. The safety processor 11004 and/or the primary processor 11006 are configured to interact with one or more additional circuit segments 11002c-11002g to control operation of the powered surgical instrument 2000. The primary processor 11006 comprises a plurality of inputs coupled to, for example, one or more circuit segments 11002c-11002g, a battery 11008, and/or a plurality of switches 11058a-11070. The segmented circuit 11000 may be implemented by any suitable circuit, such as, for example, a printed circuit board assembly (PCBA) within the powered surgical instrument 2000. It should be understood that the term processor as used herein includes any microprocessor, microcontroller, or other basic computing device that incorporates the functions of a computer's central processing unit (CPU) on an integrated circuit or at most a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one embodiment, the main processor 11006 may be any single core or multicore processor such as those known under the trade name ARM Cortex by Texas Instruments. In one embodiment, the safety processor 11004 may be a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one embodiment, the safety processor 11004 may be configured specifically for IEC 61508 and ISO 26262 safety critical applications, among others, to provide advanced integrated safety features while delivering scalable performance, connectivity, and memory options.

In certain instances, the main processor 11006 may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet. Other processors may be readily substituted and, accordingly, the present disclosure should not be limited in this context.

In one embodiment, the segmented circuit 11000 comprises an acceleration segment 11002c (Segment 3). The acceleration segment 11002c comprises an acceleration sensor 11022. The acceleration sensor 11022 may comprise, for example, an accelerometer. The acceleration sensor 11022 is configured to detect movement or acceleration of the powered surgical instrument 2000. In some embodiments, input from the acceleration sensor 11022 is used, for example, to transition to and from a sleep mode, identify an orientation of the powered surgical instrument, and/or identify when the surgical instrument has been dropped. In some embodiments, the acceleration segment 11002c is coupled to the safety processor 11004 and/or the primary processor 11006.

In one embodiment, the segmented circuit 11000 comprises a display segment 11002d (Segment 4). The display segment 11002d comprises a display connector 11024 coupled to the primary processor 11006. The display connector 11024 couples the primary processor 11006 to a display 11028 through one or more display driver integrated circuits 11026. The display driver integrated circuits 11026 may be integrated with the display 11028 and/or may be located separately from the display 11028. The display 11028 may comprise any suitable display, such as, for example, an organic light-emitting diode (OLED) display, a liquid-crystal display (LCD), and/or any other suitable display. In some embodiments, the display segment 11002d is coupled to the safety processor 11004.

In some embodiments, the segmented circuit 11000 comprises a shaft segment 11002e (Segment 5). The shaft segment 11002e comprises one or more controls for a shaft 2004 coupled to the surgical instrument 2000 and/or one or more controls for an end effector 2006 coupled to the shaft 2004. The shaft segment 11002e comprises a shaft connector 11030 configured to couple the primary processor 11006 to a shaft PCBA 11031. The shaft PCBA 11031 comprises a first articulation switch 11036, a second articulation switch 11032, and a shaft PCBA electrically erasable programmable read-only memory (EEPROM) 11034. In some embodiments, the shaft PCBA EEPROM 11034 comprises one or more parameters, routines, and/or programs specific to the shaft 2004 and/or the shaft PCBA 11031. The shaft PCBA 11031 may be coupled to the shaft 2004 and/or integral with the surgical instrument 2000. In some embodiments, the shaft segment 11002e comprises a second shaft EEPROM 11038. The second shaft EEPROM 11038 comprises a plurality of algorithms, routines, parameters, and/or other data corresponding to one or more shafts 2004 and/or end effectors 2006 which may be interfaced with the powered surgical instrument 2000.

In some embodiments, the segmented circuit 11000 comprises a position encoder segment 11002f (Segment 6). The position encoder segment 11002f comprises one or more magnetic rotary position encoders 11040a-11040b. The one or more magnetic rotary position encoders 11040a-11040b are configured to identify the rotational position of a motor 11048, a shaft 2004, and/or an end effector 2006 of the surgical instrument 2000. In some embodiments, the magnetic rotary position encoders 11040a-11040b may be coupled to the safety processor 11004 and/or the primary processor 11006.

In some embodiments, the segmented circuit 11000 comprises a motor segment 11002g (Segment 7). The motor segment 11002g comprises a motor 11048 configured to control one or more movements of the powered surgical instrument 2000. The motor 11048 is coupled to the primary processor 11006 by an H-Bridge driver 11042 and one or more H-bridge field-effect transistors (FETs) 11044. The H-bridge FETs 11044 are coupled to the safety processor 11004. A motor current sensor 11046 is coupled in series with the motor 11048 to measure the current draw of the motor 11048. The motor current sensor 11046 is in signal communication with the primary processor 11006 and/or the safety processor 11004. In some embodiments, the motor 11048 is coupled to a motor electromagnetic interference (EMI) filter 11050.

The segmented circuit 11000 comprises a power segment 11002h (Segment 8). A battery 11008 is coupled to the safety processor 11004, the primary processor 11006, and one or more of the additional circuit segments 11002c-11002g. The battery 11008 is coupled to the segmented circuit 11000 by a battery connector 11010 and a current sensor 11012. The current sensor 11012 is configured to measure the total current draw of the segmented circuit 11000. In some embodiments, one or more voltage converters 11014a, 11014b, 11016 are configured to provide predetermined voltage values to one or more circuit segments 11002a-11002g. For example, in some embodiments, the segmented circuit 11000 may comprise 3.3V voltage converters 11014a-11014b and/or 5V voltage converters 11016. A boost converter 11018 is configured to provide a boost voltage up to a predetermined amount, such as, for example, up to 13V. The boost converter 11018 is configured to provide additional voltage and/or current during power intensive operations and prevent brownout or low-power conditions.

In some embodiments, the safety segment 11002a comprises a motor power interrupt 11020. The motor power interrupt 11020 is coupled between the power segment 11002h and the motor segment 11002g. The safety segment 11002a is configured to interrupt power to the motor segment 11002g when an error or fault condition is detected by the safety processor 11004 and/or the primary processor 11006 as discussed in more detail herein. Although the circuit segments 11002a-11002g are illustrated with all components of the circuit segments 11002a-11002h located in physical proximity, one skilled in the art will recognize that a circuit segment 11002a-11002h may comprise components physically and/or electrically separate from other components of the same circuit segment 11002a-11002g. In some embodiments, one or more components may be shared between two or more circuit segments 11002a-11002g.

In some embodiments, a plurality of switches 11056-11070 are coupled to the safety processor 11004 and/or the primary processor 11006. The plurality of switches 11056-11070 may be configured to control one or more operations of the surgical instrument 2000, control one or more operations of the segmented circuit 11100, and/or indicate a status of the surgical instrument 2000. For example, a bail-out door switch 11056 is configured to indicate the status of a bail-out door. A plurality of articulation switches, such as, for example, a left side articulation left switch 11058a, a left side articulation right switch 11060a, a left side articulation center switch 11062a, a right side articulation left switch 11058b, a right side articulation right switch 11060b, and a right side articulation center switch 11062b are configured to control articulation of a shaft 2004 and/or an end effector 2006. A left side reverse switch 11064a and a right side reverse switch 11064b are coupled to the primary processor 11006. In some embodiments, the left side switches comprising the left side articulation left switch 11058a, the left side articulation right switch 11060a, the left side articulation center switch 11062a, and the left side reverse switch 11064a are coupled to the primary processor 11006 by a left flex connector 11072a. The right side switches comprising the right side articulation left switch 11058b, the right side articulation right switch 11060b, the right side articulation center switch 11062b, and the right side reverse switch 11064b are coupled to the primary processor 11006 by a right flex connector 11072b. In some embodiments, a firing switch 11066, a clamp release switch 11068, and a shaft engaged switch 11070 are coupled to the primary processor 11006.

The plurality of switches 11056-11070 may comprise, for example, a plurality of handle controls mounted to a handle of the surgical instrument 2000, a plurality of indicator switches, and/or any combination thereof. In various embodiments, the plurality of switches 11056-11070 allow a surgeon to manipulate the surgical instrument, provide feedback to the segmented circuit 11000 regarding the position and/or operation of the surgical instrument, and/or indicate unsafe operation of the surgical instrument 2000. In some embodiments, additional or fewer switches may be coupled to the segmented circuit 11000, one or more of the switches 11056-11070 may be combined into a single switch, and/or expanded to multiple switches. For example, in one embodiment, one or more of the left side and/or right side articulation switches 11058a-11064b may be combined into a single multi-position switch.

Figure 73A:
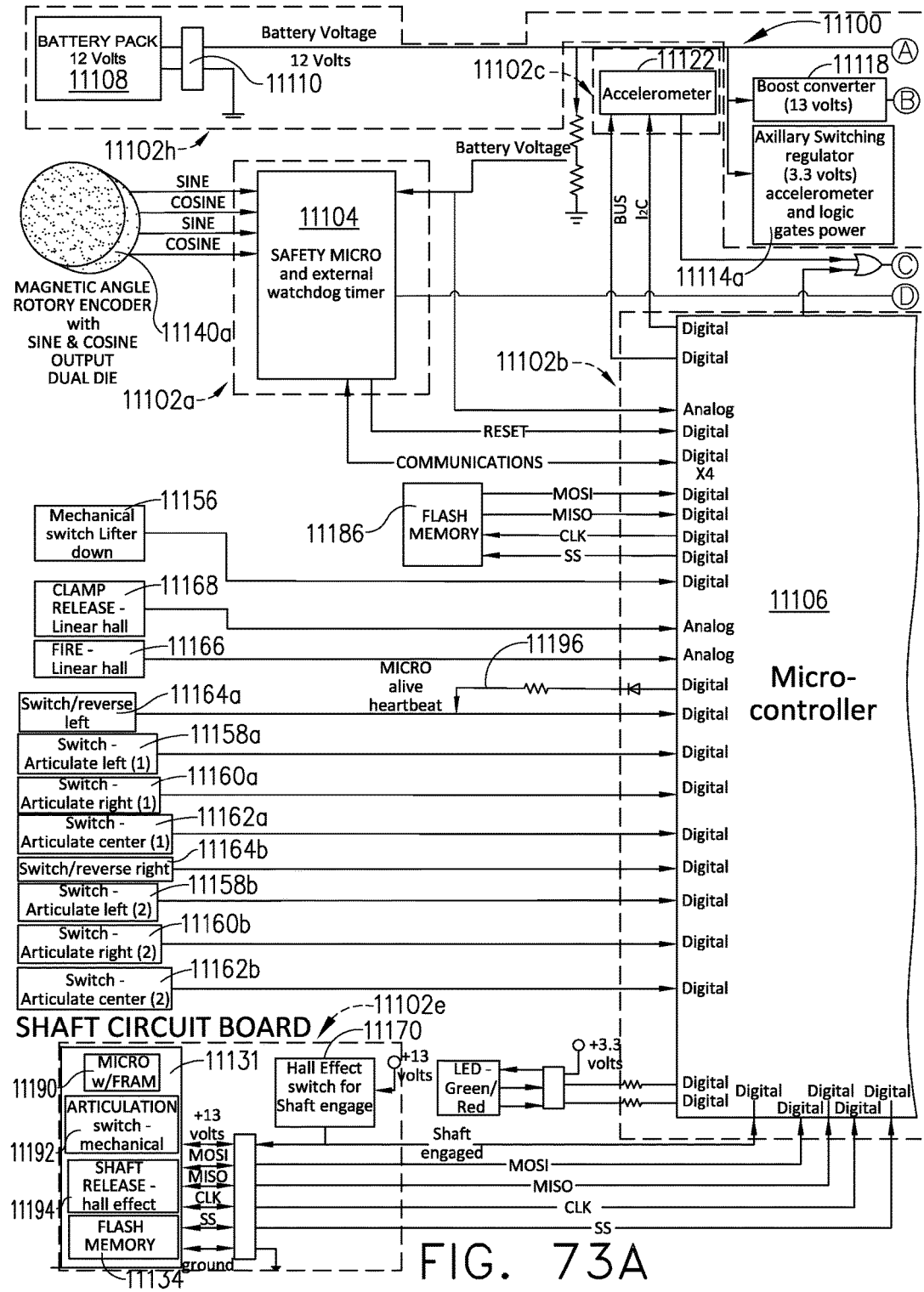
FIGS. 73A and 73B, illustrates a segmented circuit comprising a safety processor configured to implement a watchdog function.
Figure 73B:
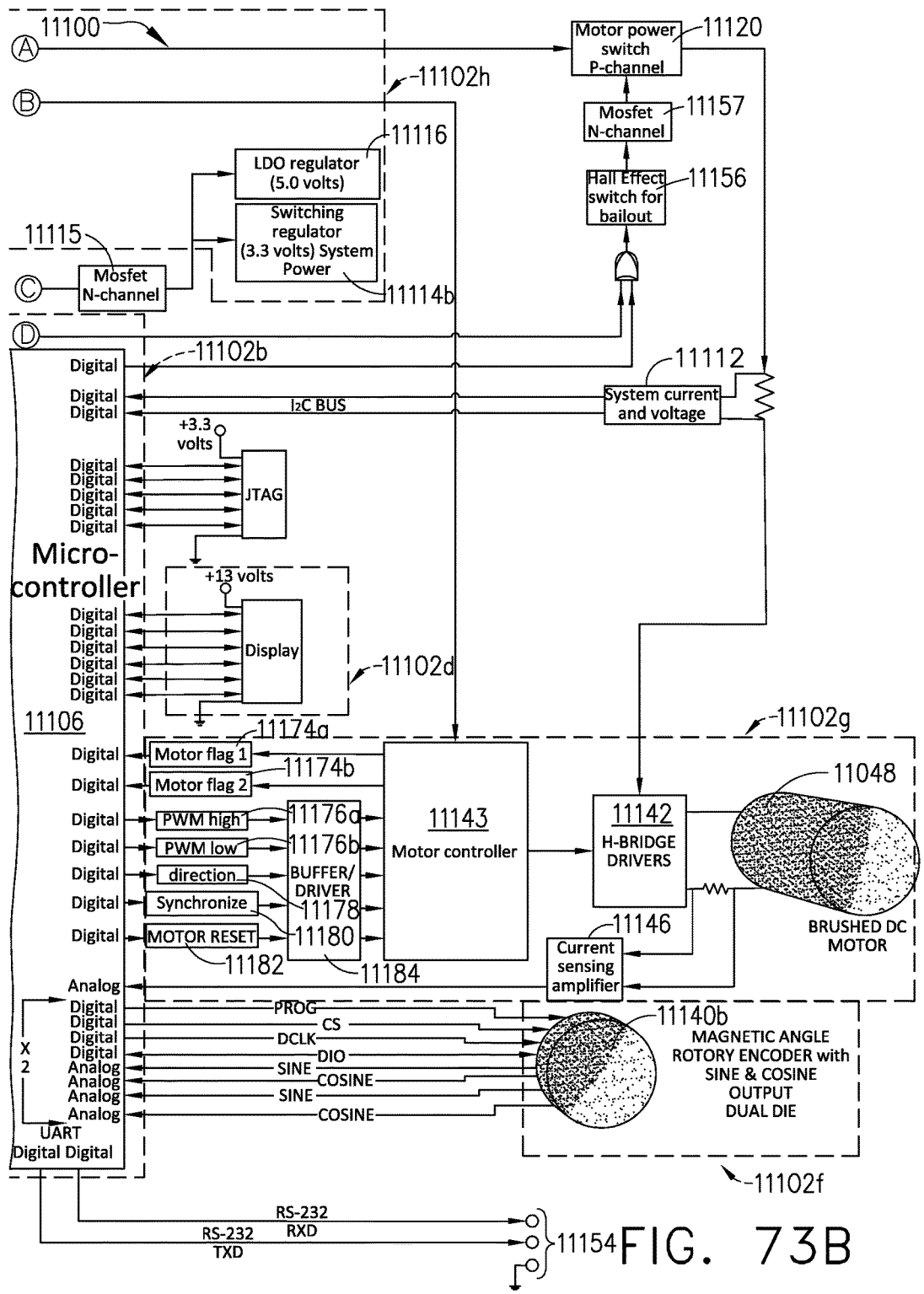

FIGS. 73A and 73B illustrate a segmented circuit 11100 comprising one embodiment of a safety processor 11104 configured to implement a watchdog function, among other safety operations. The safety processor 11004 and the primary processor 11106 of the segmented circuit 11100 are in signal communication. A plurality of circuit segments 11102c-11102h are coupled to the primary processor 11106 and are configured to control one or more operations of a surgical instrument, such as, for example, the surgical instrument 2000 illustrated in FIGS. 1-3. For example, in the illustrated embodiment, the segmented circuit 11100 comprises an acceleration segment 11102c, a display segment 11102d, a shaft segment 11102e, an encoder segment 11102f, a motor segment 11102g, and a power segment 11102h. Each of the circuit segments 11102c-11102g may be coupled to the safety processor 11104 and/or the primary processor 11106. The primary processor is also coupled to a flash memory 11186. A microprocessor alive heartbeat signal is provided at output 11196.

The acceleration segment 11102c comprises an accelerometer 11122 configured to monitor movement of the surgical instrument 2000. In various embodiments, the accelerometer 11122 may be a single, double, or triple axis accelerometer. The accelerometer 11122 may be employed to measures proper acceleration that is not necessarily the coordinate acceleration (rate of change of velocity). Instead, the accelerometer sees the acceleration associated with the phenomenon of weight experienced by a test mass at rest in the frame of reference of the accelerometer 11122. For example, the accelerometer 11122 at rest on the surface of the earth will measure an acceleration $g=9.8$ m/s$^2$ (gravity) straight upwards, due to its weight. Another type of acceleration that accelerometer 11122 can measure is g-force acceleration. In various other embodiments, the accelerometer 11122 may comprise a single, double, or triple axis accelerometer. Further, the acceleration segment 11102c may comprise one or more inertial sensors to detect and measure acceleration, tilt, shock, vibration, rotation, and multiple degrees-of-freedom (DoF). A suitable inertial sensor may comprise an accelerometer (single, double, or triple axis), a magnetometer to measure a magnetic field in space such as the earth's magnetic field, and/or a gyroscope to measure angular velocity.

The display segment 11102d comprises a display embedded in the surgical instrument 2000, such as, for example, an OLED display. In certain embodiments, the surgical instrument 2000 may comprise an output device which may include one or more devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In some aspects, the output device may comprise a display which may be included in the handle assembly 2002, as illustrated in FIG. 69. The shaft assembly controller and/or the power management controller can provide feedback to a user of the surgical instrument 2000 through the output device. An interface can be configured to connect the shaft assembly controller and/or the power management controller to the output device.

The shaft segment 11102e comprises a shaft circuit board 11131, such as, for example, a shaft PCB, configured to control one or more operations of a shaft 2004 and/or an end effector 2006 coupled to the shaft 2004 and a Hall effect switch 1170 to indicate shaft engagement. The shaft circuit board 1131 also includes a low-power microprocessor 1190 with ferroelectric random access memory (FRAM) technology, a mechanical articulation switch 1192, a shaft release Hall Effect switch 1194, and flash memory 1134. The encoder segment 11102f comprises a plurality of motor encoders 11140a, 11140b configured to provide rotational position information of a motor 11048, the shaft 2004, and/or the end effector 2006.

The motor segment 11102g comprises a motor 11048, such as, for example, a brushed DC motor. The motor 11048 is coupled to the primary processor 11106 through a plurality of H-bridge drivers 11142 and a motor controller 11143. The motor controller 11143 controls a first motor flag 11174a and a second motor flag 11174b to indicate the status and position of the motor 11048 to the primary processor 11106. The primary processor 11106 provides a pulse-width modulation (PWM) high signal 11176a, a PWM low signal 11176b, a direction signal 11178, a synchronize signal 11180, and a motor reset signal 11182 to the motor controller 11143 through a buffer 11184. The power segment 11102h is configured to provide a segment voltage to each of the circuit segments 11102a-11102g.

In one embodiment, the safety processor 11104 is configured to implement a watchdog function with respect to one or more circuit segments 11102c-11102h, such as, for example, the motor segment 11102g. In this regards, the safety processor 11104 employs the watchdog function to detect and recover from malfunctions of the primary processor 10006. During normal operation, the safety processor 11104 monitors for hardware faults or program errors of the primary processor 11104 and to initiate corrective action or actions. The corrective actions may include placing the primary processor 10006 in a safe state and restoring normal system operation. In one embodiment, the safety processor 11104 is coupled to at least a first sensor. The first sensor measures a first property of the surgical instrument 2000. In some embodiments, the safety processor 11104 is configured to compare the measured property of the surgical instrument 2000 to a predetermined value. For example, in one embodiment, a motor sensor 11140a is coupled to the safety processor 11104. The motor sensor 11140a provides motor speed and position information to the safety processor 11104. The safety processor 11104 monitors the motor sensor 11140a and compares the value to a maximum speed and/or position value and prevents operation of the motor 11048 above the predetermined values. In some embodiments, the predetermined values are calculated based on real-time speed and/or position of the motor 11048, calculated from values supplied by a second motor sensor 11140b in communication with the primary processor 11106, and/or provided to the safety processor 11104 from, for example, a memory module coupled to the safety processor 11104.

In some embodiments, a second sensor is coupled to the primary processor 11106. The second sensor is configured to measure the first physical property. The safety processor 11104 and the primary processor 11106 are configured to provide a signal indicative of the value of the first sensor and the second sensor respectively. When either the safety processor 11104 or the primary processor 11106 indicates a value outside of an acceptable range, the segmented circuit 11100 prevents operation of at least one of the circuit segments 11102c-11102h, such as, for example, the motor segment 11102g. For example, in the embodiment illustrated in FIGS. 73A and 73B, the safety processor 11104 is coupled to a first motor position sensor 11140a and the primary processor 11106 is coupled to a second motor position sensor 11140b. The motor position sensors 11140a, 11140b may comprise any suitable motor position sensor, such as, for example, a magnetic angle rotary input comprising a sine and cosine output. The motor position sensors 11140a, 11140b provide respective signals to the safety processor 11104 and the primary processor 11106 indicative of the position of the motor 11048.

The safety processor 11104 and the primary processor 11106 generate an activation signal when the values of the first motor sensor 11140a and the second motor sensor 11140b are within a predetermined range. When either the primary processor 11106 or the safety processor 11104 to detect a value outside of the predetermined range, the activation signal is terminated and operation of at least one circuit segment 11102c-11102h, such as, for example, the motor segment 11102g, is interrupted and/or prevented. For example, in some embodiments, the activation signal from the primary processor 11106 and the activation signal from the safety processor 11104 are coupled to an AND gate. The AND gate is coupled to a motor power switch 11120. The AND gate maintains the motor power switch 11120 in a closed, or on, position when the activation signal from both the safety processor 11104 and the primary processor 11106 are high, indicating a value of the motor sensors 11140a, 11140b within the predetermined range. When either of the motor sensors 11140a, 11140b detect a value outside of the predetermined range, the activation signal from that motor sensor 11140a, 11140b is set low, and the output of the AND gate is set low, opening the motor power switch 11120. In some embodiments, the value of the first sensor 11140a and the second sensor 11140b is compared, for example, by the safety processor 11104 and/or the primary processor 11106. When the values of the first sensor and the second sensor are different, the safety processor 11104 and/or the primary processor 11106 may prevent operation of the motor segment 11102g.

In some embodiments, the safety processor 11104 receives a signal indicative of the value of the second sensor 11140b and compares the second sensor value to the first sensor value. For example, in one embodiment, the safety processor 11104 is coupled directly to a first motor sensor 11140a. A second motor sensor 11140b is coupled to a primary processor 11106, which provides the second motor sensor 11140b value to the safety processor 11104, and/or coupled directly to the safety processor 11104. The safety processor 11104 compares the value of the first motor sensor 11140 to the value of the second motor sensor 11140b. When the safety processor 11104 detects a mismatch between the first motor sensor 11140a and the second motor sensor 11140b, the safety processor 11104 may interrupt operation of the motor segment 11102g, for example, by cutting power to the motor segment 11102g.

In some embodiments, the safety processor 11104 and/or the primary processor 11106 is coupled to a first sensor 11140a configured to measure a first property of a surgical instrument and a second sensor 11140b configured to measure a second property of the surgical instrument. The first property and the second property comprise a predetermined relationship when the surgical instrument is operating normally. The safety processor 11104 monitors the first property and the second property. When a value of the first property and/or the second property inconsistent with the predetermined relationship is detected, a fault occurs. When a fault occurs, the safety processor 11104 takes at least one action, such as, for example, preventing operation of at least one of the circuit segments, executing a predetermined operation, and/or resetting the primary processor 11106. For example, the safety processor 11104 may open the motor power switch 11120 to cut power to the motor circuit segment 11102g when a fault is detected.

Figure 74:
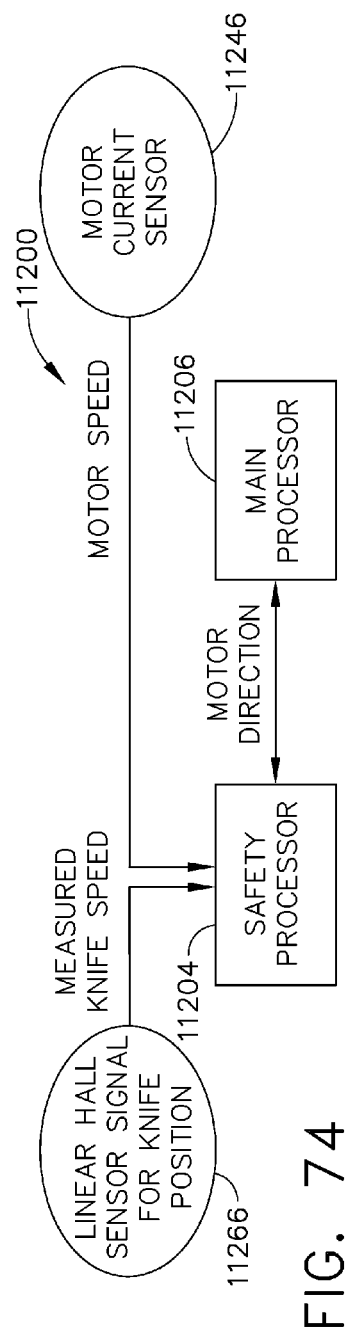
FIG. 74 illustrates a block diagram of one embodiment of a segmented circuit comprising a safety processor configured to monitor and compare a first property and a second property of a surgical instrument.

FIG. 74 illustrates a block diagram of one embodiment of a segmented circuit 11200 comprising a safety processor 11204 configured to monitor and compare a first property and a second property of a surgical instrument, such as, for example, the surgical instrument 2000 illustrated in FIGS. 1-3. The safety processor 11204 is coupled to a first sensor 11246 and a second sensor 11266. The first sensor 11246 is configured to monitor a first physical property of the surgical instrument 2000. The second sensor 11266 is configured to monitor a second physical property of the surgical instrument 2000. The first and second properties comprise a predetermined relationship when the surgical instrument 2000 is operating normally. For example, in one embodiment, the first sensor 11246 comprises a motor current sensor configured to monitor the current draw of a motor from a power source. The motor current draw may be indicative of the speed of the motor. The second sensor comprises a linear hall sensor configured to monitor the position of a cutting member within an end effector, for example, an end effector 2006 coupled to the surgical instrument 2000. The position of the cutting member is used to calculate a cutting member speed within the end effector 2006. The cutting member speed has a predetermined relationship with the speed of the motor when the surgical instrument 2000 is operating normally.

The safety processor 11204 provides a signal to the main processor 11206 indicating that the first sensor 11246 and the second sensor 11266 are producing values consistent with the predetermined relationship. When the safety processor 11204 detects a value of the first sensor 11246 and/or the second sensor 11266 inconsistent with the predetermined relationship, the safety processor 11206 indicates an unsafe condition to the primary processor 11206. The primary processor 11206 interrupts and/or prevents operation of at least one circuit segment. In some embodiments, the safety processor 11204 is coupled directly to a switch configured to control operation of one or more circuit segments. For example, with reference to FIGS. 73A and 73B, in one embodiment, the safety processor 11104 is coupled directly to a motor power switch 11120. The safety processor 11104 opens the motor power switch 11120 to prevent operation of the motor segment 11102g when a fault is detected.

Referring back to FIGS. 73A and 73B, in one embodiment, the safety processor 11104 is configured to execute an independent control algorithm. In operation, the safety processor 11104 monitors the segmented circuit 11100 and is configured to control and/or override signals from other circuit components, such as, for example, the primary processor 11106, independently. The safety processor 11104 may execute a preprogrammed algorithm and/or may be updated or programmed on the fly during operation based on one or more actions and/or positions of the surgical instrument 2000. For example, in one embodiment, the safety processor 11104 is reprogrammed with new parameters and/or safety algorithms each time a new shaft and/or end effector is coupled to the surgical instrument 2000. In some embodiments, one or more safety values stored by the safety processor 11104 are duplicated by the primary processor 11106. Two-way error detection is performed to ensure values and/or parameters stored by either of the processors 11104, 11106 are correct.

In some embodiments, the safety processor 11104 and the primary processor 11106 implement a redundant safety check. The safety processor 11104 and the primary processor 11106 provide periodic signals indicating normal operation. For example, during operation, the safety processor 11104 may indicate to the primary processor 11106 that the safety processor 11104 is executing code and operating normally. The primary processor 11106 may, likewise, indicate to the safety processor 11104 that the primary processor 11106 is executing code and operating normally. In some embodiments, communication between the safety processor 11104 and the primary processor 11106 occurs at a predetermined interval. The predetermined interval may be constant or may be variable based on the circuit state and/or operation of the surgical instrument 2000.

Figure 75:
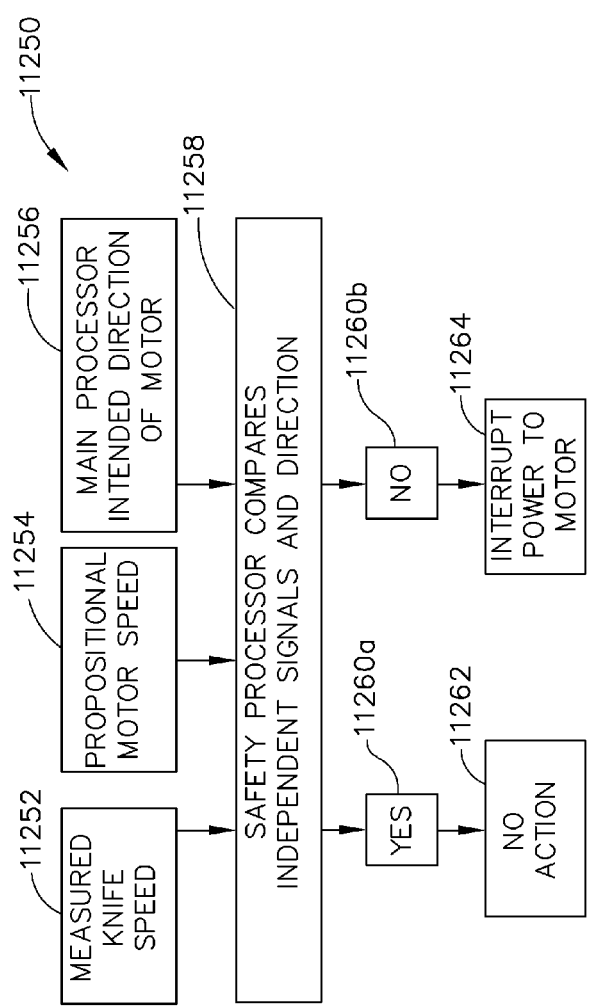
FIG. 75 illustrates a block diagram illustrating a safety process configured to be implemented by a safety processor.

FIG. 75 is a block diagram illustrating a safety process 11250 configured to be implemented by a safety processor, such as, for example, the safety process 11104 illustrated in FIGS. 73A and 73B. In one embodiment, values corresponding to a plurality of properties of a surgical instrument 2000 are provided to the safety processor 11104. The plurality of properties is monitored by a plurality of independent sensors and/or systems. For example, in the illustrated embodiment, a measured cutting member speed 11252, a propositional motor speed 11254, and an intended direction of motor signal 11256 are provided to a safety processor 11104. The cutting member speed 11252 and the propositional motor speed 11254 may be provided by independent sensors, such as, for example, a linear hall sensor and a current sensor respectively. The intended direction of motor signal 11256 may be provided by a primary processor, for example, the primary processor 11106 illustrated in FIGS. 73A and 73B. The safety processor 11104 compares 11258 the plurality of properties and determines when the properties are consistent with a predetermined relationship. When the plurality of properties comprises values consistent with the predetermined relationship 11260a, no action is taken 11262. When the plurality of properties comprises values inconsistent with the predetermined relationship 11260b, the safety processor 11104 executes one or more actions, such as, for example, blocking a function, executing a function, and/or resetting a processor. For example, in the process 11250 illustrated in FIG. 75, the safety processor 11104 interrupts operation of one or more circuit segments, such as, for example, by interrupting power 11264 to a motor segment.

Figure 76:
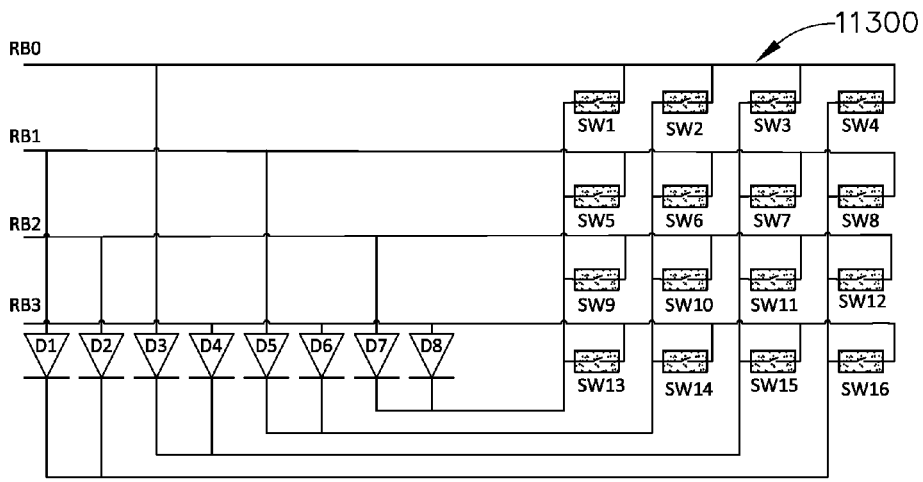
FIG. 76 illustrates one embodiment of a four by four switch bank comprising four input/output pins.

Referring back to FIGS. 73A and 73B, the segmented circuit 11100 comprises a plurality of switches 11156-11170 configured to control one or more operations of the surgical instrument 2000. For example, in the illustrated embodiment, the segmented circuit 11100 comprises a clamp release switch 11168, a firing trigger 11166, and a plurality of switches 11158a-11164b configured to control articulation of a shaft 2004 and/or end effector 2006 coupled to the surgical instrument 2000. The clamp release switch 11168, the fire trigger 11166, and the plurality of articulation switches 11158a-11164b may comprise analog and/or digital switches. In particular, switch 11156 indicates the mechanical switch lifter down position, switches 11158a, 11158b indicate articulate left (1) and (2), switch 11160a, 1160b indicate articulate right (1) and (2), switches 11162a, 11162b indicate articulate center (1) and (2), and switches 11164a, 11164b indicate reverse/left and reverse/right. For example, FIG. 76 illustrates one embodiment of a switch bank 11300 comprising a plurality of switches SW1-SW16 configured to control one or more operations of a surgical instrument. The switch bank 11300 may be coupled to a primary processor, such as, for example, the primary processor 11106. In some embodiments, one or more diodes D1-D8 are coupled to the plurality of switches SW1-SW16. Any suitable mechanical, electromechanical, or solid state switches may be employed to implement the plurality of switches 11156-11170, in any combination. For example, the switches 11156-11170 may limit switches operated by the motion of components associated with the surgical instrument 2000 or the presence of an object. Such switches may be employed to control various functions associated with the surgical instrument 2000. A limit switch is an electromechanical device that consists of an actuator mechanically linked to a set of contacts. When an object comes into contact with the actuator, the device operates the contacts to make or break an electrical connection. Limit switches are used in a variety of applications and environments because of their ruggedness, ease of installation, and reliability of operation. They can determine the presence or absence, passing, positioning, and end of travel of an object. In other implementations, the switches 11156-11170 may be solid state switches that operate under the influence of a magnetic field such as Hall-effect devices, magneto-resistive (MR) devices, giant magneto-resistive (GMR) devices, magnetometers, among others. In other implementations, the switches 11156-11170 may be solid state switches that operate under the influence of light, such as optical sensors, infrared sensors, ultraviolet sensors, among others. Still, the switches 11156-11170 may be solid state devices such as transistors (e.g., FET, Junction-FET, metal-oxide semiconductor-FET (MOSFET), bipolar, and the like). Other switches may include wireless switches, ultrasonic switches, accelerometers, inertial sensors, among others.

Figure 77:
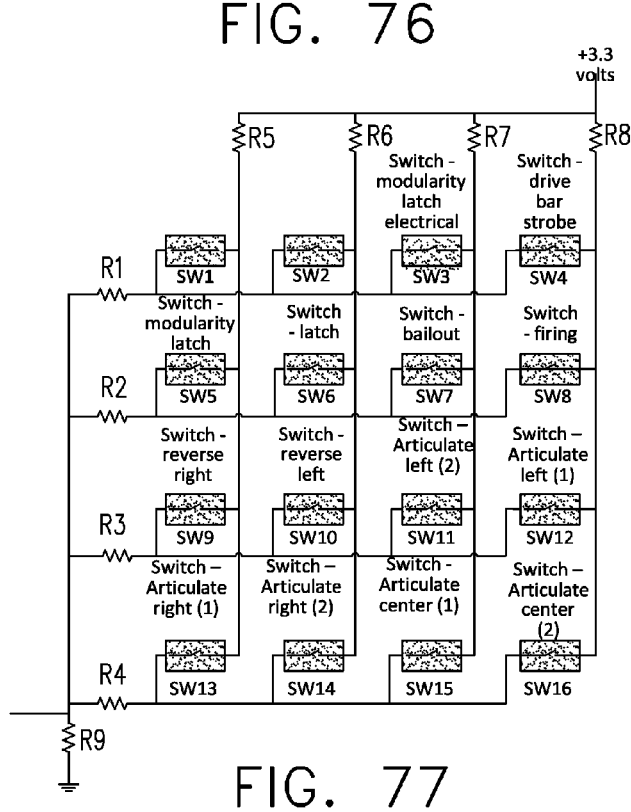
FIG. 77 illustrates one embodiment of a four by four bank circuit comprising one input/output pin.

FIG. 77 illustrates one embodiment of a switch bank 11350 comprising a plurality of switches. In various embodiments, one or more switches are configured to control one or more operations of a surgical instrument, such as, for example, the surgical instrument 2000 illustrated in FIGS. 69-71B. A plurality of articulation switches SW1-SW16 is configured to control articulation of a shaft 2004 and/or an end effector 2006 coupled to the surgical instrument 2000. A firing trigger 11366 is configured to fire the surgical instrument 2000, for example, to deploy a plurality of staples, translate a cutting member within the end effector 2006, and/or deliver electrosurgical energy to the end effector 2006. In some embodiments, the switch bank 11350 comprises one or more safety switches configured to prevent operation of the surgical instrument 2000. For example, a bailout switch 11356 is coupled to a bailout door and prevents operation of the surgical instrument 2000 when the bailout door is in an open position.

Figure 78A:
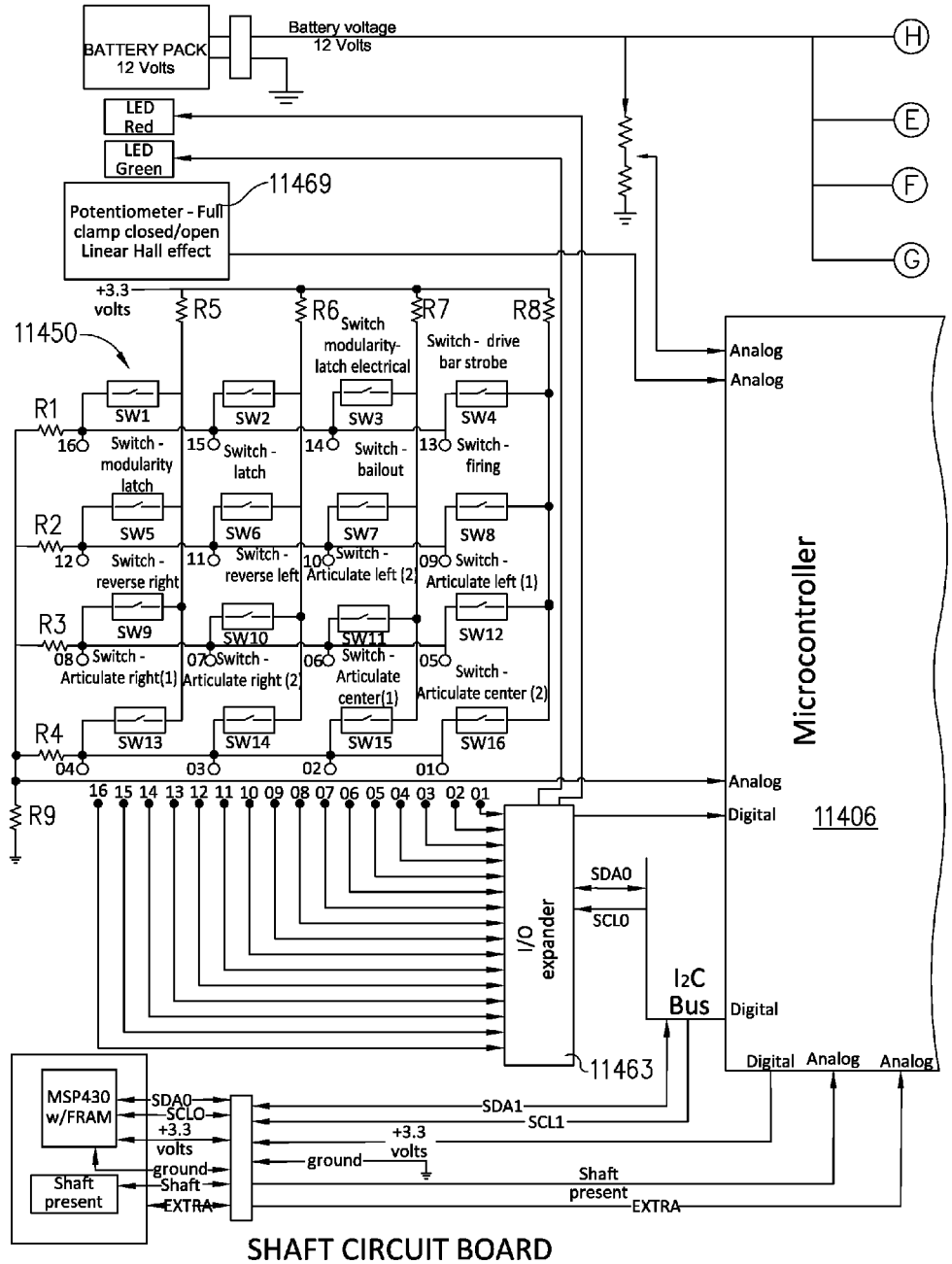
FIGS. 78A and 78B, illustrates one embodiment of a segmented circuit comprising a four by four switch bank coupled to a primary processor.
Figure 78B:
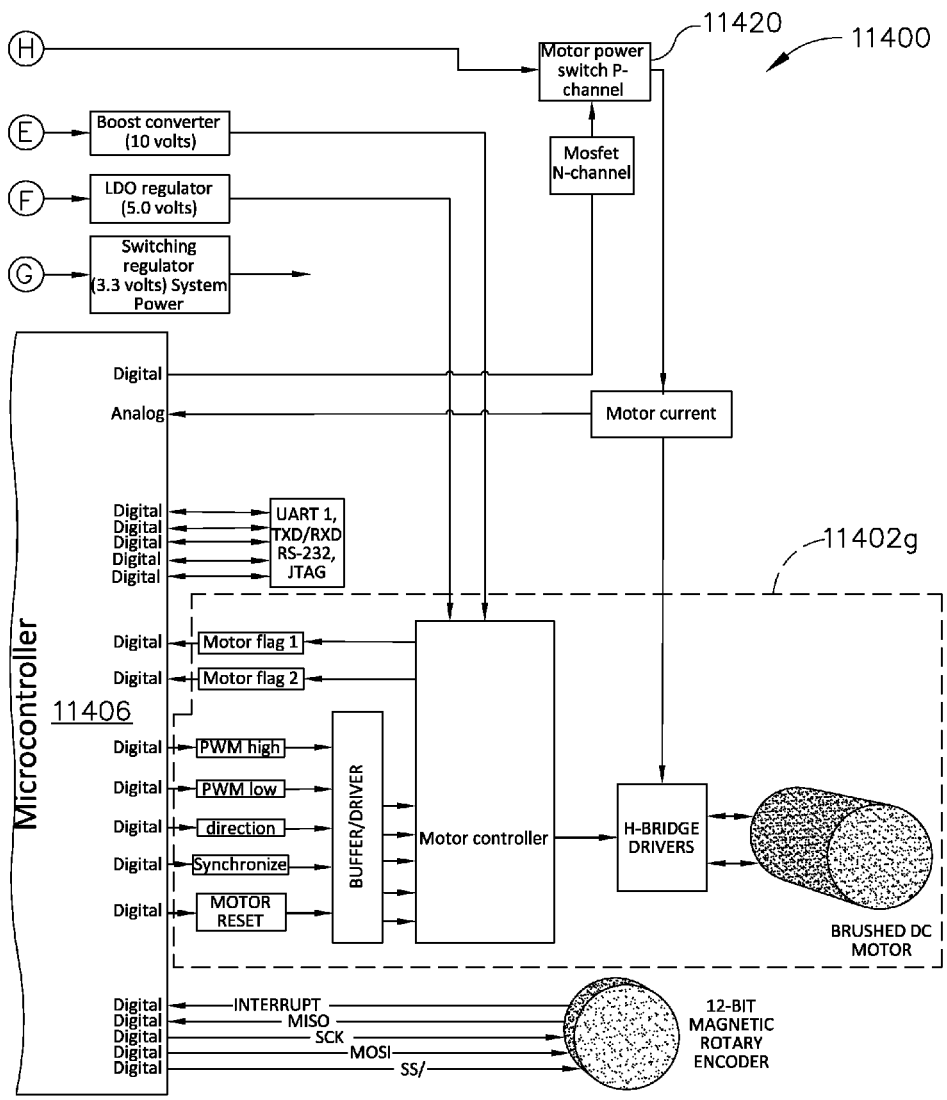

FIGS. 78A and 78B illustrate one embodiment of a segmented circuit 11400 comprising a switch bank 11450 coupled to the primary processor 11406. The switch bank 11450 is similar to the switch bank 11350 illustrated in FIG.

77. The switch bank 11450 comprises a plurality of switches SW1-SW16 configured to control one or more operations of a surgical instrument, such as, for example, the surgical instrument 2000 illustrated in FIGS. 69-71B. The switch bank 11450 is coupled to an analog input of the primary processor 11406. Each of the switches within the switch bank 11450 is further coupled to an input/output expander 11463 coupled to a digital input of the primary processor 11406. The primary processor 11406 receives input from the switch bank 11450 and controls one or more additional segments of the segmented circuit 11400, such as, for example, a motor segment 11402g in response to manipulation of one or more switches of the switch bank 11450.

In some embodiments, a potentiometer 11469 is coupled to the primary processor 11406 to provide a signal indicative of a clamp position of an end effector 2006 coupled to the surgical instrument 2000. The potentiometer 11469 may replace and/or supplement a safety processor (not shown) by providing a signal indicative of a clamp open/closed position used by the primary processor 11106 to control operation of one or more circuit segments, such as, for example, the motor segment 11102g. For example, when the potentiometer 11469 indicates that the end effector is in a fully clamped position and/or a fully open position, the primary processor 11406 may open the motor power switch 11420 and prevent further operation of the motor segment 11402g in a specific direction. In some embodiments, the primary processor 11406 controls the current delivered to the motor segment 11402g in response to a signal received from the potentiometer 11469. For example, the primary processor 11406 may limit the energy that can be delivered to the motor segment 11402g when the potentiometer 11469 indicates that the end effector is closed beyond a predetermined position.

Referring back to FIGS. 73A and 73B, the segmented circuit 11100 comprises an acceleration segment 11102c. The acceleration segment comprises an accelerometer 11122. The accelerometer 11122 may be coupled to the safety processor 11104 and/or the primary processor 11106. The accelerometer 11122 is configured to monitor movement of the surgical instrument 2000. The accelerometer 11122 is configured to generate one or more signals indicative of movement in one or more directions. For example, in some embodiments, the accelerometer 11122 is configured to monitor movement of the surgical instrument 2000 in three directions. In other embodiments, the acceleration segment 11102c comprises a plurality of accelerometers 11122, each configured to monitor movement in a signal direction.

In some embodiments, the accelerometer 11122 is configured to initiate a transition to and/or from a sleep mode, e.g., between sleep-mode and wake-up mode and vice versa. Sleep mode may comprise a low-power mode in which one or more of the circuit segments 11102a-11102g are deactivated or placed in a low-power state. For example, in one embodiment, the accelerometer 11122 remains active in sleep mode and the safety processor 11104 is placed into a low-power mode in which the safety processor 11104 monitors the accelerometer 11122, but otherwise does not perform any functions. The remaining circuit segments 11102b-11102g are powered off. In various embodiments, the primary processor 11104 and/or the safety processor 11106 are configured to monitor the accelerometer 11122 and transition the segmented circuit 11100 to sleep mode, for example, when no movement is detected within a predetermined time period. Although described in connection with the safety processor 11104 monitoring the accelerometer 11122, the sleep-mode/wake-up mode may be implemented by the safety processor 11104 monitoring any of the sensors, switches, or other indicators associated with the surgical instrument 2000 as described herein. For example, the safety processor 11104 may monitor an inertial sensor, or a one or more switches.

In some embodiments, the segmented circuit 11100 transitions to sleep mode after a predetermined period of inactivity. A timer is in signal communication with the safety processor 11104 and/or the primary processor 11106. The timer may be integral with the safety processor 11104, the primary processor 11106, and/or may be a separate circuit component. The timer is configured to monitor a time period since a last movement of the surgical instrument 2000 was detected by the accelerometer 11122. When the counter exceeds a predetermined threshold, the safety processor 11104 and/or the primary processor 11106 transitions the segmented circuit 11100 into sleep mode. In some embodiments, the timer is reset each time the accelerometer 11122 detects movement.

In some embodiments, all circuit segments except the accelerometer 11122, or other designated sensors and/or switches, and the safety processor 11104 are deactivated when in sleep mode. The safety processor 11104 monitors the accelerometer 11122, or other designated sensors and/or switches. When the accelerometer 11122 indicates movement of the surgical instrument 2000, the safety processor 11104 initiates a transition from sleep mode to operational mode. In operational mode, all of the circuit segments 11102a-11102h are fully energized and the surgical instrument 2000 is ready for use. In some embodiments, the safety processor 11104 transitions the segmented circuit 11100 to the operational mode by providing a signal to the primary processor 11106 to transition the primary processor 11106 from sleep mode to a full power mode. The primary processor 11106, then transitions each of the remaining circuit segments 11102d-11102h to operational mode.

The transition to and/or from sleep mode may comprise a plurality of stages. For example, in one embodiment, the segmented circuit 11100 transitions from the operational mode to the sleep mode in four stages. The first stage is initiated after the accelerometer 11122 has not detected movement of the surgical instrument for a first predetermined time period. After the first predetermined time period the segmented circuit 11100 dims a backlight of the display segment 11102d. When no movement is detected within a second predetermined period, the safety processor 11104 transitions to a second stage, in which the backlight of the display segment 11102d is turned off. When no movement is detected within a third predetermined time period, the safety processor 11104 transitions to a third stage, in which the polling rate of the accelerometer 11122 is reduced. When no movement is detected within a fourth predetermined time period, the display segment 11102d is deactivated and the segmented circuit 11100 enters sleep mode. In sleep mode, all of the circuit segments except the accelerometer 11122 and the safety processor 11104 are deactivated. The safety processor 11104 enters a low-power mode in which the safety processor 11104 only polls the accelerometer 11122. The safety processor 11104 monitors the accelerometer 11122 until the accelerometer 11122 detects movement, at which point the safety processor 11104 transitions the segmented circuit 11100 from sleep mode to the operational mode.

In some embodiments, the safety processor 11104 transitions the segmented circuit 11100 to the operational mode only when the accelerometer 11122 detects movement of the surgical instrument 2000 above a predetermined threshold. By responding only to movement above a predetermined threshold, the safety processor 11104 prevents inadvertent transition of the segmented circuit 11100 to operational mode when the surgical instrument 2000 is bumped or moved while stored. In some embodiments, the accelerometer 11122 is configured to monitor movement in a plurality of directions. For example, the accelerometer 11122 may be configured to detect movement in a first direction and a second direction. The safety processor 11104 monitors the accelerometer 11122 and transitions the segmented circuit 11100 from sleep mode to operational mode when movement above a predetermined threshold is detected in both the first direction and the second direction. By requiring movement above a predetermined threshold in at least two directions, the safety processor 11104 is configured to prevent inadvertent transition of the segmented circuit 11100 from sleep mode due to incidental movement during storage.

In some embodiments, the accelerometer 11122 is configured to detect movement in a first direction, a second direction, and a third direction. The safety processor 11104 monitors the accelerometer 11122 and is configured to transition the segmented circuit 11100 from sleep mode only when the accelerometer 11122 detects oscillating movement in each of the first direction, second direction, and third direction. In some embodiments, oscillating movement in each of a first direction, a second direction, and a third direction correspond to movement of the surgical instrument 2000 by an operator and therefore transition to the operational mode is desirable when the accelerometer 11122 detects oscillating movement in three directions.

In some embodiments, as the time since the last movement detected increases, the predetermined threshold of movement required to transition the segmented circuit 11100 from sleep mode also increases. For example, in some embodiments, the timer continues to operate during sleep mode. As the timer count increases, the safety processor 11104 increases the predetermined threshold of movement required to transition the segmented circuit 11100 to operational mode. The safety processor 11104 may increase the predetermined threshold to an upper limit. For example, in some embodiments, the safety processor 11104 transitions the segmented circuit 11100 to sleep mode and resets the timer. The predetermined threshold of movement is initially set to a low value, requiring only a minor movement of the surgical instrument 2000 to transition the segmented circuit 11100 from sleep mode. As the time since the transition to sleep mode, as measured by the timer, increases, the safety processor 11104 increases the predetermined threshold of movement. At a time T, the safety processor 11104 has increased the predetermined threshold to an upper limit. For all times T+, the predetermined threshold maintains a constant value of the upper limit.

In some embodiments, one or more additional and/or alternative sensors are used to transition the segmented circuit 11100 between sleep mode and operational mode. For example, in one embodiment, a touch sensor is located on the surgical instrument 2000. The touch sensor is coupled to the safety processor 11104 and/or the primary processor 11106. The touch sensor is configured to detect user contact with the surgical instrument 2000. For example, the touch sensor may be located on the handle of the surgical instrument 2000 to detect when an operator picks up the surgical instrument 2000. The safety processor 11104 transitions the segmented circuit 11100 to sleep mode after a predetermined period has passed without the accelerometer 11122 detecting movement. The safety processor 11104 monitors the touch sensor and transitions the segmented circuit 11100 to operational mode when the touch sensor detects user contact with the surgical instrument 2000. The touch sensor may comprise, for example, a capacitive touch sensor, a temperature sensor, and/or any other suitable touch sensor. In some embodiments, the touch sensor and the accelerometer 11122 may be used to transition the device between sleep mode and operation mode. For example, the safety processor 11104 may only transition the device to sleep mode when the accelerometer 11122 has not detected movement within a predetermined period and the touch sensor does not indicate a user is in contact with the surgical instrument 2000. Those skilled in the art will recognize that one or more additional sensors may be used to transition the segmented circuit 11100 between sleep mode and operational mode. In some embodiments, the touch sensor is only monitored by the safety processor 11104 when the segmented circuit 11100 is in sleep mode.

In some embodiments, the safety processor 11104 is configured to transition the segmented circuit 11100 from sleep mode to the operational mode when one or more handle controls are actuated. After transitioning to sleep mode, such as, for example, after the accelerometer 11122 has not detected movement for a predetermined period, the safety processor 11104 monitors one or more handle controls, such as, for example, the plurality of articulation switches 11158a-11164b. In other embodiments, the one or more handle controls comprise, for example, a clamp control 11166, a release button 11168, and/or any other suitable handle control. An operator of the surgical instrument 2000 may actuate one or more of the handle controls to transition the segmented circuit 11100 to operational mode. When the safety processor 11104 detects the actuation of a handle control, the safety processor 11104 initiates the transition of the segmented circuit 11100 to operational mode. Because the primary processor 11106 is in not active when the handle control is actuated, the operator can actuate the handle control without causing a corresponding action of the surgical instrument 2000.

Figure 84:
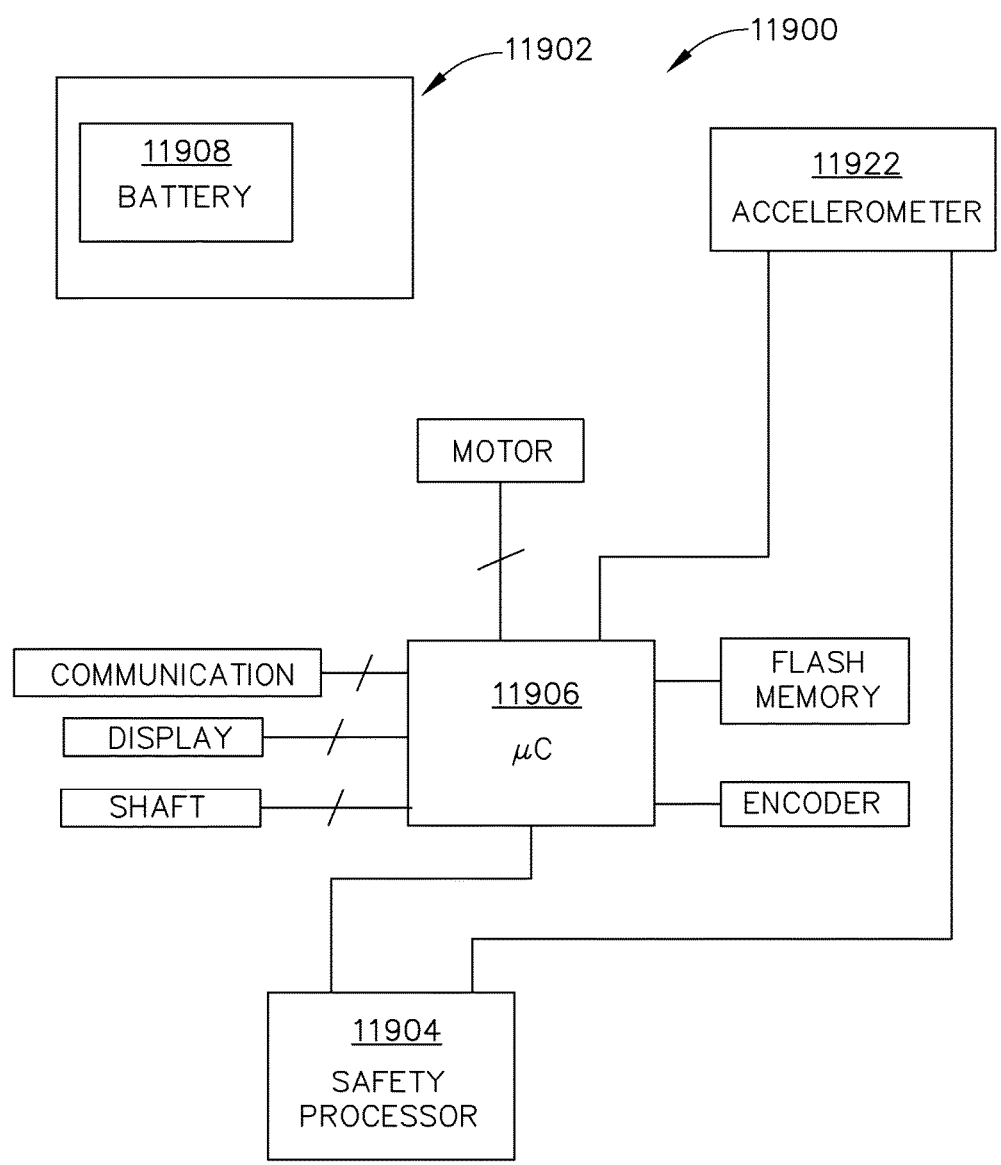
FIG. 84 illustrates one embodiment of a segmented circuit comprising an accelerometer.

FIG. 84 illustrates one embodiment of a segmented circuit 11900 comprising an accelerometer 11922 configured to monitor movement of a surgical instrument, such as, for example, the surgical instrument 2000 illustrated in FIGS. 69-71B. A power segment 11902 provides power from a battery 11908 to one or more circuit segments, such as, for example, the accelerometer 11922. The accelerometer 11922 is coupled to a processor 11906. The accelerometer 11922 is configured to monitor movement the surgical instrument 2000. The accelerometer 11922 is configured to generate one or more signals indicative of movement in one or more directions. For example, in some embodiments, the accelerometer 11922 is configured to monitor movement of the surgical instrument 2000 in three directions.

In certain instances, the processor 11906 may be an LM 4F230H5QR, available from Texas Instruments, for example. The processor 11906 is configured to monitor the accelerometer 11922 and transition the segmented circuit 11900 to sleep mode, for example, when no movement is detected within a predetermined time period. In some embodiments, the segmented circuit 11900 transitions to sleep mode after a predetermined period of inactivity. For example, a safety processor 11904 may transitions the segmented circuit 11900 to sleep mode after a predetermined period has passed without the accelerometer 11922 detecting movement. In certain instances, the accelerometer 11922 may be an LIS331DLM, available from STMicroelectronics, for example. A timer is in signal communication with the processor 11906. The timer may be integral with the processor 11906 and/or may be a separate circuit component. The timer is configured to count time since a last movement of the surgical instrument 2000 was detected by the accelerometer 11922. When the counter exceeds a predetermined threshold, the processor 11906 transitions the segmented circuit 11900 into sleep mode. In some embodiments, the timer is reset each time the accelerometer 11922 detects movement.

In some embodiments, the accelerometer 11922 is configured to detect an impact event. For example, when a surgical instrument 2000 is dropped, the accelerometer 11922 will detect acceleration due to gravity in a first direction and then a change in acceleration in a second direction (caused by impact with a floor and/or other surface). As another example, when the surgical instrument 2000 impacts a wall, the accelerometer 11922 will detect a spike in acceleration in one or more directions. When the accelerometer 11922 detects an impact event, the processor 11906 may prevent operation of the surgical instrument 2000, as impact events can loosen mechanical and/or electrical components. In some embodiments, only impacts above a predetermined threshold prevent operation. In other embodiments, all impacts are monitored and cumulative impacts above a predetermined threshold may prevent operation of the surgical instrument 2000.

With reference back to FIGS. 73A and 73B, in one embodiment, the segmented circuit 11100 comprises a power segment 11102*h*. The power segment 11102*h* is configured to provide a segment voltage to each of the circuit segments 11102*a*-11102*g*. The power segment 11102*h* comprises a battery 11108. The battery 11108 is configured to provide a predetermined voltage, such as, for example, 12 volts through battery connector 11110. One or more power converters 11114*a*, 11114*b*, 11116 are coupled to the battery 11108 to provide a specific voltage. For example, in the illustrated embodiments, the power segment 11102*h* comprises an axillary switching converter 11114*a*, a switching converter 11114*b*, and a low-drop out (LDO) converter 11116. The switch converters 11114*a*, 11114*b* are configured to provide 3.3 volts to one or more circuit components. The LDO converter 11116 is configured to provide 5.0 volts to one or more circuit components. In some embodiments, the power segment 11102*h* comprises a boost converter 11118. A transistor switch (e.g., N-Channel MOSFET) 11115 is coupled to the power converters 11114*b*, 11116. The boost converter 11118 is configured to provide an increased voltage above the voltage provided by the battery 11108, such as, for example, 13 volts. The boost converter 11118 may comprise, for example, a capacitor, an inductor, a battery, a rechargeable battery, and/or any other suitable boost converter for providing an increased voltage. The boost converter 11118 provides a boosted voltage to prevent brownouts and/or low-power conditions of one or more circuit segments 11102*a*-11102*g* during power-intensive operations of the surgical instrument 2000. The embodiments, however, are not limited to the voltage range(s) described in the context of this specification.

Figure 79:
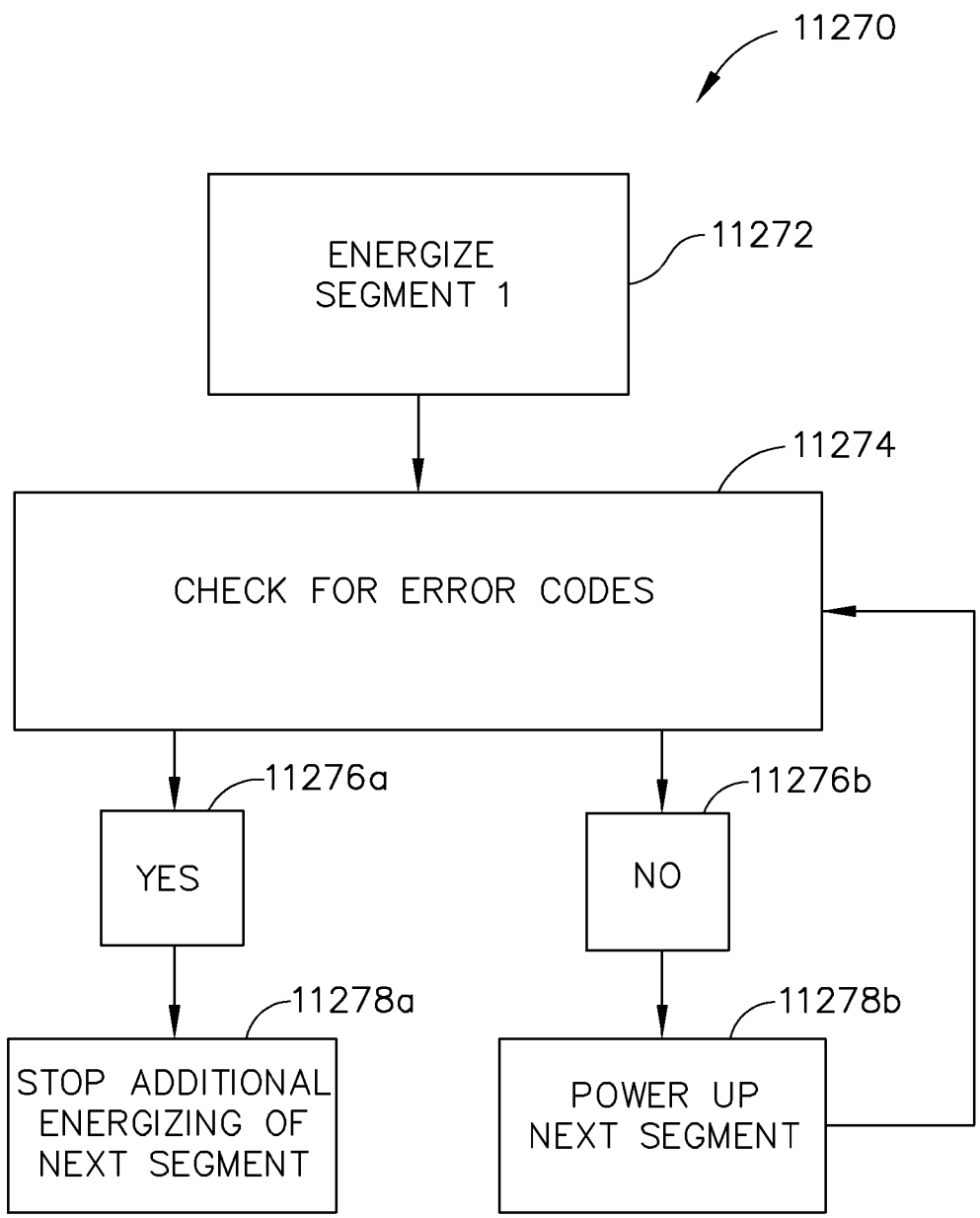
FIG. 79 illustrates one embodiment of a process for sequentially energizing a segmented circuit.

In some embodiments, the segmented circuit 11100 is configured for sequential start-up. An error check is performed by each circuit segment 11102*a*-11102*g* prior to energizing the next sequential circuit segment 11102*a*-11102*g*. FIG. 79 illustrates one embodiment of a process for sequentially energizing a segmented circuit 11270, such as, for example, the segmented circuit 11100. When a battery 11108 is coupled to the segmented circuit 11100, the safety processor 11104 is energized 11272. The safety processor 11104 performs a self-error check 11274. When an error is detected 11276*a*, the safety processor stops energizing the segmented circuit 11100 and generates an error code 11278*a*. When no errors are detected 11276*b*, the safety processor 11104 initiates 11278*b* power-up of the primary processor 11106. The primary processor 11106 performs a self-error check. When no errors are detected, the primary processor 11106 begins sequential power-up of each of the remaining circuit segments 11278*b*. Each circuit segment is energized and error checked by the primary processor 11106. When no errors are detected, the next circuit segment is energized 11278*b*. When an error is detected, the safety processor 11104 and/or the primary process stops energizing the current segment and generates an error 11278*a*. The sequential start-up continues until all of the circuit segments 11102*a*-11102*g* have been energized. In some embodiments, the segmented circuit 11100 transitions from sleep mode following a similar sequential power-up process 11250.

Figure 80:
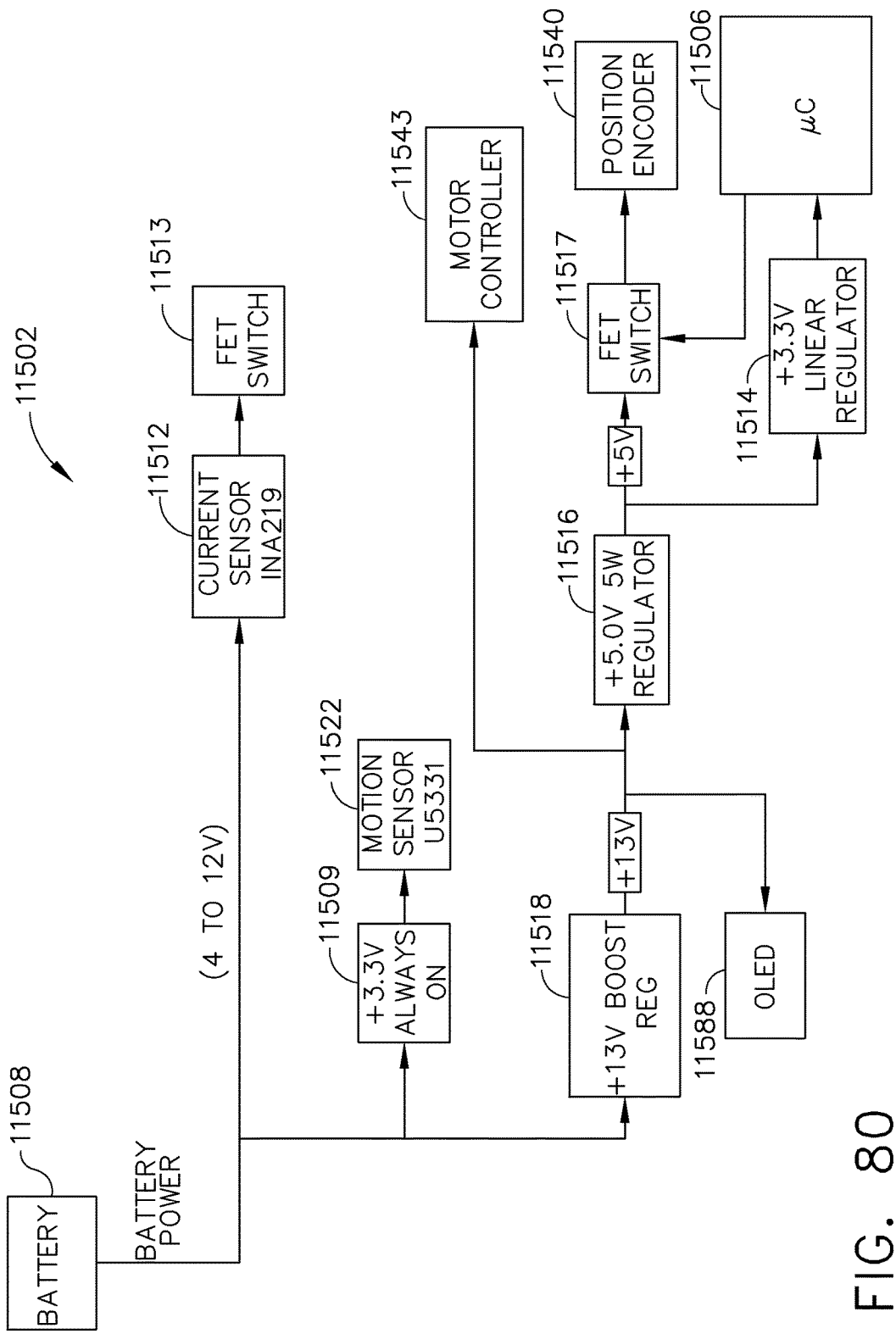
FIG. 80 illustrates one embodiment of a power segment comprising a plurality of daisy chained power converters.

FIG. 80 illustrates one embodiment of a power segment 11502 comprising a plurality of daisy chained power converters 11514, 11516, 11518. The power segment 11502 comprises a battery 11508. The battery 11508 is configured to provide a source voltage, such as, for example, 12V. A current sensor 11512 is coupled to the battery 11508 to monitor the current draw of a segmented circuit and/or one or more circuit segments. The current sensor 11512 is coupled to an FET switch 11513. The battery 11508 is coupled to one or more voltage converters 11509, 11514, 11516. An always on converter 11509 provides a constant voltage to one or more circuit components, such as, for example, a motion sensor 11522. The always on converter 11509 comprises, for example, a 3.3V converter. The always on converter 11509 may provide a constant voltage to additional circuit components, such as, for example, a safety processor (not shown). The battery 11508 is coupled to a boost converter 11518. The boost converter 11518 is configured to provide a boosted voltage above the voltage provided by the battery 11508. For example, in the illustrated embodiment, the battery 11508 provides a voltage of 12V. The boost converter 11518 is configured to boost the voltage to 13V. The boost converter 11518 is configured to maintain a minimum voltage during operation of a surgical instrument, for example, the surgical instrument 2000 illustrated in FIGS. 69-71B. Operation of a motor can result in the power provided to the primary processor 11506 dropping below a minimum threshold and creating a brownout or reset condition in the primary processor 11506. The boost converter 11518 ensures that sufficient power is available to the primary processor 11506 and/or other circuit components, such as the motor controller 11543, during operation of the surgical instrument 2000. In some embodiments, the boost converter 11518 is coupled directly one or more circuit components, such as, for example, an OLED display 11588.

The boost converter 11518 is coupled to a one or more step-down converters to provide voltages below the boosted voltage level. A first voltage converter 11516 is coupled to the boost converter 11518 and provides a first stepped-down voltage to one or more circuit components. In the illustrated embodiment, the first voltage converter 11516 provides a voltage of 5V. The first voltage converter 11516 is coupled to a rotary position encoder 11540. A FET switch 11517 is coupled between the first voltage converter 11516 and the rotary position encoder 11540. The FET switch 11517 is controlled by the processor 11506. The processor 11506 opens the FET switch 11517 to deactivate the position encoder 11540, for example, during power intensive operations. The first voltage converter 11516 is coupled to a second voltage converter 11514 configured to provide a second stepped-down voltage. The second stepped-down voltage comprises, for example, 3.3V. The second voltage converter 11514 is coupled to a processor 11506. In some embodiments, the boost converter 11518, the first voltage converter 11516, and the second voltage converter 11514 are coupled in a daisy chain configuration. The daisy chain configuration allows the use of smaller, more efficient converters for generating voltage levels below the boosted voltage level. The embodiments, however, are not limited to the particular voltage range(s) described in the context of this specification.

Figure 81:
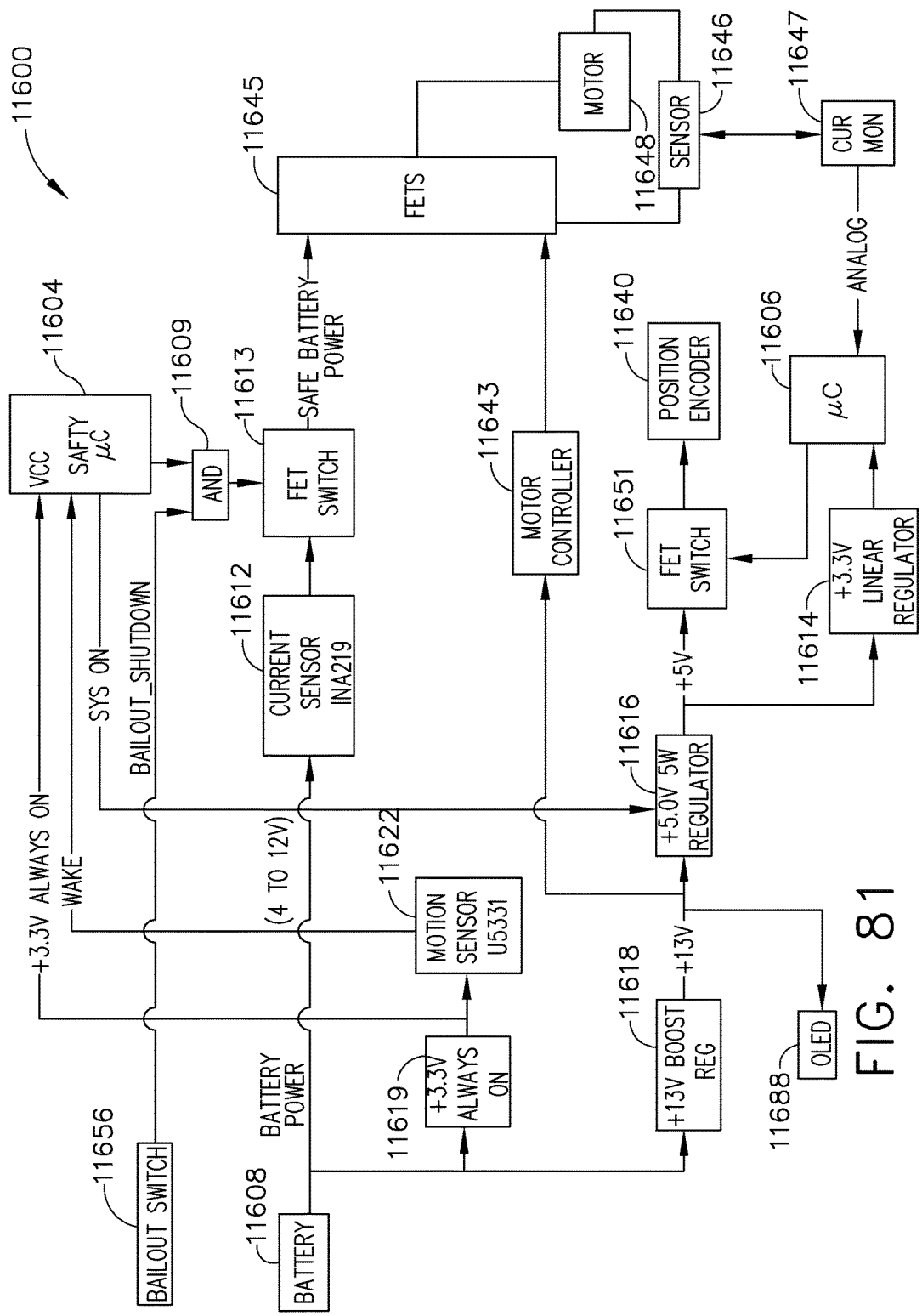
FIG. 81 illustrates one embodiment of a segmented circuit configured to maximize power available for critical and/or power intense functions.

FIG. 81 illustrates one embodiment of a segmented circuit 11600 configured to maximize power available for critical and/or power intense functions. The segmented circuit 11600 comprises a battery 11608. The battery 11608 is configured to provide a source voltage such as, for example, 12V. The source voltage is provided to a plurality of voltage converters 11609, 11618. An always-on voltage converter 11609 provides a constant voltage to one or more circuit components, for example, a motion sensor 11622 and a safety processor 11604. The always-on voltage converter 11609 is directly coupled to the battery 11608. The always-on converter 11609 provides a voltage of, for example, 3.3V. The embodiments, however, are not limited to the particular voltage range(s) described in the context of this specification.

The segmented circuit 11600 comprises a boost converter 11618. The boost converter 11618 provides a boosted voltage above the source voltage provided by the battery 11608, such as, for example, 13V. The boost converter 11618 provides a boosted voltage directly to one or more circuit components, such as, for example, an OLED display 11688 and a motor controller 11643. By coupling the OLED display 11688 directly to the boost converter 11618, the segmented circuit 11600 eliminates the need for a power converter dedicated to the OLED display 11688. The boost converter 11618 provides a boosted voltage to the motor controller 11643 and the motor 11648 during one or more power intensive operations of the motor 11648, such as, for example, a cutting operation. The boost converter 11618 is coupled to a step-down converter 11616. The step-down converter 11616 is configured to provide a voltage below the boosted voltage to one or more circuit components, such as, for example, 5V. The step-down converter 11616 is coupled to, for example, an FET switch 11651 and a position encoder 11640. The FET switch 11651 is coupled to the primary processor 11606. The primary processor 11606 opens the FET switch 11651 when transitioning the segmented circuit 11600 to sleep mode and/or during power intensive functions requiring additional voltage delivered to the motor 11648. Opening the FET switch 11651 deactivates the position encoder 11640 and eliminates the power draw of the position encoder 11640. The embodiments, however, are not limited to the particular voltage range(s) described in the context of this specification.

The step-down converter 11616 is coupled to a linear converter 11614. The linear converter 11614 is configured to provide a voltage of, for example, 3.3V. The linear converter 11614 is coupled to the primary processor 11606. The linear converter 11614 provides an operating voltage to the primary processor 11606. The linear converter 11614 may be coupled to one or more additional circuit components. The embodiments, however, are not limited to the particular voltage range(s) described in the context of this specification.

The segmented circuit 11600 comprises a bailout switch 11656. The bailout switch 11656 is coupled to a bailout door on the surgical instrument 2000. The bailout switch 11656 and the safety processor 11604 are coupled to an AND gate 11619. The AND gate 11619 provides an input to a FET switch 11613. When the bailout switch 11656 detects a bailout condition, the bailout switch 11656 provides a bailout shutdown signal to the AND gate 11619. When the safety processor 11604 detects an unsafe condition, such as, for example, due to a sensor mismatch, the safety processor 11604 provides a shutdown signal to the AND gate 11619. In some embodiments, both the bailout shutdown signal and the shutdown signal are high during normal operation and are low when a bailout condition or an unsafe condition is detected. When the output of the AND gate 11619 is low, the FET switch 11613 is opened and operation of the motor 11648 is prevented. In some embodiments, the safety processor 11604 utilizes the shutdown signal to transition the motor 11648 to an off state in sleep mode. A third input to the FET switch 11613 is provided by a current sensor 11612 coupled to the battery 11608. The current sensor 11612 monitors the current drawn by the circuit 11600 and opens the FET switch 11613 to shut-off power to the motor 11648 when an electrical current above a predetermined threshold is detected. The FET switch 11613 and the motor controller 11643 are coupled to a bank of FET switches 11645 configured to control operation of the motor 11648.

A motor current sensor 11646 is coupled in series with the motor 11648 to provide a motor current sensor reading to a current monitor 11647. The current monitor 11647 is coupled to the primary processor 11606. The current monitor 11647 provides a signal indicative of the current draw of the motor 11648. The primary processor 11606 may utilize the signal from the motor current 11647 to control operation of the motor, for example, to ensure the current draw of the motor 11648 is within an acceptable range, to compare the current draw of the motor 11648 to one or more other parameters of the circuit 11600 such as, for example, the position encoder 11640, and/or to determine one or more parameters of a treatment site. In some embodiments, the current monitor 11647 may be coupled to the safety processor 11604.

In some embodiments, actuation of one or more handle controls, such as, for example, a firing trigger, causes the primary processor 11606 to decrease power to one or more components while the handle control is actuated. For example, in one embodiment, a firing trigger controls a firing stroke of a cutting member. The cutting member is driven by the motor 11648. Actuation of the firing trigger results in forward operation of the motor 11648 and advancement of the cutting member. During firing, the primary processor 11606 closes the FET switch 11651 to remove power from the position encoder 11640. The deactivation of one or more circuit components allows higher power to be delivered to the motor 11648. When the firing trigger is released, full power is restored to the deactivated components, for example, by closing the FET switch 11651 and reactivating the position encoder 11640.

In some embodiments, the safety processor 11604 controls operation of the segmented circuit 11600. For example, the safety processor 11604 may initiate a sequential power-up of the segmented circuit 11600, transition of the segmented circuit 11600 to and from sleep mode, and/or may override one or more control signals from the primary processor 11606. For example, in the illustrated embodiment, the safety processor 11604 is coupled to the step-down converter 11616. The safety processor 11604 controls operation of the segmented circuit 11600 by activating or deactivating the step-down converter 11616 to provide power to the remainder of the segmented circuit 11600.

Figure 82:
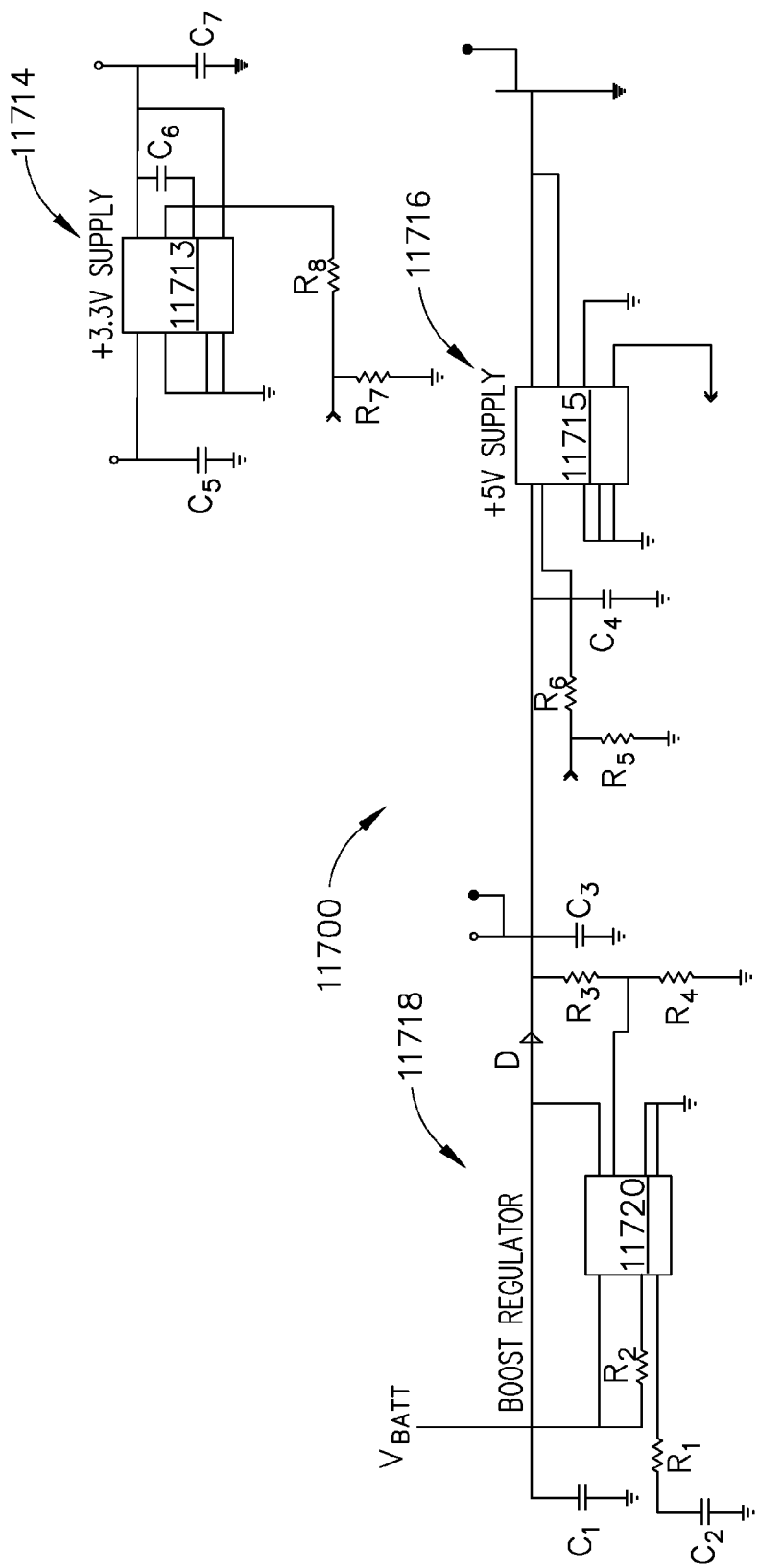
FIG. 82 illustrates one embodiment of a power system comprising a plurality of daisy chained power converters configured to be sequentially energized.

FIG. 82 illustrates one embodiment of a power system 11700 comprising a plurality of daisy chained power converters 11714, 11716, 11718 configured to be sequentially energized. The plurality of daisy chained power converters 11714, 11716, 11718 may be sequentially activated by, for example, a safety processor during initial power-up and/or transition from sleep mode. The safety processor may be powered by an independent power converter (not shown). For example, in one embodiment, when a battery voltage $V_{BATT}$ is coupled to the power system 11700 and/or an accelerometer detects movement in sleep mode, the safety processor initiates a sequential start-up of the daisy chained power converters 11714, 11716, 11718. The safety processor activates the 13V boost section 11718. The boost section 11718 is energized and performs a self-check. In some embodiments, the boost section 11718 comprises an integrated circuit 11720 configured to boost the source voltage and to perform a self check. A diode D prevents power-up of a 5V supply section 11716 until the boost section 11718 has completed a self-check and provided a signal to the diode D indicating that the boost section 11718 did not identify any errors. In some embodiments, this signal is provided by the safety processor. The embodiments, however, are not limited to the particular voltage range(s) described in the context of this specification.

The 5V supply section 11716 is sequentially powered-up after the boost section 11718. The 5V supply section 11716 performs a self-check during power-up to identify any errors in the 5V supply section 11716. The 5V supply section 11716 comprises an integrated circuit 11715 configured to provide a step-down voltage from the boost voltage and to perform an error check. When no errors are detected, the 5V supply section 11716 completes sequential power-up and provides an activation signal to the 3.3V supply section 11714. In some embodiments, the safety processor provides an activation signal to the 3.3V supply section 11714. The 3.3V supply section comprises an integrated circuit 11713 configured to provide a step-down voltage from the 5V supply section 11716 and perform a self-error check during power-up. When no errors are detected during the self-check, the 3.3V supply section 11714 provides power to the primary processor. The primary processor is configured to sequentially energize each of the remaining circuit segments. By sequentially energizing the power system 11700 and/or the remainder of a segmented circuit, the power system 11700 reduces error risks, allows for stabilization of voltage levels before loads are applied, and prevents large current draws from all hardware being turned on simultaneously in an uncontrolled manner. The embodiments, however, are not limited to the particular voltage range(s) described in the context of this specification.

In one embodiment, the power system 11700 comprises an over voltage identification and mitigation circuit. The over voltage identification and mitigation circuit is configured to detect a monopolar return current in the surgical instrument and interrupt power from the power segment when the monopolar return current is detected. The over voltage identification and mitigation circuit is configured to identify ground floatation of the power system. The over voltage identification and mitigation circuit comprises a metal oxide varistor. The over voltage identification and mitigation circuit comprises at least one transient voltage suppression diode.

Figure 83:
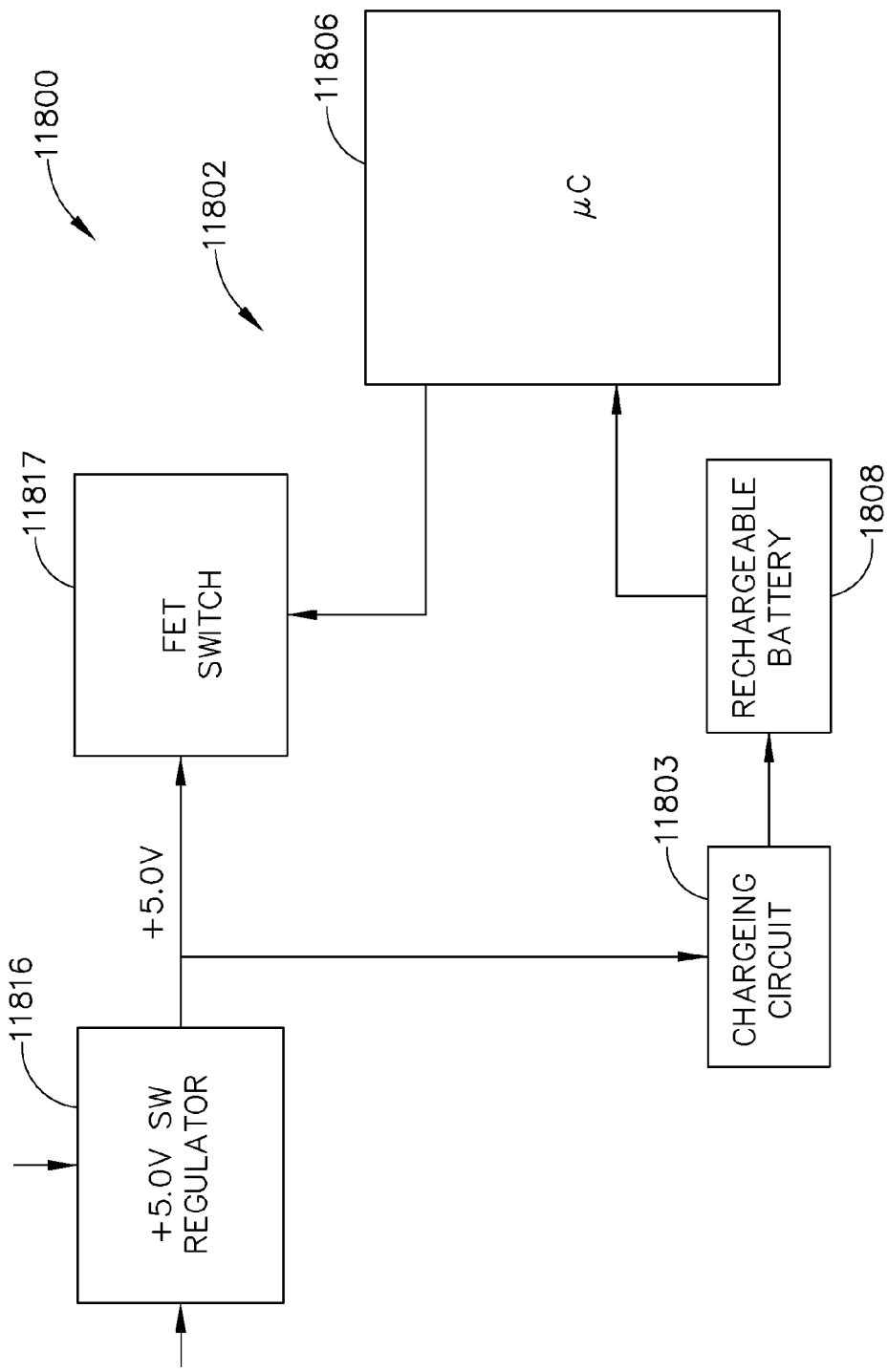
FIG. 83 illustrates one embodiment of a segmented circuit comprising an isolated control section.

FIG. 83 illustrates one embodiment of a segmented circuit 11800 comprising an isolated control section 11802. The isolated control section 11802 isolates control hardware of the segmented circuit 11800 from a power section (not shown) of the segmented circuit 11800. The control section 11802 comprises, for example, a primary processor 11806, a safety processor (not shown), and/or additional control hardware, for example, a FET Switch 11817. The power section comprises, for example, a motor, a motor driver, and/or a plurality of motor MOSFETS. The isolated control section 11802 comprises a charging circuit 11803 and a rechargeable battery 11808 coupled to a 5V power converter 11816. The charging circuit 11803 and the rechargeable battery 11808 isolate the primary processor 11806 from the power section. In some embodiments, the rechargeable battery 11808 is coupled to a safety processor and any additional support hardware. Isolating the control section 11802 from the power section allows the control section 11802, for example, the primary processor 11806, to remain active even when main power is removed, provides a filter, through the rechargeable battery 11808, to keep noise out of the control section 11802, isolates the control section 11802 from heavy swings in the battery voltage to ensure proper operation even during heavy motor loads, and/or allows for real-time operating system (RTOS) to be used by the segmented circuit 11800. In some embodiments, the rechargeable battery 11808 provides a stepped-down voltage to the primary processor, such as, for example, 3.3V. The embodiments, however, are not limited to the particular voltage range(s) described in the context of this specification.

Figure 85:
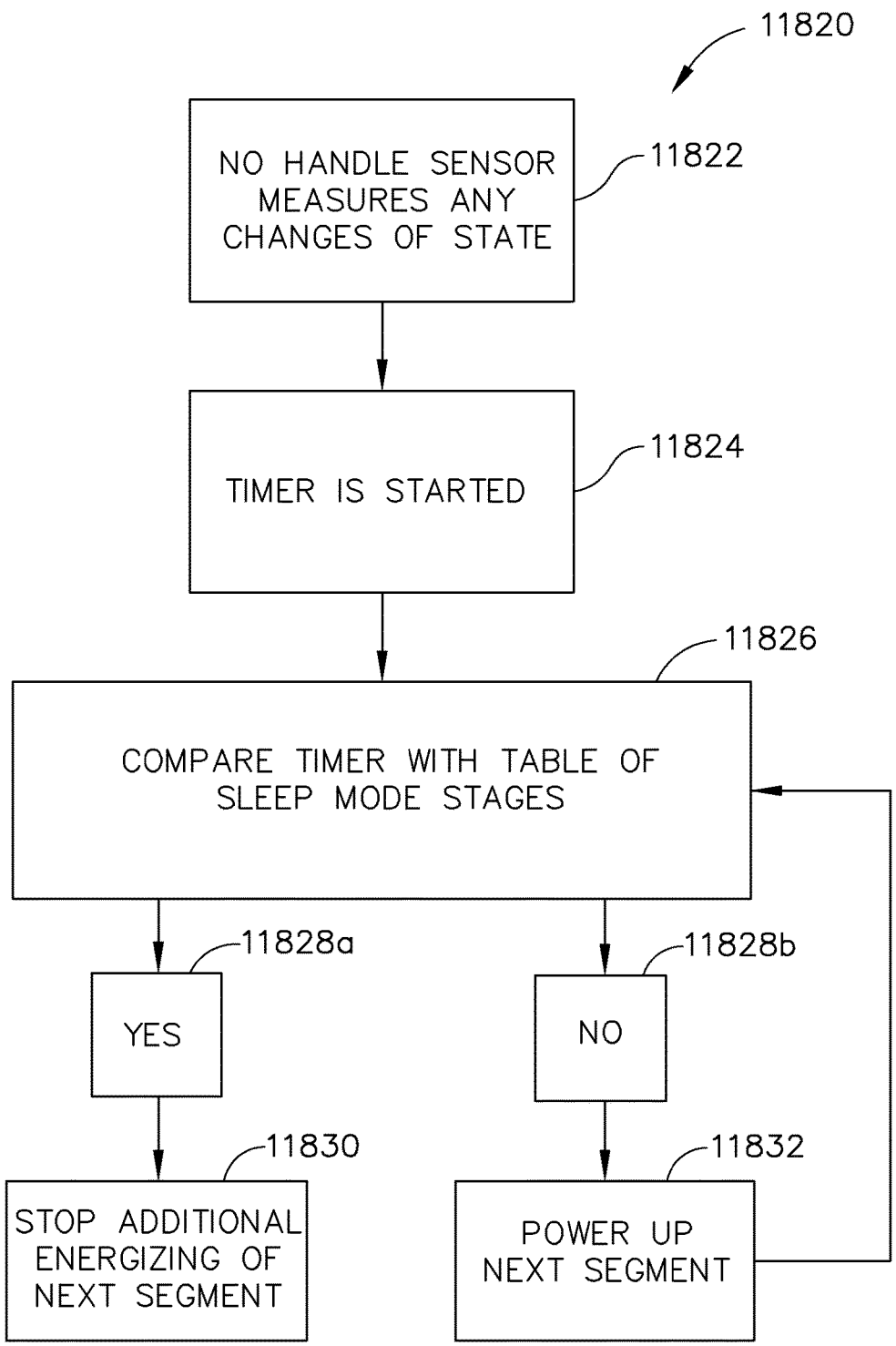
FIG. 85 illustrates one embodiment of a process for sequential start-up of a segmented circuit.

FIG. 85 illustrates one embodiment of a process for sequential start-up of a segmented circuit, such as, for example, the segmented circuit 11100 illustrated in FIGS. 73A and 73B. The sequential start-up process 11820 begins when one or more sensors initiate a transition from sleep mode to operational mode. When the one or more sensors stop detecting state changes 11822, a timer is started 11824. The timer counts the time since the last movement/interaction with the surgical instrument 2000 was detected by the one or more sensors. The timer count is compared 11826 to a table of sleep mode stages by, for example, the safety processor 11104. When the timer count exceeds one or more counts for transition to a sleep mode stage 11828*a*, the safety processor 11104 stops energizing 11830 the segmented circuit 11100 and transitions the segmented circuit 11100 to the corresponding sleep mode stage. When the timer count is below the threshold for any of the sleep mode stages 11828*b*, the segmented circuit 11100 continues to sequentially energize the next circuit segment 11832.

With reference back to FIGS. 73A and 73B, in some embodiments, the segmented circuit 11100 comprises one or more environmental sensors to detect improper storage and/or treatment of a surgical instrument. For example, in one embodiment, the segmented circuit 11100 comprises a temperature sensor. The temperature sensor is configured to detect the maximum and/or minimum temperature that the segmented circuit 11100 is exposed to. The surgical instrument 2000 and the segmented circuit 11100 comprise a design limit exposure for maximum and/or minimum temperatures. When the surgical instrument 2000 is exposed to temperatures exceeding the limits, for example, a temperature exceeding the maximum limit during a sterilization technique, the temperature sensor detects the overexposure and prevents operation of the device. The temperature sensor may comprise, for example, a bi-metal strip configured to disable the surgical instrument 2000 when exposed to a temperature above a predetermined threshold, a solid-state temperature sensor configured to store temperature data and provide the temperature data to the safety processor 11104, and/or any other suitable temperature sensor.

In some embodiments, the accelerometer 11122 is configured as an environmental safety sensor. The accelerometer 11122 records the acceleration experienced by the surgical instrument 2000. Acceleration above a predetermined threshold may indicate, for example, that the surgical instrument has been dropped. The surgical instrument comprises a maximum acceleration tolerance. When the accelerometer 11122 detects acceleration above the maximum acceleration tolerance, safety processor 11104 prevents operation of the surgical instrument 2000.

In some embodiments, the segmented circuit 11100 comprises a moisture sensor. The moisture sensor is configured to indicate when the segmented circuit 11100 has been exposed to moisture. The moisture sensor may comprise, for example, an immersion sensor configured to indicate when the surgical instrument 2000 has been fully immersed in a cleaning fluid, a moisture sensor configured to indicate when moisture is in contact with the segmented circuit 11100 when the segmented circuit 11100 is energized, and/or any other suitable moisture sensor.

In some embodiments, the segmented circuit 11100 comprises a chemical exposure sensor. The chemical exposure sensor is configured to indicate when the surgical instrument 2000 has come into contact with harmful and/or dangerous chemicals. For example, during a sterilization procedure, an inappropriate chemical may be used that leads to degradation of the surgical instrument 2000. The chemical exposure sensor may indicate inappropriate chemical exposure to the safety processor 11104, which may prevent operation of the surgical instrument 2000.

The segmented circuit 11100 is configured to monitor a number of usage cycles. For example, in one embodiment, the battery 11108 comprises a circuit configured to monitor a usage cycle count. In some embodiments, the safety processor 11104 is configured to monitor the usage cycle count. Usage cycles may comprise surgical events initiated by a surgical instrument, such as, for example, the number of shafts 2004 used with the surgical instrument 2000, the number of cartridges inserted into and/or deployed by the surgical instrument 2000, and/or the number of firings of the surgical instrument 2000. In some embodiments, a usage cycle may comprise an environmental event, such as, for example, an impact event, exposure to improper storage conditions and/or improper chemicals, a sterilization process, a cleaning process, and/or a reconditioning process. In some embodiments, a usage cycle may comprise a power assembly (e.g., battery pack) exchange and/or a charging cycle.

The segmented circuit 11100 may maintain a total usage cycle count for all defined usage cycles and/or may maintain individual usage cycle counts for one or more defined usage cycles. For example, in one embodiment, the segmented circuit 11100 may maintain a single usage cycle count for all surgical events initiated by the surgical instrument 2000 and individual usage cycle counts for each environmental event experienced by the surgical instrument 2000. The usage cycle count is used to enforce one or more behaviors by the segmented circuit 11100. For example, usage cycle count may be used to disable a segmented circuit 11100, for example, by disabling a battery 11108, when the number of usage cycles exceeds a predetermined threshold or exposure to an inappropriate environmental event is detected. In some embodiments, the usage cycle count is used to indicate when suggested and/or mandatory service of the surgical instrument 2000 is necessary.

Figure 86:
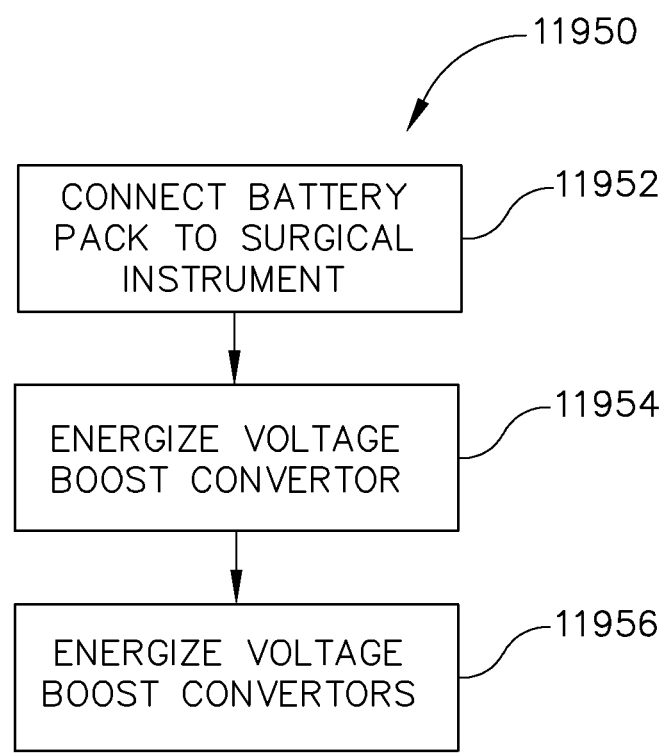
FIG. 86 illustrates one embodiment of a method 1950 for controlling a surgical instrument comprising a segmented circuit, such as, for example, the segmented control circuit 1602 illustrated in FIG. 80.

FIG. 86 illustrates one embodiment of a method 11950 for controlling a surgical instrument comprising a segmented circuit, such as, for example, the segmented control circuit 11602 illustrated in FIG. 80. At 11952, a power assembly 11608 is coupled to the surgical instrument. The power assembly 11608 may comprise any suitable battery, such as, for example, the power assembly 2006 illustrates in FIGS. 69-71B. The power assembly 11608 is configured to provide a source voltage to the segmented control circuit 11602. The source voltage may comprise any suitable voltage, such as, for example, 12V. At 11954, the power assembly 11608 energizes a voltage boost convertor 11618. The voltage boost convertor 11618 is configured to provide a set voltage. The set voltage comprises a voltage greater than the source voltage provided by the power assembly 11608. For example, in some embodiments, the set voltage comprises a voltage of 13V. In a third step 11956, the voltage boost convertor 11618 energizes one or more voltage regulators to provide one or more operating voltages to one or more circuit components. The operating voltages comprise a voltage less than the set voltage provided by the voltage boost convertor.

In some embodiments, the boost convertor 11618 is coupled to a first voltage regulator 11616 configured to provide a first operating voltage. The first operating voltage provided by the first voltage regulator 11616 is less than the set voltage provided by the voltage boost convertor. For example, in some embodiments, the first operating voltage comprises a voltage of 5V. In some embodiments, the boost convertor is coupled to a second voltage regulator 11614. The second voltage regulator 11614 is configured to provide a second operating voltage. The second operating voltage comprises a voltage less than the set voltage and the first operating voltage. For example, in some embodiments, the second operating voltage comprises a voltage of 3.3V. In some embodiments, the battery 11608, voltage boost convertor 11618, first voltage regulator 11616, and second voltage regulator 11614 are configured in a daisy chain configuration. The battery 11608 provides the source voltage to the voltage boost convertor 11618. The voltage boost convertor 11618 boosts the source voltage to the set voltage. The voltage boost convertor 11618 provides the set voltage to the first voltage regulator 11616. The first voltage regulator 11616 generates the first operating voltage and provides the first operating voltage to the second voltage regulator 11614. The second voltage regulator 11614 generates the second operating voltage.

In some embodiments, one or more circuit components are energized directly by the voltage boost convertor 11618. For example, in some embodiments, an OLED display 11688 is coupled directly to the voltage boost convertor 11618. The voltage boost convertor 11618 provides the set voltage to the OLED display 11688, eliminating the need for the OLED to have a power generator integral therewith. In some embodiments, a processor, such as, for example, the safety processor 11604 illustrated in FIGS. 73A and 73B, is verifies the voltage provided by the voltage boost convertor 11618 and/or the one or more voltage regulators 11616, 11614. The safety processor 11604 is configured to verify a voltage provided by each of the voltage boost convertor 11618 and the voltage regulators 11616, 11614. In some embodiments, the safety processor 11604 verifies the set voltage. When the set voltage is equal to or greater than a first predetermined value, the safety processor 11604 energizes the first voltage regulator 11616. The safety processor 11604 verifies the first operational voltage provided by the first voltage regulator 11616. When the first operational voltage is equal to or greater than a second predetermined value, the safety processor 11604 energizes the second voltage regulator 11614. The safety processor 11604 then verifies the second operational voltage. When the second operational voltage is equal to or greater than a third predetermined value, the safety processor 11604 energizes each of the remaining circuit components of the segmented circuit 11600.

Various aspects of the subject matter described herein relate to methods of controlling power management of a surgical instrument through a segmented circuit and variable voltage protection. In one embodiment, a method of controlling power management in a surgical instrument comprising a primary processor, a safety processor, and a segmented circuit comprising a plurality of circuit segments in signal communication with the primary processor, the plurality of circuit segments comprising a power segment, the method comprising providing, by the power segment, variable voltage control of each segment. In one embodiment, the method comprises providing, by the power segment comprising a boost converter, power stabilization for at least one of the segment voltages. The method also comprises providing, by the boost converter, power stabilization to the primary processor and the safety processor. The method also comprises providing, by the boost converter, a constant voltage to the primary processor and the safety processor above a predetermined threshold independent of a power draw of the plurality of circuit segments. The method also comprises detecting, by an over voltage identification and mitigation circuit, a monopolar return current in the surgical instrument and interrupting power from the power segment when the monopolar return current is detected. The method also comprises identifying, by the over voltage identification and mitigation circuit, ground floatation of the power system.

In another embodiment, the method also comprises energizing, by the power segment, each of the plurality of circuit segments sequentially and error checking each circuit segment prior to energizing a sequential circuit segment. The method also comprises energizing the safety processor by a power source coupled to the power segment, performing an error check, by the safety processor, when the safety processor is energized, and performing, and energizing, the safety processor, the primary processor when no errors are detected during the error check. The method also comprises performing an error check, by the primary processor when the primary processor is energized, and wherein when no errors are detected during the error check, sequentially energizing, by the primary processor, each of the plurality of circuit segments. The method also comprises error checking, by the primary processor, each of the plurality of circuit segments.

In another embodiment, the method comprises, energizing, by the boost convertor the safety processor when a power source is connected to the power segment, performing, by the safety processor an error check, and energizing the primary processor, by the safety processor, when no errors are detected during the error check. The method also comprises performing an error check, by the primary process, and sequentially energizing, by the primary processor, each of the plurality of circuit segments when no errors are detected during the error check. The method also comprises error checking, by the primary processor, each of the plurality of circuit segments.

In another embodiment, the method also comprises, providing, by a power segment, a segment voltage to the primary processor, providing variable voltage protection of each segment, providing, by a boost converter, power stabilization for at least one of the segment voltages, an over voltage identification, and a mitigation circuit, energizing, by the power segment, each of the plurality of circuit segments sequentially, and error checking each circuit segment prior to energizing a sequential circuit segment.

Various aspects of the subject matter described herein relate to methods of controlling an surgical instrument control circuit having a safety processor. In one embodiment, a method of controlling a surgical instrument comprising a control circuit comprising a primary processor, a safety processor in signal communication with the primary processor, and a segmented circuit comprising a plurality of circuit segments in signal communication with the primary processor, the method comprising monitoring, by the safety processor, one or more parameters of the plurality of circuit segments. The method also comprises verifying, by the safety processor, the one or more parameters of the plurality of circuit segments and verifying the one or more parameters independently of one or more control signals generated by the primary processor. The method further comprises verifying, by the safety processor, a velocity of a cutting element. The method also comprises monitoring, by a first sensor, a first property of the surgical instrument, monitoring, by a second sensor a second property of the surgical instrument, wherein the first property and the second property comprise a predetermined relationship, and wherein the first sensor and the second sensor are in signal communication with the safety processor. The method also comprises preventing, by the safety processor, operation of at least one of the plurality of circuit segments when the fault is detected, wherein a fault comprises the first property and the second property having values inconsistent with the predetermined relationship. The method also comprises, monitoring, by a Hall-effect sensor, a cutting member position and monitoring, by a motor current sensor, a motor current.

In another embodiment, the method comprises disabling, by the safety processor, at least one of the plurality of circuit segments when a mismatch is detected between the verification of the one or more parameters and the one or more control signals generated by the primary processor. The method also comprises preventing by the safety processor, operation of a motor segment and interrupting power flow to the motor segment from the power segment. The method also comprises preventing, by the safety processor, forward operation of a motor segment and when the fault is detected allowing, by the safety processor, reverse operation of the motor segment.

In another embodiment the segmented circuit comprises a motor segment and a power segment, the method comprising controlling, by the motor segment, one or more mechanical operations of the surgical instrument and monitoring, by the safety processor, one or more parameters of the plurality of circuit segments. The method also comprises verifying, by the safety processor, the one or more parameters of the plurality of circuit segments and the independently verifying, by the safety processor, the one or more parameters independently of one or more control signals generated by the primary processor.

In another embodiment, the method also comprises independently verifying, by the safety processor, the velocity of a cutting element. The method also comprises monitoring, by a first sensor, a first property of the surgical instrument, monitoring, by a second sensor, a second property of the surgical instrument, wherein the first property and the second property comprise a predetermined relationship, and wherein the first sensor and the second sensor are in signal communication with the safety processor, wherein a fault comprises the first property and the second property having values inconsistent with the predetermined relationship, and preventing, by the safety processor, the operation of at least one of the plurality of circuit segments when the fault is detected by the safety processor. The method also comprises monitoring, by a Hall-effect sensor, a cutting member position and monitoring, by a motor current sensor, a motor current.

In another embodiment, the method comprises disabling, by the safety processor, at least one of the plurality of circuit segments when a mismatch is detected between the verification of the one or more parameters and the one or more control signals generated by the primary processor. The method also comprises preventing, by the safety processor, operation of the motor segment and interrupting power flow to the motor segment from the power segment. The method also comprises preventing, by the safety processor, forward operation of the motor segment and allowing, by the safety processor, reverse operation of the motor segment when the fault is detected.

In another embodiment, the method comprises monitoring, by the safety processor, one or more parameters of the plurality of circuit segments, verifying, by the safety processor, the one or more parameters of the plurality of circuit segments, verifying, by the safety processor, the one or more parameters independently of one or more control signals generated by the primary processor, and disabling, by the safety processor, at least one of the plurality of circuit segments when a mismatch is detected between the verification of the one or more parameters and the one or more control signals generated by the primary processor. The method also comprises monitoring, by a first sensor, a first property of the surgical instrument, monitoring, by a second sensor, a second property of the surgical instrument, wherein the first property and the second property comprise a predetermined relationship, and wherein the first sensor and the second sensor are in signal communication with the safety processor, wherein a fault comprises the first property and the second property having values inconsistent with the predetermined relationship, and wherein when the fault is detected, preventing, by the safety processor, operation of at least one of the plurality of circuit segments. The method also comprises preventing, by the safety processor, operation of a motor segment by interrupting power flow to the motor segment from the power segment when a fault is detected prevent.

Various aspects of the subject matter described herein relate to methods of controlling power management of a surgical instrument through sleep options of segmented circuit and wake up control, the surgical instrument comprising a control circuit comprising a primary processor, a safety processor in signal communication with the primary processor, and a segmented circuit comprising a plurality of circuit segments in signal communication with the primary processor, the plurality of circuit segments comprising a power segment, the method comprising transitioning, by the safety processor, the primary processor and at least one of the plurality of circuit segments from an active mode to a sleep mode and from the sleep mode to the active mode. The method also comprises tracking, by a timer, a time from a last user initiated event and wherein when the time from the last user initiated event exceeds a predetermined threshold, transitioning, by the safety processor, the primary processor and at least one of the plurality of circuit segments to the sleep mode. The method also comprises detecting, by an acceleration segment comprising an accelerometer, one or more movements of the surgical instrument. The method also comprises tracking, by the timer, a time from the last movement detected by the acceleration segment. The method also comprises maintaining, by the safety processor, the acceleration segment in the active mode when transitioning the plurality of circuit segments to the sleep mode.

In another embodiment, the method also comprises transitioning to the sleep mode in a plurality of stages. The method also comprises transitioning the segmented circuit to a first stage after a first predetermined period and dimming a backlight of the display segment, transitioning the segmented circuit to a second stage after a second predetermined period and turning the backlight off, transitioning the segmented circuit to a third stage after a third predetermined period and reducing a polling rate of the accelerometer, and transitioning the segmented circuit to a fourth stage after a fourth predetermined period and turning a display off and transitioning the surgical instrument to the sleep mode.

In another embodiment comprising detecting, by a touch sensor, user contact with a surgical instrument and transitioning, by the safety processor, the primary processor and a plurality of circuit segments from a sleep mode to an active mode when the touch sensor detects a user in contact with surgical instrument. The method also comprises monitoring, by the safety processor, at least one handle control and transitioning, by the safety processor, the primary processor and the plurality of circuit segments from the sleep mode to the active mode when the at least one handle control is actuated.

In another embodiment, the method comprises transitioning, by the safety processor, the surgical device to the active mode when the accelerometer detects movement of the surgical instrument above a predetermined threshold. The method also comprises monitoring, by the safety processor, the accelerometer for movement in at least a first direction and a second direction and transitioning, by the safety processor, the surgical instrument from the sleep mode to the operational mode when movement above a predetermined threshold is detected in at least the first direction and the second direction. The method also comprises monitoring, by the safety processor, the accelerometer for oscillating movement above the predetermined threshold in the first direction, the second direction, and a third direction, and transitioning, by the safety processor, the surgical instrument from the sleep mode to the operational mode when oscillating movement is detected above the predetermined threshold in the first direction, second direction, and third direction. The method also comprises increasing the predetermined as the time from the previous movement increases.

In another embodiment, the method comprises transitioning, by the safety processor, the primary processor and at least one of the plurality of circuit segments from an active mode to a sleep mode and from the sleep mode to the active mode when a time from the last user initiated event exceeds a predetermined threshold, tracking, by a timer, a time from the last movement detected by the acceleration segment, and transitioning, by the safety processor, the surgical device to the active mode when the acceleration segment detects movement of the surgical instrument above a predetermined threshold.

In another embodiment, a method of controlling a surgical instrument comprises tracking a time from a last user initiated event and disabling, by the safety processor, a backlight of a display when the time from the last user initiated event exceeds a predetermined threshold. The method also comprises flashing, by the safety processor, the backlight of the display to indicate to a user to look at the display.

Various aspects of the subject matter described herein relate to methods of verifying the sterilization of a surgical instrument through a sterilization verification circuit, the surgical instrument comprising a control circuit comprising a primary processor, a safety processor in signal communication with the primary processor and a segmented circuit comprising a plurality of circuit segments in signal communication with the primary processor, the plurality of circuit segments comprising a storage verification segment, the method comprising indicating when a surgical instrument has been properly stored and sterilized. The method also comprises detecting, by at least one sensor, one or more improper storage or sterilization parameters. The method also comprises sensing, by a drop protection sensor, when the instrument has been dropped and preventing, by the safety processor, operation of at least one of the plurality of circuit segments when the drop protection sensor detects that the surgical instrument has been dropped. The method also comprises preventing, by the safety processor, operation of at least one of the plurality of circuit segments when a temperature above a predetermined threshold is detected by a temperature sensor. The method also comprises preventing, by the safety processor, operation of at least one of the plurality of circuit segments when the temperature sensor detects a temperature above a predetermined threshold.

In another embodiment, the method comprises controlling, by the safety processor, operation of at least one of the plurality of circuit segments when a moisture detection sensor detects moisture. The method also comprises detecting, by a moisture detection sensor, an autoclave cycle and preventing, by the safety processor, operation of the surgical instrument unless the autoclave cycle has been detected. The method also comprises preventing, by the safety processor, operation of the at least one of the plurality of circuit segments when moisture is detected during a staged circuit start-up.

In another embodiment, the method comprises indicating, by the plurality of circuit segments comprising a sterilization verification segment, when a surgical instrument has been properly sterilized. The method also comprises detecting, by at least one sensor of the sterilization verification segment, sterilization of the surgical instrument. The method also comprises indicating, by a storage verification segment, when a surgical instrument has been properly stored. The method also comprises detecting, by at least one sensor of the storage verification segment, improper storage of the surgical instrument.

Figure 87:
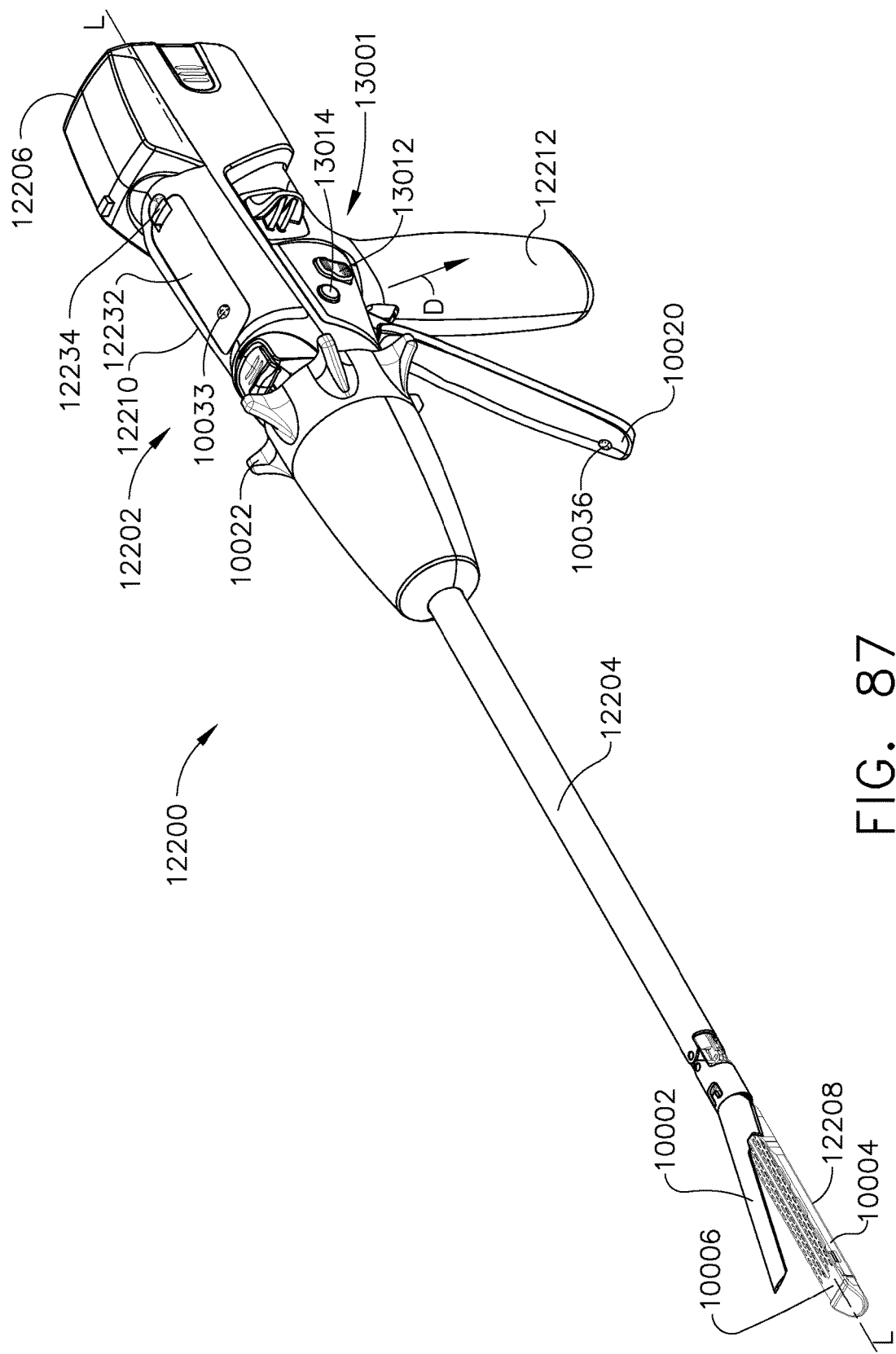
FIG. 87 is a perspective view of a surgical instrument comprising a handle assembly and a shaft assembly including an end effector.

FIG. 87 generally depicts a motor-driven surgical instrument 12200. In certain circumstances, the surgical instrument 12200 may include a handle assembly 12202, a shaft assembly 12204, and a power assembly 12206 (or "power source" or "power pack"). The shaft assembly 12204 may include an end effector 12208 which, in certain circumstances, can be configured to act as an endocutter for clamping, severing, and/or stapling tissue, although, in other circumstances, different types of end effectors may be used, such as end effectors for other types of surgical devices, graspers, cutters, staplers, clip appliers, access devices, drug/gene therapy devices, ultrasound, RF and/or laser devices, etc. Several RF devices may be found in U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL FASTENING AND CUTTING INSTRUMENT HAVING RF ELECTRODES, filed Feb. 14, 2008. The entire disclosures of U.S. Pat. No. 5,403,312, entitled ELECTROSURGICAL HEMOSTATIC DEVICE, which issued on Apr. 4, 1995, and U.S. patent application Ser. No. 12/031,573, entitled SURGICAL FASTENING AND CUTTING INSTRUMENT HAVING RF ELECTRODES, filed Feb. 14, 2008, are incorporated herein by reference in their entirety.

Referring again to FIG. 87, the handle assembly 12202 may comprise a housing 12210 that includes a handle 12212 that may be configured to be grasped, manipulated, and/or actuated by a clinician. However, it will be understood that the various unique and novel arrangements of the housing 12210 may also be effectively employed in connection with robotically-controlled surgical systems. Thus, the term "housing" may also encompass a housing or similar portion of a robotic system that houses or otherwise operably supports at least one drive system that is configured to generate and apply at least one control motion which could be used to actuate the shaft assembly 12204 disclosed herein and its respective equivalents. For example, the housing 12210 disclosed herein may be employed with various robotic systems, instruments, components, and methods disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719. The disclosure of U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719, is incorporated by reference herein in its entirety.

In certain instances, the surgical instrument 12200 may include several operable systems that extend, at least partially, through the shaft 12204 and are in operable engagement with the end effector 12208. For example, the surgical instrument 12200 may include a closure assembly that may transition the end effector 12208 between an open configuration and a closed configuration, an articulation assembly that may articulate the end effector 12208 relative to the shaft 12204, and/or a firing assembly that may fasten and/or cut tissue captured by the end effector 12208. In addition, the housing 12210 may be separably couplable to the shaft 12204 and may include complimenting closure, articulation, and/or firing drive systems for operating the closure, articulation, and firing assemblies, respectively.

In use, an operator of the surgical instrument 12200 may desire to reset the surgical instrument 12200 and return one or more of the assemblies of the surgical instrument 12200 to a default position. For example, the operator may insert the end effector 12208 into a surgical site within a patient through an access port and may then articulate and/or close the end effector 12208 to capture tissue within the cavity. The operator may then choose to undo some or all of the previous actions and may choose to remove the surgical instrument 12200 from the cavity, for instance. The surgical instrument 12200 may include one more systems configured to facilitate a reliable return of one or more of the assemblies described above to a home state with minimal input from the operator thereby allowing the operator to remove the surgical instrument from the cavity.

Figure 89:
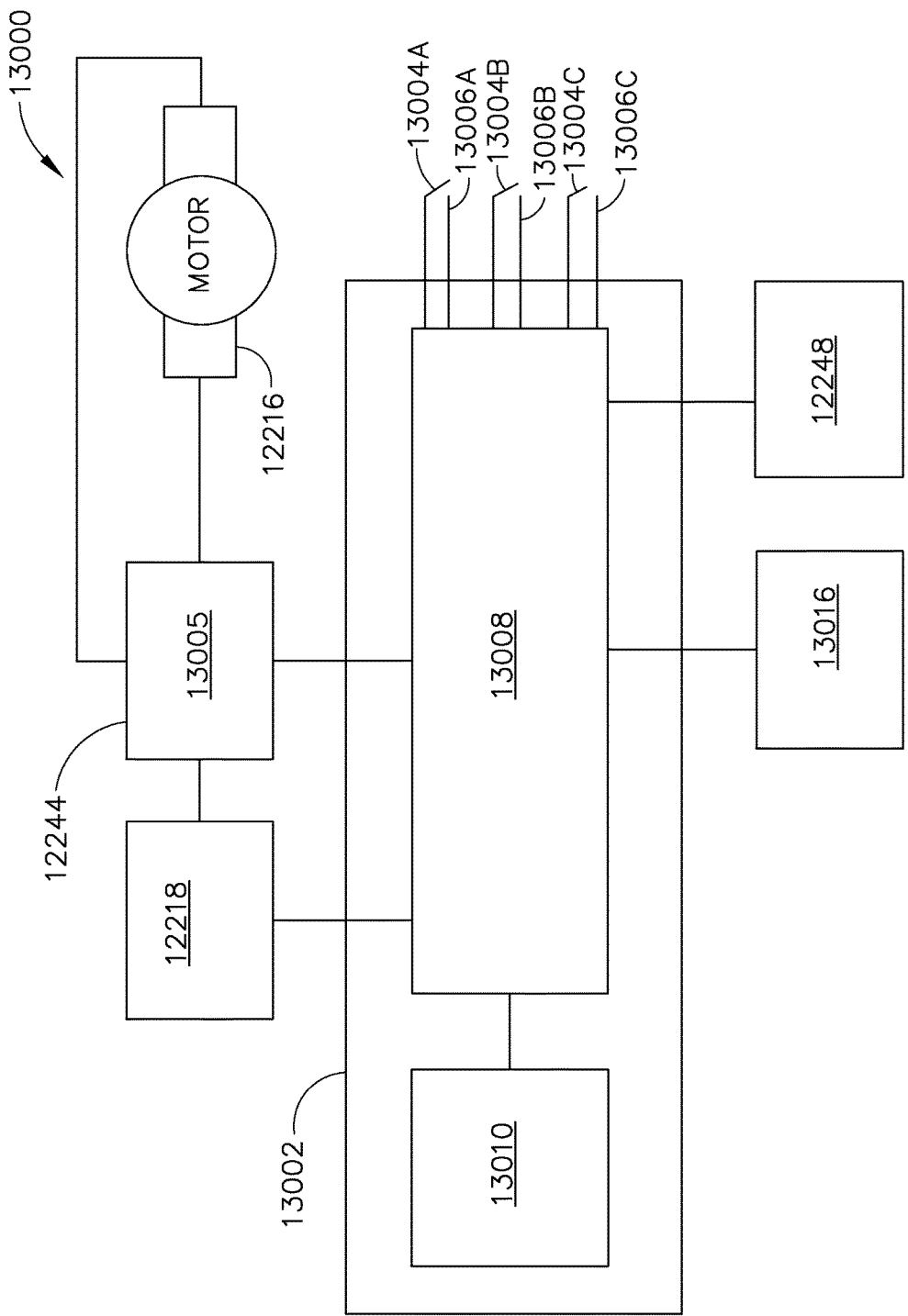
FIG. 89 is a schematic block diagram of a control system of the surgical instrument of FIG. 87.

Referring to FIGS. 87 and 89, the surgical instrument 12200 may include a control system 13000. A surgical operator may utilize the control system 13000 to articulate the end effector 12208 relative to the shaft 12204 between an articulation home state position and an articulated position, for example. In certain instances, the surgical operator may utilize the control system 13000 to reset or return the articulated end effector 12208 to the articulation home state position. The control system 13000 can be positioned, at least partially, in the housing 12210. In certain instances, as illustrated in FIG. 89, the control system 13000 may comprise a microcontroller 13002 ("controller") which can be configured to receive an input signal and, in response, activate a motor 12216 to cause the end effector 12208 to articulate in accordance with such an input signal, for example.

Further to the above, the end effector 12208 can be positioned in sufficient alignment with the shaft 12204 in the articulation home state position, also referred to herein as an unarticulated position such that the end effector 12208 and at least a portion of shaft 12204 can be inserted into or retracted from a patient's internal cavity through an access port such as, for example, a trocar positioned in a wall of the internal cavity without damaging the access port. In certain instances, the end effector 12208 can be aligned, or at least substantially aligned, with a longitudinal axis "LL" passing through the shaft 12204 when the end effector 12208 is in the articulation home state position, as illustrated in FIG. 87. In at least one instance, the articulation home state position can be at any angle up to and including 5°, for example, with the longitudinal axis "LL" on either side of the longitudinal axis "LL". In another instance, the articulation home state position can be at any angle up to and including 3°, for example, with the longitudinal axis "LL" on either side of the longitudinal axis "LL". In yet another instance, the articulation home state position can be at any angle up to and including 7°, for example, with the longitudinal axis "LL" on either side of the longitudinal axis "LL".

The control system 13000 can be operated to articulate the end effector 12208 relative to the shaft 12204 in a plane extending along the longitudinal axis "LL" in a first direction such as, for example, a clockwise direction and/or a second direction such as, for example, a counterclockwise direction. In at least one instance, the control system 13000 can be operated to articulate the end effector 12208 in the clockwise direction form the articulation home state position to an articulated position 10 degrees to the right of the longitudinal axis "LL", for example. In another example, the control system 13000 can be operated to articulate the end effector 12208 in the counterclockwise direction form the articulated position at 10 degrees to the right of the longitudinal axis "LL" to the articulation home state position. In yet another example, the control system 13000 can be operated to articulate the end effector 12208 relative to the shaft 12204 in the counterclockwise direction from the articulation home state position to an articulated position 10 degrees to the left of the longitudinal axis "LL", for example. The reader will appreciate that the end effector can be articulated to different angles in the clockwise direction and/or the counterclockwise direction.

Figure 88:
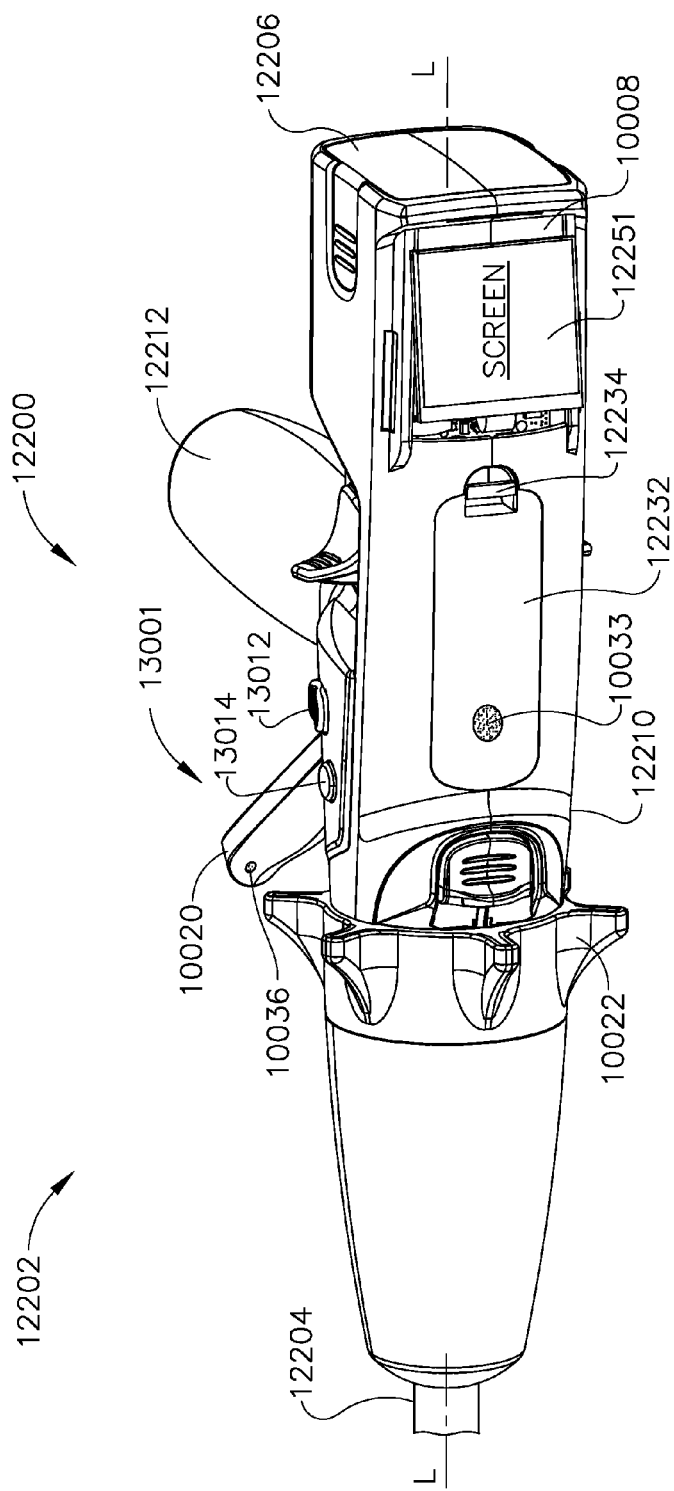
FIG. 88 is a perspective view of the handle assembly of the surgical instrument of FIG. 87.

Referring to FIGS. 87 and 88, the housing 12210 of the surgical instrument 12200 may comprise an interface 13001 which may include a plurality of controls that can be utilized by the operator to operate the surgical instrument 12200. In certain instances, the interface 13001 may comprise a plurality of switches which can be coupled to the controller 13002 via electrical circuits, for example. In certain instances, as illustrated in FIG. 89, the interface 13001 comprises three switches 13004A-C, wherein each of the switches 13004A-C is coupled to the controller 13002 via electrical circuits such as, for example electrical circuits 13006A-C, respectively. The reader will appreciate that other combinations of switches and circuits can be utilized with the interface 13001.

Referring to FIG. 89, the controller 13002 may generally comprise a microprocessor 13008 ("processor") and one or more memory units 13010 operationally coupled to the processor 13008. By executing instruction code stored in the memory 13010, the processor 13008 may control various components of the surgical instrument 12200, such as the motor 12216, various drive systems, and/or a user display, for example. The controller 13002 may be implemented using integrated and/or discrete hardware elements, software elements, and/or a combination of both. Examples of integrated hardware elements may include processors, microprocessors, microcontrollers, integrated circuits, application specific integrated circuits (ASIC), programmable logic devices (PLD), digital signal processors (DSP), field programmable gate arrays (FPGA), logic gates, registers, semiconductor devices, chips, microchips, chip sets, microcontrollers, system-on-chip (SoC), and/or system-in-package (SIP). Examples of discrete hardware elements may include circuits and/or circuit elements such as logic gates, field effect transistors, bipolar transistors, resistors, capacitors, inductors, and/or relays. In certain instances, the controller 13002 may include a hybrid circuit comprising discrete and integrated circuit elements or components on one or more substrates, for example.

In certain instances, the microcontroller 13002 may be an LM 4F230H5QR, available from Texas Instruments, for example. In certain instances, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available. Other microcontrollers may be readily substituted for use with the present disclosure. Accordingly, the present disclosure should not be limited in this context.

In various forms, the motor 12216 may be a DC brushed driving motor having a maximum rotation of, approximately, 25,000 RPM, for example. In other arrangements, the motor 12216 may include a brushless motor, a cordless motor, a synchronous motor, a stepper motor, or any other suitable electric motor. A battery 12218 (or "power source" or "power pack"), such as a Li ion battery, for example, may be coupled to the housing 12212 to supply power to the motor 12216, for example.

Referring again to FIG. 89, the surgical instrument 12200 may include a motor controller 13005 in operable communication with the controller 13002. The motor controller 13005 can be configured to control a direction of rotation of the motor 12216. In certain instances, the motor controller 13005 may be configured to determine the voltage polarity applied to the motor 12216 by the battery 12218 and, in turn, determine the direction of rotation of the motor 12216 based on input from the controller 13002. For example, the motor 12216 may reverse the direction of its rotation from a clockwise direction to a counterclockwise direction when the voltage polarity applied to the motor 12216 by the battery 12218 is reversed by the motor controller 13005 based on input from the controller 13002. In addition, the motor 12216 can be operably coupled to an articulation drive which can be driven by the motor 12216 distally or proximally depending on the direction in which the motor 12216 rotates, for example. Furthermore, the articulation drive can be operably coupled to the end effector 12208 such that, for example, the axial translation of the articulation drive proximally may cause the end effector 12208 to be articulated in the counterclockwise direction, for example, and/or the axial translation of the articulation drive distally may cause the end effector 12208 to be articulated in the clockwise direction, for example.

Figure 93:
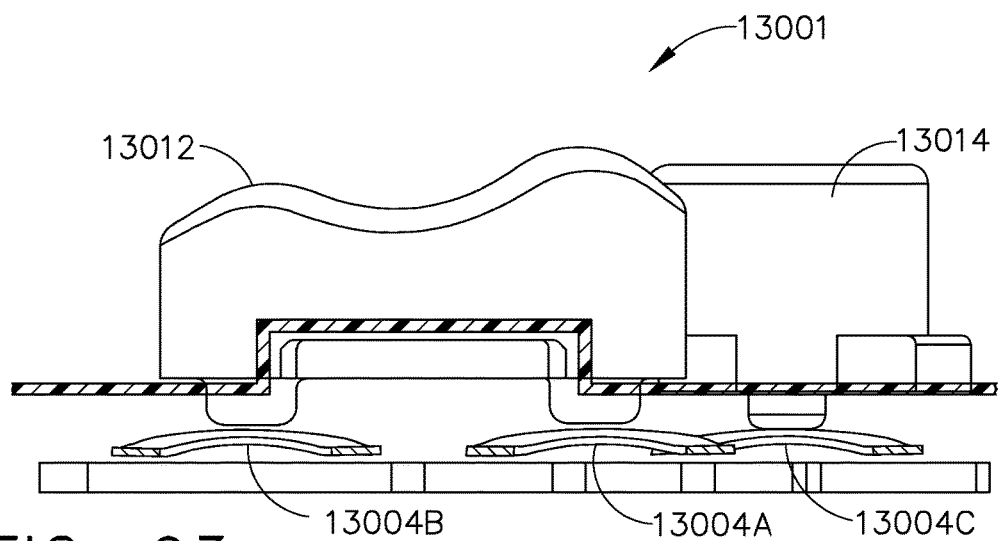
FIG. 93 is a schematic illustration of an interface of the surgical instrument of FIG. 87 in an inactive or neutral configuration.

In various instances, referring to FIGS. 87-89, the interface 13001 can be configured such that the switch 13004A can be dedicated to the clockwise articulation of the end effector 12208, for example, and the switch 13004B can be dedicated to the counterclockwise articulation of the end effector 12208, for example. In such instances, the operator may articulate the end effector 12208 in the clockwise direction by closing the switch 13004A and may articulate the end effector 12208 in the counterclockwise direction by closing the switch 13004B. In various instances, the switches 13004A-C can comprise open-biased dome switches, as illustrated in FIG. 93. Other types of switches can also be employed such as, for example, capacitive switches.

Figure 94:
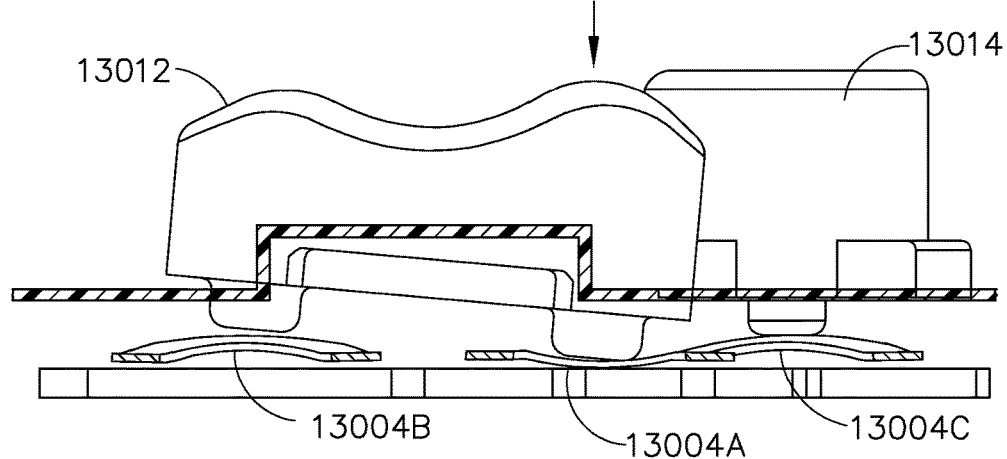
FIG. 94 is a schematic illustration of the interface of FIG. 93 activated to articulate an end effector.

Referring to FIG. 93, the dome switches 13004A and 13004B can be controlled by a rocker 13012. Other means for controlling the switches 13004A and 13004B are contemplated by the present disclosure. In the neutral position, as illustrated in FIG. 93, both of the switches 13004A and 13004B are biased in the open position. The operator, for example, may articulate the end effector 12208 in the clockwise direction by tilting the rocker forward thereby depressing the dome switch 13004A, as illustrated in FIG. 94. In result, the circuit 13006A (FIG. 89) may be closed signaling the controller 13002 to activate the motor 12216 to articulate the end effector 12208 in the clockwise direction, as described above. The motor 12216 may continue to articulate the end effector 12208 until the operator releases the rocker 13012 thereby allowing the dome switch 13004A to return to the open position and the rocker 13012 to the neutral position. In some circumstances, the controller 13002 may be able to identify when the end effector 12208 has reached a predetermined maximum degree of articulation and, at such point, interrupt power to the motor 12216 regardless of whether the dome switch 13004A is being depressed. In a way, the controller 13002 can be configured to override the operator's input and stop the motor 12216 when a maximum degree of safe articulation is reached. Alternatively, the operator may articulate the end effector 12208 in the counterclockwise direction by tilting the rocker 13012 back thereby depressing the dome switch 13004B, for example. In result, the circuit 13006B may be closed signaling the controller 13002 to activate the motor 12216 to articulate the end effector 12208 in the counterclockwise direction, as described above. The motor 12216 may continue to articulate the end effector 12208 until the operator releases the rocker 13012 thereby allowing the dome switch 13004B to return to the open position and the rocker 13012 to the neutral position. In some circumstances, the controller 13002 may be able to identify when the end effector 12208 has reached a predetermined maximum degree of articulation and, at such point, interrupt power to the motor 12216 regardless of whether the dome switch 13004B is being depressed. In a way, the controller 13002 can be configured to override the operator's input and stop the motor 12216 when a maximum degree of safe articulation is reached.

As described above in greater detail, an operator may desire to return the end effector 12208 to the articulation home state position to align, or at least substantially align, the end effector 12208 with the shaft 12204 in order to retract the surgical instrument 12200 from a patient's internal cavity, for example. In various instances, the control system 13000 may include a virtual detent that may alert the operator when the end effector 12208 has reached the articulation home state position. In certain instances, the control system 13000 may be configured to stop the articulation of the end effector 12208 upon reaching the articulation home state position, for example. In certain instances, the control system 13000 may be configured to provide feedback to the operator when the end effector 12208 reaches the articulation home state position, for example.

Figure 90:
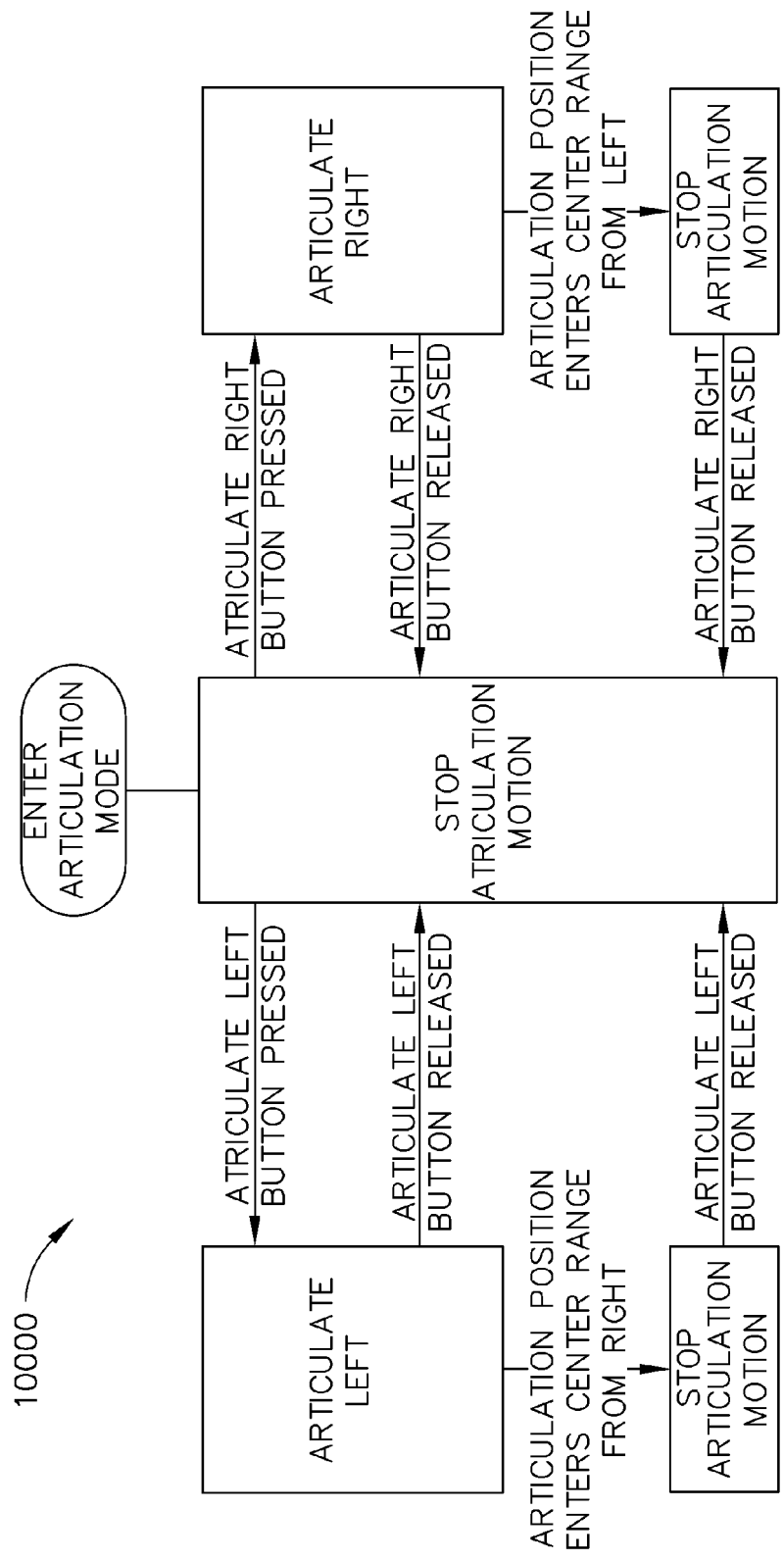
FIG. 90 is a schematic block diagram of a module for use with the surgical instrument of FIG. 87.

In certain instances, the control system 13000 may comprise various executable modules such as software, programs, data, drivers, and/or application program interfaces (APIs), for example. FIG. 90 depicts an exemplary virtual detent module 10000 that can be stored in the memory 13010, for example. The module 10000 may include program instructions, which when executed may cause the processor 13008, for example, to alert the operator of the surgical instrument 12200 when the end effector 12208 reaches the articulation home state position during the articulation of the end effector 12208 from an articulated position, for example.

As described above, referring primarily to FIGS. 89, 93, and 94, the operator may use the rocker 13012 to articulate the end effector 12208, for example. In certain instances, the operator may depress the dome switch 13004A of the rocker 13012 to articulate the end effector 12208 in a first direction such as a clockwise direction to the right, for example, and may depress the dome switch 13004B to articulate the end effector 12208 in a second direction such as a counterclockwise direction to the left, for example. In various instances, as illustrated in FIG. 90, the module 10000 may modulate the response of the processor 13008 to input signals from the dome switches 13004A and/or 13004B. For example, the processor 13008 can be configured to activate the motor 12216 to articulate the end effector 12208 to the right, for example, while the dome switch 13004A is depressed; and the processor 13008 can be configured to activate the motor 12216 to articulate the end effector 12208 to the left, for example, while the dome switch 13004B is depressed. In addition, the processor 13008 may be configured to stop the articulation of the end effector 12208 by causing the motor 12216 to stop, for example, when input signals from the dome switches 13004A and/or 13004B are stopped such as when the operator releases the dome switches 13004A and/or 13004B, respectively.

In various instances, as described above, the articulation home state position may comprise a range of positions. In certain instances, the processor 13008 can configured to detect when the end effector 12208 enters the range of positions defining the articulation home state position. In certain instances, the surgical instrument 12200 may comprise one or more positioning systems (not shown) for sensing and recording the articulation position of the end effector 12208. The processor 13008 can be configured to employ the one or more positioning systems to detect when the end effector 12208 enters the articulation home state position.

As illustrated in FIG. 90, in certain instances, upon reaching the articulation home state position, the processor 13008 may stop the articulation of the end effector 12208 to alert the operator that the articulation home state position is reached; the processor 13008, in certain instances, may stop the articulation in the articulation home state position even if the operator continues to depress the rocker 13012. In certain instances, in order to continue past the articulation home state position, the operator may release the rocker 13012 and then tilt it again to restart the articulation. In at least one such instance, the operator may push the rocker 13012 to depress dome switch 13004A, for example, to rotate the end effector 12208 toward its home state position until the end effector 12208 reaches its home state position and the processor 13008 stops the articulation of the end effector 12208, wherein the operator can then release the rocker 13012 and, then, push the rocker 13012 to depress the dome switch 13004A once again in order to continue the articulation of the end effector 12208 in the same direction.

Figure 91:
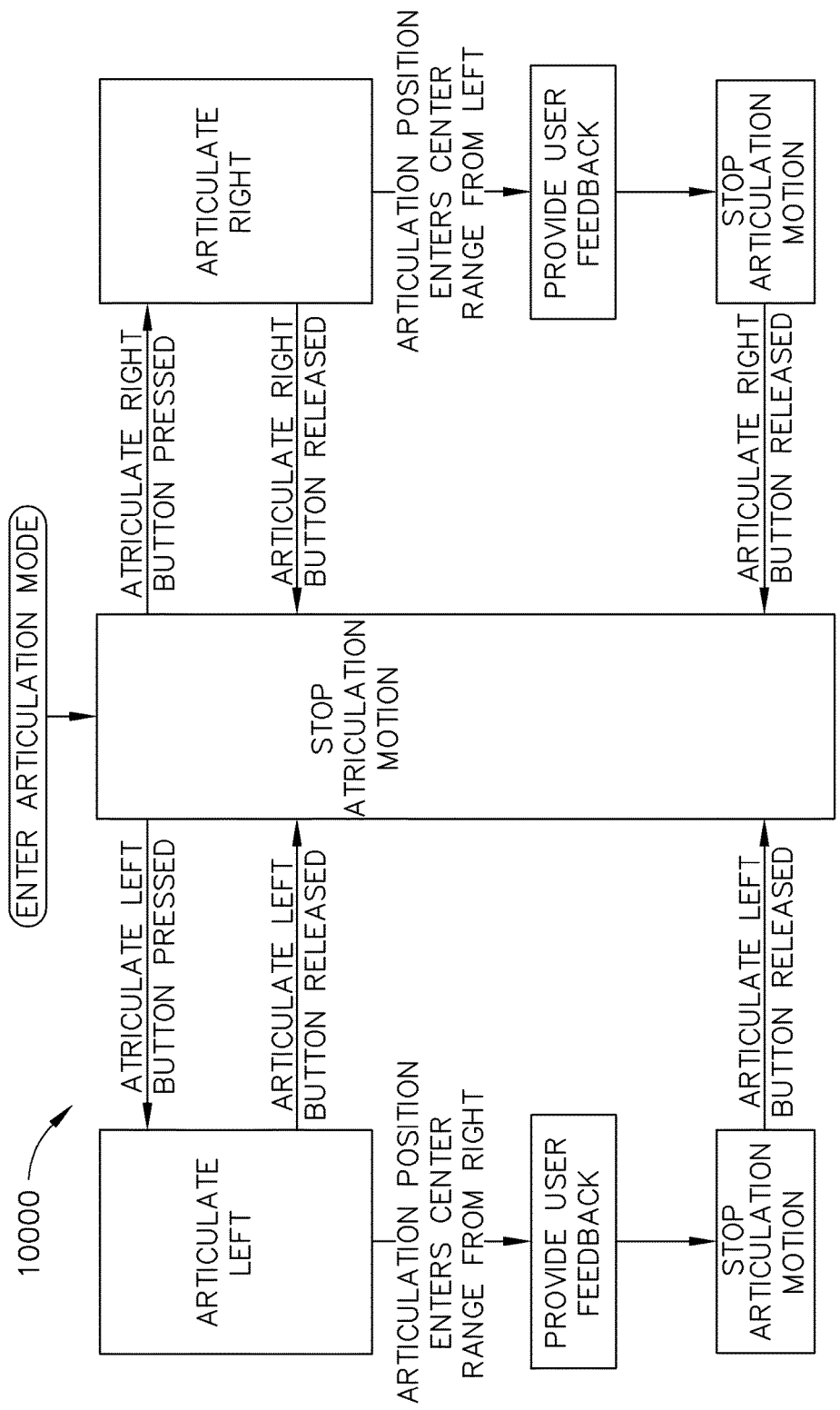
FIG. 91 is a schematic block diagram of a module for use with the surgical instrument of FIG. 87.

In certain instances, as illustrated in FIG. 91, the module 10000 may comprise a feedback mechanism to alert the operator when the articulation home state position is reached. Various feedback devices 12248 (FIG. 89) can be employed by the processor 13008 to provide sensory feedback to the operator. In certain instances, the devices 12248 may comprise, for example, visual feedback devices such as display screens and/or LED indicators, for example. In certain instances, the devices 12248 may comprise audio feedback devices such as speakers and/or buzzers, for example. In certain instances, the devices 12248 may comprise tactile feedback devices such as a mechanical detent, for example, which can provide haptic feedback, for example. In some instances, haptic feedback can be provided by a vibrating motor, for example, that can provide a pulse of vibrations to the handle of the surgical instrument, for example. In certain instances, the devices 12248 may comprise combinations of visual feedback devices, audio feedback devices, and/or tactile feedback devices, for example.

In certain instances, the processor 13008 can be configured to stop the articulation of the end effector 12208 and provide feedback to the operator when the articulation home state position is reached, for example. In certain instances, the processor 13008 may provide feedback to the operator but may not stop the articulation of the end effector 12208 when the articulation home state position is reached. In at least one instance, the end effector 12208 can be moved from a position on a first side of the home state position toward the home state position, pass through the home state position, and continue moving in the same direction on the other side of the home state position. During such movement, the operator may be supplied with some form of feedback at the moment the end effector 12208 passes through the home state position. In certain instances, the processor 13008 may stop the articulation of the end effector 12208 but may not provide feedback to the operator when the articulation home state position is reached, for example. In certain instances, the processor 13008 may pause the end effector 12208 as it passes through its center position and then continue past its center position. In at least one instance, the end effector 12208 can temporarily dwell in its center position for about 2 seconds, for example, and then continue its articulation so long as the articulation switch 13012 remains depressed.

In various instances, an operator of the surgical instrument 12200 may attempt to articulate the end effector 12208 back to its unarticulated position utilizing the rocker switch 13012. As the reader will appreciate, the operator may not be able to accurately and/or repeatably align the end effector 12208 with the longitudinal axis of the surgical instrument shaft. In various instances, though, the operator can readily position the end effector 12208 within a certain range of the center position. For instance, an operator may push the rocker switch 13012 to rotate the end effector 12208 toward its center position and then release the rocker switch 13012 when the operator believes that the end effector 12208 has reached its center position or is close to its center position. The processor 13008 can interpret such circumstances as an attempt to recenter the end effector 12208 and, in the event that the end effector 12208 is not in its center position, the processor 13008 can automatically center the end effector 12208. In at least one example, if the operator of the surgical instrument releases the rocker switch 13012 when the end effector 12208 is within about 10 degrees on either side of the center position, for example, the processor 13008 may automatically recenter the end effector 12208.

Figure 92:
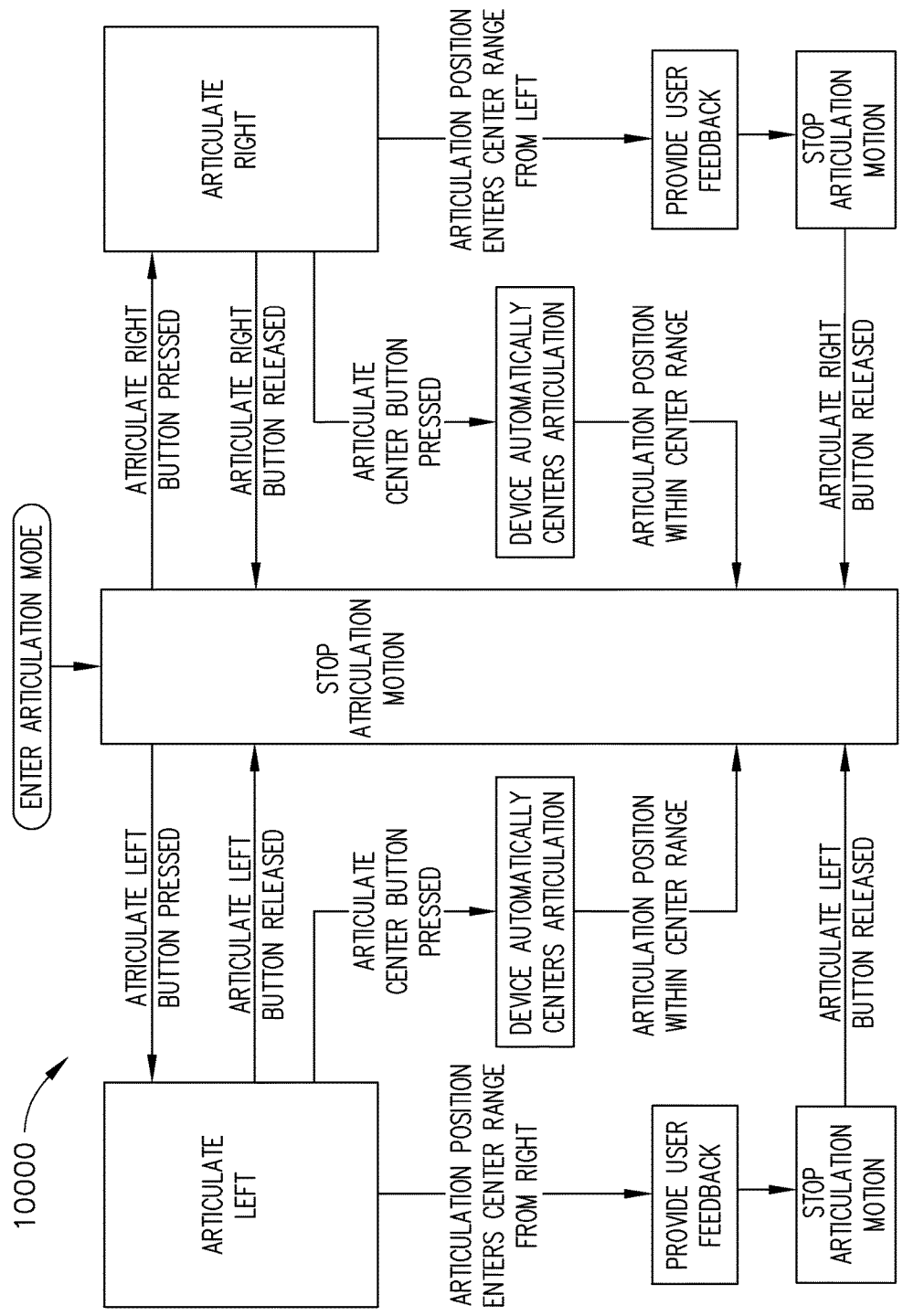
FIG. 92 is a schematic block diagram of a module for use with the surgical instrument of FIG. 87.
Figure 95:
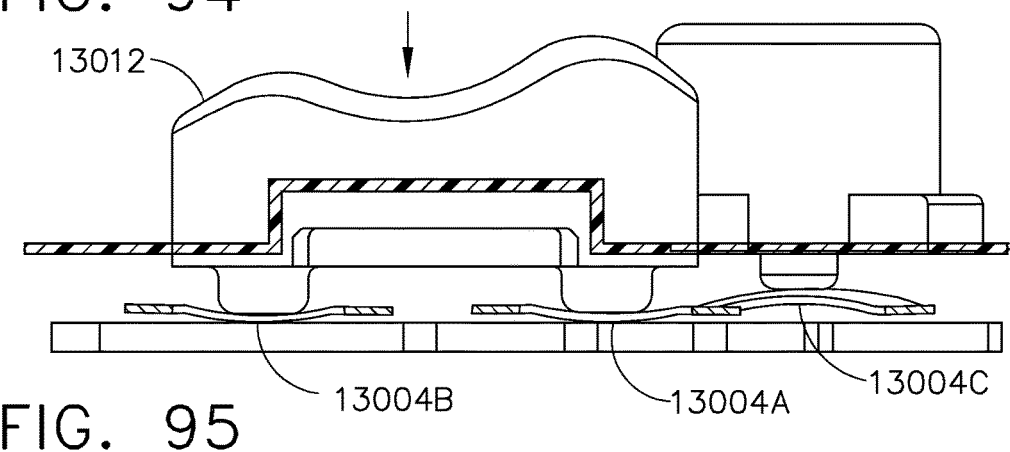
FIG. 95 is a schematic illustration of the interface of FIG. 93 activated to return the end effector to an articulation home state position.

In various instances, referring primarily to FIGS. 89, 92, and 95, the module 10000 may comprise an articulation resetting or centering mechanism. In certain instances, the control system 13000 may include a reset input which may reset or return the end effector 12208 to the articulation home state position if the end effector 12208 is in an articulated position. For example, upon receiving a reset input signal, the processor 13008 may determine the articulation position of the end effector 12208 and, if the end effector 12208 is in the articulation home state position, the processor 13008 may take no action to change the articulation position of the end effector 12208. However, if the end effector 12208 is in an articulated position when the processor 13008 receives a reset input signal, the processor 13008 may activate the motor 12216 to return the end effector 12208 to the articulation home state position. As illustrated in FIG. 95, the operator may depress the rocker 13012 downward to close the dome switches 13004A and 13004B simultaneously, or at least within a short time period from each other, which may transmit the reset input signal to the processor 13008 to reset or return the end effector 12208 to the articulation home state position. The operator may then release the rocker 13012 to allow the rocker 13012 to return to the neutral position and the switches 13004A and 13004B to the open positions. Alternatively, the interface 13001 of the control system 13000 may include a separate reset switch such as, for example, another dome switch which can be independently closed by the operator to transmit the articulation reset input signal to the processor 13008.

Referring again to FIG. 87, the end effector 12208 of the surgical instrument 12200 may include a first jaw comprising an anvil 10002 and a second jaw comprising a channel 10004 configured to receive a staple cartridge 10006 which may include a plurality of staples. In certain instances, the end effector 12208 can be transitioned between an open configuration and a closed configuration to capture tissue between the anvil 10002 and the staple cartridge 10006, for example. Furthermore, the surgical instrument 12200 may include a firing member which can be moved axially between a firing home state position and a fired position to deploy the staples from the staple cartridge 10006 and/or cut the tissue captured between the anvil 10002 and the staple cartridge 10006 when the end effector 12208 is in the closed configuration.

As discussed above, the end effector 12208 can be transitioned between an open configuration and a closed configuration to clamp tissue therein. In at least one embodiment, the anvil 10002 can be moved between an open position and a closed position to compress tissue against the staple cartridge 10006. In various instances, the pressure or force that the anvil 10002 can apply to the tissue may depend on the thickness of the tissue. For a given gap distance between the anvil 10002 and the staple cartridge 10006, the anvil 10002 may apply a larger compressive pressure or force to thicker tissue than thinner tissue. The surgical instrument can include a sensor, such as a load cell, for example, which can detect the pressure or force being applied to the tissue. In certain instances, the thickness and/or composition of the tissue may change while pressure or force is being applied thereto. For instance, fluid, such as blood, for example, contained within the compressed tissue may flow outwardly into the adjacent tissue. In such circumstances, the tissue may become thinner and/or the compressive pressure or force applied to the tissue may be reduced. The sensor configured to detect the pressure of force being applied to the tissue may detect this change. The sensor can be in signal communication with the processor 13008 wherein the processor 13008 can monitor the pressure or force being applied to the tissue and/or the change in the pressure of force being applied to the tissue. In at least one instance, the processor 13008 can evaluate the change in the pressure or force and communicate to the operator of the surgical instrument when the pressure or force has reached a steady state condition and is no longer changing. The processor 13008 can also determine when the change in the pressure or force is at and/or below a threshold value, or rate. For instance, when the change in the pressure or force is above about 10 percent per second, the processor 13008 can illuminate a caution indicator associated with the firing actuator, for example, and when the change in the pressure or force is at or below about 10 percent per second, the processor can illuminate a ready-to-fire indicator associated with the firing actuator, for example. In some circumstances, the surgical instrument may prohibit the firing member from being advanced distally through the end effector 12208 until the change in pressure or force is at and/or below the threshold rate, for example.

In certain instances, the operator of the surgical instrument may elect to deploy only some of the staples stored within the end effector 12208. After the firing member has been sufficiently advanced, in such circumstances, the firing member can be retracted. In various other instances, the operator of the surgical instrument may elect to deploy all of the staples stored within the end effector 12208. In either event, the operator of the surgical instrument can depress a firing actuator extending from the handle assembly 12210 to actuate the motor 12216 and advance the firing member distally. The motor 12216 can be actuated once the firing actuator has been sufficiently depressed. In at least one mode of operation, further depression of the firing actuator may not affect the operation of the motor 12216. The motor 12216 may be operated in the manner dictated by the processor 13008 until the firing actuator is released. In at least one other mode of operation, the degree or amount in which the firing actuator is depressed may affect the manner in which the motor 12216 is operated. For instance, an initial depression of the firing actuator can be detected by the processor 13008 and, in response thereto, the processor 13008 can operate the motor 12216 at a first speed, wherein additional depression of the firing actuator can be detected by the processor 13008 and, in response thereto, the processor 13008 can operate the motor 12216 at a second speed, such as a faster speed, for example. In certain instances, the change in the depression of the firing actuator can be proportional to the change in the motor speed. In at least one instance, the change in the depression of the firing actuator can be linearly proportional to the change in the motor speed. In various circumstances, the further the firing actuator is pulled, the faster the motor 12216 is operated. In certain embodiments, the amount of pressure or force applied to the firing actuator may affect the manner in which the motor 12216 is operated. For instance, an initial pressure or force applied to the firing actuator can be detected by the processor 13008 and, in response thereto, the processor 13008 can operate the motor 12216 at a first speed, wherein additional pressure or force applied to the firing actuator can be detected by the processor 13008 and, in response thereto, the processor 13008 can operate the motor 12216 at a second speed, such as a faster speed, for example. In certain instances, the change in the pressure or force applied to the firing actuator can be proportional to the change in the motor speed. In at least one instance, the change in the pressure or force applied to the firing actuator can be linearly proportional to the change in the motor speed. The disclosure of U.S. Pat. No. 7,845,537, entitled SURGICAL INSTRUMENT HAVING RECORDING CAPABILITIES, which issued on Dec. 7, 2010, is incorporated by reference in its entirety.

As discussed above, the operator of the surgical instrument may elect to deploy all of the staples stored within the end effector 12208. In such circumstances, the operator may depress the firing actuator and then release the actuator when they believe that all of the staples have been deployed during a firing stroke of the firing member. In some instances, the surgical instrument can include an indicator which can be illuminated by the processor 13008 when the firing stroke has been completed. A suitable indicator can comprise a light emitting diode (LED), for example. In certain instances, the operator may believe that a firing stroke has been fully completed even though it may have only been nearly completed. The surgical instrument can comprise at least one sensor configured to detect the position of the firing member within its firing stroke wherein the sensor can be in signal communication with the processor 13008. In the event that the firing stroke is ended at a nearly completed position, the processor 13008 can command the motor 12216 to finish the firing stroke of the firing member. For instance, if the firing member has completed all but the last 5 mm of the firing stroke, for example, the processor 13008 can assume that the operator meant to complete the firing stroke and automatically complete the firing stroke.

Referring again to FIG. 87, the interface 13001 of the surgical instrument 12200 may include a home state input 13014. The operator may utilize the home state input to transmit a home state input signal to the processor 13008 to return the surgical instrument 12200 to home state which may include returning the end effector 12208 to the articulation home state position and/or the firing member to the firing home state position. As illustrated in FIGS. 89 and 93, the home state input 13014 may include a cap or a cover, for example, which can be depressed by the operator to close the switch 13004C and transmit the home state input signal through the circuit 13006C to the processor 13008. In certain instances, the home state input 13014 can be configured to return the end effector 12208 to the articulation home state position, and a separate input can be utilized to return the firing member to the firing home state position. In certain instances, the home state input 13014 can be configured to return the firing member to the firing home state position, and a separate input can be utilized to return the end effector 12208 to the articulation home state position such as, for example, the rocker 13012.

In various instances, the processor 13008 can be configured to cause the firing member to return to the firing home state position and the end effector 12208 to return to the articulation home state position upon receiving the home state input signal from the home state input 13014. In certain instances, the response of the processor 13008 to the home state input signal may depend on whether the surgical instrument 12200 is in a firing mode or an articulation mode; if the processor 13008 determines that the surgical instrument 12200 is in the articulation mode, the processor 13008 may cause the end effector 12208 to return to the articulation home state position in response to the home state input signal, for example; and if the processor 13008 determines that the surgical instrument 12200 is in the firing mode, the processor 13008 may cause the firing member to return to the firing home state position in response to the home state input signal, for example. In certain instances, the firing member can be advanced axially to fire the staples from the staple cartridge 10006 only when the end effector 12208 is in the closed configuration. In such instances, the surgical instrument 12200 can be in the firing mode only when the end effector 12208 is in the closed configuration. In certain instances, the end effector 12208 can be articulated only when the end effector 12208 is in the open configuration. In such instances, the surgical instrument 12200 can be in the articulation mode only when the end effector 12208 is in the open configuration. Accordingly, in certain instances, the processor 13008 can be configured to determine whether the surgical instrument 12200 is in the articulation mode or the firing mode by determining whether the end effector 12208 is in the open configuration or the closed configuration. In certain instances, one or more sensors 13016 (FIG. 89) can be employed by the processor 13008 to determine whether the end effector 12208 is in the open configuration or closed configuration.

Figure 96:
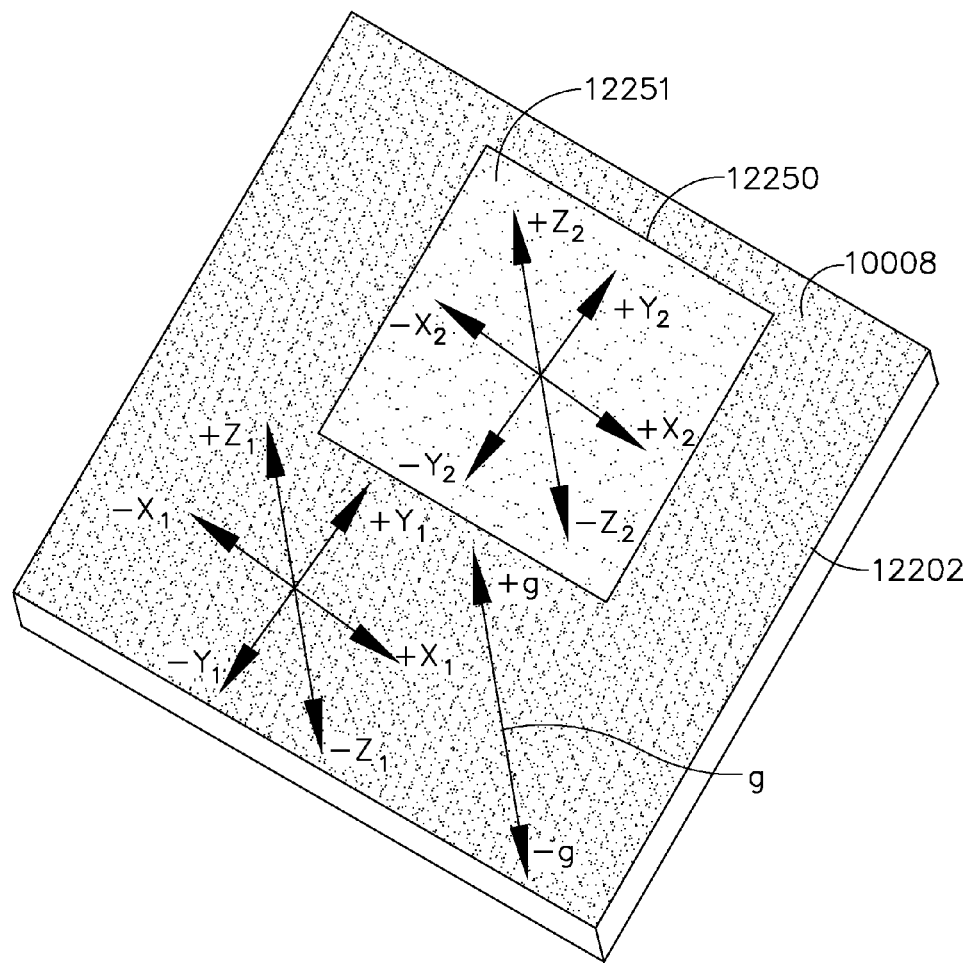
FIG. 96 is a schematic illustration of a partial view of a handle assembly of the surgical instrument of FIG. 87 depicting a display.

Referring now to FIGS. 87 and 96, the surgical instrument 12200 may comprise a screen 12251 which may be included in the handle assembly 12202, for example. The screen 12251 can be employed by one or more of the microcontrollers described herein to alert, guide, and/or provide feedback to the operator of the surgical instrument 12200, for example. The screen 12251 can produce an output display 12250. In use, the operator may tilt, flip, and/or rotate the handle assembly 12202, for example, and, in response, the microcontroller can change the orientation of the output display 12250 to improve, align, and/or adjust the orientation of the output display 12250 with respect to the view of the operator of the surgical instrument 12200 and/or any suitable frame of reference, such as an inertial, or at least substantially inertial, frame of reference, for example. A fixed frame of reference can be defined, at least in part, by gravity. In some instances, the downward acceleration of Earth's gravity can be represented by the vector $-g$ in FIG. 96. In certain instances, a processor, such as the processor 13008, for example, may be configured to detect the changes in the position of the handle assembly 12202 with respect to the frame of reference and adopt one of a plurality of orientations of the screen 12251 in accordance with the relative position of the screen 12251 with respect to the frame of reference.

In certain instances, as illustrated in FIG. 96, the screen 12251 can be disposed on a top surface 10008 of the handle assembly 12202. In various instances, the surface 10008 may extend in a first plane defined by coordinates X1 and Y1 of a first set of Cartesian coordinates representing the handle assembly 12202. In various instances, the screen 12251 may be positioned within the first plane. In some instances, the screen 12251 may be positioned within a plane which extends parallel to the first plane and/or any suitable plane in a fixed relationship relative to the first plane. For the purposes of convenience herein, it will be assumed that the first set of Cartesian coordinates representing the handle assembly are aligned with the screen 12251 and, thus, referred to as a screen set of Cartesian coordinates. The output display 12250 can reside in a second plane defined by coordinates X2 and Y2 of a second, or display, set of Cartesian coordinates. In certain instances, as illustrated in FIG. 96, the first plane can be coplanar with the second plane, for example. Moreover, the first, or screen, set of Cartesian coordinates can be aligned with the second, or display, set of Cartesian coordinates, in at least some instances. For example, +X1 can be aligned with or parallel to +X2, +Y1 can be aligned with or parallel to +Y2, and +Z1 can be aligned with or parallel to +Z2. Correspondingly, in such instances, -X1 can be aligned with or parallel to -X2, -Y1 can be aligned with or parallel to -Y2, and -Z1 can be aligned with or parallel to -Z2. As will be described in greater detail below, the second, or display, set of Cartesian coordinates can be realigned with respect to the first, or screen, set of Cartesian coordinates in certain instances. In various instances, a certain arrangement of the display Cartesian coordinates can be preferred. For instance, a neutral position of the surgical instrument 12200 can coincide with the +Z1 axis of the screen coordinates being aligned with the +g vector. As will be described in greater detail below, the processor 13008 can tolerate a certain amount of deviation between the screen coordinates at the reference frame without changing the alignment of the display coordinates; however, beyond a certain deviation between the screen coordinates at the reference frame, the processor can change the alignment of the display coordinates relative to the screen coordinates.

Figure 97:
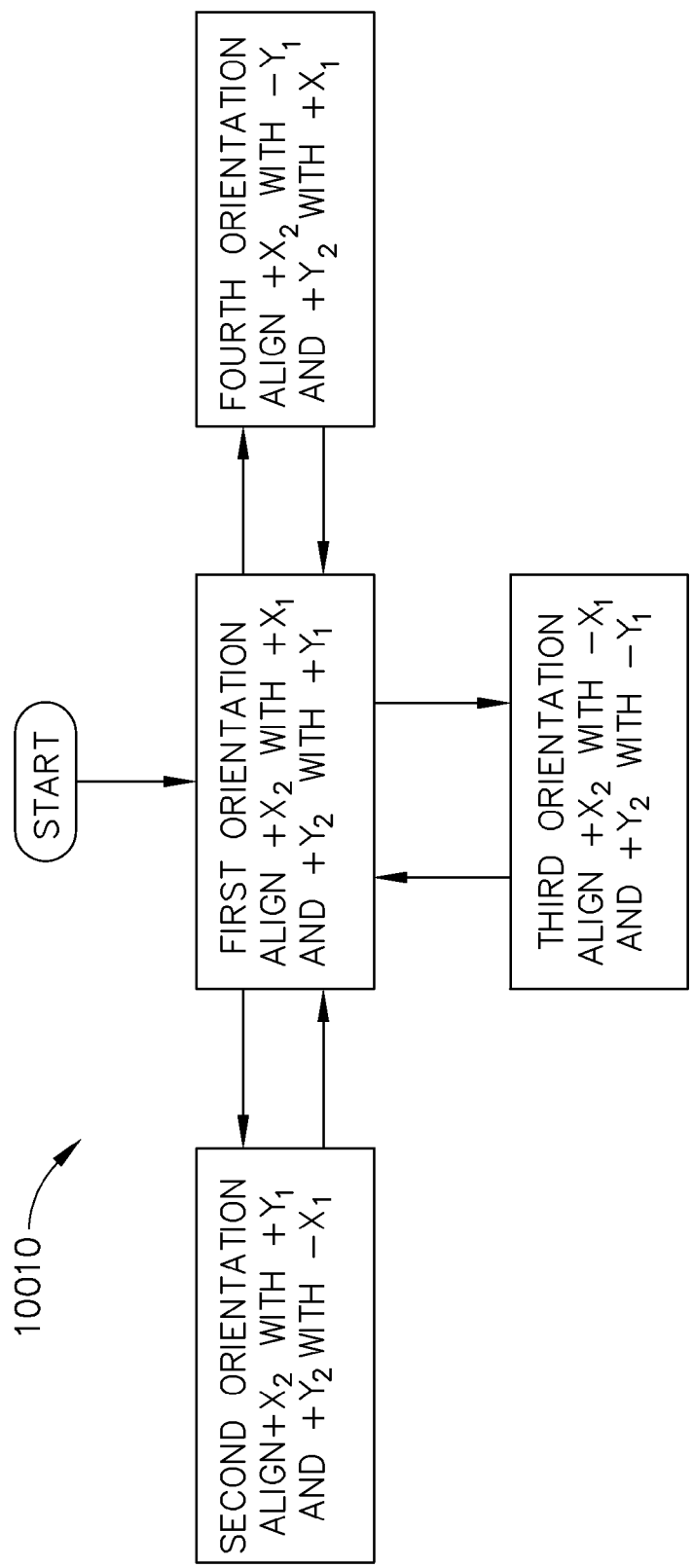
FIG. 97 depicts a module of the surgical instrument of FIG. 87.
Figure 98A:
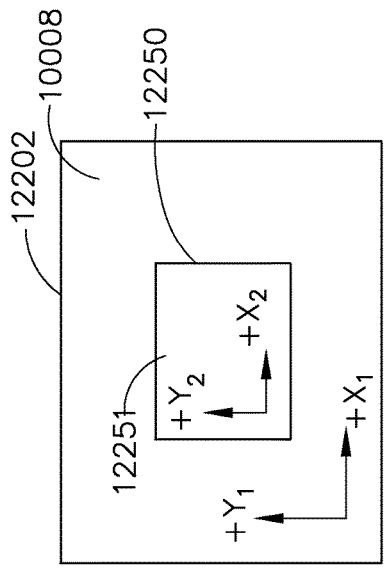
FIG. 98A is a schematic illustration of a screen orientation of the display of FIG. 96.
Figure 98B:
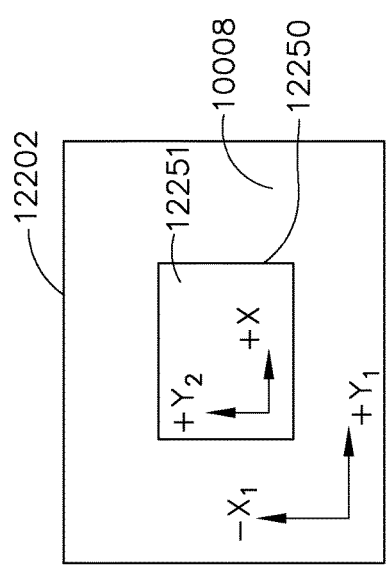
FIG. 98B is a schematic illustration of a screen orientation of the display of FIG. 96.
Figure 98C:
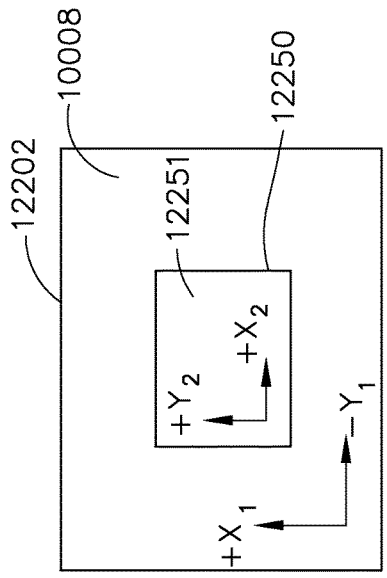
FIG. 98C is a schematic illustration of a screen orientation of the display of FIG. 96.
Figure 98D:
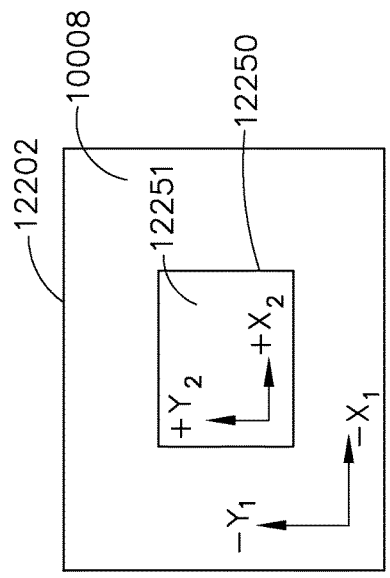
FIG. 98D is a schematic illustration of a screen orientation of the display of FIG. 96.

Referring to FIGS. 97-98D, a module 10010 can be configured to change or alter the orientation of the output display 12250 between a plurality of orientations in response to the changes in the position of the handle assembly 12202 which can be monitored through input from one or more accelerometers (not shown) that can be housed within the handle assembly 12202, for example. As discussed above, and as illustrated in FIG. 98A, the output display 12250 may adopt a first orientation wherein the +X2 and +Y2 vectors of the display set of Cartesian coordinates are aligned, or at least substantially aligned, with the +X1 and +Y1 vectors, respectively, of the screen set of Cartesian coordinates when the surgical instrument is in its neutral position. In certain instances, as illustrated in FIG. 98B, the output display 12250 may adopt a second orientation wherein the +Y2 and +X2 vectors of the display set of Cartesian coordinates are aligned, or at least substantially aligned, with the +Y1 and -X1 vectors, respectively, of the screen set of Cartesian coordinates, for example. In certain instances, as illustrated in FIG. 98C, the output display 12250 may adopt a third orientation wherein the +X2 and +Y2 vectors of the display set of Cartesian coordinates are aligned, or at least substantially aligned, with the -X1 and -Y1 vectors, respectively, of the screen set of Cartesian coordinates, for example. In certain instances, as illustrated in FIG. 98D, the output display 12250 may adopt a fourth orientation wherein the +X2 and +Y2 vectors of the second set of Cartesian coordinates are aligned, or at least substantially aligned, with the -Y1 and +X1 vectors, respectively, of the screen set of Cartesian coordinates, for example. Other orientations are possible.

Referring to FIGS. 97-98D, the processor 13008 can be configured to toggle the orientation of the output display 12250 between a plurality of orientations including the first orientation, the second orientation, the third orientation, and/or the fourth orientation, for example, to accommodate changes in the position of the handle assembly 12202, for example. In certain instances, the module 10010 may include a hysteresis control algorithm to prevent dithering of the orientation while toggling between the first, second, third, and/or fourth orientations, for example. A hysteresis control algorithm can produce a lag between an initial detection of an event that would result in a display orientation change and the processor command to change the display orientation. As such, the hysteresis control algorithm can ignore events which would result in a potentially transient orientation and optimally wait to reorient the display until a steady state, or sufficiently steady state, condition has been reached. In certain instances, the processor 13008 can be configured to orient the output display 12250 in the first orientation when an angle between the +Z1 vector of the Z1 axis and the −g vector of the gravity axis g is less than or equal to a maximum angle, for example. In certain instances, the processor 13008 can be configured to orient the output display 12250 in the second orientation when an angle between the +X1 vector of the X1 axis and the +g vector of the gravity axis g is less than or equal to a maximum angle, for example. In certain instances, the processor 13008 can be configured to orient the output display 12250 in the third orientation when an angle between the +Y1 vector of the Y1 axis and the +g vector of the gravity g axis is less than or equal to a maximum angle, for example. In certain instances, the processor 13008 can be configured to orient the output display 12250 in the fourth orientation when an angle between the +X1 vector of the X1 axis and the −g vector of the gravity axis g is less than or equal to a maximum angle, for example. In certain instances, the maximum angle can be any angle selected from a range of about 0 degrees, for example, to about 10 degrees, for example. In certain instances, the maximum angle can be any angle selected from a range of about 0 degrees, for example, to about 5 degrees, for example. In certain instances, the maximum angle can be about 5 degrees, for example. The maximum angles described above are exemplary and are not intended to limit the scope of the present disclosure.

Referring to FIGS. 97-98D, in certain instances, the processor 13008 can be configured to orient the output display 12250 in the first orientation when the +Z1 vector of the Z1 axis and the −g vector of the gravity axis g are aligned, or at least substantially aligned with each other, for example. In certain instances, the processor 13008 can be configured to orient the output display 12250 in the second orientation when the +X1 vector of the X1 axis and the +g vector of the gravity axis g are aligned, or at least substantially aligned with each other, for example. In certain instances, the processor 13008 can be configured to orient the output display 12250 in the third orientation when the +Y1 vector of the Y1 axis and the +g vector of the gravity g axis are aligned, or at least substantially aligned with each other, for example. In certain instances, the processor 13008 can be configured to orient the output display 12250 in the fourth orientation when the +X1 vector of the X1 axis and the −g vector of the gravity axis g are aligned, or at least substantially aligned with each other, for example.

Referring to FIGS. 97-98D, in certain instances, the processor 13008 can be configured to rotate the output display 12250 from the first orientation to the second orientation if the handle 12212 is rotated clockwise about the longitudinal axis LL (FIG. 87) by an angle selected from a range of about 80 degrees, for example, to about 100 degrees, for example. If the handle 12212 is rotated clockwise about the longitudinal axis LL by less than 80 degrees, the processor 13008 may not reorient the output display 12250, in this example. In certain instances, the processor 13008 can be configured to rotate the display 12250 from the first orientation to the fourth orientation if the handle 12212 is rotated counterclockwise about the longitudinal axis LL by an angle selected from a range of about 80 degrees, for example, to about 100 degrees, for example. If the handle 12212 is rotated counterclockwise about the longitudinal axis LL by less than 80 degrees, the processor 13008 may not reorient the output display 12250, in this example.

As described above, the operator may use the rocker 13012 to articulate the end effector 12208, for example. In certain instances, the operator may move their finger in a first direction to tilt the rocker 13012 to depress the dome switch 13004A to articulate the end effector 12208 in a clockwise direction to the right, for example; and the operator may move their finger in a second direction, opposite the first direction, to depress the dome switch 13004B to articulate the end effector 12208 in a counterclockwise direction to the left, for example.

Depending on the position and/or orientation of the rocker 13012 with respect to the interface 13001 and/or the handle assembly 12202, in certain instances, in a first or neutral position of the handle assembly 12202, the first direction can be an upward direction, for example, and the second direction can be a downward direction, for example, as illustrated in FIGS. 87 and 100A. In such instances, the operator of the surgical instrument 12200 may become accustomed to moving their finger up, for example, to articulate the end effector 12208 to the right, for example; and the operator may become accustomed to moving their finger down, for example, to articulate the end effector 12208 to the left, for example. In certain instances, however, the operator may change the position of the handle assembly 12202 to a second position such as an upside down position, for example, as illustrated in FIG. 100B. In such instances, if the operator does not remember to reverse the direction of movement of their finger, the operator may unintentionally articulate the end effector 12208 in an opposite direction to the direction the operator intended.

Figure 99:
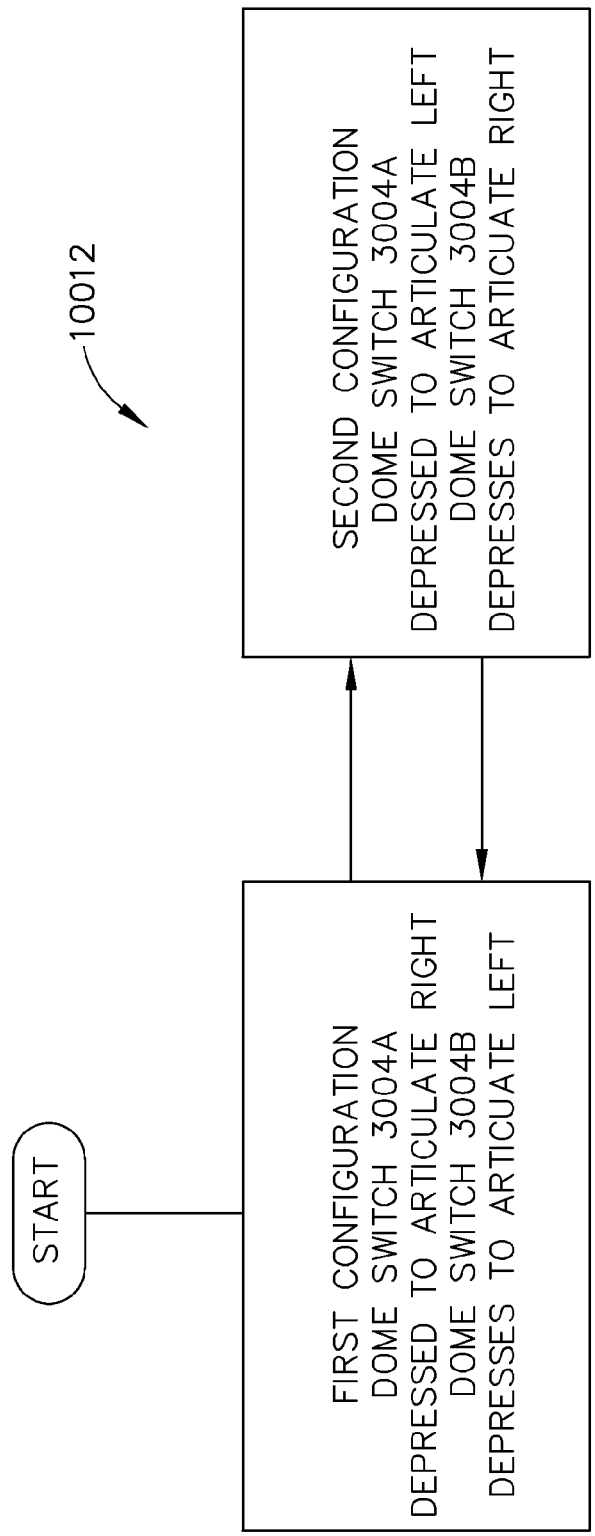
FIG. 99 depicts a module of the surgical instrument of FIG. 87.

Referring to FIG. 99, the surgical instrument 12200 may comprise a module 10012 which may allow the operator to maintain the directions of movement to which a surgeon may have become accustomed with respect to the operation of the surgical instrument 12200. As discussed above, the processor 13008 can be configured to toggle between a plurality of configurations in response to changes in the position and/or orientation of the handle assembly 12202, for example. In certain instances, as illustrated in FIG. 99, the processor 13008 can be configured to toggle between a first configuration of the interface 13001 associated with a first position and/or orientation of the handle assembly 12202, and a second configuration of the interface 13001 associated with a second position and/or orientation of the handle assembly 12202.

In certain instances, in the first configuration, the processor 13008 can be configured to command an articulation motor to articulate the end effector 12208 to the right when the dome switch 13004A is depressed, for example, and the processor 13008 can be configured to command an articulation motor to articulate the end effector 12208 to the left when the dome switch 13004B is depressed, for example. In the second configuration, the processor 3008 can command an articulation motor to articulate the end effector 12208 to the left when the dome switch 13004A is depressed, for example, and the processor 13008 can command an articulation motor to articulate the end effector 12208 to the right when the dome switch 13004B is depressed, for example. In various embodiments, a surgical instrument can comprise one motor to articulate the end effector 12208 in both directions while, in other embodiments, the surgical instrument can comprise a first motor configured to articulate the end effector 12208 in a first direction and a second motor configured to articulate the end effector 12208 in a second direction.

Referring to FIGS. 99-100B, the processor 13008 can be configured to adopt the first configuration while the handle assembly 12202 is in the first position and/or orientation, for example, and adopt the second configuration while the handle assembly 12202 is in the second position and/or orientation, for example. In certain instances, the processor 13008 can be configured to detect the orientation and/or position of the handle assembly 12202 through input from one or more accelerometers (not shown) which can be housed within the handle assembly 12202, for example. Such accelerometers, in various instances, can detect the orientation of the handle assembly 12202 with respect to gravity, i.e., up and/or down.

In certain instances, the processor 13008 can be configured to adopt the first configuration while an angle between a vector D (FIG. 87) extending through the handle assembly 12202 and the gravity vector g is any angle in the range of about 0 degrees, for example, to about 100 degrees, for example. In certain instances, the processor 13008 can be configured to adopt the first configuration while the angle between the vector D and the gravity vector g is any angle in the range of about 0 degrees, for example, to about 90 degrees, for example. In certain instances, the processor 13008 can be configured to adopt the first configuration while the angle between the vector D and the gravity vector g is less than or equal to about 80 degrees, for example.

In certain instances, the processor 13008 can be configured to adopt the second configuration while the angle between the vector D and the gravity vector g is greater than or equal to about 80 degrees, for example. In certain instances, the processor 13008 can be configured to adopt the second configuration while the angle between the vector D and the gravity vector g is greater than or equal to about 90 degrees, for example. In certain instances, the processor 13008 can be configured to adopt the second configuration while the angle between the vector D and the gravity vector g is greater than or equal to about 100 degrees, for example.

The reader will appreciate that the described orientations and/or positions of the handle assembly 12202 and their corresponding configurations which are adopted by the processor 13008 are exemplary in nature and are not intended to limit the scope of the present disclosure. The processor 13008 can be configured to adopt various other configurations in connection with various other orientations and/or positions of the handle assembly 12202.

Referring to FIG. 101, in certain instances, the surgical instrument 12200 can be controlled and/or operated, or at least partially controlled and/or operated, by input from an operator received through a display such as, for example, the display 12250; the display 12250 may comprise a touchscreen adapted to receive the input from the operator which can be in the form of one or more touch gestures. In various instances, the display 12250 may be coupled to a processor such as, for example, the processor 13008 which can be configured to cause the surgical instrument 12200 to perform various functions in response to the touch gestures provided by the operator. In certain instances, the display 12250 may comprise a capacitive touchscreen, a resistive touchscreen, or any suitable touchscreen, for example.

Referring again to FIG. 101, the display 12250 may comprise a plurality of icons which can be associated with a plurality of functions that can be performed by the surgical instrument 12200. In certain instances, the processor 13008 can be configured to cause the surgical instrument 12200 to perform a function when an icon representing such function is selected, touched, and/or pressed by the operator of the surgical instrument 12200. In certain instances, a memory such as, for example, the memory 13010 may comprise one or more modules for associating the plurality of icons with the plurality of functions.

In certain instances, as illustrated in FIG. 101, the display 12250 may include a firing icon 10014, for example. The processor 13008 can be configured to detect a firing input signal when the operator touches and/or presses the firing icon 10014. In response to the detection of the firing input signal, the processor 13008 can be configured to activate the motor 12216 to motivate a firing member of the surgical instrument 12200 to fire the staples from the staple cartridge 10006 and/or cut tissue captured between the anvil 10002 and the staple cartridge 10006, for example. In certain instances, as illustrated in FIG. 101, the display 12250 may include an articulation icon 10016 for articulating the end effector 12208 in a first direction such as, for example, a clockwise direction, for example; the display 12250 may also include an articulation icon 10018 for articulating the end effector 12208 in a second direction such as, for example, a counterclockwise direction. The reader will appreciate that the display 12250 may comprise various other icons associated with various other functions that the processor 13008 may cause the surgical instrument 12200 to perform when such icons are selected, touched, and/or pressed by the operator of the surgical instrument 12200, for example.

In certain instances, one or more of the icons of the display 12250 may comprise words, symbols, and/or images representing the function that can be performed by touching or pressing the icons, for example. In certain instances, the articulation icon 10016 may show an image of the end effector 12208 articulated in the clockwise direction. In certain instances, the articulation icon 10018 may show an image of the end effector 12208 articulated in the counterclockwise direction. In certain instances, the firing icon 10014 may show an image of the staples being fired from the staple cartridge 10006.

Figure 102:
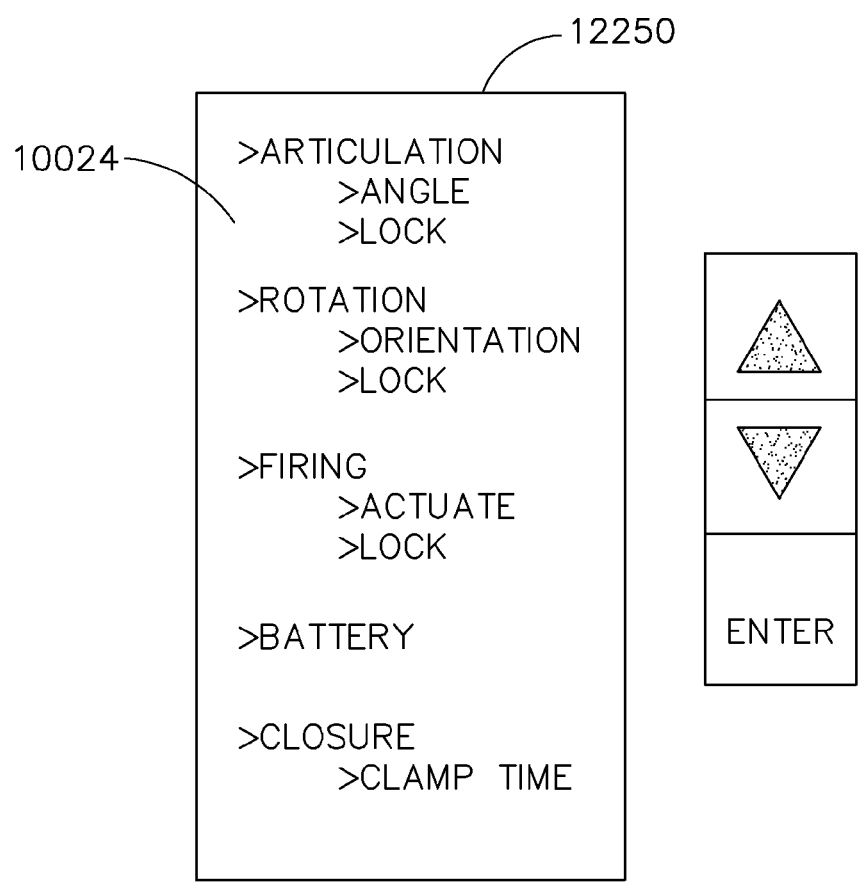
FIG. 102 is a schematic illustration of the display of FIG. 96 showing a navigational menu.
Figure 103:
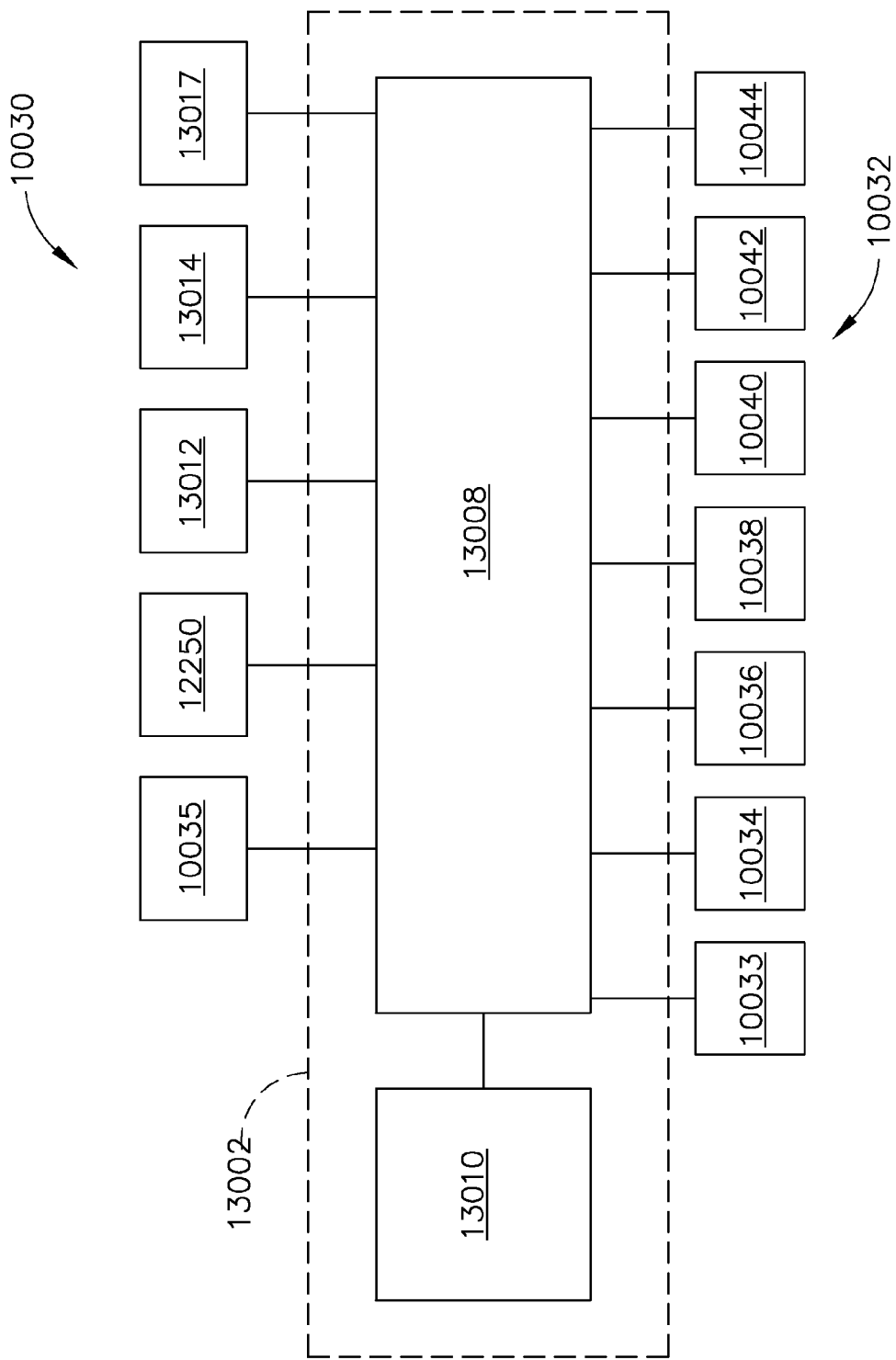
FIG. 103 is a schematic block diagram of an indicator system of the surgical instrument of FIG. 87.

Referring to FIGS. 87 and 102, the interface 13001 of the surgical instrument 12200 may comprise a plurality of operational controls such as, for example, a closure trigger 10020, a rotation knob 10022, the articulation rocker 13012, and/or a firing input 13017 (FIG. 103). In certain instances, various operational controls of the interface 13001 of the surgical instrument 12200 may serve, in addition to their operational functions, as navigational controls. In certain instances, the surgical instrument 12200 may comprise an operational mode and a navigational mode. In the operational mode, some or all of the controls of the surgical instrument 12200 may be configured to perform operational functions; and in the navigational mode, some or all of the controls of the surgical instrument 12200 may be configured to perform navigational functions. In various instances, the navigational functions performed by some or all of the controls of the surgical instrument 12200 can be related to, associated with, and/or connected to the operational functions performed by the controls. In other words, the operational functions performed by the controls of the surgical instrument 12200 may define the navigational functions performed by such controls.

Referring to FIGS. 87 and 102, in certain instances, a processor such as, for example, the processor 13008 can be configured to toggle between a primary interface configuration while the surgical instrument 12200 is in the operational mode and a secondary interface configuration while the surgical instrument 12200 is in the navigational mode; the processor 13008 can be configured to assign operational functions to some or all of the controls of the interface 13001 in the operational mode and assign navigational functions to such controls in the navigational mode, for example. In certain instances, the navigational functions of the controls in the secondary interface configuration are defined by the operational functions of the controls in the primary interface configuration, for example.

Referring to FIG. 102, in certain instances, the operator of the surgical instrument 12200 may activate the navigational mode by opening or activating a navigational menu 10024 in the display 12250, for example. In certain instances, the surgical instrument 12200 may comprise a navigational mode button or a switch (not shown) for activating the navigational mode. In any event, the processor 13008 may switch the controls of the interface 13001 from the primary interface configuration to the secondary interface configuration upon receiving a navigational mode input signal.

As illustrated in FIG. 102, the navigational menu 10024 may comprise various selectable categories, menus, and/or folders and/or various subcategories, sub-menus, and/or subfolders. In certain instances, the navigational menu 10024 may comprise an articulation category, a firing category, a closure category, a battery category and/or, rotation category, for example.

In certain instances, the articulation rocker 13012 can be utilized to articulate the end effector 12208, in the operational mode, as described above, and can be utilized to select the articulation category, and/or launch and/or navigate an articulation menu in the navigational mode, for example. In certain instances, the firing input 13017 (FIG. 103) can be utilized to fire the staples, in the operational mode, as described above, and can be utilized to select the firing category, and/or launch and/or navigate a firing menu in the navigational mode, for example. In certain instances, the closure trigger 10020 can be utilized to transition the end effector 12208 between an open configuration and an approximated configuration in the operational mode, as described above, and can be utilized to select the closure category, and/or launch and/or navigate a closure menu in the navigational mode, for example. In certain instances, the rotation knob 10022 can be utilized to rotate the end effector 12208 relative to the elongate shaft 12204 in the operational mode, and can be utilized to select the rotation category, and/or launch and/or navigate a rotation menu in the navigational mode, for example.

Referring primarily to FIGS. 87 and 103, the operation of the surgical instrument 12200 may involve a series or a sequence of steps, actions, events, and/or combinations thereof. In various circumstances, as illustrated in FIG. 103, the surgical instrument 12200 may include an indicator system 10030 which can be configured to guide, alert, and/or provide feedback to the operator of the surgical instrument 12200 with respect to the various steps, actions, and/or events.

In various instances, the indicator system 10030 may include a plurality of indicators 10032. In certain instances, the indicators 10032 may comprise, for example, visual indicators such as a display screens, backlights, and/or LEDs, for example. In certain instances, the indicators 10032 may comprise audio indicators such as speakers and/or buzzers, for example. In certain instances, the indicators 10032 may comprise tactile indicators such as haptic actuators, for example. In certain instances, the indicators 10032 may comprise combinations of visual indicators, audio indicators, and/or tactile indicators, for example.

Referring to FIG. 103, the indicator system 10030 may include one or more microcontrollers such as, for example, the microcontroller 13002 which may comprise one or more processors such as, for example, the processor 13008 and/or one or more memory units such as, fore example, the memory 13010. In various instances, the processor 13008 may be coupled to various sensors 10035 and/or feedback systems which may be configured to provide feedback to the processor 13008 regarding the status of the surgical instrument 12200 and/or the progress of the steps, actions, and/or events pertaining to the operation of the surgical instrument 12200, for example.

In various instances, the operation of the surgical instrument 12200 may include various steps including an articulation step, a closure step, a firing step, a firing reset step, a closure reset step, an articulation reset step, and/or combinations thereof, for example. In various instances, the articulation step may involve articulating the end effector 12208 relative to the elongate shaft 12204 to an articulated position, for example; and the articulation reset step may involve returning the end effector 12208 to an articulation home state position, for example. In various instances, the closure step may involve transitioning the end effector 12208 to a closed configuration, for example; and the closure reset step may involve transitioning the end effector 12208 to an open configuration, for example. In various instances, the firing step may involve advancing a firing member to deploy staples from the staple cartridge 10006 and/or cut tissue captured by the end effector 12208, for example. In various instances, the firing reset step may involve retraction of the firing member to a firing home state position, for example.

Referring to FIG. 103, one or more of the indicators 10032 of the indicator system 10030 can be associated with one or more of the various steps performed in connection with the operation of the surgical instrument 12200. In various instances, as illustrated in FIG. 103, the indicators 10032 may include a bailout indicator 10033 associated with the bailout assembly 12228, an articulation indicator 10034 associated with the articulation step, a closure indicator 10036 associated with the closure step, a firing indicator 10038 associated with the firing step, an articulation reset indicator 10040 associated with the articulation reset step, a closure reset indicator 10042 associated with the closure reset step, and/or a firing reset indicator 10044 associated with the firing reset step, for example. The reader will appreciate that the above described steps and/or indicators are exemplary in nature and are not intended to limit the scope of the present disclosure. Various other steps and/or indicators are contemplated by the present disclosure.

Referring to FIG. 87, in various instances, one or more of the controls of the interface 13001 can be employed in one or more of the steps of operation of the surgical instrument 12200. In certain instances, the closure trigger 10020 can be employed in the closure step, for example. In certain instance, the firing input 13017 (FIG. 103) can be employed in the firing step, for example. In certain instances, the articulation rocker 13012 can be employed in the articulation step and/or the articulation reset step, for example. In certain instances, the home state input 13014 can be employed in the firing reset step, for example.

Referring to FIG. 103, in various instances, the indicators 10032 associated with one of the steps of operation of the surgical instrument 10030 may also be associated with the controls employed in such steps. For example, the articulation indicator 10034 can be associated with the articulation rocker 13012, the closure indicator 10036 can be associated with the closure trigger 10020, the firing indicator 10038 can be associated with the firing input 13017, and/or the firing reset indicator 10044 can be associated with the home state input 13014. In certain instances, associating an indicator with a control of the interface 13001 may include placing or positioning the indicator on, within, partially within, near, and/or in close proximity to the control, for example, to aid the operator in associating the indicator with the control. The reader will appreciate that the above described controls and/or the indicators associated with such controls are exemplary in nature and are not intended to limit the scope of the present disclosure. Various other controls and the indicators associated with such controls are contemplated by the present disclosure.

In various instances, the processor 13008 can be configured to activate the indicators 10032 in one or more sequences defined by the order of the steps associated with the indicators 10032. For example, the operator may need to operate the surgical instrument 12200 in a series of steps starting with the articulation step followed by the closure step, and further followed by the firing step. In such example, the processor 13008 can be configured to guide the operator through the sequence of steps by activating the corresponding articulation indicator 10034, closure indicator 10036, and firing indicator 10038 in the same order as the order of the steps. In other words, the processor 13008 can be configured to first activate the articulation indicator 10034 followed by the closure indicator 10036, and further followed by the firing indicator 10038, for example. In certain instances, the surgical instrument 12200 may comprise a bypass switch (not shown) which may be configured to allow the operator to bypass a step that is recommended but not required, for example. In such instances, pressing the bypass switch may signal the processor 13008 to activate the next indicator in the sequence.

In various instances, the processor 13008 can be configured to toggle the indicators 10032 between a plurality of indicator configurations to guide, alert, and/or provide feedback to the operator of the surgical instrument 12200. In various instances, the processor 13008 may provide visual cues to the operator of the surgical instrument 12200 by the toggling of the indicators 10032 between the plurality of indicator configurations which may include activated and/or deactivated configurations, for example. In certain instances, one or more of the indicators 10032 may comprise a light source which can be activated in a first indicator configuration, for example, to alert the operator to perform a step associated with the indicators 10032, for example; and the light source can be deactivated in a second indicator configuration, for example, to alert the operator when the step is completed, for example.

In certain instances, the light source can be a blinking light which can be transitioned by the processor 13008 between a blinking configuration and a non-blinking configuration. In certain instances, the blinking light, in the non-blinking configuration, may be transitioned to solid illumination or turned off, for example. In certain instances, the blinking light, in the blinking configuration, may represent a waiting period while a step is in progress, for example.

In certain instances, the blinking frequency of the blinking light may be changed to provide various visual cues. For example, the blinking frequency of the blinking light that represents a waiting period may be increased or decreased as the waiting period approaches its completion. The reader will appreciate that the waiting period can be a forced waiting period and/or a recommended waiting period, for example. In certain instances, forced waiting periods can be represented by a blinking configuration different from recommended waiting periods. In certain instances, the blinking light may comprise a first color representing a forced waiting period and a second color representing a recommended waiting period, wherein the first color is different from the second color. In certain instances, the first color can be a red color, for example, and the second color can be a yellow color, for example.

In various instances, one or more of the indicators 10032 can be toggled by the processor 13008 between a first indicator configuration representing controls that are available for use in a standard next step of the steps of operation of the surgical instrument 12200, a second indicator configuration representing controls that are available for use in a non-standard next step of the steps of operation of the surgical instrument 12200, and/or a third indicator configuration representing controls that are not available for use in a next step of the steps of operation of the surgical instrument 12200, for example. For instance, when the end effector 12208 of the surgical instrument 12000 is in an open configuration, the articulation indicator 10034 and the closure indicator 10036 can be illuminated indicating to the operator of the surgical instrument 12200 that those two functions, i.e., end effector articulation and end effector closure, are available to the operator at that moment. In such a state, the firing indicator 10038 may not be illuminated indicating to the operator that the firing function is not available to the operator at that moment. Once the end effector 12208 has been placed in a closed and/or clamped configuration, the articulation indicator 10034 may be deilluminated indicating to the operator that the articulation function is no longer available at that moment. In such a state, the illumination of the closure indicator 10036 may be reduced indicating to the operator that the closing function can be reversed at that moment. Moreover, in such a state, the firing indicator 10038 can become illuminated indicating to the operator that the firing function is available to the operator at that moment. Once the firing member has been at least partially advanced, the closure indicator 10036 may be deilluminated indicating that the closing function cannot be reversed at that moment. When the firing member is retracted back to its unfired position, the illumination of the firing indicator 10038 may be reduced indicating to the operator that the firing member can be readvanced, if needed. Alternatively, once the firing member has been retracted, the firing indicator 10038 may be deilluminated indicating to the operator that the firing member cannot be readvanced at that moment. In either event, the closure indicator 10036 can be reilluminated after the firing member has been retracted back to its unfired position indicating to the operator that the closing function can be reversed at that moment. The articulation indicator 10034 may remain deilluminated indicating that the articulation function is not available at that moment. Once the end effector 12208 has been opened, the firing indicator 10038 can be deilluminated, if it hadn't been deilluminated already, indicating to the operator that the firing function is not available at that moment, the closing indicator 10036 can remain illuminated or its illumination can be reduced indicating to the operator that the closing function is still available at that moment, and the articulation indicator 10034 can be reilluminated indicating to the operator that the articulation function is available at that moment. The example provided above is exemplary and other embodiments are possible.

In certain instances, the one or more of the indicators 10032 may include a light source that can be toggled by the processor 13008 between a first color in the first indicator configuration, a second color in the second indicator configuration, and/or a third color in the third indicator configuration, for example. In certain instances, the indicators 10032 can be toggled by the processor 13008 between the first indicator configuration, the second indicator configuration, and/or the third indicator configuration by changing the light intensity of the light source or scanning through the color spectrum, for example. In certain instances, the first indicator configuration may comprise a first light intensity, for example, the second indicator configuration may comprise a second light intensity, for example, and/or the third indicator configuration may comprise a third indicator configuration, for example.

In various instances, in the firing step of operation of the surgical instrument 12200, the firing member can be motivated to deploy the plurality of staples from the staple cartridge 10006 into tissue captured between the anvil 10002 and the staple cartridge 10006, and advance a cutting member (not shown) to cut the captured tissue. The reader will appreciate that advancing the cutting member to cut the captured tissue in the absence of a staple cartridge or in the presence of a spent staple cartridge may be undesirable. Accordingly, in various instances, the surgical instrument 12200 may comprise a lockout mechanism (not shown) which can be activated to prevent advancement of the cutting member in the absence of a staple cartridge or in the presence of a spent staple cartridge, for example.

Figure 104:
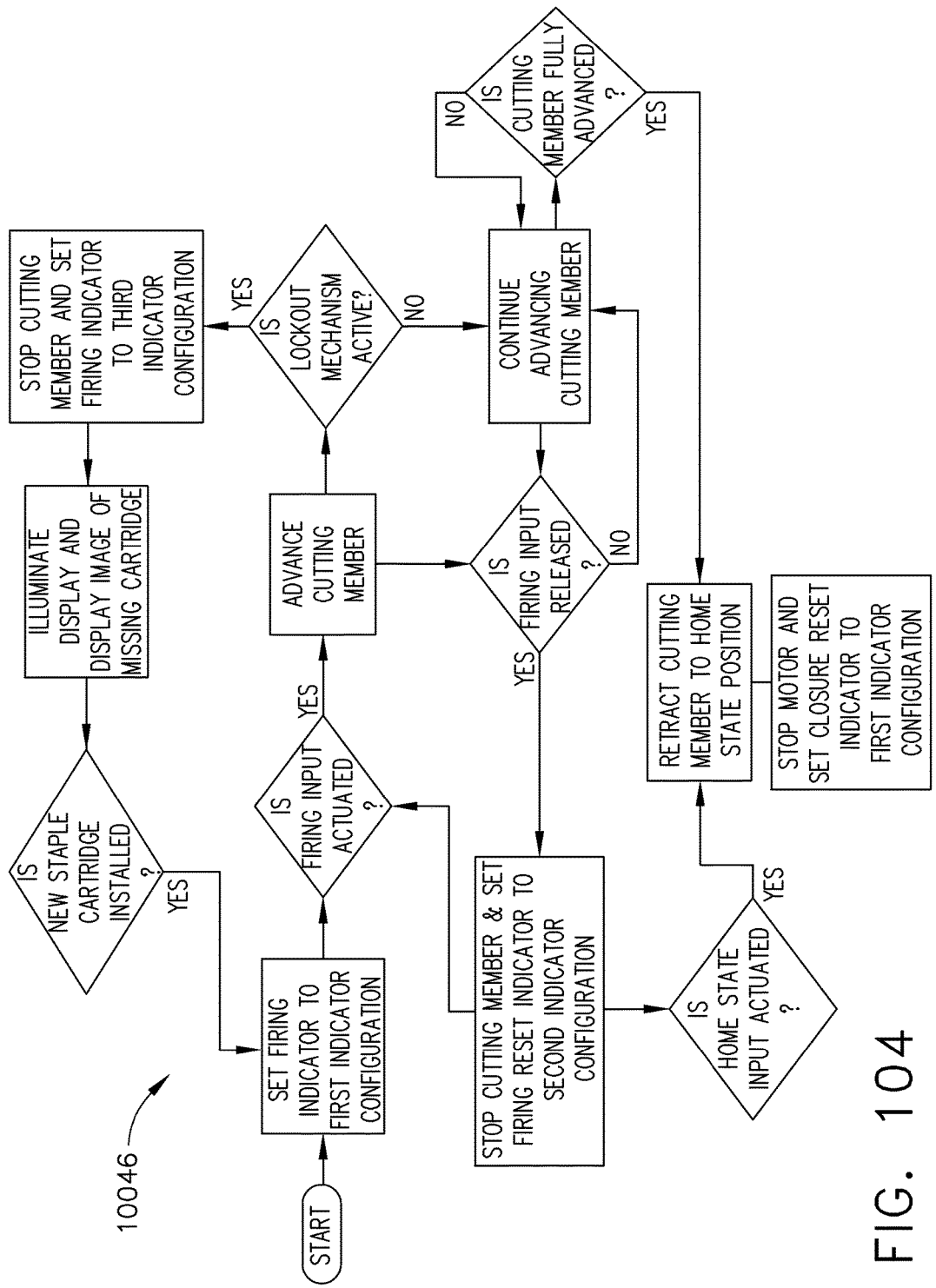
FIG. 104 is a module of the surgical instrument of FIG. 87.

Referring to FIG. 104, a module 10046 can be employed by an indicator system such as, for example, the indicator system 10030 (FIG. 103). In various instances, the module 10046 may comprise program instructions stored in one or more memory units such as, for example, the memory 13010, which when executed may cause the processor 13008 to employ the indicators 10032 to alert, guide, and/or provide feedback to the operator of the surgical instrument 12200 during the firing step of operation of the surgical instrument 12200, for example. In certain instances, one or more of the indicators 10032 such as the firing indicator 10038 and/or the firing reset indicator 10044, for example, can be toggled by the processor 13008 between the first indicator configuration, the second indicator configuration, and/or the third indicator configuration to alert, guide, and/or provide feedback to the operator of the surgical instrument 12200 during the firing step of operation of the surgical instrument 12200, for example.

Referring to FIGS. 103 and 104, the operator of the surgical instrument 12200 may actuate the firing input 13017 to cause the processor 13008 to activate the motor 12216, for example, to motivate the firing member to deploy the plurality of staples from the staple cartridge 10006 into the captured tissue and advance the cutting member to cut the captured tissue. In certain instances, the firing indicator 10038 can be set to the first indicator configuration to alert the operator that the firing input 13017 is available for use and/or is one of the standard control options available for completion of the firing step.

In certain instances, as illustrated in FIGS. 103 and 104, if the processor 13008 detects that the lockout mechanism is active, the processor 13008 may stop the advancement of the cutting member by stopping and/or deactivating the motor 12216, for example. In addition, the processor 13008 can be configured to transition the firing indicator 10038 from the first indicator configuration to the third indicator configuration to caution the operator that the firing input 13017 is not available for use. In certain instances, the processor 13008 may also be configured to illuminate the display 12250 and display an image of a missing staple cartridge, for example. In certain instances, the processor 13008 may also set the firing reset indicator 10044 to the first indicator configuration, for example, to inform the operator that home state input 13014 is available for use to motivate the firing member to retract the cutting member to the firing home state position, for example. In certain instances, the processor 13008 can be configured to detect the installation of a new staple cartridge, through the sensors 10035 for example, and in response, return the firing indicator 10038 to the first indicator configuration, for example.

In certain instances, as illustrated in FIG. 104, if the operator releases the firing input 13017 before completion of the firing step, the processor 13008 can be configured to stop the motor 12216. In certain instances, the processor 13008 may also maintain the firing indicator 10038 in the first indicator configuration, for example, to alert the operator that the firing input 13017 is available for use as the standard control option available for completion of the firing step of operation of the surgical instrument 12200, for example. In certain instances, the processor 13008 may also set the firing reset indicator 10044 to the second indicator configuration, for example, to inform the operator that home state input 13014 is available for use as a non-standard control option available for use to retract the cutting member to the firing home state position, for example, if the operator decides to abort the firing step of operation of the surgical instrument 12200, for example.

Further to the above, as illustrated in FIG. 104, if the firing input 13017 is re-actuated by the operator, the processor 13008 may, in response, reactivate the motor 12216 to continue advancing the cutting member until the cutting member is fully advanced. In certain instances, the processor 13008 may employ the sensors 10035 to detect when the cutting member is fully advanced; the processor 13008 may then reverse the direction of rotation of the motor 12216, for example, to motivate the firing member to retract the cutting member to the firing home state position, for example. In certain instances, the processor 13008 can be configured to stop the motor 12216, for example, and/or set the closure reset indicator 10042 to the first indicator configuration, for example, if the processor detects that the cutting member has reached the firing home state position, for example.

As described herein, a surgical instrument can enter into various operational states, modes, and/or configurations. In certain instances, the instrument may enter into an operational state, mode, and/or configuration that is undesired by the operator who may be unsure as to how to remove the instrument from that undesired state, mode, and/or configuration. In at least one instance, the surgical instrument can include a reset button which, when actuated, can place the instrument in a default state, mode, and/or configuration. For instance, the default state, mode, and/or configuration can comprise an operational mode, and not a navigational mode. In at least one instance, the default state and/or configuration can comprise a certain orientation of the display output 12250, for example. The reset button can be in signal communication with the processor 13008 which can place the surgical instrument in the default state, mode, and/or configuration. In certain instances, the processor 13008 can be configured to hold the surgical instrument in the default state, mode, and/or configuration. In at least one instance, the surgical instrument can include a lock button which, when actuated, can lock the surgical instrument in its default state, mode, and/or configuration. In certain instance, a lock button can lock the surgical instrument in its current state, mode, and/or configuration. The operational state, mode, and/or configuration can be unlocked by actuating the lock button once again. In various embodiments, the surgical instrument can include at least one accelerometer in signal communication with the processor 13008 which can determine when the instrument handle is being shaken or being moved back and forth quickly. When such shaking is sensed, the processor 13008 can place the surgical instrument into a default operation state, mode, and/or configuration.

Figure 105:
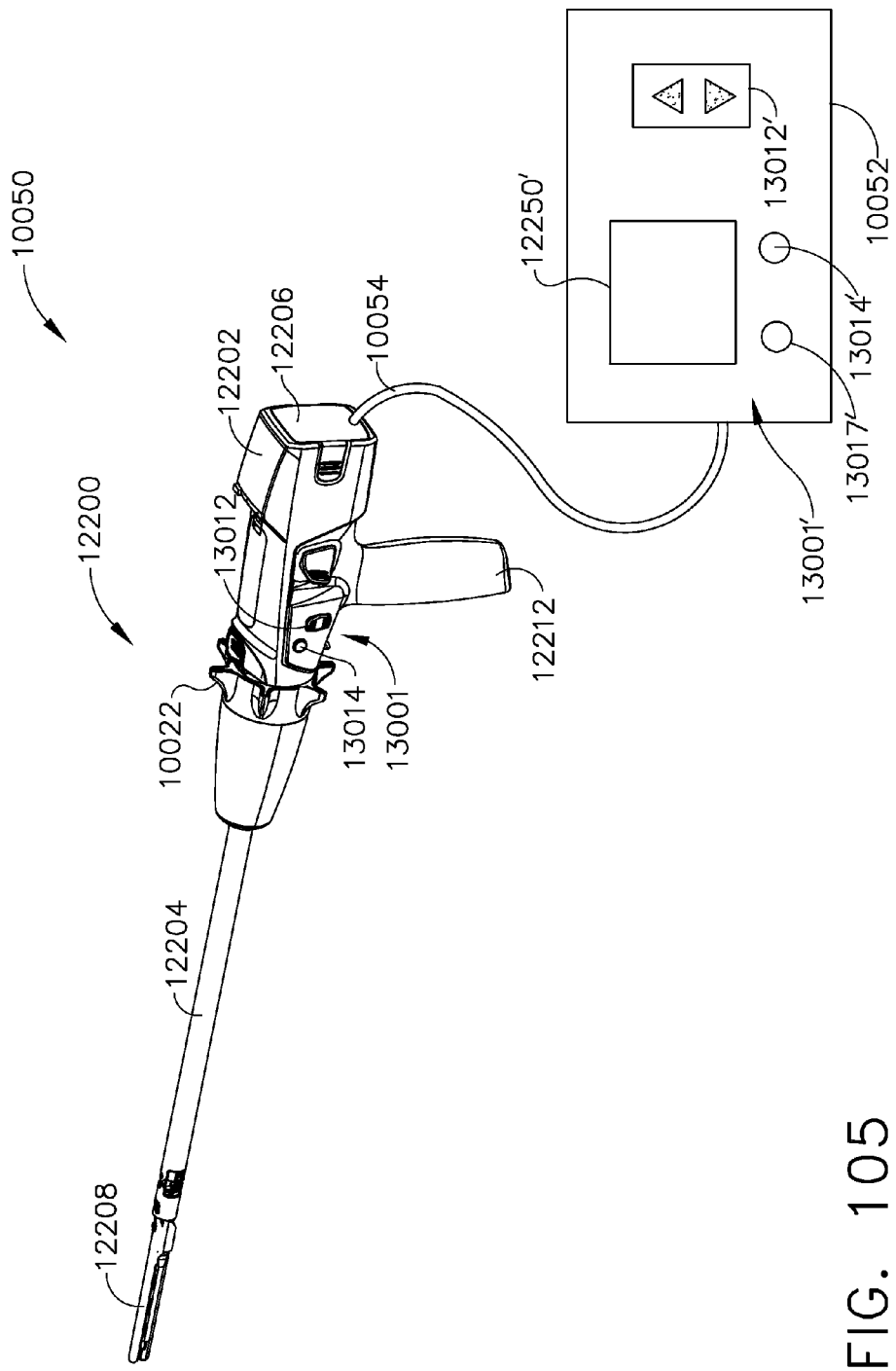
FIG. 105 is a perspective view of the surgical instrument of FIG. 87 coupled to a remote operating unit.

Referring to FIG. 105, in various instances, a surgical assembly 10050 may include a surgical instrument such as, for example, the surgical instrument 12200 and a remote operating unit 10052. In certain instances, the surgical instrument 12200 may comprise a primary interface such as, for example, the interface 13001 which may reside in the handle assembly 12202, as illustrated in FIG. 87. In certain instances, the interface 13001 may include a plurality of primary controls such as, for example, the closure trigger 10020 (FIG. 87), the rotation knob 10022, the articulation rocker 13012, the home state input 13014, and/or the firing input 13017 (FIG. 103).

In various instances, an operator of the surgical instrument 12200 may manually operate the primary controls of the interface 13001 to perform a surgical procedure, for example. As described above, the operator may actuate the articulation rocker 13012 to activate the motor 12216 to articulate the end effector 12208 between an unarticulated position and an articulated position, for example. In certain instances, the operator may actuate the closure trigger 10020 to transition the end effector 12208 between an open configuration and a closed configuration, for example. In certain instances, the operator may actuate the firing input 13017 to activate the motor 12216 to motivate the firing member of the surgical instrument 12200 to fire the staples from the staple cartridge 10006 and/or cut tissue captured between the anvil 10002 and the staple cartridge 10006, for example.

In various instances, the operator of the surgical instrument 12200 may not be sufficiently close in proximity to the handle assembly 12202 to be able to manually operate the interface 13001. For example, the operator may operate the surgical instrument 12200 together with a robotically-controlled surgical system, which may be controlled from a remote location. In such instances, the operator may need to operate the surgical instrument 12200 from the remote location where the operator operates the robotically-controlled surgical system, for example; the operator may employ the remote operating unit 10052 to operate the surgical instrument 12200 remotely, for example. Various robotic systems, instruments, components, and methods are disclosed in U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719, which is incorporated by reference herein in its entirety.

Figure 106:
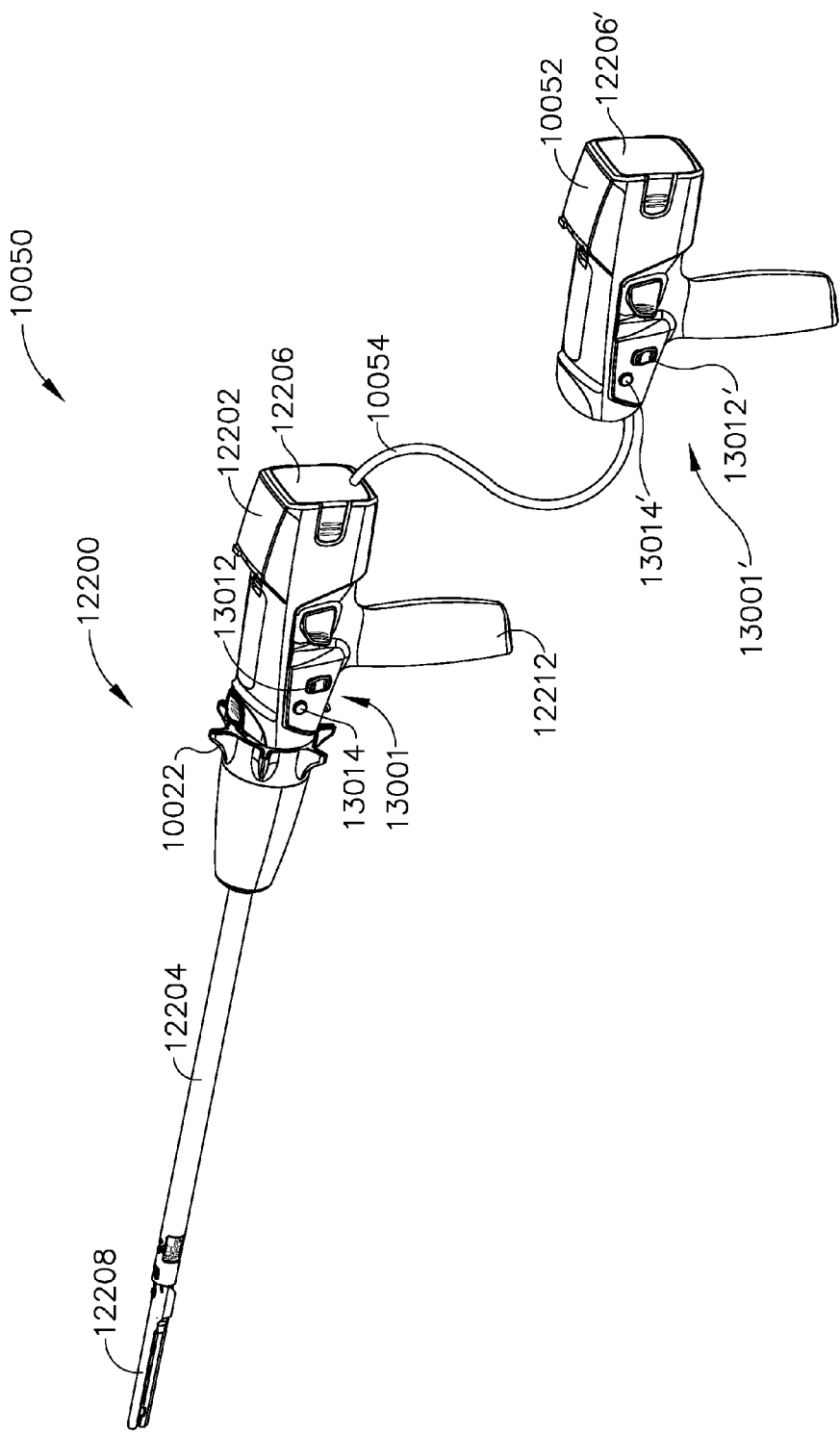
FIG. 106 is a perspective view of the surgical instrument of FIG. 87 coupled to a remote operating unit.

Referring to FIGS. 105 and 106, the remote operating unit 10052 may include a secondary interface 13001', a display 12250', and/or a power assembly 12206' (or "power source" or "power pack"), for example. In various instances, the secondary interface 13001' may include a plurality of secondary controls which may correspond to the primary controls of the primary interface 13001'. In certain instances, the remote operating unit 10052 may include a remote articulation rocker 13012' corresponding to the articulation rocker 13012, for example. In certain instances, the remote operating unit 10052 may include a remote firing input 13017' corresponding to the firing input 13017 of the surgical instrument 12200, for example. In certain instances, the remote operating unit 10052 may include a remote home state input 13014' corresponding to the home state input 13014 of the surgical instrument 12200, for example.

In certain instances, as illustrated in FIG. 105, the remote operating unit 10052, the interface 13001', and/or the plurality of secondary controls may comprise a different shape and/or design from the handle assembly 12202, the interface 13001, and/or the plurality of primary controls, respectively. In certain instances, as illustrated in FIG. 106, the remote operating unit 10052, the interface 13001', and/or the plurality of secondary controls may comprise the same, or at least substantially the same, shape and/or design to the handle assembly 12202, the interface 13001, and/or the plurality of primary controls, respectively.

Figure 107:
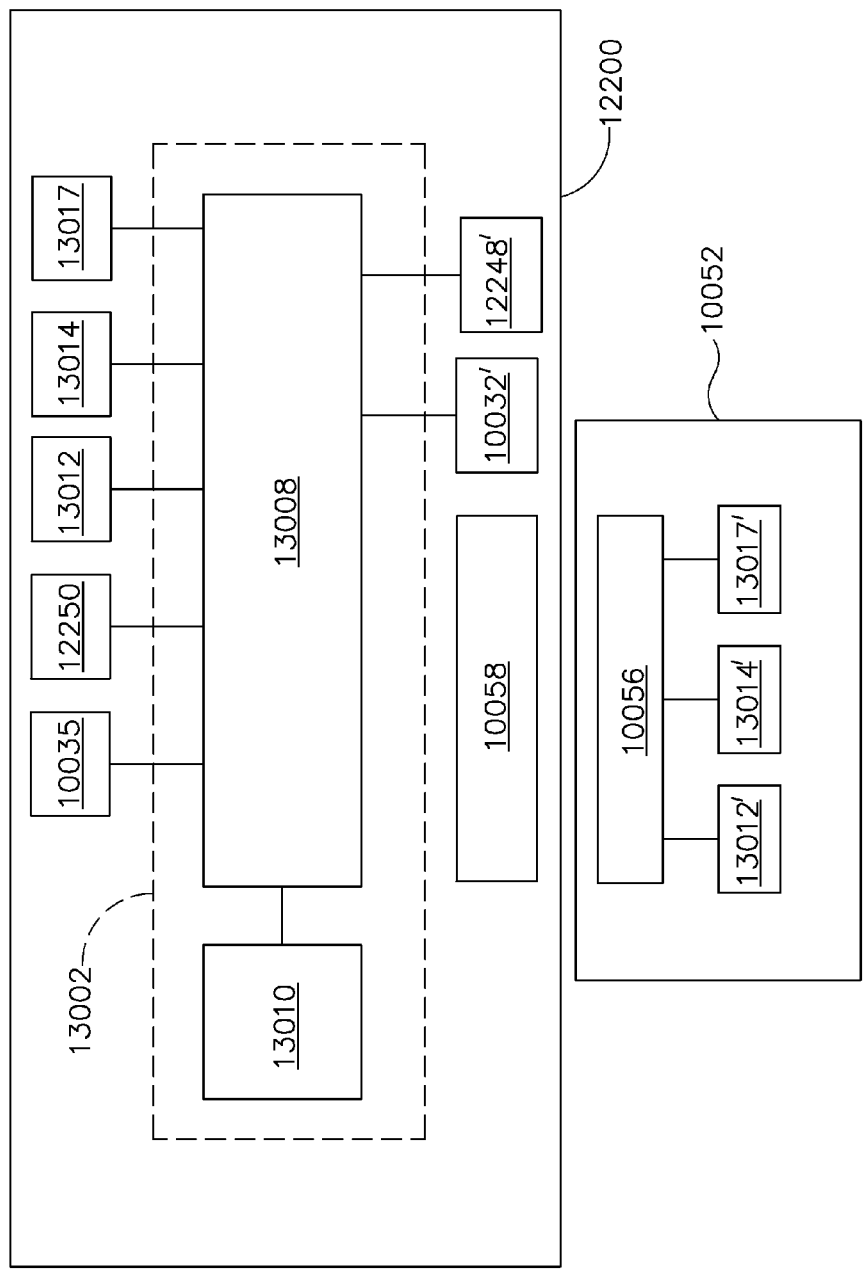
FIG. 107 is a schematic block diagram of the surgical instrument of FIG. 87 in wireless communication with a remote operating unit.

In various instances, as illustrated in FIGS. 105 and 106, the remote operating unit 10052 can be coupled to the handle assembly 12202 of the surgical instrument 12200 via an elongate flexible cable 10054, for example, which can be configured to transmit various actuation signals to the processor 13008 of the surgical instrument 12200, for example; the various actuation signals can be generated by actuating the plurality of secondary controls of the interface 13001', for example. In certain instances, as illustrated in FIG. 107, the remote operating unit 10052 may comprise a transmitter 10056 which can be configured to wirelessly transmit the actuation signals generated by the secondary controls of the secondary interface 13001' from the remote operating unit 10052 to the processor 13001, for example, through a receiver 10058 which can be located in the handle assembly 12202, for example.

In various instances, the surgical instrument 12200 and/or the remote operating unit 10052 may include communication activation inputs (not shown). In certain instances, actuating the communication activation inputs may be a precursory step to establishing communication between the surgical instrument 12200 and the remote operating unit 10052, for example; once communication is established, the operator may employ the remote operating unit 10052 to remotely control the surgical instrument 12200, for example.

In various instances, the memory 13010 may include program instructions for a puppet mode, which when executed may cause the processor 13008 to respond to the actuation signals generated by the plurality of secondary controls of the secondary interface 13001' in the same, or at least similar, manner to the response of the processor 13008 to the actuation signals generated by the plurality of primary controls of the primary interface 13001. In other words, the responses of the processor 13008 to the actuation signals generated by the plurality of secondary controls can be configured to mimic the responses of the processor 13008 to the actuation signals generated by the plurality of primary controls, for example.

In certain instances, actuation of the remote firing input 13017' may solicit the same, or at least a similar, response from the processor 13008 as the actuation of the firing input 13017; the solicited response may include activation of the motor 12216 to motivate the firing member to fire the staples from the staple cartridge 10006 and/or cut tissue captured between the anvil 10002 and the staple cartridge 10006, for example. In certain instances, actuation of the remote articulation rocker 13012' may solicit the same, or at least a similar, response from the processor 13008 as the actuation of the articulation rocker 13012; the solicited response may include activation of the motor 12216 to articulate the end effector 12208 relative to the elongate shaft 12204, for example.

In certain instances, the processor 13008 can be configured to require input actuation signals from both of the primary controls of the primary interface 13001 and the corresponding secondary controls of the secondary interface 13001' to perform the function solicited by such controls. In such instances, the remote operator of the remote operating unit 10052 may need the assistance of an additional operator who can be employed to manually actuate the primary controls of the primary interface 13001 while the remote operator actuates the secondary controls of the secondary interface 13001', for example.

In various instances, as described above, an operator may operate the surgical instrument 12200 together with a robotically-controlled surgical system, which may be controlled by a robotic control system from a remote location. In certain instances, the remote operating unit 10052 can be configured to work in tandem with the robotic control system. In certain instances, the robotic control system may include one or more control ports; and the remote operating unit 10052 may comprise connection means for coupling engagement with the control ports of the robotic control system. In such instances, the operator may operate the surgical instrument 12200 through an interface of the robotic control system, for example. In various instances, the control ports may comprise unique mechanical and/or electrical configurations which may require the use of original equipment manufacturer components to ensure consistent product quality and performance, for example.

In various instances, the remote operating unit 10052 may include various indicators 10032' which can be similar in many respects to the indicators 10032 of the handle assembly 12202. In certain instances, the indicators 10032' of the remote operating unit 10052 can be employed by the processor 13008 in the same, or at least substantially the same, manner as the indicators 10032 to guide, alert, and/or provide feedback to the operator with respect to the various steps of operation of the surgical instrument 12200.

In various instances, the remote operating unit 10052 may include various feedback devices 12248' which can be similar in many respects to the feedback devices 12248 of the handle assembly 12202. In certain instances, the feedback devices 12248' of the remote operating unit 10052 can be employed by the processor 13008 in the same, or at least substantially the same, manner as the feedback devices 12248 to provide sensory feedback to the operator with respect to the various steps of operation of the surgical instrument 12200. Similar to the feedback devices 12248, the feedback devices 12248' may include, for example, visual feedback devices, audio feedback devices, tactile feedback devices, and/or combinations thereof.

Figure 108:
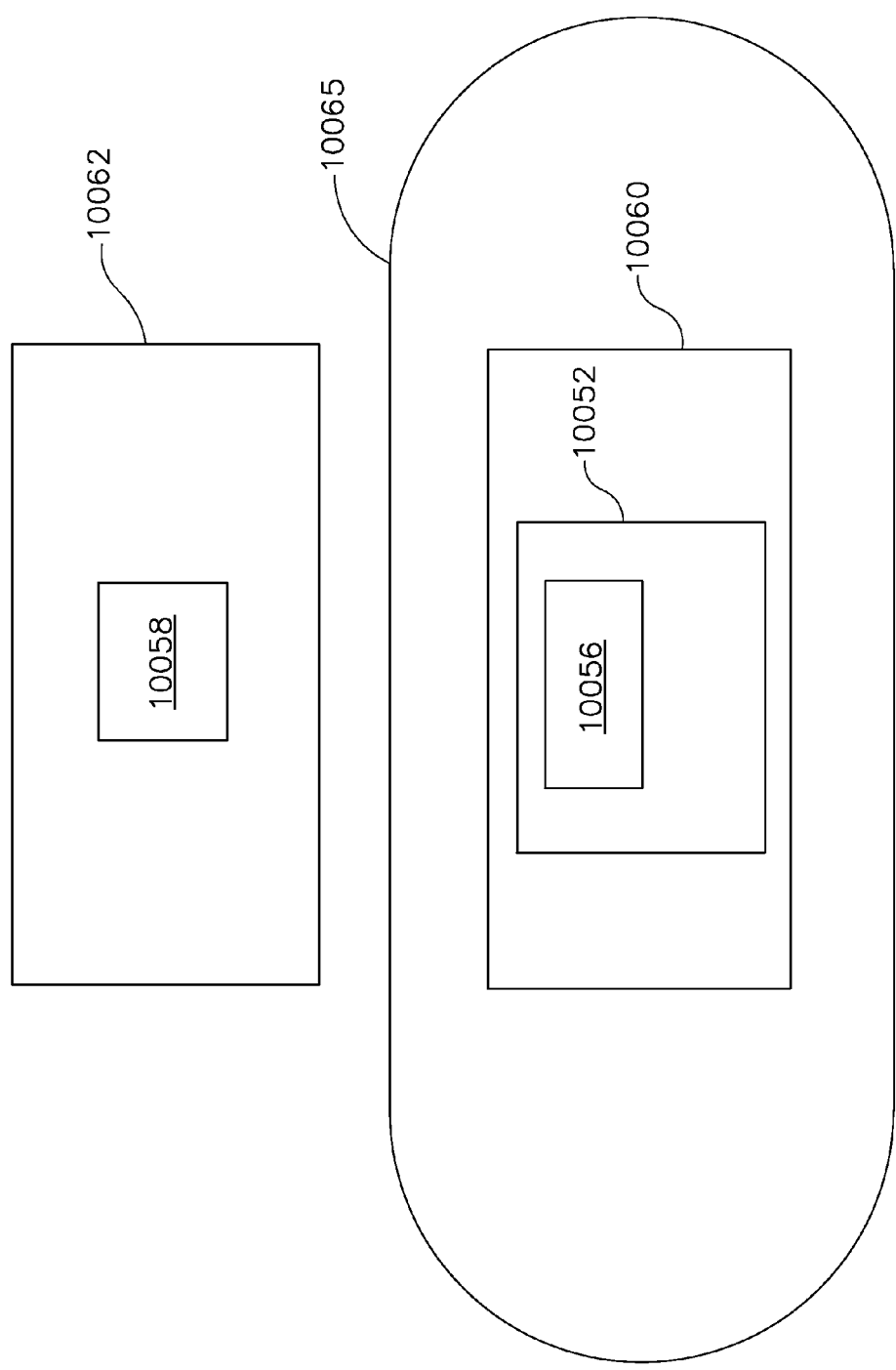
FIG. 108 is a schematic illustration of a first surgical instrument including a remote operating unit for controlling a second surgical instrument.

In various instances, as illustrated in FIG. 108, the remote operating unit 10052 can be included or integrated with a first surgical instrument 10060 and can be utilized to operate a second surgical instrument 10062, for example. In certain instances, the first surgical instrument 10060 can reside in a surgical field 10065 and can be manually operated by the operator from within the surgical field 10065, for example; and the second surgical instrument 10062 can reside outside the surgical field 10065. In certain instances, to avoid exiting the surgical field 10065, the operator may use the remote operating unit 10052 to remotely operate the second surgical instrument 10062 from within the surgical field 10065, for example. In certain instances, the second surgical instrument 10062 may be a circular stapler, for example. The entire disclosure of U.S. Pat. No. 8,360,297, entitled SURGICAL CUTTING AND STAPLING INSTRUMENT WITH SELF ADJUSTING ANVIL, which issued on Jan. 29, 2013, is incorporated by reference herein.

In various instances, the first surgical instrument 10060 and/or the second surgical instrument 10062 may include communication activation inputs (not shown). In such instances, actuating the communication activation inputs may be a precursory step to establishing communication between the first surgical instrument 10060 and the second surgical instrument 10062, for example; once communication is established, the operator may employ the remote operating unit 10052 to remotely control the second surgical instrument 10062, for example.

In various instances, a surgical system can include modular components that can be attached and/or combined together to form a surgical instrument. In certain instances, the modular components can be designed, manufactured, programmed, and/or updated at different times and/or in accordance with different software and/or firmware revisions and updates. For example, referring primarily to FIGS. 109 and 110, a surgical instrument 14100 can include a first modular component 14110, such as a handle, for example, and a second modular component 14120, such as a shaft 14122 and an end effector 14124, for example, which are described in greater detail herein. In various circumstances, the first modular component 14110 and the second modular component 14120 can be assembled together to form the modular surgical instrument 14100 or at least a portion thereof. Optionally, a different modular component may be coupled to the first modular component 14110, such as shaft having different dimensions and/or features than those of the second modular component 14120, for example. In various instances, the surgical instrument can include additional modular components, such as a modular battery, for example. Components of the modular surgical instrument 14100 can include a control system that is designed and configured to control various elements and/or functions of the surgical instrument 14100. For example, the first modular component 14110 and the second modular component 14120 can each comprise a control system, and the control systems of each modular component 14110, 14120 can communicate and/or cooperate. In various instances, the first modular component 14110 may have been designed, manufactured, programmed, and/or updated at a different time and/or with different software and/or firmware than the second modular component 14120, for example.

Figure 111:
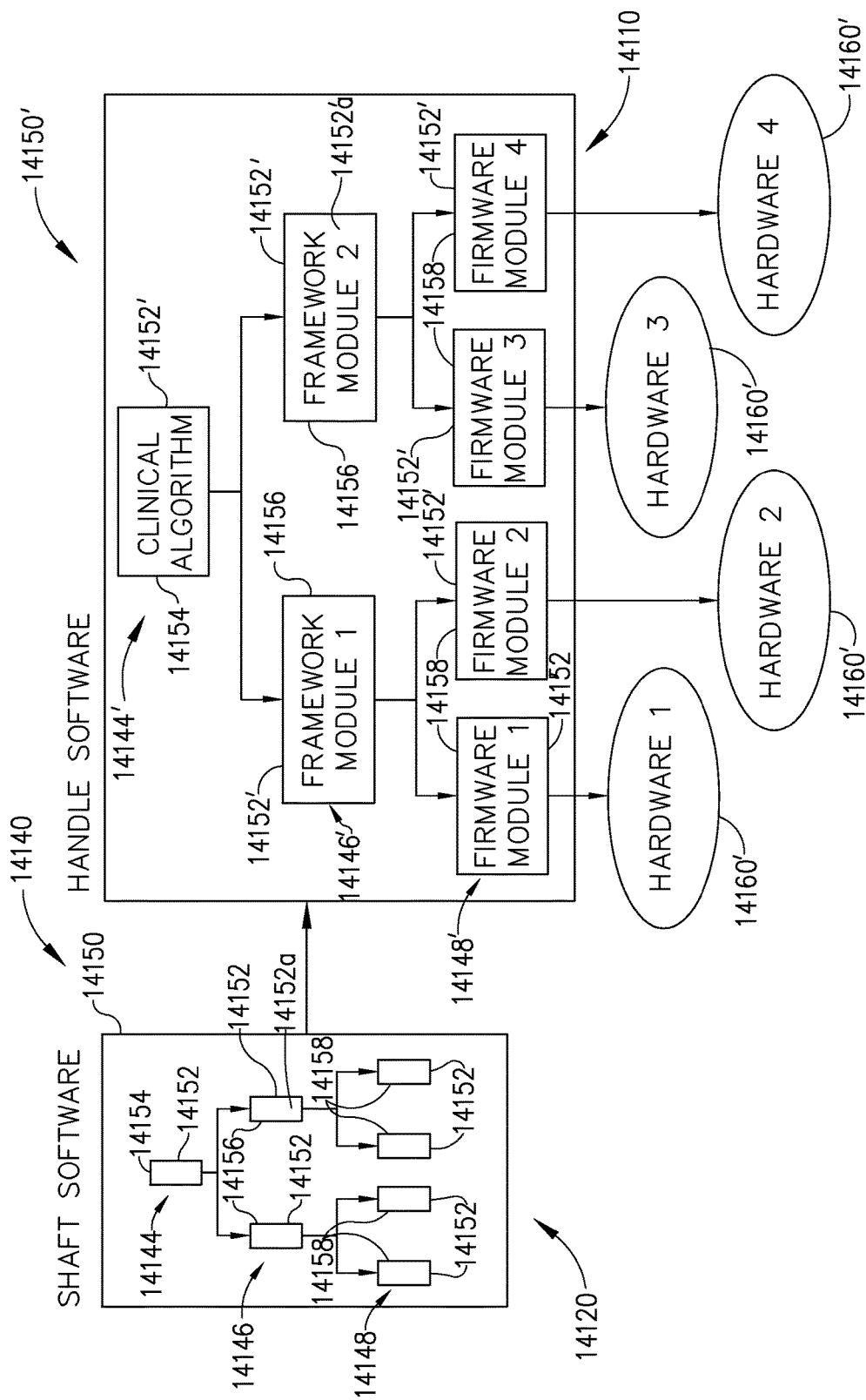

Referring now to FIG. 111, the assembled surgical system can include a first control system 14150' and a second control system 14150. The control systems 14150', 14150 can be in signal communication, for example. In various instances, the second modular component 14120 can comprise the control system 14150, for example, which can include a plurality of control modules 14152. The control modules 14152 can affect a surgical function with and/or by an element or subsystem of the surgical instrument 14100, for example. The control modules 14152 can affect a surgical function based on a pre-programmed routine, operator input, and/or system feedback, for example. In various instances, the first modular component 14110 can also comprise a control system 14150', for example, which can include a plurality of control modules 14152'. The control system 14150' and/or one of the control modules 14152' of the first modular component 14110 may be different than the control system 14150 and/or one of the control modules 14152 of the second modular component 14120. Though the control systems 14150 and 14150' can be different, the control systems 14150 and 14150' can be configured to control corresponding functions. For example, the control module 14152(a) and the control module 14152(a)' can both issue commands to firmware modules 14158 to implement a firing stroke, for example. In various instances, one of the control systems 14150, 14150' and/or a control module 14152, 14152' thereof may include updated software and/or firmware and/or can have a more-recent effective date, as described in greater detail herein.

A control module 14152, 14152' can comprise software, firmware, a program, a module, and/or a routine, for example, and/or can include multiple software, firmware, programs, control modules, and/or routines, for example. In various circumstances, the control systems 14150, 14150' can include multiple tiers and/or levels of command. For example, the control system 14150 can include a first tier 14144 of control modules 14152, a second tier 14146 of control modules 14152, and/or a third tier 14148 of control modules 14152. Control modules 14152 of the first tier 14144 can be configured to issue commands to the control modules 14152 of the second tier 14146, for example, and the control modules 14152 of the second tier 14146 can be configured to issue commands to the control modules 14152 of the third tier 14148. In various instances, the control systems 14150, 14150' can include less than three tiers and/or more than three tiers, for example.

Referring still to FIG. 111, the control module(s) 14152 in the first tier 14144 can comprise high-level software, or a clinical algorithm 14154. The clinical algorithm 14154 can control the high-level functions of the surgical instrument 14100, for example. In certain instances, the control module(s) 14152 in the second tier 14146 can comprise intermediate software, or framework module(s) 14156, which can control the intermediate-level functions of the surgical instrument 14100, for example. In certain instances, the clinical algorithm 14154 of the first tier 14144 can issue abstract commands to the framework module(s) 14156 of the second tier 14146 to control the surgical instrument 14100. Furthermore, the control modules 14152 in the third tier 14148 can comprise firmware modules 14158, for example, which can be specific to a particular hardware component 14160, or components, of the surgical instrument 14100. For example, the firmware modules 14158 can correspond to a particular cutting element, firing bar, trigger, sensor, and/or motor of the surgical instrument 14100, and/or can correspond to a particular subsystem of the surgical instrument 14100, for example. In various instances, a framework module 14156 can issue commands to a firmware module 14158 to implement a surgical function with the corresponding hardware component 14160. Accordingly, the various control modules 14152 of the surgical system 14100 can communicate and/or cooperate during a surgical procedure.

Referring still to FIG. 111, the control system 14150 of the second component 14120 can correspond to the control system 14150' of the first component 14110, and the various control modules 14152 of the second component 14120 can correspond to the control modules 14152' of the first component 14110. Stated differently, each control module 14152 can include a parallel, or corresponding control module 14152', and both control modules 14152 and 14152' can be configured to perform identical, similar and/or related functions and/or to provide identical, similar and/or related commands. Referring still to FIG. 111, the control module 14152a can correspond to the control module 14152a'. For example, the control modules 14152a and 14152a' can both control the firing stroke of a cutting element; however, control module 14152a can be configured to control a first cutting element design or model number and control module 14152a' can be configured to control a different cutting element design or model number, for example. In other instances, the control module 14152a' can comprise a software program and control module 14152a can comprise an updated or revised version of the software program, for example.

In various instances, the first component 14110 of the surgical instrument 14100 can include a clinical algorithm 14154' that is different than the clinical algorithm 14154 of the second component 14120. Additionally and/or alternatively, the first component 14110 can include a framework module 14156' that is different than a corresponding framework module 14156 of the second component 14120, and/or the first component 14110 can include a firmware module 14158' that is different than a corresponding firmware module 14158 of the second component 14120.

In various instances, corresponding control modules 14152, 14152' can comprise different effective dates. A person having ordinary skill in the art will appreciate that the effective date of a control module 14152, 14152' can correspond to a date that the control module 14152, 14152' was designed, created, programmed, and/or updated, for example. The effective date of a control module can be recorded or stored in the program code of the control module, for example. In certain instances, a control module of the surgical instrument 14100 can be outdated. Furthermore, an out-of-date, or less-recently updated, control module may be incompatible with, disjointed from, and/or disconnected from an up-to-date and/or more-recently updated, control module. Accordingly, in certain instances, it may be desirable to update out-of-date control modules to ensure proper and effective operation of the surgical instrument 14100.

In various instances, a modular component of the surgical system can include a predetermined default, or master, control system. In such instances, if the control systems of the assembled modular components are different, the default control system can update, overwrite, revise, and/or replace the non-default control systems. In other words, if corresponding control modules are different, incompatible, or inconsistent, for example, the non-default control module can be updated and the default control module can be preserved. For example, if the handle 14110 comprises the control system 14150', which is the non-default control system, and the shaft 14120 comprises the control system 14150, which is the master control system, the control system 14150' of the handle 14110 can be updated based on the control system 14150 of the shaft 14120.

It may be desirable to program a shaft component 14120 of the surgical instrument to include the default control system in circumstances where shaft components are more frequently updated and/or modified than handle components. For example, if new generations and/or iterations of shaft components 14120 are introduced more frequently than new generations and/or iterations of handle components 14110, it may be advantageous to include a default, or master, control system in the shaft component 14120 of the modular surgical instrument 14100. Various circumstances described throughout the present disclosure relate to updating control modules of a handle component based on control modules of the shaft component; however, a person of skill in the art will readily appreciate that, in other contemplated circumstances, the control modules of the shaft component and/or a different modular component may be updated instead of or in addition to the control modules of the handle component.

Figure 112:
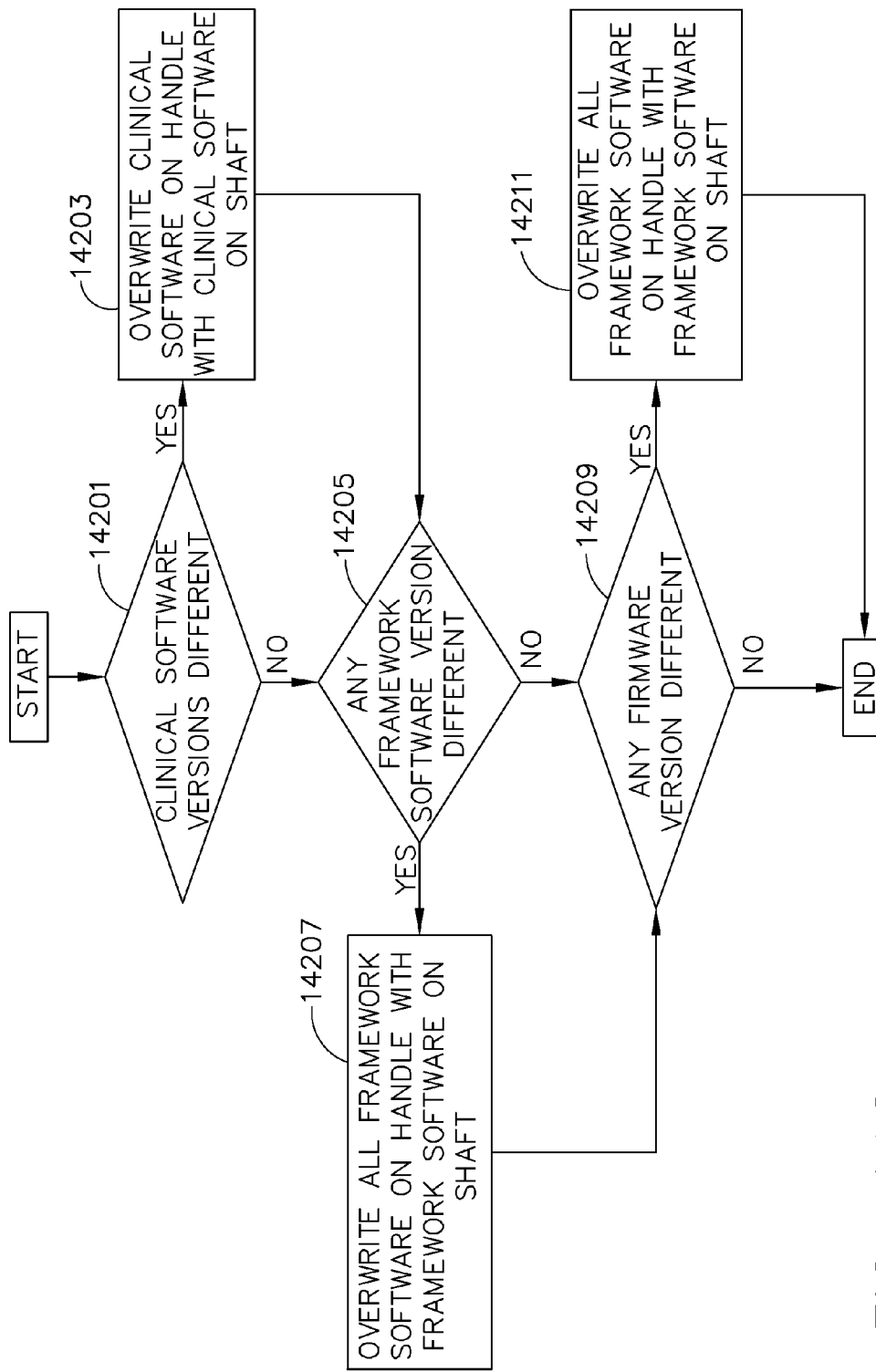

In various instances, the surgical instrument 14100 (FIGS. 109 and 110) can compare the control module(s) 14152' at each tier or level in the control system 14150' to the control module(s) 14152 at each corresponding tier or level in the control system 14150. If the control modules 14152 and 14152' in corresponding tiers are different, a control system 14150, 14150' can update the non-default control module(s), for example. Referring to FIG. 112, at step 14201, the control system 14150 and/or the control system 14150' can compare the control module(s) 14152' of the first tier 14144' of the first component 14110 to the control module(s) 14152 of the first tier 14144 of the second component 14120. Where the first tiers 14144, 14144' comprise high-level clinical algorithms 14154, 14154', respectively, the control system 14150 and/or the control system 14150' can compare the clinical algorithms 14154 and 14154', for example. Furthermore, at step 14203, if the control modules 14152, 14152' in the first tiers 14144, 14144' are different, the control system 14150 and/or the control system 14150' can update the module(s) 14152' of the first tier 14144' with the default module(s) 14152 of the first tier 14144, for example. In various instances, the control system 14150 can compare and/or update a control system and/or control modules and, in other circumstances, the control system 14150' can compare and update a control system and/or control modules, for example. In various instances, one of the control systems 14150, 14150' can be configured to compare and/or update a control system and/or control modules and, in other instances, both control systems 14150, 14150' can be configured to compare and/or update a control system and/or control modules.

At step 14205, the control system 14150 and/or the control system 14150' can compare the control modules 14152' of the second tier 14146' of the first component 14110 to the control modules 14152 of the second tier 14146 of the second component 14120. For example, where the second tiers 14146, 14146' comprise mid-level framework algorithms 14156, 14156', the control systems 14150, 14150' can compare the framework algorithms 14156 and 14156', for example. At step 14207, if the modules 14152, 14152' in the second tiers 14146, 14146' are different, the control systems 14150, 14150' can update the control modules 14152' of the second tier 14146' with the default control modules 14152 of the second tier 14146. In various instances, though one or more of the control modules 14152' in the second tier 14146' can be the same as a corresponding module 14152 in the second tier 14146, all control modules 14152' of the second tier 14146' can be updated if any corresponding second tier modules 14152, 14152' are different. In other instances, as described in greater detail herein, only the control module(s) 14152' that is/are different than the corresponding module(s) 14152 may be updated.

At step 14209, the control systems 14150 and/or the control system 14150' can compare the control modules 14152' of the third tier 14148' of the first component 14110 to the control modules 14152 of the third tier 14148 of the second component 14120. For example, where the third tiers 14148, 14148' comprise firmware modules 14158, 14158', the control system 14150 and/or the control system 14150' can compare the firmware modules 14158 and 14158', for example. If the modules 14152, 14152' in the third tiers 14148, 14148' are different, the control system 14150 and/or the control system 14150' can update the control modules 14152' of the third tier 14148' with the default control modules 14152 of the third tier 14148 at step 211. In various instances, though one or more of the control modules 14152' in the third tier 14148' can be the same as a corresponding control module 14152 in the third tier 14148, all modules 14152' of the third tier 14148' can be updated if any corresponding third tier modules 14152, 14152' are different. In other instances, only the control module(s) 14152' that is/are different than the corresponding control module(s) 14152 may be updated, as described in greater detail herein. Referring still to FIG. 112, the first tier control modules 14154, 14154' can be updated prior to the second tier control modules 14156, 14156', for example, and the second tier control modules 14156, 14156' can be updated prior to the third tier control modules 14158, 14158', for example. In other instances, as described in greater detail herein, the third tier control modules 14158, 14158' can be updated prior to the second tier control modules 14156, 14156', for example, and the second tier control modules 14156, 14156' can be updated before the first tier control modules 14154, 14154', for example.

As described above, the control system 14150 and/or the control system 14150' may compare the control system 14150, 14150' and/or the control modules 14152, 14152' thereof prior to updating, replacing and/or overwriting an outdated control module 14152, 14152' and/or control systems 14150, 14150'. A reader will appreciate that this step can reduce the instrument startup time when software updates and/or upgrades are unnecessary or unmerited. Alternatively, the comparison steps 14201, 14205, and 14209 could be eliminated, and the control systems 14150, 14150' may automatically update, replace, revise and/or overwrite the control module(s) 14152' of the first modular component 14110 and/or specific, predetermined control module(s) 14152 of the first modular component 14110, for example.

In various instances, the control modules 14152, 14152' can be compared and updated on a tier-by-tier basis and, in other instances, the control systems 14150, 14150' can be compared and updated on a system-by-system basis. In still other instances, the control modules 14152, 14152' can be updated on a module-by-module basis. For example, referring now to FIG. 113, at step 14221, a third tier module 14158' of the first control system 14150' can be compared to a corresponding third tier module 14158 of the second control system 14150. In various instances, the effective date of the third tier module 14158' can be compared to the effective date of the corresponding third tier module 14158. Moreover, the control system 14150 and/or the control system 14150' can determine if the effective date of the third tier module 14158' postdates the effective date of the third tier module 14158. If the third tier module 14158' is newer than the third tier module 14158, for example, the third tier module 14158' can be preserved at step 14225. Conversely, if the third tier module 14158' is not newer than the third tier module 14158, i.e., the third tier module 14158 predates the corresponding third tier module 14158 or the third tier module 14158 and the corresponding third tier module 14158' have the same effective date, the third tier module 14158' can be updated, replaced, revised, and/or overwritten by the corresponding third tier module 14158, for example. Furthermore, in various instances, steps 14221 and either 14223 or 14225 can be repeated for each module 14158, 14158' in the third tier of the control systems 14150, 14150'. Accordingly, the modules 14158' in the third tier 14148' may be updated on a module-by-module basis, and in various instances, only outdated modules 14158' can be updated and/or overwritten, for example.

Figure 113:
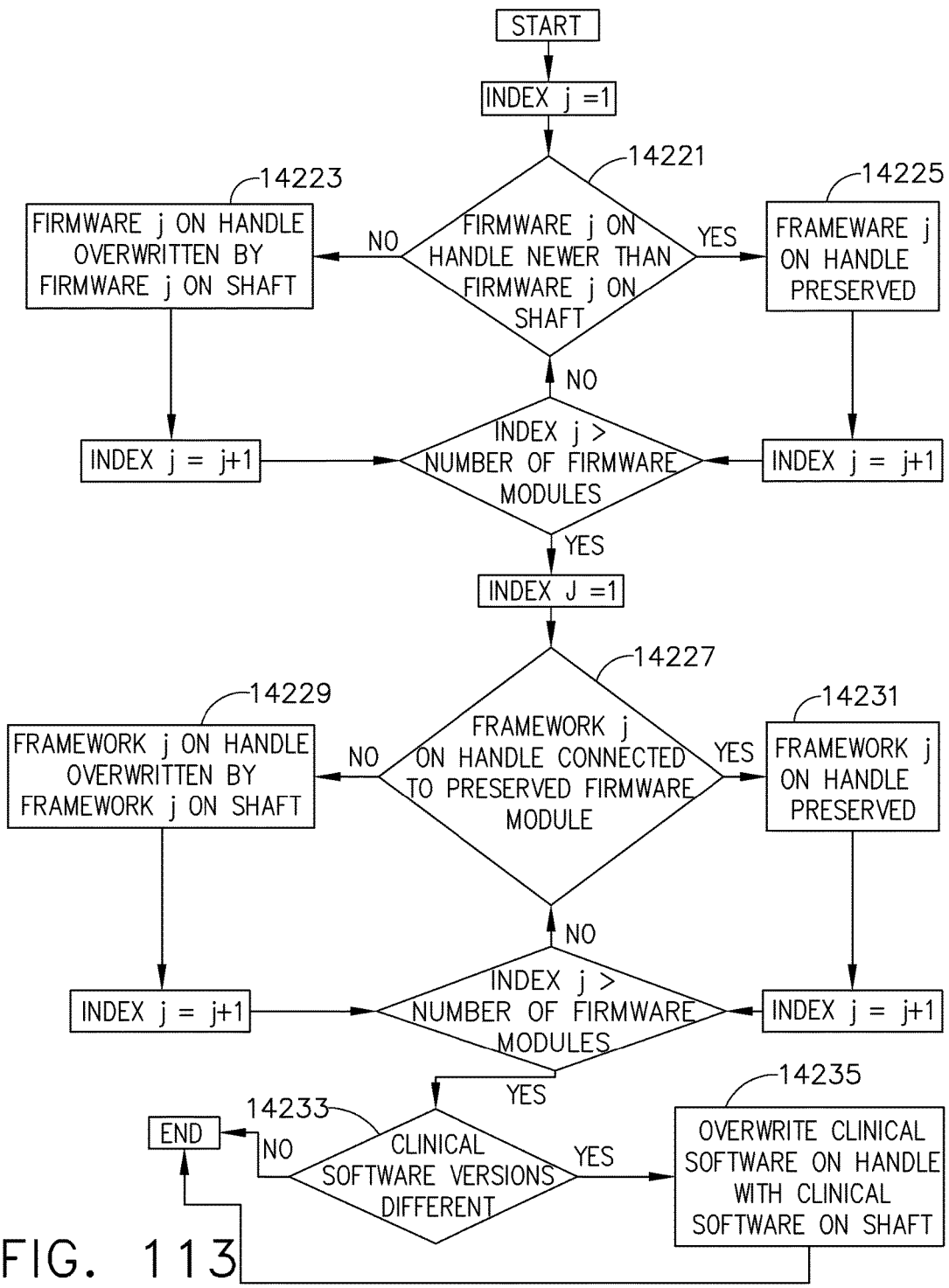

Referring still to FIG. 113, after all third tier modules 14158, 14158' have been compared and possibly updated, the control systems 14150, 14150' can progress to step 14227. At step 14227, the control system 14150 and/or the control system 14150' can confirm that a third tier module 14158' of the first control system 14150' is connected and/or in proper communication with a second tier module 14156' of the control system 14150'. For example, in circumstances where the third tier module 14158' was updated at step 14223, the second tier module 14156' may be disconnected from the updated third tier module 14158'. If the third tier module 14158' is disconnected from the second tier module 14156', for example, the second tier module 14156' can be updated, replaced, revised, and/or overwritten at step 14229. The second tier module 14156' can be replaced by the corresponding second tier module 14156 of the second control system 14150, for example. Conversely, if the third tier module 14158' is properly connected and/or in communication with the second tier module 14156', the second tier module 14156' can be preserved. Furthermore, in various instances, steps 14227 and either 14229 or 14231 can be repeated for each module 14158, 14158' in the third tier of the control systems 14150, 14150'. Accordingly, the modules 14156' in the second tier 14146' may be updated on a module-by-module basis, and in various instances, only disconnected modules 14156' can be updated or overwritten, for example.

After updating any outdated third tier modules 14158' (steps 14221 and 14223) and ensuring all updated third tier modules 14158', if any, are connected to the appropriate second tier module 14156' on the first modular component 14110 (steps 14227, 14229, and 14231), the control systems 14150, 14150' can progress to step 14233, wherein the first tier module 14154' of the first control system 14150' can be compared to a corresponding first tier module 14154 of the second control system 14150. If the first tier modules 14154, 14154' are the same, the updating and/or revising process can be complete. Conversely, if the first tier modules 14154, 14154' are different, the first tier module 14154' of the first control system 14150' can be updated, replaced, revised, and/or overwritten by the first tier module 14154 of the second control system 14150.

As described herein, the software and/or firmware modules of the modular components 14110, 14120 can be updated, revised, and/or replaced on a module-by-module, tier-by-tier, and/or system-by-system basis. In certain instances, the updating and/or revision process can be automatic when the modular components are attached and/or operably coupled. In other circumstances, an operator of the surgical instrument 14100 can initiate or trigger the updating and/or revision process described herein.

Figure 109:
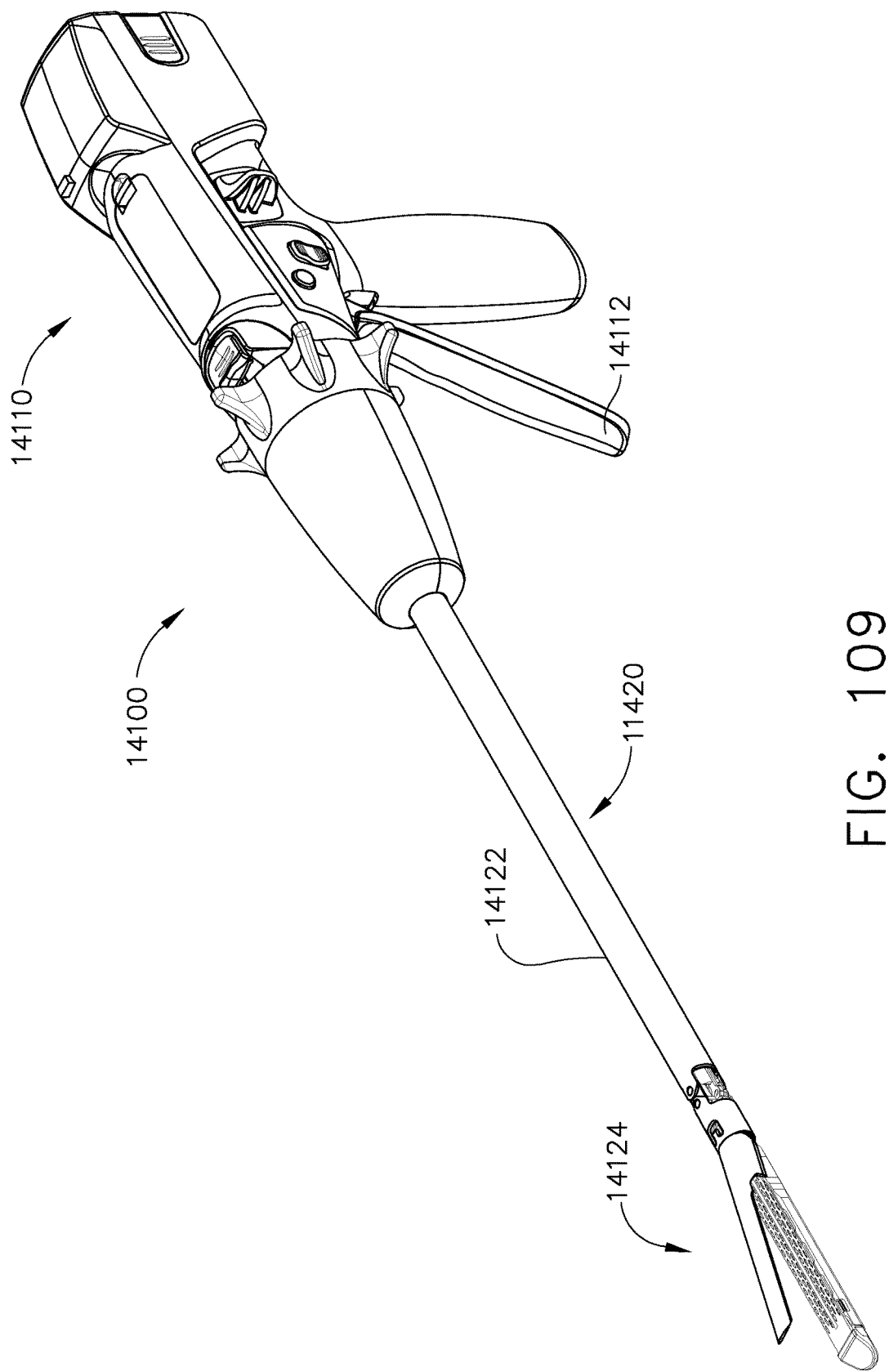
FIG. 109 is a perspective view of a modular surgical instrument according to various embodiments of the present disclosure.
Figure 110:
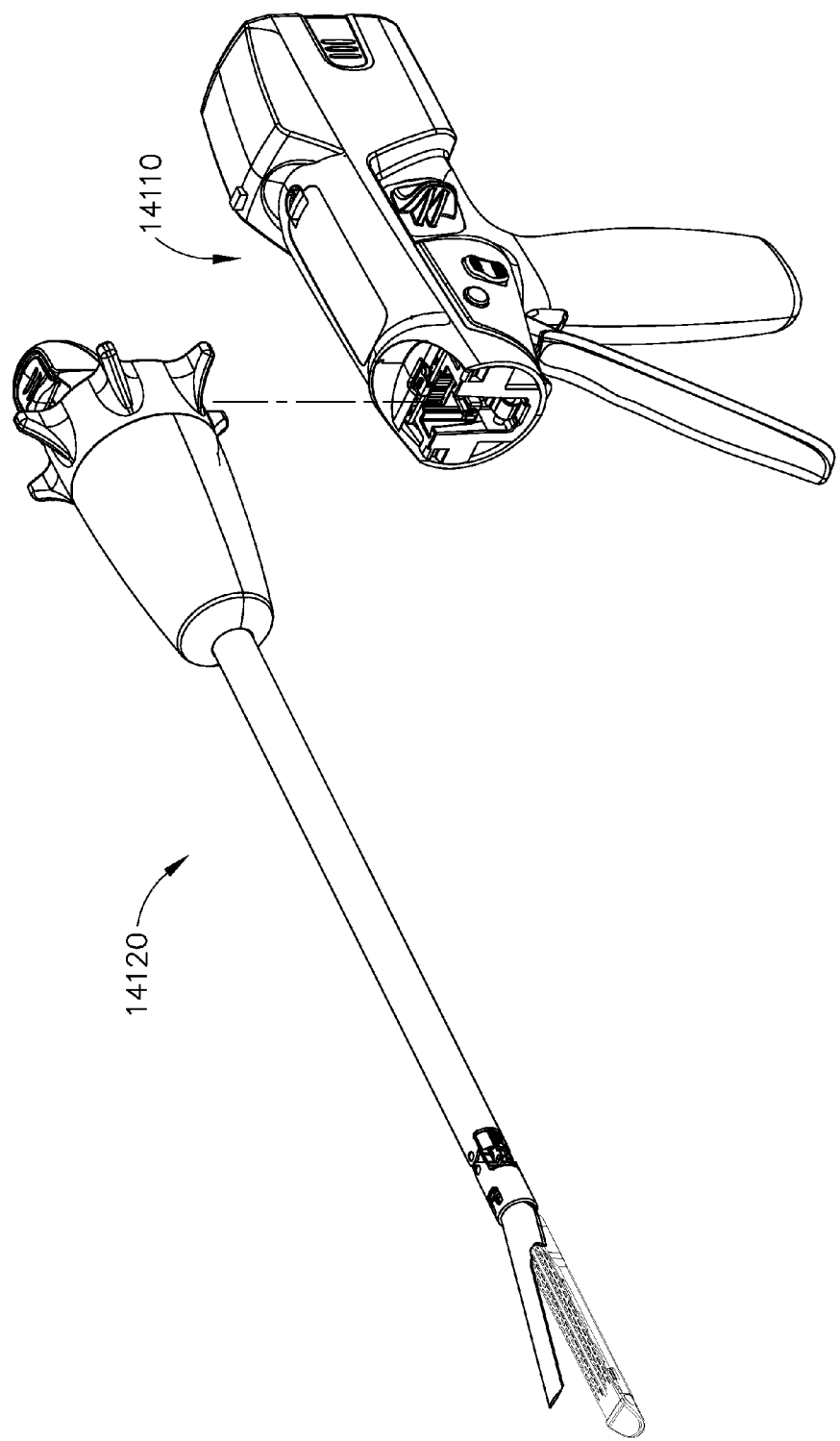

In various instances, a modular surgical instrument, such as the modular surgical instrument 14100 (FIGS. 109 and 110), for example, can include a microcontroller in signal communication with an engagement sensor and a display. In various instances, the engagement sensor can detect the relative positioning of modular components of the surgical system. Referring again to FIGS. 109 and 110, where the first modular component 14110 comprises a handle and the second modular component 14120 comprises a shaft, for example, an engagement sensor can detect whether the shaft 14120 is engaged with and/or operably coupled to the handle 14110. In various instances, the shaft 14120 can be moveable between engagement with the handle 14110 (FIG. 109) and disengagement from the handle 14110 (FIG. 110).

Referring primarily to FIGS. 114(A) and 114(B), an engagement sensor, such as the engagement sensor 14602, for example, can be in signal communication with a microcontroller, such as the microcontroller 14604, for example, of a surgical system. In various instances, the engagement sensor 14602 can detect whether the modular components 14110, 14120 are engaged or disengaged, for example, and can communicate the engagement or lack thereof to the microcontroller 14604, for example. When the engagement sensor 14602 indicates that the shaft 14120 is engaged with the handle 14110, for example, the microcontroller 14604 can permit a surgical function by the modular surgical instrument 14100 (FIG. 109). If the modular components 14110, 14120 are operably coupled, for example, an actuation of the firing trigger 14112 (FIG. 109) on the handle 14110 can affect, or at least attempt to affect, a firing motion in the shaft 14120, for example. Conversely, if the engagement sensor 14602 indicates that the shaft 14120 is disengaged from the handle 14110, the microcontroller 14604 can prevent a surgical function. For example, if the modular components 14110, 14120 are disconnected, an actuation of the firing trigger 14612 may not affect, or not attempt to affect, a firing motion in the shaft 14120.

In various instances, the modular surgical instrument 14100 can include a display, such as the display 14606 (FIG. 114(B)), for example. The display 14606 can be integrated into one of the modular components 14110, 14120 of the surgical instrument 14100 and/or can be external to the modular components 14110, 14120 and in signal communication with the microcontroller 14604 of the surgical instrument 14100. In various instances, the microcontroller 14604 can communicate the information detected by the engagement sensor 14602 to the display 14606. For example, the display 14606 can depict engagement and/or non-engagement of the modular components 14110, 14120. Moreover, in various instances, the display 14606 can provide instructions and/or guidance regarding how to (a) properly attach, couple, and/or engage the disengaged components 14110, 14120 of the surgical instrument 14100, and/or how to (b) properly un-attach, decouple, and/or disengage the engaged components 14110, 14120 of the surgical instrument 14100. Referring again to FIG. 114(A), in various instances, the engagement sensor 14604 can comprise a Hall Effect switch, and in other instances, the engagement sensor can comprise a different and/or additional sensor and/or switch, for example.

In certain circumstances, the engagement sensor 14604 can detect the degree of engagement between modular components of a surgical instrument. In instances where the first component comprises the handle 14110, for example, and the second component comprises the shaft 14120, for example, the handle 14110 and the shaft 14120 can move between a disengaged position, a partially-engaged position, and an engaged position. The partially-engaged position can be intermediate the disengaged position and the engaged position, for example, and there may be multiple partially-engaged positions intermediate the engaged position and the disengaged position, for example. In various instances, the engagement sensor 14604 can include a plurality of sensors, which can detect the partially-engaged position(s) of the components 14110, 14120. For example, the engagement sensor 14606 can comprise a plurality of sensors and/or electrical contacts, for example, which can be staggered along an attachment portion of at least one of the modular components 14110, 14120, for example. In certain instances, the engagement sensor(s) 14604 can comprise a Hall Effect sensor, for example.

In certain instances, referring primarily to FIGS. 115(A) and 115(B), the surgical system 14100 can include multiple sensors in signal communication with a microcontroller, such as the microcontroller 14614, for example. The multiple sensors can include a first sensor 14612 (FIG. 115(A)), which can detect the presence of the first component 14120, and can communicate the presence of the first component 14120 to the microcontroller 14614, for example. In various instances, the first sensor 14612 may not detect and/or communicate the degree of engagement between the first component 14110 and the second component 14120, for example. In various instances, a second sensor 14613 (FIG. 115(A)) can also be in signal communication with the microcontroller 14614. The second sensor 14613 can detect the degree of engagement between the modular components 14110, 14120, for example.

Similar to the control system depicted in FIGS. 114(A) and 114(B), the microcontroller 14614 can issue commands based on the feedback received from the sensors 14612 and 14613, and/or can be in signal communication with a display to display the feedback and/or otherwise communicate with an operator of the surgical system. For example, the microcontroller 14614 can prevent a surgical function until the modular components 14110, 14120 are in the engaged position, and can prevent a surgical function when the modular components 14110, 14120 are partially-engaged, for example. Furthermore, the microcontroller 14614 can communicate the information detected by the engagement sensor to a display. For example, the display can depict engagement, partial-engagement and/or non-engagement of the modular components 14110, 14120. Moreover, in various instances, the display can provide instructions and/or guidance regarding how to properly attach, couple, and/or engage disengaged and/or partially-engaged components 14110, 14120 of the surgical instrument, for example.

In various instances, a surgical instrument can include a microprocessor such as the microprocessor 14604 (FIGS. 114(A) and 114(B)) or 14614 (FIGS. 115(A) and 115(B)), for example, which can be in signal communication with a memory chip or memory unit. The microprocessor can communicate data and/or feedback detected and/or calculated by the various sensors, programs, and/or circuits of the surgical instrument to the memory chip, for example. In various instances, recorded data can relate to the time and/or duration of the surgical procedure, as well as the time and/or duration of various functions and/or portions of the surgical procedure, for example. Additionally or alternatively, recorded data can relate to conditions at the treatment site and/or conditions within the surgical instrument, for example. In certain instances, recordation of data can be automatic and, in other instances, the microprocessor may not record data unless and/or until instructed to record data. For example, it may be preferable to record data during a surgical procedure, maintain or store the recorded data in the memory chip, and/or transfer the recorded data to a secure site. In other circumstances, it may be preferable to record data during a surgical procedure and delete the recorded data thereafter, for example.

A surgical instrument and/or microcontroller thereof can comprise a data storage protocol. The data storage protocol can provide rules for recording, processing, storing, transferring, and/or deleting data, for example. In various instances, the data storage protocol can be preprogrammed and/or updated during the lifecycle of the surgical instrument. In various instances, the data storage protocol can mandate deletion of the recorded data after completion of a surgical function and/or surgical operation and, in other instances, the data storage protocol can mandate deletion of the recorded data after the elapse of a predefined period of time. For example, recorded data can be deleted, in accordance with the data storage protocol, one minute, one hour, one day, one week, one month or one year after the surgical function. The predefined period of time can be any suitable and appropriate period permitted by the circumstances.

In certain circumstances, the data storage protocol can mandate deletion of the recorded data after a predefined number of surgical functions, such as firing strokes, for example. In still other instances, the data storage protocol can mandate deletion of the recorded data when the surgical instrument is powered off. For example, referring to FIG. 117, if the surgical instrument is powered off, the microcontroller can proceed to step 14709, wherein the microcontroller can determine if an error or major issue, such as an instrument, component or subsystem failure, for example, occurred during the surgical procedure. In various instances, if an error is detected, the microcontroller can proceed to step 14713, wherein the data can be stored in the memory chip, for example. Moreover, in certain instances, if an error is not detected, the microcontroller can proceed to step 14711, wherein the data can be deleted, for example. In other instances, the data storage protocol may not comprise the step 14709, and the data storage protocol can continue without checking for a major error or failure, for example.

In still other instances, the data storage protocol can mandate deletion of the recorded data after a predefined period of inactivity or stillness of the surgical instrument. For example, if the surgical instrument is set down and/or put into storage, the data storage protocol can mandate deletion of the recorded data after the surgical instrument has been still or idle for a predefined period of time. The requisite period of stillness can be one minute, one hour, one day, one week, one month, or one year, for example. The predefined period of stillness can be any suitable and appropriate period permitted by the circumstances. In various instances, the surgical instrument can include an accelerometer, for example, which can detect movement and stillness of the surgical instrument. Referring again to FIG. 117, when the surgical instrument has not been powered off at step 14701, the accelerometer can be set to detect movement of the surgical instrument. If movement is detected at step 14703, prior to lapsing of the predefined idle period at step 14707, the predefined idle time count can be restarted at step 14705. Conversely, if movement is not detected by the accelerometer prior to lapsing of the predefined idle period at step 14707, the microprocessor can proceed to step 14709, for example. In other circumstances, the microprocessor can proceed directly to step 14711 or 14713, depending on the data storage protocol, without checking for an instrument error or failure, for example.

As described herein, the data storage protocol can include one of more default rules for deleting recorded data. In certain instances, however, it may be desirable to override the default rule or procedure. For example, for research and/or development purposes, it may be desirable to store recorded data for a longer period of time. Additionally or alternatively, it may be desirable to store recorded data for teaching and/or investigative purposes. Moreover, in various instances, the data storage protocol may not include an error-checking step and, in such instances, it may be desirable to override the data storage protocol and ensure storage of data when the operator detects or suspects an error and/or anomaly during a surgical procedure, for example. The recovered data can facilitate review of the procedure and/or a determination of the cause of the error, for example. In various instances, a key or input may be required to overcome or override the standard data storage protocol. In various instances, the key can be entered into the surgical instrument and/or a remote storage device, and can be entered by an operator and/or user of the surgical instrument, for example.

In various instances, a surgical system may prompt the user or instrument operator to select either data deletion or data storage for each surgical procedure or function. For example, the data storage protocol may mandate solicitation of instructions from the user, and may command subsequent action in accordance with the user's instructions. The surgical system may solicit instructions from the user upon the occurrence of a particular trigger event, such as powering down of the instrument, the elapse of a predefined period of time, or the completion of a particular surgical function, for example.

In certain instances, the surgical system can request input from a user when the surgical instrument is powered down, for example. Referring to FIG. 116, when a user initiates powering off of a surgical instrument at step 14801, for example, the surgical system can request data storage instructions from the user. For example, at step 14803, a display of the surgical system can ask, "KEEP DATA Y/N?" In various instances, the microcontroller of the surgical system can read the user input at step 14805. If the user requests storage of the data, the microcontroller can proceed to step 14809, wherein the data is stored in a memory unit or memory chip of the surgical system. If the user requests deletion of the data, the microcontroller can proceed to step 14811, wherein the data is erased. In various instances, the user may not enter input. In such instances, the data storage protocol can mandate a particular process at step 14813. For example, the data storage protocol may mandate "Process I", "Process II", or an alternative process, for example. In certain instances, "Process I" can command the deletion of data at step 14813(a), and "Process II" can command the storage of data at step 14813(b), for example. In various circumstances, the user can provide instructions to the surgical instrument before instruction have been solicited, for example. Additionally or alternatively, a display associated with the surgical system can request instruction from the user prior to initiating the surgical function and/or at different time(s) during instrument use, for example.

If data is stored in the memory of the surgical instrument, the data can be securely stored. For example, a code or key may be required to access the stored data. In certain instances, the access key can comprise an identification code. For example, the identification code can be specific to the operator, user, or owner of the surgical instrument. In such instances, only an authorized person can obtain a licensed identification code, and thus, only authorized personnel can access the stored data. Additionally or alternatively, the access key can be specific to the instrument and/or can be a manufacturer's code, for example. In certain instances, the access key can comprise a secure server, and data can be transferred and/or accessed by an approved Bluetooth and/or radio frequency (RF) transmission, for example. In still other circumstances, the access key can comprise a physical key, such as memory key and/or a data exchange port connector, which can be physically coupled to a data exchange port of the surgical instrument. In such instances, the access key can be preprogrammed to obtain access to the secure data, and to securely store and/or transfer the data, for example. In various circumstances, an access key can correspond to a specific surgical instrument, for example.

In various instances, data extraction from the memory device of a surgical instrument can be restricted by various security measures. In certain instances, the memory device of the surgical instrument can comprise a secure data connection or data exchange port. For example, the data exchange port can have a proprietary geometry or shape, and only authorized personnel can obtain a corresponding port key designed and structured to fit the proprietary geometry or shape, for example. In various instances, the data exchange port can comprise a mechanical lock, which can comprise a plug, a plurality of pins, and/or a plurality of springs, for example. In various instances, a physical key or extraction device can unlock the mechanical lock of the data exchange port. For example, the physical key can contact the plurality of pins, deform the plurality of springs, and/or bias the plug from a locked orientation to an unlocked orientation to unlock the data exchange port, for example.

In various instances, the data exchange port can comprise at least one connection pin, which can be biased and/or held in a first position. When a physical key is inserted into and/or engages the data exchange port, the physical key can bias the connection pin from the first position to a second position, for example. In various instances, the first position can comprise a retracted position, for example, and the second position can comprise an extended position, for example. Moreover, when the connection pin is moved to the second position, the connection pin can operably interface with a data connection port in the physical key, for example. Accordingly, the data exchange port of the memory device can move into signal communication with the data exchange port of the physical key via the connection pin, for example, such that data can be exchanged and/or transferred therebetween. In various instances, the physical key can comprise a modular component, for example, which can be configured to removably attach to the modular surgical instrument. In certain instances, the physical key can replace or mimic a modular component 14110, 14120 of a surgical instrument 14100 (FIGS. 109 and 110). For example, the physical key can attach to an attachment portion of the handle 14110 in lieu of a shaft attachment 14120, for example, for the transfer of data from a memory device in the handle 14120.

Additionally or alternatively, the key or extraction device can comprise a security token. In various instances, the data exchange port can be encrypted, for example, and/or the key can provide information or codes to the data exchange port to verify that the key is authorized and/or approved to extract data from the data exchange port. In certain circumstances, the key can comprise a specialized data reader, for example, and data can be transferred via an optical data transmission arrangement, for example.

Referring now to FIGS. 118(A)-118(C), before data access is granted to a proposed data reader, the data reader may need to be verified and/or confirmed by the surgical instrument. For example, the proposed data reader can request and read a checksum value of the surgical instrument at step 14821. As depicted in the surgical instrument flowchart depicted in FIG. 118(C), the surgical instrument can first receive the proposed data reader request at step 14841, and can then send the checksum value to the proposed data reader at step 14843. Referring again to FIG. 118(A), at step 14823, the proposed data reader can calculate or determine an appropriate return code based on the checksum value provided by the surgical instrument. The proposed data reader can have access to a code table, for example, and, if the proposed data reader is appropriately attempting to access the data, the appropriate return code can be available in the code table. In such instances, the proposed data reader can pull or calculate the return code at step 14823 and can send the return code to the surgical instrument at step 14825. Referring again to FIG. 118(C), upon receiving the return code from the proposed data reader at step 14845, the surgical instrument can verify that the return code is correct at step 14847. If the code is incorrect, the microprocessor of the surgical instrument can proceed to step 14849, for example, and the surgical instrument can be shut down, or access to the stored data can be otherwise denied. However, if the code is correct, the microprocessor can proceed to step 14851, for example, and the surgical instrument can provide data access to the proposed data reader. For example, the data can be securely transferred to the data reader at step 14851. Thereafter, at step 14827 (FIG. 118(A)), the proposed data reader can read the data from the surgical instrument, for example. In various instances, the transferred data can be encrypted, for example, and the data reader may need to decrypt the unintelligible data prior to reading it, for example.

Referring primarily to FIG. 118(B), an alternate data extraction security method can be similar to the method depicted in FIG. 118(A), for example, and can also require the consideration of a reader-specific code. Although the reader can read the checksum of the device at step 14831 and the return code can be based on the checksum, in various circumstances, the proposed data reader can have a reader-specific code, and the appropriate return code from the code table can be based on the reader-specific code. For example, the proposed data reader can consider the reader-specific code at step 14832, and can determine the appropriate return code at step 14833 based on the reader-specific code and the code table, for example. The proposed data reader can provide the reader-specific code and the return code to the surgical instrument at step 14835, for example. In such instances, referring again to FIG. 118(C), the microcontroller of the surgical instrument can verify the return code and reader-specific code, at step 14845. Moreover, if these codes are correct, the surgical instrument can provide access to the proposed data reader. Thereafter, at step 14827, the proposed data reader can read the data from the surgical instrument, for example. If one or both of the codes are incorrect, the surgical instrument can prevent the reader from reading the data. For example, the surgical instrument can shut down or otherwise restrict the transfer of data to the reader.

Referring now to FIG. 119, in various instances, a surgical system can comprise a surgical instrument 21600, which can be formed from a plurality of modular components. As described in greater detail herein, a handle component can be compatible with a plurality of different shaft components, for example, and the handle component and/or the shaft components can be reusable, for example. Moreover, a microcontroller of the surgical instrument 21600 can include a locking circuit, for example. In various instances, the locking circuit can prevent actuation of the surgical instrument until the locking circuit has been unlocked, for example. In various circumstances, the operator can enter a temporary access code into the surgical system to unlock the locking circuit of the microcontroller, for example.

In various circumstances, the operator can purchase or otherwise obtain the temporary access code for entering into the surgical system. For example, the instrument manufacturer or distributor can offer access codes for sale, and such access codes can be required in order to unlock, and thus use, the surgical instrument 21660. In various instances, the access code can unlock the locking circuit for a predefined period of time. The instrument manufacturer or distributor can offer different durations of use for purchase, and the user can select and purchase or acquire, a desired or preferable duration of use. For example, the user may acquire ten minutes of use, one hour of use, or one day of use. In other instances, additional and/or different suitable periods of use can be offered for sale or authorization. In various instances, after the acquired period of use expires, the locking circuit can be relocked. In other instances, an access code can unlock the locking circuit for a predefined number of surgical functions. For example, a user may purchase or otherwise obtain a single instrument firing or multiple firings, for example. Moreover, after the user has fired the instrument the purchased or authorized number of times, the locking circuit can be relocked. In still other instances, an access code can permanently unlock the locking circuit, for example.

In various instances, the operator can enter the temporary access code directly into the surgical system via a keypad or other suitable input arrangement. In other instances, the locking circuit can be unlocked by coupling a nonvolatile memory unit to the surgical instrument 21600, wherein the nonvolatile memory unit comprises a preprogrammed access code. In various instances, the nonvolatile memory unit can be loaded into a battery 21650 of the surgical instrument 21660, for example. Moreover, the nonvolatile memory unit can be reloaded and/or replaced. For example, the user can purchase replacement nonvolatile memory units. Additionally or alternatively, new codes can be purchased and uploaded to the nonvolatile memory unit, for example, after the previously-obtained access codes expire or lapse. In various instances, new codes can be loaded onto the nonvolatile memory unit when the battery 1650 is coupled to a power source and/or external computer 21670, for example.

In other instances, the temporary access code can be entered into an external or remote access code input, such as a display screen, computer, and/or heads up display. For example, a temporary access code can be purchased via a computer 21660, and can be transmitted to a radio frequency (RF) device 21680 coupled to the computer 21660. In various instances, the surgical instrument 21600 can comprise a receiver or antenna, which can be in signal communication with the radio frequency device 21680, for example. In such instances, the radio frequency device 21680 can transmit the acquired temporary access code(s) to the surgical instrument 21600 receiver, for example. Accordingly, the locking circuit can be unlocked, and the operator can use the surgical instrument 21600 for the purchased time period and/or number of surgical functions, for example.

In various instances, a modular surgical instrument may be compatible with an external display for depicting data and/or feedback from the surgical instrument. For example, the surgical instrument can comprise an instrument display for displaying feedback from the surgical procedure. In various instances, the instrument display can be positioned on the handle of the instrument, for example. In certain instances, the instrument display can depict a video feed viewed from an endoscope, for example. Additionally or alternatively, the display can detect sensed, measured, approximated, and/or calculated characteristics of the surgical instrument, surgical operation, and/or surgical site, for example. In various instances, it may be desirable to transmit the feedback to an external display. The external display can provide an enlarged view of the duplicated and/or reproduced feedback, for example, which can allow multiple operators and/or assistants to simultaneously view the feedback. In various instances, it may be desirable to select the surgical instrument for connection to the external display, for example, and, in other instances, the selection of a surgical instrument may be automatic.

Referring to FIG. 120, an external display 21700 can depict an end effector 21720 of a surgical instrument and/or the surgical site, for example. The external display 21700 can also depict feedback and/or data sensed and/or measured by the surgical instrument, for example. In various instances, the external display 21700 can duplicate feedback provided on the display of the surgical instrument. In certain circumstances, the surgical instrument can automatically connect with the external display 21700 and/or a wireless receiver in signal communication with the external, or operating room, display 21700, for example. In such instances, an operator can be notified if multiple surgical instruments are attempting to connect to the external display 21700. As described herein, the operator can select the desired surgical instrument(s) from a menu on the external display 21700, for example. In still other instances, the operator can select the desired surgical instrument by providing an input to the surgical instrument. For example, the operator can issue a command, control sequence, or input a code to select the surgical instrument. In various instances, the operator may complete a specific control sequence with the surgical instrument to select that surgical instrument. For example, the operator may power on the surgical instrument and, within a predefined period of time, hold down the reverse button for a predefined period of time, for example, to select the surgical instrument. When an instrument is selected, the feedback on the selected instrument display can be rebroadcast or duplicated on the external display 21700, for example.

In certain instances, the surgical system can include a proximity sensor. For example, the external display and/or wireless receiver can comprise a proximity sensor, which can detect when a surgical instrument is brought within a predefined range thereof. Referring primarily to FIGS. 121 and 122, when the display 21700 and/or wireless receiver detect a surgical instrument, the display can notify the user. In certain circumstances, the display and/or wireless receiver may detect multiple surgical instruments. Referring to FIG. 121, the display 21700 can include a non-obtrusive notification 21704, for example, which can communicate to the user that a surgical instrument, or multiple surgical instruments, have been detected in the proximity of the display 21700. Accordingly, using the controls for the display 21700, such as a computer, for example, the user can click the notification 21704 to open the menu 21706 of instrument selections (FIG. 122). The menu 21706 can depict the available surgical instruments, for example, and the user can select the preferred surgical instrument for broadcasting on the display 21700. For example, the menu 21706 can depict the serial numbers and/or names of the available surgical instruments.

In certain instances, the selected surgical instrument can provide feedback to the operator to confirm its selection. For example, the selected surgical instrument can provide auditory or haptic feedback, for example. Additionally, the selected surgical instrument can broadcast at least a portion of its feedback to the external display 21700. In certain instances, the operator can select multiple surgical instruments and the display 21700 can be shared by the selected surgical instruments. Additionally or alternatively, the operating room can include multiple displays and at least one surgical instrument can be selected for each display, for example. Various surgical system features and/or components are further described in U.S. patent application Ser. No. 13/974,166, filed Aug. 23, 2013, and titled FIRING MEMBER RETRACTION DEVICES FOR POWERED SURGICAL INSTRUMENTS, which is hereby incorporated by reference in its entirety.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/249,117, entitled POWERED SURGICAL CUTTING AND STAPLING APPARATUS WITH MANUALLY RETRACTABLE FIRING SYSTEM, now U.S. Patent Application Publication No. 2010/0089970;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009;

U.S. patent application Ser. No. 12/893,461, entitled STAPLE CARTRIDGE, filed Sep. 29, 2012, now U.S. Patent Application Publication No. 2012/0074198;

U.S. patent application Ser. No. 13/036,647, entitled SURGICAL STAPLING INSTRUMENT, filed Feb. 28, 2011, now U.S. Patent Application Publication No. 2011/0226837;

U.S. patent application Ser. No. 13/118,241, entitled SURGICAL STAPLING INSTRUMENTS WITH ROTATABLE STAPLE DEPLOYMENT ARRANGEMENTS, now U.S. Patent Application Publication No. 2012/0298719;

U.S. patent application Ser. No. 13/524,049, entitled ARTICULATABLE SURGICAL INSTRUMENT COMPRISING A FIRING DRIVE, filed on Jun. 15, 2012;

U.S. patent application Ser. No. 13/800,025, entitled STAPLE CARTRIDGE TISSUE THICKNESS SENSOR SYSTEM, filed on Mar. 13, 2013;

U.S. patent application Ser. No. 13/800,067, entitled STAPLE CARTRIDGE TISSUE THICKNESS SENSOR SYSTEM, filed on Mar. 13, 2013;

U.S. Patent Application Pub. No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, are hereby incorporated by reference herein.

In accordance with various embodiments, the surgical instruments described herein may comprise one or more processors (e.g., microprocessor, microcontroller) coupled to various sensors. In addition, to the processor(s), a storage (having operating logic) and communication interface, are coupled to each other.

The processor may be configured to execute the operating logic. The processor may be any one of a number of single or multi-core processors known in the art. The storage may comprise volatile and non-volatile storage media configured to store persistent and temporal (working) copy of the operating logic.

In various embodiments, the operating logic may be configured to process the collected biometric associated with motion data of the user, as described above. In various embodiments, the operating logic may be configured to perform the initial processing, and transmit the data to the computer hosting the application to determine and generate instructions. For these embodiments, the operating logic may be further configured to receive information from and provide feedback to a hosting computer. In alternate embodiments, the operating logic may be configured to assume a larger role in receiving information and determining the feedback. In either case, whether determined on its own or responsive to instructions from a hosting computer, the operating logic may be further configured to control and provide feedback to the user.

In various embodiments, the operating logic may be implemented in instructions supported by the instruction set architecture (ISA) of the processor, or in higher level languages and compiled into the supported ISA. The operating logic may comprise one or more logic units or modules. The operating logic may be implemented in an object oriented manner. The operating logic may be configured to be executed in a multi-tasking and/or multi-thread manner. In other embodiments, the operating logic may be implemented in hardware such as a gate array.

In various embodiments, the communication interface may be configured to facilitate communication between a peripheral device and the computing system. The communication may include transmission of the collected biometric data associated with position, posture, and/or movement data of the user's body part(s) to a hosting computer, and transmission of data associated with the tactile feedback from the host computer to the peripheral device. In various embodiments, the communication interface may be a wired or a wireless communication interface. An example of a wired communication interface may include, but is not limited to, a Universal Serial Bus (USB) interface. An example of a wireless communication interface may include, but is not limited to, a Bluetooth interface.

For various embodiments, the processor may be packaged together with the operating logic. In various embodiments, the processor may be packaged together with the operating logic to form a System in Package (SiP). In various embodiments, the processor may be integrated on the same die with the operating logic. In various embodiments, the processor may be packaged together with the operating logic to form a System on Chip (SoC).

Various embodiments may be described herein in the general context of computer executable instructions, such as software, program modules, and/or engines being executed by a processor. Generally, software, program modules, and/or engines include any software element arranged to perform particular operations or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, program modules, and/or engines may be located in both local and remote computer storage media including memory storage devices. A memory such as a random access memory (RAM) or other dynamic storage device may be employed for storing information and instructions to be executed by the processor. The memory also may be used for storing temporary variables or other intermediate information during execution of instructions to be executed by the processor.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more of the modules described herein may comprise one or more embedded applications implemented as firmware, software, hardware, or any combination thereof. One or more of the modules described herein may comprise various executable modules such as software, programs, data, drivers, application program interfaces (APIs), and so forth. The firmware may be stored in a memory of the controller 2016 and/or the controller 2022 which may comprise a nonvolatile memory (NVM), such as in bit-masked read-only memory (ROM) or flash memory. In various implementations, storing the firmware in ROM may preserve flash memory. The nonvolatile memory (NVM) may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a general purpose processor or application specific processor. The embodiments, however, are not limited in this context.

The functions of the various functional elements, logical blocks, modules, and circuits elements described in connection with the embodiments disclosed herein may be implemented in the general context of computer executable instructions, such as software, control modules, logic, and/or logic modules executed by the processing unit. Generally, software, control modules, logic, and/or logic modules comprise any software element arranged to perform particular operations. Software, control modules, logic, and/or logic modules can comprise routines, programs, objects, components, data structures and the like that perform particular tasks or implement particular abstract data types. An implementation of the software, control modules, logic, and/or logic modules and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, control modules, logic, and/or logic modules may be located in both local and remote computer storage media including memory storage devices.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

It is worthy to note that any reference to "one embodiment" or "an embodiment" means that a particular feature, structure, or characteristic described in connection with the embodiment is comprised in at least one embodiment. The appearances of the phrase "in one embodiment" or "in one aspect" in the specification are not necessarily all referring to the same embodiment.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

It is worthy to note that some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, application program interface (API), exchanging messages, and so forth.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The disclosed embodiments have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and when necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device also may be sterilized using any other technique known in the art, including but not limited to beta or gamma radiation, ethylene oxide, or steam.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely examples and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated also can be viewed as being "operably connected," or "operably coupled," to each other to achieve the desired functionality, and any two components capable of being so associated also can be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that when a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even when a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

What is claimed is:

1. A surgical instrument, comprising:
    a handle;
    a first sensor configured to detect a condition of said surgical instrument;
    a second sensor configured to detect said condition; and
    a processor, wherein said first sensor and said second sensor are in signal communication with said processor, wherein said processor receives a first signal from said first sensor, wherein said processor receives a second signal from said second sensor, wherein said processor is configured to utilize said first signal and said second signal to determine said condition, wherein said processor is configured to communicate instructions to said surgical instrument in view of said condition, wherein said processor is configured to compare at least one first datum from said first signal to a range of data, wherein said processor is configured to ignore said first signal if said at least one first datum is not within said range of data, wherein said processor is configured to compare at least one second datum from said second signal to said range of data, and wherein said processor is configured to ignore said second signal if said at least one second datum is not within said range of data.

2. A surgical instrument, comprising:
    a handle;
    a first sensor configured to detect a condition of said surgical instrument;
    a second sensor configured to detect said condition; and
    a processor, wherein said first sensor and said second sensor are in signal communication with said processor, wherein said processor receives a first signal from said first sensor, wherein said processor receives a second signal from said second sensor, wherein said processor is configured to utilize said first signal and said second signal to determine said condition, wherein said processor is configured to communicate instructions to said surgical instrument in view of said condition, wherein said processor is configured to compare at least one first datum from said first signal and at least one second datum from said second signal, and wherein said processor is configured to determine whether said at least one first datum is different than said at least one second datum.

3. The surgical instrument of claim 2, wherein said processor is in signal communication with said first sensor and said second sensor, wherein said processor is configured to selectively send a first calibration signal to said first sensor, and wherein said processor is configured to selectively send a second calibration signal to said second sensor.

4. The surgical instrument of claim 2, further comprising a memory device, wherein a calibration lookup table comprising data is stored on said memory device, wherein said processor is in signal communication with said memory device, wherein said processor is configured to access said calibration lookup table, wherein said processor is configured to calibrate said first sensor using at least one datum from said calibration lookup table, and wherein said processor is configured to calibrate said second sensor using at least one datum from said calibration lookup table.

5. The surgical instrument of claim 2, wherein said processor is configured to modify a first gain applied to said at least one first datum if said first signal is not within a predefined range, and wherein said processor is configured to modify a second gain applied to said at least one second datum if said second signal is not within a predefined range.

6. The surgical instrument of claim 2, wherein said processor comprises an algorithm configured to determine said condition from said first signal and said second signal, and wherein said condition is not determinable from only one of said first signal and said second signal.

7. The surgical instrument of claim 2, wherein said instructions modify the operation of the surgical instrument.

8. The surgical instrument of claim 2, further comprising a shaft assembly extending from said handle, wherein said first sensor is positioned in said handle, and wherein said second sensor is positioned in said shaft assembly.

9. The surgical instrument of claim 8, wherein said shaft assembly includes a proximal end and a distal end, wherein said proximal end is engageable with said handle, wherein said condition includes the position of said distal end relative to said proximal end.

10. The surgical instrument of claim 2, wherein said condition includes the electrical power being utilized by said surgical instrument.

11. The surgical instrument of claim 2, wherein said second sensor comprises a redundant sensor to said first sensor.

12. The surgical instrument of claim 2, further comprising a staple cartridge.

13. A surgical instrument, comprising:
a handle;
a first sensor configured to detect a condition of said surgical instrument;
a second sensor configured to detect said condition; and
a processor, wherein said first sensor and said second sensor are in signal communication with said processor, wherein said processor receives a first signal from said first sensor, wherein said processor receives a second signal from said second sensor, wherein said processor is configured to utilize said first signal and said second signal to determine said condition, wherein said processor is configured to communicate instructions to said surgical instrument in view of said condition, wherein said first sensor comprises a first orientation sensor positioned in a first portion of said surgical instrument, wherein said second sensor comprises a second orientation sensor positioned in a second portion of said surgical instrument, and wherein said condition includes the relative movement of said first portion relative to said second portion.

14. A surgical instrument, comprising:
a handle;
a first sensor configured to detect a condition of said surgical instrument;
a second sensor configured to detect said condition; and
a first processor, wherein said first sensor and said second sensor are in signal communication with said first processor, wherein said first processor receives a first signal from said first sensor, wherein said first processor receives a second signal from said second sensor, wherein said first processor is configured to utilize said first signal and said second signal to determine said condition, and wherein said first processor is configured to communicate instructions to said surgical instrument in view of said condition, wherein the surgical instrument further comprises a second processor, wherein said second processor receives said first signal from said first sensor, wherein said second processor receives said second signal from said second sensor, and wherein said second processor is configured to utilize said first signal and said second signal to determine said condition.

15. The surgical instrument of claim 14, wherein said second processor is in signal communication with said first processor, and wherein said second processor is configured to determine whether the condition determined by said first processor is the same as the condition determined by said second processor.

16. The surgical instrument of claim 15, wherein said second processor is configured to deactivate said first processor.

17. A surgical instrument assembly, comprising:
a first sensor configured to detect an operating condition of said surgical instrument assembly;
a second sensor configured to detect the same operating condition of said surgical instrument assembly; and
a controller, wherein said first sensor and said second sensor are in signal communication with said controller, wherein said controller is configured to receive a first signal from said first sensor, wherein said controller is configured to receive a second signal from said second sensor, wherein said controller is configured to utilize said first signal to determine said operating condition and, independently, said second signal to determine said operating condition, and wherein said controller is configured to communicate instructions to said surgical instrument assembly in response to said operating condition.

18. A surgical instrument assembly, comprising:
a first sensor system;
a second sensor system; and
a controller, wherein said first sensor system and said second sensor system are in signal communication with said controller, wherein said controller is configured to receive a first signal from said first sensor system, wherein said controller is configured to receive a second signal from said second sensor system, wherein said controller is configured to concurrently utilize said first signal and said second signal to determine an operating condition of said surgical instrument assembly, and wherein said controller is configured to communicate instructions to said surgical instrument assembly in response to said operating condition.

* * * * *